United States Patent
Byun et al.

(10) Patent No.: US 12,110,305 B2
(45) Date of Patent: Oct. 8, 2024

(54) PRODRUGS OF PHOSPHONAMIDE NUCLEOTIDE ANALOGUES AND THEIR PHARMACEUTICAL USE

(71) Applicant: Gilead Sciences, Inc., Foster City, CA (US)

(72) Inventors: Daniel H. Byun, Foster City, CA (US); Byoung-Kwon Chun, Pleasanton, CA (US); Michael O. Clarke, Redwood City, CA (US); Petr Jansa, Foster City, CA (US); Devan Naduthambi, San Bruno, CA (US); Neil H. Squires, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 2 days.

(21) Appl. No.: 17/394,630

(22) Filed: Aug. 5, 2021

(65) Prior Publication Data
US 2022/0119426 A1    Apr. 21, 2022

Related U.S. Application Data

(60) Provisional application No. 63/062,899, filed on Aug. 7, 2020.

(51) Int. Cl.
| | |
|---|---|
| *C07F 9/36* | (2006.01) |
| *A61K 45/06* | (2006.01) |
| *A61P 31/18* | (2006.01) |
| *A61P 31/20* | (2006.01) |
| *C07F 9/6561* | (2006.01) |

(52) U.S. Cl.
CPC ............. *C07F 9/36* (2013.01); *A61K 45/06* (2013.01); *A61P 31/18* (2018.01); *A61P 31/20* (2018.01); *C07F 9/65616* (2013.01)

(58) Field of Classification Search
None
See application file for complete search history.

(56) References Cited

U.S. PATENT DOCUMENTS

| | | | | |
|---|---|---|---|---|
| 2018/0362562 | A1* | 12/2018 | Raheem | .............. A61K 45/06 |
| 2023/0303599 | A1 | 9/2023 | Byun et al. | |

FOREIGN PATENT DOCUMENTS

| | | |
|---|---|---|
| CN | 103232490 A | 8/2013 |
| CN | 104804042 A | 7/2015 |
| CN | 105330700 A | 2/2016 |
| CN | 106167504 A | 11/2016 |
| CN | 106565785 A | 4/2017 |
| CN | 108101942 A | 6/2018 |
| CN | 108690080 A | 10/2018 |
| CN | 109400647 A | 3/2019 |
| WO | WO-1995/07919 A1 | 3/1995 |
| WO | WO-2005/066189 A1 | 7/2005 |
| WO | WO-2007/084157 A2 | 7/2007 |
| WO | WO-2014/026582 A1 | 2/2014 |
| WO | WO-2015/148746 A1 | 10/2015 |
| WO | WO-2017/007701 A1 | 1/2017 |
| WO | WO-2017/027434 A1 | 2/2017 |
| WO | WO-2017/048956 A1 | 3/2017 |
| WO | WO-2017/100108 A1 | 6/2017 |
| WO | WO-2017/106069 A1 | 6/2017 |
| WO | WO-2017/203395 A1 | 11/2017 |
| WO | WO-2018/039157 A1 | 3/2018 |
| WO | WO-2018/118826 A1 | 6/2018 |
| WO | WO-2018/119013 A1 | 6/2018 |
| WO | WO-2018/172416 A1 | 9/2018 |
| WO | WO-2019/120084 A1 | 6/2019 |
| WO | WO-2020/030781 A1 | 2/2020 |

OTHER PUBLICATIONS

Intl. Search Report-Written Opinion dated Oct. 22, 2021 for Intl. Appl. No. PCT/US2021/044615.
Remenar, J. (2014) "Making the Leap from Daily Oral Dosing to Long-Acting Injectables: Lessons from the Antipsychotics" *Molecular Pharmaceutics* 11:1739-1749.
McGuigan, C et al. (2011) "Phosphorodiamidates as a Promising New Phosphate Prodrug Motif for Antiviral Drug Discovery: Application to Anti-HCV Agents", Journal of Medicinal Chemistry 54(24): 8632-8645.
Tichy, T. et al. (2011) "New prodrugs of Adefovir and Cidofovir", Bioorganic & Medicinal Chemistry 19(11): 3527-3539.
Hecker, S.J. et al. (2008) "Prodrugs of Phosphates and Phosphonates", Journal of Medicinal Chemistry 51(8): 2328-2345.
Redasani & Bari. (2015) Pro Drug Design—Perspectives, Approaches and Applications in Medicinal Chemistry, Elsevier Inc., 84 pages.
Office Action dated Oct. 26, 2022 for Taiwanese Appl. No. 110129079, 11 pages.
Third Party Observation dated Jul. 12, 2022 for Intl. Appl. No. PCT/US2021/044615, 11 pages.
International Preliminary Report on Patentability dated Feb. 16, 2023 for Intl. Appl. No. PCT/US2021/044615, 7 pages.
Notice of Opposition dated Jun. 5, 2023 for Colombian Appl. No. NC2023/0001308, 27 pages.
Office Action dated May 31, 2023 for Taiwanese Appl. No. 110129079, 9 pages.
Dang, Q. et al. (2008) "Discovery of Phosphonic Diamide Prodrugs and Their Use for the Oral Delivery of a Series of Fructose 1,6-Bisphosphatase Inhibitors", Journal of Medicinal Chemistry, Jun. 21, 2008, vol. 51, No. 14, p. 4331-4339.
Office Action dated Apr. 3, 2024 for Japanese Appl. No. 2023-507948, 10 pages.
Office Action dated Apr. 10, 2024 for European Appl. No. 21762257. 0, 6 pages.
Office Action dated 2024 for Eurasian Appl. No. 202390439, 6 pages.
Kitamura, M. (2017) "Hepatitis B therapeutic agent—nucleic acid analog formulation: tenofovir", Oto-Rhino-Laryngology, Tokyo (2017), vol. 60, No. 2, p. 107-109.
Office Action dated Jun. 24, 2024 for Saudi Arabian Appl. No. 523442468.

* cited by examiner

*Primary Examiner* — Po-Chih Chen

(57) ABSTRACT

Compounds, compositions, and method useful for treating a viral infection, such as human immunodeficiency virus (HIV) and/or hepatitis B virus (HBV) infection, are disclosed. In particular, prodrugs of phosphonamide nucleotide analogues and methods for their preparation and use as therapeutic or prophylactic agents are disclosed.

45 Claims, No Drawings

PRODRUGS OF PHOSPHONAMIDE NUCLEOTIDE ANALOGUES AND THEIR PHARMACEUTICAL USE

CROSS REFERENCE TO RELATED APPLICATIONS

This application claims the benefit under 35 U.S.C. § 119(e) of U.S. provisional application No. 63/062,899, filed on Aug. 7, 2020, which is hereby incorporated herein by reference in its entirety for all purposes.

FIELD

Compounds, compositions, and methods useful for treating a viral infection, such as human immunodeficiency virus (HIV) infection, are disclosed.

BACKGROUND

Human immunodeficiency virus infection and related diseases are a major public health problem worldwide. Human immunodeficiency virus encodes three enzymes that are required for viral replication: reverse transcriptase, protease, and integrase. Drugs targeting reverse transcriptase are in wide use and have shown effectiveness, particularly when employed in combination with, for example, protease inhibitors and integrase inhibitors. No HIV cure is known, and accordingly, those affected by HIV can require life-long treatments. Improved treatments for HIV and other viral infections are desirable.

SUMMARY

The present disclosure is directed to novel prodrugs of the nucleotide analogue reverse transcriptase inhibitor tenofovir and pharmaceutically acceptable salts thereof. In some embodiments, the compounds may be used to treat HIV infections, to inhibit the activity of HIV reverse transcriptase, and/or to reduce HIV replication. In some embodiments, compounds disclosed herein may be effective against a range of known drug-resistant HIV mutants. In some embodiments, compounds disclosed herein have properties that make it possible for them to be administered with less than daily frequency, for example, at weekly, monthly, or longer intervals.

In one embodiment, compounds having the following formula (I) or a pharmaceutically acceptable salt thereof are provided:

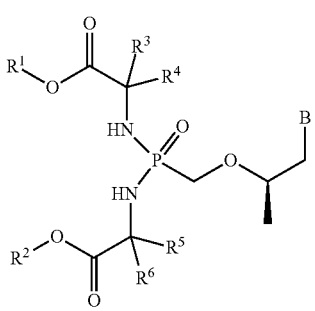

I or a pharmaceutically acceptable salt thereof, wherein $R^1$ and $R^2$ are independently chosen from $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl, bridged $C_{5-10}$bicycloalkyl-$C_{1-4}$alkylene, fused $C_{5-10}$bicycloalkyl, $C_{10-16}$dispirocycloalkyl, $C_{10-16}$dispirocycloalkyl-$C_{1-4}$alkylene, bridged $C_{9-12}$tricycloalkyl, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three $R^a$;

$R^3$, $R^4$, $R^5$, and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or optionally:

$R^3$ and $R^4$ together with the carbon atom to which they are attached form a 3- to 6-membered saturated or partially unsaturated carbocyclic ring optionally substituted with from one to three $R^b$; and $R^5$ and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or $R^3$ and $R^4$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$; or $R^3$ and $R^4$ together with the carbon atom to which they are attached form a 3- to 6-membered saturated or partially unsaturated carbocyclic ring optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$;

B is

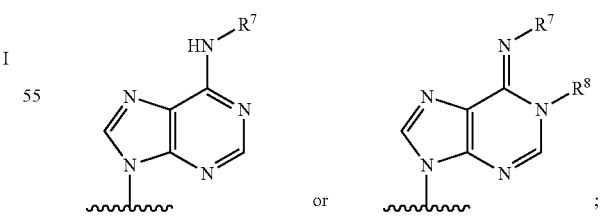

$R^7$ is hydrogen or $R^8$;

$R^8$ is -$L^1$-$(L^2)_m$-$(L^3)_n$-$R^{8a}$;

$L^1$ is chosen from a bond, —C(O)—, and —C(O)O—;

$L^2$ is $C_{1-6}$alkylene;

$L^3$ is —C(O)O— or

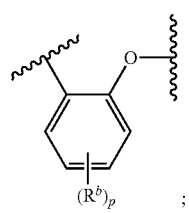

$R^{8a}$ is chosen from $C_{1-12}$alkyl, aryl, —C(O)-aryl, —C(O)—$C_{1-4}$alkyl, —S—C(O)—$C_{1-4}$alkyl,

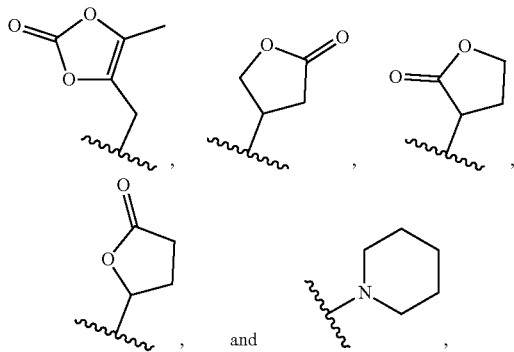

wherein aryl and —C(O)-aryl are optionally substituted with one or two $R^c$;

each $R^a$ is independently chosen from $C_{1-4}$alkyl, halo, $C_{1-4}$haloalkyl, and —O—$C_{1-4}$alkyl;

each $R^b$ is independently $C_{1-4}$alkyl;

each $R^c$ is independently $C_{1-4}$alkyl or —OC(O)—$C_{1-4}$alkyl;

m and n are independently 0 or 1; and p is 0, 1, or 2.

In another embodiment, a pharmaceutical composition is provided comprising a therapeutically effective amount of a compound of formula I, or a pharmaceutically acceptable salt thereof, and a pharmaceutically acceptable excipient.

In another embodiment, a pharmaceutical composition is provided comprising a means for maintaining the therapeutically effective concentration of TFV-DP in PBMCs for an extended period of time, and a pharmaceutically acceptable excipient, wherein the means for maintaining the therapeutically effective concentration of TFV-DP in PBMCs for an extended period of time is a compound of formula I, or a pharmaceutically acceptable salt thereof.

In another embodiment, a pharmaceutical composition is provided comprising a means for maintaining the therapeutically effective concentration of TFV-DP in PHHs for an extended period of time, and a pharmaceutically acceptable excipient, wherein the means for maintaining the therapeutically effective concentration of TFV-DP in PHHs for an extended period of time is a compound of formula I, or a pharmaceutically acceptable salt thereof.

In another embodiment, a kit or an article of manufacture is provided comprising a compound of formula I, or a pharmaceutically acceptable salt thereof, and instructions for use.

In another embodiment, a kit or an article of manufacture is provided comprising a pharmaceutical composition comprising a therapeutically effective amount of a compound of formula I, or a pharmaceutically acceptable salt thereof, and a pharmaceutically acceptable excipient, and instructions for use.

In another embodiment, a method of treating an HIV infection by administering to a subject in need thereof a therapeutically effective amount of a compound of formula I, or a pharmaceutically acceptable salt thereof, is provided.

In another embodiment, a method of treating an HIV infection, by administering to a subject in need thereof a pharmaceutical composition comprising a therapeutically effective amount of a compound of formula I, or a pharmaceutically acceptable salt thereof, and a pharmaceutically acceptable excipient, is provided.

In another embodiment, a method of preventing an HIV infection, by administering to a subject at risk thereof a therapeutically effective amount of a compound of formula I, or a pharmaceutically acceptable salt thereof, is provided.

In another embodiment, a method of preventing an HIV infection, by administering to a subject at risk thereof a pharmaceutical composition comprising a therapeutically effective amount of a compound of formula I, or a pharmaceutically acceptable salt thereof, and a pharmaceutically acceptable excipient, is provided.

In another embodiment, a method of treating an HBV infection, by administering to a subject in need thereof a therapeutically effective amount of a compound of formula I, or a pharmaceutically acceptable salt thereof, is provided.

In another embodiment, a method of treating an HBV infection, by administering to a subject in need thereof a pharmaceutical composition comprising a therapeutically effective amount of a compound of formula I, or a pharmaceutically acceptable salt thereof, and a pharmaceutically acceptable excipient, is provided.

In another embodiment, a method of preventing an HBV infection, by administering to a subject at risk thereof a therapeutically effective amount of a compound of formula I, or a pharmaceutically acceptable salt thereof, is provided.

In another embodiment, a method of preventing an HBV infection, by administering to a subject at risk thereof a pharmaceutical composition comprising a therapeutically effective amount of a compound of formula I, or a pharmaceutically acceptable salt thereof, and a pharmaceutically acceptable excipient, is provided.

In another embodiment, use of a compound of formula I, or a pharmaceutically acceptable salt thereof, for treating an HIV infection is provided.

In another embodiment, use of a pharmaceutical composition comprising a therapeutically effective amount of a compound of formula I or a pharmaceutically acceptable salt thereof, and a pharmaceutically acceptable excipient, for treating an HIV infection is provided.

In another embodiment, use of a compound of formula I, or a pharmaceutically acceptable salt thereof, in the manufacture of a medicament for treating an HIV infection is provided.

In another embodiment, a compound of formula I, or a pharmaceutically acceptable salt thereof, for use in treating an HIV infection is provided.

In another embodiment, a pharmaceutical composition comprising a therapeutically effective amount of a compound of formula I or a pharmaceutically acceptable salt thereof, and a pharmaceutically acceptable excipient, for use in treating an HIV infection is provided.

In another embodiment, use of a compound of formula I, or a pharmaceutically acceptable salt thereof, for treating an HBV infection is provided.

In another embodiment, use of a pharmaceutical composition comprising a therapeutically effective amount of a compound of formula I or a pharmaceutically acceptable salt thereof, and a pharmaceutically acceptable excipient, for treating an HBV infection is provided.

In another embodiment, use of a compound of formula I, or a pharmaceutically acceptable salt thereof, in the manufacture of a medicament for treating an HBV infection is provided.

In another embodiment, a compound of formula I, or a pharmaceutically acceptable salt thereof, for use in treating an HBV infection is provided.

In another embodiment, a pharmaceutical composition comprising a therapeutically effective amount of a compound of formula I, or a pharmaceutically acceptable salt thereof, and a pharmaceutically acceptable excipient, for use in treating an HBV infection is provided.

In another embodiment, a compound of formula I or a pharmaceutically acceptable salt thereof, for use in medical therapy is provided.

In another embodiment, a pharmaceutical composition comprising a therapeutically effective amount of a compound of formula I, or a pharmaceutically acceptable salt thereof, and a pharmaceutically acceptable excipient, for use in medical therapy is provided.

In another embodiment, the use of a compound of formula I, or a pharmaceutically acceptable salt thereof, as a research tool is provided.

In another embodiment, a method of using a compound of formula I in therapy is provided. In particular, a method of treating the proliferation of the HIV virus, treating AIDS, or delaying the onset of AIDS or ARC symptoms in a mammal (e.g., a human), comprising administering to the mammal a compound of formula I or a pharmaceutically acceptable salt thereof, and a pharmaceutically acceptable excipient, is provided.

In another embodiment, a composition comprising a compound of formula I or a pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In another embodiment, a kit or an article of manufacture comprising a composition effective to treat or prevent an HIV infection; and packaging material comprising a label which indicates that the composition can be used to treat or prevent infection by HIV, is provided. Exemplary compositions comprise a compound of formula I as disclosed herein, or a pharmaceutically acceptable salt thereof.

In another embodiment, a method of inhibiting the replication of HIV is provided. The method comprises exposing the virus to an effective amount of a compound of formula I or a salt thereof, under conditions where replication of HIV is inhibited.

In another embodiment, the use of a compound of formula I, or a pharmaceutically acceptable salt thereof to inhibit the activity of HIV reverse transcriptase is provided.

In another embodiment, the use of a compound of formula I, or a salt thereof, to inhibit the replication of HIV is provided. Other embodiments, may be set forth in the detailed description of the embodiments that follows, and in part may be apparent from the description, or may be learned by practice, of the claimed embodiments. These may be realized and attained by the processes and compositions particularly pointed out in the description and claims thereof. The foregoing Summary has been made with the understanding that it is to be considered as a brief and general synopsis of some of the embodiments disclosed herein, and is not intended to limit in any manner the scope, or range of equivalents, to which the appended claims are lawfully entitled.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present disclosure and claims, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "about" or "approximately," used in connection with a quantity is inclusive of the stated value and has the meaning dictated by the context (e.g., includes the degree of error associated with measurement of the particular quantity).

As used herein, the term "administering" or "administration" typically refers to the administration of a composition to a subject to achieve delivery of an agent that is, or is included, in a composition to a target site or a site to be treated. Those of ordinary skill in the art will be aware of a variety of routes that may, in appropriate circumstances, be used for administration to a subject, for example a human. For example, in some embodiments, administration may be parenteral. In some embodiments, administration may be by injection (e.g., intramuscular, intravenous, or subcutaneous injection). In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time). In some embodiments, administration may involve continuous dosing (e.g., perfusion) for at least a selected period of time.

"Alkyl" refers to a straight or branched chain hydrocarbon radical, which is saturated, having from one to twelve carbon atoms ($C_{1-12}$alkyl), in certain embodiments one to eight carbon atoms ($C_{1-8}$alkyl) or one to six carbon atoms ($C_{1-6}$alkyl), one to four carbon atoms ($C_{1-4}$alkyl), or five to eight carbon atoms ($C_{5-8}$alkyl), and which is attached to the rest of the molecule by a single bond, e.g., methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, hexyl, 3-methylhexyl, 2-methylhexyl, and the like.

"Alkylene" refers to a straight or branched chain hydrocarbon radical, which is saturated, having from one to twelve carbon atoms ($C_{1-12}$alkylene), in certain embodiments one to eight carbon atoms ($C_{1-4}$alkylene) or one to six carbon atoms ($C_{1-6}$alkylene), or one to four carbon atoms ($C_{1-4}$alkylene), and which is divalent. Examples include methylene (—$CH_2$—), ethylene (—$CH_2CH_2$—), propylene (—$CH_2CH_2CH_2$—), 1-methylethylene (—$CH(CH_3)CH_2$—), butylene (—$CH_2CH_2CH_2CH_2$—), 1-methylpropylene (—$CH(CH_3)CH_2CH_2$—), 1,1-dimethylethylene (—$C(CH_3)_2CH_2$—), and 1,2-dimethyl ethylene (—$CH(CH_3)CH(CH_3)$—). Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethyl ethylene.

"Amino" refers to the —$NH_2$ radical.

The term "antiviral agent" as used herein is intended to mean an agent (compound or biological) that is effective to inhibit the formation and/or replication of a virus in a subject, for example, a human, including but not limited to agents that interfere with either host or viral mechanisms necessary for the formation and/or replication of a virus in a subject, for example, a human.

"Aryl" refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho, spirocyclo, or bridged bicyclic or multicyclic radical having about 9 to 14 atoms in which at least one ring is aromatic (e.g., an aryl fused to one or more aryl or carbocycle). Such bicyclic or multicyclic rings may be optionally substituted with one or more (e.g., 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1, 2, 3, 4-tetrahydronaphthyl, anthracenyl, and the like.

"Arylalkylene" refers to an alkylene radical as defined herein which is bonded to an aryl radical as defined herein. Accordingly, the point of attachment of an arylalkylene radical is the alkylene group. The alkylene group of the "arylalkylene" is typically 1 to 6 carbon atoms (i.e., aryl$C_{1-6}$alkylene). Arylalkylene groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. The arylalkylene group typically comprises 6 to 20 carbon atoms, e.g., the alkylene moiety of the arylalkylene group is one to six carbon atoms and the aryl moiety is five to fourteen carbon atoms.

"Arylcycloalkylene" refers to a cycloalkylene radical as defined herein which is bonded to an aryl radical as defined herein. Accordingly, the point of attachment of an arylcycloalkylene radical is the cycloalkylene group. The cycloalkylene group of the "arylcycloalkylene" is typically 3 to 7 carbon atoms (i.e., aryl$C_{3-7}$cycloalkylene).

As used herein, "bicycloalkyl" refers to a hydrocarbon radical having the specified number carbon atoms and two rings, which rings may be bridged, fused, or spirocyclic relative to one another. In certain embodiments the bicycloalkyl has from seven to twelve carbon atoms, six to twelve carbon atoms, from six to ten carbon atoms, or from five to ten carbon atoms, and is saturated and attached to the rest of the molecule by a single bond. A bridged bicycloalkyl will have two rings connected via two shared atoms that are non-adjacent. A fused bicycloalkyl will have two rings connected via a shared bond. A spirocyclic bicycloalkyl (denoted "spirocyclo alkyl") will have two rings connected via a single, shared atom. For example, bicycloheptyl may be bridged bicycloheptyl, fused bicycloheptyl, or spirocyclo heptyl, respectively, as exemplified below:

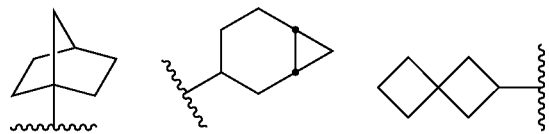

"Bridged" refers to a carbocyclic or heterocyclic ring structure described herein containing two non-adjacent atoms in a ring that are connected via a single atom or a divalent group. Exemplary bridged bicyclic compounds are bicyclo[2.2.1]heptane and 1,4-diazabicyclo[2.2.2]octane, depicted below:

A bridged ring structure may be polycyclic (i.e., bicyclic, tricyclic, etc.).

As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

A prefix such as "$C_{u-v}$" or "$(C_u-C_v)$" indicates that the following group has from u to v carbon atoms. For example, "$C_{1-6}$alkyl" indicates that the alkyl group has from one to six carbon atoms.

"Carbocyclic ring" refers to a non-aromatic hydrocarbon ring, having from three to fifteen carbon atoms, in certain embodiments having from three to ten carbon atoms or from three to seven carbon atoms, or from three to six carbon atoms, and which is saturated or partially unsaturated and attached to the rest of the molecule by a single bond. Carbocyclic rings include, for example, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane.

"Cycloalkyl" refers to a non-aromatic cyclic hydrocarbon radical, which is saturated, having from three to fifteen carbon atoms ($C_{3-15}$cycloalkyl), in certain embodiments having from three to ten carbon atoms ($C_{3-10}$cycloalkyl), from three to seven carbon atoms ($C_{3-7}$cycloalkyl), from three to six carbon atoms ($C_{3-6}$cycloalkyl), or from five to seven carbon atoms ($C_{5-7}$ cycloalkyl), and which is attached to the rest of the molecule by a single bond. Cycloalkyl includes, for example, cyclopropyl, cyclobutyl, cyclopentyl, cyclohexyl, cycloheptyl, and cyclooctyl.

"Cycloalkylene" as used herein refers to a non-aromatic cyclic hydrocarbon radical having two monovalent radical centers derived by the removal of two hydrogen atoms from the same or two different carbon atoms of a parent cycloalkane (i.e., it is divalent). Accordingly, a cyclobutylene radical includes:

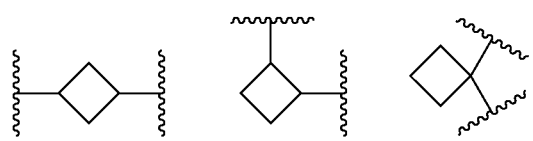 [SMILES: *C1CC(*)C1 ; *C1CCC1* ; *C1(*)CCC1]

A cycloalkylene group can have from three to fifteen carbon atoms, from three to ten carbon atoms, from three to seven carbon atoms, or from three to six carbon atoms. As used herein, cycloalkylene may be saturated or partially unsaturated. Cycloalkylene groups include, for example, cyclopropylene, cyclobutylene, cyclopentylene, cyclopentenylene, cyclohexylene, cyclohexenylene, 1,3-cyclohexadienylene, 1,4-cyclohexadienylene, cycloheptylene, cycloheptenylene, and cyclooctylene.

As used herein, the term "dosage form" refers to a physically discrete unit of an active agent (e.g., a therapeutic, prophylactic, or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a prophylactic or therapeutic dosing regimen). Those of ordinary skill in the art appreciate that the total amount of a composition or agent administered to a particular subject is determined by one or more attending physicians and may involve administration of multiple dosage forms.

"Fused" refers to a ring structure described herein containing carbocyclic, heterocyclic, aromatic, and/or heteroaromatic rings that are connected via two adjacent atoms. For example, the bicyclic compounds depicted below incorporate a cyclopropane fused to a cyclohexane, a pyrrolidine fused to a benzene, and a thiene fused to a furan, respectively:

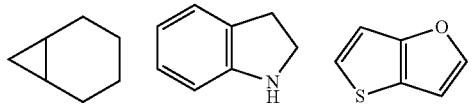

A fused ring structure may be polycyclic (i.e., bicyclic, tricyclic, etc.).

"Halo" or "halogen" refers to bromo, chloro, fluoro, and iodo.

"Haloalkyl" refers to an alkyl as defined herein, wherein one or more hydrogen atoms are each replaced by a halo substituent. For example, a $C_{1-6}$haloalkyl is a $C_{1-6}$alkyl wherein one or more of the hydrogen atoms have been replaced by a halo substituent. Such a range includes one halo substituent on the alkyl group to complete halogenation of the alkyl group. Exemplary haloalkyl groups include, but are not limited to, trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl" or "heterocyclic ring" refers to a non-aromatic radical or ring having from three to fifteen atoms wherein from one to six atoms are heteroatoms chosen from nitrogen, oxygen and sulfur and attached to the rest of the molecule by a single bond. In certain embodiments, "heterocyclyl" has from three to ten atoms, wherein from one to four atoms are heteroatoms chosen from nitrogen, oxygen and sulfur, or from three to seven atoms, wherein from one to two atoms are heteroatoms chosen from nitrogen, oxygen and sulfur. The nitrogen, carbon or sulfur atoms in the heterocyclyl may be optionally oxidized; the nitrogen atom may be optionally quaternized. As used herein, "heterocyclyl" or "heterocyclic ring" refers to rings that are saturated unless otherwise indicated, e.g., in some embodiments "heterocyclyl" or "heterocyclic ring" refers to rings that are saturated or partially saturated where specified. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

"Hydroxy" or "hydroxyl" refers to the —OH radical.

The term "inhibitor of HIV replication" as used herein is intended to mean an agent capable of reducing or eliminating the ability of HIV to replicate in a host cell, whether in vitro, ex vivo, or in vivo.

The term "inhibitor of HBV replication" as used herein is intended to mean an agent capable of reducing or eliminating the ability of HBV to replicate in a host cell, whether in vitro, ex vivo, or in vivo.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Oxo" refers to the =O substituent.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

The term "pharmaceutically acceptable salt," as used herein, refers to salts of such compounds that are appropriate for use in pharmaceutical contexts, i.e., salts which are, within the scope of sound medical judgment, suitable for use in contact with the tissues of humans and/or animals without undue toxicity, irritation, allergic response and the like, and are commensurate with a reasonable benefit/risk ratio. Pharmaceutically acceptable salts are well known in the art. For example, S. M. Berge et al. describe several pharmaceutically acceptable salts in detail in the Journal of Pharmaceutical Sciences. S. M. Berge et al., J. Pharma. Sci., 66:119 (1977).

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

"Prevention" or "preventing" means any treatment of a disease or condition that causes the clinical symptoms of the disease or condition not to develop. Compositions may, in some embodiments, be administered to a subject (including a human) who is at risk of having the disease or condition. As used herein, the terms "preventing" and "prevention" encompass the administration of a compound, composition, or pharmaceutically acceptable salt according to the embodiments disclosed herein pre- or post-exposure of the individual to HIV, or HBV, but before the appearance of symptoms of HIV infection, or HBV infection, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

"Spiro" or "spirocyclo" refers to a ring structure described herein which has two ring structures, each of which may be carbocyclic or heterocyclic, that are connected via a single, shared atom (which atom is denoted a spiro atom). Accordingly, "spirocyclo" refers to a spiro cycloalkyl radical, or a spiro heterocycloalkyl radical. "Dispiro" or dispirocyclo" refers to a ring structure described herein which has three ring structures, each of which may be carbocyclic or heterocyclic, that are connected via two spiro atoms.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

As used herein, the term "subject" refers to an organism, typically a mammal (e.g., a human). In some embodiments, a human subject is an adult, adolescent, or pediatric subject. In some embodiments, a subject is suffering from a relevant disease or condition. In some embodiments, a subject is susceptible to a disease or condition. In some embodiments, a subject displays one or more symptoms or characteristics of a disease or condition. In some embodiments, a subject does not display any symptom or characteristic of a disease or condition. In some embodiments, a subject is someone with one or more features characteristic of susceptibility to or risk of a disease or condition. In some embodiments, a subject is a patient. In some embodiments, a subject is an individual to whom diagnosis and/or therapy and/or prophylaxis is and/or has been administered.

As used herein, "therapeutically effective amount" is an amount that produces the desired effect for which it is administered. In some embodiments, the term "therapeutically effective amount" or "therapeutically effective dose" means an amount that is sufficient, when administered to a population suffering from or susceptible to a disease or condition in accordance with a therapeutic dosing regimen, to treat the disease or condition. In some embodiments, a therapeutically effective amount is one that reduces the incidence and/or severity of, stabilizes one or more characteristics of, and/or delays onset of, one or more symptoms of the disease or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease or condition) or fluids (e.g., blood, saliva, serum, sweat, tears, urine, etc.). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. As used herein, the terms "treatment" and "treating" encompass the administration of a compound, composition, or pharmaceutically acceptable salt according to the embodiments disclosed herein to alleviate or eliminate symptoms of HIV infection, or HBV infection, and/or to reduce viral load in a subject in need thereof. In some embodiments, a subject is a patient.

As used herein, "tricycloalkyl" refers to a hydrocarbon radical having the specified number carbon atoms and three rings, which rings may be bridged, fused, spirocyclo, or a combination thereof relative to one another. In certain embodiments, the tricycloalkyl has from ten to sixteen carbon atoms, or from nine to twelve carbon atoms, and is saturated and attached to the rest of the molecule by a single bond. For example, tricyclodecyl may be bridged tricyclodecyl, fused tricyclodecyl, dispirocyclo decyl, or mixed (e.g., bridged-fused) tricyclodecyl, respectively, as depicted below:

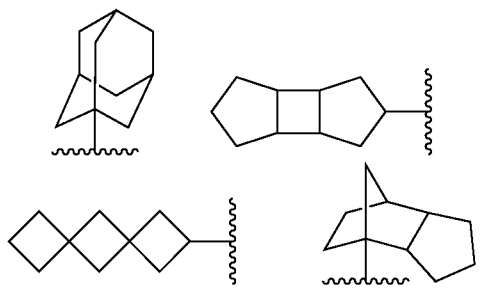

The embodiments disclosed herein are also meant to encompass all pharmaceutically acceptable compounds of formula I being isotopically labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. In certain embodiments, these radiolabeled compounds are useful to help determine or measure the effectiveness of the compounds, by characterizing, for example, the site or mode of action, or binding affinity to pharmacologically important site of action. Certain isotopically labeled compounds of formula I, for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

In certain embodiments, substitution with heavier isotopes such as deuterium, i.e., $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically labeled compounds of formula I can be prepared by techniques known to those skilled in the art or by processes analogous to those described in the Examples as set out below using an appropriate isotopically labeled reagent in place of the non-labeled reagent previously employed.

The methods, compositions, kits and articles of manufacture provided herein use or include compounds (e.g., a compound of formula I) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Allen B. Foster, Deuterium Isotope Effects in Studies of Drug Metabolism, 5 *Trends Pharmacol. Sci.* 524, 524-27 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Compounds

Provided herein are compounds that function as anti-HIV agents, or anti-HBV agents, pharmaceutical compositions comprising such compounds, optionally in combination with one or more (e.g., two, three, or four) additional therapeutic agents, and methods of using such compounds and compositions. All compound embodiments described herein include any pharmaceutically acceptable salt, stereoisomer, or mixture of stereoisomers thereof.

In one embodiment, a compound of formula (I), or a pharmaceutically acceptable salt thereof, is provided:

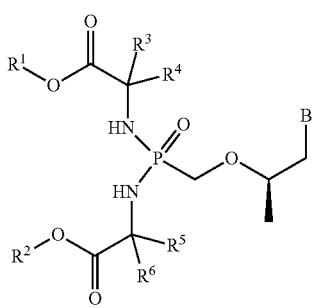

I wherein $R^1$ and $R^2$ are independently chosen from $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl, bridged $C_{5-10}$bicycloalkyl-$C_{1-4}$alkylene, fused $C_{5-10}$bicycloalkyl, $C_{10-16}$dispirocycloalkyl, $C_{10-16}$dispirocycloalkyl-$C_{1-4}$alkylene, bridged $C_{9-12}$tricycloalkyl, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three $R^a$;

$R^3$, $R^4$, $R^5$, and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or optionally:

$R^3$ and $R^4$ together with the carbon atom to which they are attached form a 3- to 6-membered saturated or partially unsaturated carbocyclic ring optionally substituted with from one to three $R^b$; and $R^5$ and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or $R^3$ and $R^4$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$; or $R^3$ and $R^4$ together with the carbon atom to which they are attached form a 3- to 6-membered saturated or partially unsaturated carbocyclic ring optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$;

B is

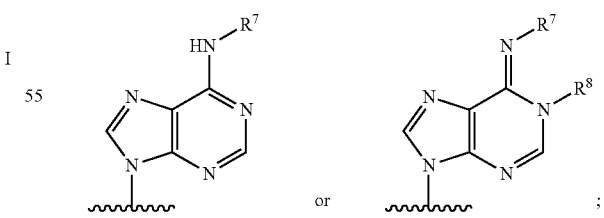

$R^7$ is hydrogen or $R^8$;

$R^8$ is -$L^1$-$(L^2)_m$-$(L^3)_n$-$R^{8a}$;

$L^1$ is chosen from a bond, —C(O)—, and —C(O)O—;

$L^2$ is $C_{1-6}$alkylene;

$L^3$ is —C(O)O— or

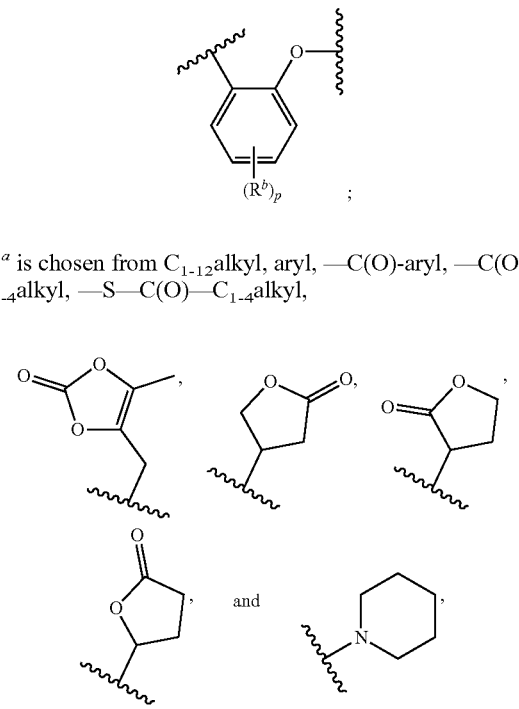

$R^{8a}$ is chosen from $C_{1-12}$alkyl, aryl, —C(O)-aryl, —C(O)—$C_{1-4}$alkyl, —S—C(O)—$C_{1-4}$alkyl,

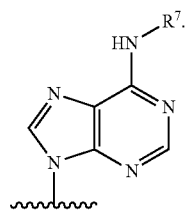

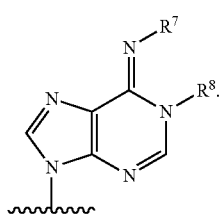

wherein aryl and —C(O)-aryl are optionally substituted with one or two $R^c$;

each $R^a$ is independently chosen from $C_{1-4}$alkyl, halo, $C_{1-4}$haloalkyl, and —O—$C_{1-4}$alkyl;

each $R^b$ is independently $C_{1-4}$alkyl;

each $R^c$ is independently $C_{1-4}$alkyl or —OC(O)—$C_{1-4}$alkyl;

m and n are independently 0 or 1; and p is 0, 1, or 2.

In some embodiments of the compound of formula I, or a pharmaceutically acceptable salt thereof, B is

[structure]

In some embodiments, B is

[structure]

In some embodiments, the compound of formula I is a compound of formula (II):

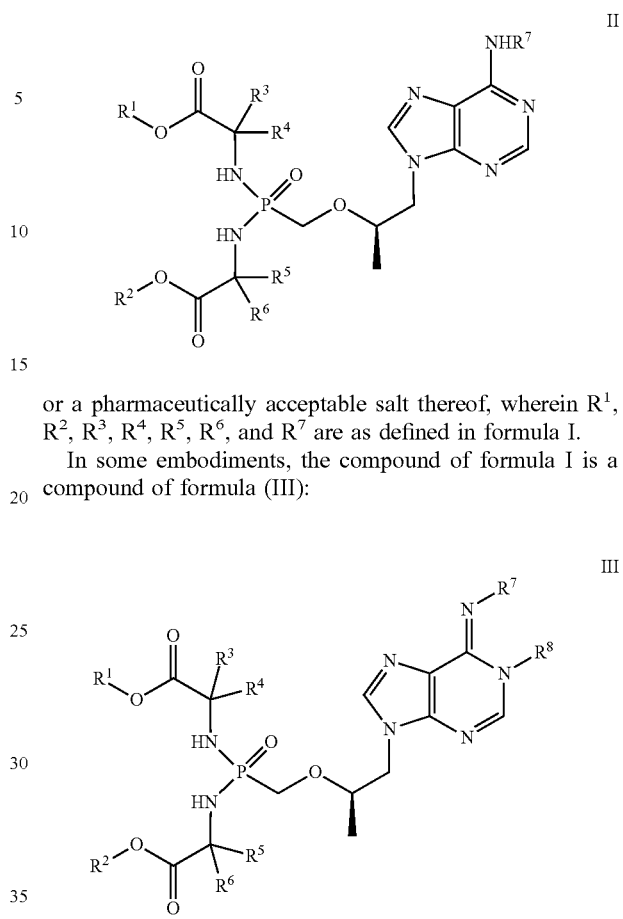

or a pharmaceutically acceptable salt thereof, wherein $R^1$, $R^2$, $R^3$, $R^4$, $R^5$, $R^6$, and $R^7$ are as defined in formula I.

In some embodiments, the compound of formula I is a compound of formula (III):

[structure III]

or a pharmaceutically acceptable salt thereof, wherein $R^1$, $R^2$, $R^3$, $R^4$, $R^5$, $R^6$, $R^7$, and $R^8$ are as defined in formula I.

In some embodiments of the compound of formula I, II, or III, or a pharmaceutically acceptable salt thereof, $R^1$ and $R^2$ are independently chosen from $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl, bridged $C_{5-10}$bicycloalkyl-$C_{1-4}$alkylene, fused $C_{5-10}$bicycloalkyl, $C_{10-16}$dispirocycloalkyl, $C_{10-16}$dispirocycloalkyl-$C_{1-4}$alkylene, bridged $C_{9-12}$tricycloalkyl, bridged $C_{9-12}$tricycloalkyl-$C_{1-4}$alkylene, $C_{3-7}$cycloalkyl-$C_{3-7}$ cycloalkylene, and 5- to 7-membered monocyclic heterocyclyl having from 1 to 3 heteroatoms chosen from N, O, and S, wherein each $C_{1-8}$alkyl, aryl-$C_{1-4}$alkylene, $C_{3-7}$cycloalkyl, $C_{3-7}$ cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three $R^a$, wherein $R^a$ is as defined above.

In some embodiments, $R^1$ and $R^2$ are independently chosen from $C_{1-8}$alkyl, aryl-$C_{1-4}$alkylene, $C_{3-7}$ cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl-$C_{1-4}$alkylene, fused $C_{5-10}$bicycloalkyl, $C_{10-16}$dispirocycloalkyl-$C_{1-4}$alkylene, bridged $C_{9-12}$tricycloalkyl-$C_{1-4}$alkylene, $C_{3-7}$cycloalkyl-$C_{3-7}$ cycloalkylene, and 5- to 7-membered monocyclic heterocyclyl having from 1 to 3 heteroatoms chosen from N, O, and S, wherein each $C_{1-8}$alkyl, aryl-$C_{1-4}$alkylene, $C_{3-7}$cycloalkyl, $C_{3-7}$ cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three $R^a$, wherein $R^a$ is as defined above. In some embodiments, $R^1$ and $R^2$ are independently chosen from $C_{1-8}$alkyl, $C_{3-7}$cycloalkyl, $C_{3-7}$cycloalkyl-$C_{1-4}$alkylene, $C_{7-12}$spirocycloalkyl, $C_{7-12}$spirocycloalkyl-$C_{1-4}$alkylene, and bridged $C_{5-10}$bicycloalkyl-$C_{1-4}$alkylene, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three $R^a$, wherein $R^a$ is as defined above. In some embodiments, $R^1$ and $R^2$ are independently chosen from $C_{5-8}$alkyl, $C_{5-7}$cycloalkyl, $C_{5-7}$cycloalkyl-$C_{1-4}$alkylene, $C_{7-9}$spirocycloalkyl, $C_{7-9}$spirocycloalkyl-$C_{1-4}$alkylene, and bridged $C_{5-7}$bicycloalkyl-$C_{1-4}$alkylene, wherein each $C_{5-8}$alkyl, $C_{5-7}$cycloalkyl, $C_{5-7}$cycloalkyl-$C_{1-4}$alkylene, $C_{7-9}$spirocycloalkyl, $C_{7-9}$spirocycloalkyl-$C_{1-4}$alkylene, and bridged $C_{5-7}$bicycloalkyl-$C_{1-4}$alkylene is optionally substituted with from one to three $R^a$, wherein $R^a$ is as defined above.

In some embodiments of the compound of formula I, II, or III, or a pharmaceutically acceptable salt thereof, $R^1$ and $R^2$ are different. In some embodiments, $R^1$ and $R^2$ are the same. In some embodiments, $R^1$ and $R^2$ are the same and chosen from $C_{1-8}$alkyl, aryl-$C_{1-4}$alkylene, $C_{3-7}$ cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl-$C_{1-4}$alkylene, fused $C_{5-10}$bicycloalkyl, $C_{10-16}$dispirocycloalkyl-$C_{1-4}$alkylene, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three $R^a$, wherein $R^a$ is as defined above. In some embodiments, $R^1$ and $R^2$ are the same and chosen from $C_{1-8}$alkyl, $C_{3-7}$cycloalkyl, $C_{3-7}$cycloalkyl-$C_{1-4}$alkylene, $C_{7-12}$spirocycloalkyl, $C_{7-12}$spirocycloalkyl-$C_{1-4}$alkylene, and bridged $C_{5-10}$bicycloalkyl-$C_{1-4}$alkylene, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three $R^a$, wherein $R^a$ is as defined above. In some embodiments, $R^1$ and $R^2$ are the same and chosen from $C_{3-7}$ cycloalkyl-$C_{1-4}$alkylene, $C_{7-12}$spirocycloalkyl, $C_{7-12}$spirocycloalkyl-$C_{1-4}$alkylene, and bridged $C_{5-10}$bicycloalkyl-$C_{1-4}$alkylene, wherein each $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three $R^a$, wherein $R^a$ is as defined above. In some embodiments, $R^1$ and $R^2$ are the same and chosen from $C_{1-8}$alkyl and $C_{3-7}$cycloalkyl, wherein each $C_{1-8}$alkyl and $C_{3-7}$cycloalkyl is optionally substituted with from one to three $R^a$, wherein $R^a$ is as defined above.

In some embodiments of the compound of formula I, II, or III, or a pharmaceutically acceptable salt thereof, R and R are independently chosen from

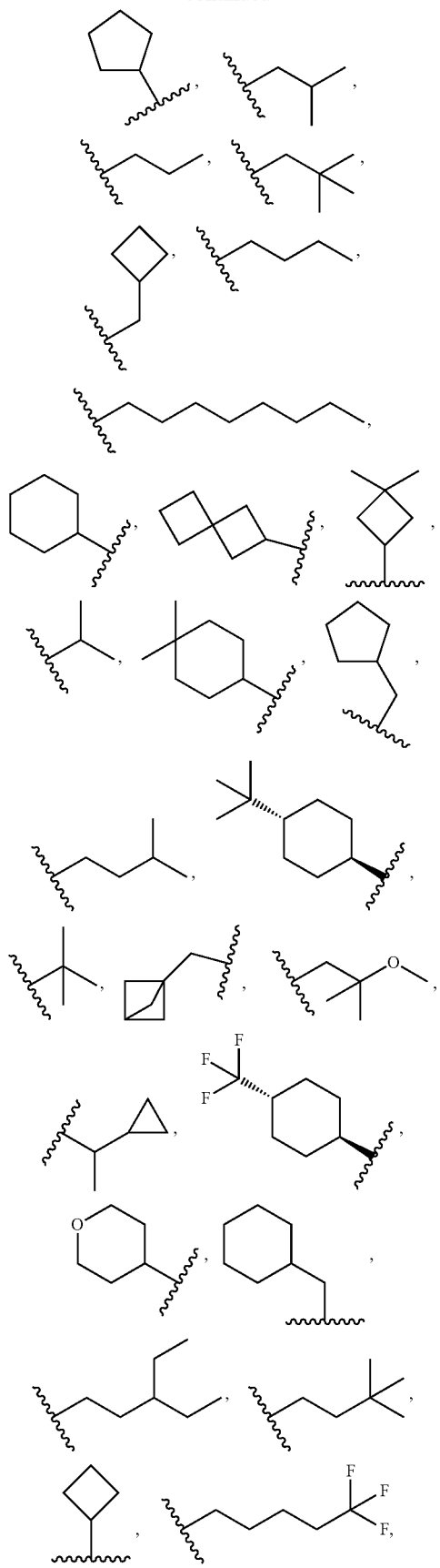

-continued
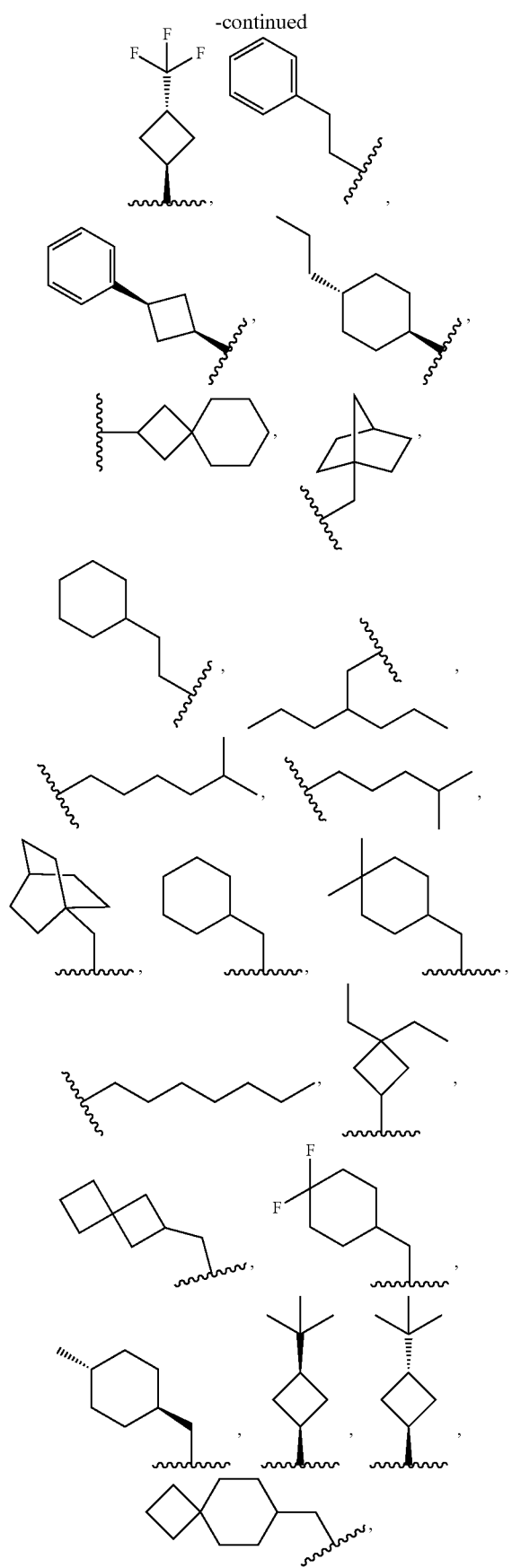
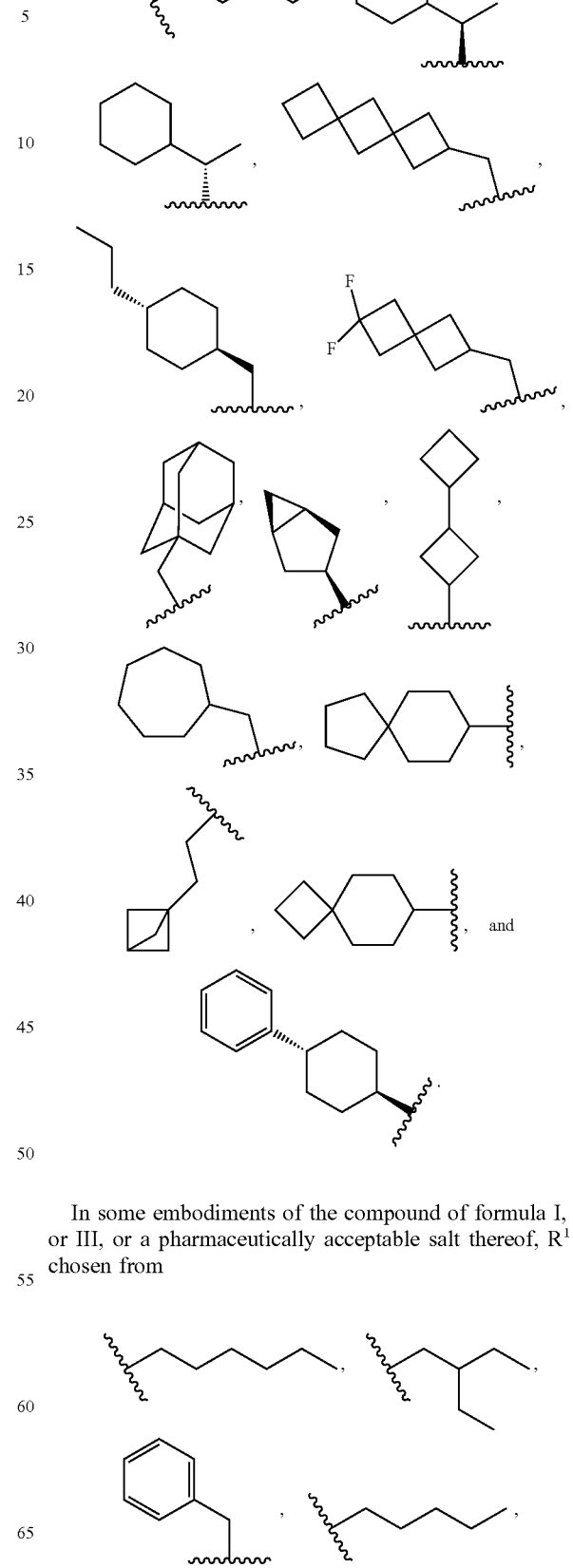
In some embodiments of the compound of formula I, II, or III, or a pharmaceutically acceptable salt thereof, $R^1$ is chosen from -continued
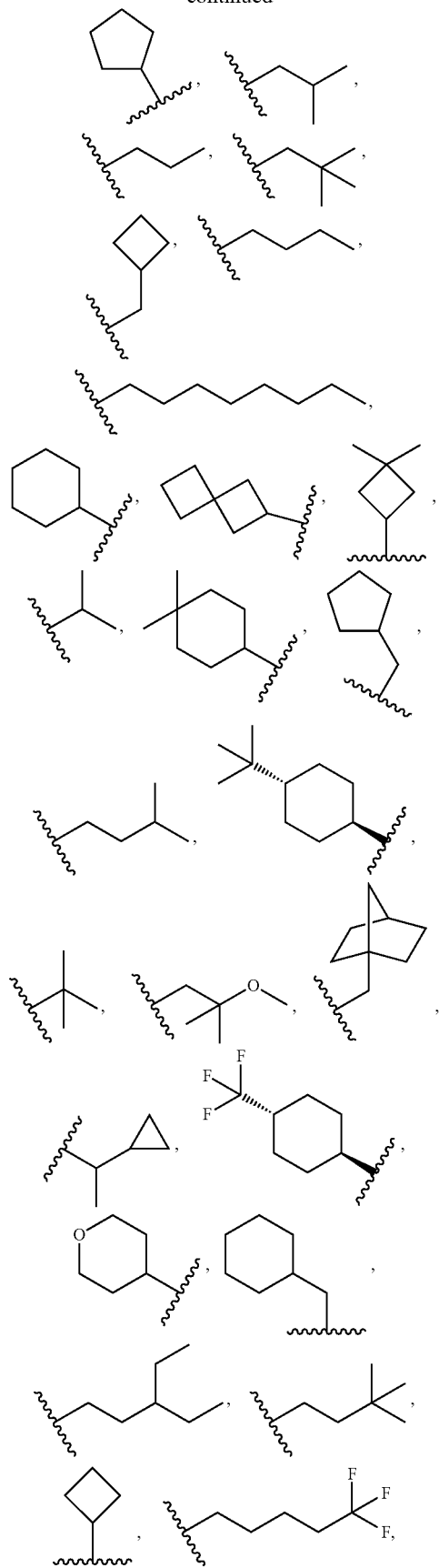
-continued
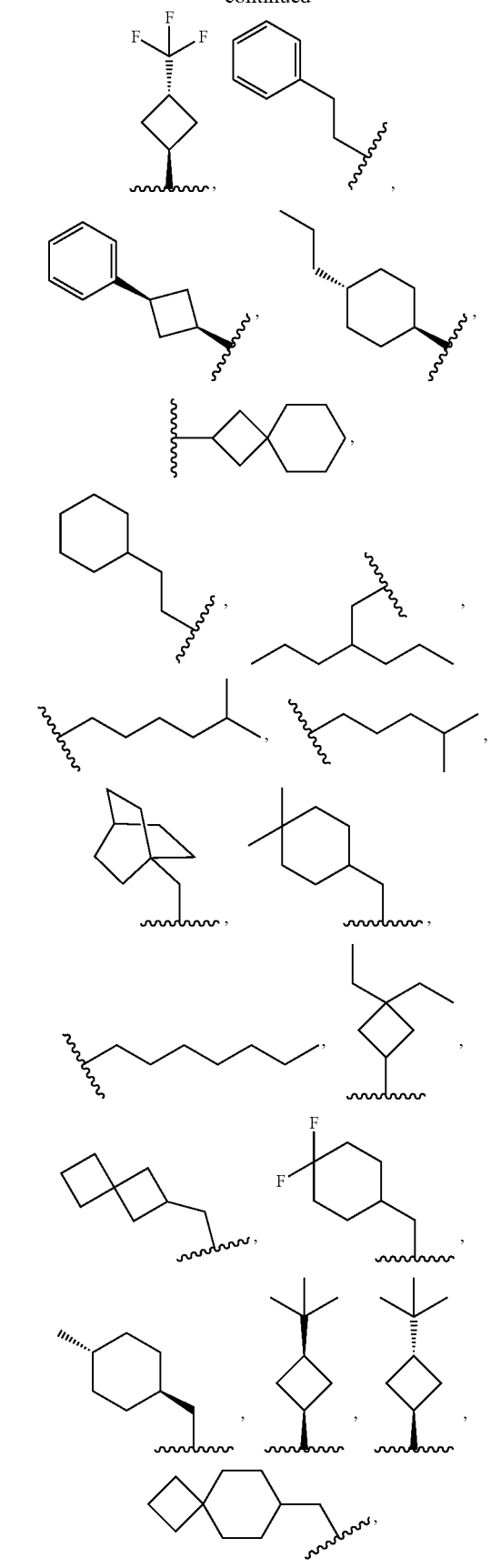

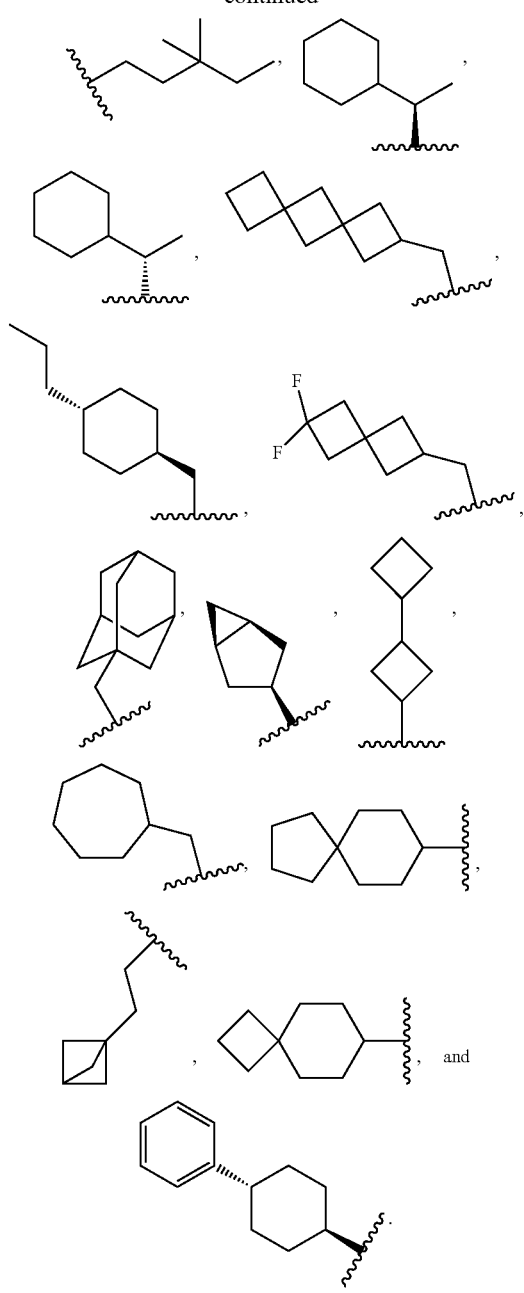
In some embodiments of the compound of formula I, II, or III, or a pharmaceutically acceptable salt thereof, R is chosen from
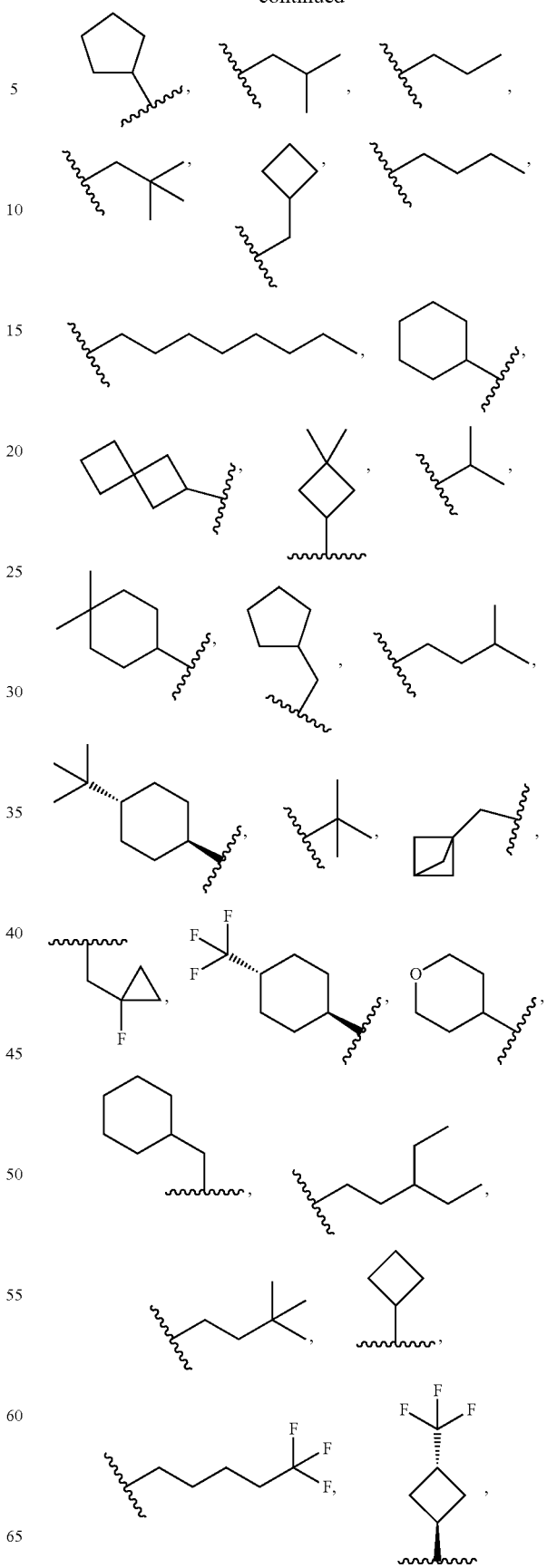

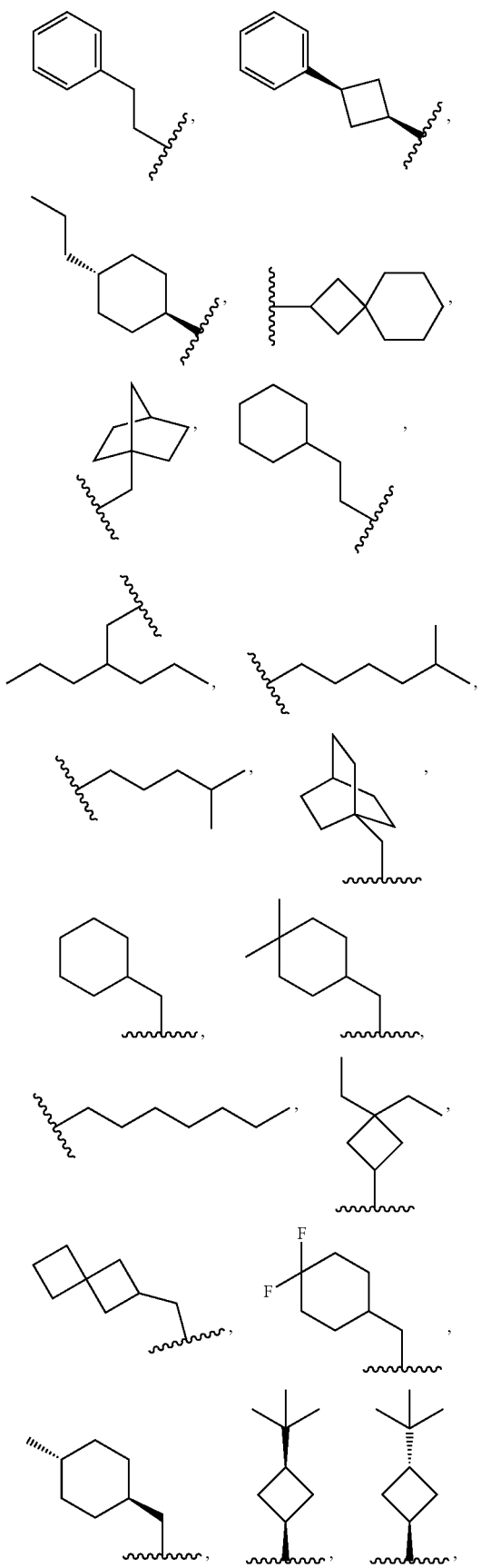
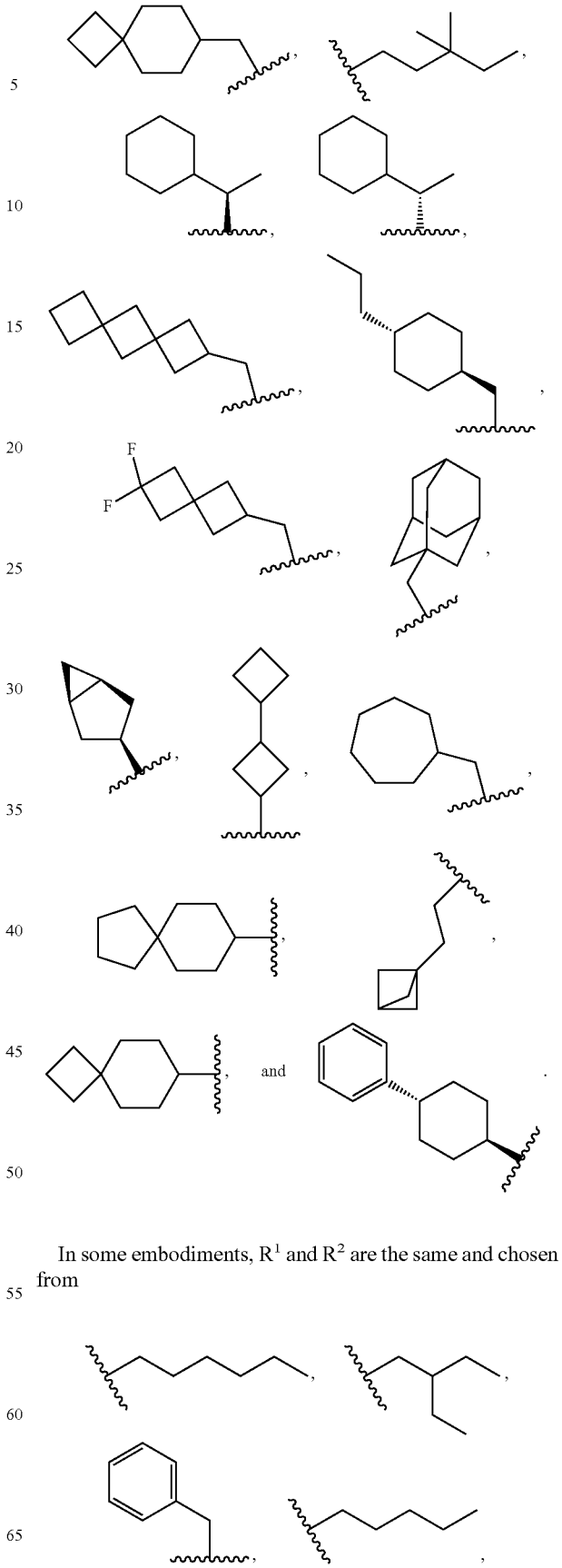
In some embodiments, $R^1$ and $R^2$ are the same and chosen from
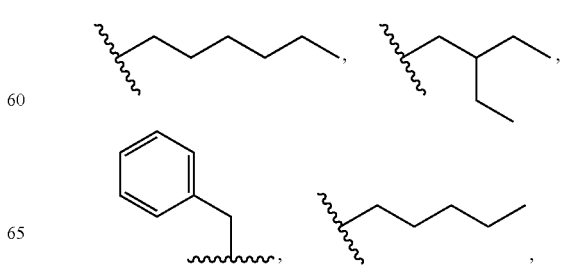

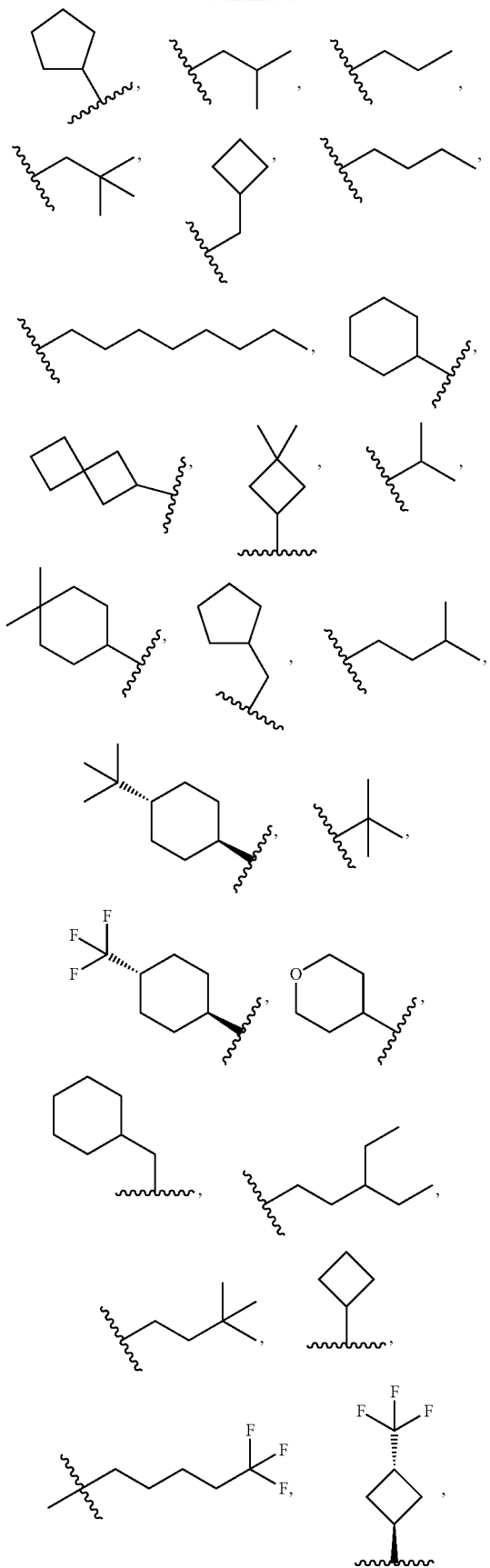
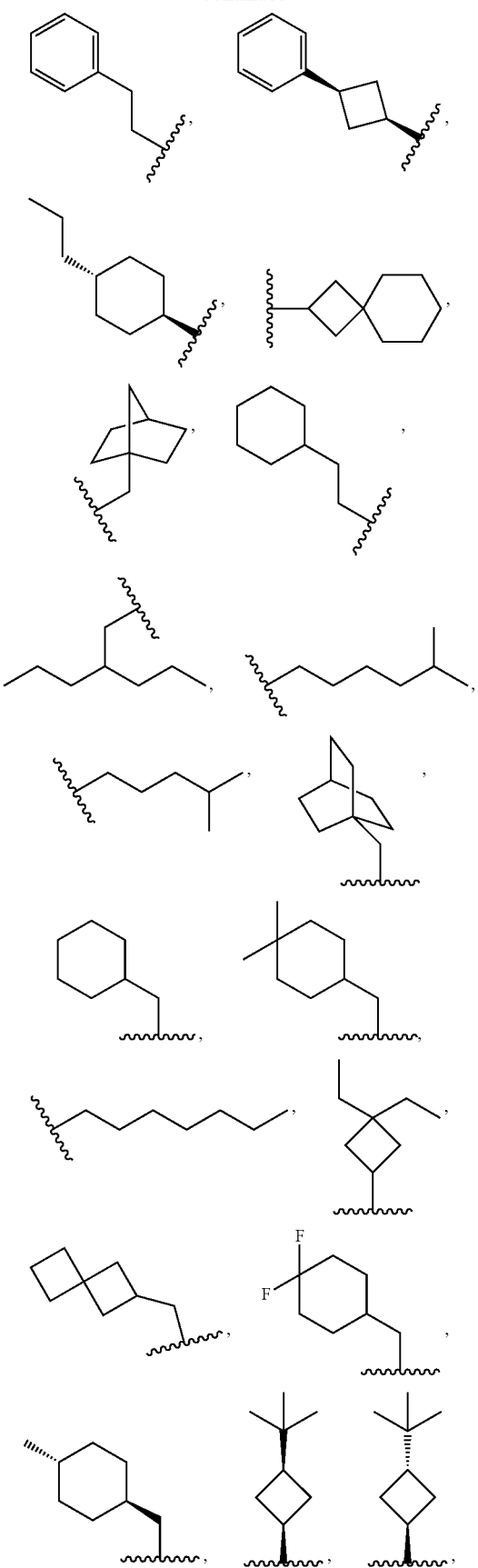

31

-continued

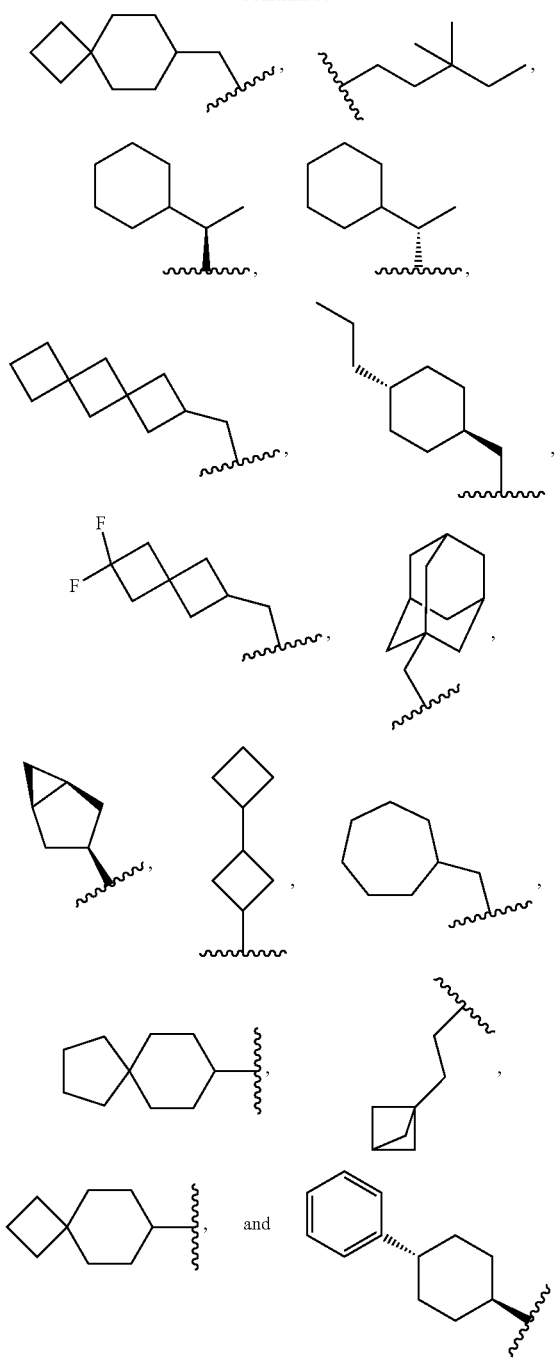

In some embodiments, $R^1$ and $R^2$ are the same and chosen from

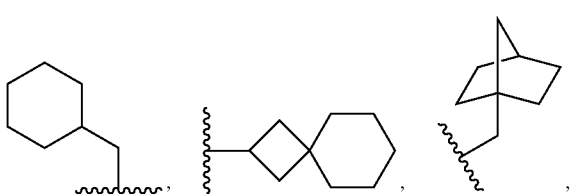

32

-continued

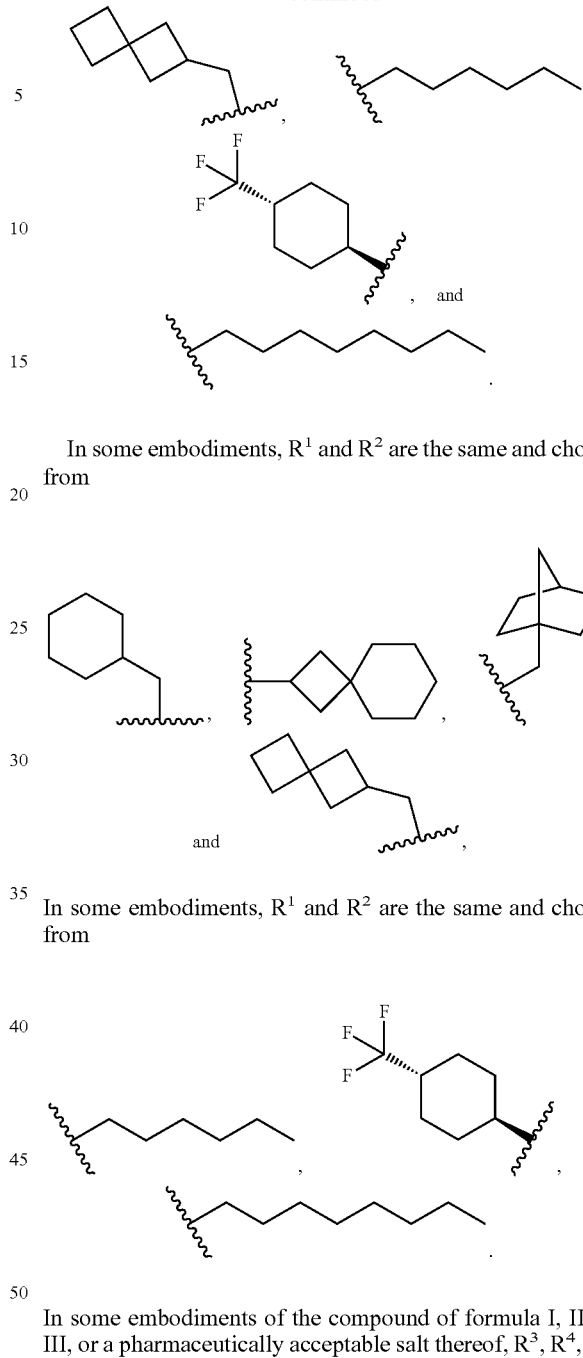

In some embodiments, $R^1$ and $R^2$ are the same and chosen from

In some embodiments of the compound of formula I, II, or III, or a pharmaceutically acceptable salt thereof, $R^3$, $R^4$, $R^5$, and $R^6$ are independently chosen from $C_{1-3}$alkyl, $C_{3-5}$cycloalkyl, and aryl-$C_{1-4}$alkylene, wherein each $C_{1-3}$alkyl, $C_{3-5}$cycloalkyl, and aryl-$C_{1-4}$alkylene is optionally substituted with from one to three $R^b$, wherein $R^b$ is as defined above. In some embodiments, $R^3$, $R^4$, $R^5$, and $R^6$ are independently chosen from methyl, ethyl, cyclopropyl, and benzyl, wherein each methyl, ethyl, cyclopropyl, and benzyl is optionally substituted with from one to three $R^b$, wherein $R^b$ is as defined above.

In some embodiments of the compound of formula I, II, or III, or a pharmaceutically acceptable salt thereof, $R^3$ and $R^5$ are the same. In some embodiments, $R^3$ and $R^5$ are both methyl. In some embodiments, $R^3$ and $R^5$ are both ethyl. In some embodiments, $R^3$ and $R^5$ are both cyclopropyl. In some embodiments, $R^3$ and $R^5$ are both benzyl.

In some embodiments of the compound of formula I, II, or III, or a pharmaceutically acceptable salt thereof, $R^4$ and $R^6$ are the same. In some embodiments, $R^4$ and $R^6$ are both ethyl or both benzyl. In some embodiments, $R^4$ and $R^6$ are both methyl. In some embodiments, $R^4$ and $R^6$ are both ethyl. In some embodiments, $R^4$ and $R^6$ are both cyclopropyl. In some embodiments, $R^4$ and $R^6$ are both benzyl.

In some embodiments of the compound of formula I, II, or III, or a pharmaceutically acceptable salt thereof, $R^3$ and $R^4$ are the same. In some embodiments, $R^3$ and $R^4$ are both methyl. In some embodiments, $R^3$ and $R^4$ are both ethyl. In some embodiments, $R^3$ and $R^4$ are both cyclopropyl. In some embodiments, $R^3$ and $R^4$ are both benzyl.

In some embodiments of the compound of formula I, II, or III, or a pharmaceutically acceptable salt thereof, $R^5$ and $R^6$ are the same. In some embodiments, $R^5$ and $R^6$ are both methyl. In some embodiments, $R^5$ and $R^6$ are both ethyl. In some embodiments, $R^5$ and $R^6$ are both cyclopropyl. In some embodiments, $R^5$ and $R^6$ are both benzyl.

In some embodiments of the compound of formula I, II, or III, or a pharmaceutically acceptable salt thereof, $R^3$ and $R^4$ together with the carbon atom to which they are attached form a 3- to 5-membered saturated or partially unsaturated carbocyclic ring optionally substituted with from one to three $R^b$; and $R^5$ and $R^6$ are independently chosen from $C_{1-4}$alkyl, $C_{3-6}$ cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$, wherein each $R^b$ is as defined above. In some embodiments, $R^3$ and $R^4$ together with the carbon atom to which they are attached form a cyclopropane ring or a cyclobutane ring, wherein the cyclopropane ring or the cyclobutane ring is optionally substituted with from one to three $R^b$, wherein $R^b$ is as defined above. In some embodiments, $R^3$ and $R^4$ together with the carbon atom to which they are attached form a cyclopropane ring optionally substituted with from one to three $R^b$. In some embodiments, $R^3$ and $R^4$ together with the carbon atom to which they are attached form a cyclobutane ring optionally substituted with from one to three $R^b$. In some embodiments, the cyclopropane ring or the cyclobutane ring is unsubstituted. In some embodiments, the cyclopropane ring or the cyclobutane ring is substituted with one $R^b$. In some embodiments, the cyclopropane ring or the cyclobutane ring is substituted with two $R^b$. In some embodiments, the cyclopropane ring or the cyclobutane ring is substituted with three $R^b$. In some embodiments, $R^5$ and $R^6$ are independently chosen from $C_{1-3}$alkyl, $C_{3-5}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$. In some embodiments, $R^5$ and $R^6$ are independently chosen from methyl, ethyl, cyclopropyl, and benzyl, wherein each methyl, ethyl, cyclopropyl, and benzyl is optionally substituted with from one to three $R^b$. In some embodiments, $R^3$ and $R^4$ together with the carbon atom to which they are attached form cyclopropane ring or a cyclobutane ring, wherein the cyclopropane ring or the cyclobutane ring is optionally substituted with from one to three $R^b$, and $R^5$ and $R^6$ are independently chosen from methyl, ethyl, cyclopropyl, and benzyl, wherein each methyl, ethyl, cyclopropyl, and benzyl is optionally substituted with from one to three $R^b$.

In some embodiments of the compound of formula I, II, or III, or a pharmaceutically acceptable salt thereof, $R^3$ and $R^4$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; and $R^5$ and $R^6$ together with the carbon atom to which they are attached form a 3- to 5-membered saturated or partially unsaturated carbocyclic ring optionally substituted with from one to three $R^b$, wherein $R^b$ is as defined above. In some embodiments, $R^5$ and $R^6$ together with the carbon atom to which they are attached form a cyclopropane ring or a cyclobutane ring, wherein the cyclopropane ring or the cyclobutane ring is optionally substituted with from one to three $R^b$, wherein $R^b$ is as defined above. In some embodiments, $R^5$ and $R^6$ together with the carbon atom to which they are attached form a cyclopropane ring optionally substituted with from one to three $R^b$. In some embodiments, $R^5$ and $R^6$ together with the carbon atom to which they are attached form a cyclobutane ring optionally substituted with from one to three $R^b$. In some embodiments, the cyclopropane ring or the cyclobutane ring is unsubstituted. In some embodiments, the cyclopropane ring or the cyclobutane ring is substituted with one $R^b$. In some embodiments, the cyclopropane ring or the cyclobutane ring is substituted with two $R^b$. In some embodiments, the cyclopropane ring or the cyclobutane ring is substituted with three $R^b$. In some embodiments, $R^3$ and $R^4$ are independently chosen from $C_{1-3}$alkyl, $C_{3-5}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$. In some embodiments, $R^3$ and $R^4$ are independently chosen from methyl, ethyl, cyclopropyl, and benzyl, wherein each methyl, ethyl, cyclopropyl, and benzyl is optionally substituted with from one to three $R^b$. In some embodiments, $R^3$ and $R^4$ are independently chosen from methyl, ethyl, cyclopropyl, and benzyl, wherein each methyl, ethyl, cyclopropyl, and benzyl is optionally substituted with from one to three $R^b$; and $R^5$ and $R^6$ together with the carbon atom to which they are attached form a cyclopropane ring or a cyclobutane ring, wherein the cyclopropane ring or the cyclobutane ring is optionally substituted with from one to three $R^b$.

In some embodiments of the compound of formula I, II, or III, or a pharmaceutically acceptable salt thereof, $R^3$ and $R^4$ together with the carbon atom to which they are attached form a 3- to 5-membered saturated or partially unsaturated carbocyclic ring optionally substituted with from one to three $R^b$; and $R^5$ and $R^6$ together with the carbon atom to which they are attached form a 3- to 5-membered saturated or partially unsaturated carbocyclic ring optionally substituted with from one to three $R^b$. In some embodiments, $R^3$ and $R^4$ together with the carbon atom to which they are attached form a cyclopropane ring or a cyclobutane ring, wherein the cyclopropane ring or the cyclobutane ring is optionally substituted with from one to three $R^b$; and $R^5$ and $R^6$ together with the carbon atom to which they are attached form a cyclopropane ring or a cyclobutane ring, wherein the cyclopropane ring or the cyclobutane ring is optionally substituted with from one to three $R^b$, wherein $R^b$ is as defined above. In some embodiments, $R^3$ and $R^4$ together with the carbon atom to which they are attached form a cyclopropane ring optionally substituted with from one to three $R^b$. In some embodiments, $R^5$ and $R^6$ together with the carbon atom to which they are attached form a cyclopropane ring. In some embodiments, $R^3$ and $R^4$ together with the carbon atom to which they are attached form a cyclobutane ring optionally substituted with from one to three $R^b$. In some embodiments, $R^5$ and $R^6$ together with the carbon atom to which they are attached form a cyclobutane ring. In some embodiments, $R^3$ and $R^4$ together with the carbon atom to which they are attached form a cyclopropane ring optionally substituted with from one to three $R^b$ and $R^5$ and $R^6$ together with the carbon atom to which they are attached form a cyclopropane ring optionally substituted with from one to three $R^b$. In some embodiments, $R^3$ and $R^4$ together with the carbon atom to which they are attached form a cyclopropane ring optionally substituted with from one to three $R^b$ and $R^5$ and $R^6$ together with the carbon atom to which they are attached form a cyclobutane ring optionally substituted with from one to three $R^b$. In some embodiments, $R^3$ and $R^4$ together with the carbon atom to which they are attached form a cyclobutane ring optionally substituted with from one to three $R^b$ and $R^5$ and $R^6$ together with the carbon atom to which they are attached form a cyclopropane ring optionally substituted with from one to three $R^b$. In some embodiments, $R^3$ and $R^4$ together with the carbon atom to which they are attached form a cyclobutane ring optionally substituted with from one to three $R^b$ and $R^5$ and $R^6$ together with the carbon atom to which they are attached form a cyclobutane ring optionally substituted with from one to three $R^b$.

In some embodiments of the compound of formula I, II, or III, or a pharmaceutically acceptable salt thereof, each $R^b$ is independently methyl, ethyl, propyl, or butyl. In some embodiments, each $R^b$ is independently methyl, ethyl, or propyl. In some embodiments, each $R^b$ is independently methyl or ethyl. In some embodiments, each $R^b$ is methyl. In some embodiments, each $R^b$ is ethyl.

In some embodiments of the compound of formula I, II, or III, or a pharmaceutically acceptable salt thereof, $R^3$, $R^4$, $R^5$, and $R^6$ are the same. In some embodiments, $R^3$, $R^4$, $R^5$, and $R^6$ are each $C_{1-3}$alkyl, $C_{3-5}$cycloalkyl, or aryl-$C_{1-4}$alkylene, wherein each $C_{1-3}$alkyl, $C_{3-5}$cycloalkyl, or aryl-$C_{1-4}$alkylene is optionally substituted with from one to three $R^b$, wherein $R^b$ is as defined above. In some embodiments, $R^3$, $R^4$, $R^5$, and $R^6$ are each methyl, ethyl, cyclopropyl, or benzyl, wherein each methyl, ethyl, cyclopropyl, or benzyl is optionally substituted with from one to three $R^b$, wherein $R^b$ is as defined above. In some embodiments, $R^3$, $R^4$, $R^5$, and $R^6$ are each methyl or cyclopropyl. In some embodiments, $R^3$, $R^4$, $R^5$, and $R^6$ are each methyl. In some embodiments, $R^3$, $R^4$, $R^5$, and $R^6$ are each ethyl. In some embodiments, $R^3$, $R^4$, $R^5$, and $R^6$ are each cyclopropyl. In some embodiments, $R^3$, $R^4$, $R^5$, and $R^6$ are each benzyl.

In some embodiments of the compound of formula I, II, or III, or a pharmaceutically acceptable salt thereof, $R^7$ is hydrogen. In some embodiments, $R^7$ is $R^8$.

In some embodiments of the compound of formula I, II, or III, $R^8$ is -$L^1$-$L^2$-$L^3$-$R^{8a}$. In some embodiments, $R^8$ is -$L^1$-$(L^3)_n$-$R^{8a}$. In some embodiments, $R^8$ is -$L^1$-$(L^2)_m$-$R^{8a}$. In some embodiments, $R^8$ is -$L^1$-$L^3$-$R^{8a}$. In some embodiments, $R^8$ is -$L^1$-$L^2$-$R^{8a}$. In some embodiments, $R^8$ is -$L^1$-$R^{8a}$. In some embodiments, $R^8$ is $R^{8a}$. In some embodiments, $R^8$ is chosen from

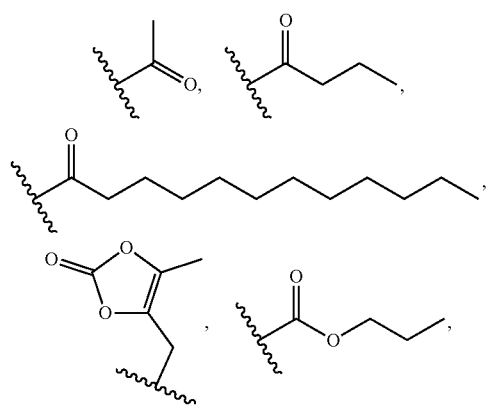

-continued

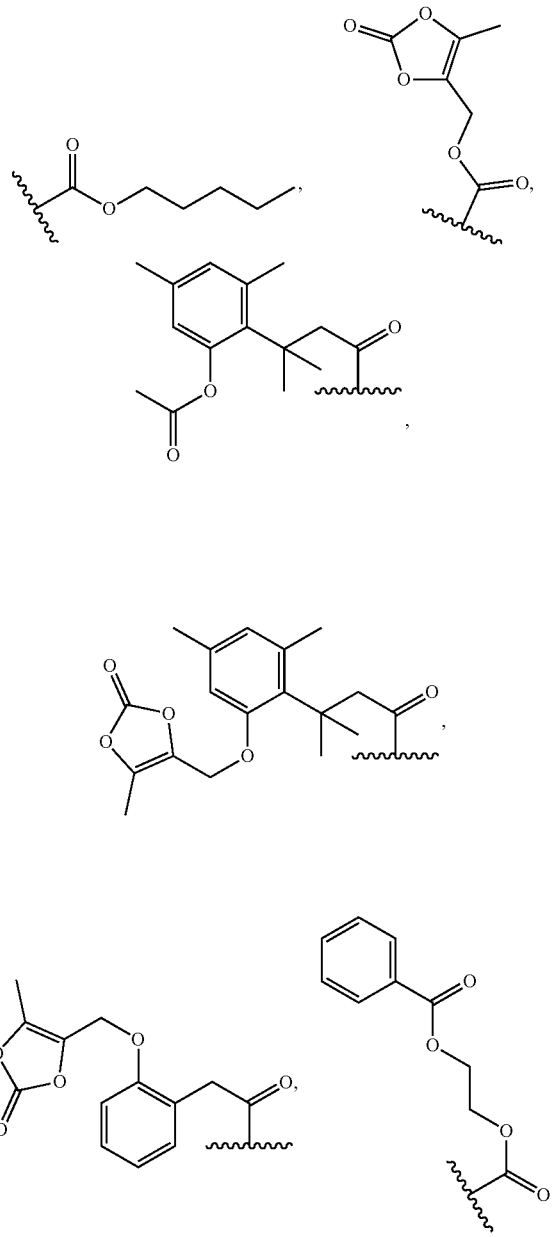

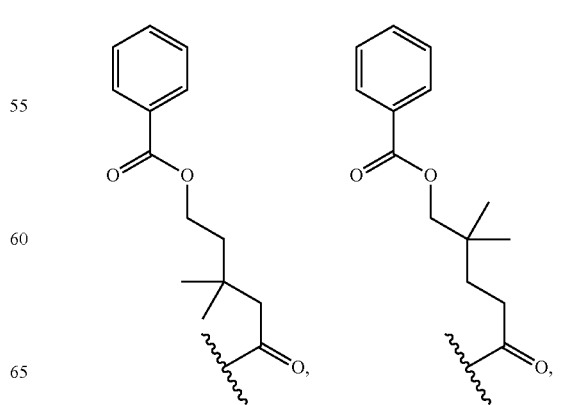

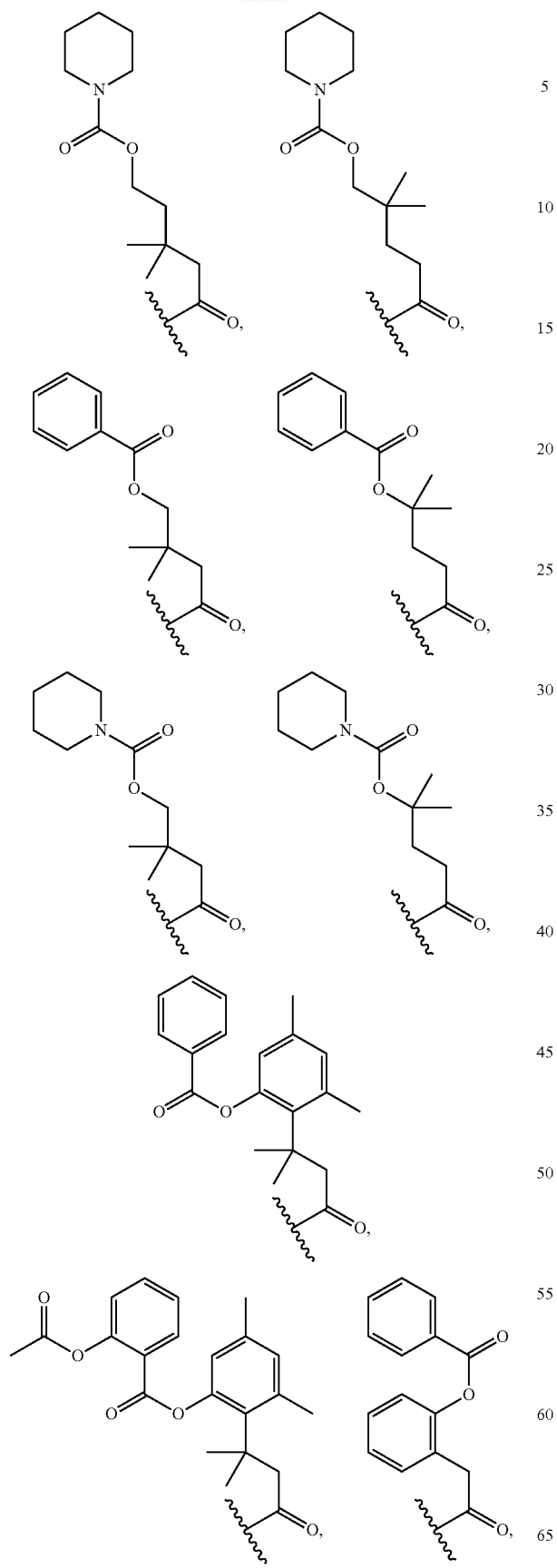
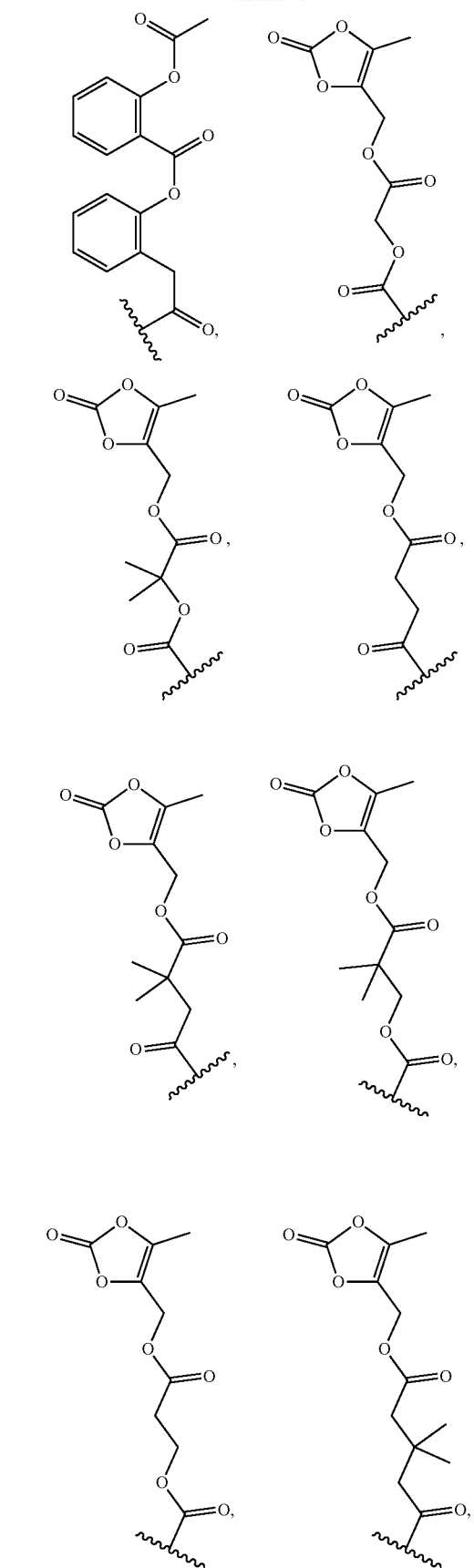

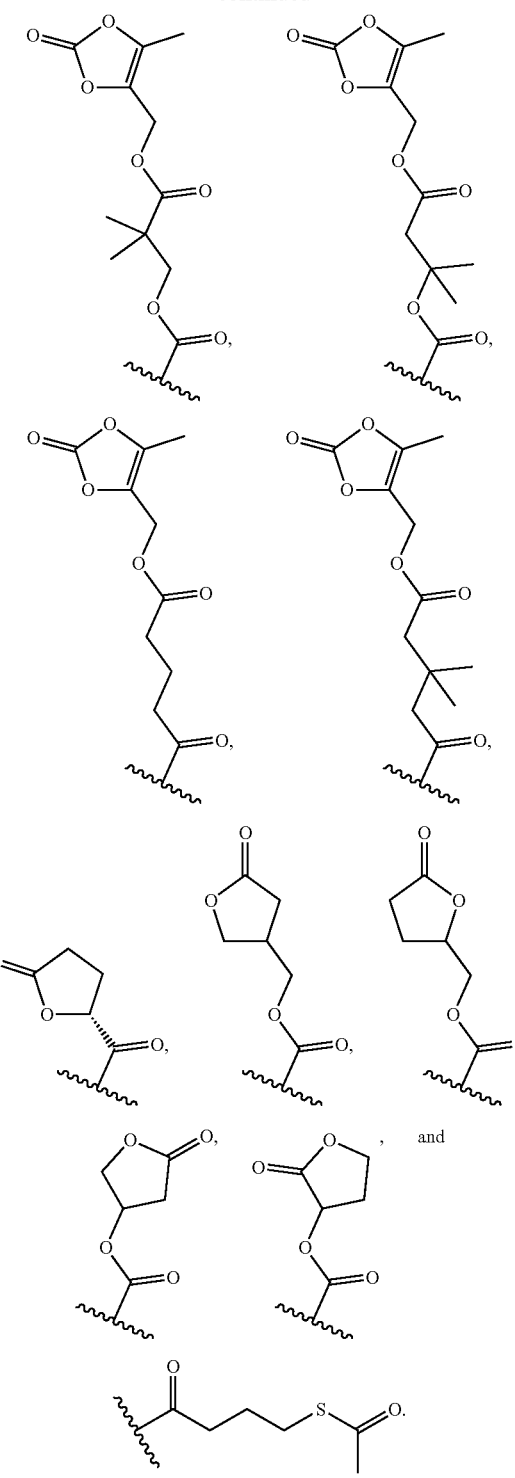
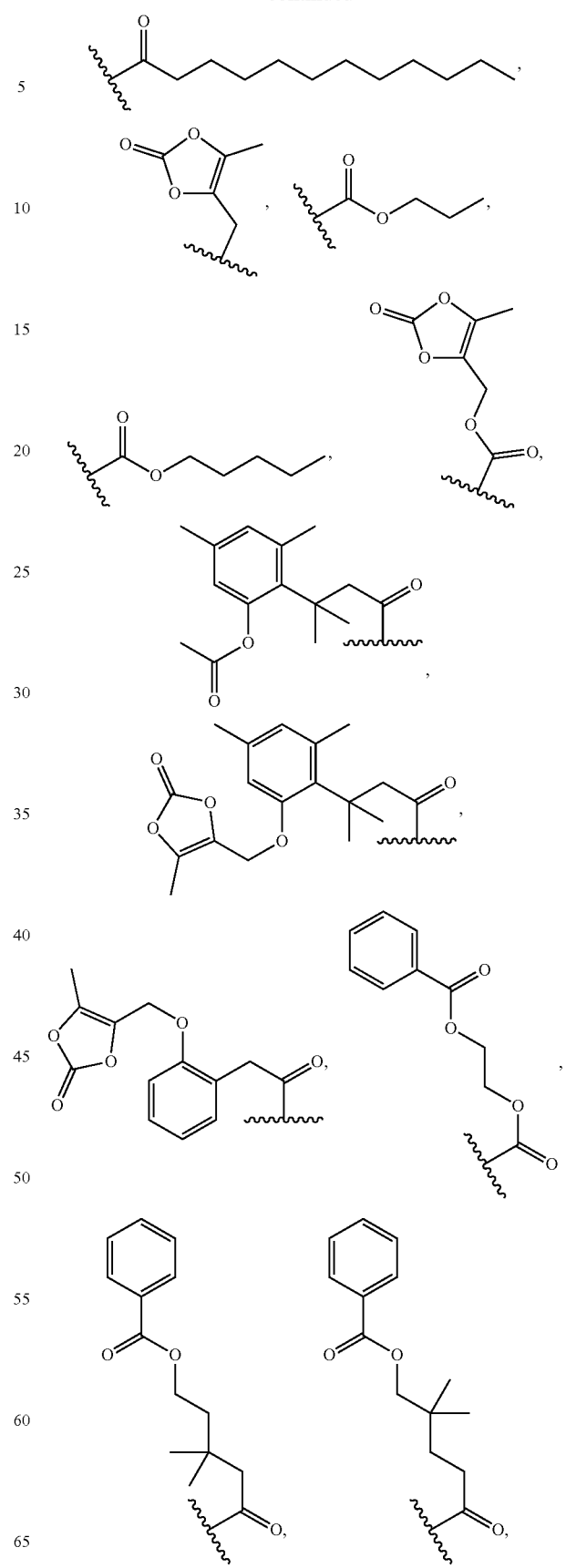
In some embodiments, $R^8$ is chosen from
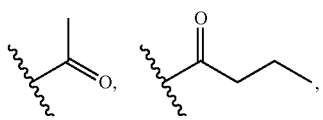

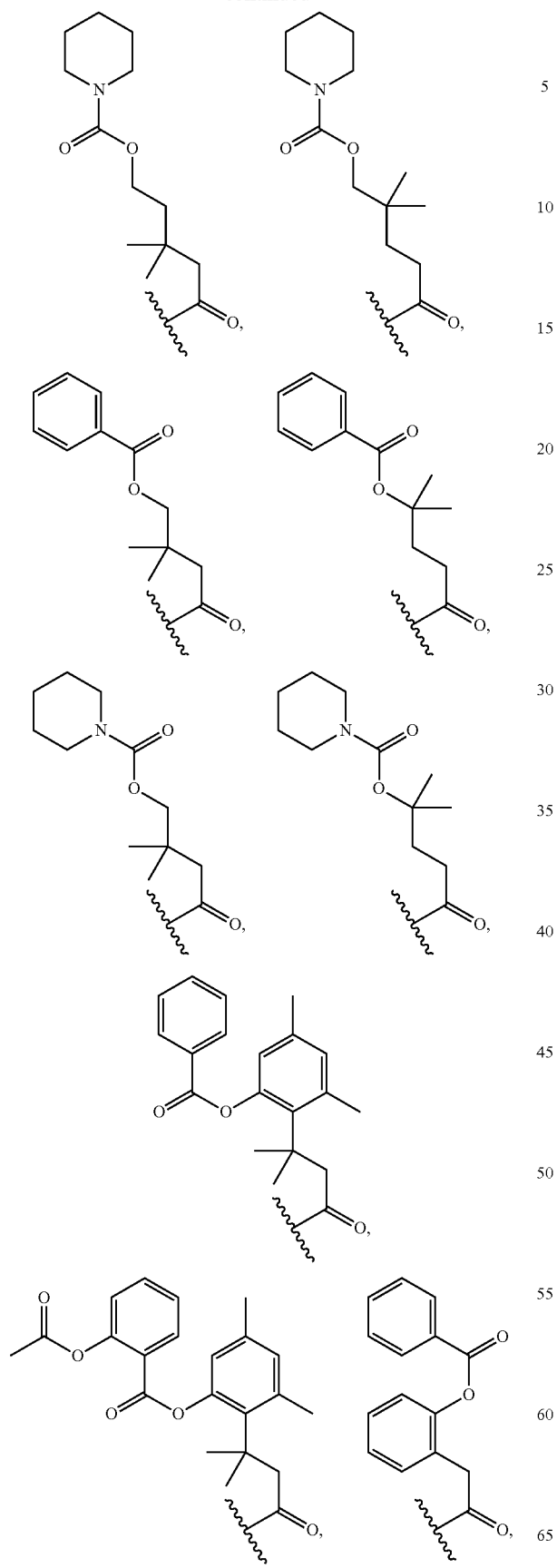
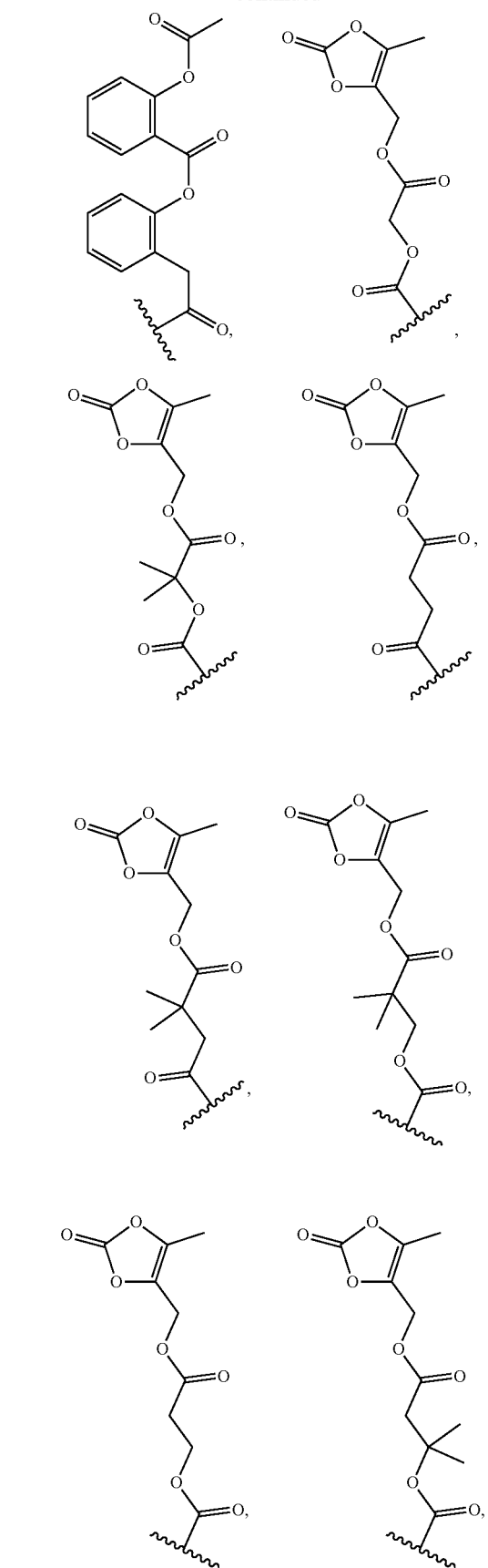

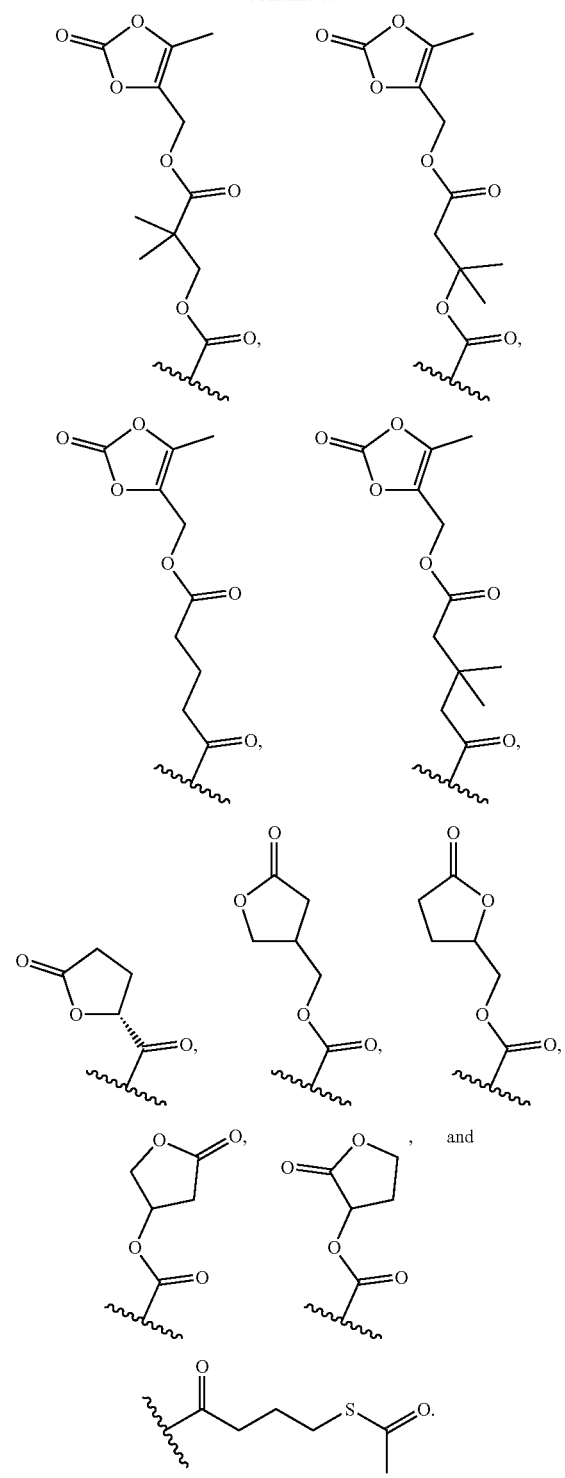
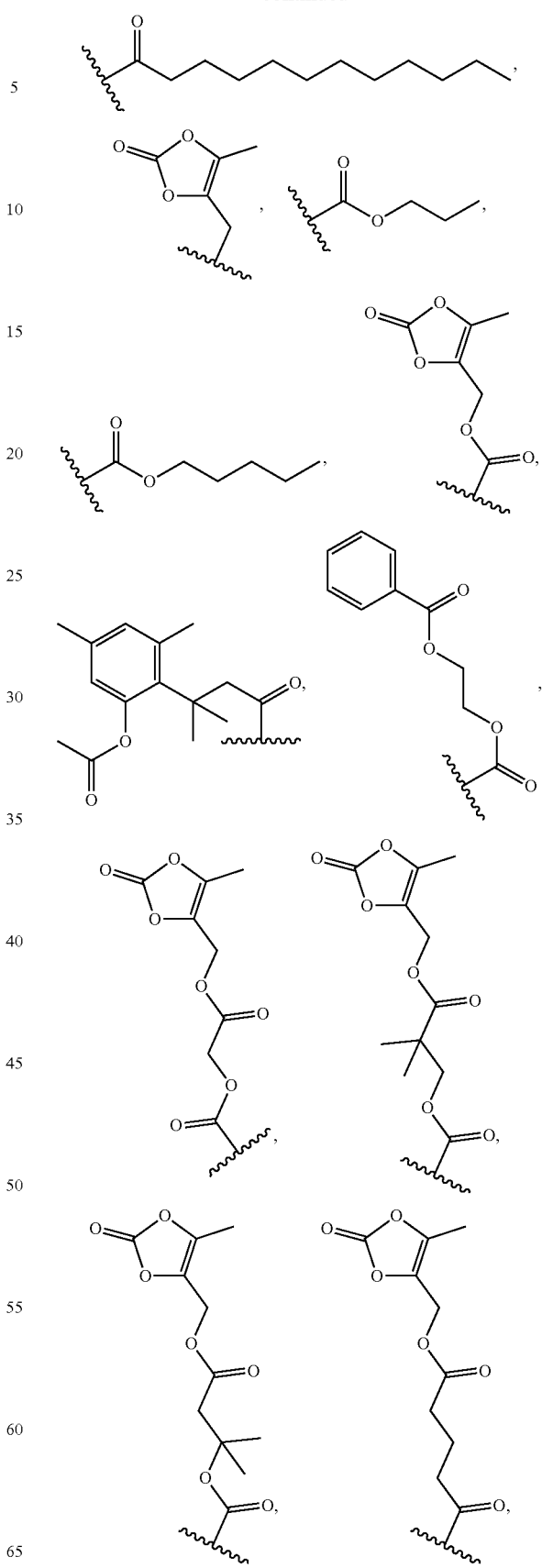
In some embodiments, R$^8$ is chosen from
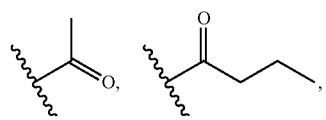

-continued

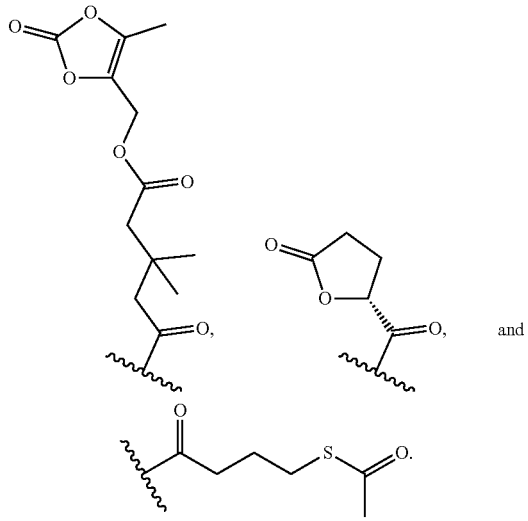

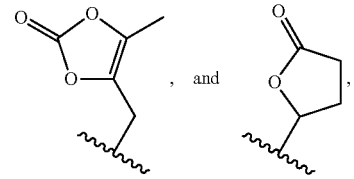

wherein aryl is optionally substituted with one or two $R^c$. In some embodiments, $R^{8a}$ is chosen from $C_{1-8}$alkyl, aryl, —C(O)—$C_{1-4}$alkyl, —S—C(O)—$C_{1-4}$alkyl,

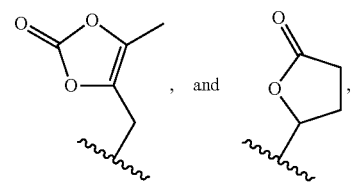

wherein aryl is optionally substituted with one or two $R^c$

In some embodiments of the compound of formula I, II, or III, or a pharmaceutically acceptable salt thereof, $L^1$ is a bond. In some embodiments, $L^1$ is —C(O)—. In some embodiments, $L^1$ is —C(O)O—.

In some embodiments of the compound of formula I, II, or III, or a pharmaceutically acceptable salt thereof, $L^2$ is chosen from —CH$_2$—, —CH$_2$—CH$_2$—, —CH$_2$—CH$_2$—CH$_2$—, —CH$_2$—CH$_2$—CH$_2$—CH$_2$—, —CH$_2$—C(CH$_3$)$_2$—, —CH$_2$—CH$_2$—CH$_2$—CH$_2$—CH$_2$—, —CH$_2$—C(CH$_3$)$_2$—CH$_2$—, —CH$_2$—CH$_2$—C(CH$_3$)$_2$—, —CH$_2$—C(CH$_3$)$_2$—CH$_2$—CH$_2$—, and —CH$_2$—CH$_2$—CH$_2$—C(CH$_3$)$_2$—. In some embodiments, $L^2$ is chosen from —CH$_2$—, —CH$_2$—CH$_2$—, —CH$_2$—CH$_2$—CH$_2$—, —CH$_2$—C(CH$_3$)$_2$—, —CH$_2$—C(CH$_3$)$_2$—CH$_2$—, —CH$_2$—CH$_2$—C(CH$_3$)$_2$—, and —CH$_2$—C(CH$_3$)$_2$—CH$_2$—CH$_2$—. In some embodiments, $L^2$ is —CH$_2$—. In some embodiments, $L^2$ is —CH$_2$—CH$_2$—. In some embodiments, $L^2$ is —CH$_2$—CH$_2$—CH$_2$—. In some embodiments, $L^2$ is —CH$_2$—C(CH$_3$)$_2$—. In some embodiments, $L^2$ is —CH$_2$—C(CH$_3$)$_2$—CH$_2$—. In some embodiments, $L^2$ is —CH$_2$—CH$_2$—C(CH$_3$)$_2$—. In some embodiments, $L^2$ is —CH$_2$—C(CH$_3$)$_2$—CH$_2$—CH$_2$—.

In some embodiments of the compound of formula I, II, or III, or a pharmaceutically acceptable salt thereof, $L^3$ is —C(O)O—. In some embodiments, $L^3$ is

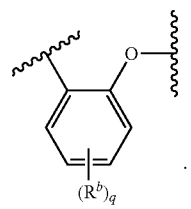

In some embodiments of the compound of formula I, II, or III, or a pharmaceutically acceptable salt thereof, $R^{8a}$ is chosen from $C_{1-12}$alkyl, aryl, —C(O)—$C_{1-4}$alkyl, —S—C(O)—$C_{1-4}$alkyl, In some embodiments of the compound of formula I, II, or III, or a pharmaceutically acceptable salt thereof, each $R^a$ is independently chosen from $C_{1-4}$alkyl, halo, and $C_{1-4}$haloalkyl. In some embodiments, each $R^a$ is independently $C_{1-4}$alkyl. In some embodiments, each $R^a$ is independently halo. In some embodiments, each $R^a$ is independently $C_{1-4}$haloalkyl. In some embodiments, each $R^a$ is independently —O—$C_{1-4}$alkyl. In some embodiments, each $R^a$ is independently chosen from methyl, ethyl, n-propyl, isopropyl, fluoro, methoxy, and trifluoromethyl.

In some embodiments of the compound of formula I, II, or III, or a pharmaceutically acceptable salt thereof, each $R^b$ is independently methyl or ethyl.

In some embodiments of the compound of formula I, II, or III, or a pharmaceutically acceptable salt thereof, each $R^c$ is independently $C_{1-4}$alkyl. In some embodiments, each $R^c$ is independently —OC(O)—$C_{1-4}$alkyl. In some embodiments, each $R^c$ is independently methyl or —OC(O)-methyl.

In some embodiments of the compound of formula I, II, or III, or a pharmaceutically acceptable salt thereof, m and n are both 0. In some embodiments, m is 0 and n is 1. In some embodiments, m is 1 and n is 0. In some embodiments, m and n are both 1.

In some embodiments of the compound of formula I, II, or III, or a pharmaceutically acceptable salt thereof, p is 0 or 2. In some embodiments, p is 0. In some embodiments, p is 1. In some embodiments, p is 2.

In some embodiments of the compound of formula I, II, or III, or a pharmaceutically acceptable salt thereof, $R^1$ and $R^2$ are the same and $R^3$, $R^4$, $R^5$, and $R^6$ are the same. In some embodiments, $R^1$ and $R^2$ are the same and $R^3$, $R^4$, $R^5$, and $R^6$ are each methyl or cyclopropyl. In some embodiments, $R^1$ and $R^2$ are the same and $R^3$, $R^4$, $R^5$, and $R^6$ are each cyclopropyl. In some embodiments, $R^1$ and $R^2$ are the same and $R^3$, $R^4$, $R^5$, and $R^6$ are each methyl.

In some embodiments of the compound of formula I, II, or III, or a pharmaceutically acceptable salt thereof, $R^7$ is hydrogen and $R^1$ and $R^2$ are the same.

In some embodiments, $R^7$ is hydrogen and $R^3$, $R^4$, $R^5$, and $R^6$ are the same. In some embodiments, $R^7$ is hydrogen and $R^3$, $R^4$, $R^5$, and $R^6$ are each methyl or cyclopropyl. In some embodiments, $R^7$ is hydrogen and $R^3$, $R^4$, $R^5$, and $R^6$ are each cyclopropyl. In some embodiments, $R^7$ is hydrogen and $R^3$, $R^4$, $R^5$, and $R^6$ are each methyl.

In some embodiments of the compound of formula I, II, or III, or a pharmaceutically acceptable salt thereof, $R^7$ is hydrogen, $R^1$ and $R^2$ are the same, and $R^3$, $R^4$, $R^5$, and $R^6$ are the same. In some embodiments, $R^7$ is hydrogen, $R^1$ and $R^2$ are the same, and $R^3$, $R^4$, $R^5$, and $R^6$ are each methyl or cyclopropyl. In some embodiments, $R^7$ is hydrogen, $R^1$ and $R^2$ are the same, and $R^3$, $R^4$, $R^5$, and $R^6$ are each cyclopropyl. In some embodiments, $R^7$ is hydrogen, $R^1$ and $R^2$ are the same, and $R^3$, $R^4$, $R^5$, and $R^6$ are each methyl.

In some embodiments, the compound of formula I or II is a compound of formula

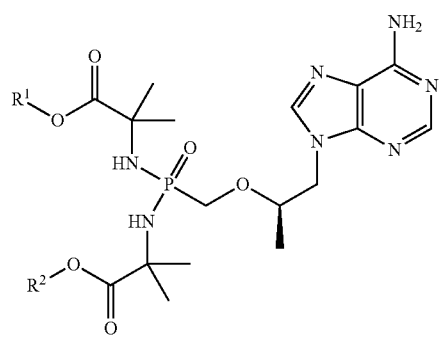

IV or a pharmaceutically acceptable salt thereof, wherein $R^1$ and $R^2$ are as defined in formula I.

In some embodiments of the compound of formula IV, $R^1$ and $R^2$ are different. In some embodiments, $R^1$ and $R^2$ are the same.

In some embodiments, the compound of formula I or III is a compound of formula (V):

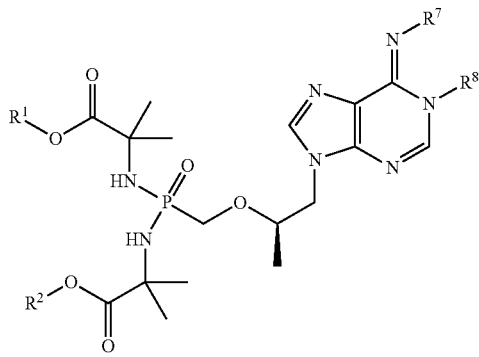

V or a pharmaceutically acceptable salt thereof, wherein $R^1$, $R^2$, $R^7$, and $R^8$ are as defined above.

In some embodiments of the compound of formula V, $R^1$ and $R^2$ are different. In some embodiments, $R^1$ and $R^2$ are the same. In some embodiments $R^7$ is H. In some embodiments, $R^7$ is $R^8$.

In some embodiments, the compounds have the formula:

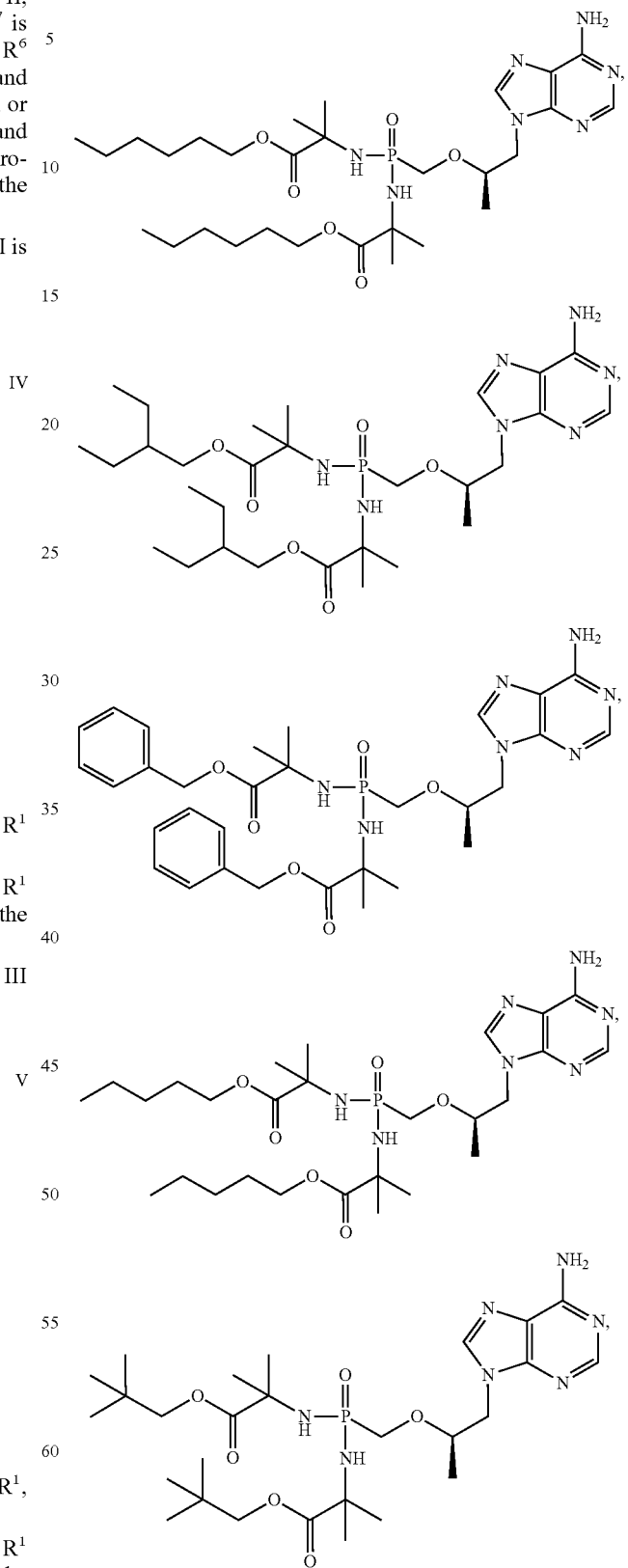

-continued
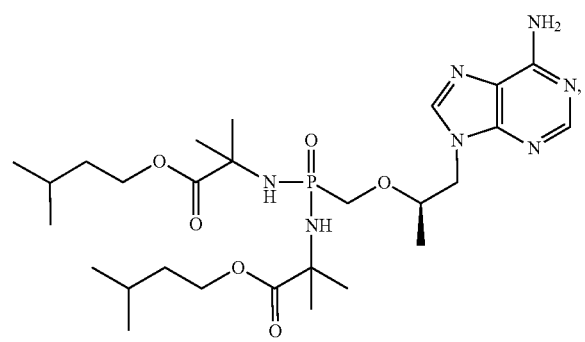
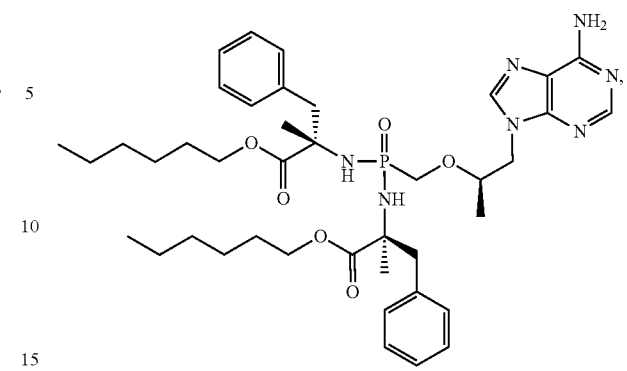
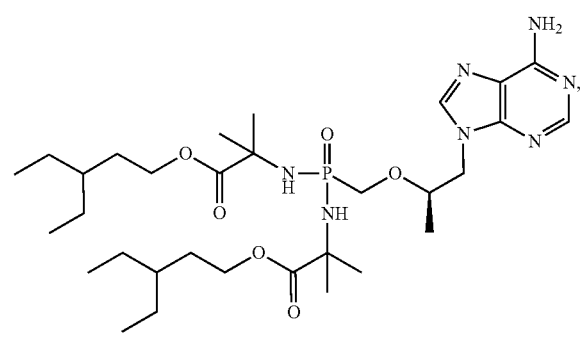
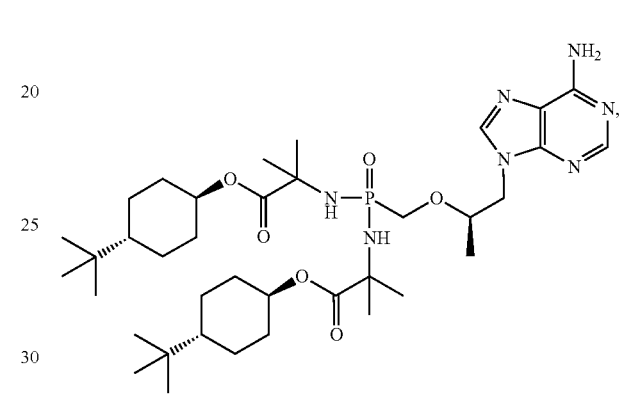
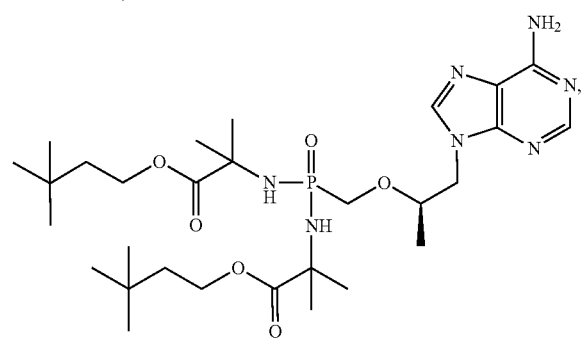
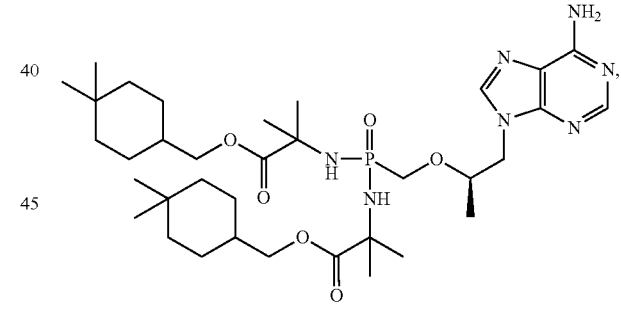
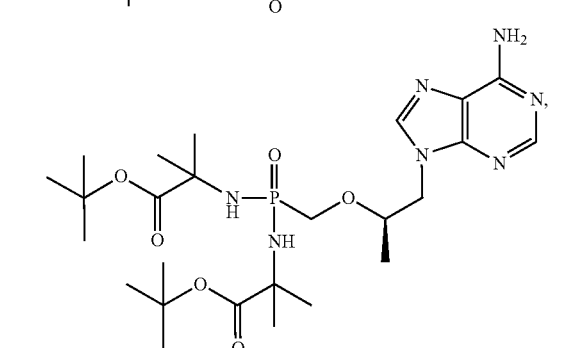
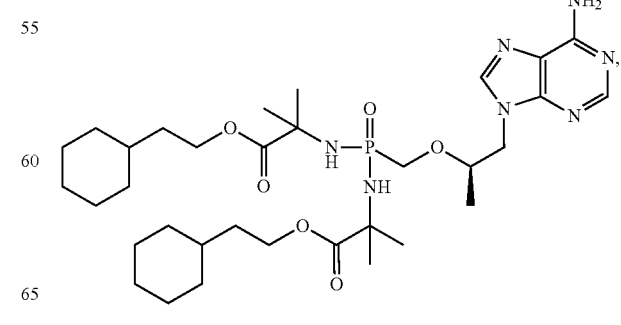

51
-continued
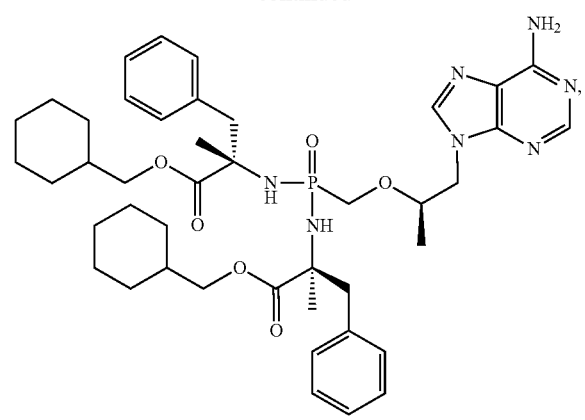
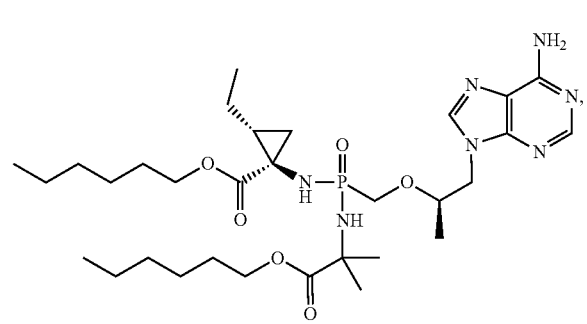
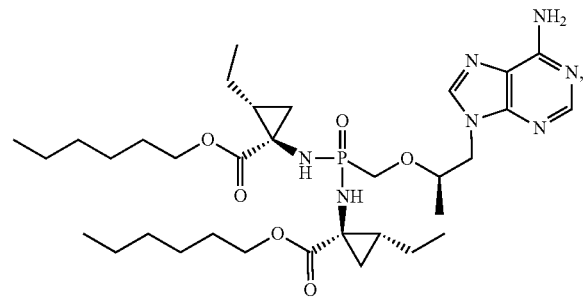
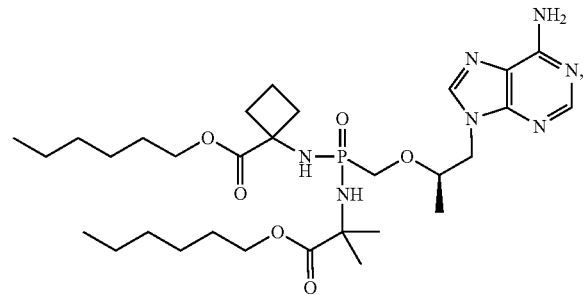
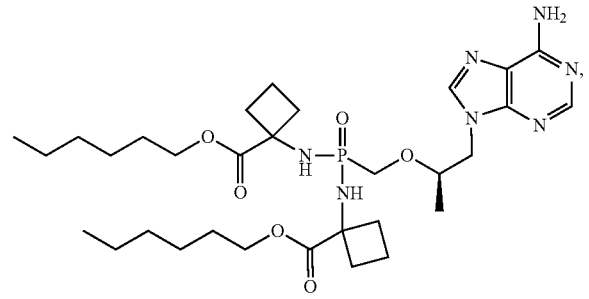
52
-continued
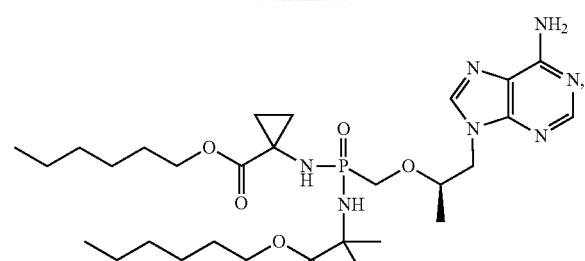
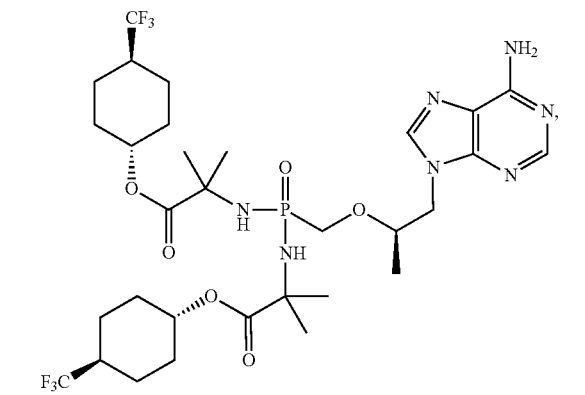
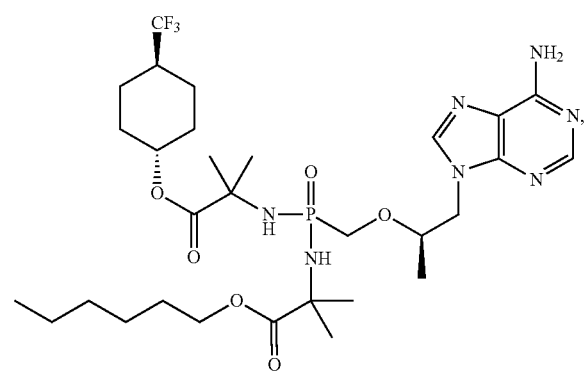
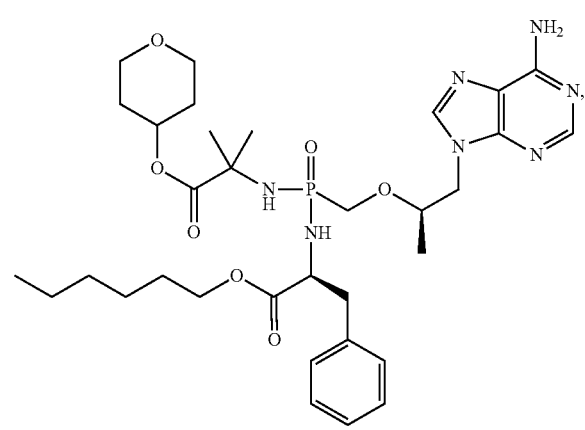

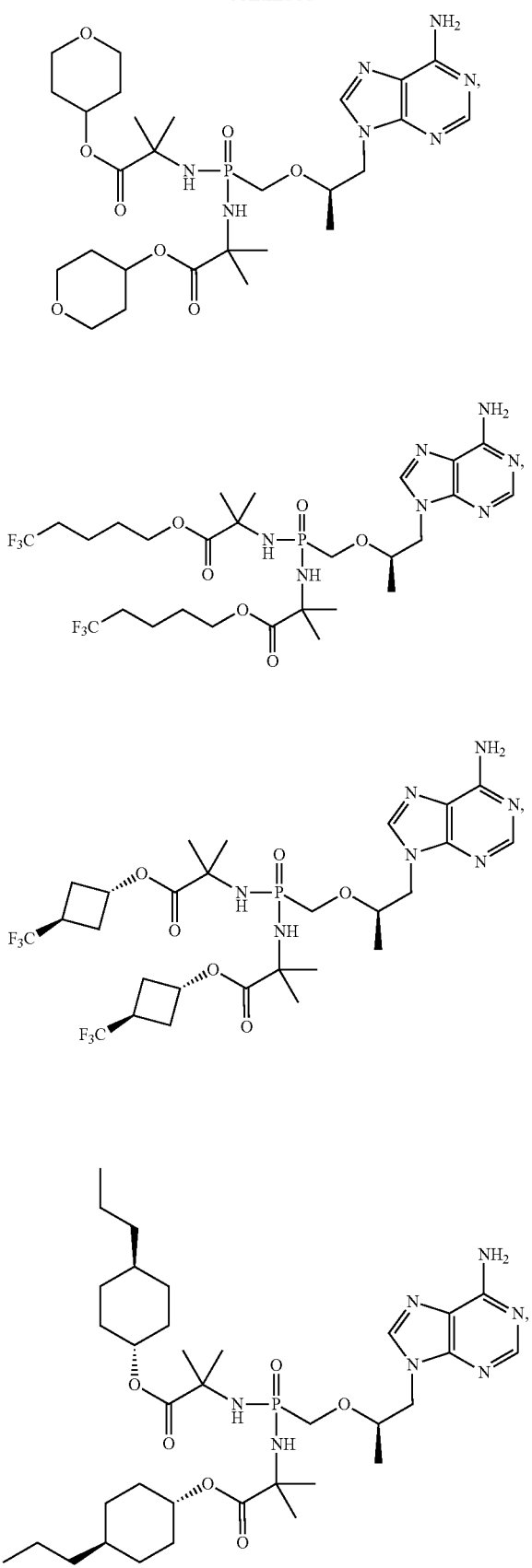
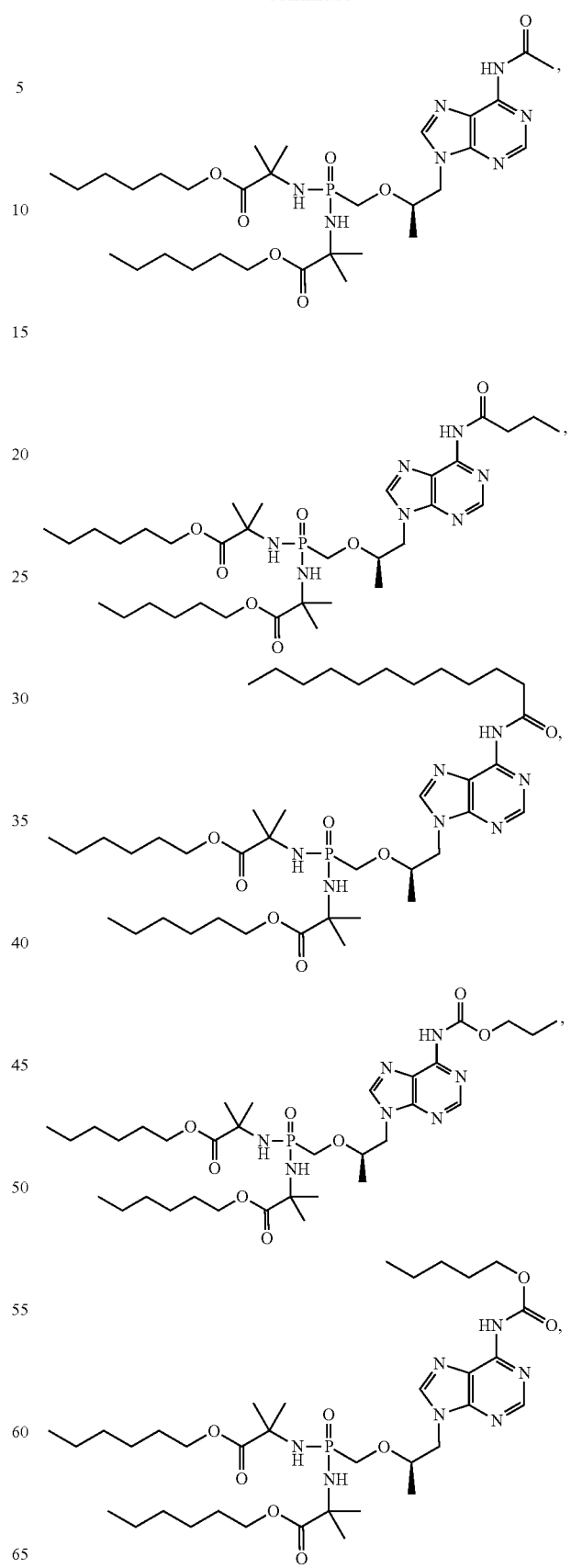

55
-continued
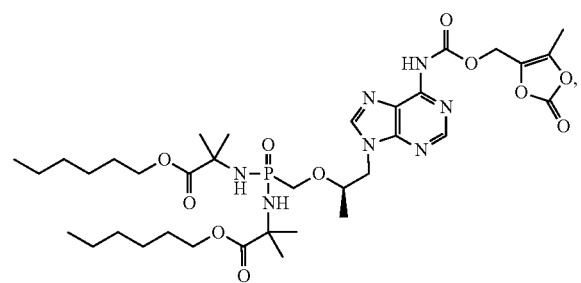
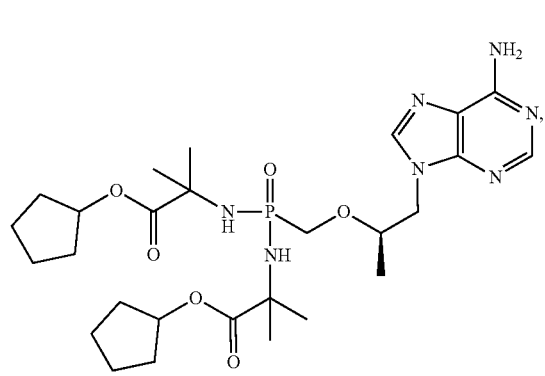
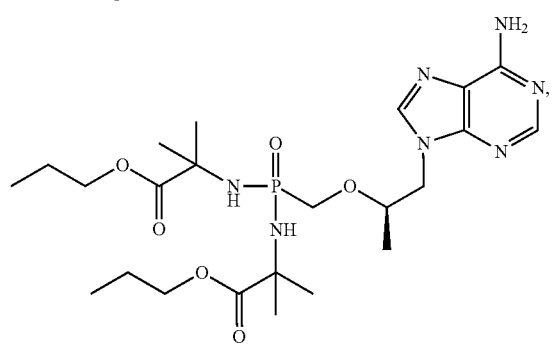
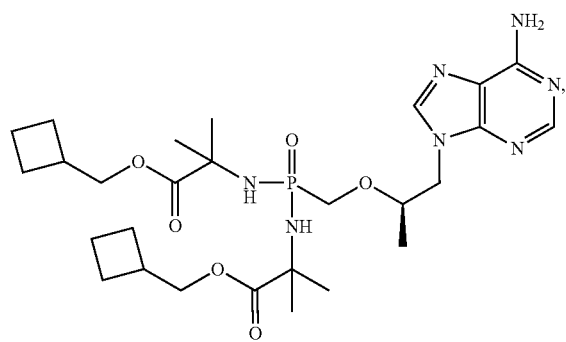
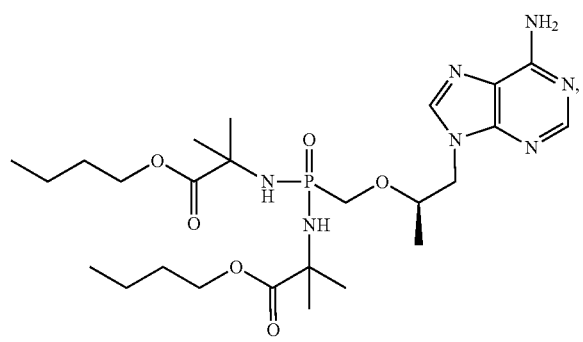
56
-continued
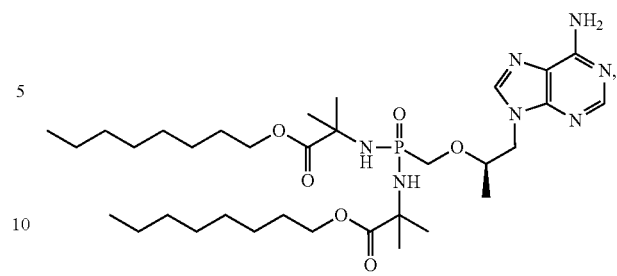
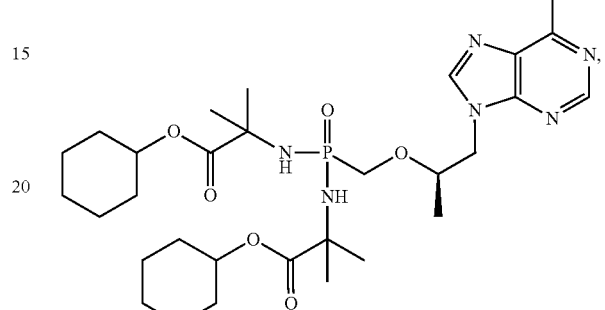
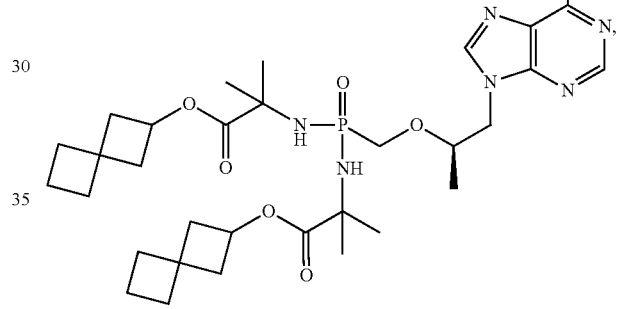
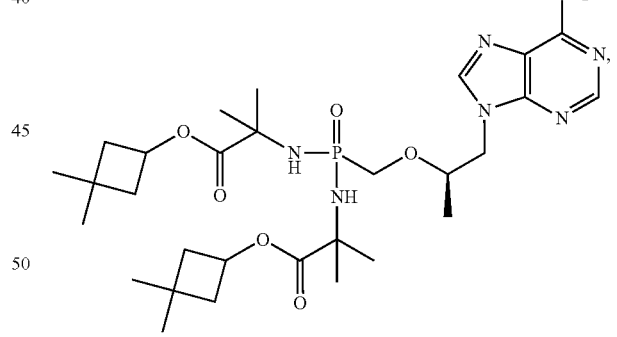
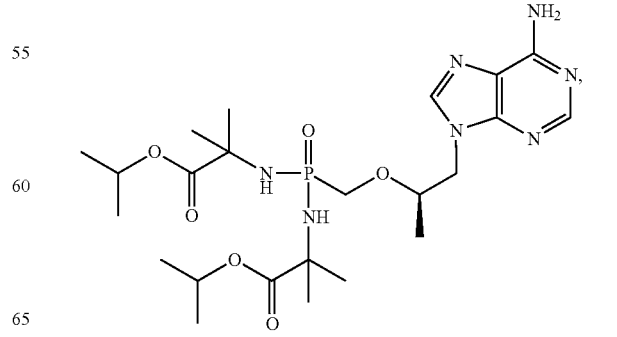

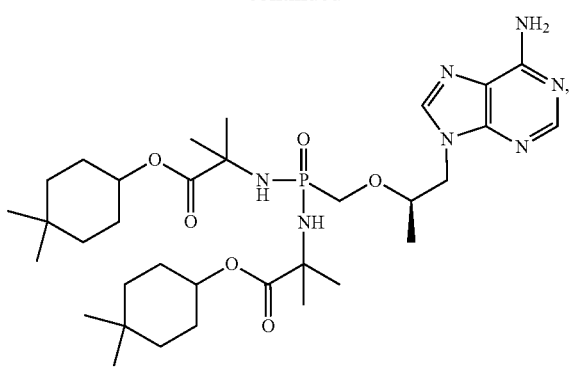
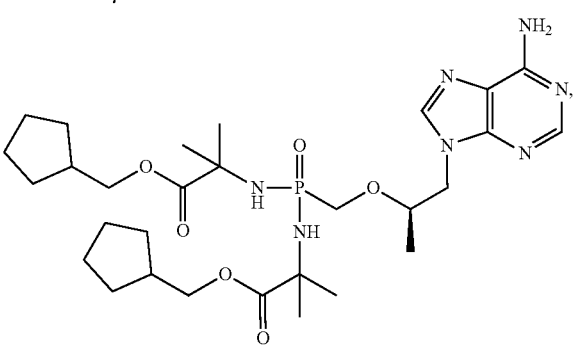
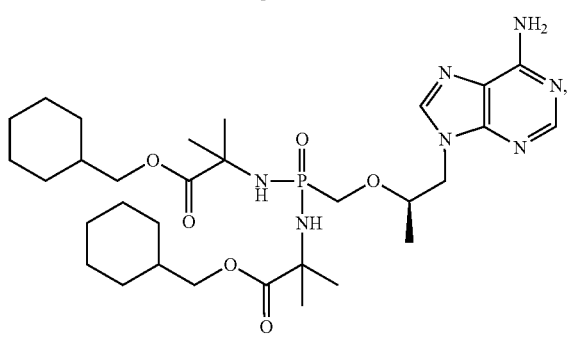
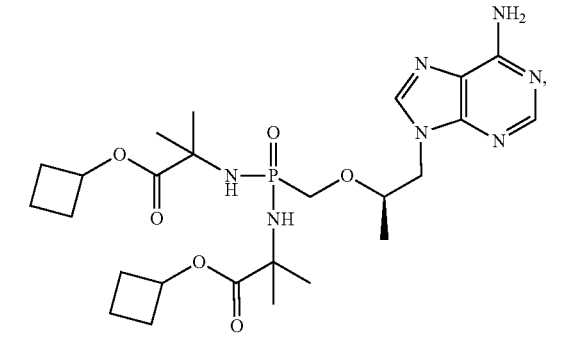
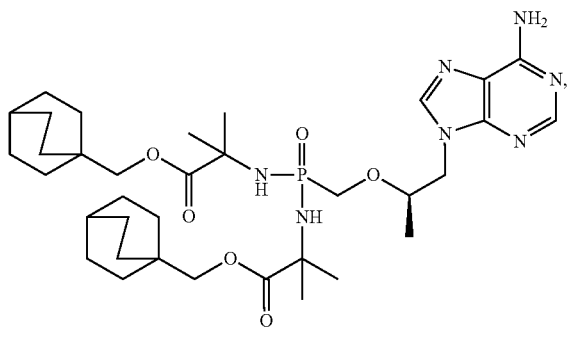
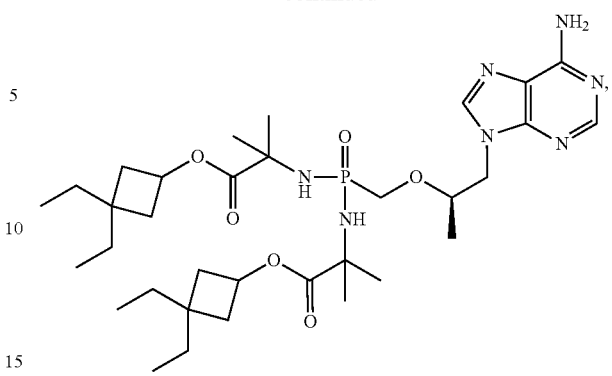
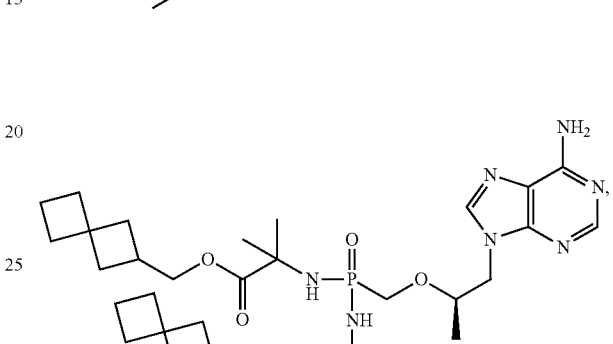
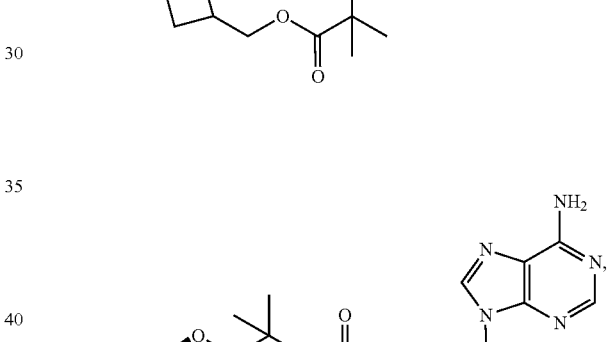
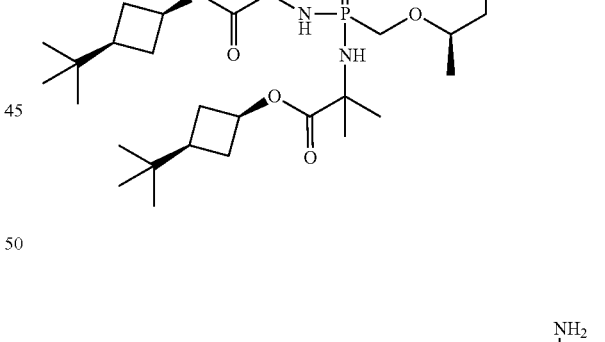
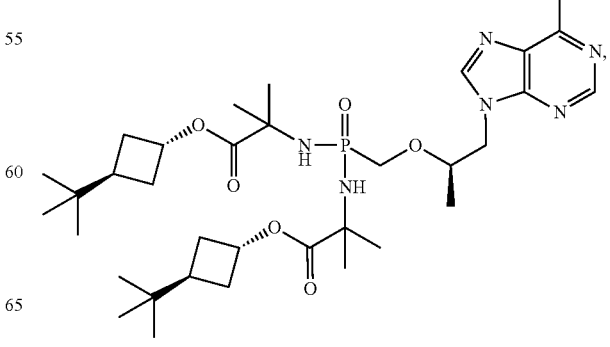

59
-continued
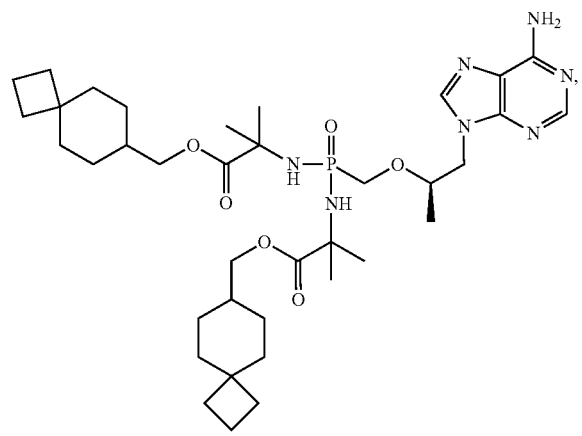
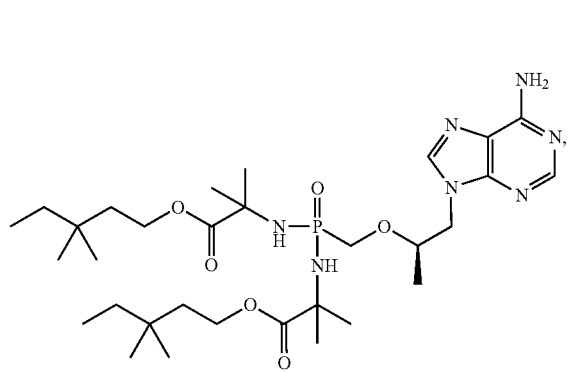
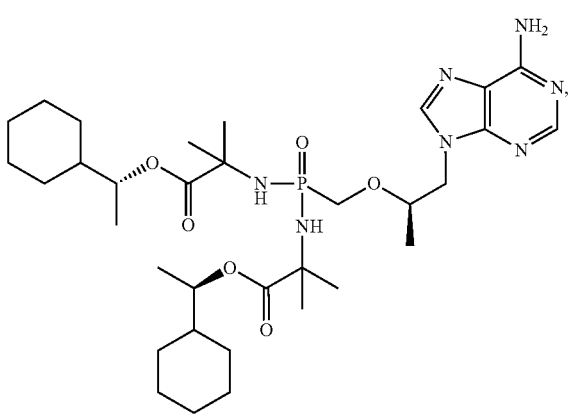
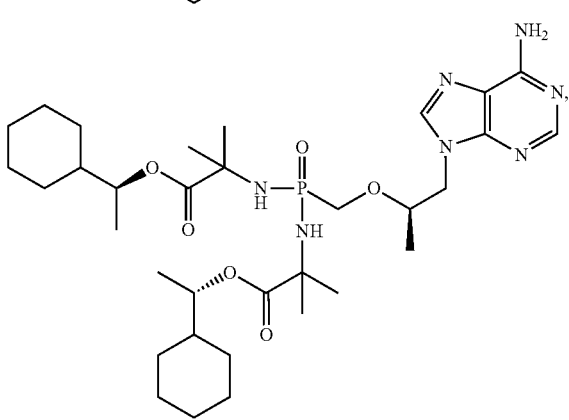
60
-continued
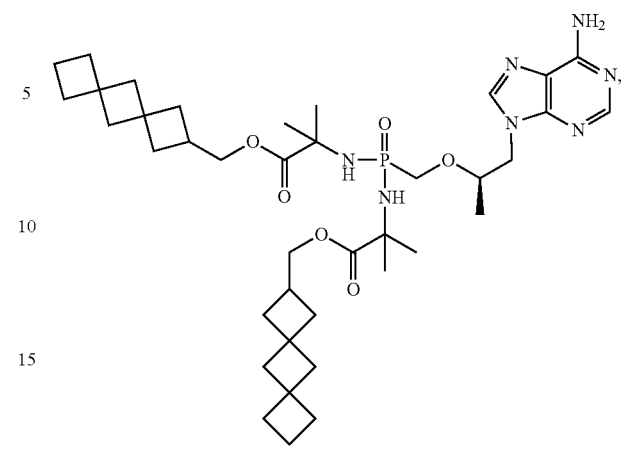
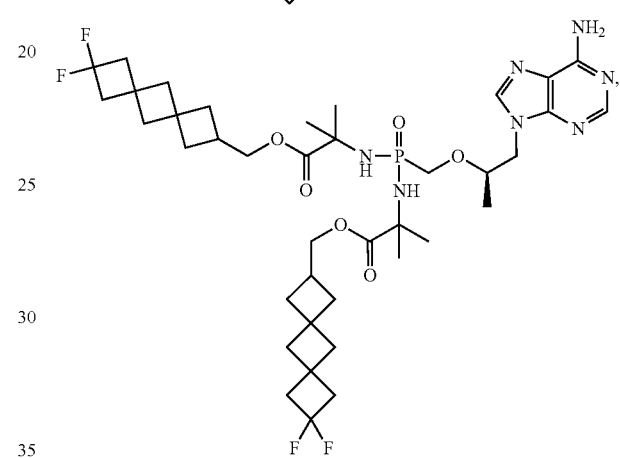
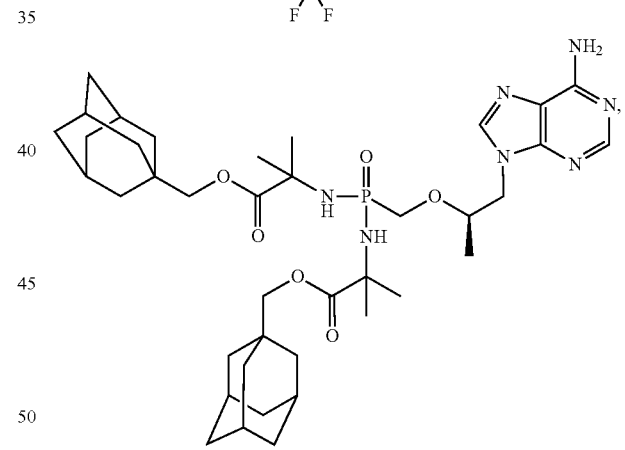
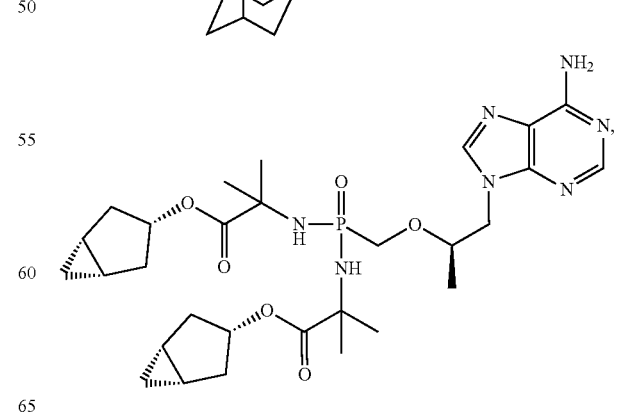

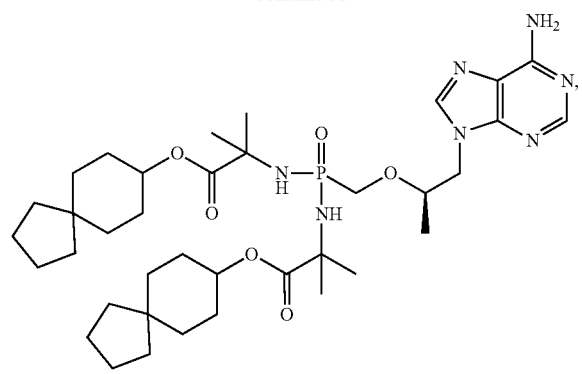
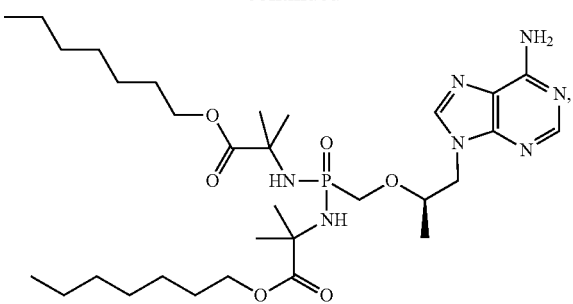
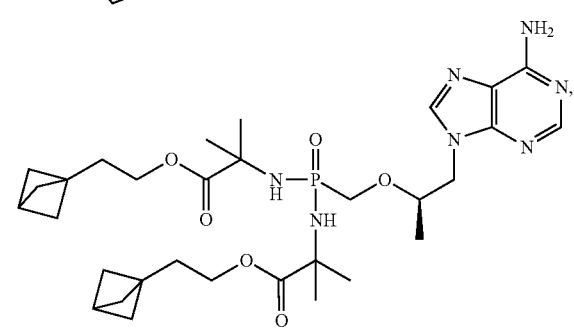
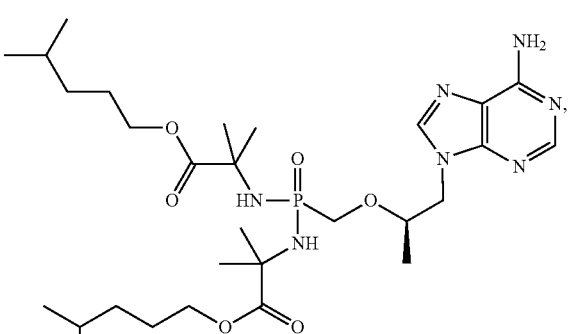
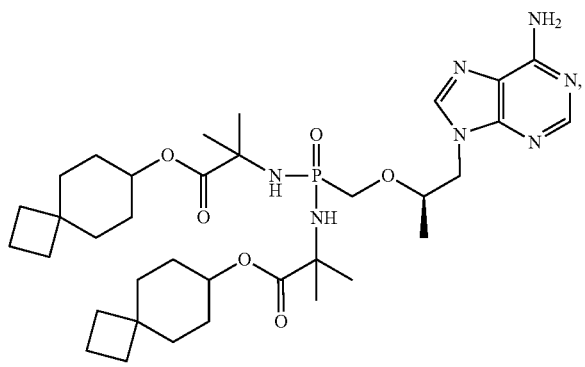
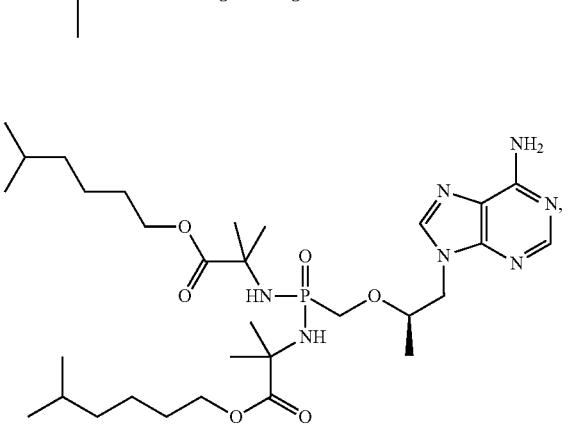
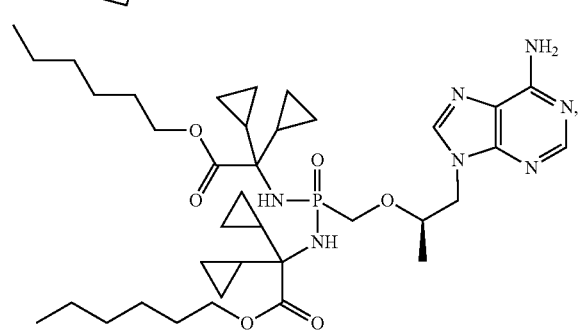
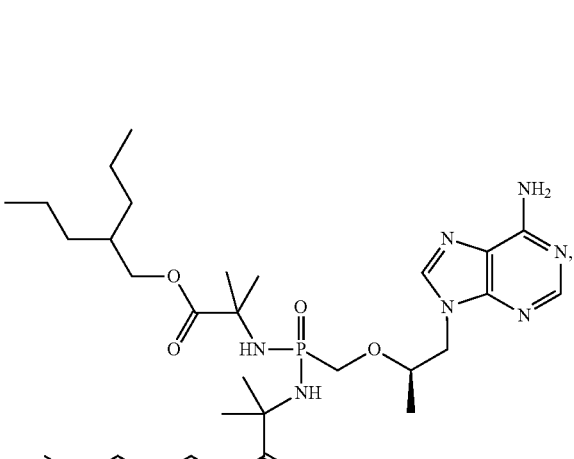
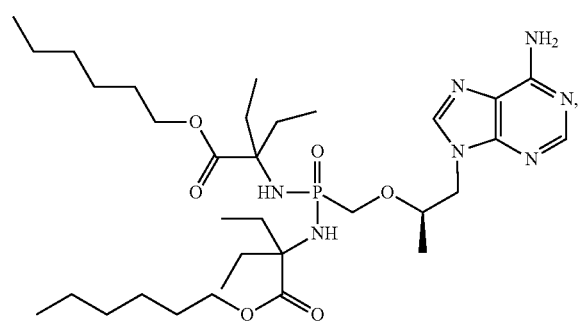

-continued
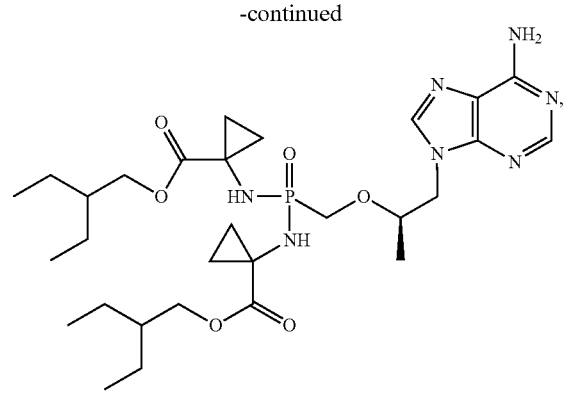
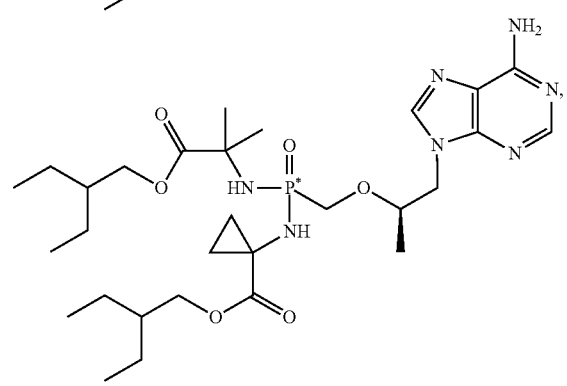
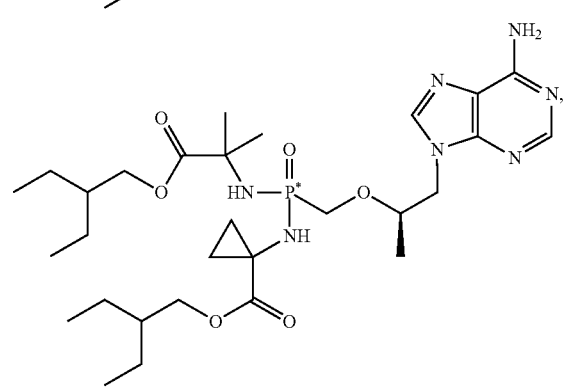
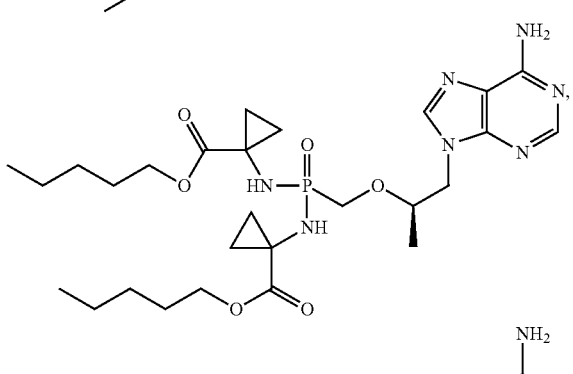
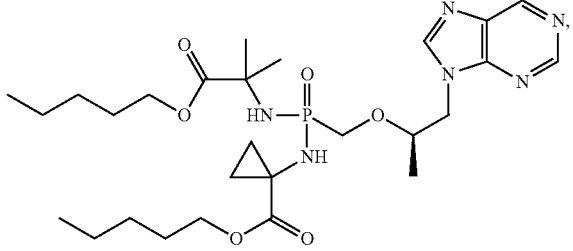
-continued
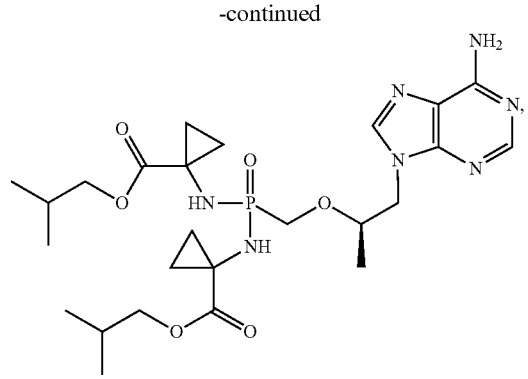
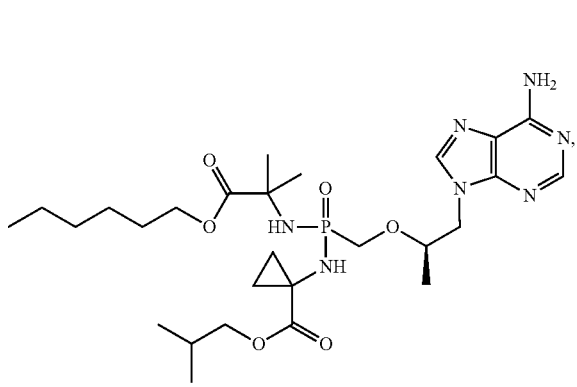
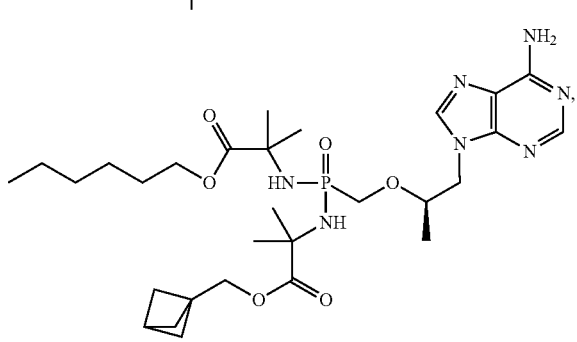
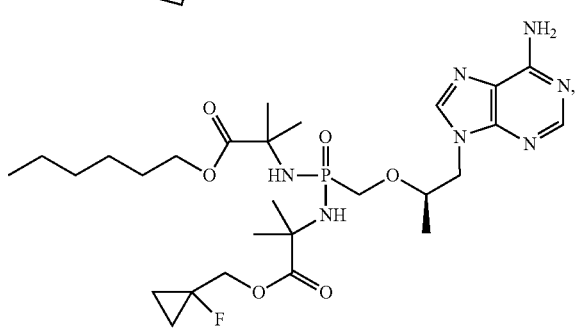
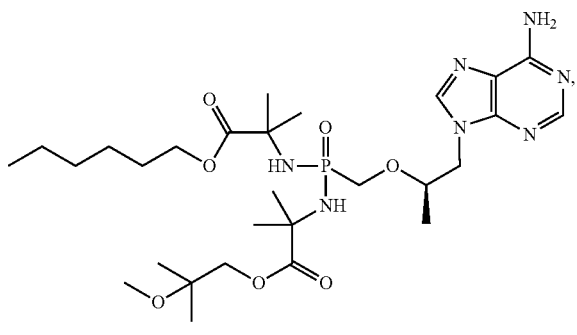

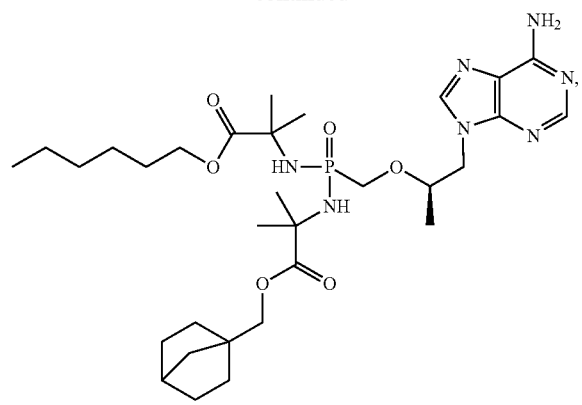
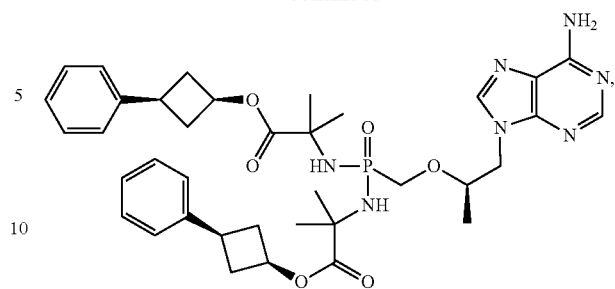
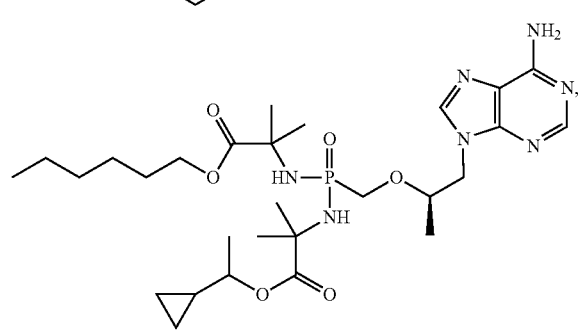
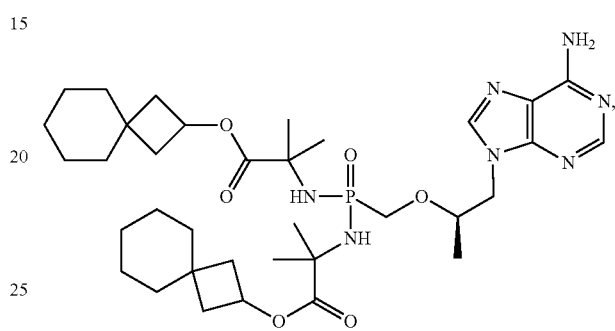
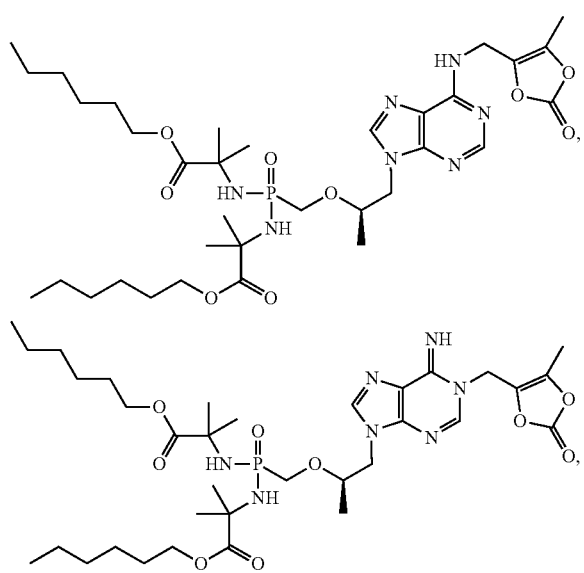
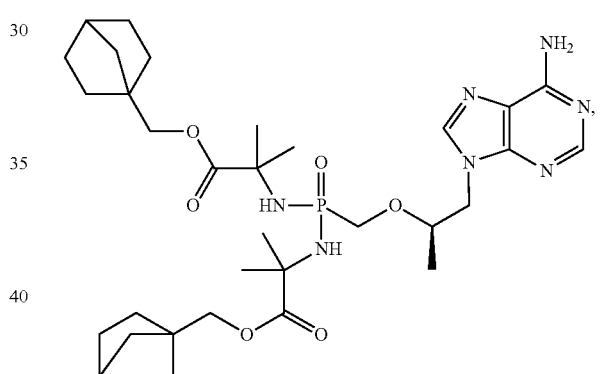
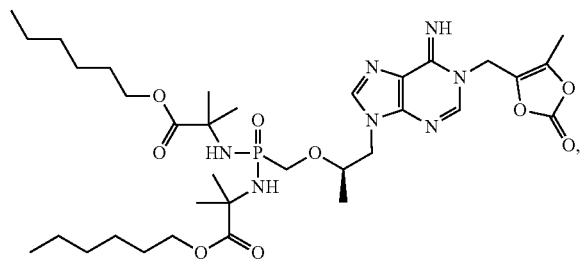
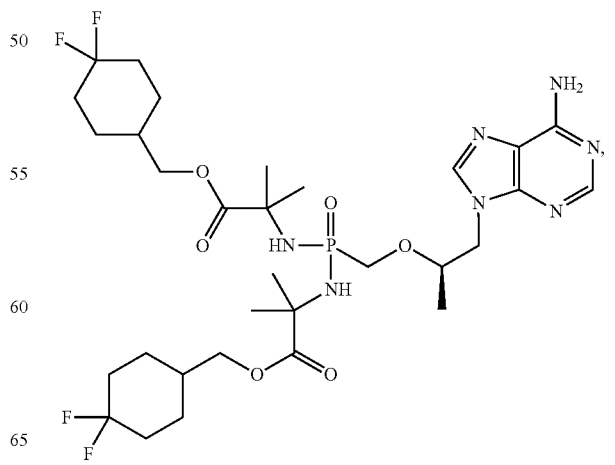

67
-continued
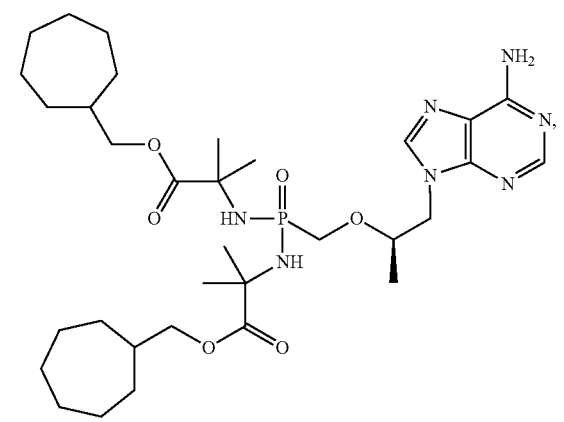
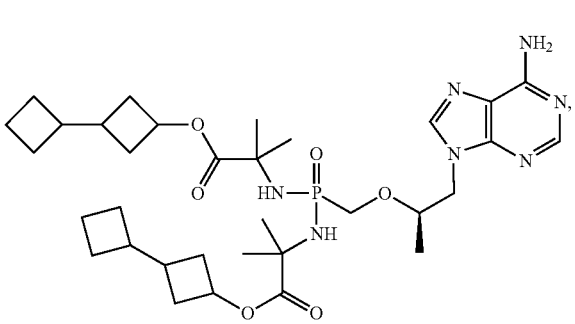
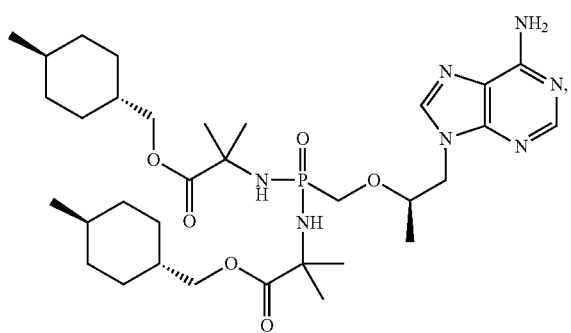
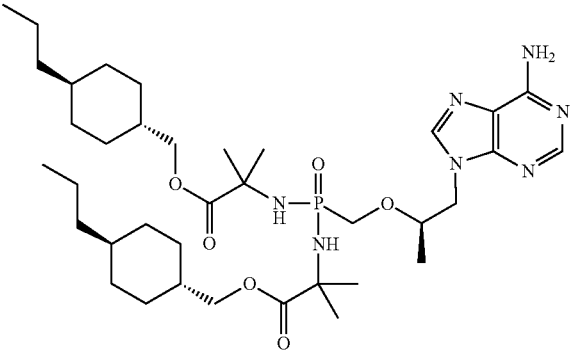
68
-continued
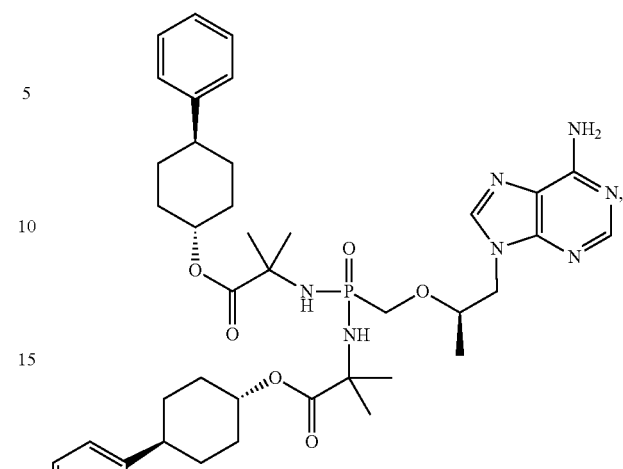
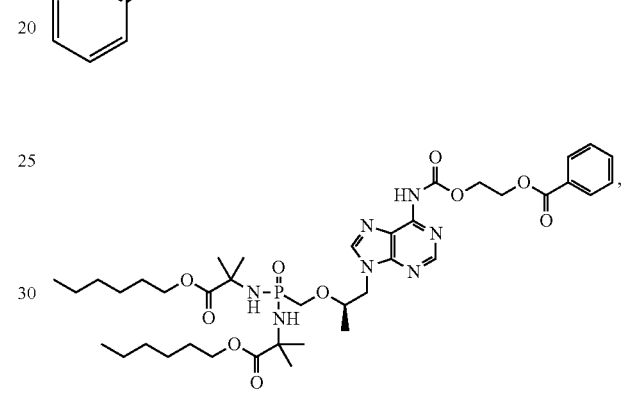
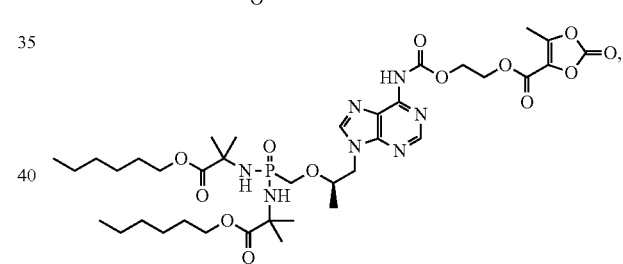
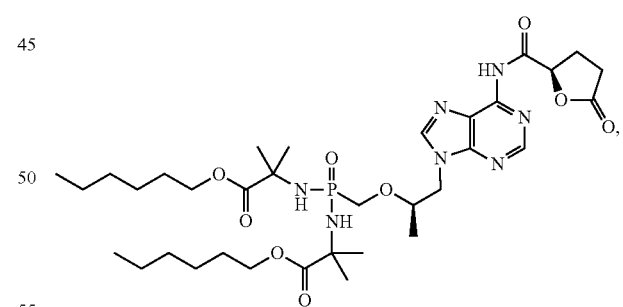
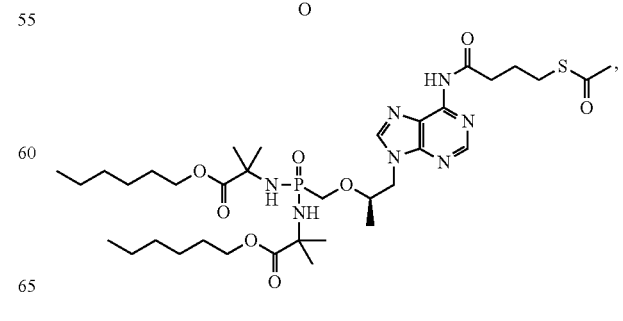

-continued
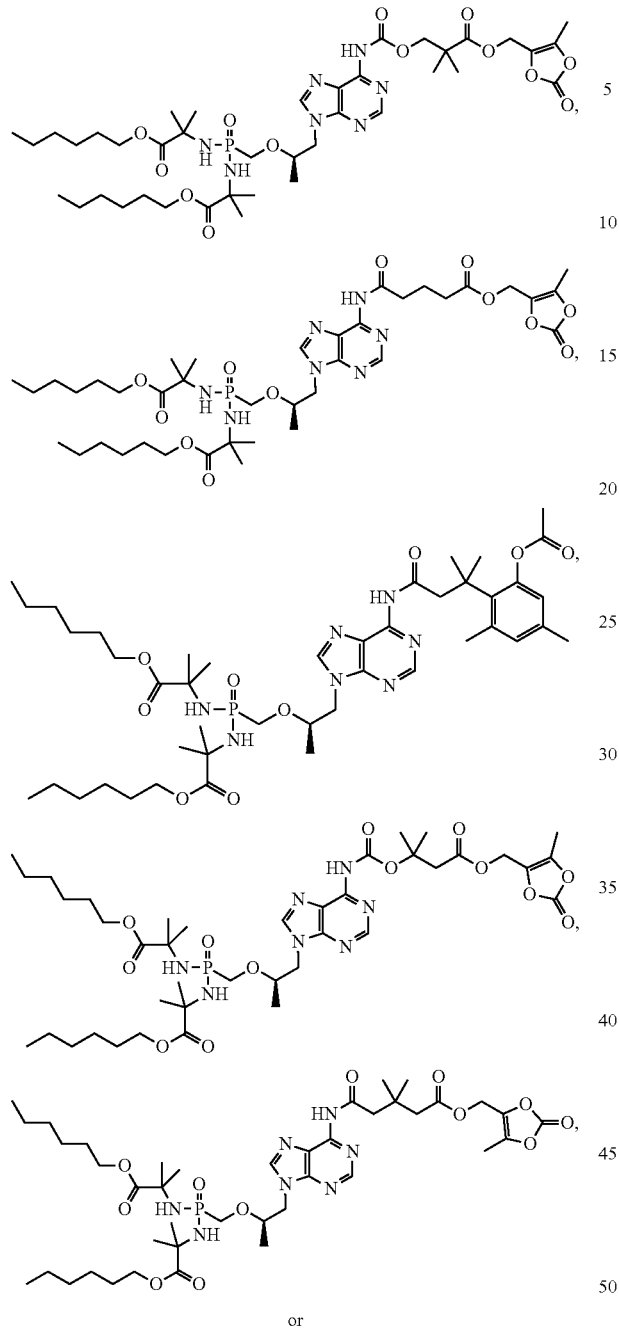
or
a pharmaceutically acceptable salt thereof.
In some embodiments, the compounds have the formula:
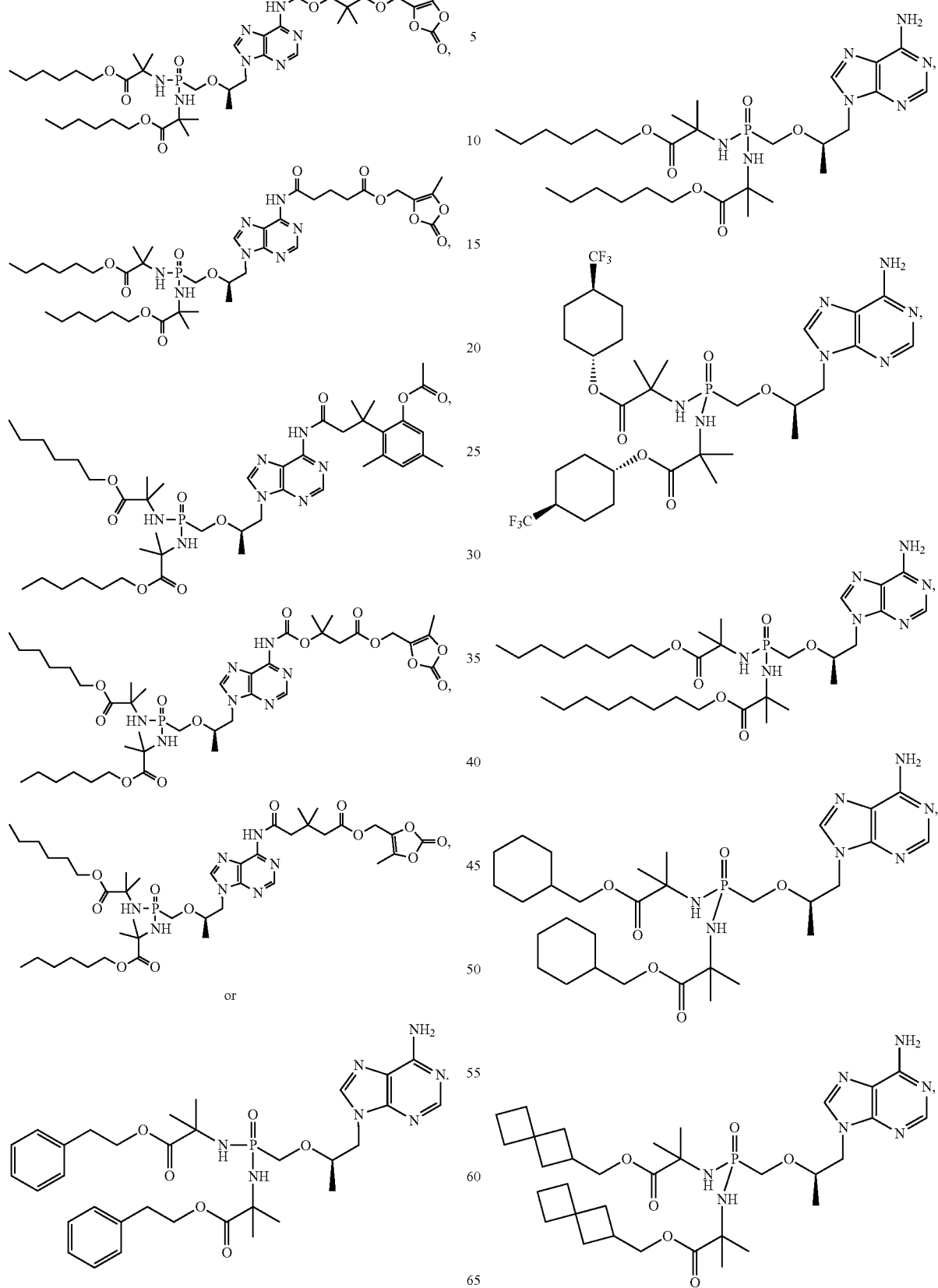

-continued

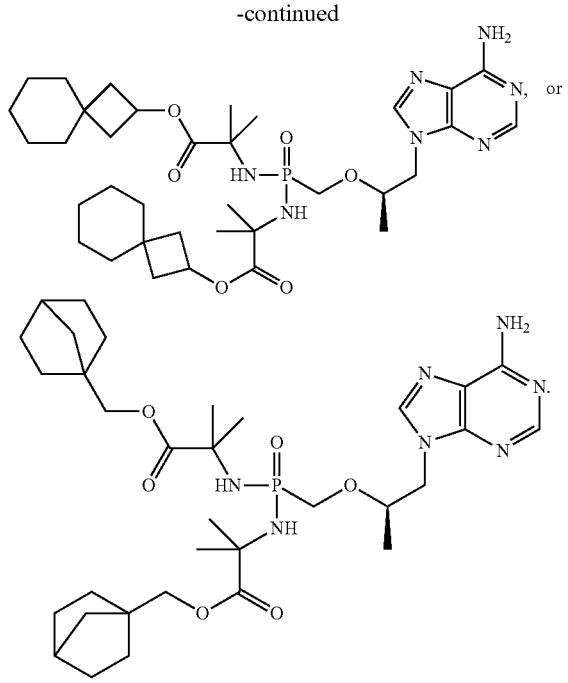

When any variable is a non-symmetrical, divalent group, both orientations of the group are intended to be covered, unless specified otherwise. For example, when $L^3$ is —C(O)O— both orientations of —C(O)O— are included (i.e., when $R^8$ is -$L^1$-$L^3$-$R^{8a}$, both -$L^1$-C(O)O—$R^{8a}$ and -$L^1$-OC(O)—$R^{8a}$ are included), or when $L^2$ is —CH$_2$—CH$_2$—C(CH$_3$)$_2$—, both orientations of —CH$_2$—CH$_2$—C(CH$_3$)$_2$— are included (i.e., when $R^8$ is -$L^1$-$L^2$-$R^{8a}$, both $R^8$ is -$L^1$-CH$_2$—CH$_2$—C(CH$_3$)$_2$—$R^{8a}$ and -$L^1$-C(CH$_3$)$_2$—CH$_2$—CH$_2$—$R^{8a}$ are included).

It is understood that any embodiment of the compounds of any one of formulas I, II, III, IV, and V, as set forth above, and any specific group or substituent set forth herein (e.g., $R^1$, $R^2$, $R^3$, $R^4$, $R^5$, $R^6$, $R^7$, $R^8$, and substituents thereof) in the compounds of formulas I, II, III, IV, and V as set forth above, may be independently combined with other embodiments and/or substituents of compounds of any one of formulas I, II, III, IV, and V, to form embodiments not specifically set forth above. In addition, in the event that a list of substituents are not listed for any particular $R^1$, $R^2$, $R^3$, $R^4$, $R^5$, $R^6$, $R^7$, and $R^8$ group in a particular embodiment and/or claim, it is understood that each individual substituent may be deleted from the particular embodiment and/or claim and that the remaining list of substituents will be considered to be within the scope of the embodiments disclosed herein.

The compounds of formulas I, II, III, IV, and V, or pharmaceutically acceptable salts thereof, are prodrugs, with the promoiety being cleaved rapidly in intracellular environments to yield tenofovir (TFV). In some embodiments, the compounds of formulas I, II, III, IV, and V, or the pharmaceutically acceptable salts thereof, are suitable for use in long-acting formulations. For certain patients, for example, those with difficult or limited access to health care, adherence to daily oral treatment or prophylactic regimens to treat or prevent viral infections (e.g., HIV infection) can be challenging. Drugs that offer favorable pharmaceutical or physicochemical properties for slow release (for example, improved potency, long acting pharmacokinetics, reduced solubility, enhanced plasma stability, and/or other properties) can be amenable to less frequent administration and can provide for better patient compliance. Such improvements can, in turn, optimize drug exposure and limit the emergence of drug resistance.

Without intending to be bound by theory, it is believed that the low solubility of the compounds of formulas I, II, III, IV, and V, or pharmaceutically acceptable salts thereof, can result in slow release of the compounds after intramuscular or subcutaneous administration and sustained intracellular levels of the pharmacologically active agent, tenofovir diphosphate (TFV-DP), making them capable of maintaining the therapeutically effective concentration of TFV-DP in relevant cell types for an extended period of time and useful as durable or long acting agents to treat or prevent viral infection. The development of poorly soluble prodrugs for safe and effective long acting injectable formulations is discussed in Remenar, *Mol. Pharmaceutics* 2014, 11, 1739-1749.

Pharmaceutical Compositions

In some embodiments, the present disclosure provides a pharmaceutical composition comprising a compound of the present disclosure, and a pharmaceutically acceptable excipient.

In some embodiments, the pharmaceutical composition comprises one, two, three, or four additional therapeutic agents, as more fully set forth below.

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition that can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

Methods of Treatment

HIV Infection

The present disclosure provides methods of treating and/or preventing human immunodeficiency virus (HIV) infection in a subject. In some embodiments, a method of treating and/or preventing HIV infection in a subject comprises administering to the subject a composition provided herein. In some embodiments, the method is for treating and/or preventing HIV-1 infection. In some embodiments, the method is for treating and/or preventing HIV-2 infection.

In some embodiments, a method of treating HIV infection in a subject in need thereof comprises administering to the subject a composition provided herein. In some such embodiments, the subject is HIV positive. In some such embodiments, the subject is of unknown HIV status. In some such embodiments, the subject is not HIV negative.

In some embodiments, a method of preventing HIV infection in a subject at risk thereof comprises administering to the subject a composition provided herein. In some such embodiments, the subject is HIV negative. In some embodiments, the subject is at risk of acquiring HIV infection.

In some embodiments, provided compositions are combined with one, two, three, or four additional therapeutic agents selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, provided compositions are combined with one, two, three, or four additional therapeutic agents selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, provided compositions are combined with one, two, three, or four additional therapeutic agents selected from dolutegravir, cabotegravir, islatravir, darunavir, bictegravir, elsulfavirine, rilpivirine, and lenacapavir, and combinations thereof.

HBV Infection

The present disclosure provides methods of treating and/or preventing hepatitis B virus (HBV) infection in a subject. In some embodiments, a method of treating and/or preventing HBV infection in a subject comprises administering to the subject a composition provided herein.

In some embodiments, a method of treating HBV infection in a subject in need thereof comprises administering to the subject a composition provided herein.

In some embodiments, a method of preventing HBV infection in a subject at risk thereof comprises administering to the subject a composition provided herein. In some such embodiments, the subject is at risk of acquiring HBV infection.

In some embodiments, provided compositions are combined with one, two, three, or four additional therapeutic agents selected from HBV combination drugs, HBV vaccines, HBV polymerase inhibitors, HBV capsid modulators, agonists of TLR7, TLR8, and TLR9, cytokines, immune checkpoint inhibitors, FLT3 ligands, interferon alpha receptor ligands, interferon alpha, interferon lambda, hyaluronidase inhibitors, hepatitis B surface antigen (HBsAg) inhibitors, HBV X protein (HBx) inhibitors, cyclophilin inhibitors, HBV viral entry inhibitors, antisense oligonucleotides, short interfering RNAs (siRNA) and DNA directed RNA interference (ddRNAi), endonuclease modulators, ribonucleotide reductase inhibitors, HBV E antigen (HBeAg) inhibitors, covalently closed circular DNA (cccDNA) inhibitors, farnesoid X receptor agonists, HBV antibodies, T cell and NK cell recruiting bispecific antibodies, chimeric T cell receptors targeting HBV antigens or peptides, CAR-T cell therapy, thymosin agonists, retinoic acid-inducible gene 1 stimulators, NOD2 stimulators, phosphatidylinositol 3-kinase (PI3K) inhibitors, indoleamine-2,3-dioxygenase (IDO1) pathway inhibitors, anti-OX40, anti-CD40, anti-CD160, HBV gene editors, PAPD5/PAPD7 inhibitors, ZCCHC14 inhibitors, Bruton's tyrosine kinase (BTK) inhibitors, epigenetic regulators, inducers of tertiary lymphoid aggregates, antagonists of IAP/XIAP, nucleic acid polymers (e.g., NAPs and STOPS), modulators of lipid metabolism or trafficking, arginase inhibitors, and other drugs for treating HBV, and combinations thereof.

In some embodiments, provided compositions are combined with one, two, three, or four additional therapeutic agents selected from adefovir, entecavir, telbivudine, lamivudine, and lenacapavir, and combinations thereof.

In some embodiments, provided compositions are combined with one, two, three, or four additional therapeutic agents selected from adefovir, entecavir, telbivudine, lamivudine, and lenacapavir.

HIV Combination Therapy

In certain embodiments, a method for treating an HIV infection is provided, comprising administering to the human a therapeutically effective amount of a compound disclosed herein, or a pharmaceutically acceptable salt thereof, in combination with a therapeutically effective amount of one, two, three, or four additional therapeutic agents. In one embodiment, a method for treating an HIV infection is provided, comprising administering to the human a therapeutically effective amount of a compound disclosed herein, or a pharmaceutically acceptable salt thereof, in combination with a therapeutically effective amount of one, two, three, or four additional therapeutic agents.

In one embodiment, pharmaceutical compositions comprising a compound disclosed herein, or a pharmaceutically acceptable salt thereof, in combination with one, two, three, or four additional therapeutic agents, and a pharmaceutically acceptable carrier, diluent, or excipient are provided.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one, two, three, or four additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with one, two, three, or four additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one, two, three, or four additional therapeutic agents. Co-administration of a compound disclosed herein with one, two, three, or four additional therapeutic agents generally refers to simultaneous or sequential administration of a compound disclosed herein and one, two, three, or four additional therapeutic agents, such that therapeutically effective amounts of the compound disclosed herein and the one, two, three, or four additional therapeutic agents are both present in the body of the patient. When administered sequentially, the combination may be administered in two or more administrations.

Co-administration includes administration of unit dosages of the compounds disclosed herein before or after administration of unit dosages of one, two, three, or four additional therapeutic agents. For example, the compound disclosed herein may be administered within seconds, minutes, or hours of the administration of the one, two, three, or four additional therapeutic agents. In some embodiments, a unit dose of a compound disclosed herein is administered first, followed within seconds or minutes by administration of a unit dose of one, two, three, or four additional therapeutic agents. Alternatively, a unit dose of one, two, three, or four additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one, two, three, or four additional therapeutic agents. In yet other embodiments, a unit dose of one, two, three, or four additional therapeutic agents is administered first, followed, after a period of hours (e.g., 1-12 hours), by administration of a unit dose of a compound disclosed herein.

In certain embodiments, a kit comprising a compound disclosed herein (e.g., a compound of formula I, II, III, IV, or V), or a pharmaceutically acceptable salt thereof, in combination with one or more (e.g., one, two, three, or four) additional therapeutic agents is provided.

In a specific embodiment, the kit includes a compound disclosed herein, or a pharmaceutically acceptable salt thereof, an HIV nucleoside or nucleotide inhibitor of reverse transcriptase and an HIV capsid inhibitor or an HIV capsid polymerization inhibitor.

HIV Combination Therapy

In the above embodiments, the additional therapeutic agent or agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, TAT protein inhibitors, Prolylendopeptidase inhibitors, Phospholipase A2 inhibitors, pharmacokinetic enhancers, HIV gene therapy, HIV vaccines, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents are chosen from dolutegravir, cabotegravir, islatravir, darunavir, bictegravir, elsulfavirine, rilpivirine, and lenacapavir, and combinations thereof.

In some embodiments, the additional therapeutic agent or agents are chosen from dolutegravir, cabotegravir, islatravir, darunavir, bictegravir, elsulfavirine, rilpivirine, and lenacapavir.

HIV Combination Drugs

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO, TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, and lamivudine; cabotegravir+rilpivirine; 3-BNC117+albuvirtide, elpida (elsulfavirine; VM-1500; VM-1500A.

Other HIV Drugs

Examples of other drugs for treating HIV include, but are not limited to, aspernigrin C, acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABX-464, AG-1105, APH-0812, bryostatin analogs, BIT-225, CYT-107, CS-TATI-1, fluoro-beta-D-arabinose nucleic acid (FANA)-modified antisense oligonucleotides, FX-101, griffithsin, HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, MK-8591 (islatravir), NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-M113V, IML-106, antiviral fc conjugate (AVC), and VIR-576.

HIV Protease Inhibitors

Examples of HIV protease inhibitors include, but are not limited to, amprenavir, atazanavir, brecanavir, darunavir, fosamprenavir, fosamprenavir calcium, indinavir, indinavir sulfate, lopinavir, nelfmavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911.

HIV Ribonuclease H Inhibitors

Examples of HIV ribonuclease H inhibitors include NSC-727447.

HIV Nef Inhibitors

Examples of HIV Nef inhibitors include FP-1.

HIV Reverse Transcriptase Inhibitors

Examples of HIV non-nucleoside or non-nucleotide inhibitors of reverse transcriptase include, but are not limited to, dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), doravirine+islatravir (fixed dose combination/oral tablet formulation, HIV-1 infection), elsulfavirine (long acting injectable nanosuspension, HIV infection), and elsulfavirine (VM-1500).

Examples of HIV nucleoside or nucleotide inhibitors of reverse transcriptase include, but are not limited to adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, islatravir, MK-8583, VM-2500, and KP-1461.

HIV Integrase Inhibitors

Examples of HIV integrase inhibitors include, but are not limited to, elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T-169, STP-0404, VM-3500 and cabotegravir.

Examples of HIV non-catalytic site, or allosteric, integrase inhibitors (NCINI) include, but are not limited to, CX-05045, CX-05168, and CX-14442.

HIV Viral Injectivity Factor Inhibitors

Examples of HIV viral infectivity factor inhibitors include 2-amino-N-(2-methoxyphenyl)-6-((4-nitrophenyl)thio)benzamide derivatives.

HIV Entry Inhibitors

Examples of HIV entry (fusion) inhibitors include, but are not limited to, AAR-501, LBT-5001, cenicriviroc, CCR5 inhibitors, gp41 inhibitors, CD4 attachment inhibitors, gp120 inhibitors, gp160 inhibitors, and CXCR4 inhibitors.

Examples of CCR5 inhibitors include, but are not limited to, aplaviroc, vicriviroc, maraviroc, maraviroc (long acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

Examples of gp41 inhibitors include, but are not limited to, albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, C13hmAb, lipuvirtide, PIE-12 trimer and sifuvirtide.

Examples of CD4 attachment inhibitors include, but are not limited to, ibalizumab and CADA analogs Examples of gp120 inhibitors include, but are not limited to, anti-HIV microbicide, Radha-108 (receptol) 3B3-PE38, BMS818251, BanLec, bentonite-based nanomedicine, fostemsavir tromethamine, IQP-0831, VVX-004, and BMS-663068.

Examples of gp160 inhibitors include fangchinoline.

Examples of CXCR4 inhibitors include, but are not limited to, plerixafor, ALT-1188, N15 peptide, and vMIP (Haimipu).

HIV Maturation Inhibitors

Examples of HIV maturation inhibitors include, but are not limited to, BMS-955176, GSK-3640254 and GSK-2838232.

Latency Reversing Agents

Examples of latency reversing agents include, but are not limited to, toll-like receptor (TLR) agonists (including TLR7 agonists, e.g, GS-9620, TLR8 agonists, and TLR9 agonists), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins, and IL-15 receptor agonists), JQ1, disulfiram, amphotericin B, and ubiquitin inhibitors such as largazole analogs, APH-0812, and GSK-343. Examples of PKC activators include indolactam, prostratin, ingenol B, and DAG-lactones.

Histone Deacetylase (HDAC) Inhibitors

In some embodiments, the agents as described herein are combined with an inhibitor of a histone deacetylase, e.g., histone deacetylase 1, histone deacetylase 9 (HDAC9, HD7, HD7b, HD9, HD AC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

Examples of capsid inhibitors include, but are not limited to, capsid polymerization inhibitors or capsid disrupting compounds, HIV nucleocapsid p7 (NCp7) inhibitors such as azodicarbonamide, HIV p24 capsid protein inhibitors, lenacapavir (GS-6207), GS-CA1, AVI-621, AVI-101, AVI-201, AVI-301, and AVI-CAN1-15 series, PF-3450074, HIV-1 capsid inhibitors (HIV-1 infection, Shandong University), and compounds described in (GSK WO2019/087016).

Immune Checkpoint Modulators

In various embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., *J Exp Clin Cancer Res*. (2018) 37:110). In various embodiments, the immune checkpoint proteins or receptors regulate NK cell responses (e.g., reviewed in Davis, et al., *Semin Immunol*. (2017) 31:64-75 and Chiossone, et al, *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In various embodiments, the agents described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In various embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (FIX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181(budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In various embodiments, the agents as described herein are combined with anti-TIGIT antibodies, such as BMS-986207, RG-6058, AGEN-1307

TNF Receptor Superfamily (TNFRSF) Member Agonists or Activators

In various embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In various embodiments, the agents as described herein, are combined with a bi-specific NK-cell engager (BiKE) or a tri-specific NK-cell engager (TriKE) (e.g., not having an Fc) or bi-specific antibody (e.g, having an Fc) against an NK cell activating receptor, e.g, CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g, 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices, et al., *Methods Mol Biol* (2016) 1441:333-346; Fang, et al., *Semin Immunol*. (2017) 31:37-54. Examples of a trispecific NK cell engager (TRiKE) include OXS-3550, HIV-TriKE, and CD16-IL-15-B7H3 TriKe.

Indoleamine-pyrrole-2,3-dioxygenase (IDO1) Inhibitors

In various embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Toll-Like Receptor (TLR) Agonists

In various embodiments, the agents as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR7/TLR8 agonists include NKTR-262, telratolimod and BDB-001. TLR8 agonists include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR9 agonists include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. TLR4 agonists include G-100 and GSK-1795091.

CDK Inhibitors or Antagonists

In some embodiments, the agents described herein are combined with an inhibitor or antagonist of CDK. In some embodiments, the CDK inhibitor or antagonist is selected from the group consisting of VS2-370.

STING Agonists, RJG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In certain embodiments, the agents as described herein are combined with an anti-TIM-3 antibody, such as TSR-022, LY-3321367, MBG-453, INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In certain embodiments, the agents described herein are combined with an interleukin agonist, such as IL-2, IL-7, IL-15, IL-10, IL-12 agonists; examples of IL-2 agonists such as proleukin (aldesleukin, IL-2); BC-IL (Cel-Sci), pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include CYT-107.

Examples of additional immune-based therapies that can be combined with an agent of this disclosure include interferon alfa; interferon alfa-2b; interferon alfa-n3; pegylated interferon alfa; interferon gamma; FLT3 agonists such as CDX-301 and GS-3583; gepon; normferon, peginterferon alfa-2a, peginterferon alfa-2b, RPI-MN Phosphatidylinositol 3-kinase (PI3K) Inhibitors Examples of PI3K inhibitors include, but are not limited to, idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, andZ-STK-474.

alpha-4/beta-7 Antagonists

Examples of Integrin alpha-4/beta-7 antagonists include, but are not limited to, PTG-100, TRK-170, abrilumab, etrolizumab, carotegrast methyl, and vedolizumab.

HIV Targeting Antibodies

Examples of HIV antibodies, bispecific antibodies, and "antibody-like" therapeutic proteins include, but are not limited to, DARTs®, DUOBODIES®, BITES®, XmAbs®, TandAbs®, Fab derivatives, bNAbs (broadly neutralizing HIV-1 antibodies), TMB-360, and those targeting HIV gp120 or gp41, antibody-Recruiting Molecules targeting HIV, anti-CD63 monoclonal antibodies, anti-GB virus C antibodies, anti-GP120/CD4, gp120 bispecific monoclonal antibody, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), PGT121.414.LS, ibalizumab, ibalizumab (second generation), Immuglo, MB-66, clone 3 human monoclonal antibody targeting KLIC (HIV infection), GS-9721, BG-HIV, VRC-HIVMAB091-00-AB.

Various bNAbs may be used. Examples include, but are not limited to, those described in U.S. Pat. Nos. 8,673,307, 9,493,549, 9,783,594, WO2014/063059, WO2012/158948, WO2015/117008, and PCT/US2015/41272, and WO2017/096221, including antibodies 12A12, 12A21, NIH45-46, bANC131, 8ANC134, IB2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., *Nature*, 492(7427): 118-22 (2012), Horwitz et al., *Proc Natl Acad Sci USA*, 110(41): 16538-43 (2013), Scheid, et al., *Science*, 333: 1633-1637 (2011), Scheid, et al., *Nature*, 458:636-640 (2009), Eroshkin et al., *Nucleic Acids Res.*, 42 (Database issue):Dl 133-9 (2014), Mascola et al., *Immunol Rev*, 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies which can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include those described in Sajadi, et al., Cell. (2018) 173(7): 1783-1795; Sajadi, et al., J Infect Dis. (2016) 213(1): 156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al., Nucleic Acids Res., 42 (Database issue):Dl 133-9 (2014), Mascola et al., Immunol Rev., 254(1):225-44 (2013), such as 2F5, 4E10, M66.6, CAP206-CH12, 10E8, 10E8v4, 10E8-5R-100cF, DH511.11P, 7b2, 10-1074, andLNOl (all of which bind the MPER of gp41).

Examples of additional antibodies include, but are not limited to, bavituximab, UB-421, BF520.1, BiIA-SG, CH01, CH59, C2F5, C4E10, C2F5+C2G12+C4E10, CAP256V2LS, 3BNC117, 3BNC117-LS, 3BNC60, DH270.1, DH270.6, D1D2, 10-1074-LS, C13hmAb, GS-9722 (elipovimab), DH411-2, BG18, GS-9721, GS-9723, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, andLNOl.

Examples of HIV bispecific and trispecific antibodies include MGD014, B12BiTe, BiIA-SG, TMB-bispecific, SAR-441236, VRC-01/PGDM-1400/10E8v4, 10E8.4/iMab, 10E8v4/PGT121-VRC01.

Examples of in vivo delivered bNAbs include AAV8-VRC07; mRNA encoding anti-HIV antibody VRC01; and engineered B-cells encoding 3BNC117 (Hartweger et al., *J. Exp. Med* 2019, 1301).

Pharmacokinetic Enhancers

Examples of pharmacokinetic enhancers include, but are not limited to, cobicistat and ritonavir.

Additional Therapeutic Agents

Examples of additional therapeutic agents include, but are not limited to, the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include, but are not limited to, peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOXl, ChAd68, ChAd3, ChAd63, ChAd83, ChAdl55, ChAdl57, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, Venezuelan equine encephalitis virus and sindbis virus; (see Lauer, *Clinical and Vaccine Immunology*, 2017, DOI: 10.1128/CVI.00298-16); LNP formulated mRNA based therapeutic vaccines; LNP-formulated self-replicating RNA/self-amplifying RNA vaccines.

Examples of vaccines include: AAVLP-HIV vaccine, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, rgp120 (AIDSVAX), ALVAC HIV (vCP 1521)/AIDSVAX B/E (gp120) (RV144), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAVl-PG9DP, GOVX-B11, GOVX-B21, GOVX-C55, TVI-HIV-1, Ad-4 (Ad4-env Clade C+Ad4-mGag), Paxvax, EN41-UGR7C, EN41-FPA2, ENOB-HV-11, PreVaxTat, AE-H, MYM-V101, CombiHIVvac, AD VAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOSl.HIV-Env, Ad26.Mod.HIV vaccine, Ad26.Mod.HIV+MV A mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNAO16-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb 12 neutralizing VRC-01 antibody-stimulating anti-CD4 vaccine, arenavirus vector-based vaccines (Vaxwave, TheraT), MVA-BN HIV-1 vaccine regimen, UBI HIV gp120, mRNA based prophylactic vaccines, VPI-211, and TBL-1203HI.

Birth Control (Contraceptive) Combination Therapy

In certain embodiments, the agents described herein are combined with a birth control or contraceptive regimen. Therapeutic agents used for birth control (contraceptive) that can be combined with an agent of this disclosure include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In a particular embodiment, a compound disclosed herein, or a pharmaceutically acceptable salt thereof, is combined with one, two, three, or four additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+ FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir alafenamide and elvitegravir; tenofovir alafenamide+elvitegravir (rectal formulation, HIV infection); tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; maraviroc; tenofovir+emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfmavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In another embodiment, an agent disclosed herein, or a pharmaceutical composition thereof, is combined with a first additional therapeutic agent chosen from dolutegravir, cabotegravir, islatravir, darunavir, bictegravir, elsulfavirine, rilpivirine, and lenacapavir and a second additional therapeutic agent chosen from emtricitabine and lamivudine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include LB-1903, ENOB-HV-01, GOVX-B01, HSPCs overexpressing ALDH1 (LV-800, HIV infection), AGT103-T, and SupT1 cell based therapy. Examples of dendritic cell therapy include AGS-004. CCR5 gene editing agents include SB-728T. CCR5 gene inhibitors include Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In certain embodiments, the agents described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include convertible CAR-T, VC-CAR-T, CMV-N6-CART, anti-CD4 CART-cell therapy, CD4 CAR+C34-CXCR4+ CCR5 ZFN T-cells, anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

TCR T-cell Therapy

In certain embodiments, the agents described herein are combined with a population of TCR-T-cells. TCR-T-cells are engineered to target HIV derived peptides present on the surface of virus-infected cells, for example, ImmTAV.

B-Cell Therapy

In certain embodiments, the antibodies or antigen-binding fragments described herein are combined with a population of B cells genetically modified to express broadly neutralizing antibodies, such as 3BNC117 (Hartweger et al., J. Exp. Med. 2019, 1301, Moffett et al., Sci. Immunol. 4, eaax0644 (2019) 17 May 2019.

A compound as disclosed herein (e.g., any compound of formula I, II, III, IV, or V) may be combined with one, two, three, or four additional therapeutic agents in any dosage amount of the compound of formula I, II, III, IV, or V (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIVNef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor. In a specific embodiment, the kit includes a compound disclosed herein, or a pharmaceutically acceptable salt thereof, an HIV nucleoside inhibitor of reverse transcriptase and an HIV capsid inhibitor. In a specific embodiment, the kit includes a compound disclosed herein, or a pharmaceutically acceptable salt thereof, and an HIV capsid inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and an HIV capsid inhibitor. In a specific embodiment, the kit includes a compound disclosed herein, or a pharmaceutically acceptable salt thereof, one, two, three or four HIV bNAbs, an HIV capsid inhibitor, and an HIV nucleoside inhibitor of reverse transcriptase.

HIV Long Acting Therapy

Examples of drugs that are being developed as long acting regimens include, but are not limited to, cabotegravir, rilpivirine, any integrase LA, VM-1500 LAI, maraviroc (LAI), tenofovir implant, islatravir implant, doravirine, raltegravir, and long acting dolutegravir.

HBV Combination Therapy

In certain embodiments, a method for treating or preventing an HBV infection is provided, comprising administering to the human a therapeutically effective amount of a composition described herein, in combination with a therapeutically effective amount of one or more (e.g., one, two, three, four, one or two, one to three, or one to four) additional therapeutic agents. In one embodiment, a method for treating an HBV infection is provided, comprising administering to the human a therapeutically effective amount of a composition described herein, in combination with a therapeutically effective amount of one or more (e.g., one, two, three, four, one or two, one to three, or one to four) additional therapeutic agents.

In certain embodiments, the present description provides a method for treating an HBV infection, comprising administering to a subject in need thereof a therapeutically effective amount of a composition described herein, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In some embodiments, the additional therapeutic agent or agents are selected from HBV combination drugs, HBV vaccines, HBV polymerase inhibitors, HBV capsid modulators, agonists of TLR7, TLR8, and TLR9, cytokines, immune checkpoint inhibitors, FLT3 ligands, interferon alpha receptor ligands, interferon alpha, interferon lambda, hyaluronidase inhibitors, hepatitis B surface antigen (HBsAg) inhibitors, HBV X protein (HBx) inhibitors, cyclophilin inhibitors, HBV viral entry inhibitors, antisense oligonucleotides, short interfering RNAs (siRNA) and DNA directed RNA interference (ddRNAi), endonuclease modulators, ribonucleotide reductase inhibitors, HBV E antigen (HBeAg) inhibitors, covalently closed circular DNA (cccDNA) inhibitors, farnesoid X receptor agonists, HBV antibodies, T cell and NK cell recruiting bispecific antibodies, chimeric T cell receptors targeting HBV antigens or peptides, CAR-T cell therapy, thymosin agonists, retinoic acid-inducible gene 1 stimulators, NOD2 stimulators, phosphatidylinositol 3-kinase (PI3K) inhibitors, indoleamine-2,3-dioxygenase (IDO1) pathway inhibitors, anti-OX40, anti-CD40, anti-CD160, HBV gene editors, PAPD5/PAPD7 inhibitors, ZCCHC14 inhibitors, Bruton's tyrosine kinase (BTK) inhibitors, epigenetic regulators, inducers of tertiary lymphoid aggregates, antagonists of IAP/XIAP, nucleic acid polymers (e.g., NAPs and STOPS), modulators of lipid metabolism or trafficking, arginase inhibitors, and other drugs for treating HBV, and combinations thereof.

In some embodiments, the additional therapeutic agent or agents are chosen from adefovir, entecavir, telbivudine, lamivudine, and lenacapavir, and combinations thereof.

In some embodiments, the additional therapeutic agent or agents are chosen from adefovir, entecavir, telbivudine, lamivudine, and lenacapavir.

HBV Combination Drugs

Examples of combination drugs for the treatment of HBV include, but are not limited to, TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include, but are not limited to, alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds described in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include, but are not limited to, Vaxelis, Hexaxim, HepI is av, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP—IPV-Hep B, HBAI-20, Infanrix-DTaP—IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include, but are not limited to, HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), fdocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include, but are not limited to, rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559,GS-9688, RO-7011785, RG-7854, AB-506, RO-6871765, AIC-649, and IR-103.

Toll-Like Receptor (TLR) Modulators

In various embodiments, the agents as described herein, are combined with an agonist of a toll-like receptor (TLR), e.g, an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262, telratolimod and BDB-001. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and U.S. Pat. No. 2,013,025 1673 (Novira Therapeutics). Example TLR9 agonists that can be co-administered include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. Examples of TLR4 agonist include G-100, and GSK-1795091Interferon Alpha Receptor Ligands Examples of interferon alpha receptor ligands include, but are not limited to, interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin interferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include, but are not limited to, astodrimer.

Hepatitis B Surface Antigen (HBsAg) Inhibitors

Examples of HBsAg inhibitors include, but are not limited to, HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include, but are not limited to, BM601.

Cytotoxic T-Lymphocyte-Associated Protein 4 (CTLA4) Inhibitors

Examples of Cytotoxic T-lymphocyte-associated protein 4 (CTLA4) inhibitors include, but are not limited to, AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include, but are not limited to, CPI-431-32, EDP-494, OCB-030, SCY-635, NVP-015, NVP-018, NVP-019, STG-175, and the compounds described in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include, but are not limited to, Myrcludex B.

Antisense Oligonucleotides

Examples of antisense oligonucleotides targeting viral mRNA include, but are not limited to, ISIS-HBVRx, IONIS-HBVRx, IONIS-GSK6-LRx, GSK-3389404, and RG-6004. Antisense oligonucleotides targeting host factors such as PD-L1 are also known.

Short Interfering RNAs (siRNA) and ddRNAi

Examples of siRNA include, but are not limited to, TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include, but are not limited to, BB-HB-331.

Endonuclease Modulators

Examples of endonuclease modulators include, but are not limited to, PGN-514.

Ribonucelotide Reductase Inhibitors

Examples of inhibitors of ribonucleotide reductase include, but are not limited to, Trimidox.

HBV E Antigen Inhibitors

Examples of HBV E antigen (HBeAg) inhibitors include, but are not limited to, wogonin.

Covalently Closed Circular DNA (cccDNA) Inhibitors

Examples of cccDNA inhibitors include, but are not limited to, BSBI-25, and CHR-101.

Farnesoid X Receptor Agonist

Examples of farnesoid x receptor agonists include, but are not limited to, EYP-001, cilofexor, EDP-305, MET-409, Tropifexor, AKN-083, RDX-023, BWD-100, LMB-763, INV-3, NTX-023-1, EP-024297 and GS-8670.

HBV Antibodies

Examples of HBV antibodies targeting the surface antigens of the hepatitis B virus include, but are not limited to, GC-1102, XTL-17, XTL-19, KN-003, IV Hepabulin SN, fully human monoclonal antibody therapy (hepatitis B virus infection, Humabs BioMed), and anti-HBsAg (small, medium, large).

Examples of HBV antibodies, including monoclonal antibodies and polyclonal antibodies, include, but are not limited to, Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include, but are not limited to, HBC-34.

CCR2 Chemokine Antagonists

Examples of CCR2 chemokine antagonists include, but are not limited to, propagermanium.

Thymosin Agonists

Examples of thymosin agonists include, but are not limited to, Thymalfasin, recombinant thymosin alpha 1 (GeneScience).

Cytokines

Examples of cytokines include, but are not limited to, interferon alpha, interferon lambda, recombinant IL-7, CYT-107, interleukin-2 (IL-2, Immunex), recombinant human interleukin-2 (Shenzhen Neptunus), IL-15, IL-21, IL-24, celmoleukin and CD4, CD8, or B cell-targeted cytokines including, but not limited to, IL-2, IL-7, IL-12, IL-15, and IL-21.

Nucleoprotein Modulators

Nucleoprotein modulators may be either HBV core or capsid protein inhibitors. Examples of nucleoprotein modulators include, but are not limited to, GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include, but are not limited to, the compounds described in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include, but are not limited to, the compounds described in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include, but are not limited to, SB-9200, SB-40, SB-44, ORI-7246, ORI-9350, ORI-7537, ORI-9020, ORI-9198, ORI-7170, and RGT-100.

NOD2 Stimulators

Examples of stimulators of NOD2 include, but are not limited to, SB-9200.

Phosphatidylinositol 3-kinase (PI3K) Inhibitors

Examples of PI3K inhibitors include, but are not limited to, idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO1) Pathway Inhibitors

In various embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916

Recombinant Thymosin Alpha-1

Examples of recombinant thymosin alpha-1 include, but are not limited to, NL-004 and PEGylated thymosin alpha-1.

Bruton's Tyrosine Kinase (BTK) Inhibitors

Examples of BTK inhibitors include, but are not limited to, ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds described in US20140330015 (Ono Pharmaceutical), US20130079327 (Ono Pharmaceutical), and US20130217880 (Ono Pharmaceutical).

KDM Inhibitors

Examples of KDM5 inhibitors include, but are not limited to, the compounds described in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include, but are not limited to, the compounds described in U.S. Pat. No. 9,186,337B2 (Oryzon Genomics), GSK-2879552, and RG-6016.

STING Agonists

Examples of STING agonists include, but are not limited to, SB-11285, AdVCA0848, STINGVAX, and the compounds described in WO 2018065360 ("Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), and WO2018060323 (Boehringer).

Non-Nucleoside Reverse Transcriptase Inhibitors (NNRTI)

Examples of NNRTI include, but are not limited to, the compounds described in WO2018118826 (Merck), WO2018080903(Merck), WO2018119013 (Merck), WO2017100108 (Idenix), WO2017027434 (Merck), WO2017007701 (Merck), and WO2008005555 (Gilead).

HBV Replication Inhibitors

Examples of hepatitis B virus replication inhibitors include, but are not limited to, isothiafludine, IQP-HBV, RM-5038, and Xingantie.

Arginase Inhibitors

Examples of arginase inhibitors include, but are not limited to, CB-1158, C-201, and resminostat.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

Examples of genome editing systems include, but are not limited to, a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA.

CAR-T Cell Therapy

CAR T cell therapy includes a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

TCR T cell therapy includes T cells expressing HBV-specific T cell receptors. TCR-T cells are engineered to target HBV derived peptides presented on the surface of virus-infected cells (e.g., peptides presented in HLA/pMHC). In some embodiments, the T-cells express HBV surface antigen (HBsAg)-specific TCR. Examples of TCR-T therapy directed to treatment of HBV include, but are not limited to, LTCR-H2-1.

In another specific embodiment, a compound described herein, or a pharmaceutically acceptable salt thereof, is combined with an HBV DNA polymerase inhibitor, one or two additional therapeutic agents chosen from immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus, including anti-HBsAg (small, medium, large), and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, arginase inhibitors, PI3K inhibitors, IDO inhibitors, and stimulators of NOD2, and one or two additional therapeutic agents chosen from HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound described herein, or a pharmaceutically acceptable salt thereof, is combined with an HBV DNA polymerase inhibitor and at least a second additional therapeutic agent chosen from: immunomodulators, TLR modulators, HBsAg inhibitors, HBV therapeutic vaccines, HBV antibodies including HBV antibodies targeting the surface antigens of the hepatitis B virus, including anti-HBsAg (small, medium, large), bispecific antibodies and "antibody-like" therapeutic proteins (such as DARTs®, DUOBODIES® BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, arginase inhibitors, PI3K inhibitors, IDO1 inhibitors, and stimulators of NOD2.

In another specific embodiment, a compound described herein, or a pharmaceutically acceptable salt thereof, is combined with an HBV DNA polymerase inhibitor and at least a second additional therapeutic agent chosen from: HBV viral entry inhibitors, NTCP inhibitors, HBx inhibitors, cccDNA inhibitors, HBV antibodies targeting the surface antigens of the hepatitis B virus, including anti-HBsAg (small, medium, large), siRNA, miRNA gene therapy agents, sshRNAs, KDM5 inhibitors, and nucleoprotein modulators (HBV core or capsid protein inhibitors).

In a particular embodiment, a compound described herein, or a pharmaceutically acceptable salt thereof, is combined with compounds such as those described in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HB V, and combinations thereof.

Administration

Routes of Administration

The compound of formula I, II, III, IV, or V, or a pharmaceutically acceptable salt thereof, (also referred to herein as the active ingredient) can be administered by any route appropriate to the condition to be treated. Suitable routes include, but are not limited to, oral, rectal, nasal, topical (including buccal and sublingual), transdermal, vaginal and parenteral (including subcutaneous, intramuscular, intravenous, intradermal, intrathecal and epidural), and the like. It will be appreciated that a suitable route may vary with, for example, the condition of the recipient. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In some embodiments, the compound of formula I, II, III, IV, or V, or a pharmaceutically acceptable salt thereof, is administered with a syringe suitable for administration of the compound. In some embodiments, the syringe is disposable. In some embodiments, the syringe is reusable. In some embodiments, the syringe is pre-filled with the compound of formula I, II, III, IV, or V, or a pharmaceutically acceptable salt thereof.

In some embodiments, the compound of formula I, II, III, IV, or V, or a pharmaceutically acceptable salt thereof, is administered with an auto-injector comprising a syringe. In some embodiments, the syringe is disposable. In some embodiments, the syringe is reusable. In some embodiments, the syringe is pre-filled with the compound formula I, II, III, IV, or V, or a pharmaceutically acceptable salt thereof.

Dosing Regimen

In some embodiments, the compound, such as a compound of formula I, II, III, IV, or V, or a pharmaceutically acceptable salt thereof, is administered to a subject in accordance with an effective dosing regimen for a desired period of time or duration, such as at least about once a day, at least about once a week, at least about once a month, at least about once every 2 months, at least about once every 3 months, at least about once every 4 months, at least about once every 6 months, or at least about once every 12 months or longer. In some embodiments, the compound is administered on a daily or intermittent schedule. In some embodiments, the compound is administered on a weekly schedule. In some embodiments, the compound is administered on a monthly schedule. In some embodiments, the compound is administered every two months. In some embodiments, the compound is administered every three months. In some embodiments, the compound is administered every four months. In some embodiments, the compound is administered every five months. In some embodiments, the compound is administered every 6 months.

In some embodiments, the compound, such as a compound of formula I, II, III, IV, or V, or a pharmaceutically acceptable salt thereof, is subcutaneously or intramuscularly administered to a subject at least about once a month. In some embodiments, the compound (e.g., a compound of formula I, II, III, IV, or V, or a pharmaceutically acceptable salt thereof), is subcutaneously or intramuscularly administered to a subject at least about once every 2 months or at least about once every 3 months, or at least about once every 4 months, or at least about once every 6 months. In some embodiments, the compound (e.g., a compound of formula I, II, III, IV, or V, or a pharmaceutically acceptable salt thereof), is subcutaneously administered to a subject at least about once a month. In some embodiments, the compound (e.g., a compound of formula I, II, III, IV, or V, or a pharmaceutically acceptable salt thereof), is subcutaneously administered to a subject at least about once every 2 months. In some embodiments, the compound (e.g., a compound of formula I, II, III, IV, or V, or a pharmaceutically acceptable salt thereof), is subcutaneously administered to a subject at least about once every 3 months.

In some embodiments, the dosage or dosing frequency of a compound of formula I, II, III, IV, or V, or a pharmaceutically acceptable salt thereof, is adjusted over the course of the treatment, based on the judgment of the administering physician.

In some embodiments, a compound as disclosed herein (e.g., a compound of formula I, II, III, IV, or V) or a pharmaceutically acceptable salt thereof, may be administered in a dosage amount that is effective. For example, the dosage amount can be from 1 mg to 1000 mg of compound.

In some embodiments, the methods disclosed herein comprise event-driven administration of the compound of formula I, II, III, IV, or V, or a pharmaceutically acceptable salt thereof, to the subject.

As used herein, the terms "event-driven" and "event-driven administration" refer to administration of the compound of formula I, II, III, IV, or V, or a pharmaceutically acceptable salt thereof, (1) prior to an event (e.g., 2 hours, 1 day, 2 days, 5 day, or 7 or more days prior to the event) that would expose the individual to HIV (or that would otherwise increase the individual's risk of acquiring HIV); and/or (2) during an event (or more than one recurring event) that would expose the individual to HIV (or that would otherwise increase the individual's risk of acquiring HIV); and/or (3) after an event (or after the final event in a series of recurring events) that would expose the individual to HIV (or that would otherwise increase the individual's risk of acquiring HIV). In some embodiments, the event driven administration is performed pre-exposure of the subject to the HIV. In some embodiments, the event driven administration is performed post-exposure of the subject to the HIV. In some embodiments, the event driven administration is performed pre-exposure of the subject to the HIV and post-exposure of the subject to the HIV.

In some embodiments, the compound of formula I, II, III, IV, or V, or a pharmaceutically acceptable salt thereof, is administered before exposure of the subject to the HIV.

An example of event driven dosing regimen includes administration of the compound of formula I, II, III, IV, or V, or a pharmaceutically acceptable salt thereof, within 24 to 2 hours prior to HIV exposure (e.g., first sexual activity with sex partner known to be HIV positive, including sexual intercourse), followed by administration of the compound of formula I, II, III, IV, or V, or a pharmaceutically acceptable salt, every 24 hours during the period of exposure (e.g., sexual activity with sex partner known to be HIV positive), followed by a further administration of the compound of formula I, II, III, IV, or V, or a pharmaceutically acceptable salt thereof, after the last exposure (e.g., sexual activity with sex partner known to be HIV positive), and one last administration of the compound of formula I, II, III, IV, or V, or a pharmaceutically acceptable salt thereof, 24 hours later.

A further example of an event driven dosing regimen includes administration of the compound of formula I, II, III, IV, or V, or a pharmaceutically acceptable salt thereof, within 24 hours before HIV exposure (e.g., sexual activity with sex partner known to be HIV positive), then daily administration during the period of exposure (e.g., sexual activity with sex partner known to be HIV positive, including the last sexual intercourse), followed by a last administration approximately 24 hours later after the last exposure (which may be an increased dose, such as a double dose).

In certain embodiments, e.g., when administered as PrEP, the compound of formula I, II, III, IV, or V, or a pharmaceutically acceptable salt thereof, is administered daily. In certain embodiments, e.g., when administered as event-driven PrEP, the compound of formula I, II, III, IV, or V, or a pharmaceutically acceptable salt thereof, is administered 1 hour to 10 days, 1 hour to 7 days, 1 hour to 5 days, 1 to 72 hours, 1 to 48 hours, 1 to 24 hours, or 12 to 12 hours prior to an event that would increase the individual's risk of acquiring HIV (e.g., prior to sex or other exposure to the HIV virus). In some embodiments, the compound of formula I, II, III, IV, or V, or a pharmaceutically acceptable salt thereof, is administered within 10 days, 7 days, 5 days, 72 hours, 60 hours, 48 hours, 24 hours, 12 hours, 9 hours, 6 hours, 4 hours, 3 hours, 2 hours, or 1 hour prior to an event that would increase the individual's risk of acquiring HIV (e.g., prior to sex or other exposure to the HIV virus). In certain embodiments, when the compound of formula I, II, III, IV, or V, or a pharmaceutically acceptable salt thereof, is administered prior to an event (e.g., administered prior to the event) that would increase the individual's risk of acquiring HIV, it is administered daily prior to the event (e.g., sexual activity). In certain embodiments, when the compound of formula I, II, III, IV, or V, or a pharmaceutically acceptable salt thereof, is administered prior to an event that would increase the individual's risk of acquiring HIV, it is administered one to three times prior to the event.

In some embodiments, e.g., when administered as part of an event-driven PrEP regimen, the compound of formula I, II, III, IV, or V, or a pharmaceutically acceptable salt thereof, is administered during the time of HIV-exposure. In certain embodiments wherein the compound of formula I, II, III, IV, or V, is administered before exposure, the compound of formula I, II, III, IV, or V, or a pharmaceutically acceptable salt thereof, is administered daily (e.g., as a single dose) during the time of HIV-exposure (e.g., during the time period of sexual activity with sex partner known to be HIV positive). In some embodiments, the compound of formula I, II, III, IV, or V, or a pharmaceutically acceptable salt thereof, is administered daily (e.g., for 1 to 7 days) after final exposure to the HIV (e.g., after a period of sexual activity with sex partner known to be HIV positive). In some embodiments, the administration is continued for 1 or 2 days after final exposure to HIV.

Additional examples of PrEP and/or PEP can be found, for example, at the clinical trial summary titled "On Demand Antiretroviral Pre-exposure Prophylaxis for HIV Infection in Men Who Have Sex With Men" (Clinical Trial #NCT01473472); the clinical trial summary titled "Prevention of HIV in Île-de-France" (Clinical Trials #NCT03113123), and at Molina, et al. *N. Engl. J. Med* 2015, 353:2237-2246, the disclosure of each of which is incorporated herein by reference in its entirety.

In some embodiments, methods for reducing the risk of acquiring HIV (e.g., HIV-1 and/or HIV-2) comprise administration of the compound of formula I, II, III, IV, or V, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In some embodiments, the reduction in risk of acquiring HIV is at least about 40%, at least about 50%, at least about 60%, at least about 70%, at least about 80%, at least about 90%, or at least about 95%. In some embodiments, the reduction in risk of acquiring HIV is at least about 75%. In some embodiments, the reduction in risk of acquiring HIV is about 80%, about 85%, or about 90%.

Formulation

Formulations suitable for parenteral administration include, but are not limited to, aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found, e.g., in *Handbook of Pharmaceutical Excipients* (eds. Rowe, Sheskey & Quinn), 6th edition 2009.

In certain embodiments, the active ingredient (e.g., a compound of formula I, II, III, IV, or V) is present as a free acid.

In certain embodiments the pharmaceutical composition disclosed herein is a parenteral formulation. In certain embodiments, the formulation is administered subcutaneously to a subject. In certain embodiments, the formulation is administered intramuscularly to a subject.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 mg to 1000 mg of active material formulated with an appropriate and convenient amount of carrier material (e.g., inactive ingredient or excipient material). In certain embodiments, the carrier material varies from about 5% to about 95% of the total compositions (weight:weight or wt:wt).

It should be understood that in addition to the ingredients particularly mentioned above the compositions of these embodiments may include other agents conventional in the art having regard to the type of composition in question, for example those suitable for oral administration may include flavoring agents.

Kits and Articles of Manufacture

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, implant, or intravenous bag.

In some embodiments, the present disclosure relates to a kit comprising a compound of formula I, II, III, IV, or V or a pharmaceutically acceptable salt thereof. In one embodiment, the kit may comprise one, two, three, or four additional therapeutic agents as described hereinbefore. The kit may further comprise instructions for use, e.g., for use in inhibiting an HIV integrase, such as for use in treating an HIV infection or AIDS, or as a research tool. The instructions for use are generally written instructions, although electronic storage media (e.g., magnetic diskette or optical disk) containing instructions are also acceptable.

In some embodiments, the present disclosure also relates to a pharmaceutical kit comprising one or more containers comprising a compound formula I, II, III, IV, or V or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

In some embodiments, disclosed herein are articles of manufacture comprising a unit dosage of a compound of formula I, II, III, IV, or V or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

Abbreviations

ACN acetonitrile
Aldrithiol-2 or Aldrithiol™-2 2,2'-dipyridyldisulfide
aq aqueous
BLQ below the limit of quantitation
Bn benzyl
Boc tert-butoxycarbonyl
$CC_{50}$ 50% cytotoxic concentration
d doublet
DCM dichloromethane
dd doublet of doublets
DMAP dimethylaminopyridine
DMF dimethylformamide
DMSO dimethyl sulfoxide
DP diphosphate
dt doublet of triplets
$EC_{50}$ half maximal effective concentration
EDCI 1-ethyl-3-(3-dimethylaminopropyl)carbodiimide or N-(3-dim ethyl aminopropyl)-N'-ethylcarbodiimide hydrochloride
ELSD evaporative light scattering detector
EtOAc ethyl acetate
FBS fetal bovine serum
GTD genotype D
h hour(s)
HBV hepatitis B virus
Hex hexane(s)
HIV human immunodeficiency virus
HPLC high performance liquid chromatography
Hz hertz
J coupling constant
LCMS liquid chromatography-mass spectrometry
M molar
m multiplet
MeOH methanol
mg milligram(s)
MHz megahertz
min minute(s)
mL or ml milliliter(s)
mm millimeter(s)
mmol millimole(s)
MT-4 or MT4 metallothionein 4 human T cell line
N normal
NAP nucleic acid polymer
NMP N-methyl-2-pyrrolidone
NMR nuclear magnetic resonance
p pentet
PBMC peripheral blood mononuclear cell
PBS phosphate buffered saline
PEG polyethylene glycol
PHH primary human hepatocytes
PMPA (R)-(((1-(6-amino-9H-purin-9-yl)propan-2-yl) oxy)methyl)phosphonic acid or (R)-9-(2-phosphonomethoxypropyl)adenine or tenofovir
prep preparative
pyr pyridine
q quartet
RPMI Roswell Park Memorial Institute (culture medium)
RT room temperature
s singlet
STOPS™ S-antigen Transport-inhibiting Oligonucleotide Polymers
t triplet
td triplet of doublets
TEA triethylamine
TFV tenofovir
TFV-DP tenofovir disphosphate
μ micron
TP triphosphate
μM micromolar
ZCCHC CCHC-type zinc finger protein The following examples are provided for purposes of illustration, not limitation.

EXAMPLES

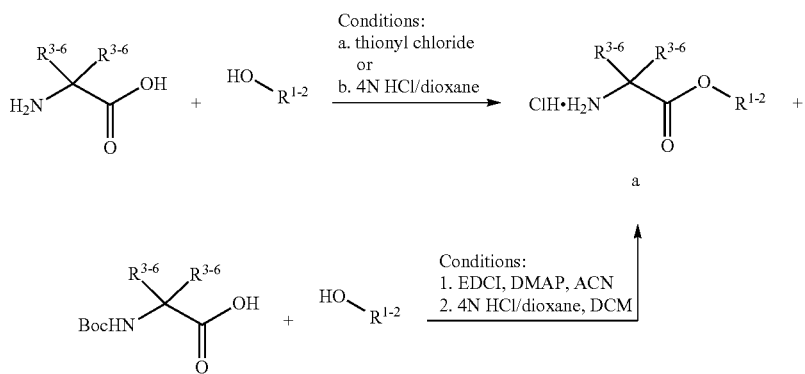

General Scheme A 109 110

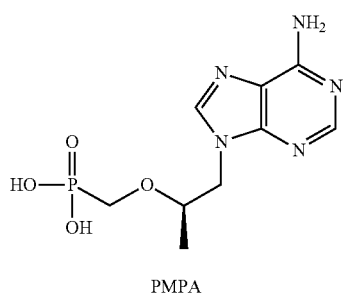

PMPA

Condition:
triphenylphosphine,
2,2'-dipyridyldisulfide,
triethylamine,
pyridine

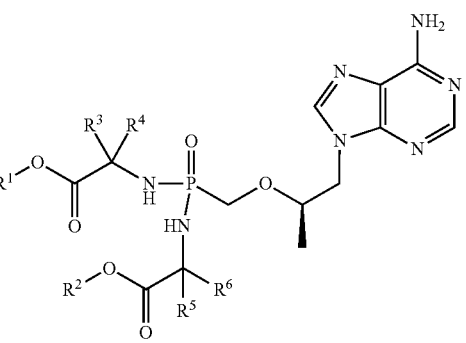

A

Compounds of formula A can be prepared in two- or three-step sequences from geminally disubstituted amino acids according to General Scheme A. Amino acids can be converted to amino ester intermediates of formula a via reaction with alcohols in the presence of thionyl chloride or 4N HCl in dioxane. Alternatively, protected amino acids can be esterified with alcohols in the presence of EDCI, DMAP and ACN. The resulting N-protected amino esters can be deprotected by treatment with 4N HCl in dioxane and DCM to yield amino ester intermediates of formula a. Intermediates of formula a can be coupled with (R)-(((1-(6-amino-9H-purin-9-yl)propan-2-yl)oxy)methyl)phosphonic acid (PMPA) using triphenylphosphine, 2,2'-dipyridyldisulfide, triethylamine and pyridine to yield compounds of formula A.

General Scheme B

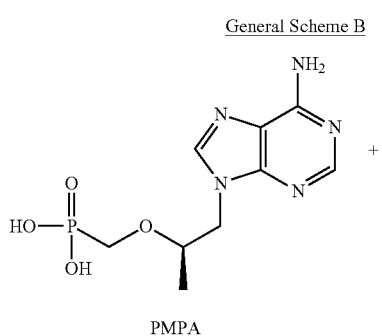

PMPA

+

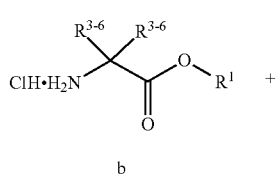

b

-continued

Condition:
triphenylphosphine,
2,2'-dipyridyldisulfide,
triethylamine,
pyridine

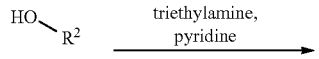

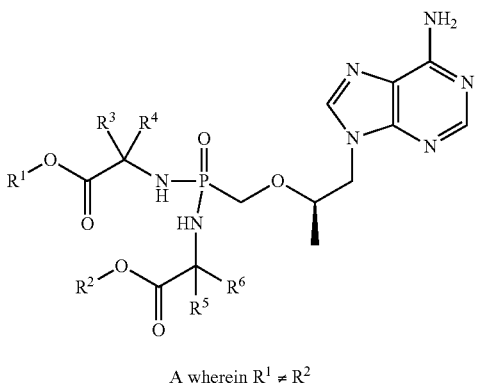

A wherein $R^1 \neq R^2$

Compounds of formula A wherein $R^1$ and $R^2$ are different can be prepared in one step from PMPA, intermediates of formula b, and alcohols different from that used to make formula b ($R^1 \neq R^2$) according to General Scheme B. This can be done by combining PMPA, intermediates of formula b and an alcohol with triphenylphosphine, 2,2'-dipyridyldisulfide, triethylamine and pyridine to yield compounds of formula A wherein $R^1$ and $R^2$ are different.

General Scheme C

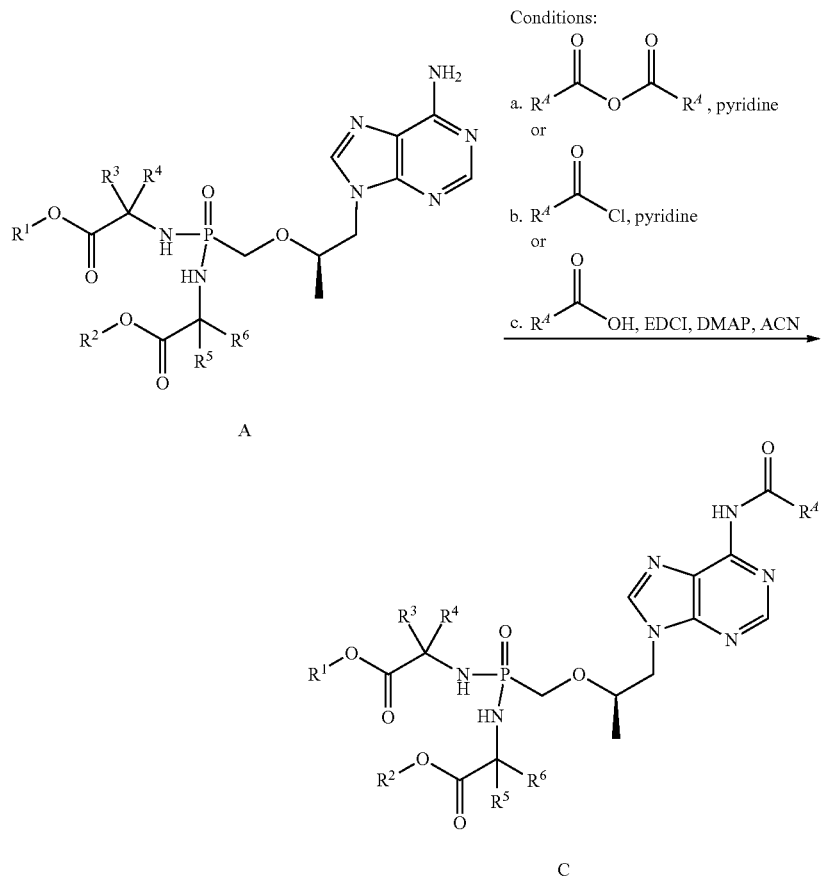

Compounds of formula C can be prepared in one step from compounds of formula A according to General Scheme C. Compounds of formula A can be mixed with anhydrides and pyridine to yield compounds of formula C. Alternatively, compounds of formula A can be mixed with acid chlorides and pyridine to yield compounds of formula C. Alternatively, compounds of formula A can be mixed with carboxylic acids, EDCI, DMAP and ACN to yield compounds of formula C. $R^4$ is defined by $R^8$ when $L^1$ is —C(O)—.

General Scheme D

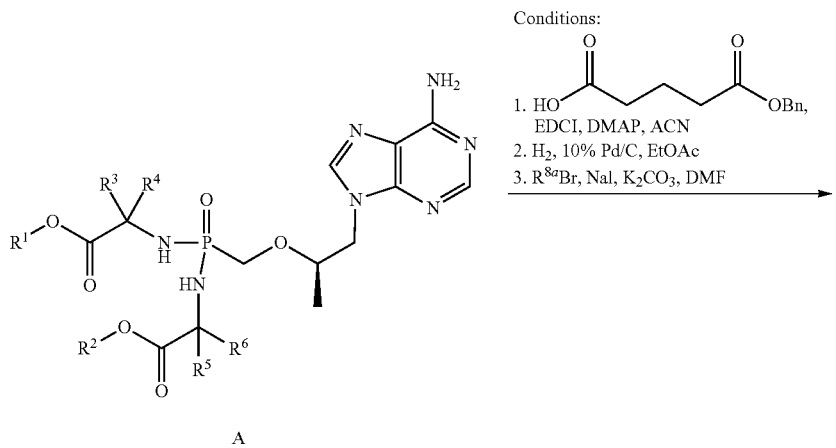

-continued

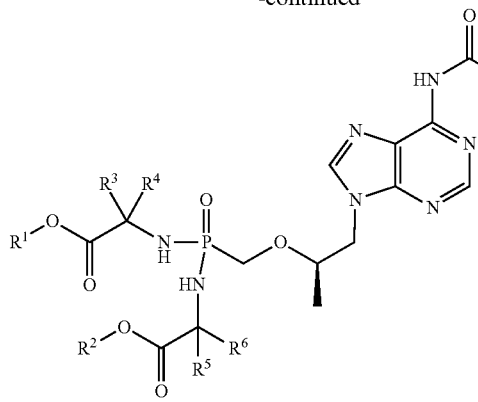

D

Compounds of formula D can be prepared in three steps from compounds of formula A according to General Scheme D (this is in addition to preparation in one step according to General Scheme C with the appropriate $R^A$). Compounds of formula A can be mixed with the monobenzyl ester of a dicarboxylic acid, EDCI, DMAP and ACN. The benzyl protecting group of the resulting product can be removed by mixing with 10% Pd/C and EtOAc under an atmosphere of $H_2$. The carboxylic acid of the resulting product can be alkylated by mixing with an alkyl halide as defined by $R^{8a}$, sodium iodide, potassium carbonate and DMF to yield compounds of formula D.

Compounds of formula E can be prepared in one step from compounds of formula A according to General Scheme E. Compounds of formula A can be mixed with chloroformates and pyridine to yield compounds of formula E. Alternatively, compounds of formula A can be mixed with alcohols, triphosgene, DMAP and DCM to yield compounds of formula E. $R^B$ is defined by $R^8$ when $L^1$ is —C(O)O—.

General Scheme E

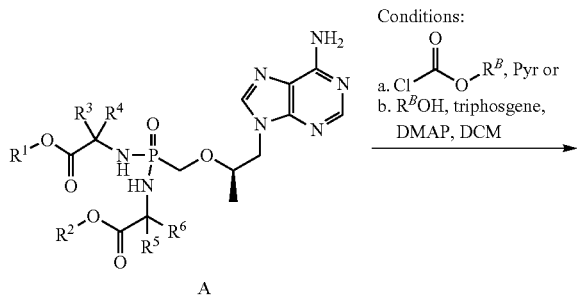

A

General Scheme F

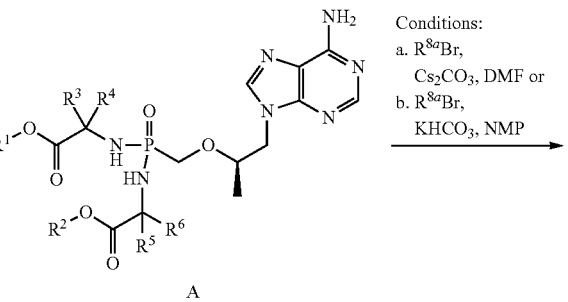

A

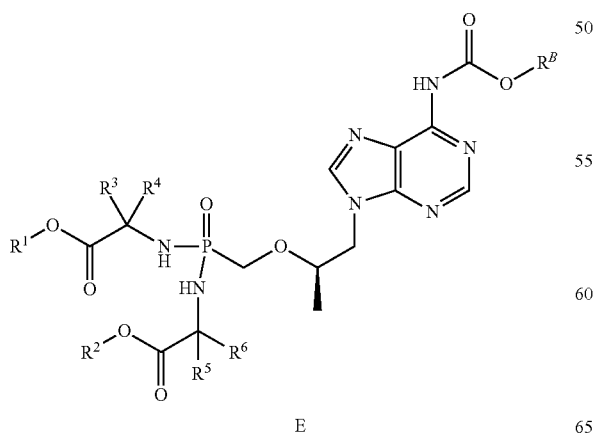

E

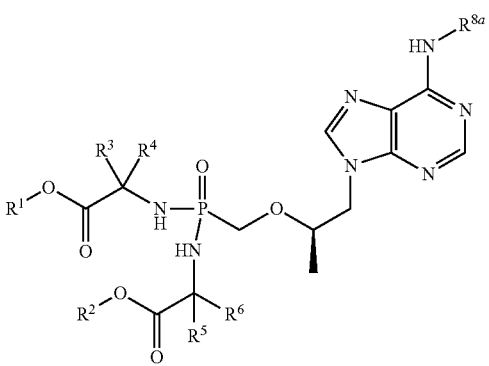

F-1

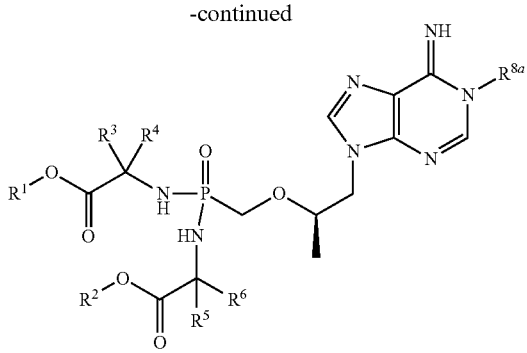

F-2

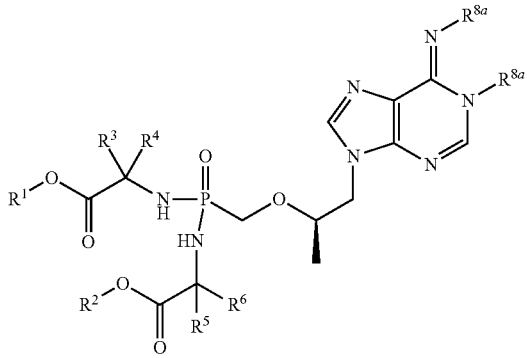

F-3

Compounds of formulas F-1, F-2, and F-3 can be prepared in one step from compounds of formula A according to General Scheme F. Compounds of formula A can be mixed with alkyl halides as defined by $R^{8a}$, cesium carbonate and DMF to yield compounds of formulas F-1, F-2, and F-3. Alternatively, compounds of formula A can be mixed with alkyl halides as defined by $R^{8a}$, potassium bicarbonate and NMP to yield compounds of formulas F-1, F-2, and F-3.

Example 1: Dihexyl 2,2'-(((((1-(6-amino-9H-purin-9-yl)propan-2-yl)oxy)methyl)phosphoryl)bis(azanediyl))(R)-bis(2-methylpropanoate) (1)

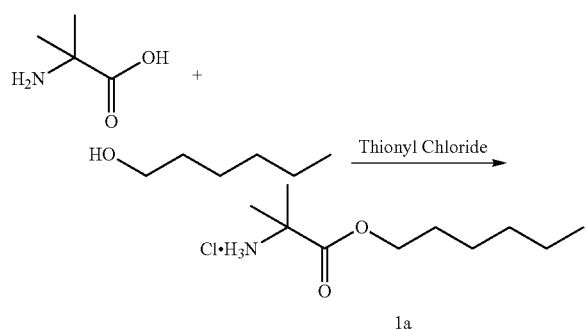

Synthesis of hexyl 2-amino-2-methylpropanoate hydrochloride (1a)

To a suspension of 2-amino-2-methyl-propanoic acid (5 g, 48.5 mmol) in 1-hexanol (49.5 g, 485 mmol) was added thionyl chloride (7.07 mL, 97 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 1a. $^1$H NMR (400 MHz, Methanol-$d_4$) δ 4.27 (t, J=6.6 Hz, 2H), 1.77-1.67 (m, 2H), 1.59 (s, 6H), 1.46-1.33 (m, 6H), 0.99-0.89 (m, 3H).

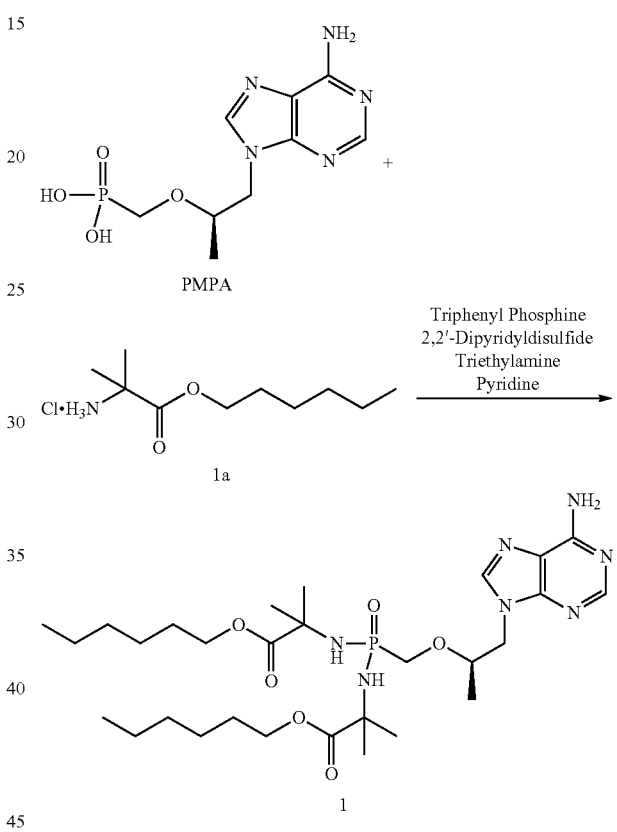

(R)-(((1-(6-amino-9H-purin-9-yl)propan-2-yl)oxy)methyl)phosphonic acid (PMPA) (100 mg, 0.35 mmol), intermediate 1a (234 mg, 1.04 mmol), triphenylphosphine (344 mg, 1.39 mmol), 2,2'-dipyridyldisulfide (307 mg, 1.39 mmol) and triethylamine (0.38 mL, 2.79 mmol) were combined in pyridine (2 mL) under argon. The reaction was heated to 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. After removal of the drying agent, the resulting solution was concentrated and was loaded onto silica gel (12 g). EtOAc (100 mL) was eluted and discarded. The product was recovered with 15% MeOH in DCM (50 mL). The product containing solution was concentrated under reduced pressure. The residue was purified by HPLC chromatography (Gemini 5 μm C18-110 Å 100×30 mm column, 25%-100% acetonitrile in water gradient over 30 min run) to afford the title compound (1). $^1$H NMR (400 MHz, DMSO-$d_6$) δ 8.17 (s, 1H), 8.13 (s, 1H), 7.19 (s, 2H), 4.33-4.14 (m, 4H), 4.11-3.91 (m, 5H), 3.63-3.48 (m, 2H), 1.61-1.51 (m, 4H), 1.40 1.46-1.35 (m, 12H), 1.33-1.19 (m, 12H), 1.06 (d, J=6.2 Hz, 3H), 0.84 (td, J=6.9, 2.1 Hz, 6H). $^{31}$P NMR (162 MHz, DMSO-d$_6$) δ 18.41 (t, J=10.2 Hz). LCMS: MS m/z=626.36 [M+1], t$_R$=1.78 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: t$_R$=3.35 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 2: Bis(2-ethylbutyl) 2,2'-(((((1-(6-amino-9H-purin-9-yl)propan-2-yl)oxy)methyl)phosphoryl)bis(azanediyl))(R)-bis(2-methylpropanoate) (2)

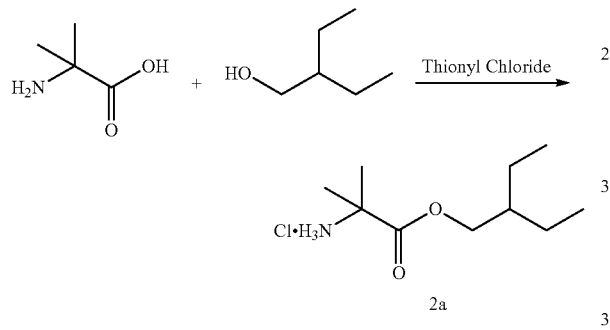

Synthesis of 2-ethylbutyl 2-amino-2-methylpropanoate hydrochloride (2a)

To a suspension of 2-amino-2-methyl-propanoic acid (20 g, 194 mmol) in 2-ethylbutan-1-ol (85.3 g, 835 mmol) was added thionyl chloride (28.3 mL, 388 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 2a. $^1$H NMR (400 MHz, DMSO-d$_6$) δ 8.77 (s, 3H), 4.08 (d, J=5.5 Hz, 2H), 1.49 (s, 7H), 1.33 (p, J=7.3 Hz, 4H), 0.86 (t, J=7.5 Hz, 6H).

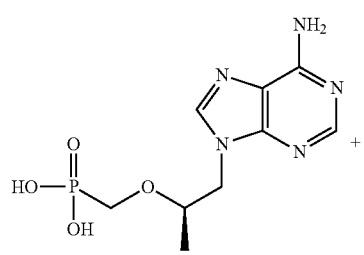

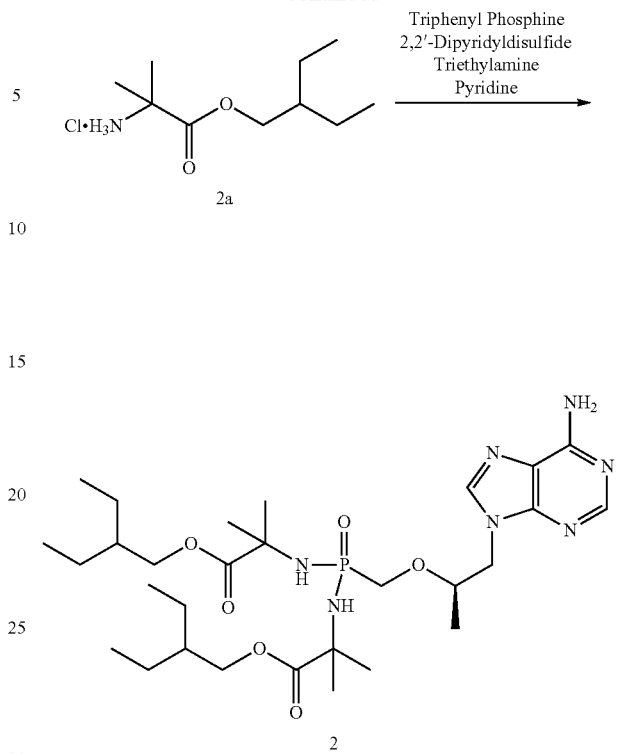

PMPA (100 mg, 0.35 mmol), intermediate 2a (195 mg, 0.87 mmol) and triethylamine (0.38 mL, 2.79 mmol) were combined in pyridine (1 mL) and heated to 70° C. for 5 min under an atmosphere of argon. A solution of triphenylphosphine (344 mg, 1.39 mmol), 2,2'-dipyridyldisulfide (307 mg, 1.39 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (2). $^1$H NMR (400 MHz, DMSO-d$_6$) δ 8.16 (s, 1H), 8.12 (s, 1H), 7.17 (s, 2H), 4.31-4.12 (m, 4H), 4.05-3.89 (m, 5H), 3.66-3.47 (m, 2H)), 1.54-1.22 (m, 22H), 1.06 (d, J=6.2 Hz, 3H), 0.83 (td, J=7.4, 3.3 Hz, 12H). $^{31}$P NMR (162 MHz, DMSO-d$_6$) δ 18.43 (t, J=10.2 Hz). LCMS: MS m/z=626.38 [M+1], t$_R$=1.74 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: t$_R$=3.31 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 3: Dibenzyl 2,2'-(((((1-(6-amino-9H-purin-9-yl)propan-2-yl)oxy)methyl)phosphoryl)bis(azanediyl))(R)-bis(2-methylpropanoate) (3)

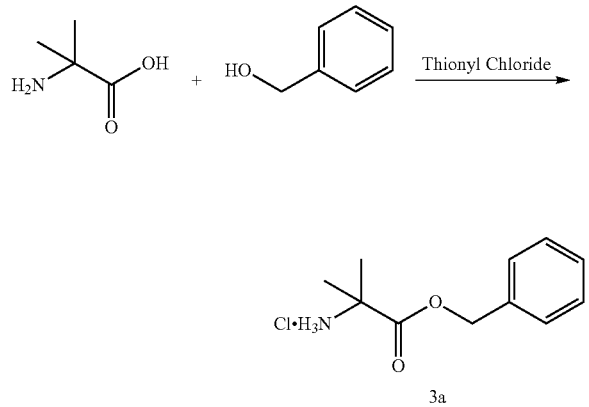

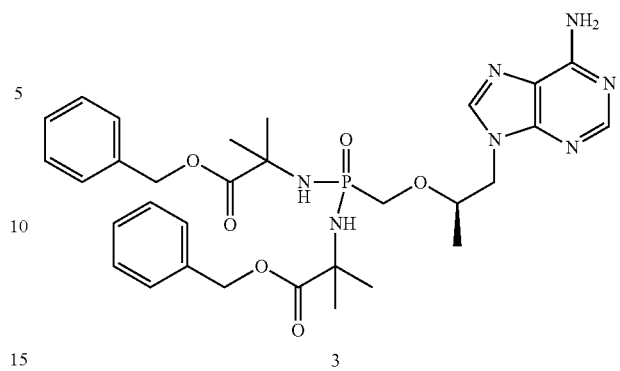

3

Synthesis of benzyl 2-amino-2-methylpropanoate hydrochloride (3a)

To a suspension of 2-amino-2-methyl-propanoic acid (2 g, 19.4 mmol) in benzyl alcohol (10.4 g, 97.0 mmol) was added thionyl chloride (2.83 mL, 38.8 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 3a. $^1$H NMR (400 MHz, DMSO-$d_6$) δ 8.46 (s, 3H), 7.46-7.33 (m, 5H), 5.26 (s, 2H), 1.49 (s, 6H).

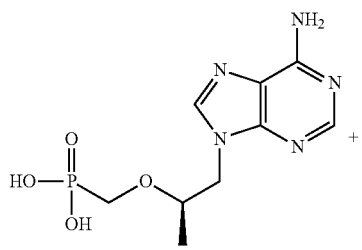

+

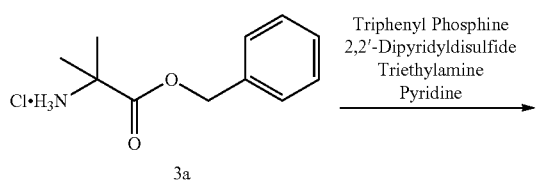

3a

PMPA (100 mg, 0.35 mmol), intermediate 3a (239 mg, 1.04 mmol) and triethylamine (0.38 mL, 2.79 mmol) were combined in pyridine (1 mL) and heated to 70° C. for 5 min under an atmosphere of argon. A solution of triphenylphosphine (344 mg, 1.39 mmol), 2,2'-dipyridyldisulfide (307 mg, 1.39 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (3). $^1$H NMR (400 MHz, DMSO-$d_6$) δ 8.13 (s, 1H), 8.12 (s, 1H), 7.39-7.28 (m, 10H), 7.22 (s, 2H), 5.17-5.03 (m, 4H), 4.28-4.06 (m, 4H), 3.91-3.83 (m, 1H), 3.63-3.45 (m, 2H), 1.39 1.44-1.34 (m, 12H), 1.00 (d, J=6.2 Hz, 3H). $^{31}$P NMR (162 MHz, DMSO-$d_6$) δ 18.71 (t, J=9.2 Hz). LCMS: MS m/z=638.13 [M+1], $t_R$=1.46 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=2.91 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 4: Dipentyl 2,2'-(((((1-(6-amino-9H-purin-9-yl)propan-2-yl)oxy)methyl)phosphoryl)bis(azanediyl))(R)-bis(2-methylpropanoate) (4)

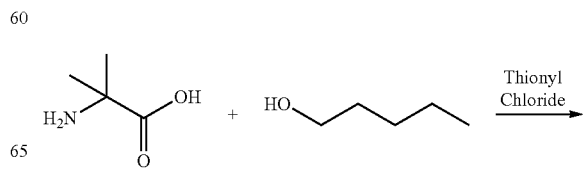

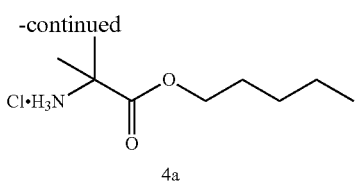

4a

Synthesis of pentyl 2-amino-2-methylpropanoate hydrochloride (4a)

To a suspension of 2-amino-2-methyl-propanoic acid (2 g, 19.4 mmol) in 1-pentanol (8.55 g, 97.0 mmol) was added thionyl chloride (2.83 mL, 38.8 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 4a. $^1$H NMR (400 MHz, DMSO-$d_6$) δ 8.56 (s, 3H), 4.17 (t, J=6.5 Hz, 2H), 1.68-1.57 (m, 2H), 1.48 (s, 6H), 1.36-1.28 (m, 4H), 0.92-0.86 (m, 3H).

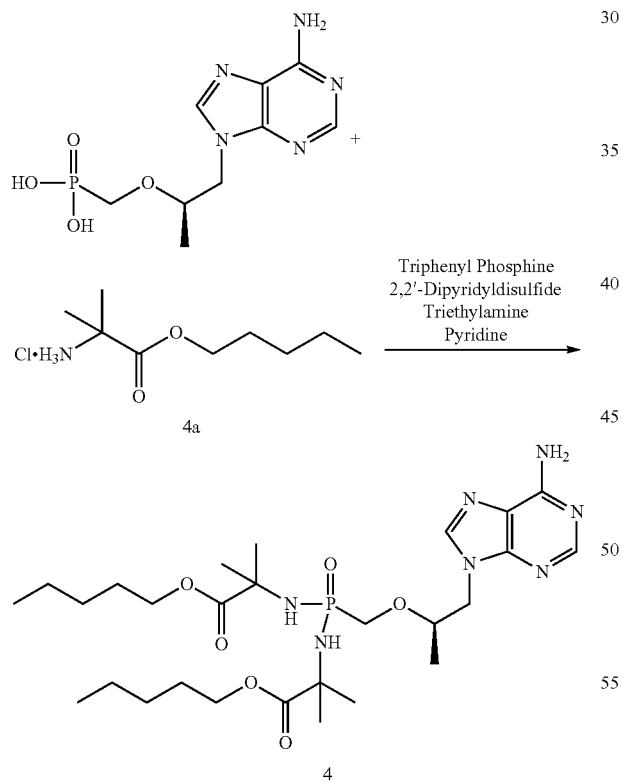

PMPA (100 mg, 0.35 mmol), intermediate 4a (219 mg, 1.04 mmol) and triethylamine (0.38 mL, 2.79 mmol) were combined in pyridine (1 mL) and heated to 70° C. for 5 min under an atmosphere of argon. A solution of triphenylphosphine (344 mg, 1.39 mmol), 2,2'-dipyridyldisulfide (307 mg, 1.39 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (4). $^1$H NMR (400 MHz, DMSO-$d_6$) δ 8.16 (s, 1H), 8.12 (s, 1H), 7.19 (s, 2H), 4.32-4.11 (m, 4H), 4.09-3.90 (m, 5H), 3.63-3.47 (m, 2H), 1.56 (q, J=6.7 Hz, 4H), 1.45-1.35 (m, 12H), 1.27 (p, J=3.6 Hz, 8H), 1.06 (d, J=6.2 Hz, 3H), 0.90-0.79 (m, 6H). $^{31}$P NMR (162 MHz, DMSO-$d_6$) δ 18.43 (t, J=10.1 Hz). LCMS: MS m/z=598.25 [M+1], $t_R$=1.61 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.11 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 5: Dipentyl 2,2'-(((((1-(6-amino-9H-purin-9-yl)propan-2-yl)oxy)methyl)phosphoryl)bis(azanediyl))(R)-bis(2-methylpropanoate) (5)

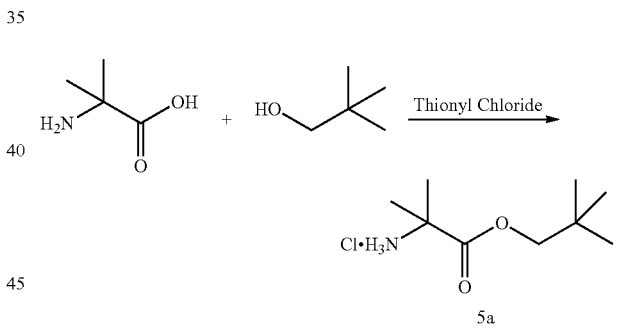

Synthesis of neopentyl 2-amino-2-methylpropanoate hydrochloride (5a)

To a suspension of 2-amino-2-methyl-propanoic acid (2 g, 19.4 mmol) in 2,2-dimethylpropan-1-ol (8.55 g, 97.0 mmol) was added thionyl chloride (2.83 mL, 38.8 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 5a. $^1$H NMR (400 MHz, DMSO-$d_6$) δ 8.67 (s, 3H), 3.88 (s, 2H), 1.51 (s, 6H), 0.94 (s, 9H).

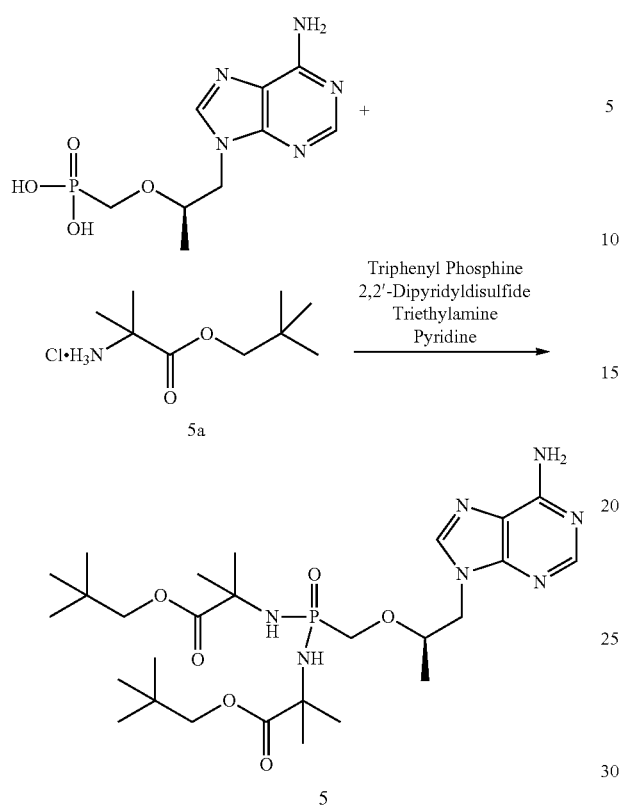

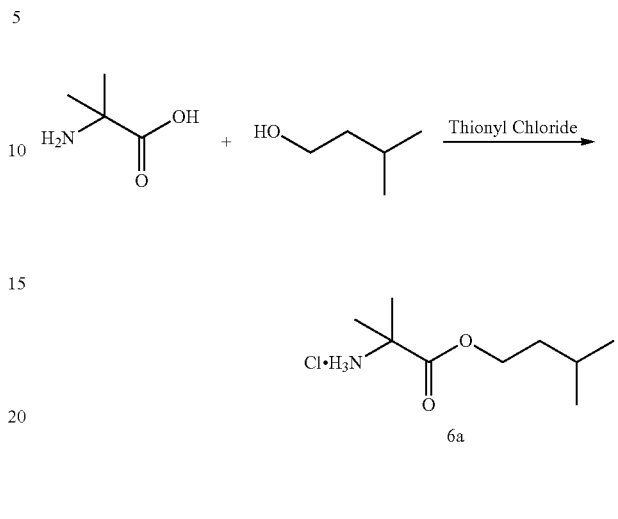

Example 6: Diisopentyl 2,2'-(((((1-(6-amino-9H-purin-9-yl)propan-2-yl)oxy)methyl)phosphoryl)bis(azanediyl))(R)-bis(2-methylpropanoate) (6)

Synthesis of isopentyl 2-amino-2-methylpropanoate hydrochloride (6a)

PMPA (100 mg, 0.35 mmol), intermediate 5a (219 mg, 1.04 mmol) and triethylamine (0.38 mL, 2.79 mmol) were combined in pyridine (1 mL) and heated to 70° C. for 5 min under an atmosphere of argon. A solution of triphenylphosphine (344 mg, 1.39 mmol), 2,2'-dipyridyldisulfide (307 mg, 1.39 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (5). $^1$H NMR (400 MHz, DMSO-$d_6$) δ 8.15 (s, 1H), 8.12 (s, 1H), 7.17 (s, 2H), 4.30-3.67 (m, 9H), 3.63-3.50 (m, 2H), 1.48-1.39 (m, 12H), 1.05 (d, J=6.2 Hz, 3H), 0.89 (d, J=5.1 Hz, 18H). $^{31}$P NMR (162 MHz, DMSO-$d_6$) δ 18.52-18.37 (m). LCMS: MS m/z=589.12 [M+1], $t_R$=1.57 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.06 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

To a suspension of 2-amino-2-methyl-propanoic acid (2 g, 19.4 mmol) in 3-methylbutan-1-ol (8.55 g, 97.0 mmol) was added thionyl chloride (2.83 mL, 38.8 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 6a. $^1$H NMR (400 MHz, DMSO-$d_6$) δ 8.71-8.54 (m, 3H), 4.20 (t, J=6.7 Hz, 2H), 1.75-1.62 (m, 1H), 1.52 (q, J=6.7 Hz, 2H), 1.48 (s, 6H), 0.90 (d, J=6.6 Hz, 6H).

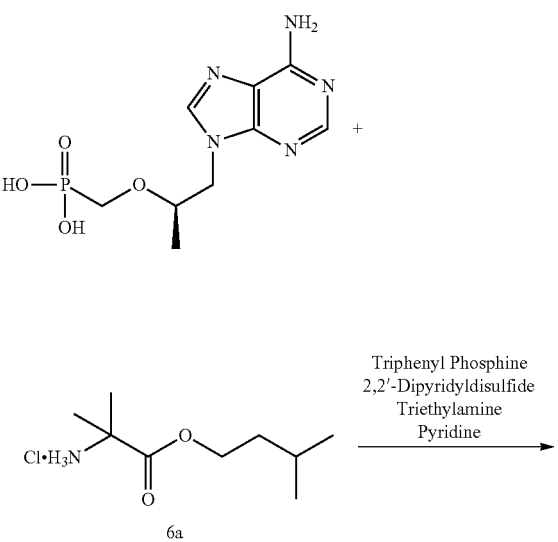

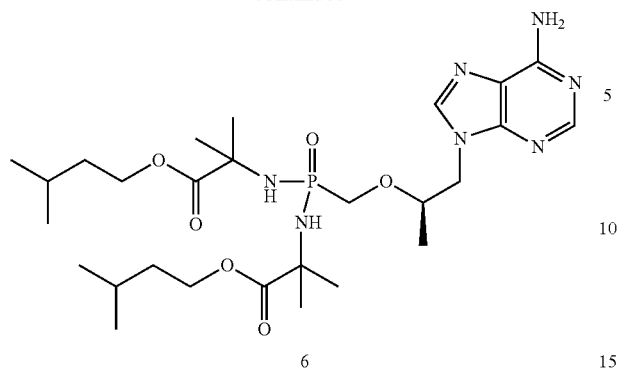

PMPA (100 mg, 0.35 mmol) and intermediate 6a (219 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and, and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to the title compound (6). $^1$H NMR (400 MHz, DMSO-$d_6$) δ 8.16 (s, 1H), 8.13 (s, 1H), 7.17 (s, 2H), 4.32-3.91 (m, 9H), 3.63-3.50 (m, 2H), 1.70-1.58 (m, 2H), 1.51-1.34 (m, 16H), 1.07 (d, J=6.3 Hz, 3H), 0.89-0.84 (m, 12H). $^{31}$P NMR (162 MHz, DMSO-$d_6$) δ 18.60-18.39 (m). LCMS: MS m/z=598.10 [M+1], $t_R$=1.60 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.14 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 7: Bis(3-ethylpentyl) 2,2'-((((((1-(6-amino-9H-purin-9-yl)propan-2-yl)oxy)methyl)phosphoryl)bis(azanediyl))(R)-bis(2-methylpropanoate) (7)

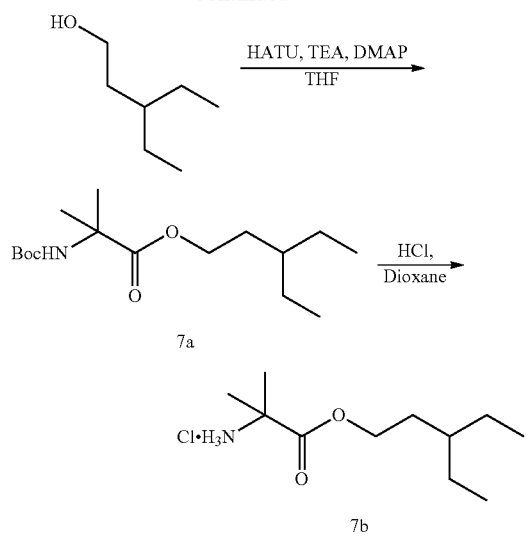

Synthesis of 3-ethylpentyl 2-amino-2-methylpropanoate hydrochloride (7b)

To a solution of 2-amino-2-methyl-propanoic acid (2 g, 9.84 mmol), 3-ethylpentan-1-ol (1.37 g, 11.8 mmol) and HATU (2.34 g, 9.84 mmol) in DCM (50 mL) was added TEA (5.37 mL, 39.4 mmol) followed by DMAP (60 mg, 0.49 mmol). After 3 h, the reaction was diluted with DCM (50 mL) and washed with a saturated sodium bicarbonate solution (50 mL), water (50 mL), and brine (50 mL). The organics were dried over sodium sulfate, filtered and concentrated. Intermediate 7a was purified by silica gel chromatography (0-50% EtOAc in Hex). Intermediate 7a was dissolved in 4N HCl in dioxane (48.5 mL, 194 mmol). After 2 h, the reaction was concentrated. The residue was taken up in water (20 mL) and concentrated (this process was repeated twice). The residue was taken up in toluene and concentrated to afford intermediate 7b. $^1$H NMR (400 MHz, DMSO-$d_6$) δ 8.57 (s, 3H), 4.20 (t, J=6.8 Hz, 2H), 1.61-1.54 (m, 2H), 1.48 (s, 5H), 1.35-1.26 (m, 6H), 0.87-0.81 (m, 6H).

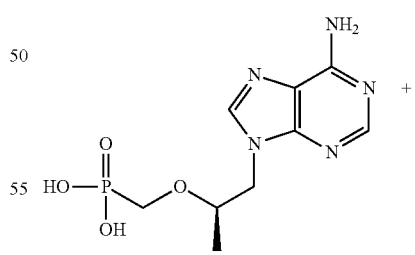

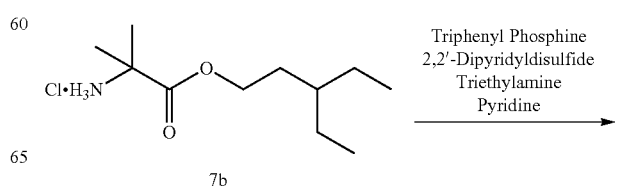

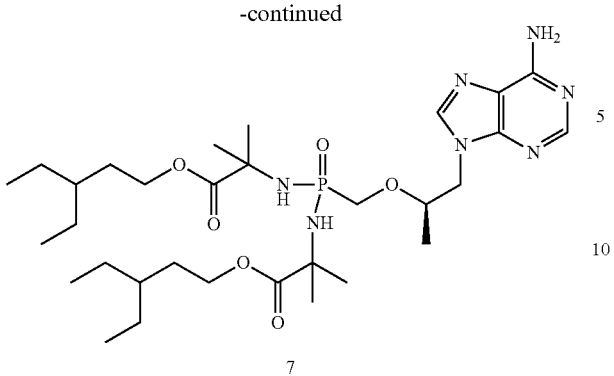

7

PMPA (100 mg, 0.35 mmol) and intermediate 7b (335 mg, 1.41 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (7). $^1$H NMR (400 MHz, DMSO-$d_6$) δ 8.16 (s, 1H), 8.12 (s, 1H), 7.17 (s, 2H), 4.32-3.90 (m, 9H), 3.63-3.48 (m, 2H), 1.55-1.48 (m, 4H), 1.46-1.35 (m, 12H), 1.29-1.22 (m, 10H), 1.06 (d, J=6.2 Hz, 3H), 0.83-0.77 (m, 12H). $^{31}$P NMR (162 MHz, DMSO-$d_6$) δ 18.44 (t, J=9.6 Hz). LCMS: MS m/z=654.17 [M+1], $t_R$=1.92 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.50 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 8: Bis(3,3-dimethylbutyl) 2,2'-(((((1-(6-amino-9H-purin-9-yl)propan-2-yl)oxy)methyl)phosphoryl)bis(azanediyl))(R)-bis(2-methylpropanoate) (8)

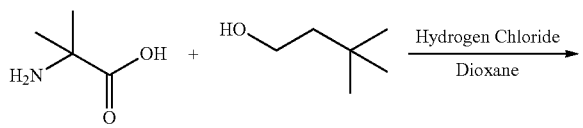

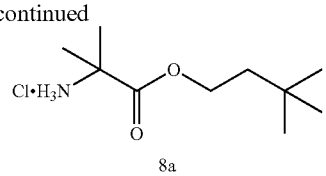

8a

Synthesis of 3,3-dimethylbutyl 2-amino-2-methyl-propanoate hydrochloride (8a)

2-amino-2-methyl-propanoic acid (2 g, 19.4 mmol) and 3,3-dimethylbutan-1-ol (9.91 g, 97.0 mmol) were taken up in 4N HCl in dioxane (19.4 mL, 77.6 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 8a. $^1$H NMR (400 MHz, DMSO-$d_6$) δ 8.47 (s, 3H), 4.23 (t, J=7.1 Hz, 2H), 1.56 (t, J=7.1 Hz, 2H), 1.46 (s, 6H), 0.93 (s, 9H).

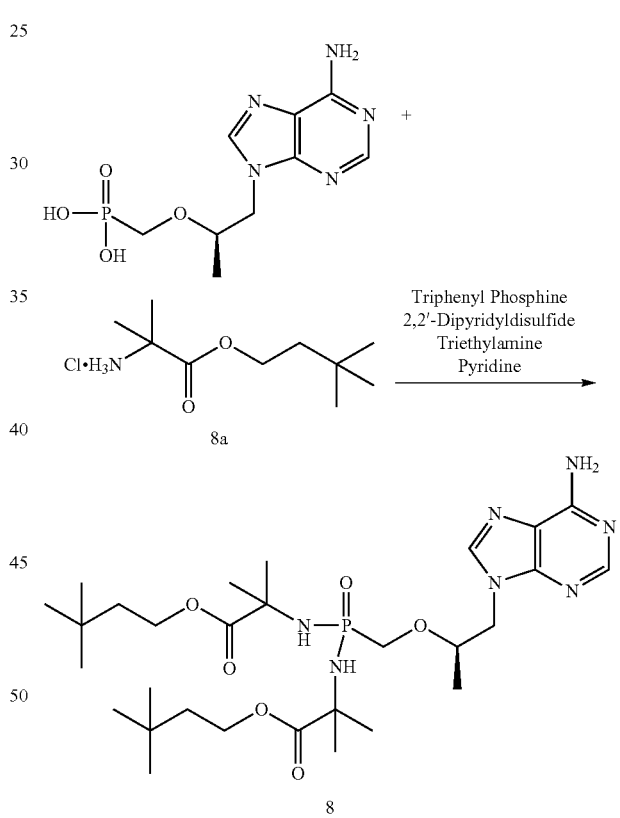

PMPA (100 mg, 0.35 mmol) and intermediate 8a (315 mg, 1.41 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (8). $^1$H NMR (400 MHz, DMSO-$d_6$) δ 8.16 (s, 1H), 8.12 (s, 1H), 7.17 (s, 2H), 4.32-3.90 (m, 9H), 3.65-3.48 (m, 2H), 1.49 (q, J=7.2 Hz, 4H), 1.45-1.34 (m, 12H), 1.06 (d, J=6.2 Hz, 3H), 0.89 (d, J=3.7 Hz, 18H). $^{31}$P NMR (162 MHz, DMSO-$d_6$) δ 18.47 (t, J=9.6 Hz). LCMS: MS m/z=626.21 [M+1], $t_R$=1.73 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=3.25 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 9: Di-tert-butyl 2,2'-((((((1-(6-amino-9H-purin-9-yl)propan-2-yl)oxy)methyl)phosphoryl)bis(azanediyl))(R)-bis(2-methylpropanoate) (9)

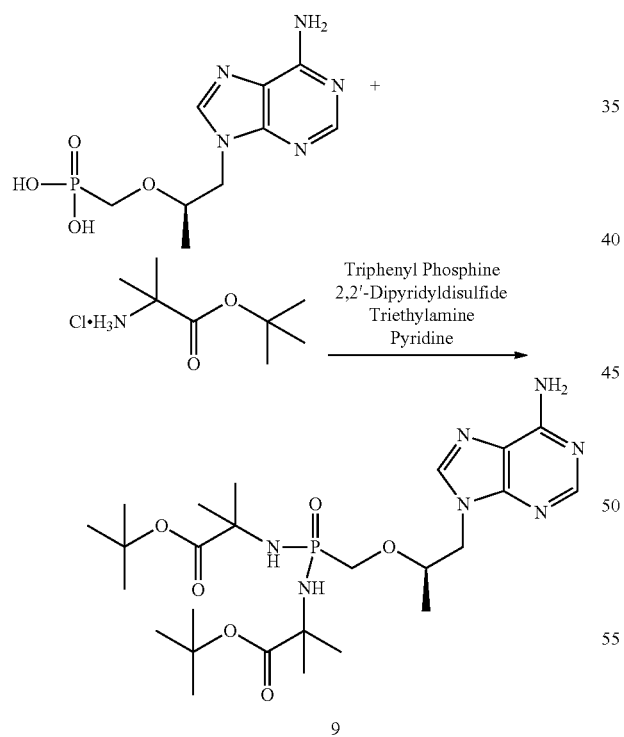

PMPA(100 mg, 0.35 mmol) and tert-butyl 2-amino-2-methylpropanoate hydrochloride (204 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (9). $^1$H NMR (400 MHz, DMSO-$d_6$) δ 8.16 (s, 1H), 8.13 (s, 1H), 7.17 (s, 2H), 4.29 (dd, J=14.3, 3.8 Hz, 1H), 4.18 (dd, J=14.4, 6.0 Hz, 1H), 4.12 (d, J=10.6 Hz, 1H), 4.02 (d, J=10.6 Hz, 1H), 3.98-3.92 (m, 1H), 1.45-1.30 (m, 30H), 1.07 (d, J=6.3 Hz, 3H). $^{31}$P NMR (162 MHz, DMSO-$d_6$) δ 18.60-18.39 (m). LCMS: MS m/z=570.27 [M+1], $t_R$=1.46 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=2.86 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 10: Dihexyl 2,2'-((((((R)-1-(6-amino-9H-purin-9-yl)propan-2-yl)oxy)methyl)phosphoryl)bis(azanediyl))(2S,2'S)-bis(2-methylbutanoate) (10)

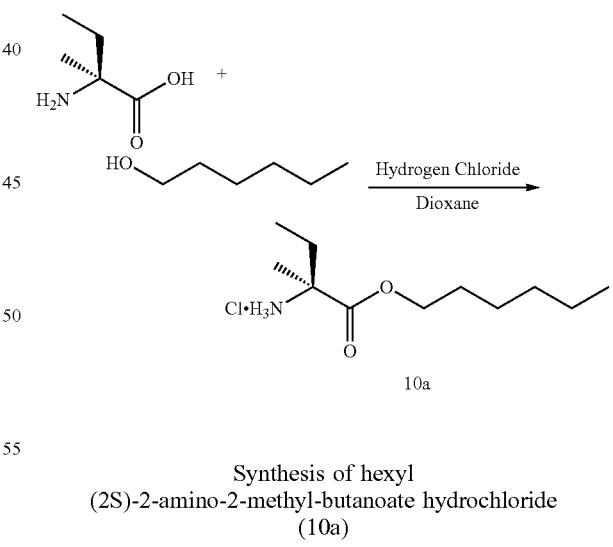

Synthesis of hexyl (2S)-2-amino-2-methyl-butanoate hydrochloride (10a)

(2S)-2-amino-2-methyl-butanoic acid (1 g, 8.6 mmol) and 1-hexanol (4.36 g, 42.7 mmol) were taken up in 4N HCl in dioxane (5.58 mL, 22.3 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 10a. $^1$H NMR (400

MHz, DMSO-d₆) δ 4.02 (t, J=6.5 Hz, 2H), 1.64-1.43 (m, 4H), 1.35-1.24 (m, 6H), 1.17 (s, 3H), 0.90-0.84 (m, 3H), 0.78 (t, J=7.5 Hz, 3H).

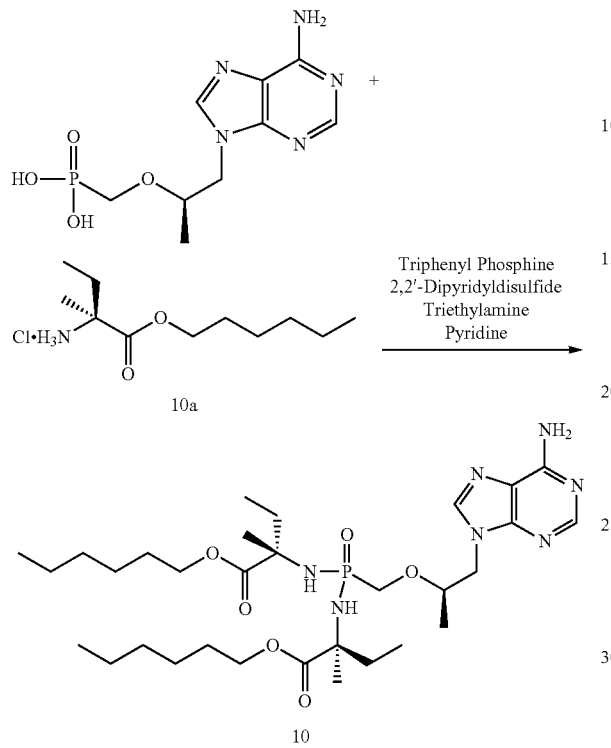

PMPA (100 mg, 0.35 mmol) and intermediate 10a (248 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 µm C18-110 Å 100×30 mm column, 25%-100% acetonitrile in water gradient over 30 min run) to afford the title compound (10). ¹H NMR (400 MHz, Acetonitrile-d₃) δ 8.24 (s, 1H), 8.04 (s, 1H), 6.14 (s, 2H), 4.33 (dd, J=14.5, 3.3 Hz, 1H), 4.23-4.06 (m, 5H), 3.98-3.92 (m, 1H), 3.73-3.43 (m, 4H), 1.90-1.60 (m, 8H), 1.57 (s, 3H), 1.42 (s, 3H), 1.39-1.28 (m, 12H), 1.19 (d, J=6.3 Hz, 3H), 0.95-0.87 (m, 6H), 0.83 (t, J=7.4 Hz, 30H), 0.78 (t, J=7.4 Hz, 3H). ³¹P NMR (162 MHz, Acetonitrile-d₃) δ 17.48 (t, J=9.8 Hz). LCMS: MS m/z=654.4 [M+1], $t_R$=1.17 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. HPLC: $t_R$=3.55 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 11: Dihexyl 2,2'-(((((R)-1-(6-amino-9H-purin-9-yl)propan-2-yl)oxy)methyl)phosphoryl)bis(azanediyl))(2S,2'S)-bis(2-methyl-3-phenylpropanoate) (11)

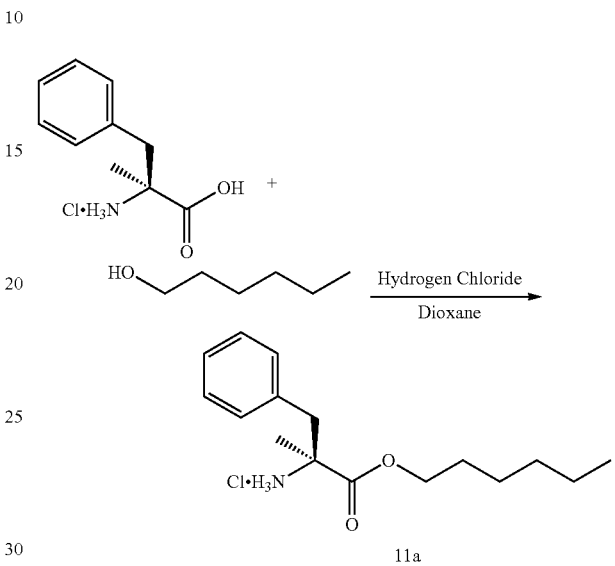

Synthesis of hexyl (2S)-2-amino-2-methyl-3-phenyl-propanoate hydrochloride (11a)

(2S)-2-amino-2-methyl-3-phenyl-propanoic acid (1 g, 5.6 mmol) and 1-hexanol (2.85 g, 27.9 mmol) were taken up in 4N HCl in dioxane (5.58 mL, 22.3 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 11a. ¹H NMR (400 MHz, DMSO-d₆) δ 7.29-7.19 (m, 3H), 7.16-7.10 (m, 2H), 4.04-3.93 (m, 2H), 2.89 (d, J=12.9 Hz, 1H), 2.76 (d, J=12.9 Hz, 1H), 1.59-1.50 (m, 2H), 1.31-1.24 (m, 6H), 1.22 (s, 3H), 0.90-0.83 (m, 3H).

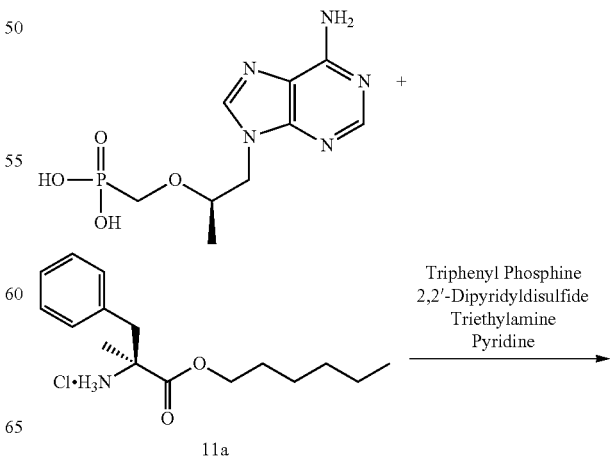

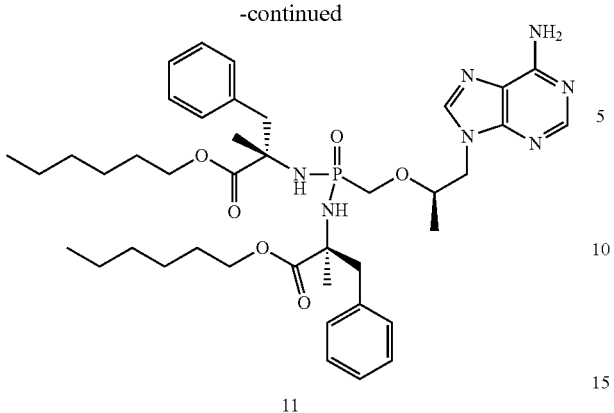

11

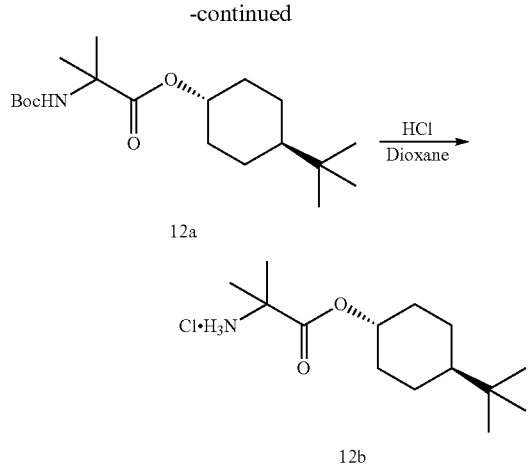

12a

12b

Synthesis of trans-4-(tert-butyl)cyclohexyl 2-amino-2-methylpropanoate hydrochloride (12b)

PMPA (100 mg, 0.35 mmol) and intermediate 11a (275 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (11). $^1$H NMR (400 MHz, DMSO-$d_6$) δ 8.12 (s, 1H), 8.04 (s, 1H), 7.30-7.08 (m, 12H), 4.27-3.82 (m, 9H), 3.61 (d, J=8.7 Hz, 2H), 3.11-2.87 (m, 4H), 1.55-1.39 (m, 10H), 1.27-1.14 (m, 12H), 0.97 (d, J=6.3 Hz, 3H), 0.86-0.78 (m, 6H). $^{31}$P NMR (162 MHz, DMSO-$d_6$) δ 18.45-18.23 (m). LCMS: MS m/z=778.4 [M+1], $t_R$=1.27 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.HPLC: $t_R$=3.86 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 12: Bis(trans-4-(tert-butyl)cyclohexyl) 2,2'-(((((R)-1-(6-amino-9H-purin-9-yl)propan-2-yl)oxy)methyl)phosphoryl)bis(azanediyl))bis(2-methylpropanoate) (12)

To a solution of 2-amino-2-methyl-propanoic acid (2 g, 9.84 mmol), trans-4-(tert-butyl)cyclohexan-1-ol (1.69 g, 10.8 mmol) and HATU (2.34 g, 9.84 mmol) in DCM (50 mL) was added TEA (5.37 mL, 39.4 mmol) followed by DMAP (60 mg, 0.49 mmol). After 3 h, the reaction was diluted with DCM (50 mL) and washed with a saturated sodium bicarbonate solution (50 mL), water (50 mL), and brine (50 mL). The organics were dried over sodium sulfate, filtered and concentrated. Intermediate 12a was purified by silica gel chromatography (0-50% EtOAc in Hex). Intermediate 12a was dissolved in 4N HCl in dioxane (48.5 mL, 194 mmol). After 2 h, the reaction was concentrated. The residue was taken up in water (20 mL) and concentrated (×2). The residue was taken up in toluene and concentrated to afford intermediate 12b. H NMR (400 MHz, DMSO-$d_6$) δ 8.50 (s, 3H), 4.71-4.59 (m, 1H), 2.02-1.93 (m, 2H), 1.81-1.75 (m, 2H), 1.41-1.27 (m, 2H), 1.19-0.95 (m, 3H), 0.85 (s, 9H).

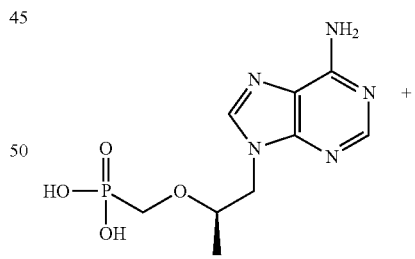

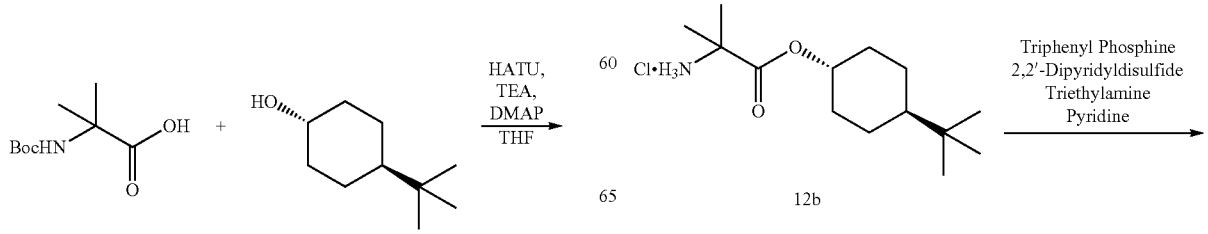

12b

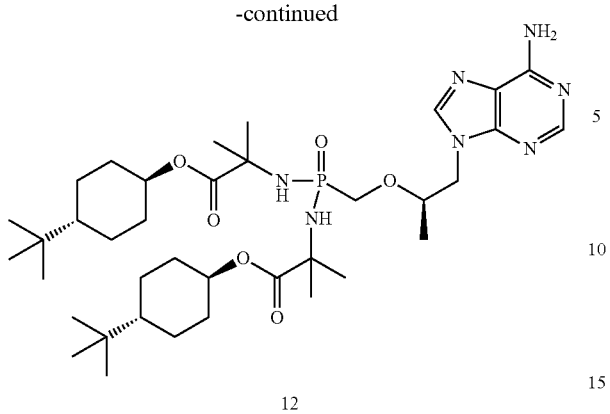

12

PMPA (100 mg, 0.35 mmol) and intermediate 12b (290 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (12). $^1$H NMR (400 MHz, DMSO-$d_6$) δ 8.16 (s, 1H), 8.12 (s, 1H), 7.16 (s, 2H), 4.57-4.44 (m, 2H), 4.28 (dd, J=14.3, 3.8 Hz, 1H), 4.21-4.06 (m, 3H), 3.98-3.91 (m, 1H), 3.63-3.48 (m, 2H), 1.96-1.86 (m, 4H), 1.79-1.68 (m, 4H), 1.44-1.32 (m, 12H), 1.29-1.17 (m, 4H), 1.13-0.90 (m, 9H), 0.82 (s, 18H). $^{31}$P NMR (162 MHz, DMSO-$d_6$) δ 18.27 (t, J=9.5 Hz). LCMS: MS m/z=734.14 [M+1], $t_R$=1.99 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min. HPLC: $t_R$=4.13 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 13: Bis((4,4-dimethylcyclohexyl)methyl) 2,2'-(((((1-(6-amino-9H-purin-9-yl)propan-2-yl)oxy)methyl)phosphoryl)bis(azanediyl))(R)-bis(2-methylpropanoate) (13)

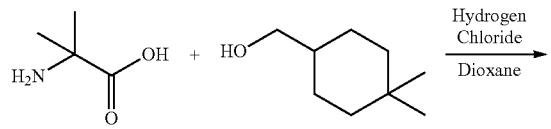

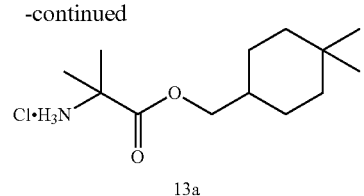

13a

Synthesis of (4,4-dimethylcyclohexyl)methyl 2-amino-2-methylpropanoate hydrochloride (13a)

2-amino-2-methyl-propanoic acid (1 g, 9.7 mmol) and (4,4-dimethylcyclohexyl)methanol (2.76 g, 19.4 mmol) were taken up in 4N HCl in dioxane (9.7 mL, 38.8 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 13a. $^1$H NMR (400 MHz, DMSO-$d_6$) δ 8.58 (s, 3H), 4.04 (d, J=6.0 Hz, 2H), 1.61-1.41 (m, 10H), 1.40-1.31 (m, 2H), 1.25-1.08 (m, 3H), 0.88 (d, J=11.2 Hz, 6H).

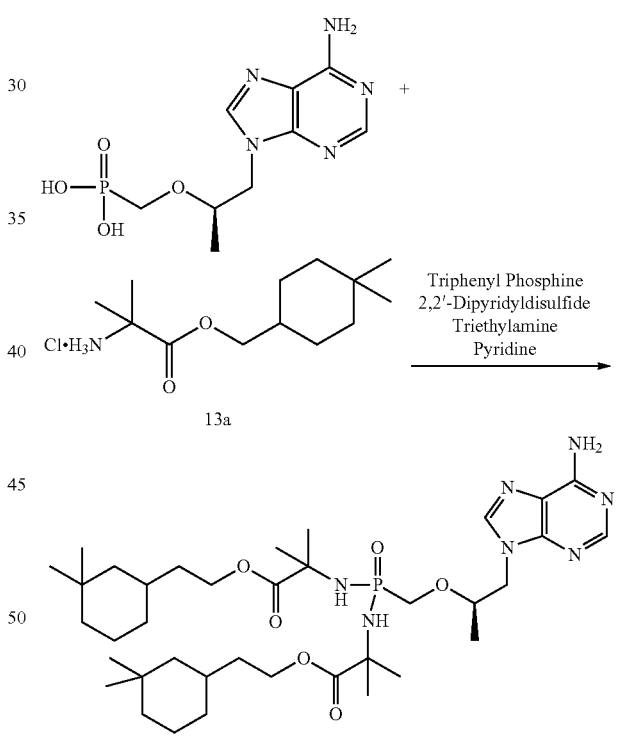

13

PMPA (100 mg, 0.35 mmol) and intermediate 13a (276 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (13). $^1$H NMR (400 MHz, DMSO-$d_6$) δ 8.16 (s, 1H), 8.13 (s, 1H), 7.17 (s, 2H), 4.32-4.14 (m, 4H), 3.98-3.82 (m, 5H), 3.65-3.49 (m, 2H), 1.55-1.27 (m, 22H), 1.12 (t, J=7.1 Hz, 8H), 1.06 (d, J=6.2 Hz, 3H), 0.87 (d, J=2.2 Hz, 6H), 0.84 (d, J=2.4 Hz, 6H). $^{31}$P NMR (162 MHz, DMSO-$d_6$) δ 18.35 (t, J=9.7 Hz). LCMS: MS m/z=706.40 [M+1], $t_R$=1.30 min; Agilent. HPLC: $t_R$=3.78 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 14: Bis(2-cyclohexylethyl) 2,2'-(((((1-(6-amino-9H-purin-9-yl)propan-2-yl)oxy)methyl)phosphoryl)bis(azanediyl))(R)-bis(2-methylpropanoate) (14)

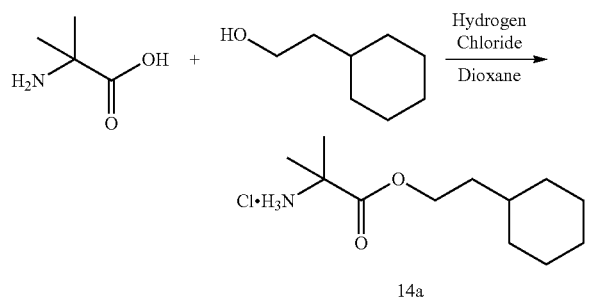

Synthesis of 2-cyclohexylethyl 2-amino-2-methylpropanoate hydrochloride (14a)

2-Amino-2-methyl-propanoic acid (1 g, 9.7 mmol) and 2-cyclohexylethanol (3.73 g, 29.1 mmol) were taken up in 4N HCl in dioxane (9.7 mL, 38.8 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 14a. $^1$H NMR (400 MHz, DMSO-$d_6$) δ 8.64 (s, 3H), 4.20 (t, J=6.7 Hz, 2H), 1.72-1.58 (m, 5H), 1.56-1.42 (m, 7H), 1.40-1.27 (m, 2H), 1.27-1.09 (m, 3H), 0.99-0.81 (m, 2H).

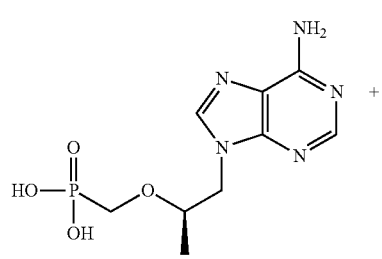

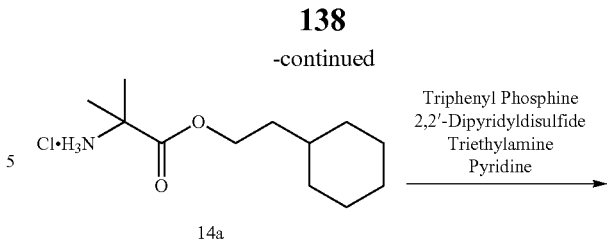

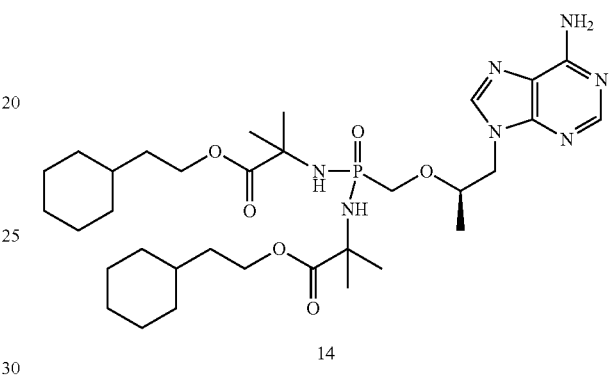

PMPA (100 mg, 0.35 mmol) and intermediate 14a (223 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (14). $^1$H NMR (400 MHz, DMSO-$d_6$) δ 8.17 (s, 1H), 8.13 (s, 1H), 7.17 (s, 2H), 4.32-3.91 (m, 9H), 3.64-3.48 (m, 2H), 1.69-1.56 (m, 10H), 1.51-1.27 (m, 18H), 1.24-1.11 (m, 6H), 1.07 (d, J=6.3 Hz, 3H), 0.96-0.82 (m, 4H). $^{31}$P NMR (162 MHz, DMSO-$d_6$) δ 18.43 (t, J=9.7 Hz). LCMS: MS m/z=678.40 [M+1], $t_R$=1.32 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. HPLC: $t_R$=3.34 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 15: Bis(cyclohexylmethyl) 2,2'-((((((R)-1-(6-amino-9H-purin-9-yl)propan-2-yl)oxy)methyl)phosphoryl)bis(azanediyl))(2S,2'S)-bis(2-methyl-3-phenylpropanoate) (15)

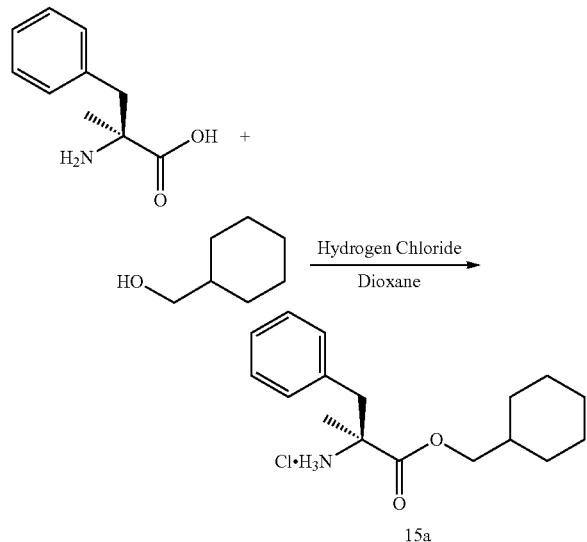

Synthesis of cyclohexylmethyl (S)-2-amino-2-methyl-3-phenylpropanoate hydrochloride (15a)

(2S)-2-Amino-2-methyl-3-phenyl-propanoic acid (1 g, 5.6 mmol) and cyclohexylmethanol (1.91 g, 16.7 mmol) were taken up in 4N HCl in dioxane (5.58 mL, 22.3 mmol) under an atmosphere of argon in a sealed tube. The reaction was heated to 90° C. for 16 h. The reaction was cooled to room temperature and concentrated. The residue was taken up in water (20 mL) and concentrated (×2). The residue was taken up in toluene and concentrated to afford intermediate 15a. $^1$H NMR (400 MHz, DMSO-d$_6$) δ 8.65 (s, 3H), 7.39-7.28 (m, 3H), 7.21-7.16 (m, 2H), 3.98 (dd, J=10.6, 6.2 Hz, 1H), 3.87 (dd, J=10.6, 6.1 Hz, 1H), 3.15 (s, 2H), 1.72-1.46 (m, 9H), 1.27-1.09 (m, 3H), 1.03-0.85 (m, 2H).

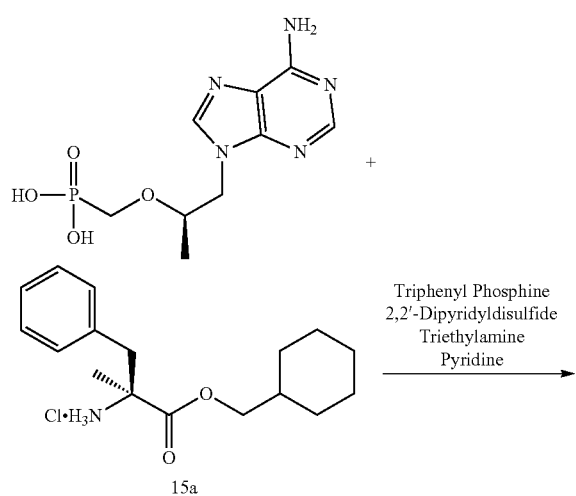

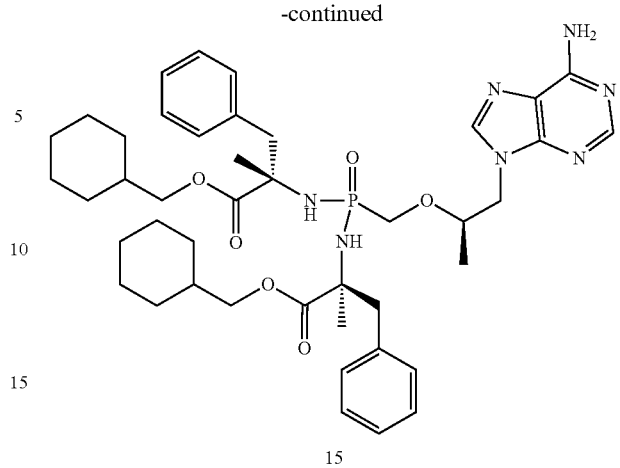

PMPA (100 mg, 0.35 mmol) and intermediate 15a (326 mg, 1.04 mmol) were suspended in 2 mL of toluene and concentrated under reduced pressure twice. Pyridine (1 mL) and triethylamine (0.38 mL, 2.79 mmol) were added and the reaction heated to 70° C. for 5 min under an atmosphere of argon. A solution of triphenylphosphine (457 mg, 1.74 mmol), 2,2'-dipyridyldisulfide (384 mg, 1.74 mmol) in pyridine (1 mL) was added. The reaction was stirred at 70° C. for 16 h. The reaction was cooled to room temperature and diluted with 5 mL of EtOAc. The organics were washed with a saturated aqueous solution of sodium bicarbonate (5 mL×2), water (5 mL), and dried over sodium sulfate. The product was loaded onto silica gel (12 g). EtOAc (100 mL) was eluted and discarded. The product was recovered with 15% MeOH in DCM (50 mL). The organics were concentrated under reduced pressure. The residue was purified by HPLC chromatography (Gemini 5 μm C18-110 Å 100×30 mm column, 25%-100% acetonitrile in water gradient over 30 min run) to afford the title compound (15). $^1$H NMR (400 MHz, Acetonitrile-d$_3$) δ 8.23 (s, 1H), 7.85 (s, 1H), 7.36-7.12 (m, 10H), 5.90 (s, 2H), 4.22 (dd, J=14.5, 3.4 Hz, 1H), 4.06-3.75 (m, 6H), 3.70-3.50 (m, 4H), 3.11-2.93 (m, 4H), 1.79-1.61 (m, 13H), 1.49 (s, 3H), 1.36-1.14 (m, 8H), 1.08 (d, J=6.2 Hz, 3H), 1.04-0.87 (m, 4H). $^{31}$P NMR (162 MHz, Acetonitrile-d$_3$) δ 17.81-17.56 (m). LCMS: MS m/z=802.30 [M+1], t$_R$=1.35 min; LC system: LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.HPLC: t$_R$=3.34 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 16: Hexyl (1R,2R)-1-((((((R)-1-(6-amino-9H-purin-9-yl)propan-2-yl)oxy)methyl)((1-(hexyloxy)-2-methyl-1-oxopropan-2-yl)amino)phosphoryl)amino)-2-ethylcyclopropane-1-carboxylate (16)

Example 17: Dihexyl 1,1'-((((((R)-1-(6-amino-9H-purin-9-yl)propan-2-yl)oxy)methyl)phosphoryl)bis(azanediyl))(1R,1'R,2R,2'R)-bis(2-ethylcyclopropane-1-carboxylate) (17)

slowly at room temperature. The resulting mixture was stirred at room temperature for 2 h, concentrated in vacuo, co-evaporated with DCM several times, and dried under high vacuum for 15 h to afford intermediate 16b. $^1$H NMR (400 MHz, Acetonitrile-d$_3$) δ 8.59 (bs, 3H), 4.21 (m, 2H), 1.97 (m, 1H), 1.87 (dd, J=10.1, 5.8 Hz, 1H), 1.75-1.61 (m, 4H), 1.54 (m, 1H), 1.47-1.25 (m, 6H), 0.98 (t, J=7.4 Hz, 3H), 0.95-0.88 (m, 3H).

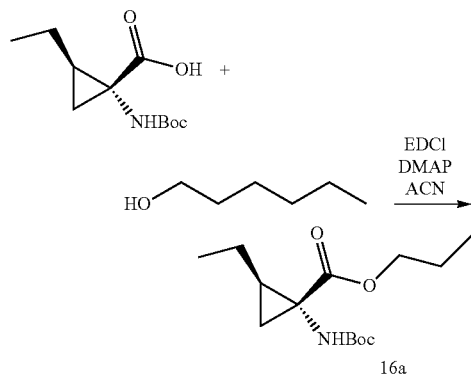

Synthesis of hexyl (1R,2R)-1-((tert-butoxycarbonyl)amino)-2-ethylcyclopropane-1-carboxylate (16a)

To a mixture of (1R,2R)-1-((tert-butoxycarbonyl)amino)-2-ethylcyclopropane-1-carboxylic acid (1.0 g, 4.36 mmol), n-hexanol (0.82 mL, 6.542 mmol), and 1-ethyl-3-(3-dimethylaminopropyl)carbodiimide hydrochloride (813 mg, 5.234 mmol) in acetonitrile (30 mL) was added DMAP (1.07 g, 8.723 mmol). The mixture was stirred at room temperature for 15 h, quenched with water, and concentrated in vacuo. The obtained residue was purified by silica gel chromatography (EtOAc 0 to 70% in hexanes) to afford intermediate 16a. $^1$H NMR (400 MHz, Acetonitrile-d$_3$) δ 5.93 (broad singlet, 1H), 4.08 (t, J=6.5 Hz, 2H), 1.68-1.51 (m, 3H), 1.50-1.28 (m, 18H), 1.13 (dd, J=8.9, 4.8 Hz, 1H), 0.94-0.82 (m, 6H).

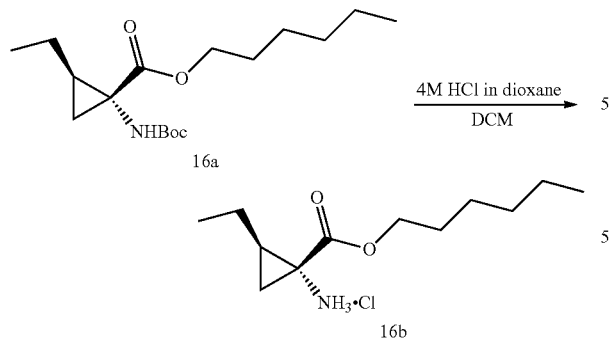

Synthesis of hexyl (1R,2R)-1-amino-2-ethylcyclopropane-1-carboxylate hydrochloride (16b)

To a solution of intermediate 16a (600 mg, 1.914 mmol) in DCM (12 mL) was added 4M HCl in dioxane (1.9 mL)

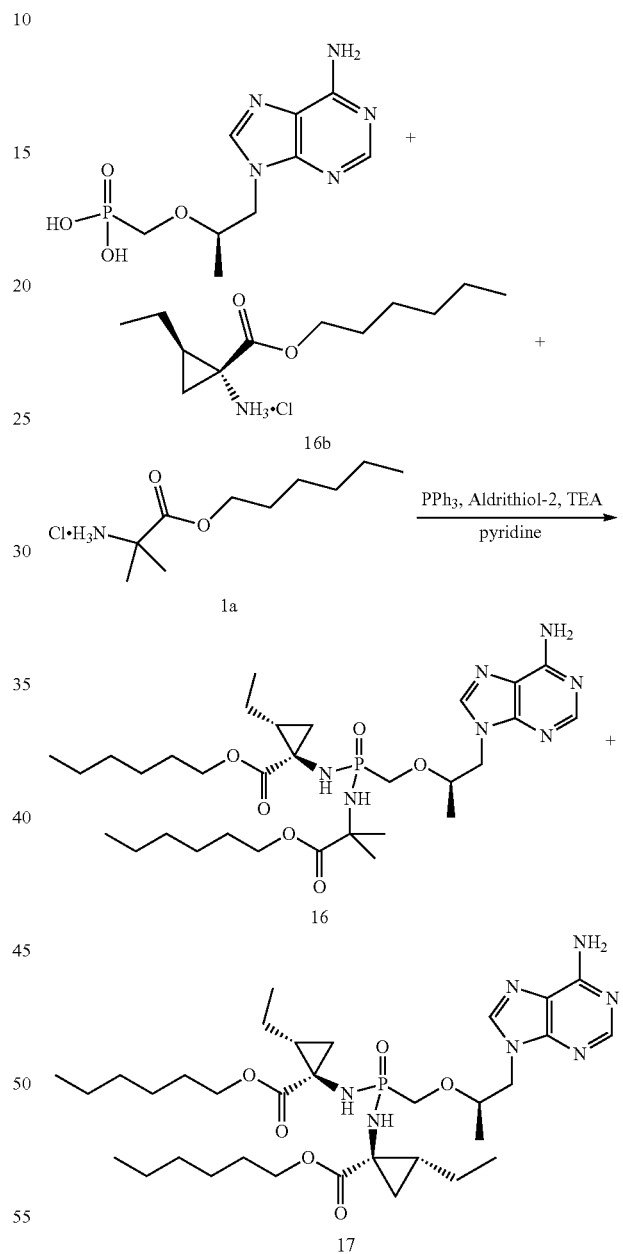

A mixture of PMPA (100 mg, 0.348 mmol), intermediate 16b (174 mg, 0.696 mmol), and triethylamine (0.73 mL, 2.785 mmol) in pyridine (1 mL) was heated to 50° C. for 5 min and a freshly prepared bright yellow solution of 2,2'-dipyridyldisulfide (460 mg, 2.089 mmol) and triphenylphosphine (548 mg, 2.089 mmol) in pyridine (1 mL) was added to the reaction mixture. The resulting reaction mixture was stirred at 90° C. for 5 hours. Intermediate 1a (234 mg, 1.045 mmol) was added. The reaction mixture was stirred at 90° C.

for 18 h, concentrated in vacuo, and purified by silica gel column chromatography (MeOH 0 to 15% in DCM) to afford a mixture of the products, which was separated by preparative HPLC (0.1% TFA-containing ACN 35% to 90% in 0.1% TFA-containing water). Each compound was dissolved in ACN (3 mL) and triethylamine (three drops) was added to generate free form and re-purified by neutral HPLC (ACN 10 to 100% in water for 12 min, 100% ACN for 5 min) to afford 16 and 17.

16: ¹H NMR (400 MHz, Acetonitrile-d₃) δ 8.24-8.21 (m, 1H), 8.05-8.02 (m, 1H), 6.13 (m, 2H), 4.32 (m, 1H), 4.23-4.04 (m, 5H), 4.02-3.84 (m, 2H), 3.78-3.59 (m, 2H), 3.47 (m, 1H), 1.76 (m, 1H), 1.68-1.52 (m, 5H), 1.51-1.22 (m, 21H), 1.17 (d, J=6.22 Hz, 3H), 0.98-0.83 (m, 9H). ³¹P NMR (162 MHz, Acetonitrile-d₃) δ 19.44, 18.94. LCMS: MS m/z=652.27 [M+1]; t_R=1.66 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: t_R=6.64 min (45%) and 6.68 min (55%); HPLC system: 1290 Infinity II.; Column: Phenomenex 2.6µ C18 100A, 100×4.6 mm; Solvents: Acetonitrile with 0.1% TFA, Water with 0.1% TFA; Gradient: 0 min-8.5 min 2-98% ACN at 1.5 mL/min.

17: ¹H NMR (400 MHz, Acetonitrile-d₃) δ 8.23 (s, 1H), 8.03 (s, 1H), 6.07 (s, 2H), 4.35 (dd, J=14.5, 3.2 Hz, 1H), 4.21-4.07 (m, 4H), 4.08-3.84 (m, 4H), 3.73 (dd, J=12.7, 8.4 Hz, 1H), 3.51 (dd, J=12.6, 10.1 Hz, 1H), 1.72-1.09 (m, 26H), 0.98-0.84 (m, 12H). ³¹P NMR (162 MHz, Acetonitrile-d₃) δ 20.76. LCMS: MS m/z=678.30 [M+1]; t_R=1.69 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: t_R=6.81 min; HPLC system: 1290 Infinity II.; Column: Phenomenex 2.6µ C18 100A, 100×4.6 mm; Solvents: Acetonitrile with 0.1% TFA, Water with 0.1% TFA; Gradient: 0 min-8.5 min 2-98% ACN at 1.5 mL/min.

Example 18: Hexyl 1-((((((R)-1-(6-amino-9H-purin-9-yl)propan-2-yl)oxy)methyl)((1-(hexyloxy)-2-methyl-1-oxopropan-2-yl)amino)phosphoryl)amino)cyclobutane-1-carboxylate (18)

Example 19: Dihexyl 1,1'-(((((1-(6-amino-9H-purin-9-yl)propan-2-yl)oxy)methyl)phosphoryl)bis(azanediyl))(R)-bis(cyclobutane-1-carboxylate) (19)

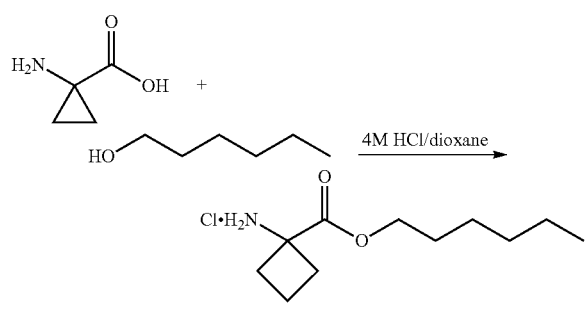

Synthesis hexyl 1-aminocyclobutane-1-carboxylate hydrochloride (18a)

To a mixture of 1-aminocyclobutane-1-carboxylic acid (1.5 g, 13.03 mmol) and n-hexanol (30 mL) was added 4M HCl in dioxane (6.5 mL, 26.06 mmol)) slowly at room temperature The resulting mixture was heated at 80° C. for 15 h, and concentrated at 65° C. under high vacuum. The solid residue was triturated with ether and the filter cake washed with ether and dried under high vacuum for 15 h to afford intermediate 18a. ¹H NMR (400 MHz, Acetonitrile-d₃) δ 8.74 (bs, 3H), 4.25 (t, J=6.5 Hz, 2H), 2.84-2.70 (m, 2H), 2.58 (m, 2H), 2.32-2.05 (m, 2H), 1.80-1.62 (m, 2H), 1.53-1.23 (m, 6H), 0.93 (m, 3H).

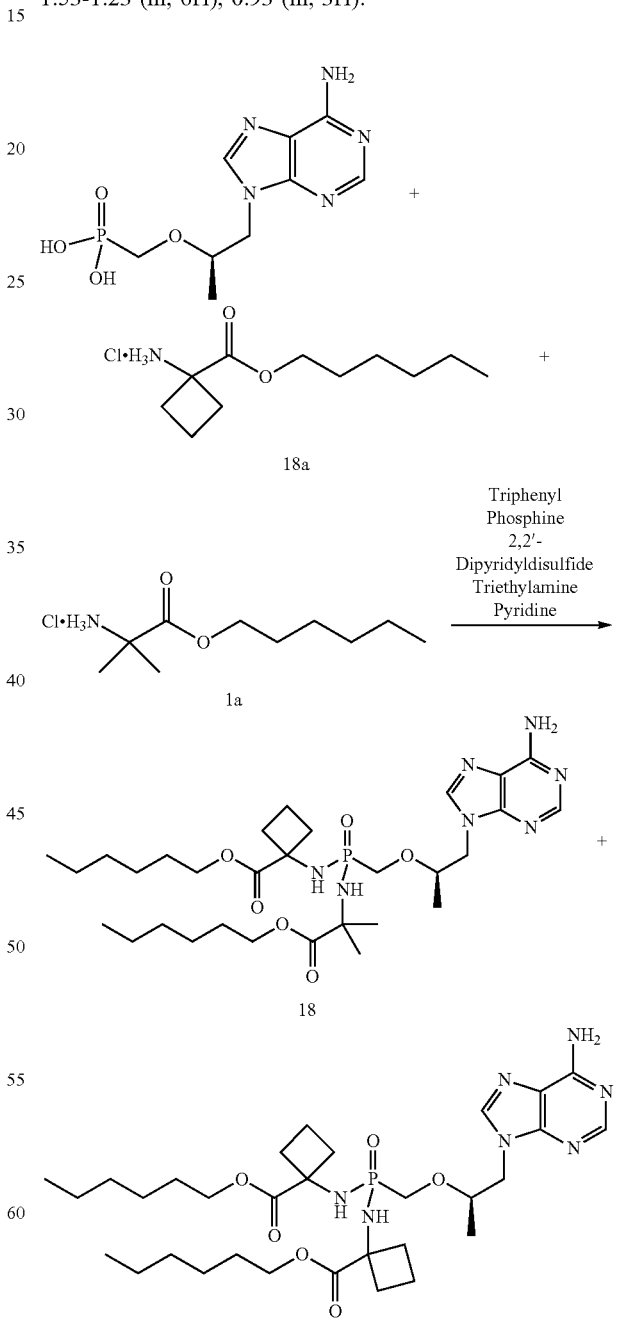

Compounds 18 and 19 were prepared from PMPA by a similar procedure used for 16 and 17.

18: $^1$H NMR (400 MHz, Acetonitrile-$d_3$) δ 8.22 (s, 1H), 8.06 (s, 1H), 6.31 (m, 2H), 4.34 (m, 1H), 4.23-4.02 (m, 5H), 4.01-3.85 (m, 2H), 3.82-3.60 (m, 2H), 3.47 (m, 1H), 2.68-2.23 (m, 4H), 2.03-1.82 (m, 2H), 1.73-1.56 (m, 4H), 1.53-1.25 (m, 18H), 1.17 (d, J=6.2 Hz, 3H), 0.96-0.84 (m, 6H). $^{31}$P NMR (162 MHz, Acetonitrile-d3) δ 18.31, 18.29. LCMS: MS m/z=638.38 [M+1]; $t_R$=1.77 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.50 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

19: $^1$H NMR (400 MHz, Acetonitrile-$d_3$) δ 8.22 (s, 1H), 8.04 (s, 1H), 6.23 (s, 2H), 4.34 (dd, J=14.5, 3.2 Hz, 1H), 4.22-4.01 (m, 5H), 4.02-3.86 (m, 2H), 3.82-3.66 (m, 2H), 3.49 (dd, J=12.7, 10.2 Hz, 1H), 2.65-2.30 (m, 8H), 2.01-1.80 (m, 4H), 1.65 (m, 4H), 1.49-1.24 (m, 12H), 1.17 (d, J=6.2 Hz, 3H), 0.98-0.85 (m, 6H). $^{31}$P NMR (162 MHz, Acetonitrile-$d_3$) δ 18.78. LCMS: MS m/z=650.37 [M+1]; $t_R$=1.79 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.56 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 20: Hexyl 1-((((((R)-1-(6-amino-9H-purin-9-yl)propan-2-yl)oxy)methyl)((1-(hexyloxy)-2-methyl-1-oxopropan-2-yl)amino)phosphoryl)amino)cyclopropane-1-carboxylate (20)

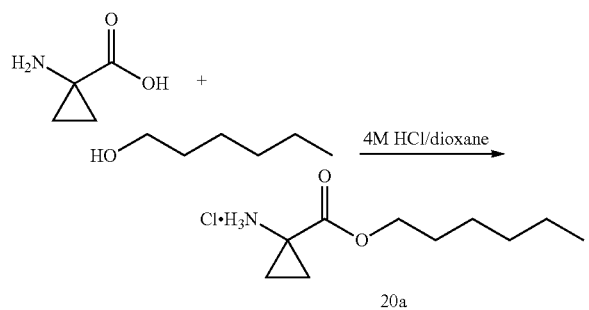

Synthesis of hexyl 1-aminocyclopropane-1-carboxylate hydrochloride (20a)

Intermediate 20a was obtained from 1-aminocyclopropane-1-carboxylic acid in a similar method shown for intermediate 18a. $^1$H NMR (400 MHz, Acetonitrile-$d_3$) δ 8.52 (bs, 3H), 4.17 (t, J=6.6 Hz, 2H), 1.75-1.58 (m, 4H), 1.52-1.42 (m, 2H), 1.43-1.28 (m, 6H), 1.03-0.82 (m, 3H).

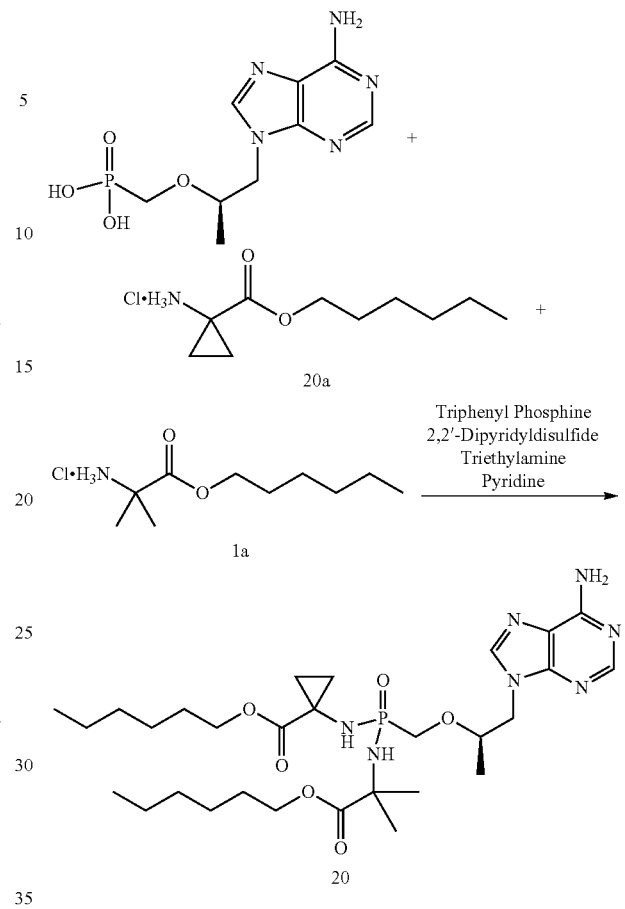

A mixture of PMPA (170 mg, 0.59 mmol), intermediate 1a (199 mg, 0.89 mmol), 2,2'-dipyridyldisulfide (782 mg, 3.55 mmol), triphenylphosphine (931 mg, 3.55 mmol), and triethylamine (0.66 mL, 4.74 mmol) in pyridine (3 mL) was heated to 70° C. for 1 h. Intermediate 20a (197 mg, 0.89 mmol) in pyridine (1 mL) was added and the reaction mixture stirred at 70° C. for 18 h. Upon concentration in vacuo the residue was purified by silica gel column chromatography (MeOH 0 to 15% in DCM) and prep. HPLC (ACN 10 to 100% in water for 12 min, 100% ACN for 5 min) to afford the title compound (20). $^1$H NMR (400 MHz, Acetonitrile-$d_3$) δ 8.25-8.20 (m, 1H), 8.10-8.06 (m, 1H), 6.48 (s, 2H), 4.42-4.26 (m, 2H), 4.24-3.82 (m, 7H), 3.71 (m, 1H), 3.57-3.42 (m, 1H), 1.73-1.21 (m, 26H), 1.16 (d, J=6.2 Hz, 3H), 0.95-0.81 (m, 6H). $^{31}$P NMR (162 MHz, Acetonitrile-$d_3$) δ 19.92, 19.85. LCMS. MS m/z=624.30 [M+1]; $t_R$=1.76 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.21 min (43%), 6.28 min (54%); HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

Example 21: Bis(trans-4-(trifluoromethyl)cyclohexyl) 2,2'-(((((R)-1-(6-amino-9H-purin-9-yl)propan-2-yl)oxy)methyl)phosphoryl)bis(azanediyl))bis(2-methylpropanoate) (21)

Example 22: Hexyl 2-(((((R)-1-(6-amino-9H-purin-9-yl)propan-2-yl)oxy)methyl)((2-methyl-1-oxo-1-((trans-4-(trifluoromethyl)cyclohexyl)oxy)propan-2-yl)amino)phosphoryl)amino)-2-methylpropanoate (22)

Synthesis of trans-4-(trifluoromethyl)cyclohexyl 2-((tert-butoxycarbonyl)amino)-2-methylpropanoate (21a)

To a mixture of 2-((tert-butoxycarbonyl)amino)-2-methylpropanoic acid (650 mg, 3.20 mmol), trans-4-(trifluoromethyl)cyclohexan-1-ol (1076 mg, 6.40 mmol), and 1-ethyl-3-(3-dimethylaminopropyl)carbodiimide, hydrochloride (993 mg, 6.40 mmol) in acetonitrile (30 mL) was added DMAP (781 mg, 6.40 mmol). The mixture was stirred at room temperature for 15 h, quenched with water, and concentrated in vacuo. The obtained residue was purified by silica gel chromatography (EtOAc 0 to 70% in hexane) to afford intermediate 21a. $^1$H NMR (400 MHz, Acetonitrile-$d_3$) δ 5.60 (bs, 1H), 4.66 (m, 1H), 2.27-2.09 (m, 1H), 2.07-1.91 (m, 4H), 1.59-1.30 (m, 19H).

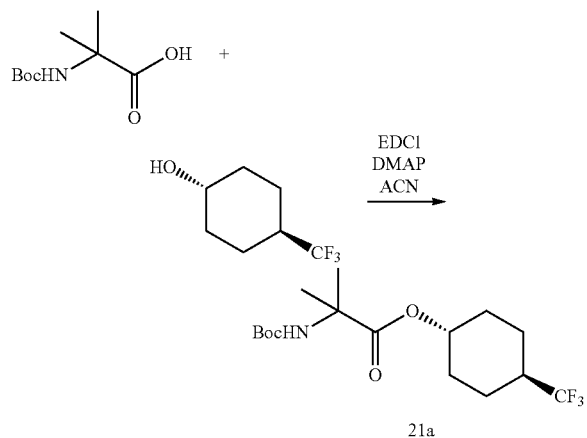

Synthesis of trans-4-(trifluoromethyl)cyclohexyl 2-amino-2-methylpropanoate hydrochloride (21b)

To a solution of intermediate 21a (451 mg, 1.28 mmol) in DCM (10 mL) was added 4M HCl in dioxane (1.6 mL) slowly at room temperature. The resulting mixture was stirred at room temperature for 15 h, concentrated in vacuo, co-evaporated with DCM several times, and dried under high vacuum for 15 h to afford intermediate 21b. $^1$H NMR (400 MHz, Acetonitrile-$d_3$) δ 8.62 (bs, 3H), 4.79 (m, 1H), 2.20 (s, 1H), 2.10 (d, J=4.9 Hz, 2H), 2.07-1.99 (m, 2H), 1.65 (s, 6H), 1.54-1.44 (m, 4H).

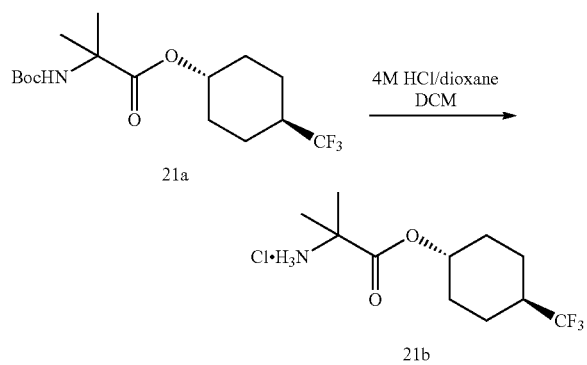

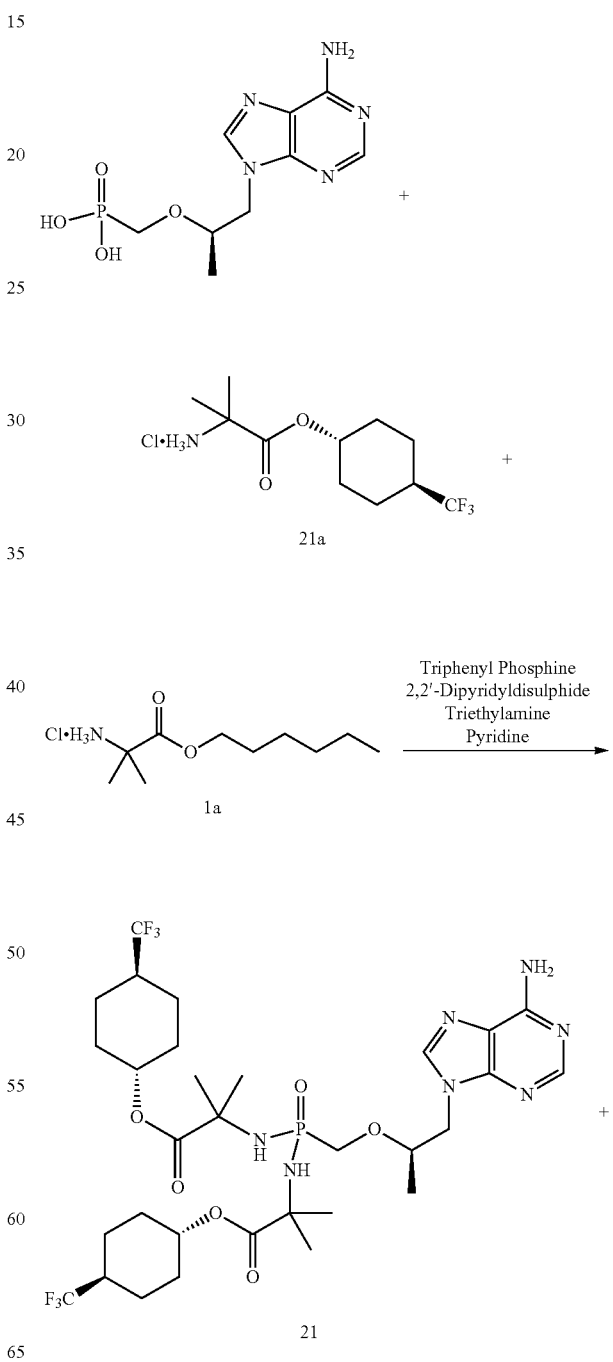

149

-continued

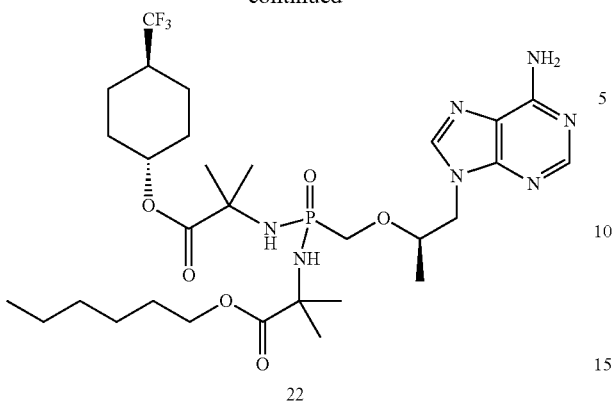

22

A mixture of PMPA (100 mg, 0.348 mmol), intermediate 21b (303 mg, 1.04 mmol), 2,2'-dipyridyldisulfide (460 mg, 2.089 mmol), triphenylphosphine (548 mg, 2.089 mmol), and triethylamine (0.4 mL, 2.785 mmol) in pyridine (2 mL) was heated at 80° C. for 3 h and intermediate 1a (117 mg, 0.522 mmol) in pyridine (0.5 mL) added. The mixture was heated at 80° C. for 15 h, concentrated in vacuo, and purified by silica gel column chromatography (MeOH 0 to 15% in DCM) to afford a mixture of two products which were separated by prep HPLC (ACN 10 to 100% in water for 12 min, 100% for 5 min) to afford 21 and 22.

21: $^1$H NMR (400 MHz, Acetonitrile-$d_3$) δ 8.24 (s, 1H), 8.07 (s, 1H), 6.35 (s, 2H), 4.66 (m, 2H), 4.34 (dd, J=14.5, 3.2 Hz, 1H), 4.17 (dd, J=14.5, 7.1 Hz, 1H), 3.94 (m, 1H), 3.77-3.62 (m, 2H), 3.55 (d, J=10.7 Hz, 1H), 3.47 (dd, J=12.6, 9.8 Hz, 1H), 2.18 (m, 2H), 2.10-1.89 (m, 8H), 1.57-1.27 (m, 20H), 1.19 (d, J=6.2 Hz, 3H). $^{31}$P NMR (162 MHz, Acetonitrile-$d_3$) δ 17.89. LCMS: MS m/z=758.27 [M+1]; $t_R$=1.70 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.12 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

22: $^1$H NMR (400 MHz, Acetonitrile-$d_3$) δ 8.23 (s, 1H), 8.06 (s, 1H), 6.17 (s, 2H), 4.75-4.55 (m, 1H), 4.37-4.30 (m, 1H), 4.24-4.01 (m, 3H), 3.93 (m, 1H), 3.75 (m, 1H), 3.67 (m, 1H), 3.56 (m, 1H), 3.45 (m, 1H), 2.26-2.11 (m, 1H), 2.10-1.90 (m, 4H), 1.63 (m, 2H), 1.56-1.23 (m, 22H), 1.18 (m, 3H), 0.96-0.80 (m, 3H). $^{31}$P NMR (162 MHz, Acetonitrile-d3) δ 17.96, 17.90. LCMS: MS m/z=692.25 [M+1]; $t_R$=1.74 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.25 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

150

Example 23: Hexyl (((((R)-1-(6-amino-9H-purin-9-yl)propan-2-yl)oxy)methyl)((2-methyl-1-oxo-1-((tetrahydro-2H-pyran-4-yl)oxy)propan-2-yl)amino) phosphoryl)-L-phenylalaninate (23)

Example 24: Bis(tetrahydro-2H-pyran-4-yl) 2,2'-(((((1-(6-amino-9H-purin-9-yl)propan-2-yl)oxy) methyl)phosphoryl)bis(azanediyl))(R)-bis(2-methylpropanoate) (24)

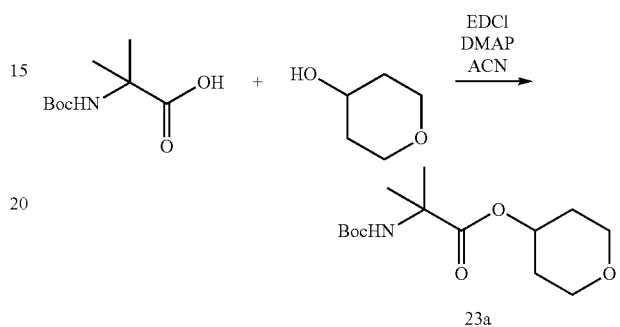

23a

Synthesis of tetrahydro-2H-pyran-4-yl-2-((tert-butoxycarbonyl)amino)-2-methylpropanoate (23a)

To a mixture of 2-((tert-butoxycarbonyl)amino)-2-methylpropanoic acid (1.0 g, 4.92 mmol), tetrahydro-2H-pyran-4-ol (0.70 mL, 7.381 mmol), and 1-ethyl-3-(3-dimethylaminopropyl)carbodiimide, hydrochloride (1.15 g, 7.381 mmol) in acetonitrile (20 mL) was added DMAP (1.20 g, 9.84 mmol). The mixture was stirred at room temperature for 15 h, quenched with water, and concentrated in vacuo. The obtained residue was purified by silica gel chromatography (EtOAc 0 to 50% in hexanes) to afford intermediate 23a. $^1$H NMR (400 MHz, Acetonitrile-$d_3$) δ 5.62 (s, 1H), 4.92 (m, 1H), 3.83 (m, 2H), 3.53 (m, 2H), 1.88 (m, 2H), 1.59 (m, 2H), 1.77-1.59 (m, 15H).

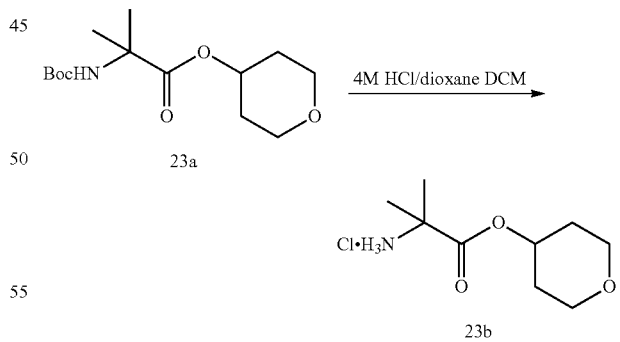

Synthesis of tetrahydro-2H-pyran-4-yl-2-amino-2-methylpropanoate hydrochloride (23b)

To a solution of intermediate 23a (490 mg, 1.71 mmol) in DCM (10 mL) was added 4M HCl in dioxane (2 mL) slowly at room temperature. The resulting mixture was stirred at room temperature for 15 h, concentrated in vacuo, co-evaporated with DCM several times, and dried under high vacuum for 15 h to afford intermediate 23b. $^1$H NMR (400 MHz, Acetonitrile-$d_3$) δ 8.48 (bs, 3H), 5.06 (m, 1H), 3.89 (m, 2H), 3.55 (m, 2H), 1.92 (m, 2H), 1.76-1.59 (m, 8H).

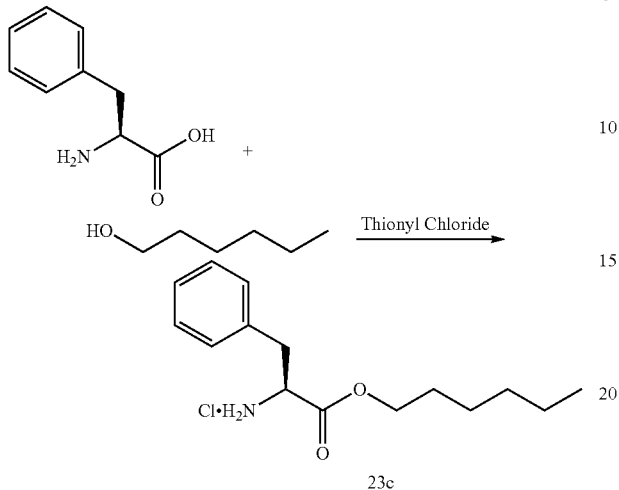

Synthesis of hexyl L-phenylalaninate hydrochloride (23c)

To a mixture of L-phenylalanine (2.5 g, 15.1 mmol) and n-hexanol (30 mL) was added $SOCl_2$ (4.4 mL, 60.5 mmol) slowly at room temperature. The resulting mixture was heated at 80° C. for 15 h and concentrated at 65° C. under high vacuum. Upon cooling, the product was precipitated and filtered. The filter cake was suspended in ether, stirred overnight, filtered, and dried under high vacuum for 24 h to afford intermediate 23c. $^1$H NMR (400 MHz, Methanol-$d_4$) δ 7.42-7.29 (m, 3H), 7.28-7.22 (m, 2H), 4.29 (t, J=7.0 Hz, 1H), 4.17 (m, 2H), 3.21 (m, 2H), 1.58 (m, 2H), 1.35-1.25 (m, 6H), 0.91 (t, J=6.85 Hz, 3H).

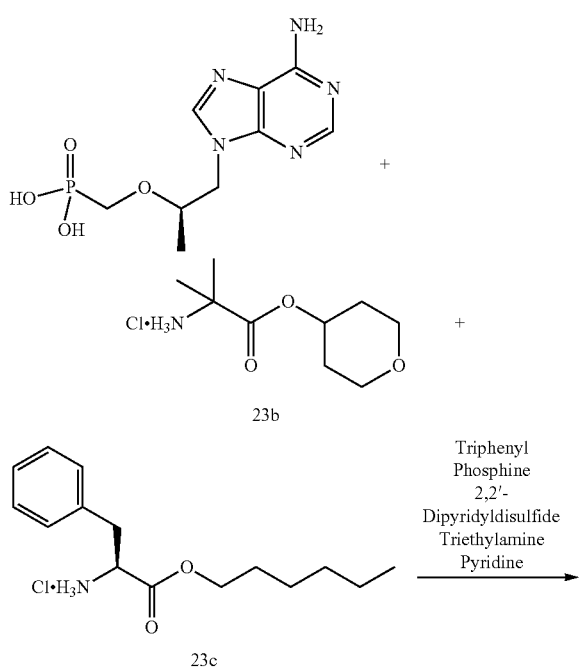

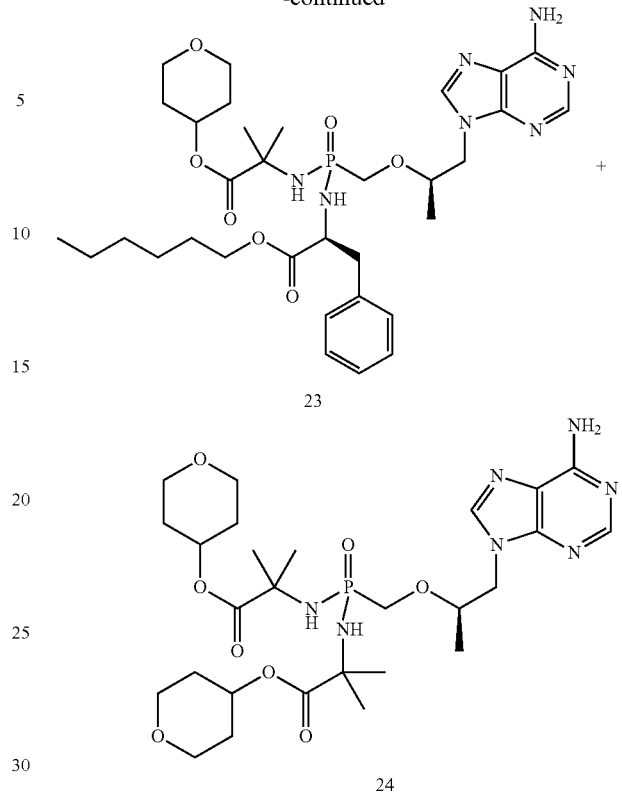

A mixture of PMPA (100 mg, 0.348 mmol) and intermediate 23b (156 mg, 0.696 mmol) was flushed with nitrogen several times and dissolved in pyridine (2 mL). Triphenylphosphine (548 mg, 2.09 mmol), 2,2'-dipyridyldisulfide (460 mg, 2.09 mmol), and triethylamine (0.39 mL, 2.79 mmol) were added. The resulting mixture was heated to 80° C. for 40 min. Intermediate 23c (299 mg, 1.04 mmol) in pyridine (0.5 mL) was added. The mixture was heated at 80° C. for 3 h, concentrated in vacuo, and purified by silica gel chromatography (MeOH 0 to 25% in DCM) to two products which were further purified by HPLC (ACN 10 to 100% in water for 12 min, ACN 100% for 5 min for 23 and ACN 10 to 100% in water for 17 min for 24) to afford 23 and 24.

23: $^1$H NMR (400 MHz, Acetonitrile-$d_3$) δ 8.27 (s, 0.5H), 8.25 (s, 0.5H), 8.08 (s, 0.5H), 8.03 (s, 0.5H), 7.33-7.16 (m, 5H), 6.87-6.55 (m, 2H), 4.89 (m, 1H), 4.39-3.95 (m, 4H), 3.94-3.68 (m, 4H), 3.61 (dd, J=12.8, 8.8 Hz, 0.5H), 3.54-3.41 (m, 3.5H), 3.24 (dd, J=12.7, 10.4 Hz, 0.5H), 3.15 (d, J=11.3 Hz, 0.5H), 3.06-2.90 (m, 1.5H), 2.82 (dd, J=13.5, 8.1 Hz, 0.5H), 1.92-1.77 (m, 2H), 1.65-1.46 (m, 4H), 1.43-1.19 (m, 12H), 1.11 (t, J=6.0 Hz, 3H), 0.92-0.83 (m, 3H). $^{31}$P NMR (162 MHz, Acetonitrile-$d_3$) δ 19.52, 19.39. LCMS: MS m/z=688.31 [M+1]; $t_R$=1.57 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=5.57 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

24: $^1$H NMR (400 MHz, Acetonitrile-d$_3$) δ 8.23 (s, 1H), 8.05 (s, 1H), 5.99 (s, 2H), 4.92 (m, 2H), 4.34 (dd, J=14.5, 3.3 Hz, 1H), 4.17 (dd, J=14.5, 7.1 Hz, 1H), 3.94 (m, 1H), 3.82 (dt, J=10.6, 5.7 Hz, 4H), 3.75 (d, J=10.7 Hz, 1H), 3.67 (dd, J=12.7, 8.8 Hz, 1H), 3.59-3.42 (m, 6H), 1.89 (m, 4H), 1.62 (m, 4H), 1.54 (s, 3H), 1.47 (s, 6H), 1.40 (s, 3H), 1.19 (d, J=6.2 Hz, 3H). $^{31}$P NMR (162 MHz, Acetonitrile-d$_3$) δ 17.90. LCMS: MS m/z=626.18 [M+1]; t$_R$=1.21 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=3.81 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 25: Bis(5,5,5-trifluoropentyl) 2,2'-(((((1-(6-amino-9H-purin-9-yl)propan-2-yl)oxy)methyl)phosphoryl)bis(azanediyl))(R)-bis(2-methylpropanoate) (25)

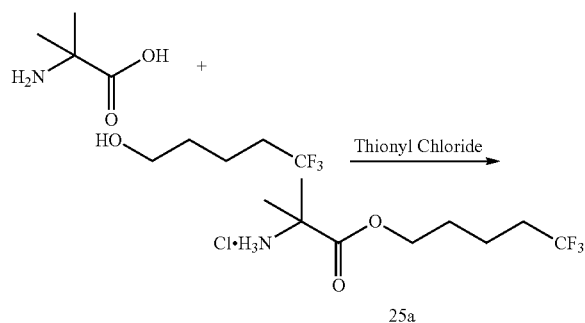

Synthesis of 5,5,5-trifluoropentyl-2-amino-2-methylpropanoate hydrochloride (25a)

To a mixture of 2-amino-2-methylpropanoic acid (600 mg, 5.82 mmol) and 5,5,5-trifluoropentan-1-ol (5.0 g, 35.2 mmol) was added SOCl$_2$ (0.72 mL, 9.89 mmol)) slowly at room temperature. The resulting mixture was heated at 80° C. for 15 h and concentrated at 70° C. under high vacuum. Hexane was added to the obtained residue which was stirred for 30 min and the precipitated solid filtered. The filter cake was washed with ether several times and dried under high vacuum for 15 h to afford intermediate 25a. $^1$H NMR (400 MHz, Acetonitrile-d$_3$) δ 8.69 (bs, 3H), 4.23 (t, J=6.2 Hz, 2H), 2.25 (m, 2H), 1.86-1.73 (m, 2H), 1.72-1.59 (m, 8H). $^{19}$F NMR (376 MHz, Acetonitrile-d$_3$) δ −67.50.

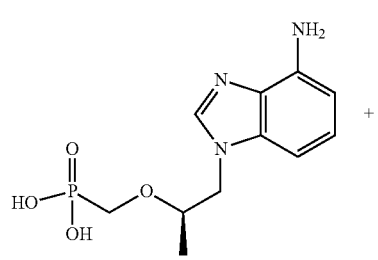

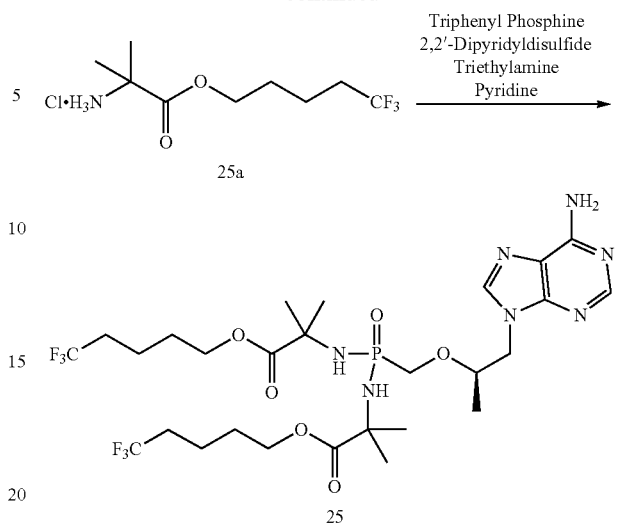

A mixture of PMPA (500 mg, 1.74 mmol), intermediate 25a (1.51 g, 5.74 mmol), 2,2'-dipyridyldisulfide (2.30 g, 10.4 mmol), triphenylphosphine (2.74 g, 10.4 mmol) was flushed with nitrogen gas several times, dissolved in pyridine (10 mL), and triethylamine (0.4 mL, 2.785 mmol) was added. The resulting mixture was heated at 90° C. for 20 h, concentrated in vacuo, and purified by silica gel column chromatography (MeOH 0 to 20% in DCM) and by prep HPLC (ACN 10 to 100% in water for 12 min, ACN 100% for 5 min) to afford the title compound (25). $^1$H NMR (400 MHz, Acetonitrile-d3) δ 8.24 (s, 1H), 8.06 (s, 1H), 6.15 (s, 2H), 4.34 (dd, J=14.4, 3.2 Hz, 1H), 4.22-4.03 (m, 5H), 3.94 (m, 1H), 3.77-3.61 (m, 2H), 3.56 (d, J=10.6 Hz, 1H), 3.44 (dd, J=12.7, 9.8 Hz, 1H), 2.22 (m, 4H), 1.82-1.56 (m, 8H), 1.53 (s, 3H), 1.46 (s, 3H), 1.45 (s, 3H), 1.39 (s, 3H), 1.19 (d, J=6.3 Hz, 3H). $^{19}$F NMR (376 MHz, Acetonitrile-d$_3$) 6-67.52 (d, J=5.3 Hz). $^{31}$P NMR (162 MHz, Acetonitrile-d3) δ 17.83. LCMS: MS m/z=706.31 [M+1]; t$_R$=1.57 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=5.53 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

Example 26: Bis(trans-3-(trifluoromethyl)cyclobutyl) 2,2'-((((((R)-1-(6-amino-9H-purin-9-yl)propan-2-yl)oxy)methyl)phosphoryl)bis(azanediyl))bis(2-methylpropanoate) (26)

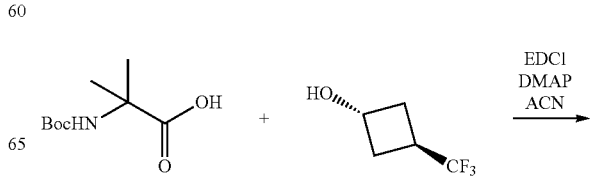

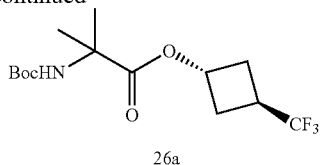

26a

Synthesis of trans-3-(trifluoromethyl)cyclobutyl-2-((tert-butoxycarbonyl)amino)-2-methylpropanoate (26a)

To a mixture of trans-3-(trifluoromethyl)cyclobutan-1-ol (1.0 g, 7.14 mmol), 2-((tert-butoxycarbonyl)amino)-2-methylpropanoic acid (2.9 g, 14.3 mmol), and DMAP (1.9 g, 15.7 mmol) in acetonitrile (30 mL) was added 1-ethyl-3-(3-dimethylaminopropyl)carbodiimide, hydrochloride (2.44 g, 15.7 mmol) at room temperature The mixture was stirred at room temperature for 2 h at room temperature, quenched with water, and concentrated in vacuo. The obtained residue was purified by silica gel chromatography (EtOAc 0 to 70% in hexane) to afford intermediate 26a. $^1$H NMR (400 MHz, Acetonitrile-d$_3$) δ 5.68 (s, 1H), 5.05 (m, 1H), 3.06 (m, 1H), 2.56 (m, 2H), 2.40 (m, 2H), 1.59-0.92 (m, 15H). $^{19}$F NMR (376 MHz, Acetonitrile-d$_3$) δ −74.34. LCMS: MS m/z=325.59 [M+1]; t$_R$=1.84 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

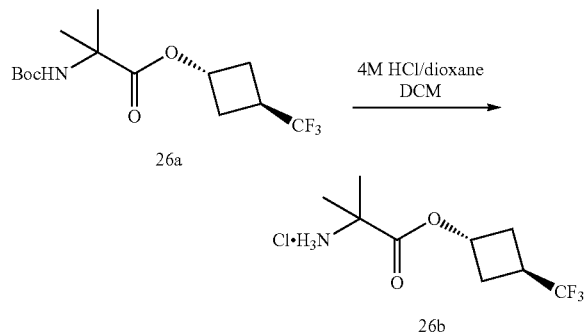

Synthesis of trans-3-(trifluoromethyl)cyclobutyl 2-amino-2-methylpropanoate hydrochloride (26b)

To a solution of intermediate 26a (1.96 g, 6.02 mmol) in DCM (10 mL) was added 4M HCl in dioxane (7.53 mL) slowly at room temperature. The resulting mixture was stirred at room temperature for 3 h, concentrated in vacuo, co-evaporated with DCM several times, suspended in ether, stirred for 5 min, and filtered. The filter cake was washed with ether several times and dried under high vacuum for 15 h to afford intermediate 26b. $^1$H NMR (400 MHz, Acetonitrile-d$_3$) δ 8.70 (bs, 3H), 5.18 (t, J=6.6 Hz, 1H), 3.20 (m, 1H), 2.66-2.49 (m, 2H), 2.40-2.25 (m, 2H), 1.74-1.57 (m, 6H). LCMS: MS m/z=226.02 [M+1-HCl]; t$_R$=0.96 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

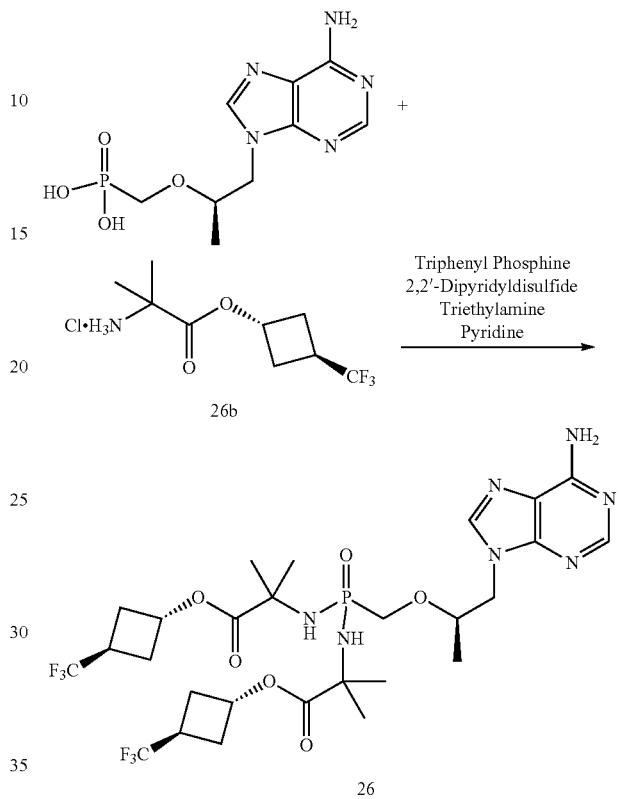

A mixture of PMPA (300 mg, 1.04 mmol), intermediate 26b (600 mg, 2.29 mmol), 2,2'-dipyridyldisulfide (768 mg, 3.48 mmol), and triphenylphosphine (914 mg, 3.48 mmol) was flushed with nitrogen several times and dissolved in pyridine (5 mL). Triethylamine (0.8 mL, 5.77 mmol) were added. The resulting mixture was stirred at 90° C. for 20 h, concentrated in vacuo, co-evaporated with toluene several times, and purified with silica gel chromatography (MeOH 0 to 20% in DCM), and by prep. HPLC (ACN 10 to 100% in water for 12 min, ACN 100% for 5 min) to afford the title compound (26). $^1$H NMR (400 MHz, Acetonitrile-d$_3$) δ 8.24 (s, 1H), 8.03 (s, 1H), 5.91 (s, 2H), 5.06 (m, 2H), 4.34 (dd, J=14.5, 3.2 Hz, 1H), 4.17 (dd, J=14.5, 7.3 Hz, 1H), 3.94 (m, 1H), 3.73-3.63 (m, 2H), 3.55-3.35 (m, 2H), 3.11 (m, 2H), 2.65-2.51 (m, 2H), 2.51-2.36 (m, 2H), 1.53 (s, 3H), 1.47 (s, 3H), 1.43 (s, 3H), 1.40 (s, 3H), 1.20 (d, J=6.2 Hz, 3H). $^{19}$F NMR (376 MHz, Acetonitrile-d$_3$) δ-74.27. $^{31}$P NMR (162 MHz, Acetonitrile-d$_3$) δ 18.10. LCMS: MS m/z=702.22 [M+1]; t$_R$=1.37 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=5.50 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 27: Bis((trans-4-propylcyclohexyl) 2,2'-(((((R)-1-(6-amino-9H-purin-9-yl)propan-2-yl)oxy)methyl)phosphoryl)bis(azanediyl))bis(2-methylpropanoate) (27)

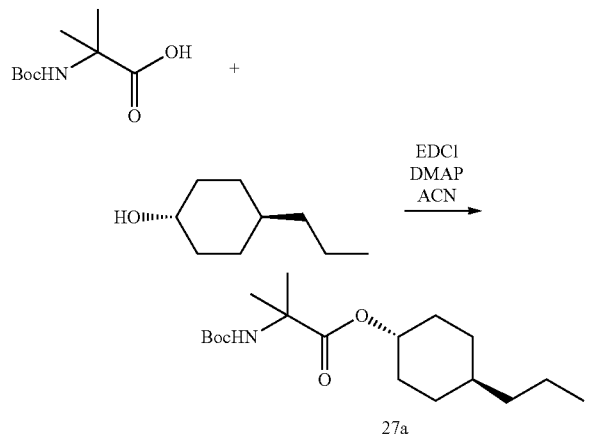

27a

Synthesis of trans-4-propylcyclohexyl 2-((tert-butoxycarbonyl)amino)-2-methylpropanoate (27a)

To a mixture of trans-4-propylcyclohexan-1-ol (1.0 g, 7.03 mmol), 2-((tert-butoxycarbonyl)amino)-2-methylpropanoic acid (2.14 g, 10.5 mmol), and DMAP (1.72 g, 14.1 mmol) in acetonitrile (30 mL) was added 1-ethyl-3-(3-dimethylaminopropyl)carbodiimide, hydrochloride (2.18 g, 14.1 mmol) at room temperature The mixture was stirred at room temperature for 15 h at room temperature, quenched with water, and concentrated in vacuo. The obtained residue was dissolved in EtOAc, washed with brine, dried with sodium sulfate, and concentrated in vacuo, and purified by silica gel chromatography (EtOAc 0 to 70% hexane) to afford intermediate 27a. $^1$H NMR (400 MHz, Acetonitrile-d$_3$) δ 5.58 (bs, 1H), 4.61 (m, 1H), 1.96-1.83 (m, 2H), 1.85-1.73 (m, 2H), 1.45-1.14 (m, 22H), 1.05 (m, 2H), 0.90 (t, J=7.3 Hz, 3H). LCMS: MS m/z=327.77 [M+1]; t$_R$=1.98 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

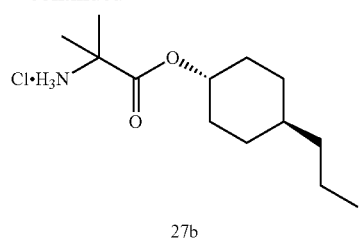

27b

Synthesis of trans-4-propylcyclohexyl 2-amino-2-methylpropanoate hydrochloride (27b)

To a solution of intermediate 27a (1.46 g, 4.46 mmol) in DCM (10 mL) was added 4M HCl in dioxane (6 mL) slowly at room temperature. The resulting mixture was stirred at room temperature for 4 h, concentrated in vacuo, co-evaporated with DCM several times, suspended in ether, stirred for 5 min, and filtered. The filter cake was washed with ether several times and dried under high vacuum for 15 h to afford intermediate 27b. $^1$H NMR (400 MHz, Chloroform-d) δ 8.98 (bs, 3H), 4.76 (m, 1H), 2.02 (m, 2H), 1.80 (m, 2H), 1.72 (s, 6H), 1.48 (m, 2H), 1.38-1.12 (m, 5H), 0.99 (m, 2H), 0.89 (t, J=7.2 Hz, 3H). LCMS: MS m/z=227.89 [M+1-HCl]; t$_R$=1.19 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

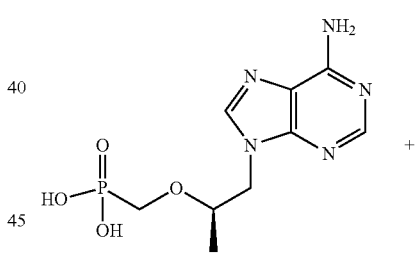

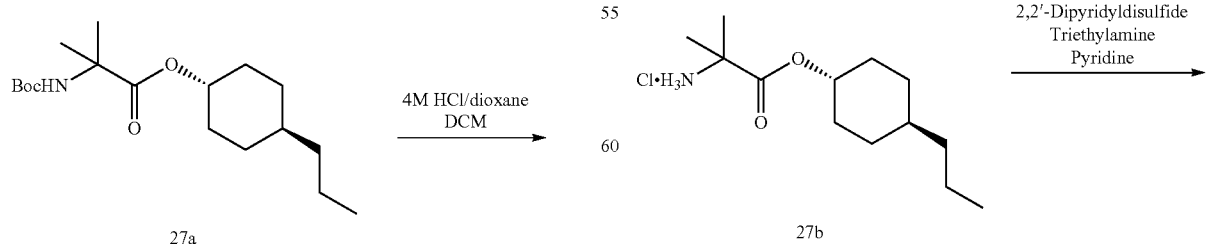

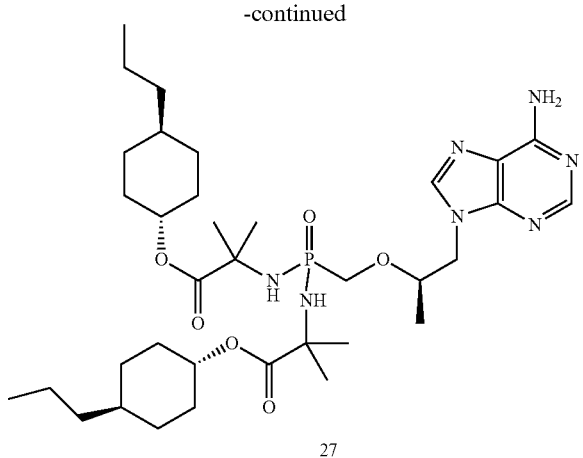

27

A mixture of PMPA (300 mg, 1.04 mmol), intermediate 27b (600 mg, 2.27 mmol), 2,2'-dipyridyldisulfide (768 mg, 3.49 mmol) and triphenylphosphine (914 mg, 3.49 mmol) was flushed with nitrogen several times and dissolved in pyridine (5 mL). Triethylamine (0.8 mL, 5.77 mmol) were added. The resulting mixture was stirred at 90° C. for 20 h, concentrated in vacuo, co-evaporated with toluene several times, and purified with silica gel (MeOH 0 to 15% in DCM) to afford the title compound (27). $^1$H NMR (400 MHz, Acetonitrile-$d_3$) δ 8.24 (s, 1H), 8.06 (s, 1H), 6.01 (s, 2H), 4.62 (m, 2H), 4.34 (dd, J=14.5, 3.2 Hz, 1H), 4.17 (dd, J=14.5, 7.0 Hz, 1H), 3.94 (m, 1H), 3.74 (d, J=10.6 Hz, 1H), 3.66 (dd, J=12.7, 8.9 Hz, 1H), 3.55 (d, J=10.7 Hz, 1H), 3.46 (dd, J=12.6, 9.8 Hz, 1H), 1.96-1.87 (m, 4H), 1.85-1.72 (m, 4H), 1.57-0.95 (m, 33H), 0.91 (t, J=7.3 Hz, 6H). $^{31}$P NMR (162 MHz, Acetonitrile-$d_3$) δ 17.59. LCMS: MS m/z=706.37 [M+1]; $t_R$=1.89 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.84 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

Example 28: Dihexyl 2,2'-(((((1-(6-acetamido-9H-purin-9-yl)propan-2-yl)oxy)methyl)phosphoryl)bis(azanediyl))(R)-bis(2-methylpropanoate) (28)

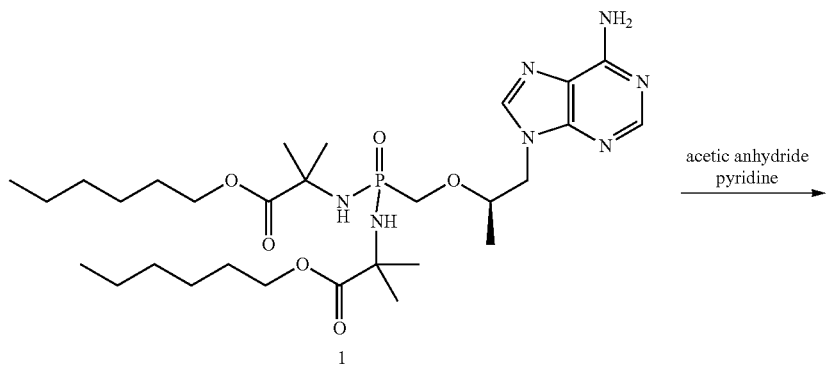

1

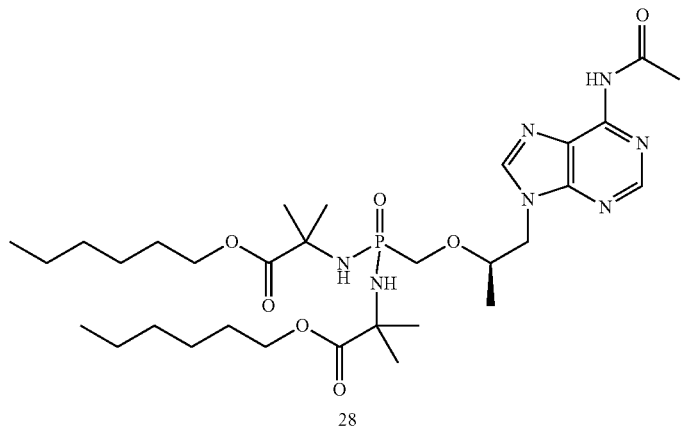

28

To a solution of 1 (100 mg, 0.210 mmol) in pyridine (1 mL) was added acetic anhydride (0.03 mL, 0.320 mmol). The resulting mixture was stirred at room temperature for 2 h and purified by prep. HPLC (ACN 10-100% in water for 8 min, ACN 100% for 18 min) to afford the title compound (28). $^1$H NMR (400 MHz, Acetonitrile-$d_3$) δ 9.13 (s, 1H), 8.61 (s, 1H), 8.34 (s, 1H), 4.43 (dd, J=14.5, 3.2 Hz, 1H), 4.26 (dd, J=14.5, 7.1 Hz, 1H), 4.17-4.01 (m, 4H), 3.97 (m, 1H), 3.75 (d, J=10.8 Hz, 1H), 3.69 (dd, J=12.8, 8.6 Hz, 1H), 3.59 (d, J=10.8 Hz, 1H), 3.45 (dd, J=12.7, 9.8 Hz, 1H), 2.48 (s, 3H), 1.62 (m, 4H), 1.52 (s, 3H), 1.45 (s, 6H), 1.42-1.23 (m, 15H), 1.20 (d, J=6.3 Hz, 3H), 0.95-0.88 (m, 6H). $^{31}$P NMR (162 MHz, Acetonitrile-d3) δ 17.75. LCMS: MS m/z=668.42 [M+1]; $t_R$=1.90 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.66 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 29: Dihexyl 2,2'-(((((1-(6-butyramido-9H-purin-9-yl)propan-2-yl)oxy)methyl)phosphoryl)bis(azanediyl))(R)-bis(2-methylpropanoate) (29)

To a solution of 1 (100 mg, 0.210 mmol) in pyridine (1 mL) was added butyryl chloride (0.033 mL, 0.320 mmol). The resulting mixture was stirred at room temperature for 2 h and purified by prep. HPLC (ACN 10-100% in water for 8 min, 100% for 15 min) to afford the title compound (29). $^1$H NMR (400 MHz, Acetonitrile-$d_3$) δ 8.98 (s, 1H), 8.61 (s, 1H), 8.32 (s, 1H), 4.43 (dd, J=14.5, 3.1 Hz, 1H), 4.25 (dd, J=14.5, 7.2 Hz, 1H), 4.17-4.01 (m, 4H), 3.96 (m, 1H), 3.78-3.64 (m, 2H), 3.57 (d, J=10.8 Hz, 1H), 3.44 (dd, J=12.7, 9.9 Hz, 1H), 2.77 (t, J=7.4 Hz, 2H), 1.74 (m, 2H), 1.63 (m, 4H), 1.52 (s, 3H), 1.48-1.42 (m, 6H), 1.43-1.23 (m, 15H), 1.20 (d, J=6.2 Hz, 3H), 1.02 (t, J=7.4 Hz, 3H), 0.96-0.84 (m, 6H). $^{31}$P NMR (162 MHz, Acetonitrile-d3) δ 17.756. LCMS: MS m/z=696.31 [M+1]; $t_R$=2.02 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.02 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

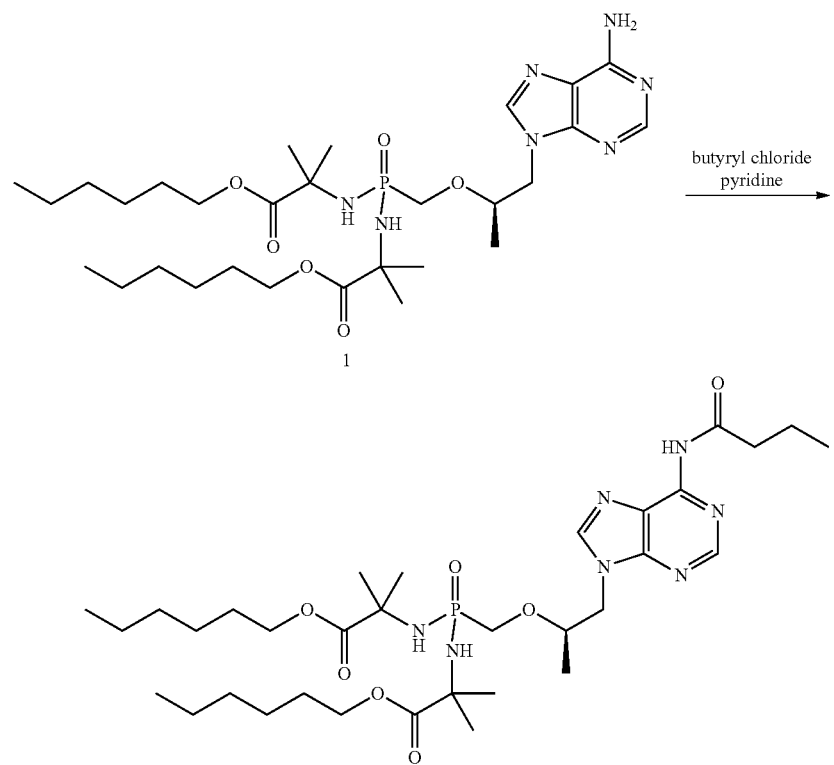

Example 30: Dihexyl 2,2'-(((((1-(6-dodecanamido-9H-purin-9-yl)propan-2-yl)oxy)methyl)phosphoryl)bis(azanediyl))(R)-bis(2-methylpropanoate) (30)

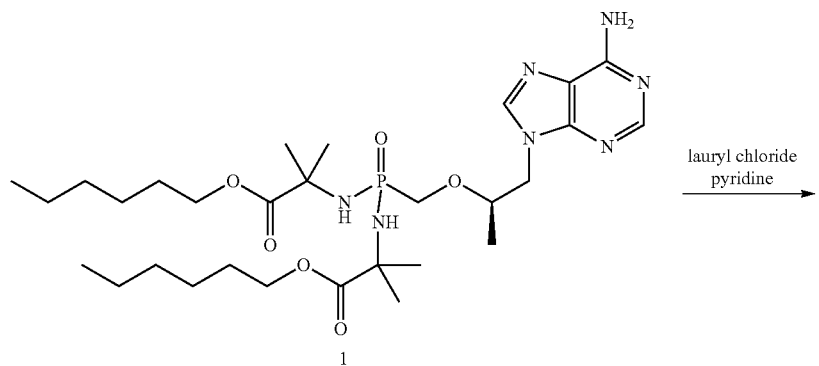

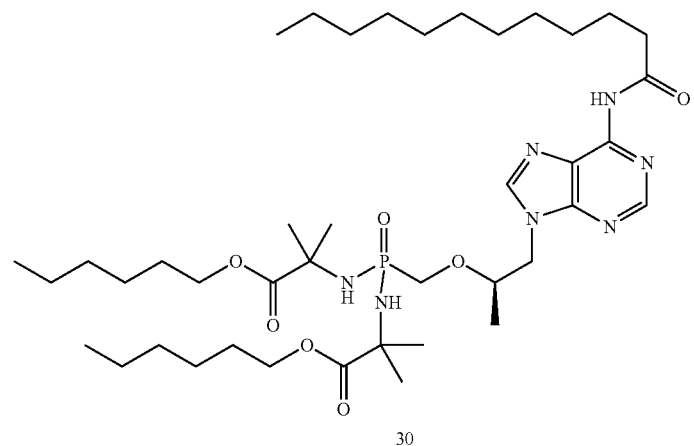

To a solution of 1 (100 mg, 0.210 mmol) in pyridine (1 mL) was added lauryl chloride (0.07 mL, 0.320 mmol). The resulting mixture was stirred at room temperature for 2 h, quenched by adding methanol, concentrated in vacuo, and purified by silica gel chromatography (MeOH 0-15% in DCM) to afford the title compound (30). $^1$H NMR (400 MHz, Acetonitrile-d$_3$) δ 8.96 (s, 1H), 8.61 (s, 1H), 8.31 (s, 1H), 4.43 (dd, J=14.5, 3.1 Hz, 1H), 4.30-4.23 (m, 1H), 4.17-4.01 (m, 4H), 3.96 (m, 1H), 3.77-3.64 (m, 2H), 3.54 (d, J=10.8 Hz, 1H), 3.43 (dd, J=12.7, 9.9 Hz, 1H), 2.78 (t, J=7.5 Hz, 2H), 1.78-1.53 (m, 6H), 1.52 (s, 3H), 1.46-1.40 (m, 6H), 1.40-1.25 (m, 31H), 1.20 (d, J=6.2 Hz, 3H), 0.93-0.83 (m, 9H). $^{31}$P NMR (162 MHz, Acetonitrile-d$_3$) δ 17.71. LCMS: MS m/z=808.83 [M+1]; t$_R$=2.58 min LC system::Dionex Ultimate 3000 UHPLC; Column: Phenomenex Kinetex 2.6µ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min. HPLC: t$_R$=8.92 min; HPLC system: 1290 Infinity II.; Column: Phenomenex 2.6µ C18 100A, 100×4.6 mm; Solvents: Acetonitrile with 0.1% TFA, Water with 0.1% TFA; Gradient: 0 min-8.5 min 2-98% ACN at 1.5 mL/min.

Example 31: Dihexyl 2,2'-((((((1-(6-((propoxycarbonyl)amino)-9H-purin-9-yl)propan-2-yl)oxy)methyl)phosphoryl)bis(azanediyl))(R)-bis(2-methylpropanoate) (31)

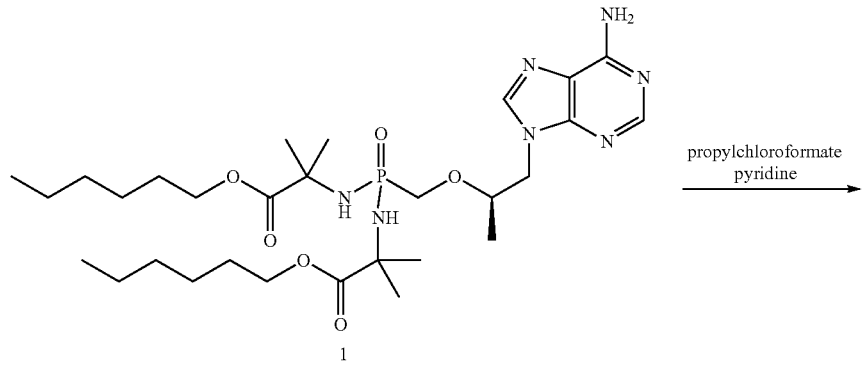

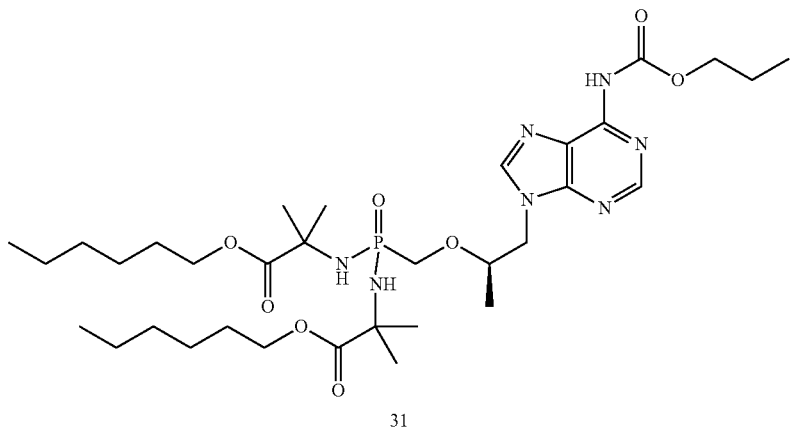

To a solution of 1 (200 mg, 0.32 mmol) in pyridine (1 mL) was added propyl chloroformate (118 mg, 0.96 mmol). The resulting mixture was stirred at room temperature for 2 h and the reaction quenched by adding water. The mixture was concentrated and purified by prep HPLC (ACN 10 to 100% in water for 5 min and ACN 100% for 18 min) to afford the title compound (31). $^1$H NMR (400 MHz, Acetonitrile-$d_3$) δ 8.88 (s, 1H), 8.61 (s, 1H), 8.31 (s, 1H), 4.43 (dd, J=14.5, 3.2 Hz, 1H), 4.25 (dd, J=14.5, 7.2 Hz, 1H), 4.20-4.01 (m, 6H), 4.01-3.91 (m, 1H), 3.75 (d, J=10.9 Hz, 1H), 3.69 (dd, J=12.8, 8.6 Hz, 1H), 3.58 (d, J=10.9 Hz, 1H), 3.44 (dd, J=12.8, 9.9 Hz, 1H), 1.73 (m, 2H), 1.69-1.58 (m, 4H), 1.52 (s, 3H), 1.45 (s, 6H), 1.41-1.26 (m, 15H), 1.20 (d, J=6.2 Hz, 3H), 1.00 (t, J=7.4 Hz, 3H), 0.93-0.83 (m, 6H). $^{31}$P NMR (162 MHz, Acetonitrile-$d_3$) δ 17.86. LCMS: MS m/z=712.31 [M+1]; $t_R$=1.84 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.12 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 32: Dihexyl 2,2'-(((((1-(6-(((pentyloxy)carbonyl)amino)-9H-purin-9-yl)propan-2-yl)oxy)methyl)phosphoryl)bis(azanediyl))(R)-bis(2-methylpropanoate) (32)

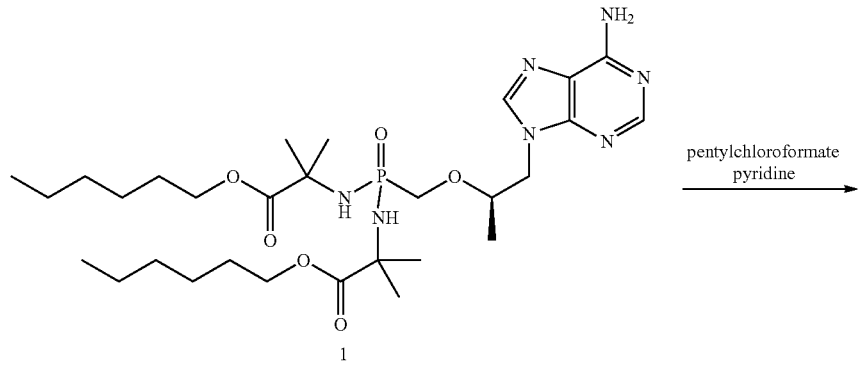

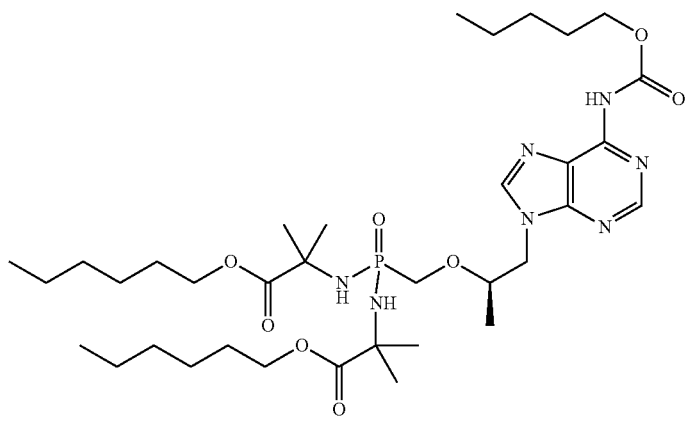

To a solution of 1 (200 mg, 0.32 mmol) in pyridine (1 mL) was added pentyl chloroformate (144 mg, 0.96 mmol). The resulting mixture was stirred at room temperature for 2 h and the reaction was quenched by adding water and purified by prep HPLC (ACN 10 to 100% in water for 5 min and ACN 100% for 18 min) to afford the title compound (32). $^1$H NMR (400 MHz, Acetonitrile-$d_3$) δ 8.74 (s, 1H), 8.61 (s, 1H), 8.30 (s, 1H), 4.43 (dd, J=14.5, 3.1 Hz, 1H), 4.30-4.17 (m, 3H), 4.17-4.01 (m, 4H), 3.96 (m, 1H), 3.74 (d, J=10.8 Hz, 1H), 3.68 (dd, J=12.8, 8.6 Hz, 1H), 3.56 (d, J=10.8 Hz, 1H), 3.43 (dd, J=12.7, 9.9 Hz, 1H), 1.77-1.56 (m, 6H), 1.52 (s, 3H), 1.47-1.26 (m, 25H), 1.20 (d, J=6.2 Hz, 3H), 0.98-0.85 (m, 9H). $^{31}$P NMR (162 MHz, Acetonitrile-$d_3$) δ 17.80. LCMS: MS m/z=740.39 [M+1]; $t_R$=1.96 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.61 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 33: Dihexyl 2,2'-(((((1-(6-((((5-methyl-2-oxo-1,3-dioxol-4-yl)methoxy)carbonyl)amino)-9H-purin-9-yl)propan-2-yl)oxy)methyl)phosphoryl)bis(azanediyl))(R)-bis(2-methylpropanoate) (33)

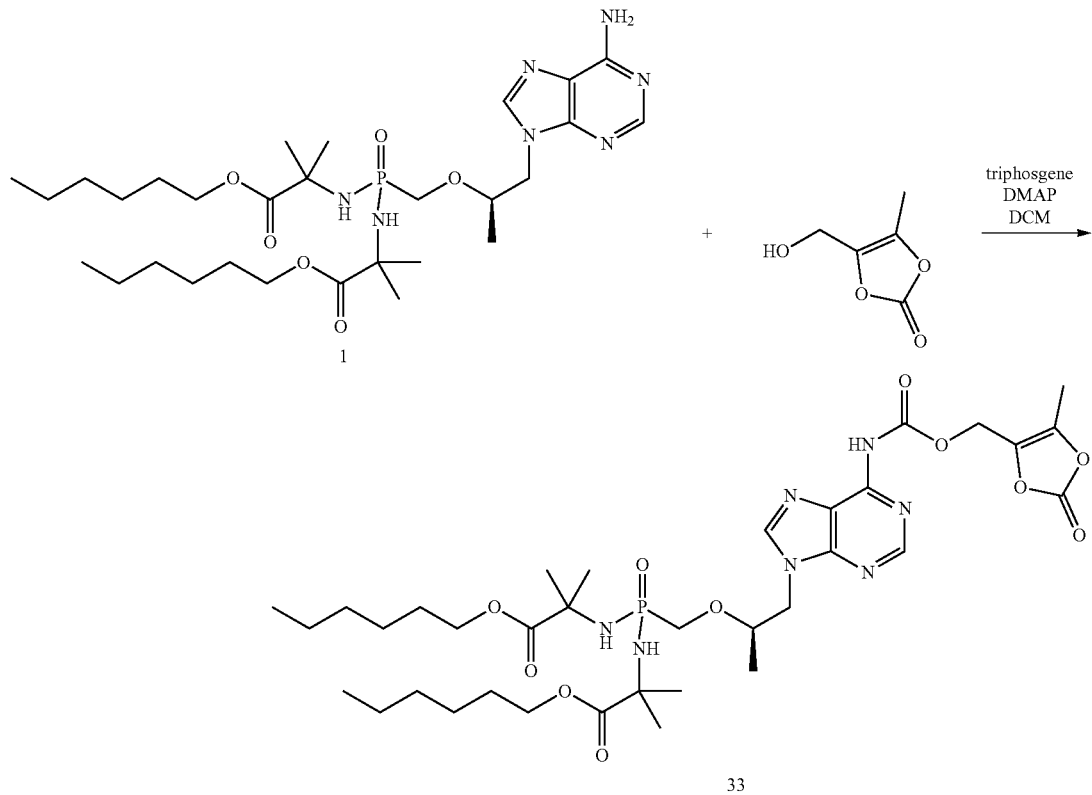

To a mixture of 1 (200 mg, 0.32 mmol) and triphosgene (38 mg, 0.128 mmol) in DCM (4 mL) was added DMAP (234 mg, 1.92 mmol) slowly portion wise at room temperature The resulting mixture was stirred at room temperature for 15 min and 4-(hydroxymethyl)-5-methyl-1,3-dioxol-2-one (60 mg, 0.46 mmol) was added at room temperature The resulting mixture was stirred for 2 h, concentrated in vacuo, and purified by silica gel column chromatography (MeOH 0 to 15% in DCM) and by prep HPLC (ACN 10 to 100% in water for 8 min, ACN 100% for 15 min) to afford the title compound (33). $^1$H NMR (400 MHz, Acetonitrile-d3) δ 8.69 (s, 1H), 8.63 (s, 1H), 8.31 (s, 1H), 5.02 (s, 2H), 4.44 (dd, J=14.5, 3.2 Hz, 1H), 4.26 (dd, J=14.5, 7.2 Hz, 1H), 4.16-4.02 (m, 4H), 3.96 (m, 1H), 3.79-3.61 (m, 2H), 3.55 (d, J=10.7 Hz, 1H), 3.44 (dd, J=12.7, 9.8 Hz, 1H), 2.21 (s, 3H), 1.70-1.55 (m, 4H), 1.52 (s, 3H), 1.45 (s, 6H), 1.42-1.26 (m, 15H), 1.20 (d, J=6.2 Hz, 3H), 0.95-0.83 (m, 6H). $^{31}$P NMR (162 MHz, Acetonitrile-d3) δ 17.63. LCMS: MS m/z=782.17 [M+1]; $t_R$=2.00 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=7.05 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 34: Dicyclopentyl 2,2'-(((((1-(6-amino-9H-purin-9-yl)propan-2-yl)oxy)methyl)phosphoryl)bis(azanediyl))(R)-bis(2-methylpropanoate) (34)

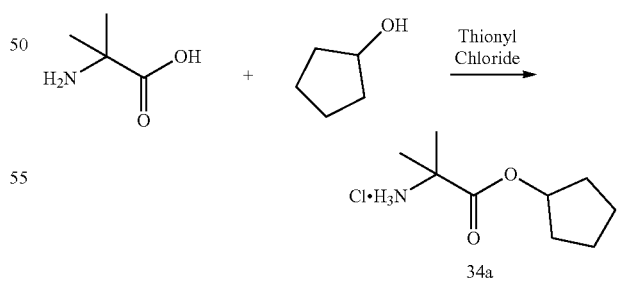

Synthesis of cyclopentyl 2-amino-2-methyl-propanoate hydrochloride (34a)

2-Amino-2-methyl-propanoic acid (1.0 g, 9.70 mmol) was suspended in cyclopentanol (17.6 mL, 194 mmol). Thionyl chloride (1.4 mL, 19.4 mmol) was added over slowly over 3 minutes. The mixture was heated at 70° C. for 3 days. The mixture was diluted with ethyl acetate/hexanes (1:1, 20 mL) and water (20 mL). The organic phase was extracted with water (20 mL). The combined aqueous phases were washed with ethyl acetate/hexanes (1:1, 3×20 mL), diethyl ether (3×20 mL) and dichloromethane (3×20 mL). Any residual solvent in the aqueous phase was removed under reduced pressure. The volume was reduced to 20 ml under reduced pressure. The aqueous phase was diluted with acetonitrile (10 mL) and subjected to lyophilization. The solid was washed stirred with hexanes for 15 minutes and isolated by filtration, providing intermediate 34a. $^1$H NMR (400 MHz, DMSO-d$_6$) δ 8.54 (s, 3H), 5.18 (m, 1H), 1.94-1.78 (m, 2H), 1.76-1.62 (m, 4H), 1.62-1.52 (m, 2H), 1.45 (s, 6H).

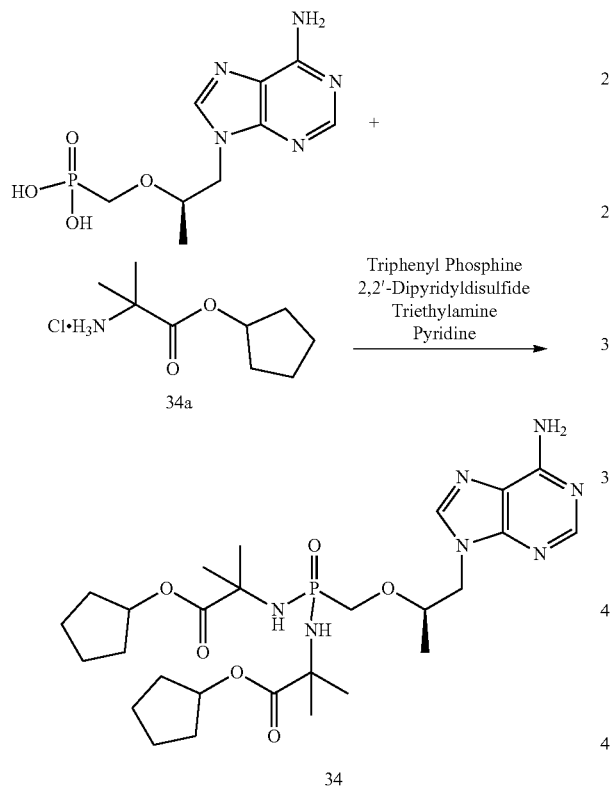

34a

PMPA (100 mg, 0.384 mmol), triphenylphosphine (344 mg, 1.39 mmol), 2,2'-dipyridyl disulfide (307 mg, 1.39 mmol) and intermediate 34a (289 mg, 1.39 mmol) were suspended in pyridine (4 mL) under argon. Triethylamine (0.38 mL, 2.79 mmol) was added. The reaction was heated at 75° C. for 3 days. The pyridine was removed under reduced pressure. The residue was co-evaporated with toluene (2×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (34). $^1$H NMR (400 MHz, Methanol-d$_4$) δ 8.30 (s, 1H), 8.23 (s, 1H), 5.20 (m, 1H), 5.15 (m, 1H), 4.43 (dd, J=14.5, 3.1 Hz, 1H), 4.34 (d, J=11.9 Hz, 0.39H), 4.27 (dd, J=14.5, 7.4 Hz, 1H), 4.12 (s, 0.24H), 4.08-3.96 (m, 1H), 3.80 (dd, J=12.8, 8.5 Hz, 1H), 3.55 (dd, J=12.8, 10.2 Hz, 1H), 1.89 (m, 5H), 1.82-1.69 (m, 6H), 1.66 (m, 5H), 1.55 (s, 3H), 1.47 (s, 3H), 1.45 (s, 3H), 1.40 (s, 3H), 1.26 (d, J=6.2 Hz, 3H). $^{31}$P NMR (162 MHz, Methanol-d$_4$) δ 20.98-20.75 (m). LCMS: MS m/z=594.58 [M+1]; t$_R$=1.145 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: t$_R$=2.706 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 35: Diisobutyl 2,2'-(((((1-(6-amino-9H-purin-9-yl)propan-2-yl)oxy)methyl)phosphoryl)bis(azanediyl))(R)-bis(2-methylpropanoate) (35)

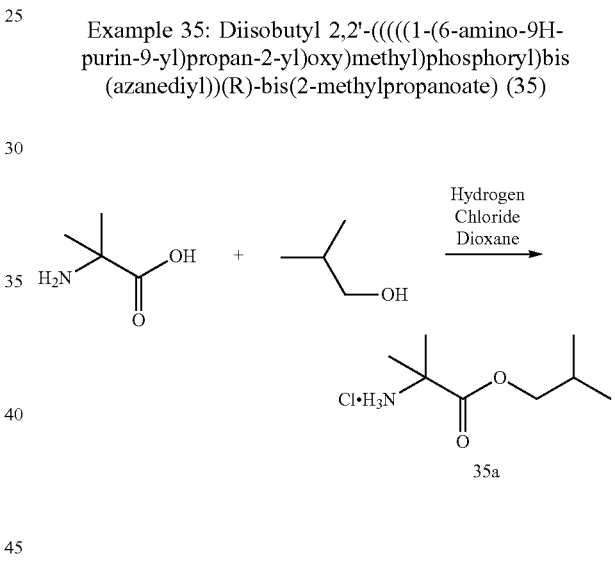

Synthesis of isobutyl 2-amino-2-methyl-propanoate hydrochloride (35a)

2-Amino-2-methylpropanoic acid (2.5 g, 24.2 mmol) was suspended in 2-methylpropan-1-ol (22 mL, 282 mmol) and a solution of hydrogen chloride in 1,4-dioxane (4N, 60 mL, 242 mmol). The mixture was heated at 65° C. for 5 days. The 1,4-dioxane was removed under reduced pressure. The mixture was diluted with ethyl acetate/hexanes (1:1, 50 mL) and water (50 mL). The organic phase was extracted with water (50 mL). The combined aqueous phases were washed with ethyl acetate/hexanes (1:1, 3×50 mL), diethyl ether (3×50 mL) and dichloromethane (3×50 mL). Any residual solvent in the aqueous phase was removed and the volume was reduced to 50 mL, under reduced pressure. The aqueous phase was diluted with acetonitrile (20 mL) and water (10 mL) and subjected to lyophilization. The solid was stirred with hexanes (20 mL) and isolated by filtration with hexanes washing to provide intermediate 35a. $^1$H NMR (400 MHz, DMSO-d$_6$) δ 8.56 (s, 3H), 3.98 (d, J=6.5 Hz, 2H), 1.93 (m, 1H), 1.49 (s, 6H), 0.92 (d, J=6.7 Hz, 6H).

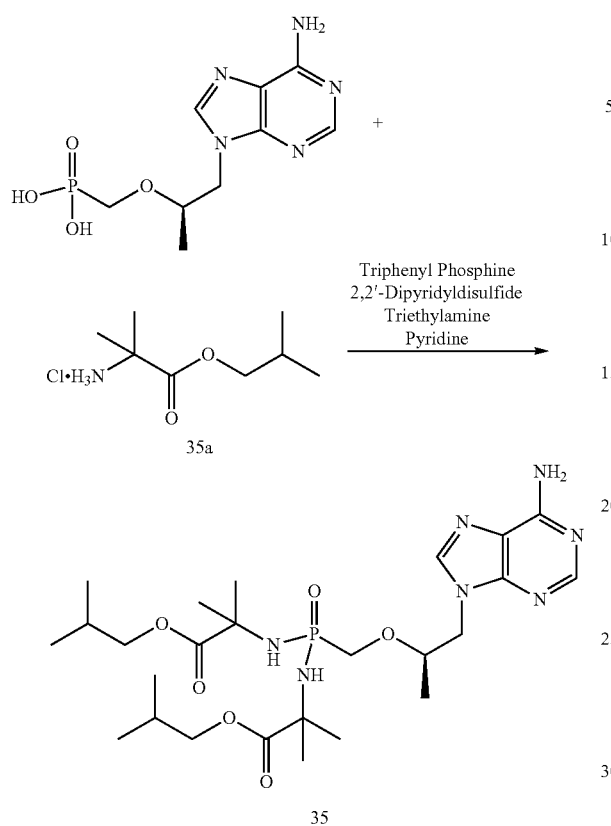

PMPA (100 mg, 0.384 mmol), triphenylphosphine (341 mg, 1.74 mmol), 2,2'-dipyridyl disulfide (307 mg, 1.39 mmol) and intermediate 35a (289 mg, 1.39 mmol) were suspended in pyridine (4 mL) under argon. Triethylamine (0.475 mL, 3.48 mmol) was added. The reaction was heated at 90° C. for 18 hours. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (35). $^1$H NMR (400 MHz, Methanol-$d_4$) δ 8.34 (s, 1H), 8.28 (s, 1H), 4.45 (dd, J=14.5, 3.0 Hz, 1H), 4.29 (dd, J=14.5, 7.4 Hz, 1H), 4.05-3.88 (m, 5H), 3.88-3.75 (m, 1H), 3.55 (dd, J=12.8, 10.2 Hz, 1H), 2.03-1.90 (m, 2H), 1.59 (s, 3H), 1.51 (s, 3H), 1.50 (s, 3H), 1.26 (d, J=6.2 Hz, 3H), 1.02-0.92 (m, 12H). $^{31}$P NMR (162 MHz, Methanol-$d_4$) δ 20.78 (t, J=9.3 Hz). LCMS: MS m/z=570.14 [M+1]; $t_R$=1.350 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min.

HPLC: $t_R$=2.673 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 36: Dipropyl 2,2'-(((((1-(6-amino-9H-purin-9-yl)propan-2-yl)oxy)methyl)phosphoryl)bis(azanediyl))(R)-bis(2-methylpropanoate) (36)

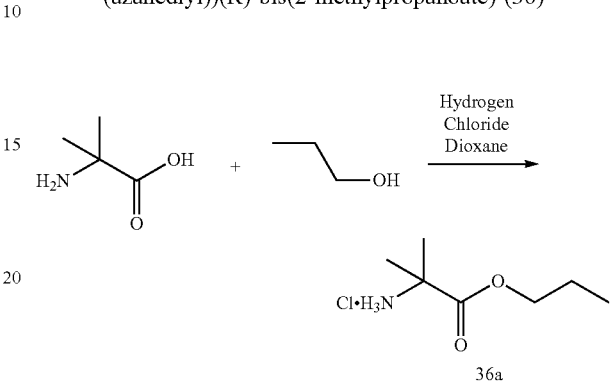

Synthesis of 2-amino-2-methyl-propanoate hydrochloride (36a)

2-Amino-2-methylpropanoic acid (1 g, 9.7 mmol) was suspended in propan-1-ol (17.6 mL, 278 mmol) and a solution of hydrogen chloride in 1,4-dioxane (4N, 12.1 mL, 48.5 mmol). The mixture was heated at 40° C. for 5 days. The 1,4-dioxane was removed under reduced pressure. The mixture was diluted with ethyl acetate/hexanes (1:1, 50 mL) and water (50 mL). The organic phase was extracted with water (50 mL). The combined aqueous phases were washed with ethyl acetate/hexanes (1:1, 3×50 mL), diethyl ether (3×50 mL) and dichloromethane (3×50 mL). Any residual solvent in the aqueous phase was removed and the volume was reduced to 50 mL, under reduced pressure. The aqueous phase was diluted with acetonitrile (20 mL) and water (10 mL) and subjected to lyophilization. The solid was stirred with hexanes (20 mL) and isolated by filtration with hexanes washing, providing intermediate 36a. $^1$H NMR (400 MHz, DMSO-$d_6$) δ 8.76-8.33 (m, 3H), 4.14 (t, J=6.5 Hz, 2H), 1.64 (m, 2H), 1.49 (s, 6H), 0.92 (t, J=7.4 Hz, 3H).

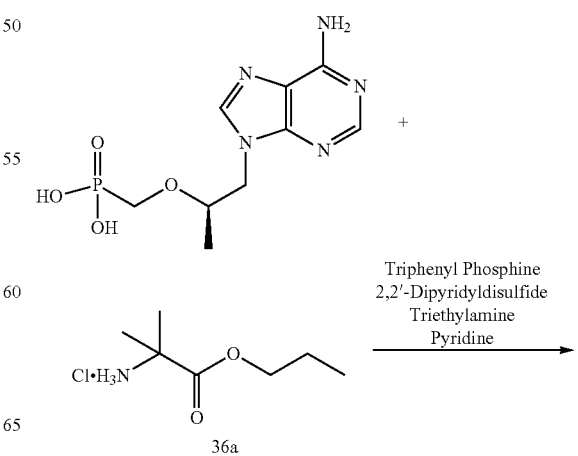

-continued

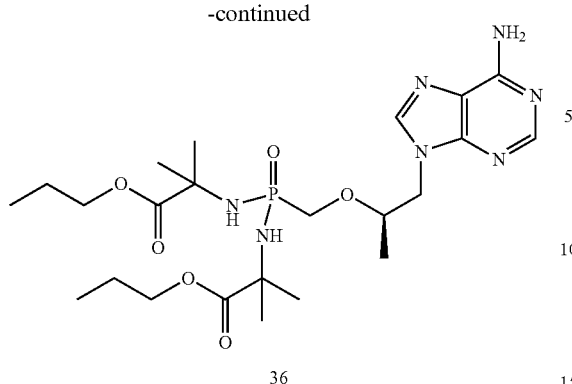

36

PMPA (100 mg, 0.384 mmol), triphenylphosphine (344 mg, 1.39 mmol), 2,2'-dipyridyl disulfide (307 mg, 1.39 mmol) and intermediate 36a (341 mg, 1.88 mmol) were suspended in pyridine (4 mL) under Argon. Triethylamine (0.475 mL, 3.48 mmol) was added. The reaction was heated at 90° C. for 16 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (36). $^1$H NMR (400 MHz, Methanol-d$_4$) δ 8.35 (s, 1H), 8.29 (s, 1H), 4.45 (dd, J=14.5, 3.1 Hz, 1H), 4.29 (dd, J=14.5, 7.5 Hz, 1H), 4.21-4.03 (m, 4H), 4.03-3.96 (m, 1H), 3.81 (dd, J=12.8, 8.4 Hz, 1H), 3.55 (dd, J=12.8, 10.2 Hz, 1H), 1.77-1.63 (m, 4H), 1.57 (s, 3H), 1.50 (s, 3H), 1.49 (s, 3H), 1.44 (s, 3H), 1.26 (d, J=6.2 Hz, 3H), 1.03-0.92 (m, 6H). $^{31}$P NMR (162 MHz, Methanol-d$_4$) δ 20.76. LCMS: MS m/z=542.11 [M+1]; t$_R$=1.240 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: t$_R$=2.402 min; HPLC system: Agilent 1100 series; Column: Gemini 5p C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 37: Bis(cyclobutylmethyl) 2,2'-(((((1-(6-amino-9H-purin-9-yl)propan-2-yl)oxy)methyl)phosphoryl)bis(azanediyl))(R)-bis(2-methylpropanoate) (37)

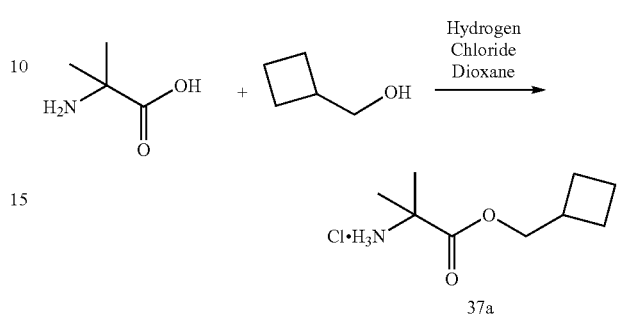

37a

Synthesis of cyclobutylmethyl 2-amino-2-methylpropanoate hydrochloride (37a)

2-Amino-2-methylpropanoic acid (1.0 g, 9.7 mmol) was suspended in cyclobutylmethanol (8.8 mL, 97 mmol) and a solution of hydrogen chloride in 1,4-dioxane (4N, 24.2 mL, 97 mmol). The mixture was heated at 65° C. for 3 days. The 1,4-dioxane was removed under reduced pressure. The mixture was diluted with ethyl acetate/hexanes (1:1, 100 mL) and water (100 mL). The organic phase was extracted with water (100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 50 mL, under reduced pressure. The aqueous phase was diluted with acetonitrile (20 mL) and water (10 mL) and subjected to lyophilization, providing intermediate 37a. $^1$H NMR (400 MHz, DMSO-d$_6$) δ 8.52 (s, 3H), 4.16 (d, J=6.4 Hz, 2H), 2.71-2.56 (m, 1H), 2.07-1.95 (m, 2H), 1.95-1.70 (m, 4H), 1.48 (s, 6H).

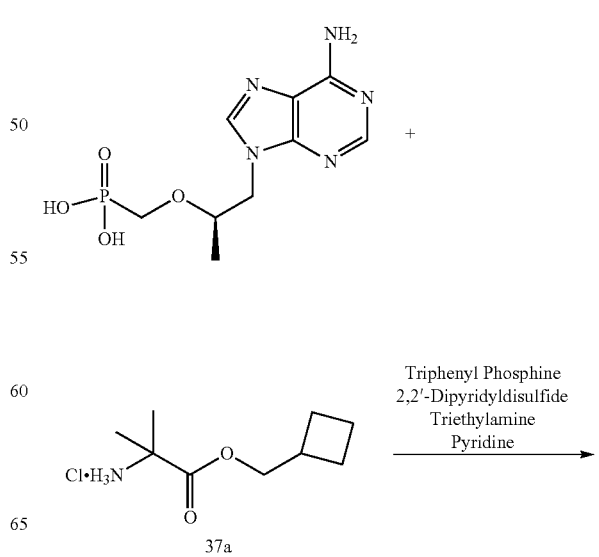

37a

-continued

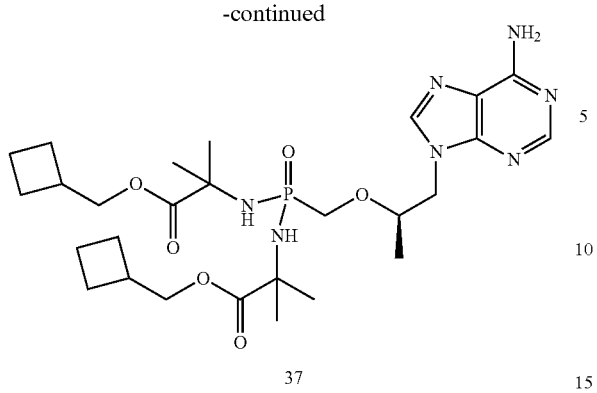

37

PMPA (100 mg, 0.384 mmol), triphenylphosphine (344 mg, 1.39 mmol), 2,2'-dipyridyl disulfide (307 mg, 1.39 mmol) and intermediate 37a (341 mg, 1.64 mmol) were suspended in pyridine (4 mL) under Argon. Triethylamine (0.475 mL, 3.48 mmol) was added. The reaction was heated at 105° C. for 19 hours. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (37). $^1$H NMR (400 MHz, Methanol-$d_4$) δ 8.29 (s, 1H), 8.23 (s, 1H), 4.46-4.35 (m, 2H), 4.33-4.24 (m, 1H), 4.11 (m, 5H), 4.02-3.94 (m, 1H), 3.81 (dd, J=12.8, 8.4 Hz, 1H), 3.54 (dd, J=12.8, 10.3 Hz, 1H), 2.77-2.56 (m, 2H), 2.16-2.02 (m, 4H), 2.02-1.88 (m, 4H), 1.88-1.74 (m, 4H), 1.58 (s, 3H), 1.50 (s, 3H), 1.47 (s, 3H), 1.43 (s, 3H), 1.26 (d, J=6.2 Hz, 3H). $^{31}$P NMR (162 MHz, Methanol-$d_4$) δ 20.87 (t, J=9.4 Hz). LCMS: MS m/z=594.54 [M+1]; $t_R$=1.203 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=2.811 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 38: Dibutyl 2,2'-(((((1-(6-amino-9H-purin-9-yl)propan-2-yl)oxy)methyl)phosphoryl)bis(azanediyl))(R)-bis(2-methylpropanoate) (38)

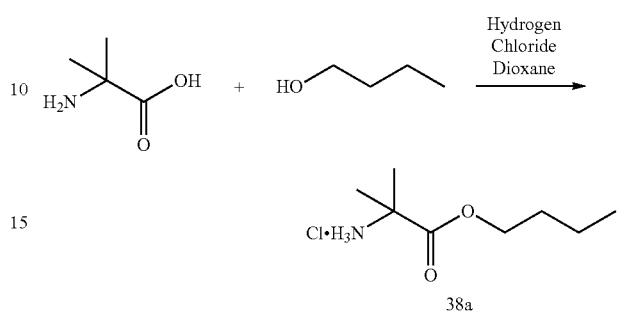

Synthesis of butyl 2-amino-2-methylpropanoate hydrochloride (38a)

2-Amino-2-methylpropanoic acid (2.5 g, 24.2 mmol) was suspended in butan-1-ol (22 mL, 240 mmol) and a solution of hydrogen chloride in 1,4-dioxane (4N, 30.3 mL, 121 mmol). The mixture was heated at 65° C. for 2 days. The 1,4-dioxane was removed under reduced pressure. The mixture was diluted with ethyl acetate/hexanes (1:1, 100 mL) and water (100 mL). The organic phase was extracted with water (2×100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 50 mL, under reduced pressure. The aqueous phase was diluted with acetonitrile (20 mL) and water (10 mL) and subjected to lyophilization, providing intermediate 38a. $^1$H NMR (400 MHz, DMSO-$d_6$) δ 8.60 (s, 3H), 4.18 (t, J=6.4 Hz, 2H), 1.68-1.54 (m, 2H), 1.48 (s, 6H), 1.42-1.28 (m, 2H), 0.91 (t, J=7.4 Hz, 3H).

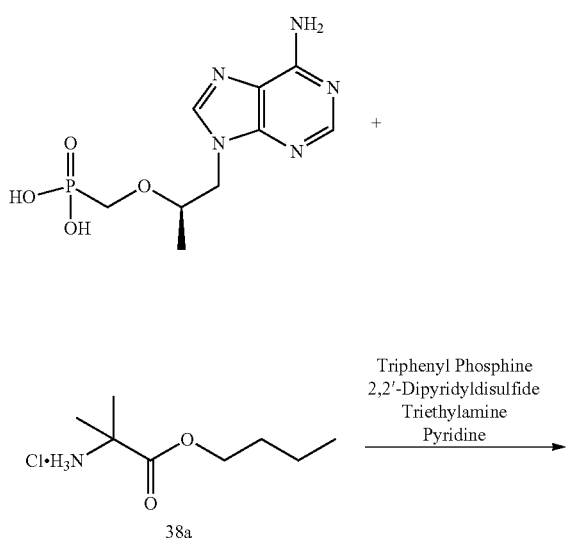

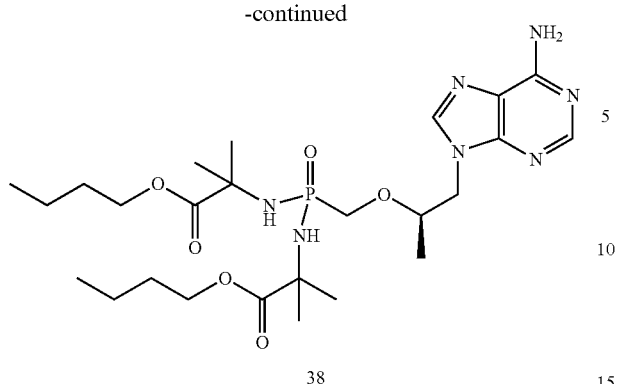

38

PMPA (100 mg, 0.384 mmol), triphenylphosphine (344 mg, 1.39 mmol), 2,2'-dipyridyl disulfide (307 mg, 1.39 mmol) and intermediate 38a (341 mg, 1.74 mmol) were suspended in pyridine (4 mL) under Argon. Triethylamine (0.475 mL, 3.48 mmol) was added. The reaction was heated at 95° C. for 16 hours, and 105° C. for 18 hours. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (38). $^1$H NMR (400 MHz, Methanol-$d_4$) δ 8.45 (s, 1H), 8.37 (s, 1H), 4.50 (dd, J=14.4, 3.1 Hz, 1H), 4.34 (dd, J=14.5, 7.4 Hz, 1H), 4.26-4.07 (m, 4H), 4.06-3.98 (m, 1H), 3.82 (dd, J=12.9, 8.3 Hz, 1H), 3.56 (dd, J=12.9, 10.2 Hz, 1H), 1.73-1.60 (m, 4H), 1.57 (s, 3H), 1.50 (s, 3H), 1.49 (s, 3H), 1.47-1.36 (m, 7H), 1.26 (d, J=6.2 Hz, 3H), 1.02-0.92 (m, 6H). $^{31}$P NMR (162 MHz, Methanol-$d_4$) δ 20.67 (t, J=9.1 Hz). LCMS: MS m/z=570.49 [M+1]; $t_R$=1.124 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=2.710 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 39: Dioctyl 2,2'-(((((1-(6-amino-9H-purin-9-yl)propan-2-yl)oxy)methyl)phosphoryl)bis (azanediyl))(R)-bis(2-methylpropanoate) (39)

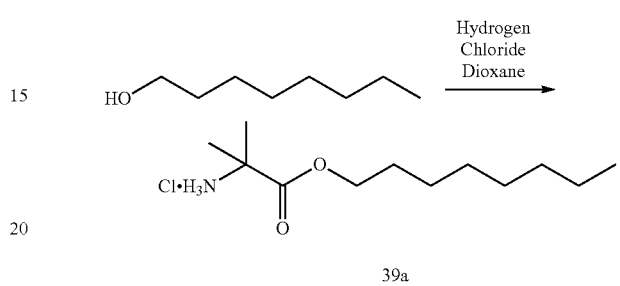

39a

Synthesis of octyl 2-amino-2-methylpropanoate hydrochloride (39a)

2-Amino-2-methylpropanoic acid (2.5 g, 24.2 mmol) was suspended in n-octanol (22.0 mL, 137 mmol) and a solution of hydrogen chloride in 1,4-dioxane (4N, 30.3 mL, 121 mmol). The mixture was heated at 65° C. for 40 h. The 1,4-dioxane was removed under reduced pressure. The mixture was diluted with ethyl acetate/hexanes (1:1, 200 mL) and water (200 mL). The organic phase was extracted with water (2×200 mL). The combined aqueous phases were washed with ethyl acetate/hexanes (1:1, 3×200 mL), diethyl ether (3×200 mL) and dichloromethane (3×200 mL). Any residual solvent in the aqueous phase was removed and the volume was reduced to 100 mL, under reduced pressure. The aqueous phase was diluted with acetonitrile (50 mL) and subjected to lyophilization, providing intermediate 39a. $^1$H NMR (400 MHz, DMSO-$d_6$) δ 8.60 (s, 3H), 4.16 (t, J=6.5 Hz, 2H), 1.68-1.57 (m, 2H), 1.48 (s, 6H), 1.40-1.18 (m, 10H), 0.93-0.79 (m, 3H).

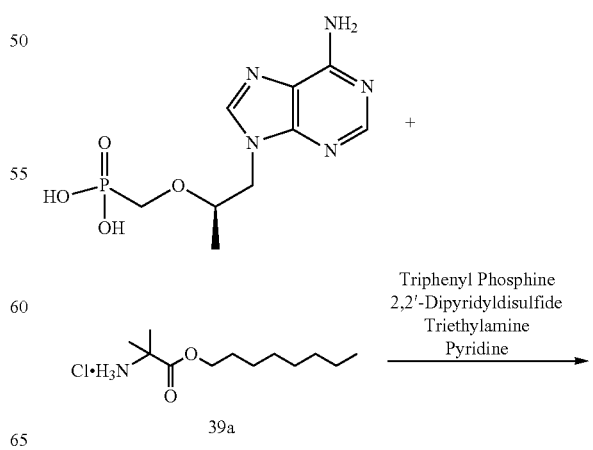

39a

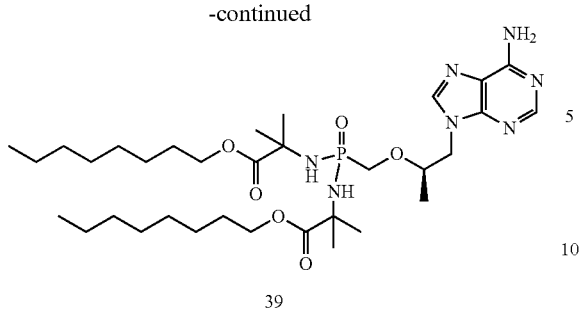

39

PMPA (100 mg, 0.384 mmol), triphenylphosphine (344 mg, 1.39 mmol), 2,2'-dipyridyl disulfide (307 mg, 1.39 mmol) and intermediate 39a (341 mg, 1.35 mmol) were suspended in pyridine (4 mL) under Argon. Triethylamine (0.475 mL, 3.48 mmol) was added. The reaction was heated at 90° C. for 16 h, and 105° C. for 6 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (39). $^1$H NMR (400 MHz, Methanol-d$_4$) δ 8.30 (s, 1H), 8.23 (s, 1H), 4.48-4.34 (m, 1.5H), 4.27 (dd, J=14.5, 7.4 Hz, 1H), 4.23-4.04 (m, 5H), 4.04-3.93 (m, 1H), 3.81 (dd, J=12.8, 8.4 Hz, 1H), 3.54 (dd, J=12.8, 10.2 Hz, 1H), 1.76-1.60 (m, 4H), 1.58 (s, 3H), 1.49 (m, 6H), 1.43 (s, 3H), 1.42-1.27 (m, 20H), 1.25 (d, J=6.2 Hz, 3H), 0.96-0.86 (m, 6H). $^{31}$P NMR (162 MHz, Methanol-d$_4$) δ 20.84 (t, J=9.3 Hz). LCMS: MS m/z=682.71 [M+1]; t$_R$=1.751 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: t$_R$=3.945 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 40: Dicyclohexyl 2,2'-((((((1-(6-amino-9H-purin-9-yl)propan-2-yl)oxy)methyl)phosphoryl)bis(azanediyl))(R)-bis(2-methylpropanoate) (40)

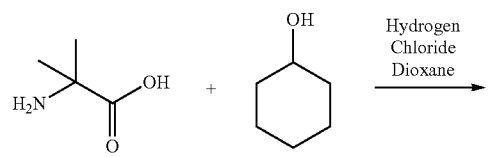

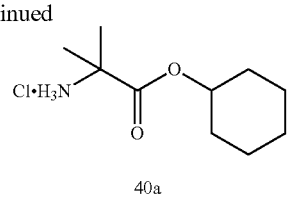

40a

Synthesis of cyclohexyl 2-amino-2-methylpropanoate hydrochloride (40a)

2-Amino-2-methylpropanoic acid (2.5 g, 24.2 mmol) was suspended in cyclohexanol (11.2 mL, 97 mmol) and a solution of hydrogen chloride in 1,4-dioxane (4N, 30.3 mL, 121 mmol). The mixture was heated at 65° C. for 3 days. The 1,4-dioxane was removed under reduced pressure. The mixture was diluted with ethyl acetate/hexanes (1:1, 200 mL) and water (200 mL). The organic phase was extracted with water (2×200 mL). The combined aqueous phases were washed with ethyl acetate/hexanes (1:1, 3×200 mL), diethyl ether (3×200 mL) and dichloromethane (3×200 mL). Any residual solvent in the aqueous phase was removed and the volume was reduced to 50 mL, under reduced pressure. The aqueous phase was diluted with acetonitrile (50 mL) and subjected to lyophilization, providing intermediate 40a. $^1$H NMR (400 MHz, DMSO-d$_6$) δ 8.60 (s, 3H), 4.83-4.78 (m, 1H), 1.83-1.73 (m, 2H), 1.73-1.61 (m, 2H), 1.58-1.43 (m, 9H), 1.43-1.18 (m, 3H).

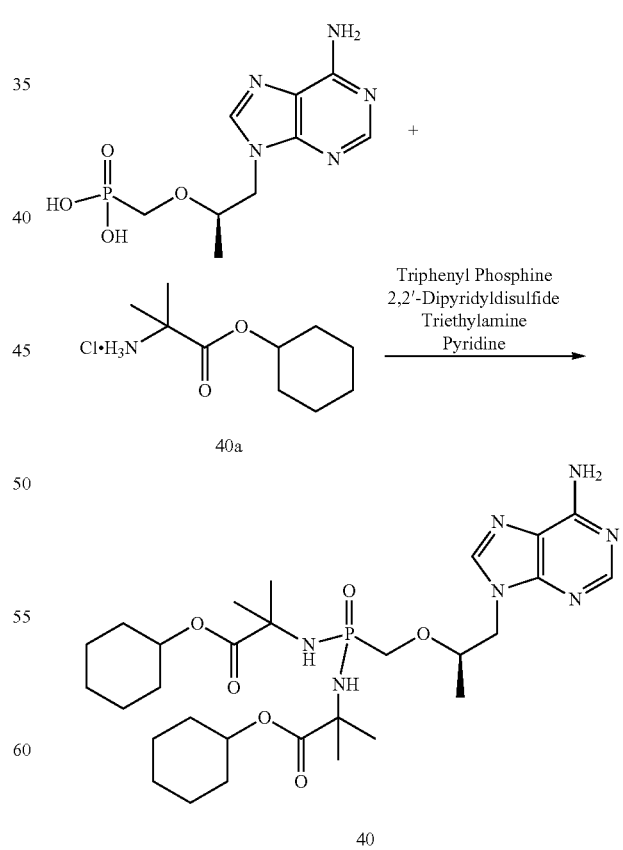

40

PMPA (100 mg, 0.384 mmol), triphenylphosphine (344 mg, 1.39 mmol), 2,2'-dipyridyl disulfide (307 mg, 1.39 mmol) and intermediate 40a (309 mg, 1.39 mmol) were suspended in pyridine (4 mL) under Argon. Triethylamine (0.475 mL, 3.48 mmol) was added. The reaction was heated at 90° C. for 16 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (40). $^1$H NMR (400 MHz, Methanol-d$_4$) δ 8.31 (s, 1H), 8.23 (s, 1H), 4.86-4.78 (m, 1H), 4.78-4.69 (m, 1H), 4.43 (dd, J=14.5, 3.0 Hz, 1H), 4.26 (dd, J=14.5, 7.4 Hz, 1H), 4.05-3.95 (m, 1H), 3.81 (dd, J=12.8, 8.5 Hz, 1H), 3.56 (dd, J=12.7, 10.3 Hz, 1H), 1.97-1.79 (m, 4H), 1.79-1.67 (m, 4H), 1.67-1.52 (m, 6H), 1.52-1.46 (m, 8H), 1.46-1.28 (m, 10H), 1.26 (d, J=6.2 Hz, 3H). $^{31}$P NMR (162 MHz, Methanol-d$_4$) δ 20.88 (t, J=9.4 Hz). LCMS: MS m/z=622.60 [M+1]; t$_R$=1.278 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: t$_R$=3.006 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 41: Di(spiro[3.3]heptan-2-yl) 2,2'-(((((1-(6-amino-9H-purin-9-yl)propan-2-yl)oxy)methyl)phosphoryl)bis(azanediyl))(R)-bis(2-methylpropanoate) (41)

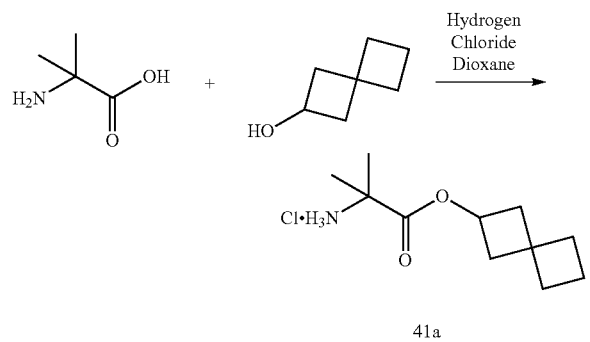

Synthesis of spiro[3.3]heptan-2-yl 2-amino-2-methylpropanoate hydrochloride (41a)

2-Amino-2-methylpropanoic acid (250 mg, 2.42 mmol) was suspended in spiro[3.3]heptan-2-ol (0.671 mL, 4.85 mmol) and a solution of hydrogen chloride in 1,4-dioxane (4N, 3.03 mL, 12.1 mmol). The mixture was heated at 65° C. for 5 days. The reaction was cooled and any solid was removed by filtration. The 1,4-dioxane was removed under reduced pressure. The mixture was diluted with ethyl acetate/hexanes (1:1, 25 mL) and water (25 mL). The organic phase was extracted with water (2×25 mL). The combined aqueous phases were washed with ethyl acetate/hexanes (1:1, 3×25 mL), diethyl ether (3×25 mL) and dichloromethane (3×25 mL). Any residual solvent in the aqueous phase was removed and the volume was reduced to 20 mL, under reduced pressure. The aqueous phase was diluted with acetonitrile (20 mL) and subjected to lyophilization, providing intermediate 41a. $^1$H NMR (400 MHz, DMSO-d$_6$) δ 8.51 (m, 3H), 4.89 (p, J=7.1 Hz, 1H), 2.46 (m, 2H), 2.08-1.94 (m, 6H), 1.85-1.75 (m, 2H), 1.46 (s, 6H).

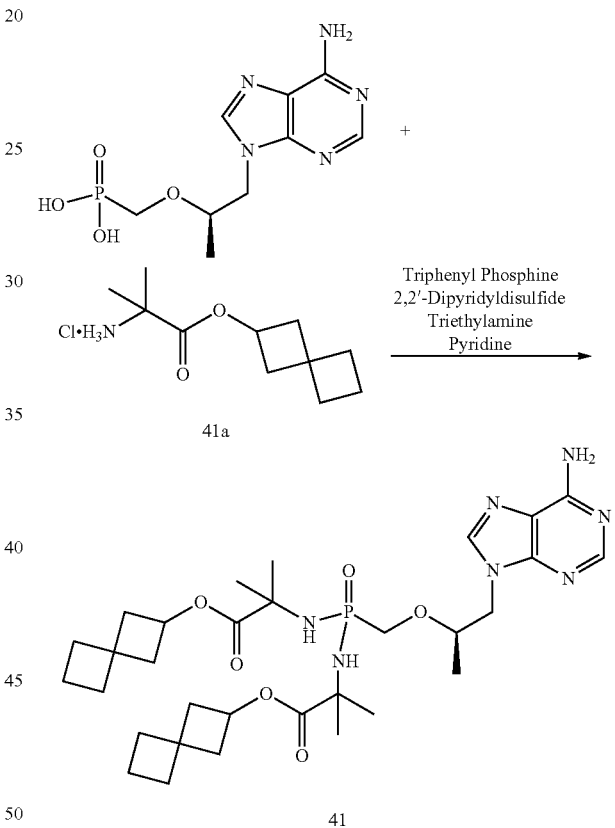

PMPA (100 mg, 0.384 mmol), triphenylphosphine (344 mg, 1.39 mmol), 2,2'-dipyridyl disulfide (307 mg, 1.39 mmol) and intermediate 41a (326 mg, 1.39 mmol) were suspended in pyridine (4 mL) under Argon. Triethylamine (0.475 mL, 3.48 mmol) was added. The reaction was heated at 90° C. for 16 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (41). $^1$H NMR (400 MHz, Methanol-d$_4$) δ 8.42 (s, 1H), 8.35 (s, 1H), 4.88-4.77 (m, 2H), 4.49 (dd, J=14.5, 3.0 Hz, 1H), 4.32 (dd, J=14.5, 7.3 Hz, 1H), 4.07-3.94 (m, 1H), 3.80 (dd, J=12.9, 8.3 Hz, 1H), 3.53 (dd, J=12.9, 10.1 Hz, 1H), 2.48 (m, 4H), 2.12-1.95 (m, 12H), 1.95-1.80 (m, 4H), 1.54 (s, 3H), 1.47 (m, 6H), 1.42 (s, 3H), 1.25 (d, J=6.2 Hz, 3H). $^{31}$P NMR (162 MHz, Methanol-d$_4$) δ 20.65 (t, J=9.3 Hz). LCMS: MS m/z=646.55 [M+1]; $t_R$=1.413 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=3.205 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 42: Bis(3,3-dimethylcyclobutyl) 2,2'-(((((1-(6-amino-9H-purin-9-yl)propan-2-yl)oxy)methyl)phosphoryl)bis(azanediyl))(R)-bis(2-methyl-propanoate) (42)

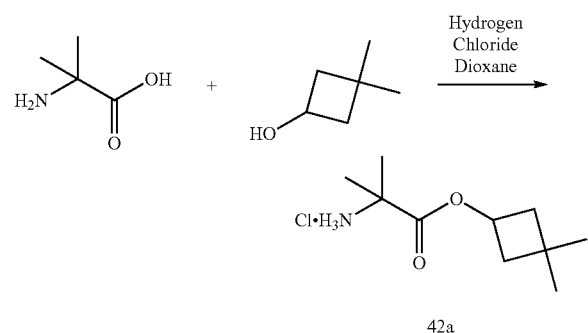

Synthesis of 3,3-dimethylcyclobutyl 2-amino-2-methylpropanoate hydrochloride (42a)

2-Amino-2-methylpropanoic acid (250 mg, 2.42 mmol) was suspended in 3,3-dimethylcyclobutanol (0.671 mL, 5.43 mmol) and a solution of hydrogen chloride in 1,4-dioxane (4N, 3.03 mL, 12.1 mmol). The mixture was heated at 65° C. for 5 days. The reaction was cooled and any solid was removed by filtration. The 1,4-dioxane was removed under reduced pressure. The mixture was diluted with ethyl acetate/hexanes (1:1, 25 mL) and water (25 mL). The organic phase was extracted with water (2×25 mL). The combined aqueous phases were washed with ethyl acetate/hexanes (1:1, 3×25 mL), diethyl ether (3×25 mL) and dichloromethane (3×25 mL). Any residual solvent in the aqueous phase was removed and the volume was reduced to 20 mL, under reduced pressure. The aqueous phase was diluted with acetonitrile (20 mL) and subjected to lyophilization, providing intermediate 42a. $^1$H NMR (400 MHz, DMSO-d$_6$) δ 8.60 (s, 3H), 5.04 (p, J=7.1 Hz, 1H), 2.22 (m, 2H), 1.94-1.79 (m, 2H), 1.47 (m, 6H), 1.15 (s, 3H), 1.13 (s, 3H).

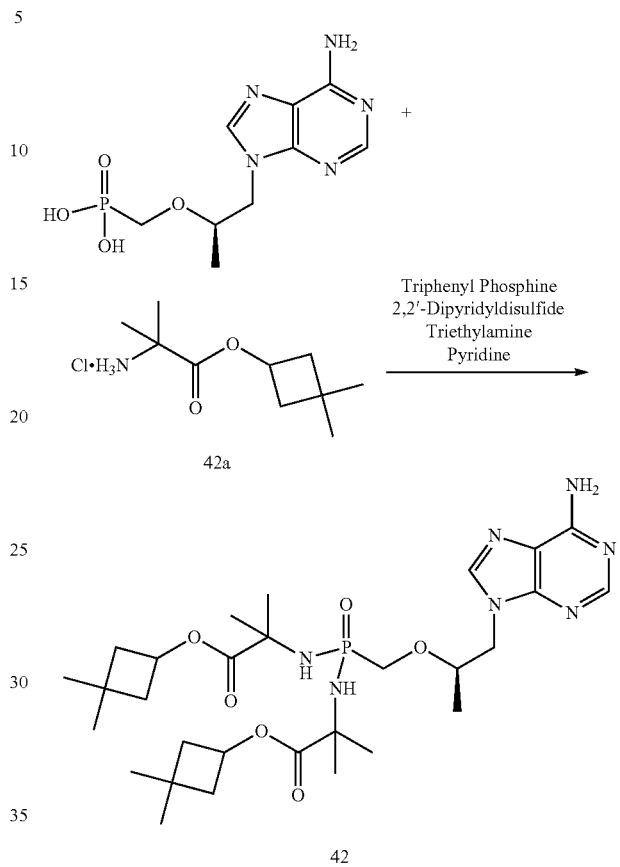

PMPA (100 mg, 0.384 mmol), triphenylphosphine (344 mg, 1.39 mmol), 2,2'-dipyridyl disulfide (307 mg, 1.39 mmol) and intermediate 42a (309 mg, 1.39 mmol) were suspended in pyridine (4 mL) under Argon. Triethylamine (0.475 mL, 3.48 mmol) was added. The reaction was heated at 90° C. for 16 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (42). $^1$H NMR (400 MHz, Methanol-d$_4$) δ 8.42 (s, 1H), 8.35 (s, 1H), 5.10-5.00 (m, 1H), 5.00-4.93 (m, 1H), 4.49 (dd, J=14.5, 3.0 Hz, 1H), 4.32 (dd, J=14.5, 7.3 Hz, 1H), 4.07-3.93 (m, 1H), 3.80 (dd, J=12.8, 8.3 Hz, 1H), 3.54 (dd, J=12.8, 10.1 Hz, 1H), 2.33-2.19 (m, 4H), 1.97-1.79 (m, 4H), 1.56 (s, 3H), 1.52-1.47 (m, 6H), 1.44 (s, 3H), 1.26 (d, J=6.2 Hz, 3H), 1.18 (m, 12H). $^{31}$P NMR (162 MHz, Methanol-d$_4$) δ 20.66 (t, J=9.2 Hz). LCMS: MS m/z=622.56 [M+1]; $t_R$=1.337 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=3.057 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 43: Diisopropyl 2,2'-(((((1-(6-amino-9H-purin-9-yl)propan-2-yl)oxy)methyl)phosphoryl)bis(azanediyl))(R)-bis(2-methylpropanoate) (43)

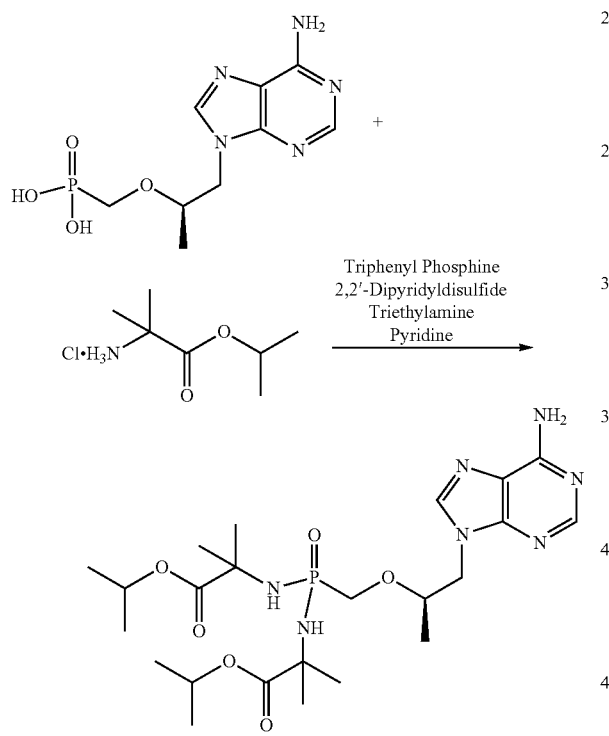

43

PMPA (100 mg, 0.384 mmol), triphenylphosphine (344 mg, 1.39 mmol), 2,2'-dipyridyl disulfide (307 mg, 1.39 mmol) and isopropyl 2-amino-2-methylpropanoate hydrochloride (341 mg, 1.88 mmol) were suspended in pyridine (4 mL) under Argon. Triethylamine (0.475 mL, 3.48 mmol) was added. The reaction was heated at 90° C. for 16 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (43). $^1$H NMR (400 MHz, Methanol-$d_4$) δ 8.31 (s, 1H), 8.23 (s, 1H), 5.11-5.01 (m, 1H), 5.01-4.93 (m, 1H), 4.42 (dd, J=14.5, 3.1 Hz, 1H), 4.35 (d, J=12.2 Hz, 0.18H), 4.27 (dd, J=14.5, 7.4 Hz, 1H), 4.12 (d, J=11.6 Hz, 0.28H), 4.07-3.95 (m, 1H), 3.81 (dd, J=12.8, 8.5 Hz, 1H), 3.55 (dd, J=12.8, 10.2 Hz, 1H), 1.56 (s, 3H), 1.48 (s, 3H), 1.46 (s, 3H), 1.41 (s, 3H), 1.29 (d, J=2.5 Hz, 3H), 1.28-1.23 (m, 12H). $^{31}$P NMR (162 MHz, Methanol-$d_4$) δ 20.81 (t, J=9.3 Hz). LCMS: MS m/z=542.33 [M+1]; $t_R$=1.000 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=2.411 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 44: Bis(4,4-dimethylcyclohexyl) 2,2'-(((((1-(6-amino-9H-purin-9-yl)propan-2-yl)oxy)methyl)phosphoryl)bis(azanediyl))(R)-bis(2-methylpropanoate) (44)

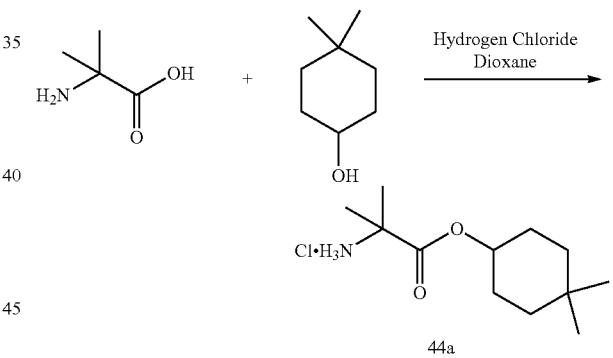

44a

Synthesis of 4,4-dimethylcyclohexyl 2-amino-2-methylpropanoate hydrochloride (44a)

2-Amino-2-methylpropanoic acid (500 mg, 2.42 mmol) was suspended in 4,4-dimethylcyclohexanol (2.15 mL, 13.6 mmol) and a solution of hydrogen chloride in 1,4-dioxane (4N, 6.06 mL, 24.2 mmol). The mixture was heated at 65° C. for 3 days. The reaction was cooled and any solid was removed by filtration. The 1,4-dioxane was removed under reduced pressure. The mixture was diluted with ethyl acetate/hexanes (1:1, 50 mL) and water (50 mL). The organic phase was extracted with water (2×50 mL). The combined aqueous phases were washed with ethyl acetate/hexanes (1:1, 3×50 mL), diethyl ether (3×50 mL) and dichloromethane (3×50 mL). Any residual solvent in the aqueous phase was removed and the volume was reduced to 50 mL, under reduced pressure. The aqueous phase was diluted with acetonitrile (20 mL) and subjected to lyophilization, providing intermediate 44a. $^1$H NMR (400 MHz, DMSO-$d_6$) δ 8.57 (s, 3H), 4.86-4.72 (m, 1H), 1.79-1.66 (m, 2H), 1.66-1.53 (m, 2H), 1.48 (s, 6H), 1.44-1.38 (m, 2H), 1.24 (m, 2H), 0.93 (s, 3H), 0.91 (s, 3H).

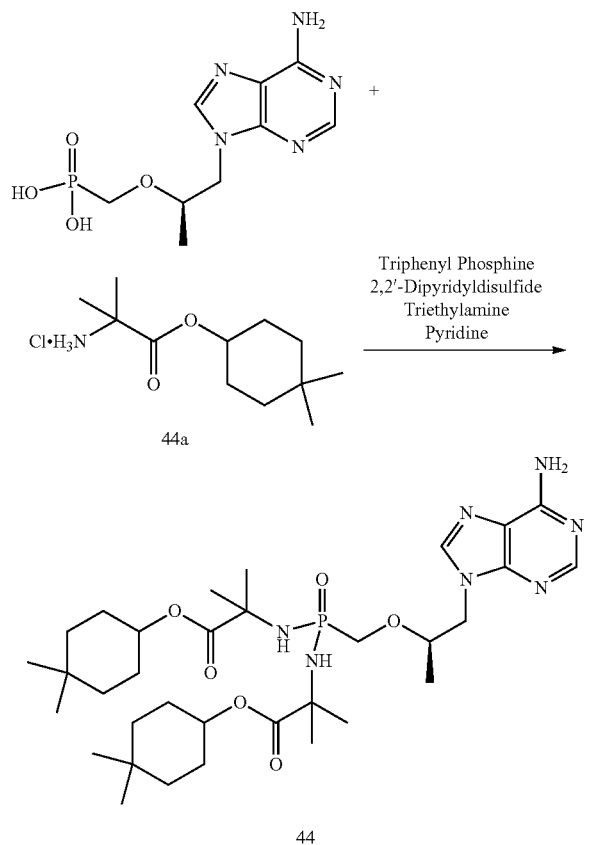

PMPA (100 mg, 0.384 mmol), triphenylphosphine (341 mg, 1.36 mmol), 2,2'-dipyridyl disulfide (307 mg, 1.39 mmol) and intermediate 44a (341 mg, 1.36 mmol) were suspended in pyridine (4 mL) under Argon. Triethylamine (0.475 mL, 3.48 mmol) was added. The reaction was heated at 90° C. for 18 h. The pyridine was removed under reduced pressure. The residue was co-evaporated with toluene (3×10 mL). The residue was subjected to a silica plug using an ISCO solid loading cartridge with a gradient of 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (44). $^1$H NMR (400 MHz, Methanol-$d_4$) δ 8.31 (s, 1H), 8.23 (s, 1H), 4.86-4.77 (m, 1H), 4.77-4.68 (m, 1H), 4.43 (dd, J=14.5, 3.0 Hz, 1H), 4.26 (dd, J=14.5, 7.4 Hz, 1H), 4.05-3.94 (m, 1H), 3.81 (dd, J=12.8, 8.4 Hz, 1H), 3.56 (dd, J=12.8, 10.3 Hz, 1H), 1.87-1.70 (m, 4H), 1.70-1.60 (m, 4H), 1.58 (s, 3H), 1.55-1.45 (m, 10H), 1.43 (s, 3H), 1.38-1.28 (m, 4H), 1.26 (d, J=6.3 Hz, 3H), 1.01-0.92 (m, 12H). $^{31}$P NMR (162 MHz, Methanol-$d_4$) δ 20.85 (t, J=9.4 Hz). LCMS: MS m/z=678.61 [M+1]; $t_R$=1.512 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=3.507 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 45: Bis(cyclopentylmethyl) 2,2'-(((((1-(6-amino-9H-purin-9-yl)propan-2-yl)oxy)methyl)phosphoryl)bis(azanediyl))(R)-bis(2-methylpropanoate) (45)

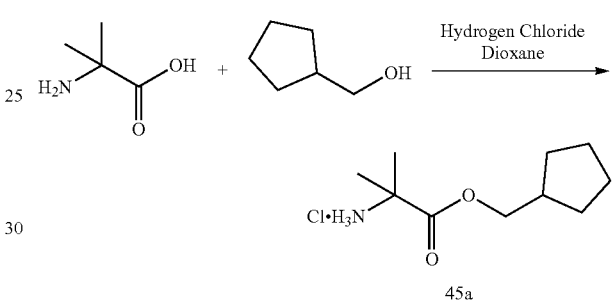

Synthesis of cyclopentylmethyl 2-amino-2-methylpropanoate hydrochloride (45a)

2-Amino-2-methylpropanoic acid (1.0 g, 9.99 mmol) was suspended in cyclopentylmethanol (4.9 mL, 40 mmol) and a solution of hydrogen chloride in 1,4-dioxane (4N, 12.5 mL, 49.9 mmol). The mixture was heated at 65° C. for 3 days. The 1,4-dioxane was removed under reduced pressure. The mixture was diluted with ethyl acetate/hexanes (1:1, 100 mL) and water (100 mL). The organic phase was extracted with water (100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 50 mL, under reduced pressure. The aqueous phase was diluted with acetonitrile (20 mL) and water (10 mL) and subjected to lyophilization, providing intermediate 45a. $^1$H NMR (400 MHz, DMSO-$d_6$) δ 8.62 (s, 4H), 4.07 (d, J=7.0 Hz, 2H), 2.20 (m, 1H), 1.79-1.66 (m, 2H), 1.66-1.51 (m, 4H), 1.49 (s, 6H), 1.25 (m, 2H).

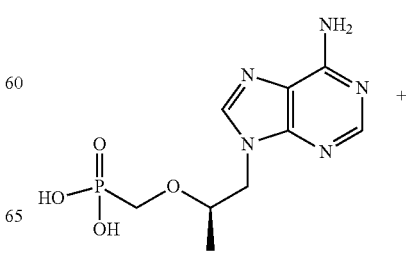

191

-continued

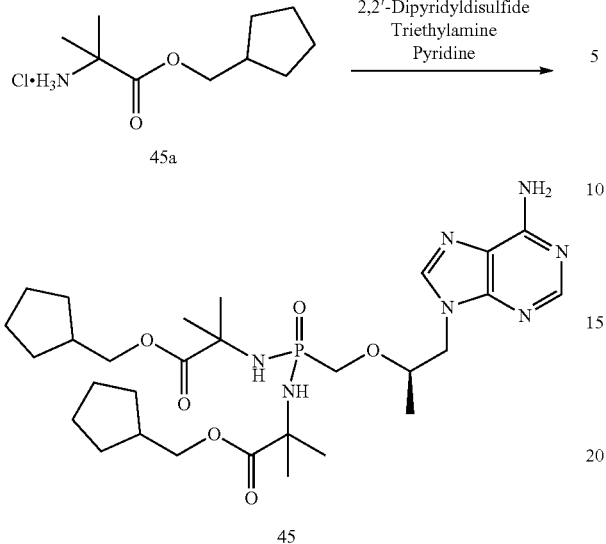

45

PMPA (100 mg, 0.384 mmol), triphenylphosphine (344 mg, 1.39 mmol), 2,2'-dipyridyl disulfide (307 mg, 1.39 mmol) and intermediate 45a (341 mg, 1.54 mmol) were suspended in pyridine (4 mL) under Argon. Triethylamine (0.475 mL, 3.48 mmol) was added. The reaction was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (45). $^1$H NMR (400 MHz, Methanol-d$_4$) δ 8.30 (s, 1H), 8.23 (s, 1H), 4.42 (dd, J=14.5, 3.0 Hz, 1H), 4.26 (dd, J=14.5, 7.4 Hz, 1H), 4.14-3.94 (m, 5H), 3.81 (dd, J=12.8, 8.4 Hz, 1H), 3.55 (dd, J=12.8, 10.3 Hz, 1H), 2.34-2.15 (m, 2H), 1.86-1.72 (m, 4H), 1.71-1.59 (m, 6H), 1.58 (m, 4H), 1.50 (s, 3H), 1.48 (s, 3H), 1.43 (s, 3H), 1.36-1.27 (m, 3H), 1.27 (s, 3H). $^{31}$P NMR (162 MHz, Methanol-d$_4$) δ 20.86 (t, J=9.3 Hz). LCMS: MS m/z=622.48 [M+1]; t$_R$=1.327 min; LC system: Thermo Accela 1250 UHPLC; MS system: Thermo LCQ Fleet; Column: Phenomenex Kinetex 2.6µ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: t$_R$=3.065 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

192

Example 46: Bis(cyclohexylmethyl) 2,2'-(((((1-(6-amino-9H-purin-9-yl)propan-2-yl)oxy)methyl)phosphoryl)bis(azanediyl))(R)-bis(2-methylpropanoate) (46)

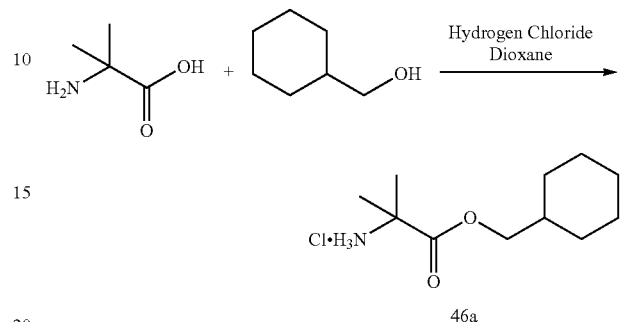

46a

Synthesis of cyclohexylmethyl 2-amino-2-methylpropanoate hydrochloride (46a)

2-Amino-2-methylpropanoic acid (1.0 g, 9.70 mmol) was suspended in cyclohexanemethanol (4.79 mL, 34 mmol) and a solution of hydrogen chloride in 1,4-dioxane (4N, 12.1 mL, 48.5 mmol). The mixture was heated at 65° C. for 5 days. The 1,4-dioxane was removed under reduced pressure. The mixture was diluted with ethyl acetate/hexanes (1:1, 100 mL) and water (100 mL). The organic phase was extracted with water (100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 50 mL, under reduced pressure. The aqueous phase was diluted with acetonitrile (20 mL) and water (10 mL) and subjected to lyophilization, providing intermediate 46a. $^1$H NMR (400 MHz, DMSO-d$_6$) δ 8.60 (s, 3H), 3.99 (d, J=6.2 Hz, 2H), 1.68 (m, 6H), 1.49 (s, 6H), 1.31-1.07 (m, 3H), 1.07-0.88 (m, 2H).

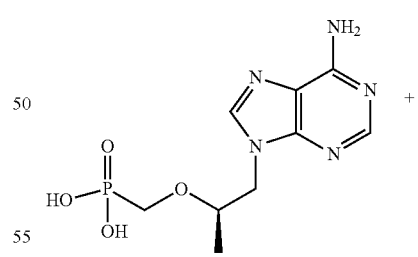

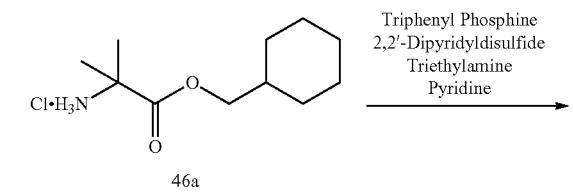

46a

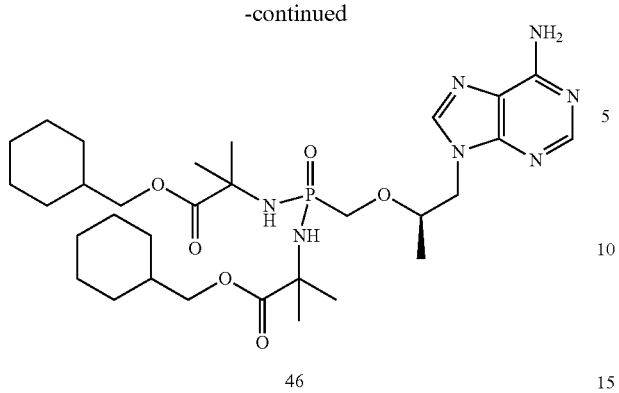

46

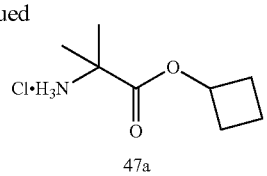

47a

Synthesis of cyclobutyl 2-amino-2-methylpropanoate hydrochloride (47a)

2-Amino-2-methylpropanoic acid (3.0 g, 29.1 mmol) was suspended in cyclobutanol (20.7 mL, 233 mmol) and a solution of hydrogen chloride in 1,4-dioxane (4N, 36.3 mL, 145 mmol). The mixture was heated at 65° C. for 24 hours. The reaction was cooled and any solid was removed by filtration. The 1,4-dioxane was removed under reduced pressure. The mixture was diluted with ethyl acetate/hexanes (1:1, 100 mL) and water (100 mL). The organic phase was extracted with water (2×100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 50 mL, under reduced pressure. The aqueous phase was diluted with acetonitrile (20 mL) and subjected to lyophilization, providing intermediate 47a. $^1$H NMR (400 MHz, DMSO-$d_6$) δ 8.65 (s, 3H), 5.06-4.94 (m, 1H), 2.39-2.25 (m, 2H), 2.17-2.01 (m, 2H), 1.85-1.71 (m, 1H), 1.71-1.59 (m, 1H), 1.48 (s, 6H).

PMPA (100 mg, 0.384 mmol) and intermediate 46a (328 mg, 1.54 mmol) were azeotroped with toluene (2×10 mL). Triphenylphosphine (344 mg, 1.39 mmol) and 2,2'-dipyridyl disulfide (307 mg, 1.39 mmol) were added followed by pyridine (4 mL) under Argon. Triethylamine (0.475 mL, 3.48 mmol) was added. The mixture was heated at 90° C. for 17 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (46). $^1$H NMR (400 MHz, Methanol-$d_4$) δ 8.37 (s, 1H), 8.29 (s, 1H), 4.46 (dd, J=14.5, 3.0 Hz, 1H), 4.30 (dd, J=14.5, 7.3 Hz, 1H), 4.06-3.86 (m, 5H), 3.81 (dd, J=12.8, 8.4 Hz, 1H), 3.55 (dd, J=12.9, 10.2 Hz, 1H), 1.88-1.61 (m, 12H), 1.58 (s, 3H), 1.53-1.46 (m, 6H), 1.44 (s, 3H), 1.37-1.16 (m, 9H), 1.12-0.94 (m, 4H). $^{31}$P NMR (162 MHz, DMSO-$d_6$) δ 18.38 (p, J=9.4 Hz). LCMS: MS m/z=650.59 [M+1]; $t_R$=1.430 min; LC system: Thermo Accela 1250 UHPLC; MS system: Thermo LCQ Fleet; Column: Phenomenex Kinetex 2.6μ XB-C18 100A, 50×3.0 mm; Solvents: Acetonitrile with 0.1% trifluoroacetic acid, water with 0.1% trifluoroacetic acid; Gradient: 0 min-0.2 min 10% acetonitrile, 0.2 min-1.85 min 10%-100% acetonitrile, 1.85 min-2.14 min 100% acetonitrile, 2.14 min-2.15 min 100%-10% acetonitrile, 2.15 min-2.25 min 10% acetonitrile at 1.8 mL/min. HPLC: $t_R$=3.351 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 47: Dicyclobutyl 2,2'-(((((1-(6-amino-9H-purin-9-yl)propan-2-yl)oxy)methyl)phosphoryl)bis(azanediyl))(R)-bis(2-methylpropanoate) (47)

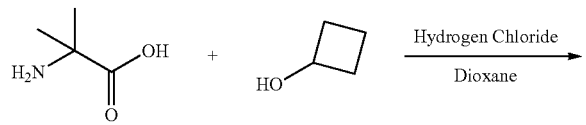

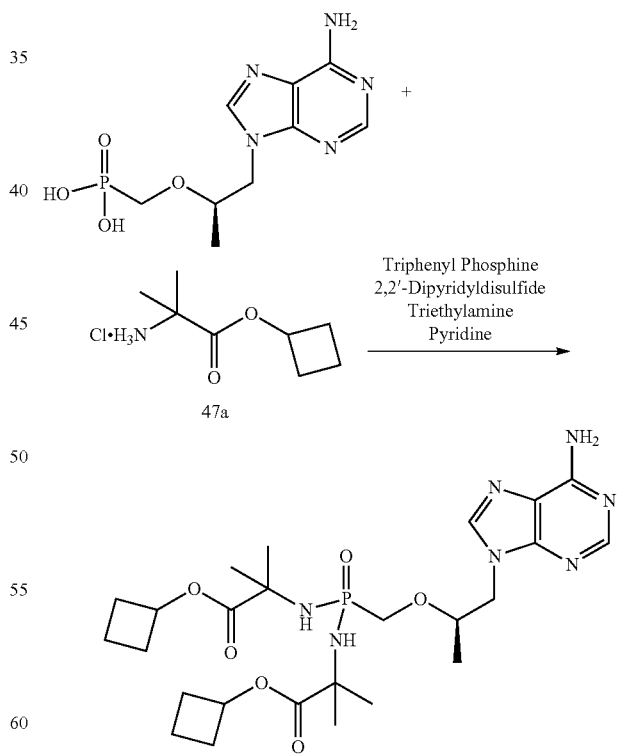

47

PMPA (200 mg, 0.696 mmol) and intermediate 47a (547 mg, 3.48 mmol) were azeotroped with toluene (2×10 mL). Triphenylphosphine (688 mg, 2.79 mmol) and 2,2'-dipyridyl disulfide (614 mg, 2.79 mmol) were added followed by pyridine (4 mL) under Argon. Triethylamine (0.950 mL, 7.05 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (47). $^1$H NMR (400 MHz, Methanol-$d_4$) δ 8.27 (s, 1H), 8.23 (s, 1H), 5.07-4.99 (m, 1H), 4.99-4.91 (m, 1H), 4.41 (dd, J=14.5, 3.1 Hz, 1H), 4.32 (d, J=12.0 Hz, 0.87H), 4.26 (dd, J=14.5, 7.5 Hz, 1H), 4.07 (d, J=11.4 Hz, 0.92H), 4.03-3.93 (m, 1H), 3.79 (dd, J=12.8, 8.4 Hz, 1H), 3.52 (dd, J=12.8, 10.1 Hz, 1H), 2.44-2.29 (m, 4H), 2.19-1.99 (m, 4H), 1.91-1.76 (m, 2H), 1.76-1.60 (m, 2H), 1.56 (s, 3H), 1.48 (s, 3H), 1.46 (s, 3H), 1.43 (s, 3H), 1.25 (d, J=6.2 Hz, 3H). $^{31}$P NMR (162 MHz, Methanol-$d_4$) δ 20.82 (q, J=10.4, 9.5 Hz). LCMS: MS m/z=566.21 [M+1]; $t_R$=1.253 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.468 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 48: Bis(bicyclo[2.2.2]octan-1-ylmethyl) 2,2'-(((((1-(6-amino-9H-purin-9-yl)propan-2-yl)oxy)methyl)phosphoryl)bis(azanediyl))(R)-bis(2-methylpropanoate) (48)

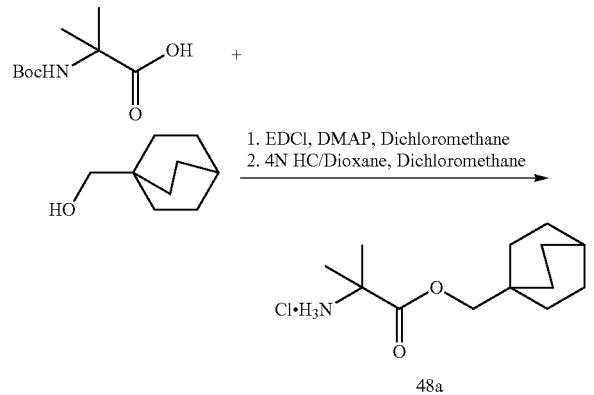

Synthesis of bicyclo[2.2.2]octan-1-ylmethyl 2-amino-2-methylpropanoate hydrochloride (48a)

2-(tert-Butoxycarbonylamino)-2-methyl-propanoic acid (1.0 g, 4.92 mmol), 1-bicyclo[2.2.2]octanylmethanol (875 mg, 6.24 mmol), 4-dimethylaminopyridine (1.8 g, 14.8 mmol) and 3-(ethyliminomethyleneamino)-N,N-dimethylpropan-1-amine hydrochloride (2.8 g mg, 14.8 mmol) were dissolved in dichloromethane (10 mL). After 16 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.2 mL, 24.6 mmol) was added to a solution of the residue in dichloromethane (5 mL). After 90 min the solvent was removed under reduced pressure. The residue was co-evaporated with dichloromethane (10 mL). The residue was subjected to high vacuum for 5 hours, providing intermediate 48a. $^1$H NMR (400 MHz, DMSO-$d_6$) δ 8.56 (s, 3H), 3.79 (s, 2H), 1.61-1.50 (m, 7H), 1.49 (s, 6H), 1.42-1.34 (m, 6H).

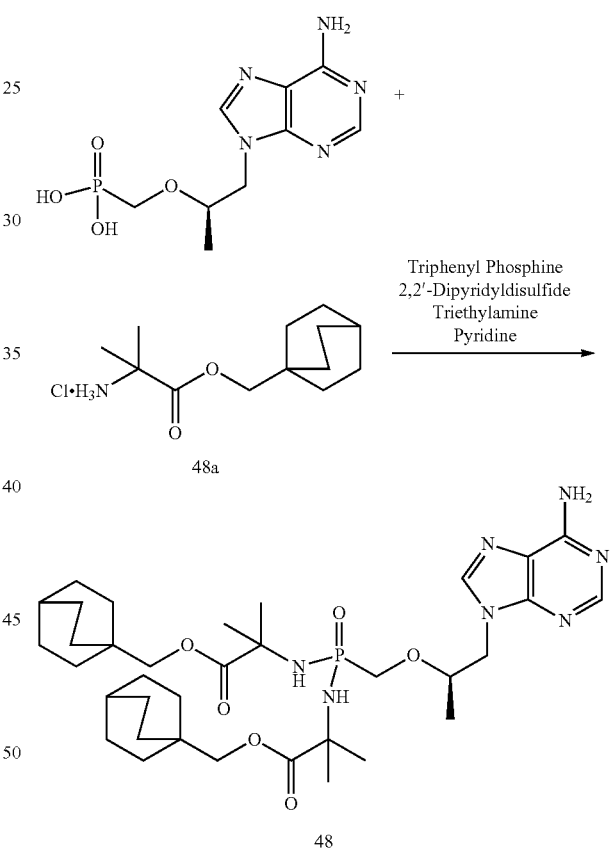

PMPA (100 mg, 0.348 mmol) and intermediate 48a (328 mg, 1.25 mmol) were azeotroped with toluene (2×10 mL). Triphenylphosphine (344 mg, 1.39 mmol) and 2,2'-dipyridyl disulfide (307 mg, 1.39 mmol) were added followed by pyridine (4 mL) under Argon. Triethylamine (0.475 mL, 3.48 mmol) was added. The mixture was heated at 90° C. for 16 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (48). $^1$H NMR (400 MHz, Methanol-$d_4$) δ 8.29 (s, 1H), 8.23 (s, 1H), 4.42 (dd, J=14.5, 3.0 Hz, 1H), 4.36 (d, J=12.1 Hz, 0.29H), 4.26 (dd, J=14.5, 7.3 Hz, 1H), 4.12 (d, J=11.5 Hz, 0.37H), 4.03-3.92 (m, 1H), 3.86-3.64 (m, 6H), 3.56 (dd, J=12.8, 10.3 Hz, 1H), 1.69-1.53 (m, 17H), 1.49 (d, J=5.2 Hz, 6H), 1.48-1.37 (m, 15H), 1.25 (d, J=6.1 Hz, 3H). $^{31}$P NMR (162 MHz, Methanol-$d_4$) δ 20.84 (q, J=10.5, 9.6 Hz). LCMS: MS m/z=702.25 [M+1]; $t_R$=1.680 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.582 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 49: Bis(3,3-diethylcyclobutyl) 2,2'-(((((1-(6-amino-9H-purin-9-yl)propan-2-yl)oxy)methyl)phosphoryl)bis(azanediyl))(R)-bis(2-methylpropanoate) (49)

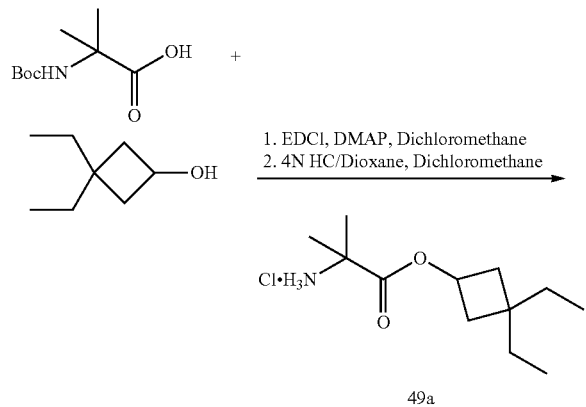

Synthesis of 3,3-diethylcyclobutyl 2-amino-2-methylpropanoate hydrochloride (49a)

2-(tert-Butoxycarbonylamino)-2-methyl-propanoic acid (1.0 g, 4.92 mmol), 3,3-diethylcyclobutanol (875 mg, 6.83 mmol), 4-dimethylaminopyridine (1.8 g, 14.8 mmol) and 3-(ethyliminomethyleneamino)-N,N-dimethyl-propan-1-amine hydrochloride (2830 mg, 14.8 mmol) were dissolved in dichloromethane (10 mL). After 18 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.2 mL, 24.6 mmol) was added to a solution of the residue in dichloromethane (5 mL). After 90 min the solvent was removed under reduced pressure. The residue was co-evaporated with dichloromethane (10 mL). The residue was subjected to high vacuum for 5 hours, providing intermediate 49a. $^1$H NMR (400 MHz, DMSO-$d_6$) δ 8.56 (s, 3H), 5.07-4.88 (m, 1H), 2.26-2.14 (m, 2H), 1.85-1.71 (m, 2H), 1.47 (s, 6H), 1.46-1.40 (m, 4H), 0.80-0.73 (m, 6H).

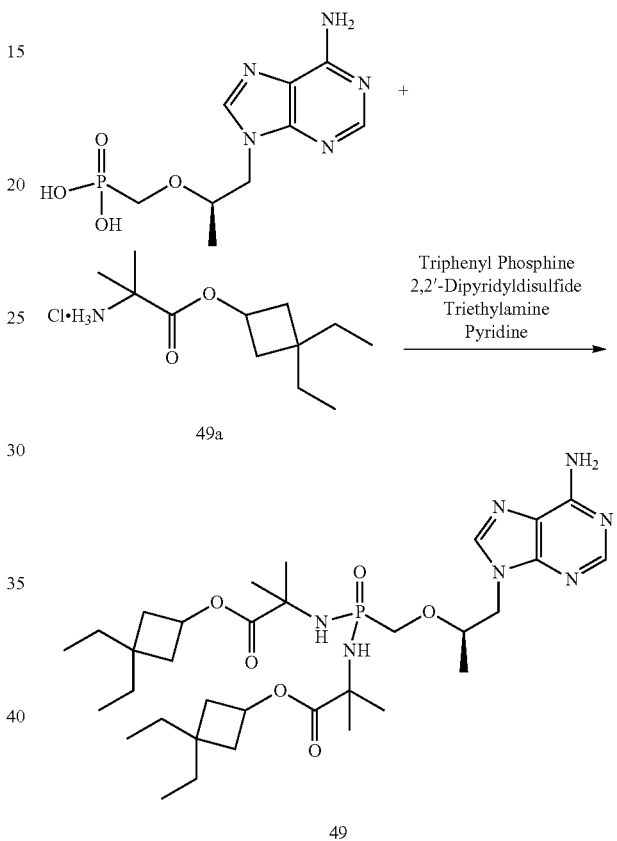

PMPA (100 mg, 0.348 mmol) and intermediate 49a (366 mg, 1.39 mmol) were azeotroped with toluene (2×10 mL). Triphenylphosphine (430 mg, 174 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 16 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (49). $^1$H NMR (400 MHz, Methanol-$d_4$) δ 8.28 (s, 1H), 8.23 (s, 1H), 5.06-4.95 (m, 1H), 4.95-4.90 (m, 1H), 4.42 (dd, J=14.5, 3.1 Hz, 1H), 4.36 (d, J=12.1 Hz, 0.06H) 4.26 (dd, J=14.5, 7.3 Hz, 1H), 4.12 (d, J=11.5 Hz, 0.06H), 4.05-3.92 (m, 1H), 3.80 (dd, J=12.8, 8.4 Hz, 1H), 3.53 (dd, J=12.8, 10.2 Hz, 1H), 2.32-2.16 (m, 4H), 1.85-1.67 (m, 4H), 1.57 (s, 3H), 1.54-1.43 (m, 14H), 1.42 (s, 3H), 1.24 (d, J=6.2 Hz, 3H), 0.90-0.81 (m, 6H), 0.81-0.72 (m, 6H). $^{31}$P NMR (162 MHz, Methanol-d$_4$) δ 20.75 (t, J=9.2 Hz, 1P). LCMS: MS m/z=678.18 [M+1]; t$_R$=1.600 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=3.470 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 50: Bis(spiro[3.3]heptan-2-ylmethyl) 2,2'-(((((1-(6-amino-9H-purin-9-yl)propan-2-yl)oxy)methyl)phosphoryl)bis(azanediyl))(R)-bis(2-methylpropanoate) (50)

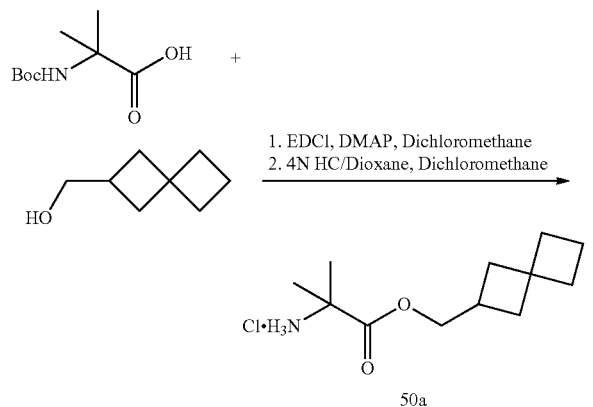

Synthesis of spiro[3.3]heptan-2-ylmethyl 2-amino-2-methylpropanoate hydrochloride (50a)

2-(tert-Butoxycarbonylamino)-2-methyl-propanoic acid (1.5 g, 7.38 mmol), spiro[3.3]heptan-2-ylmethanol (1313 mg, 10.4 mmol), 4-dimethylaminopyridine (2.7 g, 22.1 mmol) and 3-(ethyliminomethyleneamino)-N,N-dimethylpropan-1-amine hydrochloride (4.25 g, 22.1 mmol) were dissolved in dichloromethane (10 mL). After 90 minutes the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 9.2 mL, 36.9 mmol) was added to a solution of the residue in dichloromethane (5 mL). After 90 min the solvent was removed under reduced pressure. The residue was co-evaporated with dichloromethane (10 mL). The residue was subjected to high vacuum for 5 hours, providing intermediate 50a. H NMR (400 MHz, DMSO-d$_6$) δ 8.59 (s, 3H), 4.12 (d, J=6.6 Hz, 2H), 2.44 (m, 1H), 2.10-2.01 (m, 2H), 2.01-1.96 (m, 2H), 1.92-1.84 (m, 2H), 1.81-1.70 (m, 4H), 1.48 (s, 6H).

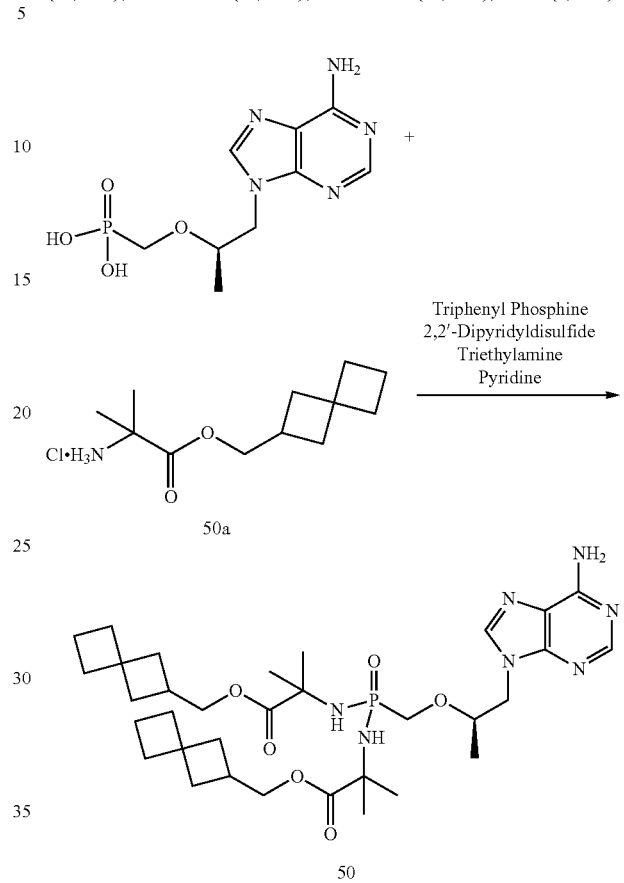

PMPA (100 mg, 0.348 mmol) and intermediate 50a (363 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 16 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (50). $^1$H NMR (400 MHz, Methanol-d$_4$) δ 8.28 (s, 1H), 8.23 (s, 1H), 4.42 (dd, J=14.5, 3.1 Hz, 1H), 4.26 (dd, J=14.5, 7.3 Hz, 1H), 4.19-3.92 (m, 5H), 3.80 (dd, J=12.8, 8.4 Hz, 1H), 3.54 (dd, J=12.8, 10.2 Hz, 1H), 2.59-2.36 (m, 2H), 2.18-1.97 (m, 8H), 1.97-1.87 (m, 4H), 1.87-1.70 (m, 8H), 1.57 (s, 3H), 1.49 (s, 3H), 1.47 (s, 3H), 1.42 (s, 3H), 1.24 (d, J=6.2 Hz, 3H). $^{31}$P NMR (162 MHz, Methanol-d$_4$) δ 20.72 (t, J=9.2 Hz). LCMS: MS m/z=674.19 [M+1]; t$_R$=1.600 min; LC system: Thermo Dionex Ultimate 3000 UHPLC+ focused;

MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.41 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 51: Bis((1S,3S)-3-(tert-butyl)cyclobutyl) 2,2'-(((((R)-1-(6-amino-9H-purin-9-yl)propan-2-yl)oxy)methyl)phosphoryl)bis(azanediyl))bis(2-methylpropanoate) (51)

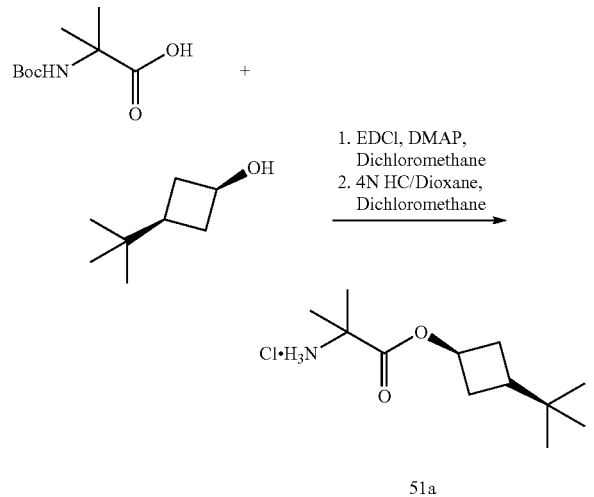

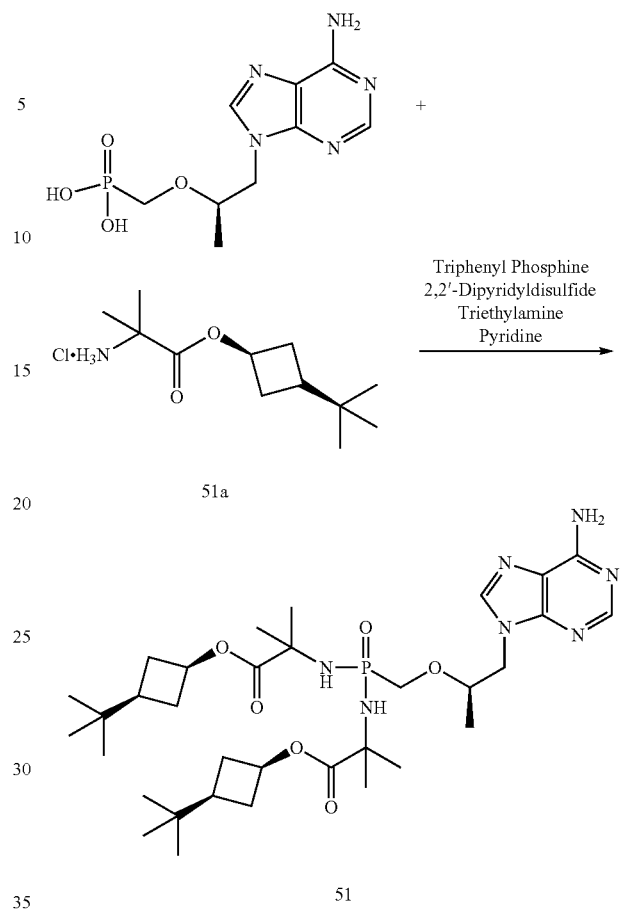

Synthesis of (1S,3S)-3-(tert-butyl)cyclobutyl 2-amino-2-methylpropanoate hydrochloride (51a)

2-(tert-Butoxycarbonylamino)-2-methyl-propanoic acid (1.0 g, 4.92 mmol), (1S,3S)-3-(tert-butyl)cyclobutan-1-ol (875 mg, 6.83 mmol), 4-dimethylaminopyridine (1.8 g, 14.8 mmol) and 3-(ethyliminomethyleneamino)-N,N-dimethylpropan-1-amine hydrochloride (2.8 g, 14.8 mmol) were dissolved in dichloromethane (10 mL). After 45 minutes the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.1 mL, 24.6 mmol) was added to a solution of the residue in dichloromethane (5 mL). After 1 h the solvent was removed under reduced pressure. The residue was co-evaporated with dichloromethane (10 mL). The residue was subjected to high vacuum for 5 hours, providing intermediate 51a. $^1$H NMR (400 MHz, DMSO-$d_6$) δ 8.46 (s, 3H), 4.84 (p, J=7.4 Hz, 1H), 2.25 (m, 2H), 1.87-1.65 (m, 3H), 1.46 (s, 6H), 0.82 (s, 9H).

PMPA (100 mg, 0.348 mmol) and intermediate 51a (366 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 21 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (51). $^1$H NMR (400 MHz, Methanol-$d_4$) δ 8.29 (s, 1H), 8.24 (s, 1H), 7.08 (s, 0.10H), 4.87-4.80 (m, 1H), 4.80-4.71 (m, 1H), 4.42 (dd, J=14.5, 3.1 Hz, 1H), 4.35 (d, J=12.0 Hz, 0.07H), 4.26 (dd, J=14.5, 7.4 Hz, 1H), 4.11 (d, J=11.4 Hz, 0.12H), 4.03-3.93 (m, 1H), 3.80 (dd, J=12.9, 8.4 Hz, 1H), 3.53 (dd, J=12.8, 10.1 Hz, 1H), 2.38-2.18 (m, 4H), 1.89-1.68 (m, 6H), 1.57 (s, 3H), 1.48 (s, 3H), 1.46 (s, 3H), 1.41 (s, 3H), 1.24 (d, J=6.2 Hz, 3H), 0.85 (s, 9H), 0.84 (s, 9H). $^{31}$P NMR (162 MHz, Methanol-$d_4$) δ 20.71 (t, J=9.2 Hz). LCMS: MS m/z=678.18 [M+1]; $t_R$=1.647 min; LC system: Thermo Dionex Ultimate 3000 UHPLC+ focused; MS system:

Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.504 min; HPLC system: Agilent 1100 series; Column: Gemini 5p C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 52: Bis((1R,3R)-3-(tert-butyl)cyclobutyl) 2,2'-(((((R)-1-(6-amino-9H-purin-9-yl)propan-2-yl)oxy)methyl)phosphoryl)bis(azanediyl))bis(2-methyl-propanoate) (52)

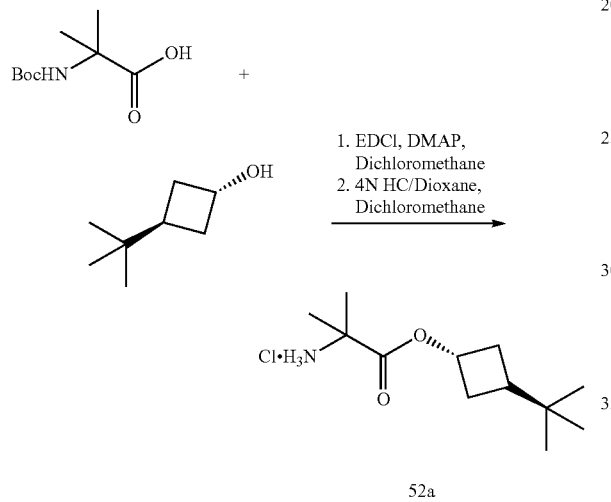

Synthesis of (1R,3R)-3-(tert-butyl)cyclobutyl 2-amino-2-methylpropanoate hydrochloride (52a)

2-(tert-Butoxycarbonylamino)-2-methyl-propanoic acid (1.5 g, 7.38 mmol), (1R,3R)-3-(-butyl)cyclobutan-1-ol (1.14 mg, 8.86 mmol), 4-dimethylaminopyridine (2.7 g, 22.1 mmol) and 3-(ethyliminomethyleneamino)-N,N-dimethyl-propan-1-amine hydrochloride (4.2 g, 22.1 mmol) were dissolved in dichloromethane (10 mL). After 3 days the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 9.2 mL, 36.9 mmol) was added to a solution of the residue in dichloromethane (5 mL). After 90 minutes the solvent was removed under reduced pressure. The residue was co-evaporated with dichloromethane (10 mL). The residue was subjected to high vacuum for 5 hours, providing intermediate 52a. $^1$H NMR (400 MHz, DMSO-d$_6$) δ 8.50 (s, 3H), 5.02-4.88 (m, 1H), 2.35-2.18 (m, 3H), 2.15-1.97 (m, 2H), 1.48 (s, 6H), 0.83 (s, 9H).

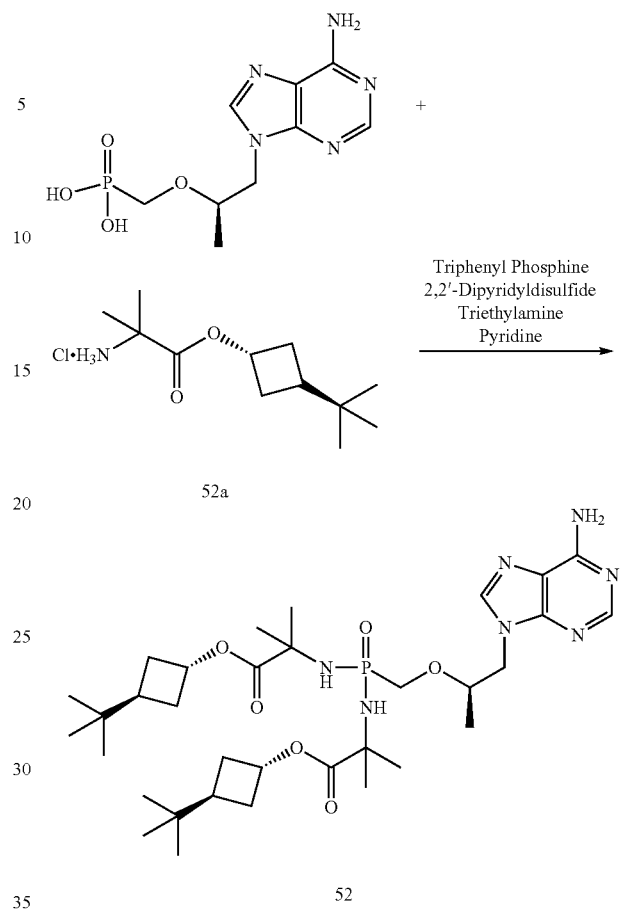

PMPA (100 mg, 0.348 mmol) and intermediate 52a (366 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 21 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (52). $^1$H NMR (400 MHz, Methanol-d$_4$) δ 8.28 (s, 1H), 8.23 (s, 1H), 4.99-4.94 (m, 1H), 4.94-4.89 (m, 1H), 4.47-4.35 (m, 1.32H), 4.26 (dd, J=14.5, 7.3 Hz, 1H), 4.16-4.12 (m, 0.41H), 4.04-3.95 (m, 1H), 3.86-3.76 (m, 1H), 3.62-3.49 (m, 1H), 2.34-2.19 (m, 6H), 2.18-1.99 (m, 4H), 1.59 (s, 3H), 1.51 (s, 3H), 1.49 (s, 3H), 1.44 (s, 3H), 1.25 (d, J=6.2 Hz, 3H), 0.87 (s, 9H), 0.86 (s, 9H). $^{31}$P NMR (162 MHz, Methanol-d$_4$) δ 20.75 (t, J=9.4 Hz). LCMS: MS m/z=678.14 [M+1]; $t_R$=1.627 min; LC system: Thermo Dionex Ultimate 3000 UHPLC+ focused; MS system: Thermo LCQ Fleet; Column: Phenomenex Kinetex 2.6µ-C18 100A, 50×2.1 mm;

Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.468 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 53: Bis(spiro[3.5]nonan-7-ylmethyl) 2,2'-(((((1-(6-amino-9H-purin-9-yl)propan-2-yl)oxy)methyl)phosphoryl)bis(azanediyl))(R)-bis(2-methyl-propanoate) (53)

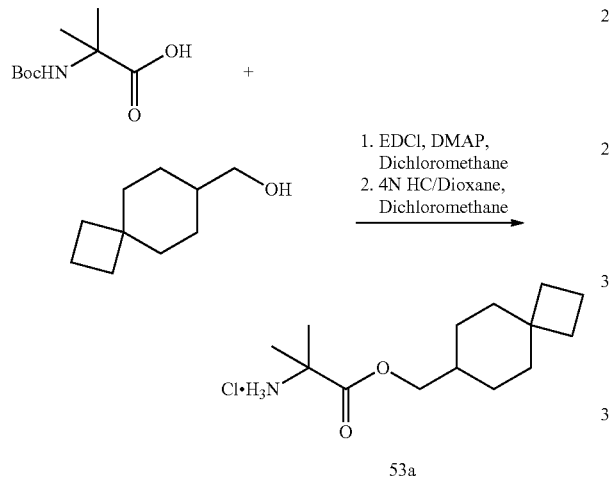

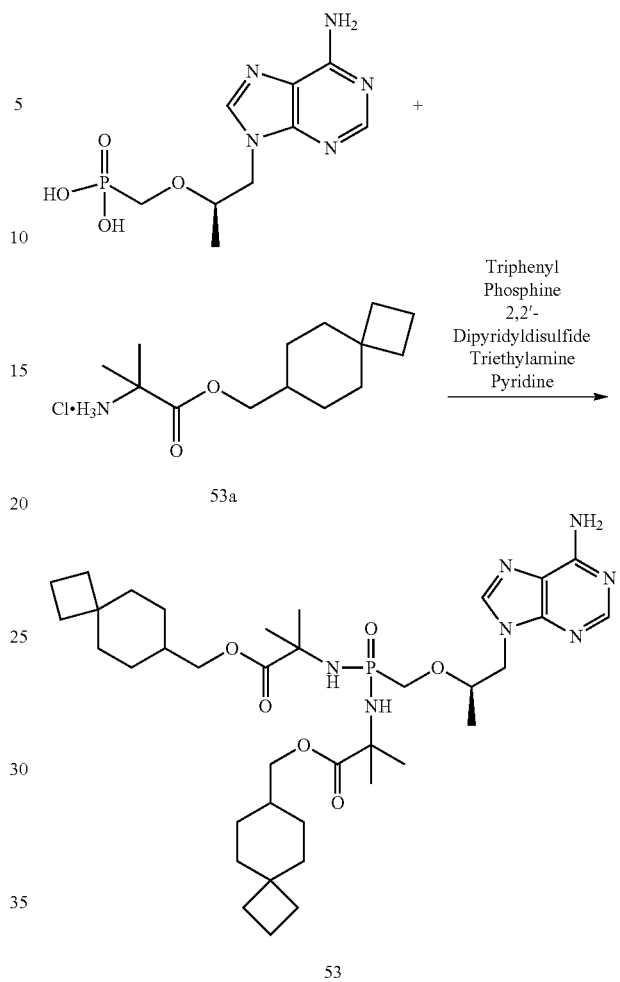

Synthesis of spiro[3.5]nonan-7-ylmethyl 2-amino-2-methylpropanoate hydrochloride (53a)

2-(tert-Butoxycarbonylamino)-2-methyl-propanoic acid (2.0 g, 9.84 mmol), spiro[3.5]nonan-7-ylmethanol (1.75 g, 11.3 mmol), 4-dimethylaminopyridine (3.6 g, 29.5 mmol) and 3-(ethyliminomethyleneamino)-N,N-dimethyl-propan-1-amine hydrochloride (5.65 g, 29.5 mmol) were dissolved in dichloromethane (10 mL). After days the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 12.3 mL, 49.2 mmol) was added to a solution of the residue in dichloromethane (5 mL). After 1 h the solvent was removed under reduced pressure. The residue was co-evaporated with dichloromethane (10 mL). The residue was subjected to high vacuum for 5 hours, providing intermediate 53a. $^1$H NMR (400 MHz, DMSO-$d_6$) δ 8.56 (s, 3H), 3.99 (d, J=6.0 Hz, 2H), 1.88-1.77 (m, 2H), 1.74 (m, 2H), 1.70-1.62 (m, 4H), 1.62-1.50 (m, 3H), 1.48 (s, 6H), 1.22 (m, 2H), 1.00 (m, 2H).

PMPA (100 mg, 0.348 mmol) and intermediate 53a (404 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 21 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (53). $^1$H NMR (400 MHz, Methanol-$d_4$) δ 8.29 (s, 1H), 8.23 (s, 1H), 4.48-4.35 (m, 1.54H), 4.26 (dd, J=14.5, 7.2 Hz, 1H), 4.16 (dd, J=11.6, 1.5 Hz, 0.46H), 4.06-3.92 (m, 4H), 3.92-3.85 (m, 1H), 3.81 (dd, J=12.8, 8.4 Hz, 1H), 3.55 (dd, J=12.8, 10.2 Hz, 1H), 1.94-1.82 (m, 4H), 1.82-1.65 (m, 11H), 1.65-1.52 (m, 10H), 1.50 (s, 3H), 1.49 (s, 3H), 1.43 (s, 3H), 1.35-1.15 (m, 7H), 1.15-0.97 (m, 4H). $^{31}$P NMR (162 MHz, Methanol-$d_4$) δ 20.77 (q, J=10.3, 9.7 Hz). LCMS: MS m/z=730.2 [M+1]; $t_R$=1.800 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.955 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 54: Bis(3,3-dimethylpentyl) 2,2'-(((((1-(6-amino-9H-purin-9-yl)propan-2-yl)oxy)methyl)phosphoryl)bis(azanediyl))(R)-bis(2-methylpropanoate) (54)

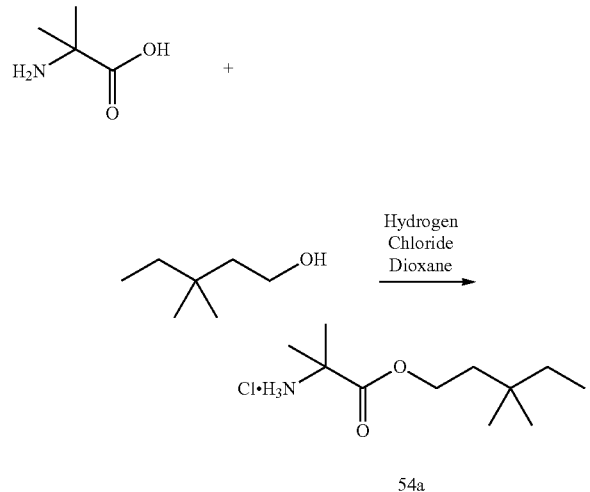

Synthesis of 3,3-dimethylpentyl 2-amino-2-methylpropanoate hydrochloride (54a)

2-Amino-2-methylpropanoic acid (0.50 g, 4.85 mmol) was suspended in 3,3-dimethylpentan-1-ol (2.08 mL, 14.5 mmol) and a solution of hydrogen chloride in 1,4-dioxane (4N, 6.06 mL, 24.2 mmol). The mixture was heated at 65° C. for 3 days. The reaction was cooled and any solid was removed by filtration. The 1,4-dioxane was removed under reduced pressure. The mixture was diluted with ethyl acetate/hexanes (1:1, 100 mL) and water (100 mL). The organic phase was extracted with water (2×100 mL). The combined aqueous phases were washed with ethyl acetate/hexanes (1:1, 3×100 mL), diethyl ether (3×100 mL) and dichloromethane (3×100 mL). Any residual solvent in the aqueous phase was removed and the volume was reduced to 10 mL, under reduced pressure. The aqueous phase was diluted with acetonitrile (8 mL) and subjected to lyophilization, providing intermediate 54a. $^1$H NMR (400 MHz, DMSO-$d_6$) δ 8.57 (m, 3H), 4.21 (t, J=7.3 Hz, 2H), 1.54 (t, J=7.3 Hz, 2H), 1.47 (s, 6H), 1.24 (q, J=7.5 Hz, 2H), 0.87 (s, 6H), 0.81 (t, J=7.5 Hz, 3H).

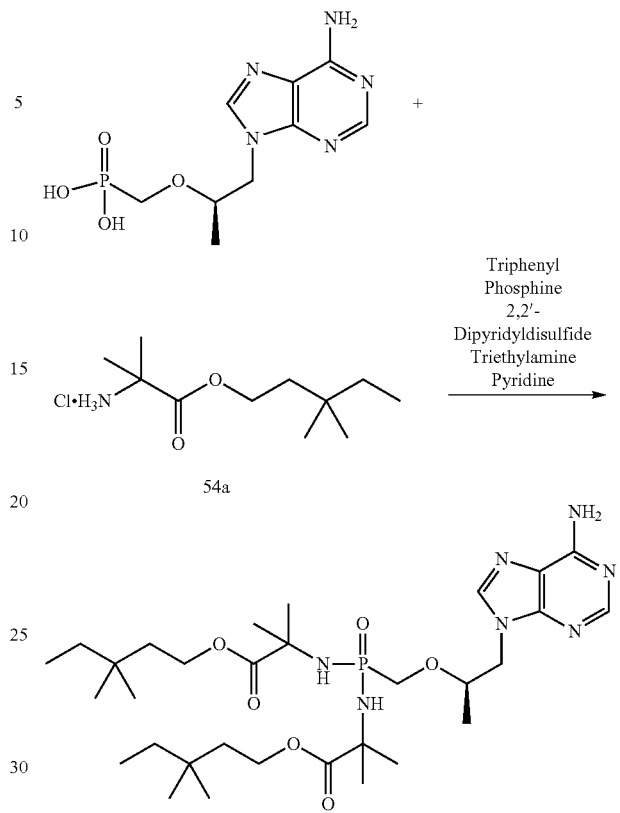

PMPA (100 mg, 0.348 mmol) and intermediate 54a (349 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 20 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (54). $^1$H NMR (400 MHz, Methanol-$d_4$) δ 8.29 (s, 1H), 8.23 (s, 1H), 4.42 (dd, J=14.5, 3.1 Hz, 1H), 4.33-4.08 (m, 5H), 4.05-3.94 (m, 1H), 3.81 (dd, J=12.8, 8.4 Hz, 1H), 3.55 (dd, J=12.8, 10.1 Hz, 1H), 1.65-1.53 (m, 7H), 1.49 (d, J=4.8 Hz, 6H), 1.42 (s, 3H), 1.35-1.27 (m, 4H), 1.25 (d, J=6.3 Hz, 3H), 0.92 (s, 6H), 0.91 (s, 6H), 0.90-0.82 (m, 6H). $^{31}$P NMR (162 MHz, Methanol-$d_4$) δ 20.80 (t, J=9.2 Hz). LCMS: MS m/z=654.19 [M+1]; $t_R$=1.617 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.416 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 55: Bis((R)-1-cyclohexylethyl) 2,2'-((((((R)-1-(6-amino-9H-purin-9-yl)propan-2-yl)oxy)methyl)phosphoryl)bis(azanediyl))bis(2-methylpropanoate) (55)

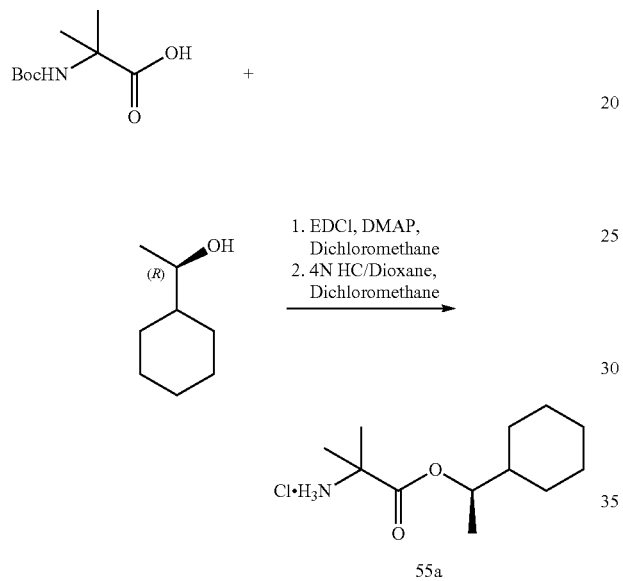

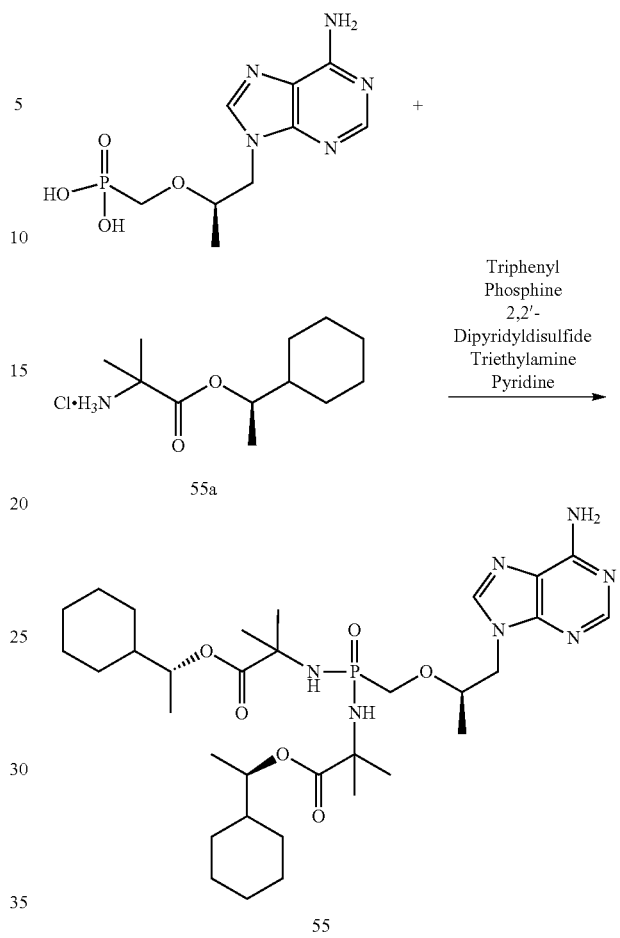

Synthesis of (R)-1-cyclohexylethyl 2-amino-2-methylpropanoate hydrochloride (55a)

2-(tert-Butoxycarbonylamino)-2-methyl-propanoic acid (1.0 g, 4.92 mmol), (R)-1-cyclohexylethan-1-ol (757 mg, 5.90 mmol), 4-dimethylaminopyridine (1.8 g, 14.8 mmol) and 3-(ethyliminomethyleneamino)-N,N-dimethyl-propan-1-amine hydrochloride (2.8 g, 14.8 mmol) were dissolved in dichloromethane (10 mL). After 19 hours the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.1 mL, 24.6 mmol) was added to a solution of the residue in dichloromethane (5 mL). After 2 h the solvent was removed under reduced pressure. The residue was co-evaporated with dichloromethane (10 mL). The residue was subjected to high vacuum for 5 hours, providing intermediate 55a. $^1$H NMR (400 MHz, DMSO-d$_6$) δ 8.46 (s, 3H), 4.74 (p, J=6.3 Hz, 1H), 1.81-1.69 (m, 4H), 1.69-1.54 (m, 3H), 1.47 (m, 7H), 1.29-1.11 (m, 4H), 1.11-0.83 (m, 2H).

PMPA (100 mg, 0.348 mmol) and intermediate 55a (366 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 24 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (55). $^1$H NMR (400 MHz, Methanol-d$_4$) δ 8.32 (s, 1H), 8.23 (s, 1H), 4.78 (p, J=6.4 Hz, 1H), 4.70 (p, J=6.3 Hz, 1H), 4.48-4.35 (m, 1.56H), 4.27 (dd, J=14.5, 7.2 Hz, 1H), 4.16 (dd, J=11.4, 1.2 Hz, 0.62H), 4.09-3.94 (m, 1H), 3.81 (dd, J=12.8, 8.4 Hz, 1H), 3.58 (dd, J=12.8, 10.2 Hz, 1H), 1.90-1.63 (m, 11H), 1.60 (s, 3H), 1.58-1.40 (m, 11H), 1.36-1.13 (m, 14H), 1.13-0.93 (m, 4H). $^{31}$P NMR (162 MHz, Methanol-d$_4$) δ 20.74 (q, J=10.4, 9.8 Hz). LCMS: MS m/z=678.21 [M+1]; $t_R$=1.650 min; LC system: Thermo Dionex Ultimate 3000 UHPLC+ focused; MS system:

Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.534 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 56: Bis((S)-1-cyclohexylethyl) 2,2'-((((((R)-1-(6-amino-9H-purin-9-yl)propan-2-yl)oxy)methyl)phosphoryl)bis(azanediyl))bis(2-methylpropanoate) (56)

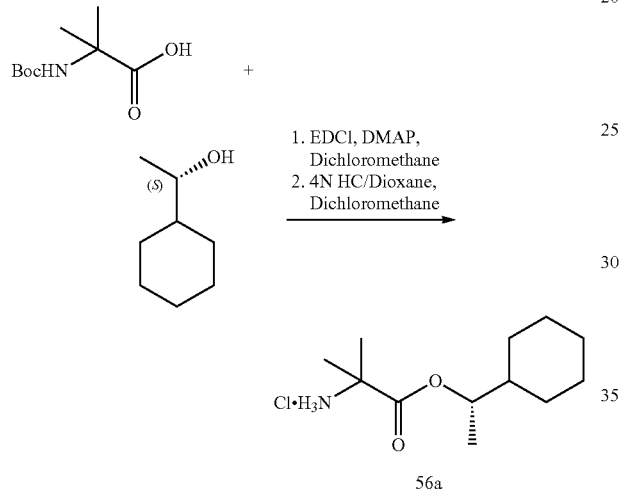

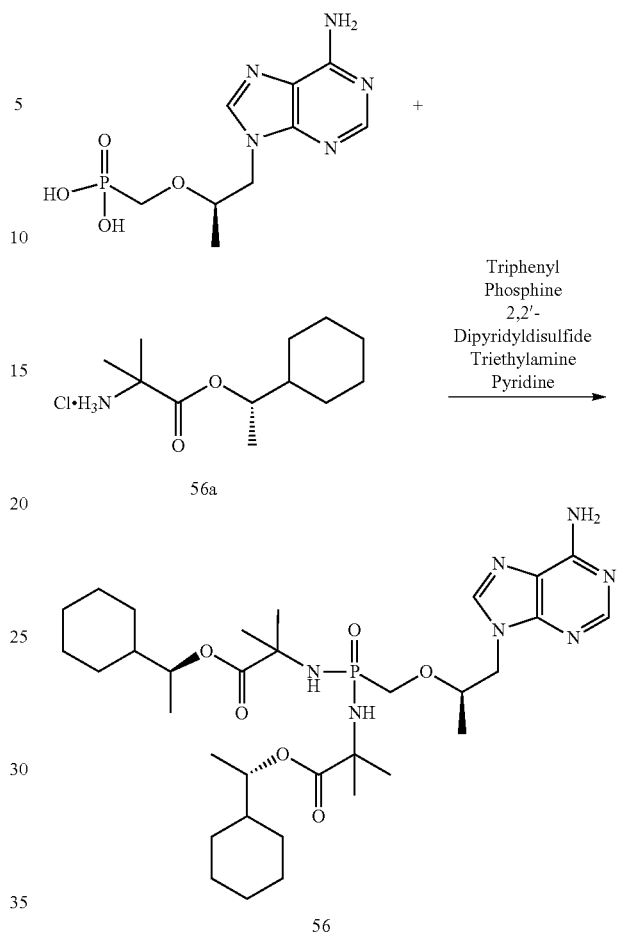

Synthesis of (S)-1-cyclohexylethyl 2-amino-2-methylpropanoate hydrochloride (56a)

2-(tert-Butoxycarbonylamino)-2-methyl-propanoic acid (1.0 g, 4.92 mmol), (S)-1-cyclohexylethan-1-ol (757 mg, 5.90 mmol), 4-dimethylaminopyridine (1.8 g, 14.8 mmol) and 3-(ethyliminomethyleneamino)-N,N-dimethyl-propan-1-amine hydrochloride (2.8 g, 14.8 mmol) were dissolved in dichloromethane (10 mL). After 19 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.1 mL, 24.6 mmol) was added to a solution of the residue in dichloromethane (5 mL). After 2 h the solvent was removed under reduced pressure. The residue was co-evaporated with dichloromethane (10 mL). The residue was subjected to high vacuum for 5 hours, providing intermediate 56a. $^1$H NMR (400 MHz, DMSO-$d_6$) δ 8.44 (s, 3H), 4.74 (p, J=6.3 Hz, 1H), 1.81-1.67 (m, 4H), 1.67-1.55 (m, 3H), 1.55-1.35 (m, 7H), 1.31-1.11 (m, 4H), 1.11-0.83 (m, 2H).

PMPA (100 mg, 0.348 mmol) and intermediate 56a (366 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 24 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (56). $^1$H NMR (400 MHz, Methanol-$d_4$) δ 8.31 (s, 1H), 8.23 (s, 1H), 4.82-4.62 (m, 2H), 4.47-4.36 (in, 1.71H), 4.27 (dd, J=14.5, 7.2 Hz, 1H), 4.18 (d, J=11.8 Hz, 0.83H), 4.07-3.93 (m, 1H), 3.81 (dd, J=12.8, 8.7 Hz, 1H), 3.56 (dd, J=12.8, 9.9 Hz, 1H), 1.89-1.61 (m, 11H), 1.57 (s, 3H), 1.55-1.45 (m, 7H), 1.43 (s, 3H), 1.33-1.13 (m, 14H), 1.13-0.90 (in, 5H). $^{31}$P NM/R (162 MHz, Methanol-$d_4$) δ 20.71 (p, J=10.5, 9.7 Hz). LCMS: MS m/z=678.20 [M+1]; $t_R$=1.657 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.527 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 57: Bis(dispiro[3.1.3⁶.1⁴]decan-2-ylmethyl) 2,2'-(((((1-(6-amino-9H-purin-9-yl)propan-2-yl)oxy)methyl)phosphoryl)bis(azanediyl))(R)-bis(2-methylpropanoate) (57)

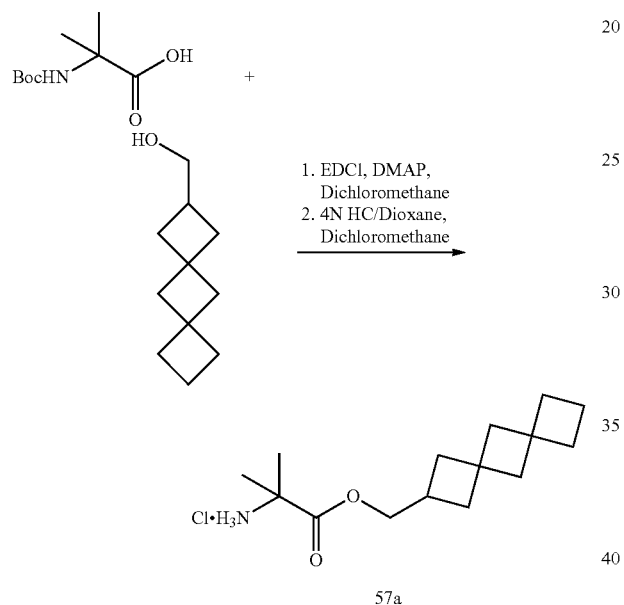

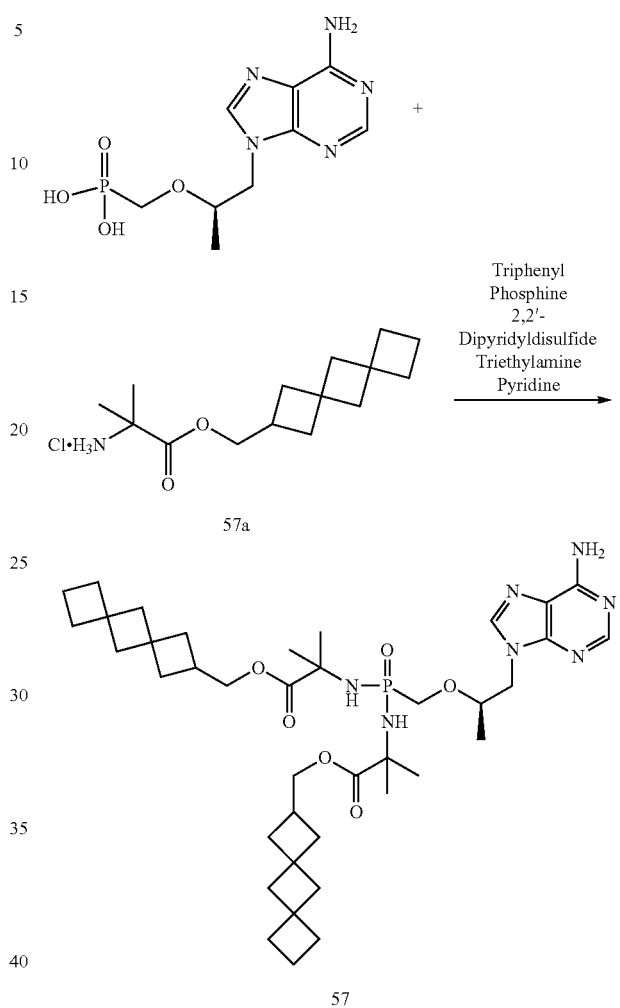

Synthesis of dispiro[3.1.36.14]decan-2-ylmethyl 2-amino-2-methylpropanoate hydrochloride (57a)

2-(tert-Butoxycarbonylamino)-2-methyl-propanoic acid (1.5 g, 7.38 mmol), dispiro[3.1.36.14]decan-2-ylmethanol (1.47 g, 8.86 mmol), 4-dimethylaminopyridine (2.7 g, 22.1 mmol) and 3-(ethyliminomethyleneamino)-N,N-dimethylpropan-1-amine hydrochloride (4.2 g, 22.1 mmol) were dissolved in dichloromethane (10 mL). After 16 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 9.2 mL, 36.9 mmol) was added to a solution of the residue in dichloromethane (5 mL). After 1 h the solvent was removed under reduced pressure. The residue was co-evaporated with dichloromethane (10 mL). The residue was subjected to high vacuum for 5 hours, providing intermediate 57a. $^1$H NMR (400 MHz, DMSO-$d_6$) δ 8.52 (s, 3H), 4.11 (d, J=6.6 Hz, 2H), 2.50-2.41 (m, 1H), 2.06-1.95 (m, 4H), 1.95-1.83 (m, 6H), 1.81-1.70 (m, 4H), 1.47 (s, 6H).

PMPA (100 mg, 0.348 mmol) and intermediate 57a (422 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (57). $^1$H NMR (400 MHz, Methanol-$d_4$) δ 8.29 (s, 1H), 8.23 (s, 1H), 4.42 (dd, J=14.5, 3.1 Hz, 1H), 4.27 (dd, J=14.5, 7.3 Hz, 1H), 4.17-3.92 (m, 5H), 3.80 (dd, J=12.8, 8.4 Hz, 1H), 3.54 (dd, J=12.8, 10.2 Hz, 1H), 2.56-2.42 (m, 2H), 2.12-1.97 (m, 8H), 1.97-1.85 (m, 12H), 1.85-1.70 (m, 8H), 1.57 (s, 3H), 1.49 (s, 3H), 1.47 (s, 3H), 1.42 (s, 3H), 1.24 (d, J=6.2 Hz, 3H). $^{31}$P NMR (162 MHz, Methanol-d$_4$) δ 20.73 (t, J=9.2 Hz). LCMS: MS m/z=754.23 [M+1]; $t_R$=1.880 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=4.210 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 58: Bis((6,6-difluorospiro[3.3]heptan-2-yl) methyl) 2,2'-(((((1-(6-amino-9H-purin-9-yl)propan-2-yl)oxy)methyl)phosphoryl)bis(azanediyl))(R)-bis (2-methylpropanoate) (58)

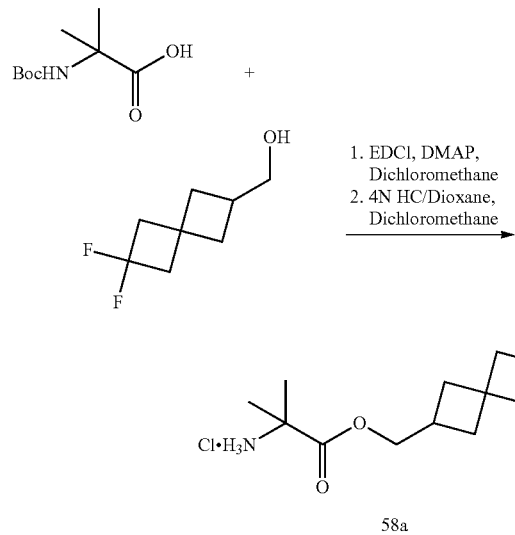

Synthesis of (6,6-difluorospiro[3.3]heptan-2-yl) methyl 2-amino-2-methylpropanoate hydrochloride (58a)

2-(tert-Butoxycarbonylamino)-2-methyl-propanoic acid (1.5 g, 7.38 mmol), (2,2-difluorospiro[3.3]heptan-6-yl) methanol (1.47 g, 9.08 mmol), 4-dimethylaminopyridine (2.7 g, 22.1 mmol) and 3-(ethyliminomethyleneamino)-N,N-dimethyl-propan-1-amine hydrochloride (4.2 g, 22.1 mmol) were dissolved in dichloromethane (10 mL). After 16 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 9.2 mL, 36.9 mmol) was added to a solution of the residue in dichloromethane (5 mL). After 1 h the solvent was removed under reduced pressure. The residue was co-evaporated with dichloromethane (10 mL). The residue was subjected to high vacuum for 5 hours, providing intermediate 58a. $^1$H NMR (400 MHz, DMSO-d$_6$) δ 8.57 (s, 3H), 4.14 (d, J=6.5 Hz, 2H), 2.75-2.58 (m, 2H), 2.58-2.52 (m, 3H), 2.23-2.10 (m, 2H), 2.03-1.91 (m, 2H), 1.48 (s, 6H). $^{19}$F NMR (376 MHz, DMSO-d$_6$) δ −89.58 (p, J=12.6 Hz).

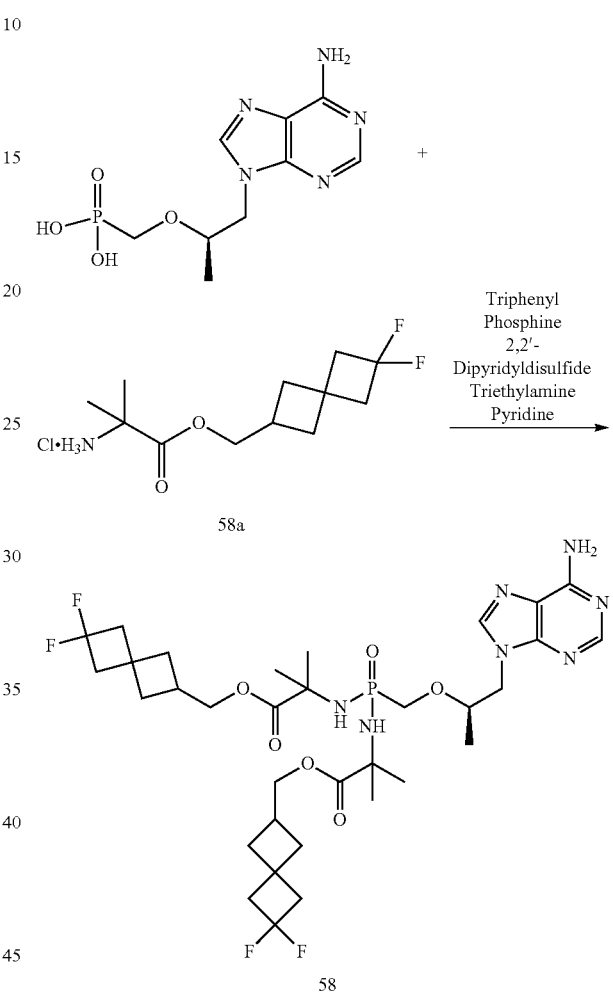

PMPA (100 mg, 0.348 mmol) and intermediate 58a (416 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (58). ¹H NMR (400 MHz, Methanol-d₄) δ 8.27 (s, 1H), 8.24 (s, 1H), 4.42 (dd, J=14.5, 3.1 Hz, 1H), 4.26 (dd, J=14.5, 7.4 Hz, 1H), 4.22-4.02 (m, 4H), 4.02-3.93 (m, 1H), 3.81 (dd, J=12.8, 8.4 Hz, 1H), 3.54 (dd, J=12.8, 10.2 Hz, 1H), 2.69-2.54 (m, 6H), 2.54-2.41 (m, 4H), 2.27-2.12 (m, 4H), 2.04-1.86 (m, 4H), 1.57 (s, 3H), 1.50 (s, 3H), 1.47 (s, 3H), 1.42 (s, 3H), 1.25 (d, J=6.2 Hz, 3H). ³¹P NMR (162 MHz, Methanol-d₄) δ 20.77 (t, J=9.4 Hz). ¹⁹F NMR (376 MHz, Methanol-d₄) δ -92.77 (pd, J=12.4, 4.8 Hz). LCMS: MS m/z=746.23 [M+1]; t_R=1.467 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t_R=3.072 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 59: Bis(((1S,3S)-adamantan-1-yl)methyl) 2,2'-((((((R)-1-(6-amino-9H-purin-9-yl)propan-2-yl)oxy)methyl)phosphoryl)bis(azanediyl))bis(2-methyl-propanoate) (59)

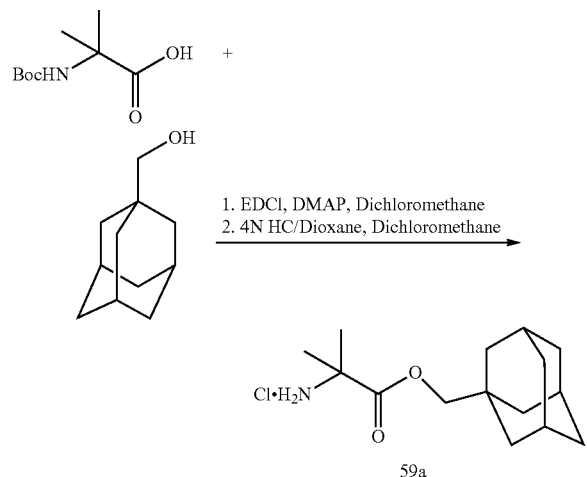

Synthesis of 1-adamantylmethyl 2-amino-2-methyl-propanoate hydrochloride (59a)

2-(tert-Butoxycarbonylamino)-2-methyl-propanoic acid (2.0 g, 9.84 mmol), 1-adamantylmethanol (1.96 g, 11.8 mmol), 4-dimethylaminopyridine (3.6 g, 29.5 mmol) and 3-(ethyliminomethyleneamino)-N,N-dimethyl-propan-1-amine hydrochloride (5.6 g, 29.5 mmol) were dissolved in dichloromethane (10 mL). After 1 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 12.3 mL, 49.2 mmol) was added to a solution of the residue in dichloromethane (5 mL). After 1 h the solvent was removed under reduced pressure. The residue was co-evaporated with dichloromethane (10 mL). The residue was subjected to high vacuum for 5 hours, providing intermediate 59a. ¹H NMR (400 MHz, DMSO-d₆) δ 8.54 (s, 3H), 3.78 (s, 2H), 2.00-1.91 (m, 3H), 1.77-1.60 (m, 6H), 1.53 (m, 6H), 1.50 (s, 6H).

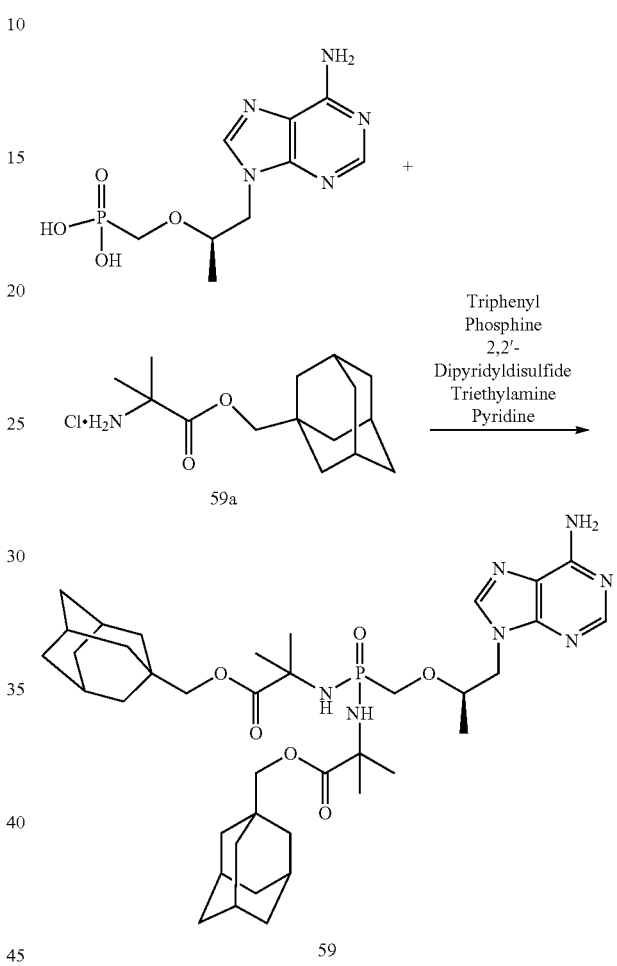

PMPA (100 mg, 0.348 mmol) and intermediate 59a (416 mg, 1.37 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å 250×30 mm column, 40%-100% acetonitrile/water gradient over 20 minutes). The fractions containing product were combined and subjected to lyophilization, providing the title compound (59). ¹H NMR (400 MHz, Methanol-d₄) δ 8.30 (s, 1H), 8.23

(s, 1H), 4.48-4.36 (m, 1.34H), 4.26 (dd, J=14.5, 7.2 Hz, 1H), 4.16 (d, J=11.5 Hz, 0.42H), 4.06-3.95 (m, 1H), 3.88-3.63 (m, 5H), 3.57 (dd, J=12.7, 10.3 Hz, 1H), 2.03-1.92 (m, 6H), 1.85-1.74 (m, 6H), 1.74-1.64 (m, 6H), 1.63-1.58 (m, 9H), 1.58-1.54 (m, 6H), 1.54-1.49 (m, 6H), 1.46 (s, 3H), 1.24 (d, J=6.2 Hz, 3H). $^{31}$P NMR (162 MHz, Methanol-d$_4$) δ 20.78 (t, J=9.8 Hz). LCMS: MS m/z=754.33 [M+1]; t$_R$=1.825 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=3.948 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 60: Di((1R,3R,5S)-bicyclo[3.1.0]hexan-3-yl) 2,2'-((((((R)-1-(6-amino-9H-purin-9-yl)propan-2-yl)oxy)methyl)phosphoryl)bis(azanediyl))bis(2-methylpropanoate) (60)

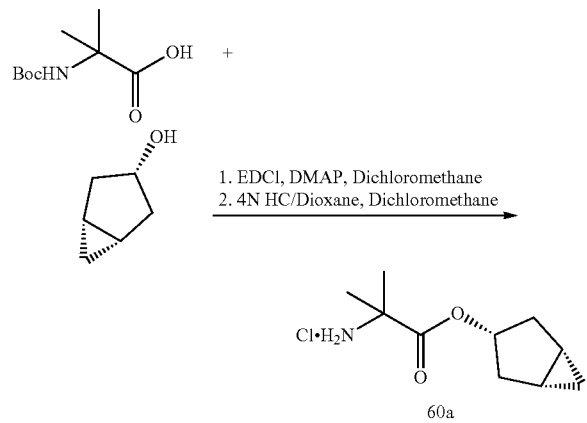

Synthesis of (1R,3R,5S)-bicyclo[3.1.0]hexan-3-yl 2-amino-2-methylpropanoate hydrochloride (60a)

2-(tert-Butoxycarbonylamino)-2-methyl-propanoic acid (5.0 g, 24.6 mmol), (1R,5S)-bicyclo[3.1.0]hexan-3-ol (2.89 g, 29.5 mmol), 4-dimethylaminopyridine (6.01 g, 29.5 mmol) and 3-(ethyliminomethyleneamino)-N,N-dimethyl-propan-1-amine hydrochloride (9.4 g, 49.2 mmol) were dissolved in dichloromethane (20 mL). After 2 h the reaction was diluted with DCM (20 mL). The solution was washed with water (3×20 mL), saturated ammonium chloride (20 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 15.3 mL, 61.0 mmol) was added to a solution of the residue in dichloromethane (5 mL). After 90 min the solvent was removed under reduced pressure. The residue was co-evaporated with dichloromethane (10 mL). The residue was subjected to high vacuum for 5 hours, providing intermediate 60a that was used as is in the next reaction.

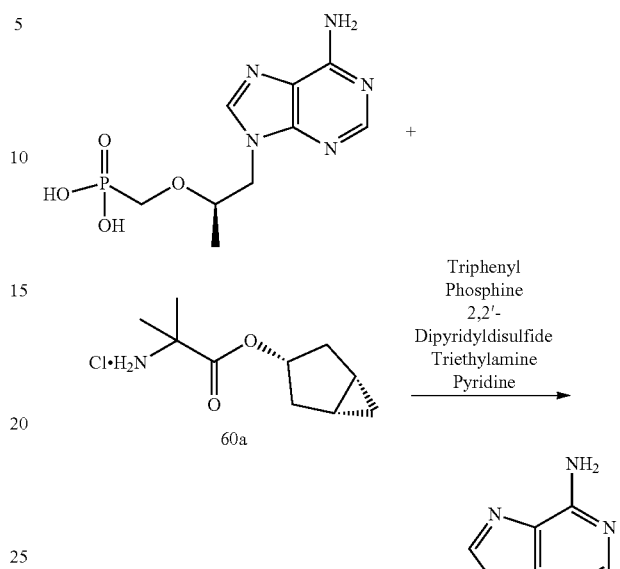

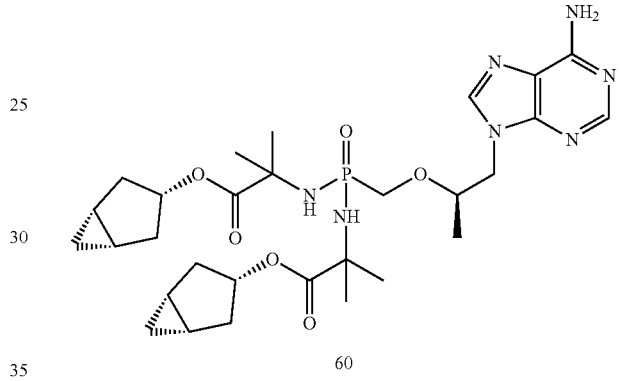

PMPA (100 mg, 0.348 mmol) and intermediate 60a (322 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 24 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (60). $^1$H NMR (400 MHz, Methanol-d$_4$) δ 8.28 (s, 1H), 8.23 (s, 1H), 5.26 (t, J=6.8 Hz, 1H), 5.19 (t, J=6.8 Hz, 1H), 4.42 (dd, J=14.5, 3.1 Hz, 1H), 4.26 (dd, J=14.5, 7.4 Hz, 1H), 4.04-3.94 (m, 1H), 3.80 (dd, J=12.8, 8.5 Hz, 1H), 3.54 (dd, J=12.8, 10.2 Hz, 1H), 2.32-2.12 (m, 5H), 1.90-1.77 (m, 4H), 1.53 (s, 3H), 1.45 (s, 3H), 1.43 (s, 4H), 1.38 (s, 3H), 1.37-1.29 (m, 3H), 1.25 (d, J=6.2 Hz, 3H), 0.58-0.46 (m, 2H), 0.38-0.34 (m, 1H), 0.33-0.30 (m, 1H). $^{31}$P NMR (162 MHz, Methanol-d$_4$) δ 20.90 (t, J=9.4 Hz). LCMS: MS m/z=618.09 [M+1]; t$_R$=1.360 min; LC system: Thermo Dionex Ultimate 3000 UHPLC+ focused; MS system:

Example 61: Di(spiro[4.5]decan-8-yl) 2,2'-(((((1-(6-amino-9H-purin-9-yl)propan-2-yl)oxy)methyl)phosphoryl)bis(azanediyl))(R)-bis(2-methylpropanoate) (61)

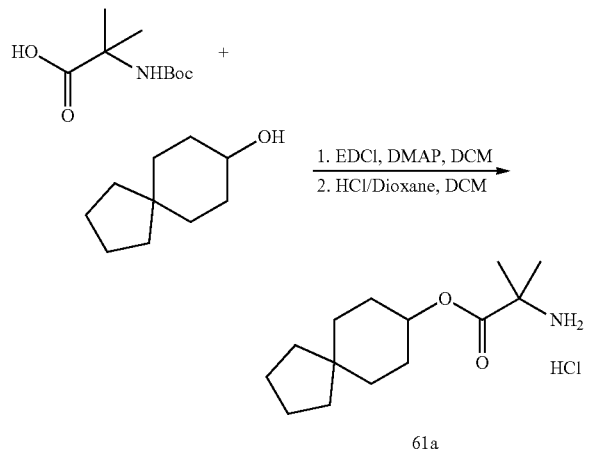

Synthesis of spiro[4.5]decan-8-yl 2-amino-2-methylpropanoate hydrochloride (61a)

2-(tert-Butoxycarbonylamino)-2-methyl-propanoic acid (1.0 g, 4.92 mmol), spiro[4.5]decan-8-ol (835 mg, 5.41 mmol), 4-dimethylaminopyridine (1.8 g, 14.8 mmol) and 3-(ethyliminomethyleneamino)-N,N-dimethyl-propan-1-amine hydrochloride (2.8 g, 14.8 mmol) were dissolved in dichloromethane (10 mL). After 20 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.1 mL, 24.6 mmol) was added to a solution of the residue in dichloromethane (5 mL). After 1 hour the solvent was removed under reduced pressure. The residue was co-evaporated with dichloromethane (10 mL). The residue was subjected to high vacuum for 5 hours, providing intermediate 61a. $^1$H NMR (400 MHz, DMSO-$d_6$) δ 8.48 (s, 3H), 4.81 (m, 1H), 1.75 (m, 2H), 1.63-1.48 (m, 7H), 1.47 (s, 6H), 1.43-1.27 (m, 7H).

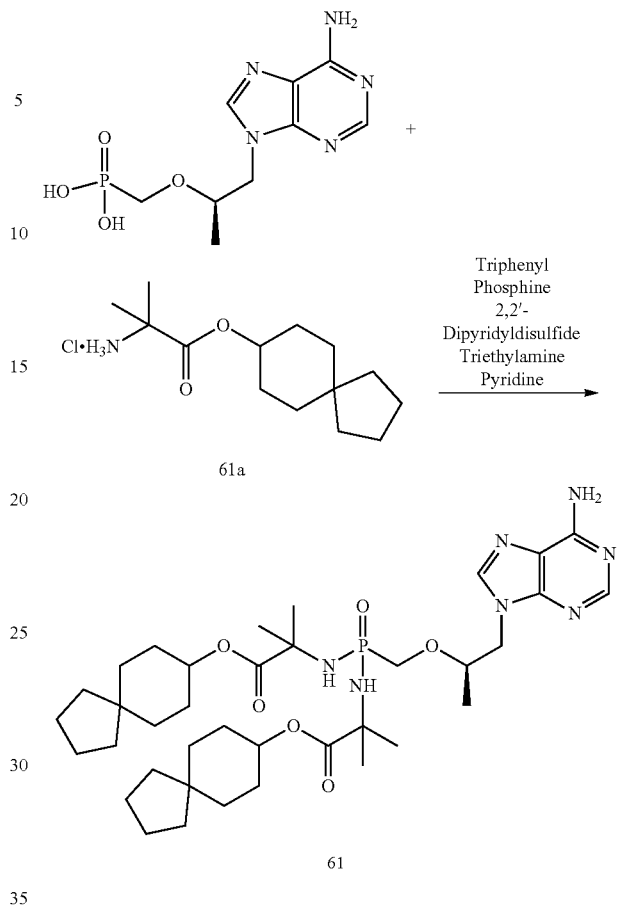

PMPA (100 mg, 0.348 mmol) and intermediate 61a (404 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 24 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (61). $^1$H NMR (400 MHz, Methanol-$d_4$) δ 8.30 (s, 1H), 8.23 (s, 1H), 4.85-4.77 (m, 1H), 4.77-4.67 (m, 1H), 4.42 (dd, J=14.5, 3.0 Hz, 1H), 4.37 (d, J=12.0 Hz, 0.83H), 4.27 (dd, J=14.5, 7.3 Hz, 1H), 4.13 (d, J=11.4 Hz, 0.85H), 4.03-3.96 (m, 1H), 3.81 (dd, J=12.8, 8.4 Hz, 1H), 3.57 (dd, J=12.8, 10.2 Hz, 1H), 1.87-1.69 (m, 4H), 1.69-1.51 (m, 18H), 1.51-1.48 (m, 6H), 1.48-1.28 (m, 16H), 1.25 (d, J=6.2 Hz, 3H). $^{31}$P NMR (162 MHz, Methanol-$d_4$) δ 20.80 (q, J=10.4 Hz). LCMS: MS m/z=730.20 [M+1]; $t_R$=1.790 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.823 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 62: Bis(2-(bicyclo[1.1.1]pentan-1-yl)ethyl) 2,2'-(((((1-(6-amino-9H-purin-9-yl)propan-2-yl)oxy)methyl)phosphoryl)bis(azanediyl))(R)-bis(2-methylpropanoate) (62)

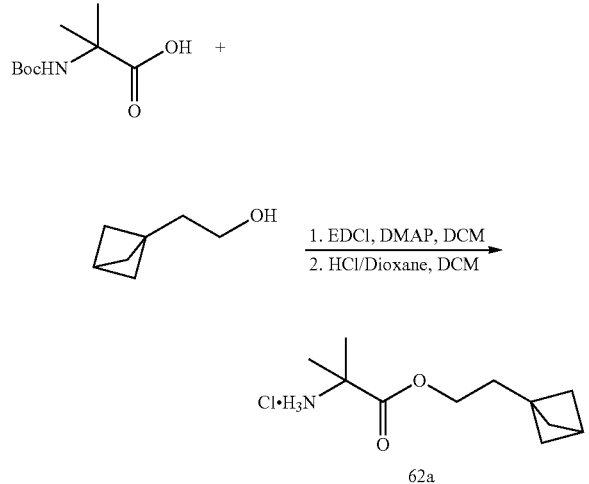

Synthesis of 2-(bicyclo[1.1.1]pentan-1-yl)ethyl 2-amino-2-methylpropanoate hydrochloride (62a)

2-(tert-Butoxycarbonylamino)-2-methyl-propanoic acid (1.8 g, 8.86 mmol), 2-(bicyclo[1.1.1]pentan-1-yl)ethan-1-ol (993 mg, 8.86 mmol), 4-dimethylaminopyridine (2.1 g, 17.7 mmol) and 3-(ethyliminomethyleneamino)-N,N-dimethylpropan-1-amine hydrochloride (3.4 g, 17.7 mmol) were dissolved in dichloromethane (10 mL). After 90 min the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 11.1 mL, 44.3 mmol) was added to a solution of the residue in dichloromethane (5 mL). After 90 min the solvent was removed under reduced pressure. The residue was co-evaporated with dichloromethane (10 mL). The residue was subjected to high vacuum for 5 hours, providing intermediate 62a. H NMR (400 MHz, DMSO-$d_6$) δ 8.56 (s, 3H), 4.16 (t, J=6.3 Hz, 2H), 2.47 (s, 1H), 1.77 (t, J=6.2 Hz, 2H), 1.70 (s, 6H), 1.48 (s, 6H).

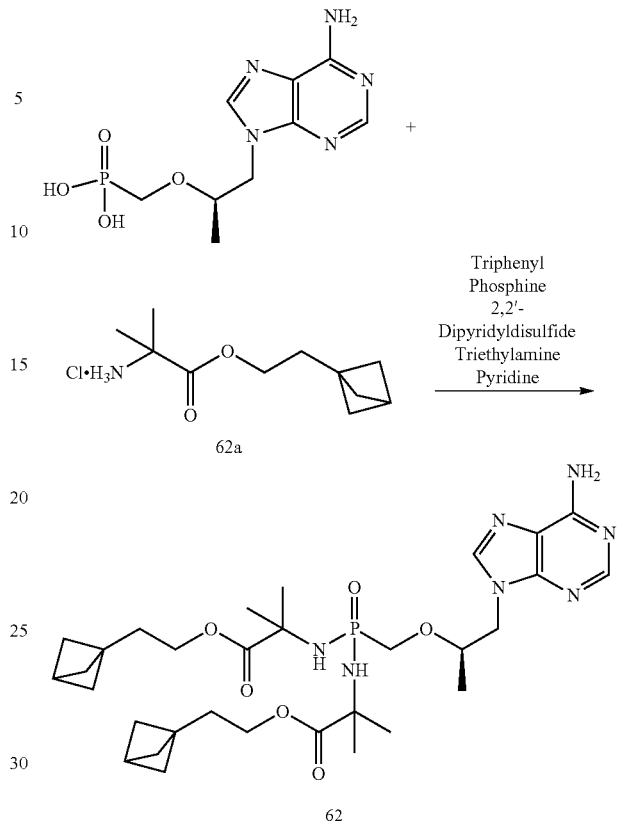

PMPA (100 mg, 0.348 mmol) and intermediate 62a (343 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (62). $^1$H NMR (400 MHz, Methanol-$d_4$) δ 8.29 (s, 1H), 8.24 (s, 1H), 4.42 (dd, J=14.5, 3.0 Hz, 1H), 4.26 (dd, J=14.5, 7.4 Hz, 1H), 4.22-4.03 (m, 4H), 4.03-3.92 (m, 1H), 3.81 (dd, J=12.8, 8.4 Hz, 1H), 3.55 (dd, J=12.8, 10.2 Hz, 1H), 2.46 (s, 1H), 2.45 (s, 1H), 1.84-1.76 (m, 2H), 1.75 (m, 7H), 1.73 (m, 7H), 1.57 (s, 3H), 1.49 (s, 3H), 1.48 (s, 3H), 1.42 (s, 3H), 1.25 (d, J=6.2 Hz, 3H). $^{31}$P NMR (162 MHz, Methanol-$d_4$) δ 20.78 (t, J=9.2 Hz). LCMS: MS m/z=646.11 [M+1]; $t_R$=1.537 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.115 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 63: Di(spiro[3.5]nonan-7-yl) 2,2'-(((((1-(6-amino-9H-purin-9-yl)propan-2-yl)oxy)methyl)phosphoryl)bis(azanediyl))(R)-bis(2-methylpropanoate) (63)

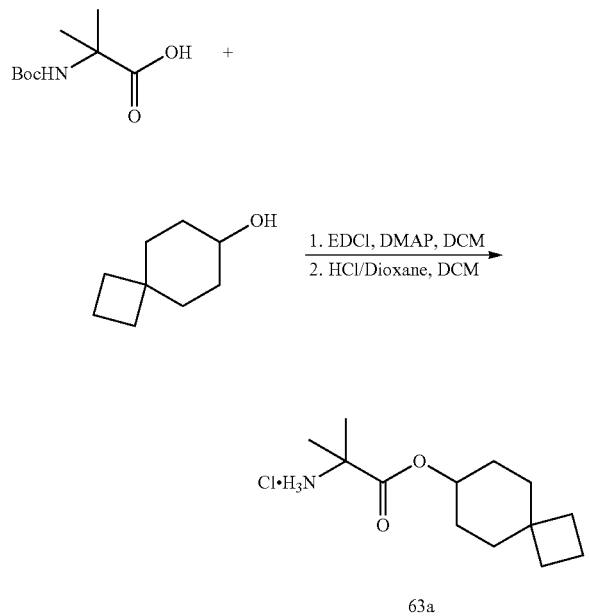

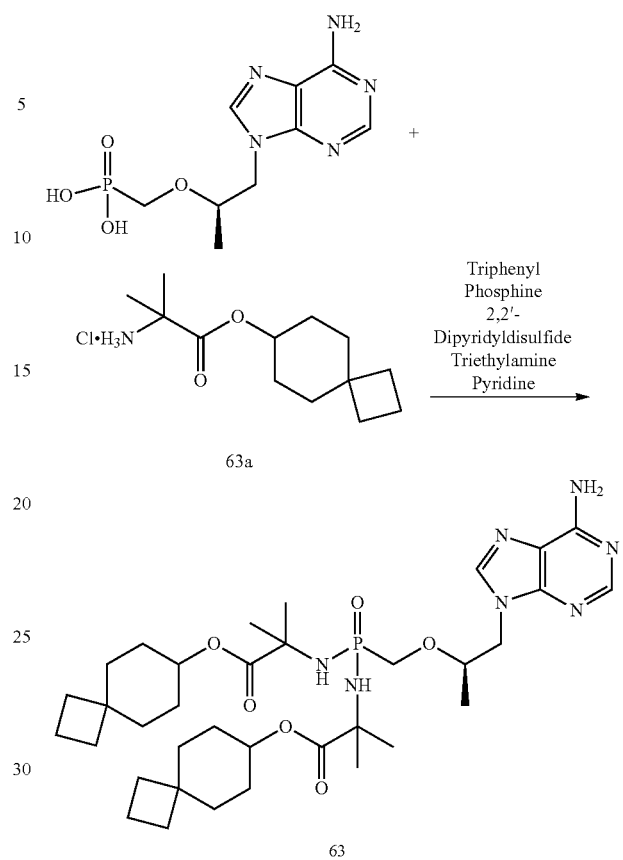

Synthesis of spiro[3.5]nonan-7-yl 2-amino-2-methylpropanoate hydrochloride (63a)

2-(tert-Butoxycarbonylamino)-2-methyl-propanoic acid (2.9 g, 14.3 mmol), spiro[3.5]nonan-7-ol (2.0 g, 14.3 mmol), 4-dimethylaminopyridine (2.6 g, 21.4 mmol) and 3-(ethyl-iminomethyleneamino)-N,N-dimethyl-propan-1-amine hydrochloride (4.1 g, 21.4 mmol) were dissolved in dichloromethane (25 mL). After 18 h the reaction was diluted with DCM (10 mL). The solution was washed with water (3×10 mL), saturated ammonium chloride (10 mL), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 17.8 mL, 71.3 mmol) was added to a solution of the residue in dichloromethane (5 mL). After 3 h the solvent was removed under reduced pressure. The residue was co-evaporated with dichloromethane (10 mL). The residue was subjected to high vacuum for 5 hours, providing intermediate 63a. $^1$H NMR (400 MHz, DMSO-$d_6$) δ 8.50 (s, 3H), 4.77 (d, J=8.4 Hz, 1H), 1.94-1.77 (m, 2H), 1.77-1.60 (m, 8H), 1.57-1.34 (m, 10H).

PMPA (100 mg, 0.348 mmol) and intermediate 63a (384 mg, 1.39 mmol) were azeotroped with toluene (2×10 mL). Triphenylphosphine (430 mg, 1.74 mmol) and 2,2'-dipyridyl disulfide (384 mg, 1.74 mmol) were added followed by pyridine (4 mL) under Argon. Triethylamine (0.475 mL, 3.48 mmol) was added. The mixture was heated at 90° C. for 18 h. The pyridine was removed under reduced pressure. The residue was co-evaporated with toluene (3×10 mL). The residue was subjected to a silica plug using an ISCO solid loading cartridge with 40% then 100% ethyl acetate/hexanes. The material remaining on the solid loading cartridge was subjected to flash chromatography (0-20% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization, providing the title compound (63). $^1$H NMR (400 MHz, Methanol-$d_4$) δ 8.31 (s, 1H), 8.25 (s, 1H), 7.20 (s, 0.09H), 4.81-4.73 (m, 1H), 4.73-4.64 (m, 1H), 4.43 (dd, J=14.5, 3.0 Hz, 1H), 4.36 (d, J=12.0 Hz, 0.05H), 4.27 (dd, J=14.5, 7.3 Hz, 1H), 4.12 (d, J=11.5 Hz, 0.05H), 4.05-3.95 (m, 1H), 3.81 (dd, J=12.8, 8.4 Hz, 1H), 3.57 (dd, J=12.8, 10.2 Hz, 1H), 1.97-1.82 (m, 4H), 1.82-1.62 (m, 16H), 1.57 (s, 3H), 1.54-1.44 (m, 13H), 1.44-1.36 (m, 4H), 1.24 (d, J=6.2 Hz, 3H). $^{31}$P NMR (162 MHz, Methanol-$d_4$) δ 20.74 (t, J=9.4 Hz). LCMS: MS m/z=702.22 [M+1]; $t_R$=1.703 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.557 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 64: Dihexyl 2,2'-(((((1-(6-amino-9H-purin-9-yl)propan-2-yl)oxy)methyl)phosphoryl)bis(azanediyl))(R)-bis(2,2-dicyclopropylacetate) (64)

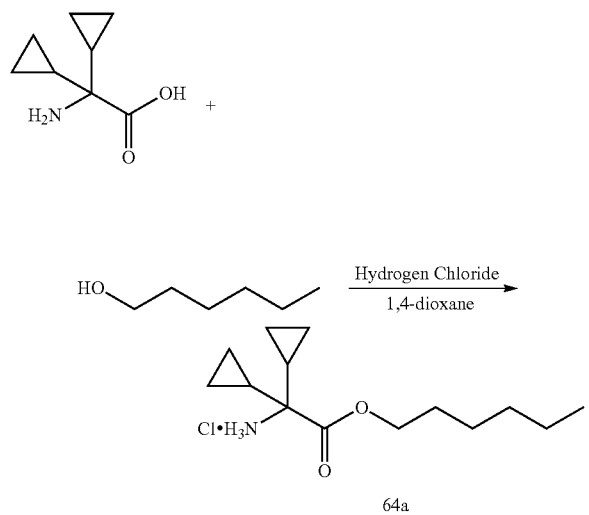

Synthesis of hexyl 2-amino-2,2-dicyclopropylacetate hydrochloride (64a)

2-Amino-2,2-dicyclopropylacetic acid (2 g, 10.4 mmol) and 1-hexanol (5.3 g, 52.2 mmol) were taken up in 4N HCl in 1,4-dioxane (13 mL, 52 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 64a. $^1$H NMR (400 MHz, DMSO-$d_6$) δ 8.43 (bs, 3H), 4.16 (t, J=6.4 Hz, 2H), 1.69-1.51 (m, 2H), 1.43-1.23 (m, 5H), 1.21-1.05 (m, 3H), 0.92-0.81 (m, 3H), 0.77-0.42 (m, 8H). LCMS: MS m/z=240.2 [M+1], $t_R$=0.70 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

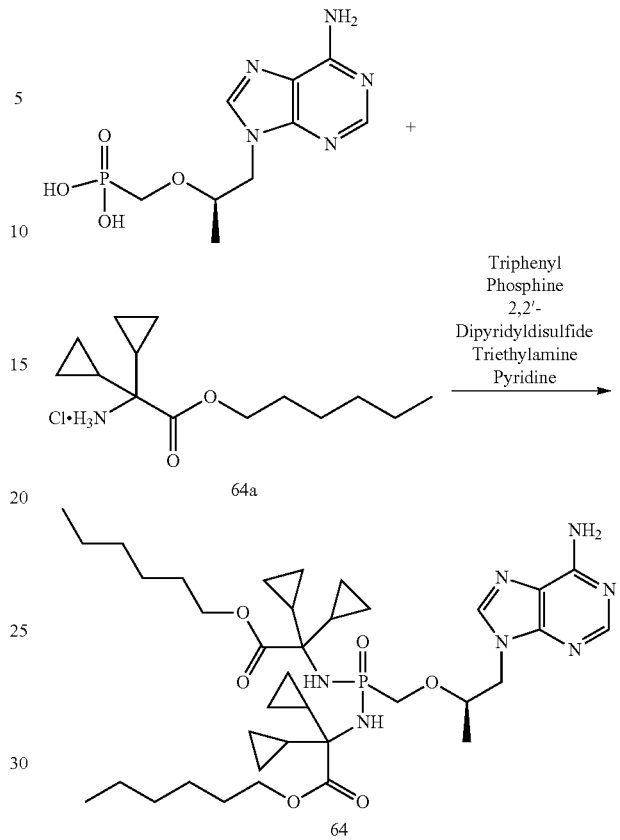

PMPA (100 mg, 0.35 mmol), intermediate 64a (384 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. Hexane (0.5 volume equivalent) was added, and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 μm C18-110 Å 100×30 mm column, 25%-100% acetonitrile in water gradient over 30 min run) to afford the title compound (64). $^1$H NMR (400 MHz, DMSO-$d_6$) δ 8.17-7.97 (m, 2H), 7.15 (bs, 2H), 4.32-4.12 (m, 2H), 4.10-3.89 (m, 5H), 3.80-3.58 (m, 4H), 1.69-1.47 (m, 4H), 1.41-1.20 (m, 14H), 1.15-0.95 (m, 5H), 0.91-0.77 (m, 6H), 0.71-0.56 (m, 2H), 0.55-0.20 (m, 14H). $^{31}$P NMR (162 MHz, DMSO-$d_6$) δ 19.18 (m). LCMS: MS m/z=730.4 [M+1], $t_R$=1.28 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. HPLC: $t_R$=3.73 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 65: Dihexyl 2,2'-(((((1-(6-amino-9H-purin-9-yl)propan-2-yl)oxy)methyl)phosphoryl)bis(azanediyl))(R)-bis(2-ethylbutanoate) (65)

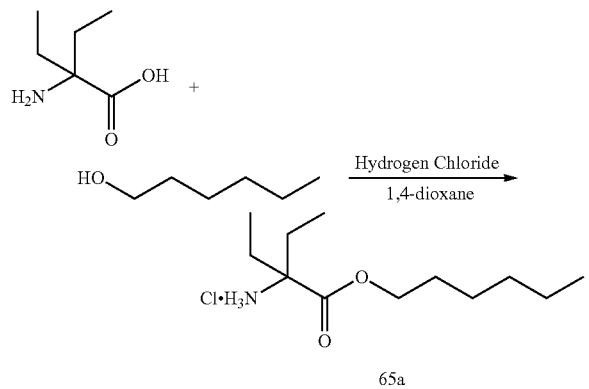

Synthesis of hexyl 2-amino-2-ethylbutanoate hydrochloride (65a)

2-Amino-2-ethylbutanoic acid (1.7 g, 10.1 mmol) and 1-hexanol (5.2 g, 50.7 mmol) were taken up in 4N HCl in 1,4-dioxane (12.7 mL, 50.7 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 65a. $^1$H NMR (400 MHz, DMSO-$d_6$) δ 8.59 (bs, 3H), 4.19 (t, J=6.5 Hz, 2H), 1.97-1.76 (m, 4H), 1.71-1.52 (m, 2H), 1.43-1.16 (m, 6H), 0.98-0.77 (m, 9H). LCMS: MS m/z=216.2 [M+1], $t_R$=0.68 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

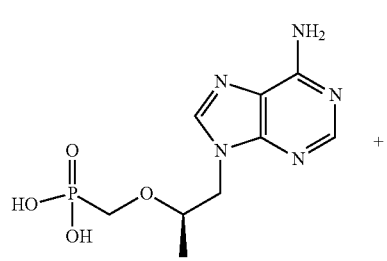

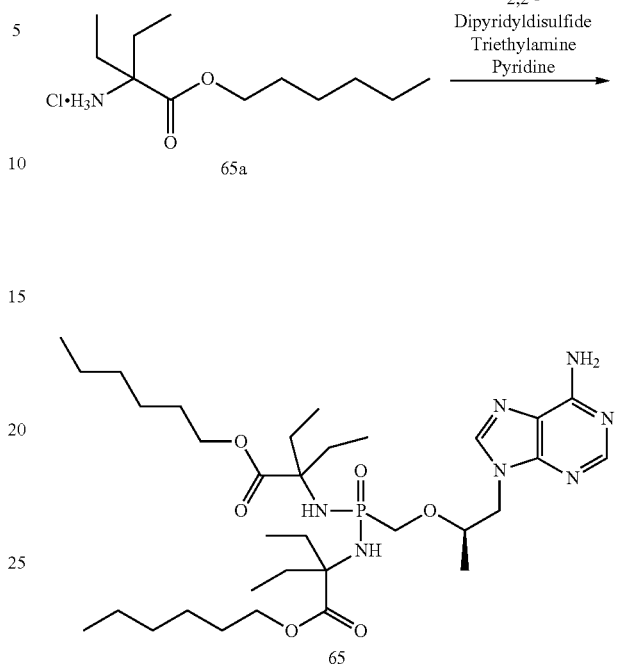

PMPA (100 mg, 0.35 mmol), intermediate 65a (350 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. 0.5 volume equivalent of hexane was added and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 μm C18-110 Å 100×30 mm column, 25%-100% acetonitrile in water gradient over 30 min run) to afford the title compound (65). $^1$H NMR (400 MHz, DMSO-$d_6$) δ 8.12 (s, 1H), 8.10 (s, 1H), 7.16 (bs, 2H), 4.30-4.15 (m, 2H), 4.13-4.01 (m, 4H), 4.01-3.92 (m, 2H), 3.84 (d, J=11.0 Hz, 1H), 3.67-3.47 (m, 2H), 2.18-1.94 (m, 2H), 1.93-1.48 (m, 10H), 1.38-1.17 (m, 12H), 1.07 (d, J=6.2 Hz, 3H), 0.90-0.58 (m, 18H). $^{31}$P NMR (162 MHz, DMSO-$d_6$) δ 16.75 (m). LCMS: MS m/z=682.4 [M+1], $t_R$=1.31 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. HPLC: $t_R$=3.76 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 66: Diheptyl 2,2'-(((((1-(6-amino-9H-purin-9-yl)propan-2-yl)oxy)methyl)phosphoryl)bis(azanediyl))(R)-bis(2-methylpropanoate) (66)

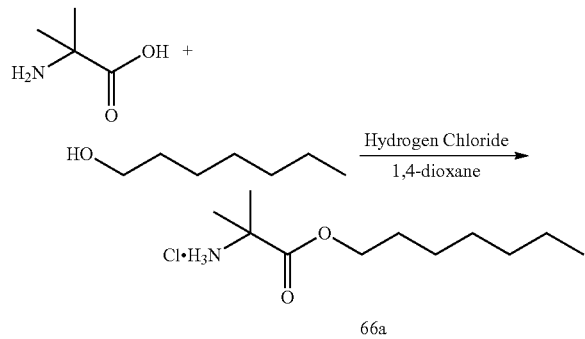

Synthesis of heptyl 2-amino-2-methylpropanoate hydrochloride (66a)

2-Amino-2-methylpropanoic acid (1.5 g, 10.7 mmol) and 1-heptanol (6.2 g, 53.7 mmol) were taken up in 4N HCl in 1,4-dioxane (13.4 mL, 53.7 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 66a. $^1$H NMR (400 MHz, DMSO-$d_6$) δ 8.53 (s, 3H), 4.16 (t, J=6.5 Hz, 2H), 1.71-1.47 (m, 2H), 1.47 (s, 6H), 1.35-1.18 (m, 8H), 0.89-0.81 (m, 3H). LCMS: MS m/z=202.2 [M+1], $t_R$=0.66 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

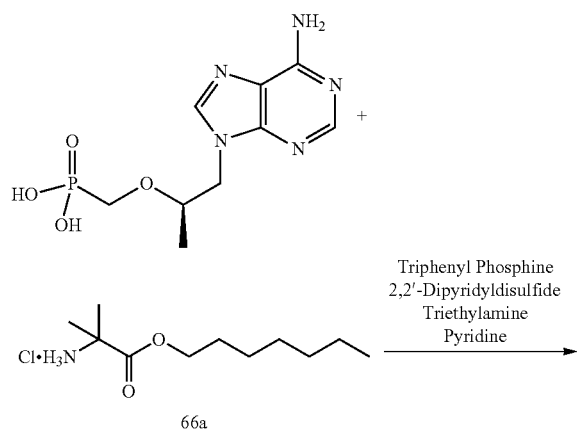

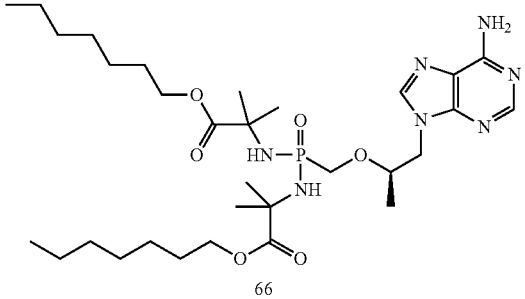

PMPA (100 mg, 0.35 mmol), intermediate 66a (331 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. Hexane (0.5 volume equivalent) was added and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 μm C18-110 Å 100×30 mm column, 25%-100% acetonitrile in water gradient over 30 min run) to afford the title compound (66). $^1$H NMR (400 MHz, DMSO-$d_6$) δ 8.16 (s, 1H), 8.12 (s, 1H), 7.16 (s, 2H), 4.36-4.09 (m, 4H), 4.09-3.90 (m, 5H), 3.67-3.43 (m, 2H), 1.67-1.50 (m, 4H), 1.46-1.33 (m, 12H), 1.32-1.17 (m, 16H), 1.06 (d, J=6.2 Hz, 3H), 0.87-0.74 (m, 6H). $^{31}$P NMR (162 MHz, DMSO-$d_6$) δ 18.42 (m). LCMS: MS m/z=654.4 [M+1], $t_R$=1.25 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. HPLC: $t_R$=3.59 min; HPLC system: Agilent 1100 series; Column: Gemini 5μ C18 110Å, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 67: Bis(4-methylpentyl) 2,2'-(((((1-(6-amino-9H-purin-9-yl)propan-2-yl)oxy)methyl)phosphoryl)bis(azanediyl))(R)-bis(2-methylpropanoate) (67)

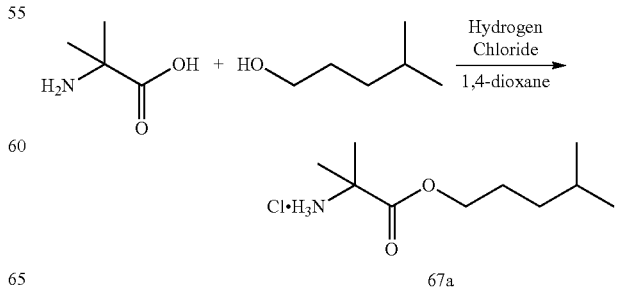

Synthesis of 4-methylpentyl 2-amino-2-methylpropanoate hydrochloride (67a)

2-Amino-2-methylpropanoic acid (1.5 g, 10.7 mmol) and 4-methylpentan-1-ol (5.49 g, 53.7 mmol) were taken up in 4N HCl in 1,4-dioxane (13.4 mL, 53.7 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 67a. H NMR (400 MHz, DMSO-$d_6$) δ 8.65 (bs, 3H), 4.15 (t, J=6.5 Hz, 2H), 1.67-1.48 (m, 3H), 1.48 (s, 6H), 1.27-1.14 (m, 2H), 0.87 (d, J=6.6 Hz, 6H). LCMS: MS m/z=188.2 [M+1], $t_R$=0.61 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min.

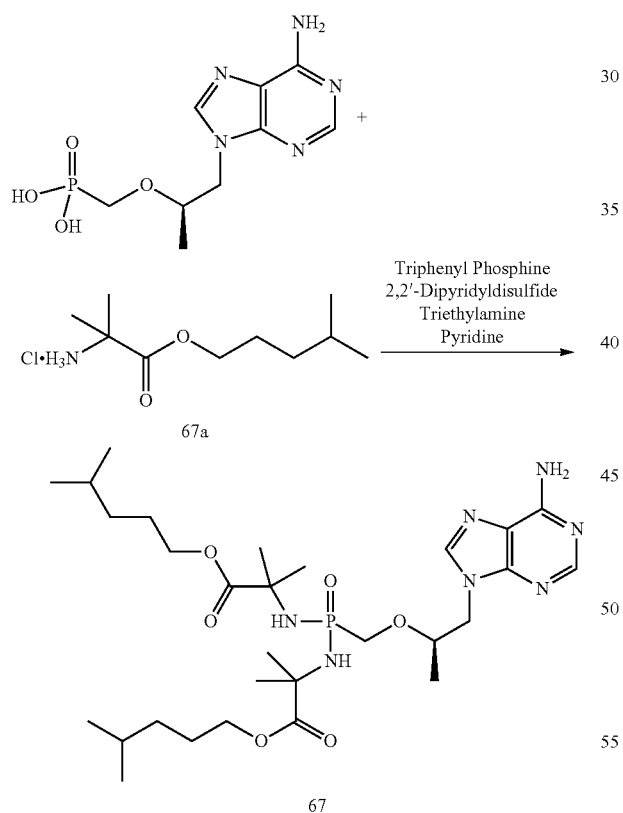

67a

67

PMPA (100 mg, 0.35 mmol), intermediate 67a (312 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. 0.5 volume equivalent of hexane was added and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 µm C18-110 Å 100×30 mm column, 25%-100% acetonitrile in water gradient over 30 min run) to afford the title compound (67). $^1$H NMR (400 MHz, DMSO-$d_6$) δ 8.16 (s, 1H), 8.12 (s, 1H), 7.16 (bs, 2H), 4.35-4.11 (m, 4H), 4.09-3.89 (m, 5H), 3.66-3.47 (m, 2H), 1.61-1.46 (m, 6H), 1.45-1.32 (m, 12H), 1.26-1.12 (m, 4H), 1.06 (d, J=6.2 Hz, 3H), 0.87-0.80 (m, 12H). $^{31}$P NMR (162 MHz, DMSO-$d_6$) δ 18.42 (m). LCMS: MS m/z=626.3 [M+1], $t_R$=1.11 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 µL/min. HPLC: $t_R$=3.29 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 68: Bis(5-methylhexyl) 2,2'-(((((1-(6-amino-9H-purin-9-yl)propan-2-yl)oxy)methyl)phosphoryl)bis(azanediyl))(R)-bis(2-methylpropanoate) (68)

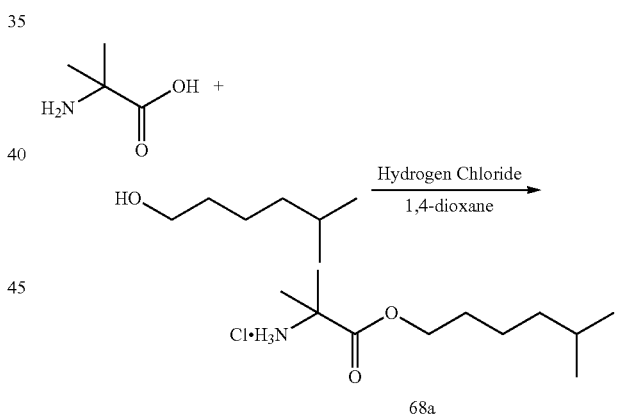

68a

Synthesis of 5-methylhexyl 2-amino-2-methylpropanoate hydrochloride (68a)

2-Amino-2-methylpropanoic acid (1.5 g, 10.7 mmol) and 5-methylhexan-1-ol (6.24 g, 53.7 mmol) were taken up in 4N HCl in 1,4-dioxane (13.4 mL, 53.7 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 68a. ¹H NMR (400 MHz, DMSO-d₆) δ 8.61 (bs, 3H), 4.16 (t, J=6.5 Hz, 2H), 1.65-1.49 (m, 3H), 1.48 (s, 6H), 1.38-1.26 (m, 2H), 1.22-1.11 (m, 2H), 0.86 (d, J=6.6 Hz, 6H). LCMS: MS m z=202.2 [M+1], $t_R$=0.63 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

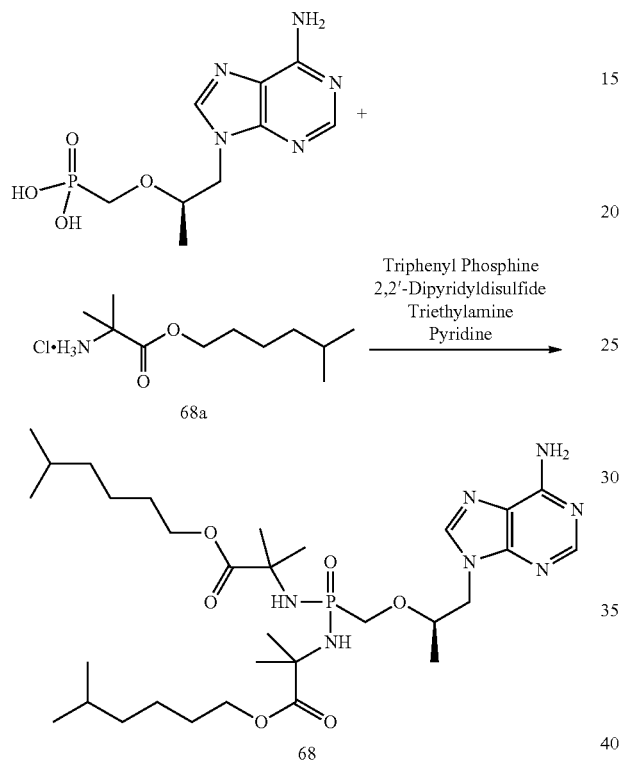

PMPA (100 mg, 0.35 mmol), intermediate 68a (331 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. 0.5 volume equivalent of hexane was added and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 μm C18-110 Å 100×30 mm column, 25%-100% acetonitrile in water gradient over 30 min run) to afford the title compound (68). ¹H NMR (400 MHz, DMSO-d₆) δ 8.16 (s, 1H), 8.12 (s, 1H), 7.16 (bs, 2H), 4.33-4.11 (m, 4H), 4.10-3.86 (m, 5H), 3.66-3.46 (m, 2H), 1.60-1.45 (m, 6H), 1.45-1.34 (m, 12H), 1.33-1.21 (m, 4H), 1.18-1.09 (m, 4H), 1.06 (d, J=6.2 Hz, 3H), 0.85-0.79 (m, 12H). ³¹P NMR (162 MHz, DMSO-d₆) δ 18.41 (m). LCMS: MS m/z=654.4 [M+1], $t_R$=1.21 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min. HPLC: $t_R$=3.52 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 69: Bis(2-propylpentyl) 2,2'-(((((1-(6-amino-9H-purin-9-yl)propan-2-yl)oxy)methyl)phosphoryl)bis(azanediyl))(R)-bis(2-methylpropanoate) (69)

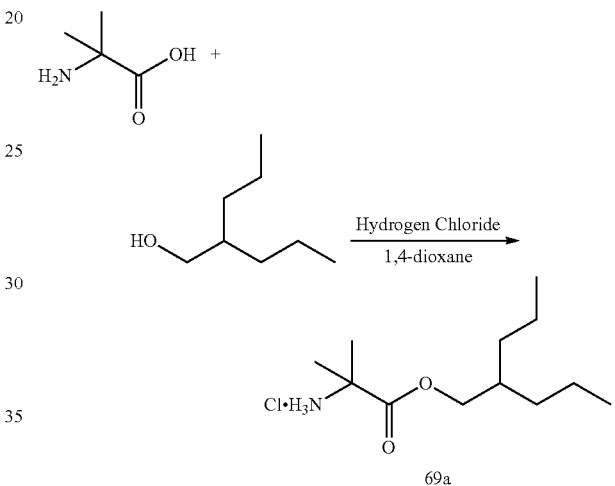

Synthesis of 2-propylpentyl 2-amino-2-methylpropanoate hydrochloride (69a)

2-Amino-2-methylpropanoic acid (1.5 g, 10.7 mmol) and 2-propylpentan-1-ol (6.3 g, 48.4 mmol) were taken up in 4N HCl in 1,4-dioxane (13.4 mL, 53.7 mmol) under an atmosphere of argon in a sealed tube. The reaction was heated to 90° C. for 16 h. The reaction was cooled to room temperature, solids were filtered off and the solution was concentrated down under reduced pressure. The residue was taken up in water (40 mL) and concentrated down under reduced pressure, taken up in water (40 mL) and concentrated down under reduced pressure. That residue was taken up in toluene and concentrated down under reduced pressure. The residue was taken up in water and lyophilized over the weekend to afford intermediate 69a. ¹H NMR (400 MHz, DMSO-d₆) δ 8.62 (bs, 3H), 4.08 (d, J=5.4 Hz, 2H), 1.77-1.60 (m, 1H), 1.48 (s, 6H), 1.35-1.20 (m, 8H), 0.94-0.80 (m, 6H). LCMS: MS m/z=216.2 [M+1], $t_R$=0.62 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

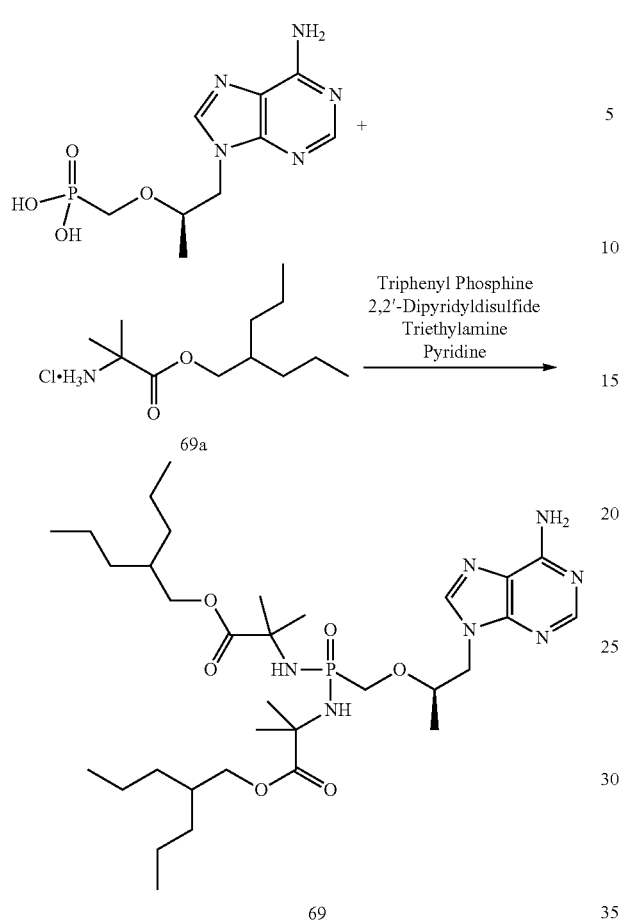

µL/min. HPLC: $t_R$=3.78 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 70: Bis(2-ethylbutyl) 1,1'-(((((1-(6-amino-9H-purin-9-yl)propan-2-yl)oxy)methyl)phosphoryl)bis(azanediyl))(R)-bis(cyclopropane-1-carboxylate) (70)

Example 71: 2-Ethylbutyl 1-(((R)-((((R)-1-(6-amino-9H-purin-9-yl)propan-2-yl)oxy)methyl)((1-(2-ethylbutoxy)-2-methyl-1-oxopropan-2-1)amino)phosphoryl)amino)cyclopropane-1-carboxylate (71)

Example 72: 2-Ethylbutyl 1-(((S)-((((R)-1-(6-amino-9H-purin-9-yl)propan-2-yl)oxy)methyl)((1-(2-ethylbutoxy)-2-methyl-1-oxopropan-2-yl)amino)phosphoryl)amino)cyclopropane-1-carboxylate (72)

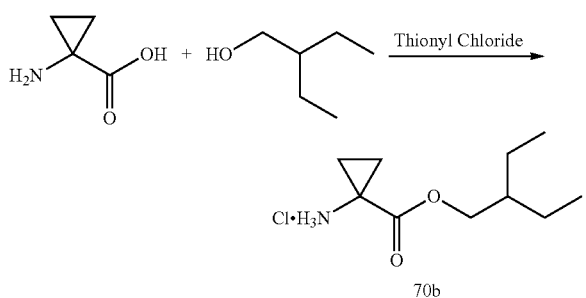

Synthesis of 2-ethylbutyl 2-amino-2-methylpropanoate hydrochloride (70a)

PMPA (100 mg, 0.35 mmol), intermediate 69a (351 mg, 1.39 mmol), and triethylamine (0.30 mL, 2.09 mmol) were combined in pyridine (1 mL) under argon and heated at 50° C. for 5 min. A freshly prepared bright yellow solution of triphenylphosphine (457 mg, 1.74 mmol), 2,2'-dipyridyldisulfide (384 mg, 1.74 mmol) in pyridine (1 mL) was added to the above reaction mixture. The reaction was stirred at 85° C. overnight. The reaction was cooled to room temperature and diluted with 20 mL of EtOAc. The organics were washed with a saturated aqueous solution of sodium bicarbonate (2×10 mL), brine (10 mL) and, and dried over sodium sulfate. 0.5 volume equivalent of hexane was added and the mixture was applied on a 3 cm layer of silica gel and washed with ethyl acetate, the desired product was eluted using 10% methanol in DCM. The organics were concentrated under reduced pressure. The residue was purified by HPLC chromatography (Gemini 5 µm C18-110 Å 100×30 mm column, 25%-100% acetonitrile in water gradient over 30 min run) to afford the title compound (69). $^1$H NMR (400 MHz, DMSO-$d_6$) δ 8.16 (s, 1H), 8.13 (s, 1H), 7.20 (bs, 2H), 4.37-4.10 (m, 4H), 4.05-3.82 (m, 5H), 3.66-3.46 (m, 2H), 1.72-1.51 (m, 2H), 1.48-1.35 (m, 12H), 1.30-1.19 (m, 16H), 1.06 (d, J=6.2 Hz, 3H), 0.87-0.80 (m, 12H). $^{31}$P NMR (162 MHz, DMSO-$d_6$) δ 18.34 (m). LCMS: MS m/z=682.3 [M+1], $t_R$=1.29 min; LC system: Agilent 1260 Infinity II HPLC; MS system: G6124B Single Quad; Column: Kinetix 2.6 u C18 100A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2

2-amino-2-methylpropanoic acid (5 g, 48.5 mmol) in a 250 mL round bottom flask charged with stir bar was added 2-ethylbutan-1-ol (29.7 mL, 291 mmol). To a well stirred mixture at room temperature was added thionyl chloride (7.08 mL, 97.0 mmol) dropwise over 5 minutes under argon (Temperature maintained below 25° C.). The reaction was refluxed at 90° C. 24 h. The reaction was cooled to room temperature and concentrated under reduced pressure at 65° C., co evaporated with THF (50 mL×2) and once with DCM (50 mL). Crude product was taken up in water (100 mL) and washed with 1:1 EtOAc:Hexanes (50 mL×2) and once with DCM (40 mL). The aqueous solution was frozen and concentrated using lyophilizer (30 h) to afford intermediate 70a as white solid. $^1$H NMR (400 MHz, DMSO-$d_6$) δ 8.80 (s, 3H), 4.09 (d, J=5.5 Hz, 2H), 1.50 (s, 7H), 1.37-1.30 (m, 4H), 0.86 (t, J=7.4 Hz, 6H).

Synthesis of 2-ethylbutyl 1-aminocyclopropane-1-carboxylate hydrochloride (70b)

Intermediate 70b was synthesized in the same manner as intermediate 70a using 1-aminocyclopropanecarboxylic acid (2.5 g, 24.7 mmol), 2-ethylbutan-1-ol (18.6 mL, 148 mmol) and thionyl chloride (3.61 mL, 49.5 mmol) to afford intermediate 70b. $^1$H NMR (400 MHz, DMSO-$d_6$) δ 9.11 (s, 3H), 4.05 (d, J=5.6 Hz, 2H), 1.53-1.46 (m, 3H), 1.39-1.25 (m, 6H), 0.85 (t, J=7.4 Hz, 7H).

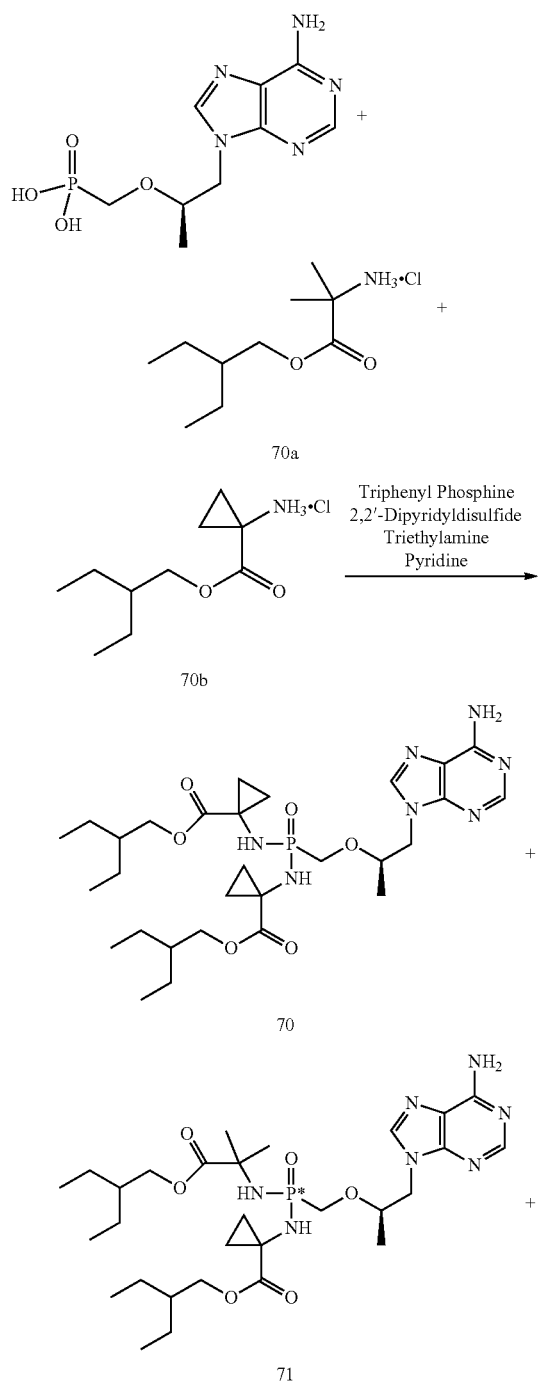

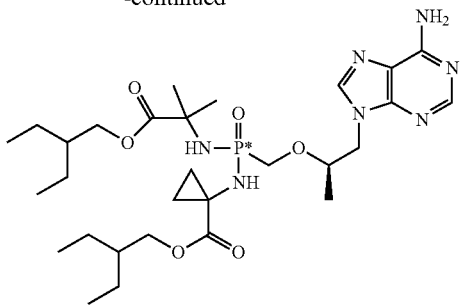

72

PMPA (100 mg, 0.348 mmol), intermediate 70a (156 mg, 0.696), intermediate 70b (154 mg, 0.696) were taken in a 8 ml vial, charged with stir bar. To this mixture was added triethylamine (0.5 mL) followed by Pyridine (1.2 mL), capped and stirred at 70° C. 10 min. 2,2'-Dipyridyldisulfide (307 mg, 1.39 mmol) and triphenylphosphine (365 mg, 139 mmol) were mixed in another 8 mL vial, added pyridine (1.4 mL), sonicated to complete dissolution under argon, the clear yellow solution was transferred to stirred suspension Reaction mixture was stirred at 70° C. overnight. The reaction mixture was cooled to room temperature, concentrated, and co-evaporated with toluene (20 mL×2). The residue was dissolved in DCM, loaded on 24 g column, dried the column by passing nitrogen over 2 min (to dry DCM) and eluted with 100% EtOAc over 6 min, 0-15% MeOH/DCM over 15 min to afford mixture of 3 products. This mixture was dissolved in MeOH, filtered and purified by preparative HPLC (Gemini, 10 uM, NX-C18, 110 Å250×30 mm column, 20%-100% acetonitrile/water gradient over 20 min run) and isolated 70, 71, and 72.

70: $^1$H NMR (400 MHz, Acetonitrile-$d_3$) δ 8.23 (s, 1H), 8.04 (s, 1H), 6.14 (s, 2H), 4.43-4.09 (m, 4H), 4.04-3.85 (m, 5H), 3.79 (dd, J=12.8, 8.0 Hz, 1H), 3.52 (dd, J=12.8, 10.4 Hz, 1H), 1.46 (dq, J=10.4, 6.0 Hz, 2H), 1.38-1.24 (m, 14H), 1.23-1.10 (m, 6H), 0.94-0.80 (m, 12H). LCMS: MS m/z=622.3 [M+1]; $t_R$=1.5 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.98 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

71: $^1$H NMR (400 MHz, Acetonitrile-$d_3$) δ 8.23 (s, 1H), 8.06 (s, 1H), 6.09 (s, 2H), 4.39-4.23 (m, 2H), 4.17 (dd, J=14.6, 7.2 Hz, 1H), 4.09-3.93 (m, 4H), 3.93-3.83 (m, 2H), 3.73 (dd, J=12.8, 8.2 Hz, 1H), 3.45 (dd, J=12.7, 10.4 Hz, 1H), 1.58-1.43 (m, 3H), 1.41 (d, J=1.7 Hz, 6H), 1.38-1.27 (m, 10H), 1.19 (d, J=6.2 Hz, 3H), 1.15-1.07 (m, 1H), 0.89 (td, J=7.5, 3.8 Hz, 12H). LCMS: MS m/z=624.3 [M+1]; $t_R$=1.52 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.81 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

72: $^1$H NMR (400 MHz, Acetonitrile-$d_3$) δ 8.23 (s, 1H), 8.05 (d, J=8.0 Hz, 1H), 6.15 (s, 2H), 4.48-4.12 (m, 3H), 4.12-3.83 (m, 6H), 3.79-3.61 (m, 1H), 3.59-3.34 (m, 1H), 1.63-1.24 (m, 18H), 1.22-1.07 (m, 4H), 0.93-0.72 (m, 12H). LCMS: MS m/z=624.3 [M+1]; $t_R$=1.53 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.85 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 73: Dipentyl 1,1'-(((((1-(6-amino-9H-purin-9-yl)propan-2-yl)oxy)methyl)phosphoryl)bis(azanediyl))(R)-bis(cyclopropane-1-carboxylate) (73)

Example 74: Pentyl 1-((((((R)-1-(6-amino-9H-purin-9-yl)propan-2-yl)oxy)methyl)((2-methyl-1-oxo-1-(pentyloxy)propan-2-yl)amino)phosphoryl)amino)cyclopropane-1-carboxylate (74)

Synthesis of pentyl 1-aminocyclopropanecarboxylate hydrochloride (73a)

Intermediate 73a was synthesized in the same manner as intermediate 70a using 1-aminocyclopropanecarboxylic acid (2.5 g, 24.7 mmol), pentan-1-ol (16.1 mL, 148 mmol) and SOCl$_2$ (3.61 mL, 49.5 mmol) to afford intermediate 73a. $^1$H NMR (400 MHz, DMSO-$d_6$) δ 9.14 (s, 3H), 4.11 (t, J=6.5 Hz, 2H), 1.58 (dq, J=10.7, 6.8, 5.2 Hz, 2H), 1.53-1.47 (m, 2H), 1.39-1.33 (m, 2H), 1.29 (h, J=3.7 Hz, 4H), 0.93-0.79 (m, 3

Synthesis of pentyl 2-amino-2-methyl-propanoate hydrochloride (73b)

Intermediate 73b was synthesized in the same manner as intermediate 70a using 2-amino-2-methylpropanoic acid (2.5 g, 24.7 mmol), pentan-1-ol (15.8 mL, 145 mmol) and SOCl$_2$ (3.54 mL, 48.5 mmol) to afford intermediate 73b. $^1$H NMR (400 MHz, DMSO-$d_6$) δ 9.06 (s, 3H), 3.92 (d, J=6.5 Hz, 2H), 1.89 (dq, J=13.3, 6.6 Hz, 1H), 1.60-1.28 (m, 4H), 0.90 (d, J=6.7 Hz, 6H).

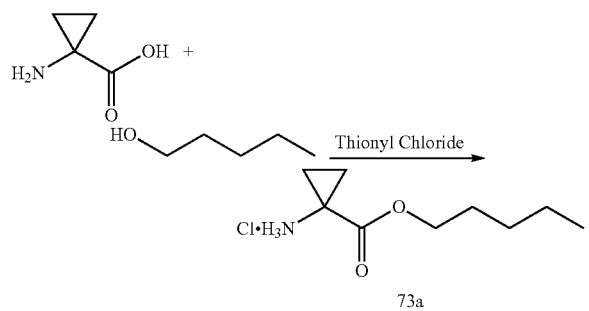

-continued

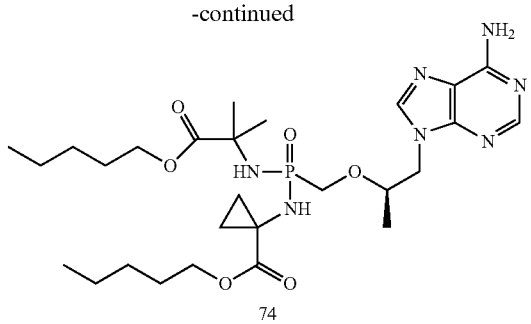

74

PMPA (100 mg, 0.348 mmol), intermediate 73a (145 mg, 0.696 mmol), intermediate 73b (146 mg, 0.696 mmol), were taken in 8 ml vial, charged with stir bar. To this mixture was added triethylamine (0.5 mL) followed by pyridine (1.2 mL), capped and stirred at 70° C. 10 min. 2,2'-Dipyridyldisulfide (307 mg, 1.39 mmol) and triphenylphosphine (365 mg, 1.39 mmol) were mixed in another 8 mL vial, added pyridine (1.4 mL), sonicated to complete dissolution under argon, the clear yellow solution was transferred to stirred suspension Reaction mixture was stirred at 70° C. overnight. Reaction was cooled to room temperature, concentrated under reduced pressure, ad co-evaporated with toluene (20 mL×2). The residue was dissolved in dichloromethane, loaded on 24 g column and dried the column by passing nitrogen over 2 min (to dry DCM) and elute with 100% EtOAc 6 min, 0-15% MeOH/DCM for 15 min to afford mixture of 3 products. This mixture was dissolved in MeOH, filtered and purified by preparative HPLC (Gemini, 10 uM, NX-C18, 110 Å 250×30 mm column, 20%-100% acetonitrile/water gradient over 20 min run) and isolated 73 and 74.

73: $^1$H NMR (400 MHz, Methanol-$d_4$) δ 8.30 (s, 1H), 8.20 (s, 1H), 4.41 (dd, J=14.5, 3.0 Hz, 1H), 4.21 (dd, J=14.5, 7.7 Hz, 1H), 4.08 (tt, J=7.9, 4.0 Hz, 3H), 4.02-3.78 (m, 5H), 3.59 (dd, J=12.8, 11.7 Hz, 1H), 1.65-1.50 (m, 4H), 1.40-1.26 (m, 10H), 1.24 (d, J=6.2 Hz, 3H), 1.20-1.08 (m, 4H), 0.90 (q, J=6.7 Hz, 6H). $^{31}$P NMR (162 MHz, Methanol-$d_4$) δ 25.55. LCMS: MS m/z=594.25 [M+1]; $t_R$=1.38 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

74: $^1$H NMR (400 MHz, Methanol-$d_4$) δ 8.27 (d, J=6.0 Hz, 1H), 8.20 (d, J=2.3 Hz, 1H), 4.40 (dt, J=14.4, 3.0 Hz, 1H), 4.23 (dt, J=14.4, 7.1 Hz, 1H), 4.18-4.10 (m, 2H), 4.07 (qd, J=6.6, 2.2 Hz, 2H), 4.02-3.91 (m, 2H), 3.82 (ddd, J=13.1, 7.9, 5.4 Hz, 1H), 3.56 (ddd, J=15.8, 12.8, 10.7 Hz, 1H), 1.69-153 (m, 4H), 1.48 (d, J=10.1 Hz, 4H), 1.40 (d, J=6.3 Hz, 4H), 1.38-1.26 (m, 6H), 1.23 (dd, J=6.2, 1.9 Hz, 4H), 1.20-1.10 (m, 1H), 0.90 (qd, J=7.1, 4.2 Hz, 7H). $^{31}$P NMR (162 MHz, Methanol-$d_4$) δ 23.09 (d, J=12.3 Hz). LCMS: MS m/z=596.23 [M+1]; $t_R$=1.43 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.88 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 75: Diisobutyl 1,1'-(((((1-(6-amino-9H-purin-9-yl)propan-2-yl)oxy)methyl)phosphoryl)bis(azanediyl))(R)-bis(cyclopropane-1-carboxylate) (75)

Example 76: Isobutyl 1-((((((R)-1-(6-amino-9H-purin-9-yl)propan-2-yl)oxy)methyl)((1-(hexyloxy)-2-methyl-1-oxopropan-2-yl)amino)phosphoryl)amino)cyclopropane-1-carboxylate (76)

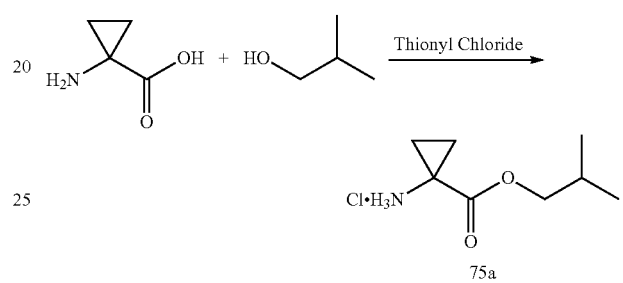

75a

Synthesis of isobutyl 1-aminocyclopropane-1-carboxylate hydrochloride (75a)

Intermediate 75a was synthesized in the same manner as Intermediate 1a using 1-aminocyclopropanecarboxylic acid (2.5 g, 24.7 mmol), 2-methylpropan-1-ol (13.5 mL, 148 mmol) and thionyl chloride (3.61 mL, 49.5 mmol) to afford intermediate 75a. $^1$H NMR (400 MHz, DMSO-$d_6$) δ 9.06 (s, 3H), 3.92 (d, J=6.5 Hz, 2H), 1.93-1.84 (m, 1H), 1.60-1.28 (m, 4H), 0.90 (d, J=6.7 Hz, 6H).

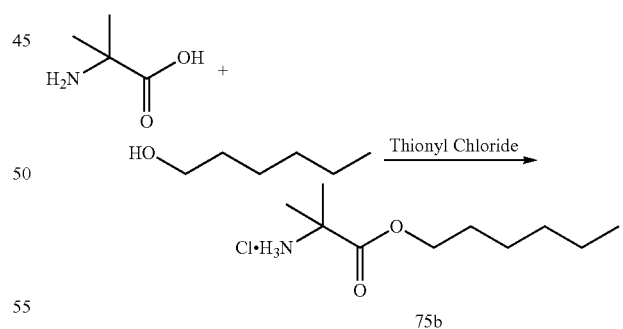

75b

Synthesis of hexyl 2-amino-2-methylpropanoate hydrochloride (75b)

To a suspension of 2-amino-2-methyl-propanoic acid (5 g, 48.5 mmol) in 1-hexanol (49.5 g, 485 mmol) was added thionyl chloride (7.07 mL, 97 mmol) over 10 min at 5° C. under an atmosphere of argon in a sealed tube. After addition was complete, the reaction was allowed to warm to room temperature and stirred for 30 min. The reaction was heated to 90° C. for 16 h. The reaction was cooled to room temperature and the reaction was quenched with water (100 mL). The aqueous layer was washed with 1:1 EtOAc:Hex (50 mL×2) and concentrated. The residue was taken up in water (20 mL) and concentrated (×2). The residue was taken up in toluene and concentrated to afford intermediate 75b. $^1$H NMR (400 MHz, Methanol-$d_4$) δ 4.27 (t, J=6.6 Hz, 2H), 1.77-1.67 (m, 2H), 1.59 (s, 6H), 1.46-1.33 (m, 6H), 0.99-0.89 (m, 3H).

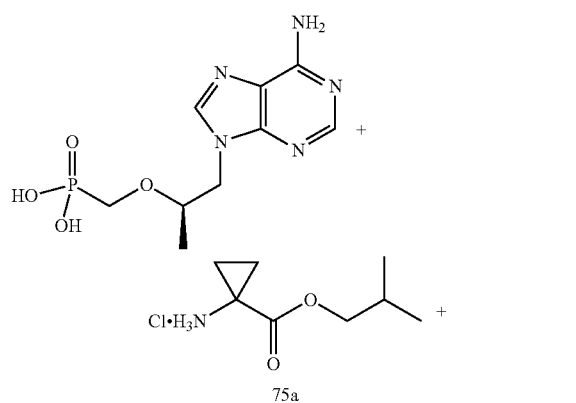

75a

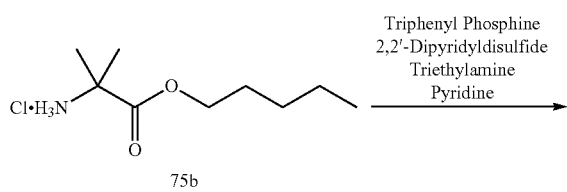

75b

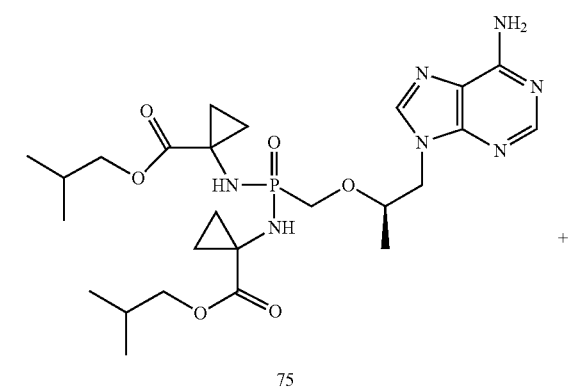

75

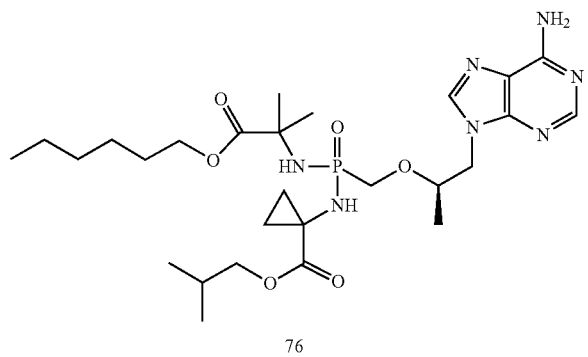

76

PMPA (100 mg, 0.348 mmol), isobutyl 1-aminocyclopropanecarboxylate hydrochloride (75a) (135 mg, 0.696 mmol), hexyl 2-amino-2-methylpropanoate hydrochloride (75b) (146 mg, 0.696 mmol), were taken in a 8 ml microwave vial, charged with stir bar. To this mixture was added TEA (0.5 mL) followed by pyridine (1.2 mL), capped and stirred at 70° C. 10 min. 2,2'-Dipyridyldisulfide (307 mg, 1.39 mmol) and triphenylphosphine (365 mg, 1.39 mmol) were mixed in a another 8 mL vial, added pyridine (1.4 mL), sonicated to complete dissolution under argon, the clear yellow solution was transferred to stirred suspension of above mixture. Reaction mixture was stirred at 70° C. overnight. Reaction was cooled to room temperature, concentrated, and co-evaporated with toluene (20 mL×2). The residue was dissolved in DCM, loaded on 24 g column, dried the column by passing nitrogen over 2 min (to dry DCM) and elute with 100% EtOAc over 6 min, 0-15% MeOH/DCM over 15 min to afford mixture of 3 products. This mixture was dissolved in MeOH, filtered and purified by preparative HPLC (Gemini, 10 uM, NX-C18, 110 Å 250×30 mm column, 20%-100% acetonitrile/water gradient in 20 min run) and isolated 75 and 76.

75: $^1$H NMR (400 MHz, Methanol-$d_4$) δ 8.31 (s, 1H), 8.20 (s, 1H), 4.41 (dd, J=14.5, 2.9 Hz, 1H), 4.20 (dd, J=14.5, 7.9 Hz, 1H), 4.03-3.93 (m, 1H), 3.93-3.81 (m, 4H), 3.68 (d, J=6.6 Hz, 2H), 3.65-3.54 (m, 1H), 1.93-1.77 (m, 2H), 1.42-1.29 (m, 6H), 1.24 (d, J=6.3 Hz, 3H), 1.21-1.06 (m, 3H), 0.91 (d, J=6.7 Hz, 6H), 0.86 (dd, J=6.7, 1.9 Hz, 6H). $^{31}$P NMR (162 MHz, Methanol-$d_4$) δ 25.67. LCMS: MS m/z=566.22 [M+1]; $t_R$=1.27 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=2.70 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

76: $^1$H NMR (400 MHz, Methanol-$d_4$) δ 8.27 (d, J=6.1 Hz, 1H), 8.20 (d, J=2.1 Hz, 1H), 4.40 (dt, J=14.5, 3.1 Hz, 1H), 4.27-4.19 (m, 1H), 4.17-4.11 (m, 1H), 4.09-4.03 (m, 1H), 4.02-3.89 (m, 1H), 3.88-3.68 (m, 3H), 3.61-3.48 (m, 1H), 1.94-1.79 (m, 1H), 1.70-1.54 (m, 2H), 1.48 (d, J=10.0 Hz, 4H), 1.40 (d, J=7.9 Hz, 4H), 1.37-1.26 (m, 5H), 1.25-1.11 (m, 5H), 0.97-0.82 (m, 10H). $^{31}$P NMR (162 MHz, Methanol-$d_4$) δ 23.19, 23.09. LCMS: MS m/z=596.23 [M+1]; $t_R$=1.43 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 77: Bicyclo[1.1.1]pentan-1-ylmethyl 2-((((((R)-1-(6-amino-9H-purin-9-yl)propan-2-yl)oxy)methyl)((1-(hexyloxy)-2-methyl-1-oxopropan-2-yl)amino)phosphoryl)amino)-2-methylpropanoate (77)

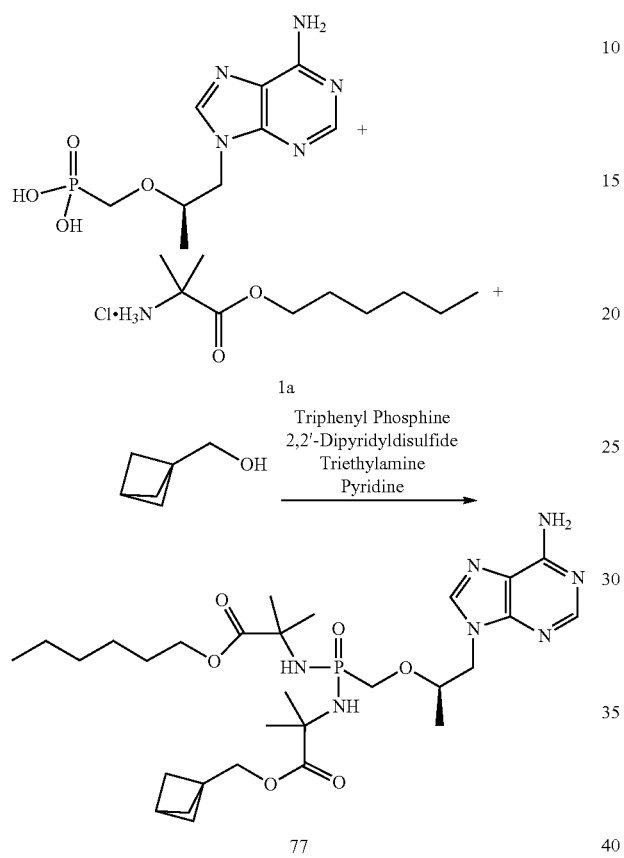

PMPA (100 mg, 0.348 mmol), 1-bicyclo[1.1.1]pentanyl-methanol (103 mg, 1.04 mmol), intermediate 1a (156 mg, 0.696 mmol), 2,2'-dipyridyldisulfide (307 mg, 1.39 mmol), triphenylphosphine (365 mg, 1.39 mmol) were taken in 8 mL vial charged with stir bar, added triethylamine (0.5 mL) and pyridine (2.4 mL). This mixture was flushed with argon, capped and stirred at 70° C. overnight. Reaction was cooled to room temperature, concentrated under reduced pressure and co-evaporated with toluene (20 mL×2). The residue was dissolved in DCM, loaded on 24 g column, dried the column by passing nitrogen over 2 min (to dry DCM and elute with 100% EtOAc 6 min, 0-15% MeOH/DCM for 15 min to afford mixture of 3 products. This mixture was dissolved in MeOH, filtered and purified by preparative HPLC (Gemini, 10 uM, NX-C18, 110 Å250×30 mm column, 20%-100% acetonitrile/water gradient in 20 min run) to afford the title compound (77) $^1$H NMR (400 MHz, Methanol-$d_4$) δ 8.21 (d, J=1.1 Hz, 1H), 8.17 (d, J=4.1 Hz, 1H), 4.45-4.33 (m, 1H), 4.26 (ddd, J=14.5, 7.2, 2.7 Hz, 1H), 4.07 (q, J=6.7 Hz, 3H), 3.92-3.61 (m, 4H), 2.48 (d, J=9.1 Hz, 1H), 1.75 (s, 3H), 1.71 (s, 3H), 1.66-1.53 (m, 2H), 1.51-1.40 (m, 14H), 1.38-1.27 (m, 4H), 1.23 (t, J=5.8 Hz, 3H), 0.96-0.82 (m, 3H). $^{31}$P NMR (162 MHz, Methanol-$d_4$) δ 26.62, 26.47. LCMS: MS m/z=622.32 [M+1]; $t_R$=1.41 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 78: (1-Fluorocyclopropyl)methyl 2-((((((R)-1-(6-amino-9H-purin-9-yl)propan-2-yl)oxy)methyl)((1-(hexyloxy)-2-methyl-1-oxopropan-2-yl)amino)phosphoryl)amino)-2-methylpropanoate (78)

PMPA (100 mg, 0.348 mmol), (1-fluorocyclopropyl)methanol (94 mg, 1.04 mmol), intermediate 1a (156 mg, 0.696 mmol), 2,2'-dipyridyldisulfide (307 mg, 1.39 mmol), triphenylphosphine (365 mg, 1.39 mmol) were taken in 8 mL microwave vial charged with stir bar, added triethylamine (0.5 mL) and pyridine (2.4 mL). This mixture was flushed with argon, capped and stirred at 70° C. overnight. Reaction was cooled to room temperature, concentrated under reduced pressure and co-evaporated with toluene (20 mL×2). The residue was dissolved in DCM, loaded on 24 g column, dried the column by passing nitrogen over 2 min (to dry DCM and elute with 100% EtOAc over 6 min, 0-15% MeOH/DCM over 15 min to afford mixture of 3 products. This mixture was dissolved in MeOH, filtered and purified by preparative HPLC (Gemini, 10 uM, NX-C18, 110 Å 250×30 mm column, 20%-100% acetonitrile/water gradient in 20 min run) to afford the title compound (78). $^1$H NMR (400 MHz, Methanol-$d_4$) δ 8.20 (s, 1H), 8.18 (d, J=3.4 Hz, 1H), 4.57 (s, 1H), 4.39 (dt, J=14.6, 3.0 Hz, 1H), 4.31-4.11 (m, 3H), 4.10-3.96 (m, 2H), 3.90 (td, J=12.7, 12.2, 8.4 Hz, 1H), 3.73 (ddd, J=18.2, 13.5, 9.1 Hz, 1H), 1.59 (d, J=8.7 Hz, 3H), 1.51-1.40 (m, 12H), 1.39-1.26 (m, 6H), 1.23 (dd, J=6.2, 1.6 Hz, 3H), 1.07 (dd, J=18.1, 8.4 Hz, 2H), 0.89 (t, J=6.6 Hz, 3H), 0.84-0.74 (m, 2H). $^{31}$P NMR (162 MHz, Methanol-d$_4$) δ 26.94, 26.80. LCMS: MS m/z=614.29 [M+1]; t$_R$=1.32 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 79: Hexyl 2-((((((R)-1-(6-amino-9H-purin-9-yl)propan-2-yl)oxy)methyl)((1-(2-methoxy-2-methylpropoxy)-2-methyl-1-oxopropan-2-yl)amino)phosphoryl)amino)-2-methylpropanoate (79)

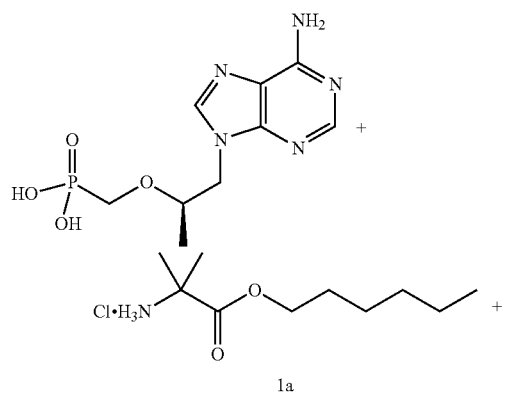

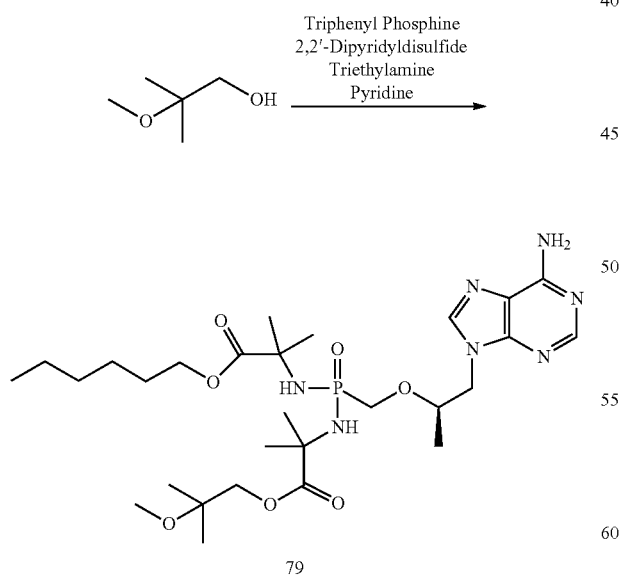

PMPA (100 mg, 0.348 mmol), 2-methoxy-2-methyl-propan-1-ol (109 mg, 1.04 mmol), intermediate 1a (156 mg, 0.696 mmol), 2,2'-dipyridyldisulfide (307 mg, 1.39 mmol), triphenylphosphine (365 mg, 1.39 mmol) were taken in 8 mL microwave vial charged with stir bar, added Triethylamine (0.5 mL) and pyridine (2.4 mL). This mixture was flushed with argon, capped and stirred at 70° C. overnight. Reaction was cooled to room temperature, concentrated by under reduced pressure, and co-evaporated with toluene (20 mL×2). The residue was dissolved in DCM, loaded on 24 g column, dried the column by passing nitrogen over 2 min (to dry DCM) and elute with 100% EtOAc 6 min, 0-15% MeOH/DCM for 15 min to afford mixture of 3 products. This mixture was dissolved in MeOH, filtered and purified by preparative HPLC (Gemini, 10 uM, NX-C18, 110 Å 250×30 mm column, 20%-100% acetonitrile/water gradient in 20 min run) to afford the title compound (79). $^1$H NMR (400 MHz, Methanol-d$_4$) δ 8.21 (s, 1H), 8.19 (d, J=2.6 Hz, 1H), 7.96 (d, J=8.6 Hz, 1H), 4.39 (ddd, J=14.5, 6.0, 3.4 Hz, 1H), 4.26 (ddd, J=14.6, 7.1, 3.0 Hz, 1H), 4.12-3.96 (m, 3H), 3.94-3.63 (m, 5H), 3.20 (d, J=10.5 Hz, 3H), 1.68-1.54 (m, 2H), 1.50-1.44 (m, 8H), 1.42 (d, J=3.2 Hz, 4H), 1.38-1.26 (m, 3H), 1.23 (dd, J=6.3, 2.6 Hz, 3H), 1.13 (dd, J=16.2, 7.4 Hz, 7H), 0.94-0.83 (m, 3H). $^{31}$P NMR (162 MHz, Methanol-d$_4$) δ 26.76, 26.57. LCMS: MS m/z=628.32 [M+1]; t$_R$=1.32 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 80: Bicyclo[2.2.1]heptan-1-ylmethyl 2-((((((R)-1-(6-amino-9H-purin-9-yl)propan-2-yl)oxy)methyl)((1-(hexyloxy)-2-methyl-1-oxopropan-2-yl)amino)phosphoryl)amino)-2-methylpropanoate (80)

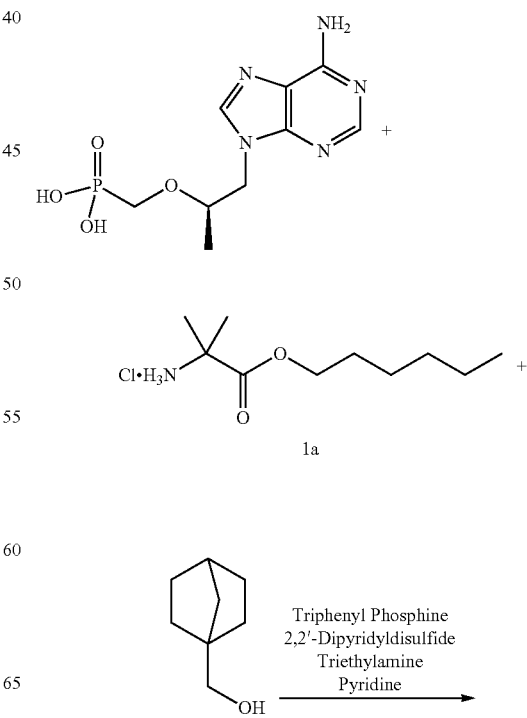

-continued

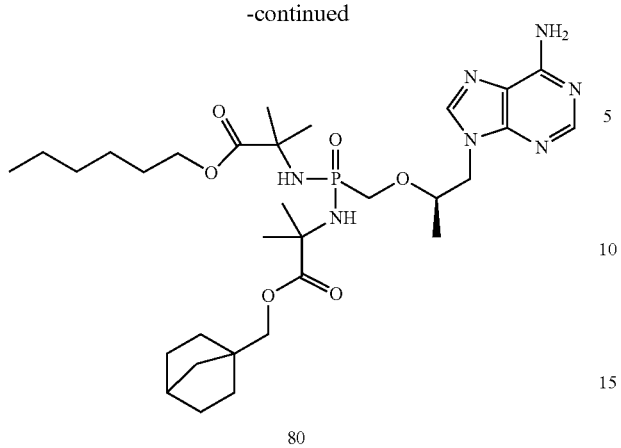

80

PMPA (100 mg, 0.348 mmol), norbornan-1-ylmethanol (132 mg, 1.04 mmol), intermediate 1a (156 mg, 0.696 mmol), 2,2'-dipyridyldisulfide (307 mg, 1.39 mmol), triphenylphosphine (365 mg, 1.39 mmol) were taken in 8 mL microwave vial charged with stir bar, added TEA (0.5 mL) and pyridine (2.4 mL). This mixture was flushed with argon, capped and stirred at 70° C. overnight. Reaction was cooled to room temperature, concentrated by reduced pressure, and co-evaporated with toluene (20 mL×2). The residue was dissolved in DCM, loaded on 24 g column, dried the column by passing nitrogen over 2 min (to dry DCM) and elute with 100% EtOAc over 6 min, 0-15% MeOH/DCM for 15 min to afford mixture of 3 products. This mixture was dissolved in MeOH, filtered and purified by preparative HPLC (Gemini, 10 uM, NX-C18, 110 Å250×30 mm column, 20%-100% acetonitrile/water gradient in 20 min run) to afford the title compound (80). $^1$H NMR (400 MHz, Methanol-$d_4$) δ 8.20 (s, 1H), 8.17 (d, J=3.3 Hz, 1H), 7.97 (d, J=9.7 Hz, 1H), 4.38 (ddd, J=14.5, 7.2, 3.2 Hz, 1H), 4.25 (ddd, J=14.4, 7.2, 3.5 Hz, 1H), 4.11-3.97 (m, 4H), 3.96-3.80 (m, 2H), 3.69 (td, J=13.4, 9.1 Hz, 1H), 2.18 (dt, J=9.7, 4.3 Hz, 1H), 1.71-1.53 (m, 5H), 1.52-1.41 (m, 13H), 1.38-1.27 (m, 7H), 1.26-1.08 (m, 6H), 0.95-0.78 (m, 4H). $^{31}$P NMR (162 MHz, Methanol-$d_4$) δ 26.38, 26.16. LCMS: MS m/z=650.37 [M+1]; $t_R$=1.49 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 81: 1-Cyclopropylethyl 2-((((((R)-1-(6-amino-9H-purin-9-yl)propan-2-yl)oxy)methyl)((1-(hexyloxy)-2-methyl-1-oxopropan-2-yl)amino)phosphoryl)amino)-2-methylpropanoate (81)

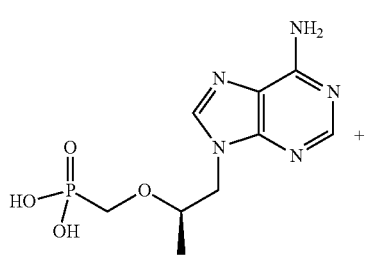

+

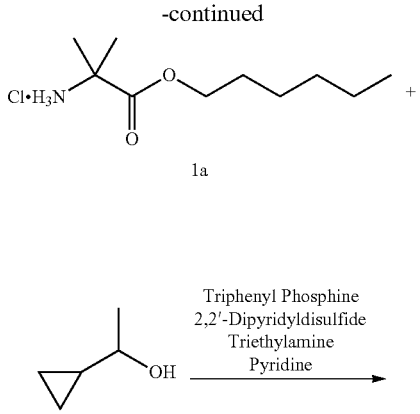

1a

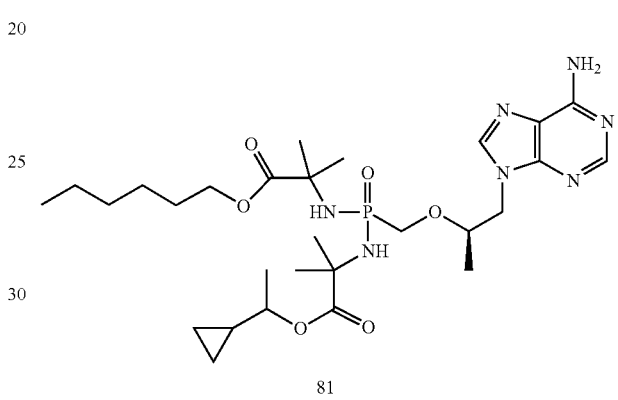

81

PMPA (100 mg, 0.348 mmol), 1-cyclopropylethanol (90 mg, 1.04 mmol), intermediate 1a (156 mg, 0.696 mmol), 2,2'-dipyridyldisulfide (307 mg, 1.39 mmol), triphenylphosphine (365 mg, 1.39 mmol) were taken in 8 mL microwave vial charged with stir bar, added triethylamine (0.5 mL) and pyridine (2.4 mL). This mixture was flushed with argon, capped and stirred at 70° C. overnight. Reaction was cooled to room temperature, concentrated by under reduced pressure, and co-evaporated with toluene (20 mL×2). The residue was dissolved in DCM, loaded on 24 g column, dried the column by passing nitrogen over 2 min (to dry DCM) and elute with 100% EtOAc over 6 min, 0-15% MeOH/DCM over 15 min to afford mixture of mixture of 3 compounds. This mixture was dissolved in MeOH, filtered and purified by preparative HPLC (Gemini, 10 uM, NX-C18, 110 Å 250×30 mm column, 20%-100% acetonitrile/water gradient in 20 min run) and isolated 81. $^1$H NMR (400 MHz, Acetonitrile-$d_3$) δ 8.24 (s, 1H), 8.02 (s, 1H), 5.98 (s, 2H), 4.41-4.10 (m, 3H), 4.05-3.96 (m, 3H), 3.92-3.70 (m, 2H), 3.68-3.45 (m, 2H), 1.70-1.51 (m, 3H), 1.47-1.25 (m, 20H), 1.24-1.14 (m, 4H), 0.95-0.82 (m, 4H), 0.56-0.17 (m, 4H). $^{31}$P NMR (162 MHz, Acetonitrile-$d_3$) δ 24.75-23.19 (m). LCMS: MS m/z=610.19 [M+1]; $t_R$=1.37 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 82: Dihexyl 2,2'-(((((1-(6-(((5-methyl-2-oxo-1,3-dioxol-4-yl)methyl)amino)-9H-purin-9-yl)propan-2-yl)oxy)methyl)phosphoryl)bis(azanediyl))(R)-bis(2-methylpropanoate) (82)

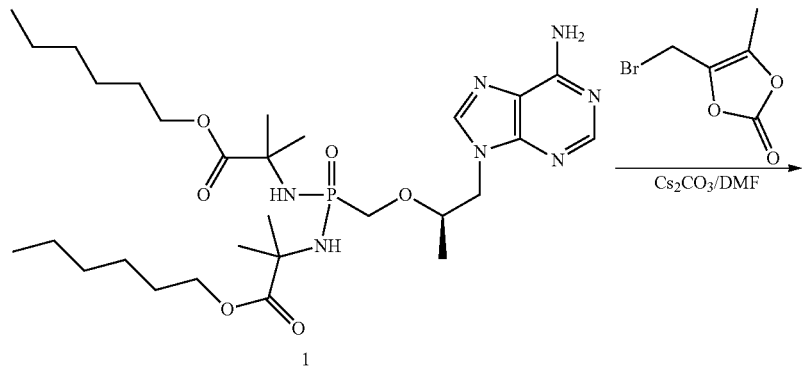

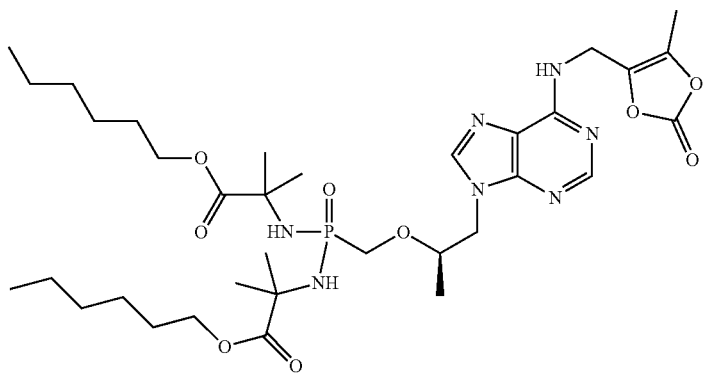

Compound 1 (50 mg, 0.079 mmol), 4-(bromomethyl)-5-methyl-1,3-dioxol-2-one (31 mg, 0.16 mmol), $Cs_2CO_3$ (130 mg, 0.4 mmol), NaI (59.9 mg, 0.4 mmol) were taken in 8 mL vial charged with stir bar and added DMF (1 mL). This mixture was flushed with argon, capped and stirred at room temperature 4 h, and heated at 80° C. 4 h. The reaction mixture was cooled to room temperature, quenched with water, extracted with DCM, dried over sodium sulfate, and concentrated. The residue was dissolved in DCM, loaded on 12 g column, and eluted with 0-20% McOH/DCM for 15 min to afford a mixture enriched in the title compound. The mixture was dissolved in MeOH (2 mL), filtered and purified by preparative HPLC (Gemini, 10 uM, NX-C18, 110 Å 250×30 mm column, 40%-100% acetonitrile/water gradient in 20 min run) to afford the title compound (82). $^1$H NMR (400 MHz, Acetonitrile-$d_3$) δ 8.33 (s, 1H), 8.06 (s, 1H), 6.61 (s, 1H), 4.60 (s, 2H), 4.35 (dd, J=14.5, 3.2 Hz, 1H), 4.24-3.99 (m, 5H), 3.97-3.90 (m, 1H), 3.81-3.60 (m, 2H), 3.58-3.31 (m, 2H), 2.20 (s, 3H), 1.71-1.56 (m, 5H), 1.52 (s, 3H), 1.44 (d, J=4.4 Hz, 6H), 1.40-1.26 (m, 14H), 1.19 (d, J=6.2 Hz, 3H), 0.98-0.80 (m, 6H). $^{31}$P NMR (162 MHz, Acetonitrile-$d_3$) δ 17.71. LCMS: MS m/z=738.30 [M+1]; $t_R$=2.01 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.80 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 83: Dihexyl 2,2'-(((((1-(6-imino-1-((5-methyl-2-oxo-1,3-dioxol-4-yl)methyl)-1,6-dihydro-9H-purin-9-yl)propan-2-yl)oxy)methyl)phosphoryl)bis(azanediyl))(R)-bis(2-methylpropanoate) (83)
Example 84: Dihexyl 2,2'-(((((1-(1-((5-methyl-2-oxo-1,3-dioxol-4-yl)methyl)-6-((((5-methyl-2-oxo-1,3-dioxol-4-yl)methyl)imino)-1,6-dihydro-9H-purin-9-yl)propan-2-yl)oxy)methyl)phosphoryl)bis(azanediyl))(R,E)-bis(2-methylpropanoate) (84)
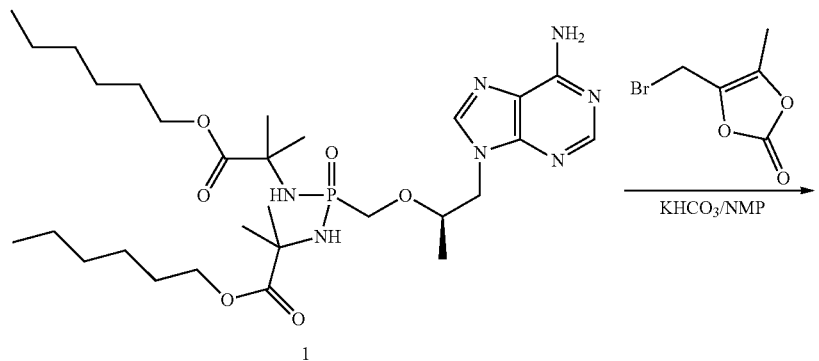
1
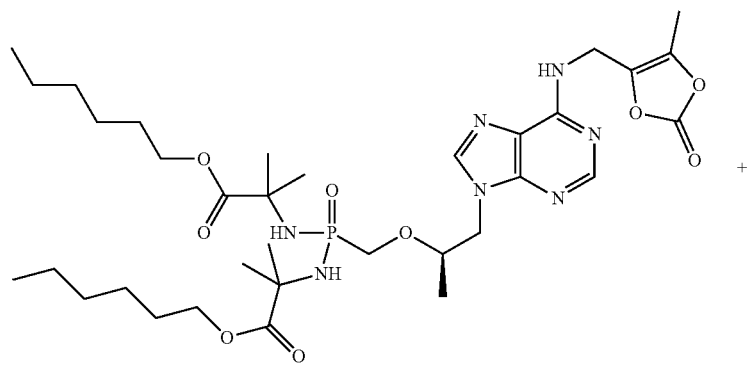
82
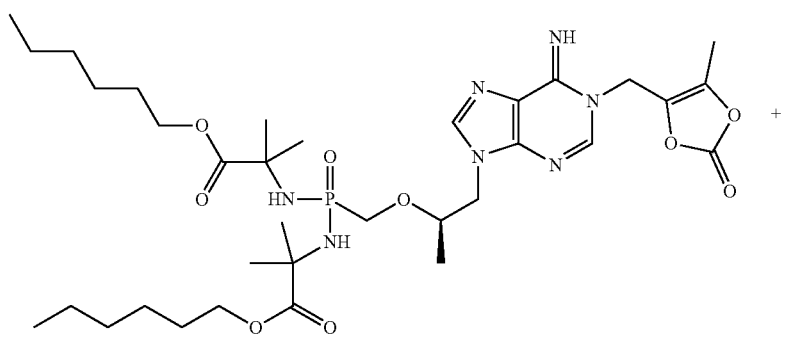
83

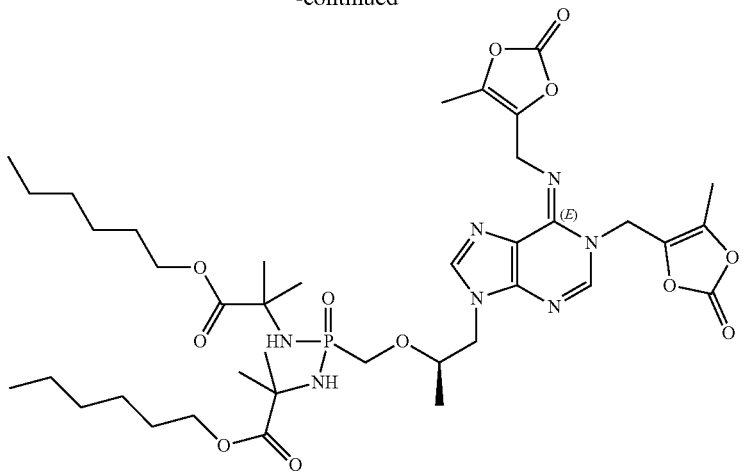

84

Compound 1 (200 mg, 0.32 mmol)) and KHCO$_3$ (64 mg, 0.64 mmol) were taken in 20 mL microwave vial charged with stir bar and added NMP (4 ml). To well stirred mixture was added 4-(bromomethyl)-5-methyl-1,3-dioxol-2-one (71 µL, 0.64 mmol) drop wise and stirred at 70° C. for 15 h. At this stage excess of KHCO$_3$ (32 mg, 0.32 mmol) and 4-(bromomethyl)-5-methyl-1,3-dioxol-2-one (36 µL, 0.32 mmol) were added and continued stirring at 70° C. for additional 12 h. The reaction mixture was cooled to 0° C., quenched with water by drop wise addition, and extracted with EtOAc (40 mL×2). The ethyl acetate layer washed once with saturated aqueous ammonium chloride, once with water, and once with brine. The combined organic layers was dried over sodium sulfate, filtered and concentrated under reduced pressure. The residue was dissolved in DCM, loaded on 12 g gold column, dried, elute with 0-20% MeOH/DCM for 15 min to afford mixture of 3 compounds. This mixture was dissolved in MeOH (4 mL), filtered and purified by preparative HPLC (Gemini, 10 uM, NX-C18, 110 Å250×30 mm column, 40%-100% acetonitrile/water gradient in 20 min run) to isolate 82, 83, and 84.

83: $^1$H NMR (400 MHz, Acetonitrile-d$_3$) δ 7.87 (s, 1H), 7.81 (s, 1H), 7.10 (s, 1H), 5.01 (s, 2H), 4.23 (dd, J=14.4, 3.3 Hz, 1H), 4.17-4.05 (m, 5H), 3.92-3.85 (m, 1H), 3.77-3.61 (m, 2H), 3.60-3.35 (m, 2H), 2.23 (s, 3H), 1.73-1.58 (m, 4H), 1.53 (s, 3H), 1.46 (d, J=3.2 Hz, 6H), 1.42-1.26 (m, 12H), 1.17 (d, J=6.2 Hz, 3H), 0.97-0.85 (m, 6H). $^{31}$P NMR (162 MHz, Acetonitrile-d$_3$) δ 17.69. LCMS: MS m/z=738.15 [M+1]; t$_R$=1.56 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=3.79 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

84: $^1$H NMR (400 MHz, Acetonitrile-d$_3$) δ 7.92 (s, 1H), 7.87 (s, 1H), 5.13-4.97 (m, 2H), 4.92 (s, 2H), 4.25 (dd, J=14.4, 3.2 Hz, 1H), 4.18-3.99 (m, 5H), 3.96-3.82 (m, 1H), 3.75-3.62 (m, 2H), 3.58-3.37 (m, 2H), 2.19 (s, 3H), 2.12 (s, 3H), 1.69-1.50 (m, 4H), 1.53 (s, 3H), 1.46 (d, J=1.6 Hz, 6H), 1.40 (s, 4H), 1.34-1.25 (m, 7H), 1.19 (d, J=6.2 Hz, 3H), 0.95-0.83 (m, 6H). $^{31}$P NMR (162 MHz, Acetonitrile-d$_3$) δ 17.65. LCMS: MS m/z=850.07 [M+1]; t$_R$=1.34 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=3.81 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 85: Bis((1s,3S)-3-phenylcyclobutyl) 2,2'-((((((R)-1-(6-amino-9H-purin-9-yl)propan-2-yl)oxy)methyl)phosphoryl)bis(azanediyl))bis(2-methylpropanoate) (85)

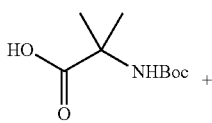

+

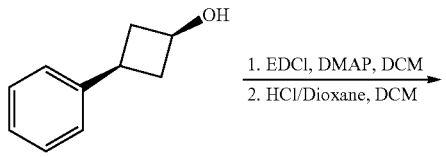

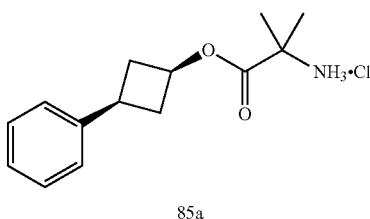

85a

Synthesis of (1S,3S)-3-phenylcyclobutyl 2-amino-2-methylpropanoate hydrochloride (85a)

2-(tert-Butoxycarbonylamino)-2-methyl-propanoic acid (0.50 g, 2.46 mmol), 3-phenylcyclobutanol (438 mg, 2.95 mmol), 4-dimethylaminopyridine (0.90 g, 7.38 mmol) and 3-(ethyliminomethyleneamino)-N,N-dimethyl-propan-1-amine hydrochloride (1.4 g, 7.38 mmol) were dissolved in dichloromethane (10 ml) and stirred at room temperature. After 17 h the reaction was diluted with DCM (10 ml). The solution was washed with water (3×10 ml), saturated ammonium chloride (10 ml), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 3.0 ml, 12.3 mmol) was added to a solution of the residue in dichloromethane (5 ml). After 18 h the solvent was removed under reduced pressure. The residue was co-evaporated with dichloromethane (10 ml). The residue was subjected to high vacuum for 5 hours, to afford intermediate 85a. $^1$H NMR (400 MHz, DMSO-d$_6$) δ 8.60 (s, 3H), 7.38-7.30 (m, 2H), 7.30-7.25 (m, 2H), 7.25-7.18 (m, 1H), 5.11-5.00 (m, 1H), 3.24-3.10 (m, 1H), 2.89-2.76 (m, 2H), 2.23-2.09 (m, 2H), 1.49 (s, 6H).

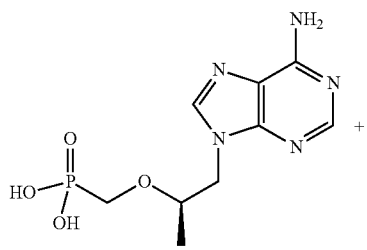

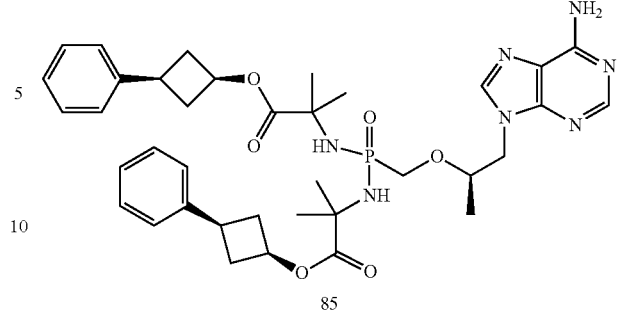

85

PMPA (100 mg, 0.348 mmol), and intermediate 85a (276 mg, 1.39 mmol) were taken up in a 8 ml vial, charged with stir bar. To this mixture was added triethylamine (0.5 mL) followed by pyridine (1.2 mL), capped and stirred at 70° C. over 10 min (not completely soluble, suspension). 2,2'-Dipyridyldisulfide (384 mg, 1.74 mmol) and triphenylphosphine (457 mg, 1.74 mmol) were mixed in another 8 mL vial, added pyridine (1.4 mL), sonicated to complete dissolution under argon, the clear yellow solution was transferred to stirred suspension of above mixture. Reaction mixture was stirred at 80° C. overnight. Reaction was cooled to room temperature, concentrated under reduced pressure and co-evaporated with toluene (20 mL×2). The residue was dissolved in DCM, loaded on 24 g gold column, dried the column by passing nitrogen over 2 min (to dry DCM) and elute with 100% EtOAc over 6 min, 0-15% MeOH/DCM over 15 min to afford a mixture. This mixture was dissolved in MeOH, filtered and purified by preparative HPLC (Gemini, 10 uM, NX-C18, 110 Å 250×30 mm column, 40%-100% acetonitrile/water gradient in 20 min run) to afford the title compound (85). $^1$H NMR (400 MHz, Acetonitrile-d$_3$) δ 8.24 (s, 1H), 8.07 (s, 1H), 7.34-3.19 (m, 10H), 6.12 (s, 2H), 4.97 (q, J=8.8 Hz, 2H), 4.47-4.02 (m, 2H), 3.99-3.33 (m, 5H), 3.17 (s, 2H), 2.94-2.68 (m, 4H), 2.53 (s, 1H), 2.18-2.07 (m, 6H), 1.46 (t, J=28.0 Hz, 10H), 1.17 (d, J=6.6 Hz, 3H). $^{31}$P NMR (162 MHz, Acetonitrile-d$_3$) δ 17.95. LCMS: MS m/z=718.34 [M+1]; t$_R$=1.51 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=2.28 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 86: Di(spiro[3.5]nonan-2-yl) 2,2'-(((((1-(6-amino-9H-purin-9-yl)propan-2-yl)oxy)methyl)phosphoryl)bis(azanediyl))(R)-bis(2-methylpropanoate) (86)

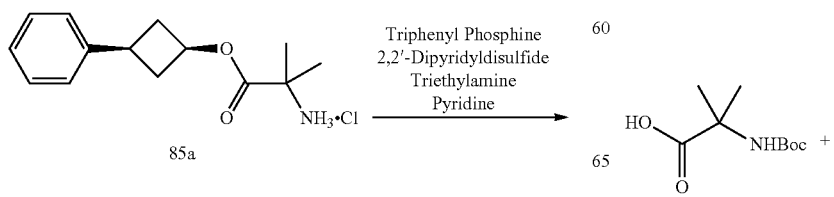

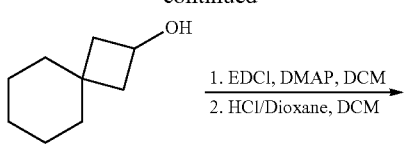
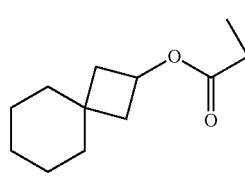
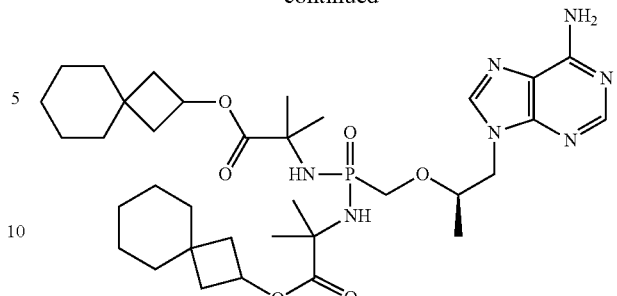

86a

86

Synthesis of spiro[3.5]nonan-2-yl 2-amino-2-methylpropanoate hydrochloride (86a)

2-(tert-Butoxycarbonylamino)-2-methyl-propanoic acid (1.0 g, 4.92 mmol), spiro[3.5]nonan-2-ol (1.03 g, 7.38 mmol), 4-dimethylaminopyridine (1.8 g, 14.8 mmol) and 3-(ethyliminomethyleneamino)-N,N-dimethyl-propan-1-amine hydrochloride (2.8 g, 14.8 mmol) were dissolved in dichloromethane (10 ml) and stirred at room temperature. After 17 h the reaction was diluted with DCM (10 ml). The solution was washed with water (3×10 ml), saturated ammonium chloride (10 ml), and dried over sodium sulfate. The solvent was removed under reduced pressure. The residue was subjected to flash chromatography (0-40% ethyl acetate/hexanes with ELSD). The fractions containing product were combined and the solvent was removed under reduced pressure.

A solution of hydrogen chloride in 1,4-dioxane (4N, 6.1 ml, 24.6 mmol) was added to a solution of the residue in dichloromethane (5 ml). After 1 h the solvent was removed under reduced pressure. The residue was co-evaporated with dichloromethane (10 ml). The residue was subjected to high vacuum for 5 hours, to afford intermediate 86a. $^1$H NMR (400 MHz, DMSO-$d_6$) δ 8.59 (s, 3H), 5.04-4.97 (m, 1H), 2.32-2.19 (m, 2H), 1.82-1.71 (m, 2H), 1.46 (d, J=6.1 Hz, 10H), 1.43-1.26 (m, 6H).

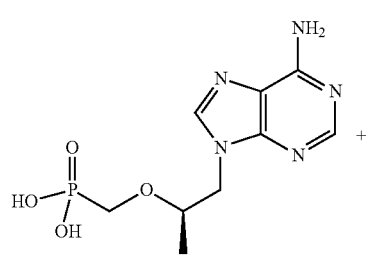

PMPA (100 mg, 0.348 mmol), intermediate 86a (273 mg, 1.04 mmol) were taken in a 8 ml microwave vial, charged with stir bar. To this mixture was added TEA (0.5 mL) followed by pyridine (1.2 mL), capped and stirred at 70° C. over 10 min (not completely soluble, suspension). 2,2'-Dipyridyldisulfide (384 mg, 1.74 mmol) and triphenylphosphine (457 mg, 1.74 mmol) were mixed in another 8 mL vial, added pyridine (1.4 mL), sonicated to complete dissolution under argon, the clear yellow solution was transferred to stirred suspension of above mixture. Reaction mixture was stirred at 80° C. overnight. Reaction was cooled to room temperature, concentrated under reduced pressure, co-evaporated with toluene (20 mL×2). The residue was dissolved in DCM, loaded on 24 g gold column, dried the column by passing nitrogen over 2 min (to dry DCM) and elute with 100% EtOAc 6 min, 0-15% MeOH/DCM for 15 min to afford a mixture. This mixture was dissolved in MeOH, filtered and purified by preparative HPLC (Gemini, 10 uM, NX-C18, 110 Å 250×30 mm column, 40%-100% acetonitrile/water gradient in 20 min run) to afford the title compound (86). $^1$H NMR (400 MHz, Acetonitrile-$d_3$) δ 8.24 (s, 1H), 8.06 (s, 1H), 6.06 (s, 2H), 4.99-4.88 (m, 2H), 4.34 (dd, J=14.5, 3.3 Hz, 1H), 4.17 (dd, J=14.5, 7.0 Hz, 1H), 3.96-3.89 (m, 1H), 3.80-3.60 (m, 2H), 3.59-3.31 (m, 2H), 2.27 (t, J=6.8 Hz, 2H), 1.79-1.70 (m, 5H), 1.56-1.41 (m, 21H), 1.37 (d, J=5.0 Hz, 13H), 1.19 (d, J=6.2 Hz, 3H). $^{31}$P NMR (162 MHz, Acetonitrile-$d_3$) δ 17.81. LCMS: MS m/z=702.23 [M+1]; $t_R$=1.55 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 87: Bis(bicyclo[2.2.1]heptan-1-ylmethyl) 2,2'-(((((1-(6-amino-9H-purin-9-yl)propan-2-yl)oxy)methyl)phosphoryl)bis(azanediyl))(R)-bis(2-methylpropanoate) (87)

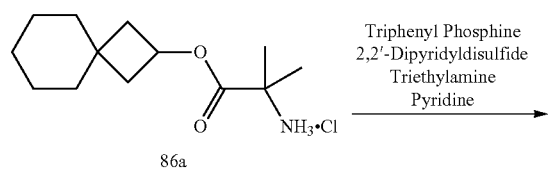
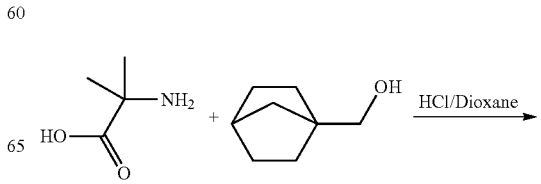

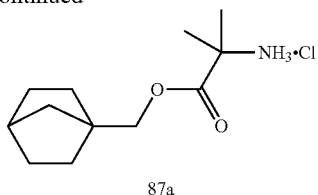

Synthesis of bicyclo[2.2.1]heptan-1-ylmethyl 2-amino-2-methylpropanoate hydrochloride (87a)

In a 40 mL seal tube charged with stir bar, 2-amino-2-methylpropanoic acid (0.5 g, 4.85 mmol) and bicyclo[2.2.1]heptan-1-ylmethanol (2.44 g, 19.4 mmol) was added solution of hydrogen chloride in 1,4-dioxane (20 mL, 4N solution in Dioxane). The mixture was stirred at 90° C. for 3 days. The 1,4-dioxane was removed under reduced pressure. The mixture was diluted with ethyl acetate/hexanes (1:1, 50 ml) and water (50 ml). The organic phase was extracted with water (50 ml). The combined aqueous phase was washed with ethyl acetate/hexanes (1:1, 2×50 ml). Any residual solvent in the aqueous phase was removed under reduced pressure. The aqueous phase was diluted with acetonitrile (10 ml) and water (10 ml) and subjected to lyophilization to afford intermediate 87a.

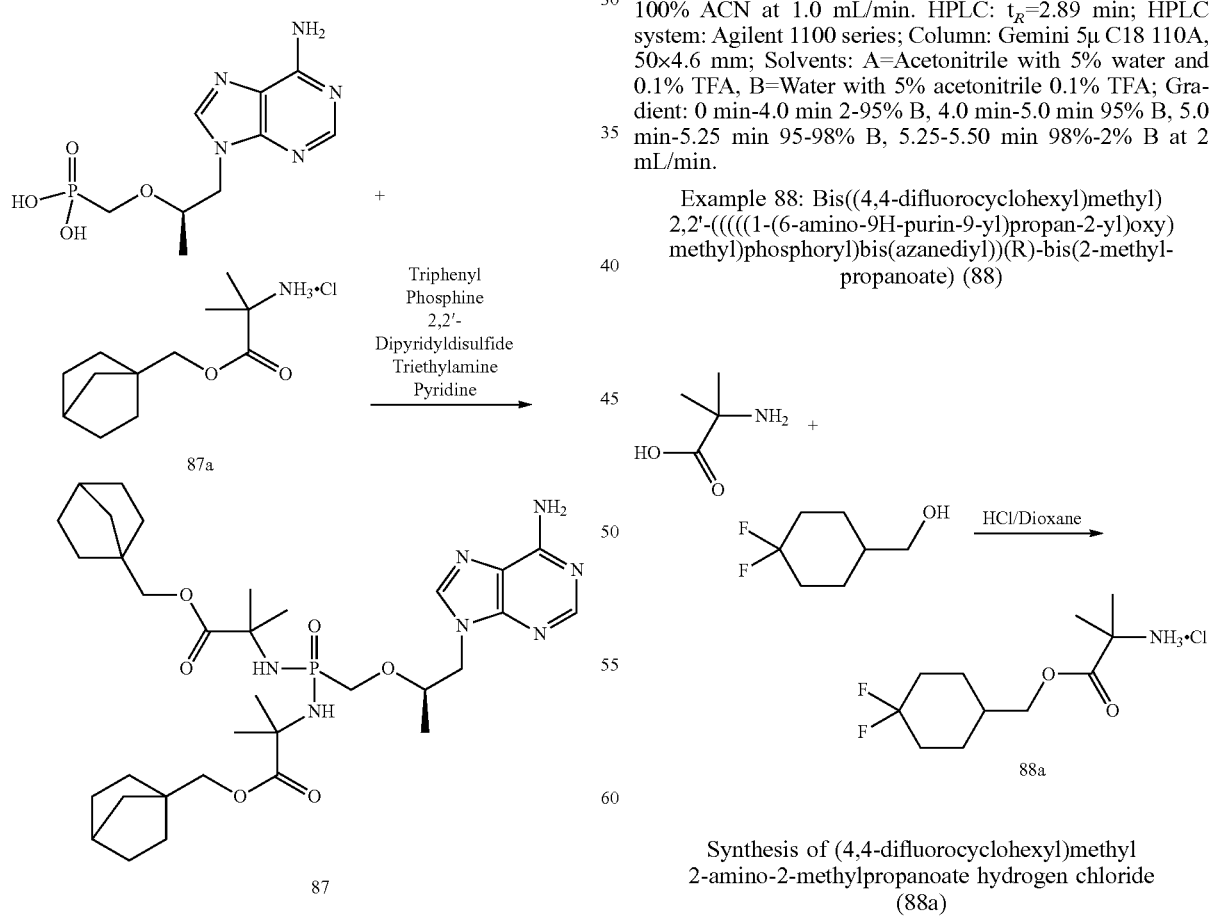

PMPA (100 mg, 0.348 mmol), intermediate 87a (259 mg, 1.04 mmol) were taken in a 8 ml-vial, charged with stir bar.

To this mixture was added TEA (0.5 mL) followed by pyridine (1.2 mL), capped and stirred at 70° C. over 10 min (not completely soluble, suspension). 2,2'-Dipyridyldisulfide (384 mg, 1.74 mmol) and triphenylphosphine (457 mg, 1.74 mmol) were mixed in another 8 mL vial, added pyridine (1.4 mL), sonicated to complete dissolution under argon, the clear yellow solution was transferred to stirred suspension of above mixture. Reaction mixture was stirred at 80° C. overnight. Reaction was cooled to room temperature, concentrated under reduced pressure, co-evaporated with toluene (20 mL×2). The residue was dissolved in DCM, loaded on 24 g gold column, dried the column by passing nitrogen over 2 min (to dry DCM) and elute with 100% EtOAc 6 min, 0-15% MeOH/DCM for 15 min to afford a mixture. This mixture was dissolved in MeOH, filtered and purified by preparative HPLC (Gemini, 10 uM, NX-C18, 110 Å250×30 mm column, 40%-100% acetonitrile/water gradient in 20 min run) to afford the title compound (87). $^1$H NMR (400 MHz, Acetonitrile-d$_3$) δ 8.24 (s, 1H), 8.06 (s, 1H), 6.05 (s, 2H), 4.43-4.10 (m, 8H), 3.97-3.90 (m, 1H), 3.77 (d, J=10.8 Hz, 1H), 3.71-3.54 (m, 2H), 3.48 (dd, J=12.6, 9.8 Hz, 1H), 1.72-1.56 (m, 6H), 1.54 (s, 3H), 1.50-1.45 (m, 10H), 1.42 (s, 3H), 1.38-1.27 (m, 6H), 1.24 (d, J=8.1 Hz, 5H), 1.18 (d, J=6.2 Hz, 3H). $^{31}$P NMR (162 MHz, Acetonitrile-d$_3$) δ 17.71. LCMS: MS m/z=674.19 [M+1]; t$_R$=1.59 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: t$_R$=2.89 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 88: Bis((4,4-difluorocyclohexyl)methyl) 2,2'-(((((1-(6-amino-9H-purin-9-yl)propan-2-yl)oxy)methyl)phosphoryl)bis(azanediyl))(R)-bis(2-methylpropanoate) (88)

Synthesis of (4,4-difluorocyclohexyl)methyl 2-amino-2-methylpropanoate hydrogen chloride (88a)

Intermediate 88a was synthesized in the same manner as intermediate 87a using 2-amino-2-methylpropanoic acid (0.5 g, 4.85 mmol), (4,4-difluorocyclohexyl)methanol (1.22 g, 8.15 mmol) and 4N HCl/Dioxane (10 mL) to afford intermediate 88a. $^1$H NMR (400 MHz, DMSO-$d_6$) δ 8.48 (s, 3H), 4.07 (d, J=6.0 Hz, 2H), 2.09-1.69 (m, 6H), 1.48 (s, 6H), 1.36-1.17 (m, 3H).

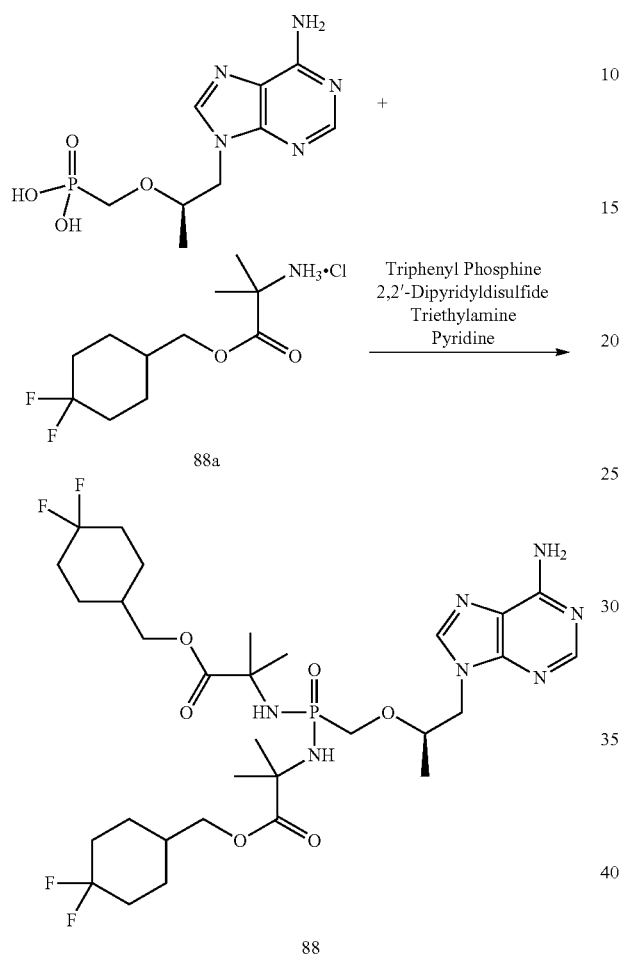

PMPA (100 mg, 0.348 mmol), intermediate 88a (246 mg, 1.05 mmol) were taken in a 8 ml vial, charged with stir bar. To this mixture was added triethylamine (0.475 mL) followed by pyridine (1.2 mL), capped and stirred at 70° C. over 10 min. 2,2'-Dipyridyldisulfide (384 mg, 1.74 mmol) and triphenylphosphine (430 mg, 1.74 mmol) were mixed in another 8 mL vial, added pyridine (1.4 mL), sonicated to complete dissolution under argon. The clear yellow solution was transferred to stirred suspension of above mixture. Reaction mixture was stirred at 80° C. overnight. Reaction was cooled to room temperature, concentrated under reduced pressure, and co-evaporated with toluene (20 mL×2). The residue was dissolved in DCM, loaded on 24 g column, and dried the column by passing nitrogen over 2 min (to dry DCM). Column was eluted with 100% EtOAc 6 min, 0-15% MeOH/DCM for 15 min to afford a mixture. This mixture was dissolved in MeOH, filtered and purified by preparative HPLC (Gemini, 10 uM, NX-C18, 110 Å 250×30 mm column, 40%-100% acetonitrile/water gradient in 20 min run) to afford the title compound (88). $^1$H NMR (400 MHz, Acetonitrile-$d_3$) δ 8.25 (d, J=1.9 Hz, 1H), 8.05-7.91 (m, 1H), 5.92 (s, 2H), 4.44-4.04 (m, 3H), 4.05-3.92 (m, 4H), 3.84-3.44 (m, 4H), 2.09 (d, J=23.7 Hz, 3H), 1.89-1.65 (m, 4H), 1.55-1.09 (m, 22H). $^{31}$P NMR (162 MHz, Acetonitrile-$d_3$) δ 17.86. LCMS: MS m/z=722.34 [M+1]; $t_R$=1.34 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 89: Bis(cycloheptylmethyl) 2,2'-(((((1-(6-amino-9H-purin-9-yl)propan-2-yl)oxy)methyl)phosphoryl)bis(azanediyl))(R)-bis(2-methylpropanoate) (89)

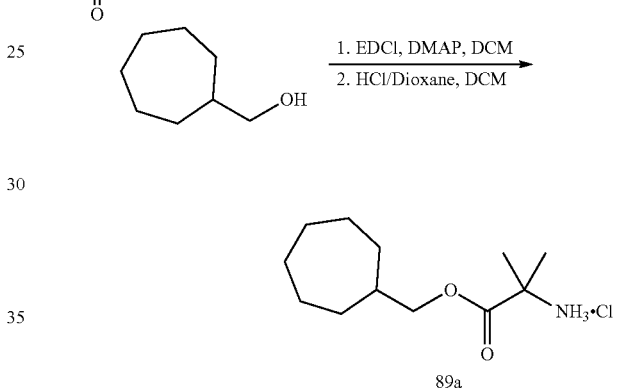

Synthesis of cycloheptylmethyl 2-(chloro-15-azanyl)-2-methylpropanoate (89a)

2-(tert-Butoxycarbonylamino)-2-methyl-propanoic acid (2.5 g, 12.3 mmol), cycloheptylmethanol (2.18 g, 17.1 mmol), 4-dimethylaminopyridine (4.5 g, 36.9 mmol) and 3-(ethyliminomethyleneamino)-N,N-dimethyl-propan-1-amine hydrochloride (7.07 g, 36.9 mmol) were dissolved in dichloromethane (30 ml) and stirred at room temperature. After 17 h the reaction was diluted with DCM (10 ml). The solution was washed with water (2×50 ml), saturated ammonium chloride (50 ml), and dried over sodium sulfate. The solvent was removed under reduced pressure. The residue was subjected to flash chromatography (0-50% ethyl acetate/hexanes with ELSD). The fractions containing product were combined and the solvent was removed under reduced pressure. A solution of hydrogen chloride in 1,4-dioxane (4N, 10 ml, 24.6 mmol) was added to a solution of the residue in dichloromethane (10 ml). After 18 h the solvent was removed under reduced pressure. The residue was co-evaporated with dichloromethane (40 ml). The residue was subjected to high vacuum for 5 hours, to afford intermediate 89a. $^1$H NMR (400 MHz, DMSO-$d_6$) δ 8.67 (s, 3H), 3.98 (d, J=6.5 Hz, 2H), 1.887-1.78 (m, 1H), 1.74-1.60 (m, 3H), 1.58-1.50 (m, 2H), 1.49 (s, 6H), 1.46-1.12 (m, 6H).

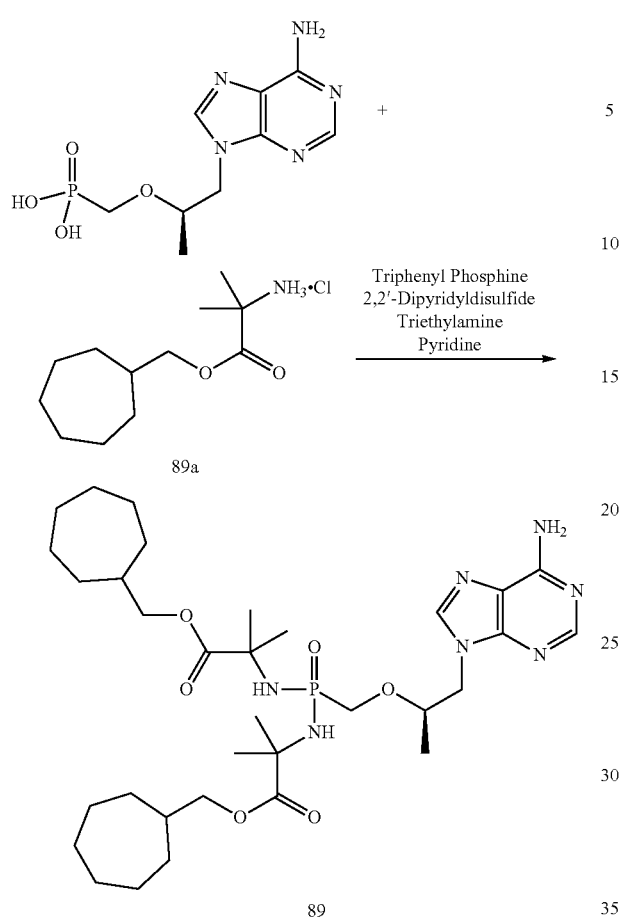

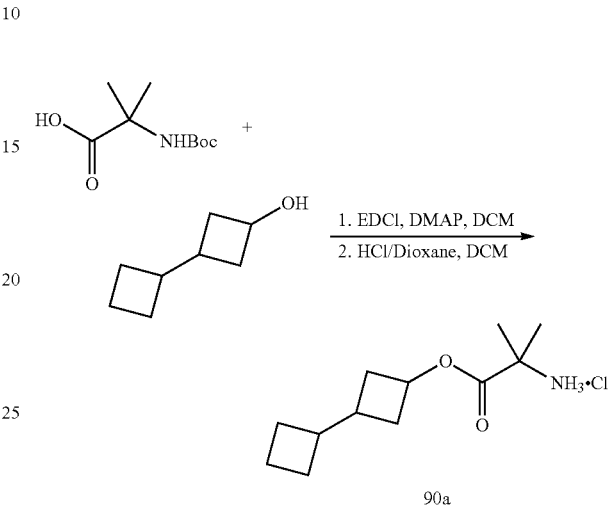

PMPA (150 mg, 0.522 mmol), and 89a (417 mg, 1.67 mmol) were taken in a 8 ml vial, charged with stir bar. To this mixture was added triethylamine (0.755 mL) followed by pyridine (3 mL), capped and stirred at 70° C., over 10 min. 2,2'-Dipyridyldisulfide (575 mg, 2.61 mmol) and triphenylphosphine (685 mg, 2.61 mmol) were mixed in another 8 mL vial, added pyridine (3 mL), and sonicated to complete dissolution under argon. The clear yellow solution was transferred to stirred suspension of above mixture. Reaction mixture was stirred at 80° C. overnight. Reaction was cooled to room temperature, concentrated under reduced pressure, and co-evaporated with toluene (30 mL×2). The residue was dissolved in DCM, loaded on 24 g flash column, dried the column by passing nitrogen over 2 min (to dry DCM) and elute with 100% EtOAc 6 min, 0-15% MeOH/DCM over 15 min to afford a mixture. This mixture was dissolved in MeOH, filtered and purified by preparative HPLC (Gemini, 10 uM, NX-C18, 110 Å 250×30 mm column, 40%-100% acetonitrile/water gradient in 20 min run) to afford the title compound (89). $^1$H NMR (400 MHz, Acetonitrile-$d_3$) δ 8.24 (s, 1H), 8.07 (s, 1H), 6.18 (s, 2H), 4.35 (dd, J=14.5, 3.2 Hz, 1H), 4.17 (dd, J=14.5, 7.0 Hz, 1H), 3.99-3.82 (m, 6H), 3.78 (d, J=10.8 Hz, 1H), 3.73-3.56 (m, 2H), 3.46 (dd, J=12.7, 9.9 Hz, 1H), 2.27 (s, 8H), 1.92-1.56 (m, 10H), 1.53 (s, 4H), 1.46 (d, J=1.7 Hz, 8H), 1.40 (s, 3H), 1.25 (ddt, J=15.0, 9.1, 2.7 Hz, 4H), 1.18 (d, J=6.3 Hz, 3H). $^{31}$P NMR (162 MHz, Acetonitrile-$d_3$) δ 17.80. LCMS: MS m/z=678.16 [M+1]; $t_R$=1.66 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 90: Di([1,1'-bi(cyclobutan)]-3-yl) 2,2'-(((((1-(6-amino-9H-purin-9-yl)propan-2-yl)oxy)methyl)phosphoryl)bis(azanediyl))(R)-bis(2-methylpropanoate) (90)

Synthesis of [1,1'-bi(cyclobutan)]-3-yl 2-amino-2-methylpropanoate (90a)

2-(tert-Butoxycarbonylamino)-2-methyl-propanoic acid (1.2 g, 5.9 mmol), [1,1'-bi(cyclobutan)]-3-ol (1.05 g, 8.32 mmol), 4-dimethylaminopyridine (2.16 g, 17.7 mmol) and 3-(ethyliminomethyleneamino)-N,N-dimethyl-propan-1-amine hydrochloride (3.39 g, 17.7 mmol) were dissolved in dichloromethane (30 ml) and stirred at room temperature. After 17 h the reaction was diluted with DCM (10 ml). The solution was washed with water (2×20 ml), saturated ammonium chloride (20 ml), and dried over sodium sulfate. The solvent was removed under reduced pressure. The residue was subjected to flash chromatography (0-50% ethyl acetate/hexanes with ELSD). The fractions containing product were combined and the solvent was removed under reduced pressure.

A solution of hydrogen chloride in 1,4-dioxane (4N, 6.2 ml, 24.6 mmol) was added to a solution of the residue in dichloromethane (6 ml). After 18 h the solvent was removed under reduced pressure. The residue was co-evaporated with dichloromethane (40 ml). The residue was subjected to high vacuum for 5 hours, to afford intermediate 90a. $^1$H NMR (400 MHz, DMSO-$d_6$) δ 8.64 (s, 3H), 4.91-4.84 (m, 1H), 2.45-2.25 (m, 3H), 2.08-1.86 (m, 3H), 1.83-1.52 (m, 6H), 1.47 (s, 6H).

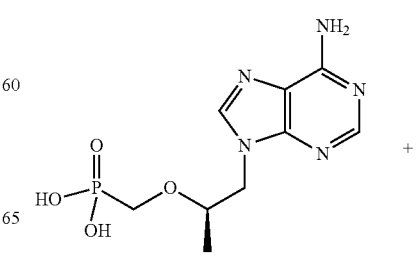

269
-continued

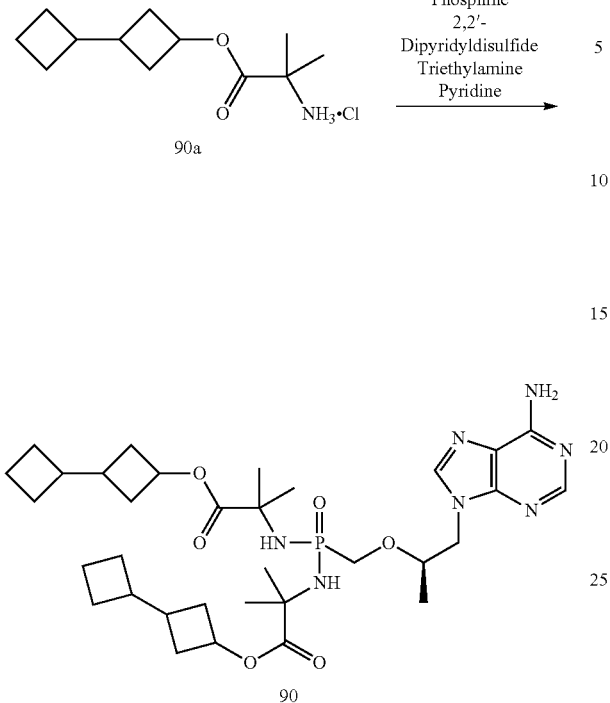

PMPA (150 mg, 0.522 mmol), intermediate 90a (410 mg, 1.66 mmol) were taken in a 8 ml vial, charged with stir bar. To this mixture was added triethylamine (0.755 mL) followed by pyridine (3 mL), capped and stirred at 70° C. over 10 min. 2,2'-Dipyridyldisulfide (575 mg, 2.61 mmol) and triphenylphosphine (685 mg, 2.61 mmol) were mixed in another 8 mL vial, added pyridine (3 mL), and sonicated to complete dissolution under argon. The clear yellow solution was transferred to stirred suspension of above mixture. Reaction mixture was stirred at 80° C. overnight. Reaction was cooled to room temperature, concentrated under reduced pressure, and co-evaporated with toluene (30 mL×2). The residue was dissolved in DCM, loaded on 24 g column, dried the column by passing nitrogen over 2 min (to dry DCM) and elute with 100% EtOAc over 6 min, 0-15% MeOH/DCM over 15 min to afford a mixture. This mixture was dissolved in MeOH, filtered and purified by preparative HPLC (Gemini, 10 uM, NX-C18, 110 Å250×30 mm column, 50%-100% acetonitrile/water gradient in 20 min run) to afford 90. $^1$H NMR (400 MHz, Acetonitrile-d3) δ 8.24 (s, 1H), 8.05 (s, 1H), 5.93 (s, 2H), 4.86-4.75 (m, 2H), 4.34 (dd, J=14.5, 3.3 Hz, 1H), 4.17 (dd, J=14.5, 7.1 Hz, 1H), 4.00-3.83 (m, 1H), 3.74-3.57 (m, 2H), 3.55-3.35 (m, 2H), 2.46-2.29 (m, 6H), 2.21-2.01 (m, 5H), 1.90-1.73 (m, 5H), 1.72-1.57 (m, 8H), 1.51 (s, 3H), 1.44 (s, 6H), 1.38 (s, 3H), 1.19 (d, J=6.2 Hz, 3H). $^{31}$P NMR (162 MHz, Acetonitrile-d$_3$) δ 17.69. LCMS: MS m/z=674.14 [M+1]; t$_R$=1.63 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

270

Example 91: Bis((trans-4-methylcyclohexyl)methyl) 2,2'-(((((R)-1-(6-amino-9H-purin-9-yl)propan-2-yl)oxy)methyl)phosphoryl)bis(azanediyl))bis(2-methylpropanoate) (91)

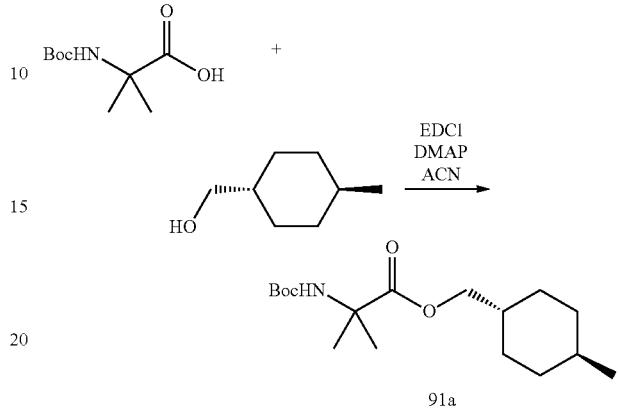

Synthesis of (trans-4-methylcyclohexyl)methyl 2-((tert-butoxycarbonyl)amino)-2-methylpropanoate (91a)

To a mixture of (trans-4-methylcyclohexyl)methanol (1.0 g, 7.80 mmol), 2-((tert-butoxycarbonyl)amino)-2-methylpropanoic acid (2.4 g, 11.7 mmol), and DMAP (1.91 g, 15.6 mmol) in acetonitrile (30 mL) was added 1-ethyl-3-(3-dimethylaminopropyl)carbodiimide, hydrochloride (2.42 g, 15.6 mmol) at room temperature. The mixture was stirred at room temperature for 15 h, quenched with water, and concentrated in vacuo. The obtained residue was dissolved in EtOAc, washed with brine, dried, and concentrated in vacuo, and the residue purified by silica gel chromatography (EtOAc 0 to 50% hexane) to afford intermediate 91a. $^1$H NMR (400 MHz, Acetonitrile-d$_3$) δ 5.62 (s, 1H), 3.88 (d, J=6.4 Hz, 2H), 1.83-1.67 (m, 4H), 1.56 (m, 1H), 1.45-1.26 (m, 16H), 1.10-0.83 (m, 7H). LCMS: MS m/z=313.83 [M+1]; t$_R$=2.12 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

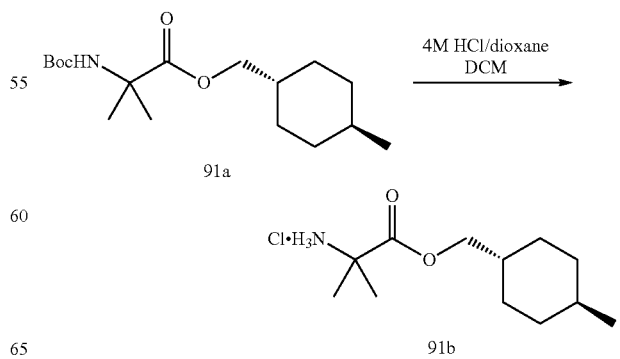

Synthesis of (trans-4-methylcyclohexyl)methyl 2-amino-2-methylpropanoate hydrochloride (91b)

To a solution of intermediate 91a (2.1 g, 6.70 mmol) in DCM (10 mL) was added 4M HCl in dioxane (10 mL) slowly at room temperature. The resulting mixture was stirred at room temperature for 3.5 h, concentrated in vacuo, co-evaporated with DCM several times, and dried high vacuum for 15 h to afford intermediate 91b. $^1$H NMR (400 MHz, Chloroform-d) δ 9.00 (bs, 3H), 4.04 (d, J=6.5 Hz, 2H), 1.91-1.58 (m, 1H), 1.32 (m, 11H), 1.09-0.85 (m, 7H). LCMS: MS m/z=214.02 [M+1-HCl]; $t_R$=1.89 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min.

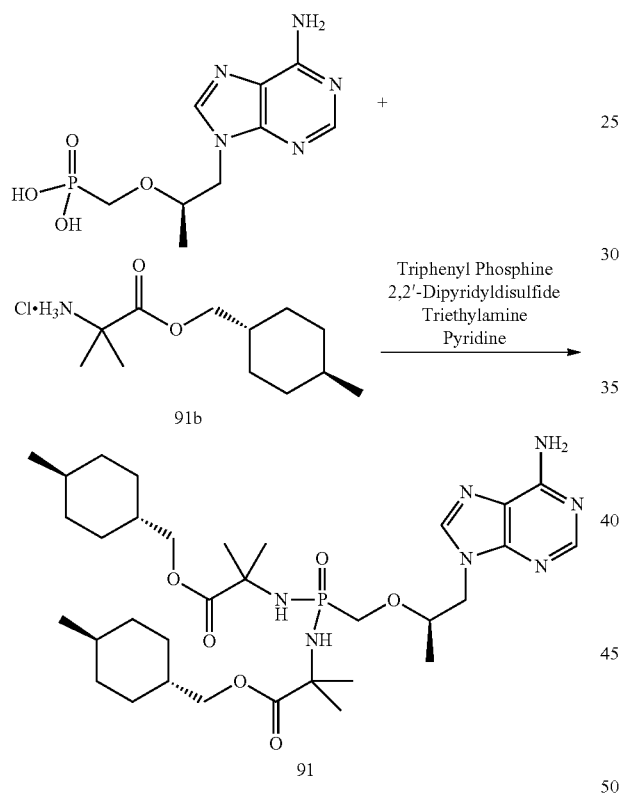

A mixture of PMPA (300 mg, 1.04 mmol), intermediate 91b (800 mg, 3.20 mmol), 2,2'-dipyridyldisulfide (1.15 g, 5.22 mmol), and triphenylphosphine (1.37 g, 5.22 mmol) was flushed with nitrogen several times and dissolved in pyridine (7 mL). TEA (1.16 mL, 8.36 mmol) was added. The resulting mixture was stirred at 90° C. for 20 h, concentrated in vacuo, co-evaporated with toluene several times, dissolved in EtOAc, vigorously washed with sat. sodium bicarbonate several times, dried with sodium sulfate, concentrated in vacuo, and purified by silica gel chromatography (MeOH 0 to 15% in DCM) and by prep. HPLC (ACN 0 to 100% for 5 min in water, and 100% for 18 min) to afford the title compound (91). $^1$H NMR (400 MHz, Acetonitrile-d$_3$) δ 8.24 (s, 1H), 8.05 (s, 1H), 5.94 (s, 2H), 4.34 (dd, J=14.5, 3.3 Hz, 1H), 4.17 (dd, J=14.5, 7.0 Hz, 1H), 4.01-3.82 (m, 5H), 3.74 (d, J=10.7 Hz, 1H), 3.66 (dd, J=12.7, 8.9 Hz, 1H), 3.56 (d, J=10.8 Hz, 1H), 3.45 (dd, J=12.7, 9.9 Hz, 1H), 1.83-1.65 (m, 8H), 1.63-1.55 (m, 2H), 1.53 (s, 3H), 1.49-1.44 (m, 6H), 1.40 (s, 3H), 1.37-1.24 (m, 2H), 1.18 (d, J=6.2 Hz, 3H), 1.11-0.83 (m, 14H). $^{31}$P NMR (162 MHz, Acetonitrile-d$_3$) δ 17.60. LCMS: MS m/z=678.36 [M+1]; $t_R$=1.94 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: $t_R$=6.95 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

Example 92: Bis(((trans-4-propylcyclohexyl)methyl) 2,2'-((((((R)-1-(6-amino-9H-purin-9-yl)propan-2-yl)oxy)methyl)phosphoryl)bis(azanediyl))bis(2-methylpropanoate) (92)

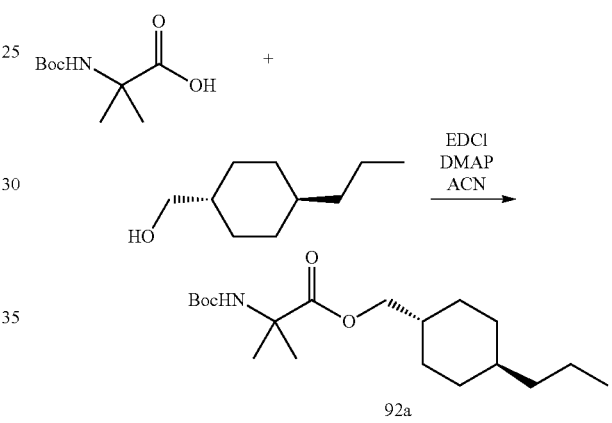

Synthesis of (trans-4-propylcyclohexyl)methyl 2-((tert-butoxycarbonyl)amino)-2-methylpropanoate (92a)

To a mixture of (trans-4-propylcyclohexyl)methanol (1.0 g, 6.40 mmol), 2-((tert-butoxycarbonyl)amino)-2-methylpropanoic acid (1.951 g, 9.60 mmol), and DMAP (1.56 g, 12.8 mmol) in acetonitrile (30 mL) was added 1-ethyl-3-(3-dimethylaminopropyl)carbodiimide, hydrochloride (1.99 g, 12.8 mmol) at room temperature. The mixture was stirred at room temperature for 15 h, quenched with water, and concentrated in vacuo. The obtained residue was dissolved in EtOAc, washed with brine, dried with sodium sulfate, concentrated in vacuo, and purified by silica gel chromatography (EtOAc 0 to 50% hexane) to afford intermediate 92a. $^1$H NMR (400 MHz, Acetonitrile-d$_3$) δ 5.55 (bs, 1H), 3.88 (d, J=6.4 Hz, 2H), 1.83-1.70 (m, 4H), 1.67-1.49 (m, 1H), 1.45-1.29 (m, 17H), 1.28-1.13 (m, 3H), 1.10-0.80 (m, 7H). LCMS: MS m/z=341.80 [M+1];]; $t_R$=2.07 min; LC system::Dionex Ultimate 3000 UHPLC; Column: Phenomenex Kinetex 2.6µ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min.

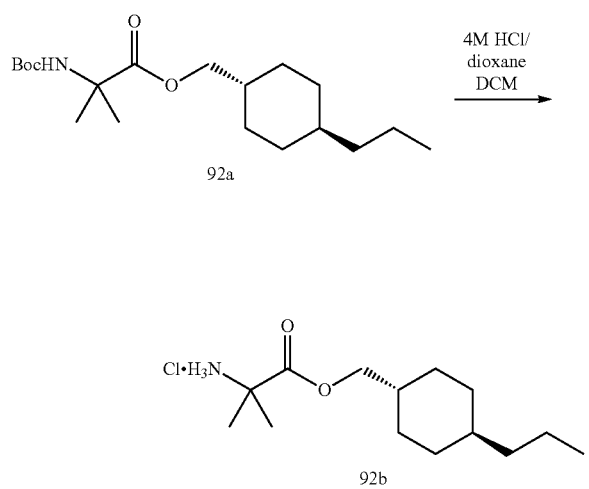

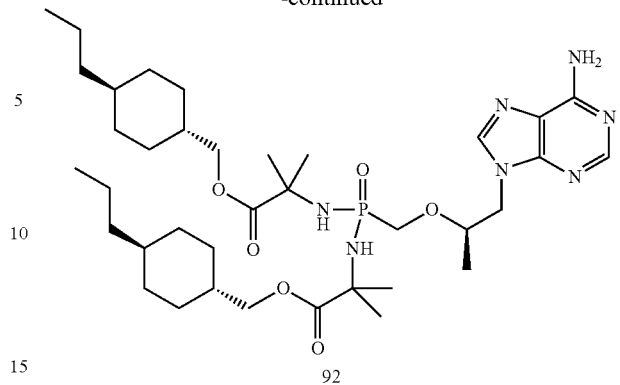

Synthesis of (trans-4-propylcyclohexyl)methyl 2-amino-2-methylpropanoate hydrochloride (92b)

To a solution of intermediate 92a (2.0 g, 5.86 mmol) in DCM (5 mL) was added 4M HCl in dioxane (4.83 mL) slowly at room temperature. The resulting mixture was stirred at room temperature for 3.5 h, concentrated in vacuo, co-evaporated with DCM several times, and dried high vacuum for 15 h to afford intermediate 92b. $^1$H NMR (400 MHz, Chloroform-d) δ 9.00 (bs, 3H), 4.04 (d, J=6.6 Hz, 2H), 1.88-1.59 (m, 11H), 1.33 (m, 2H), 1.26-1.11 (m, 3H), 1.05-0.81 (m, 7H). LCMS: MS m/z=242.05 [M+1-HCl]; $t_R$=1.38 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min.

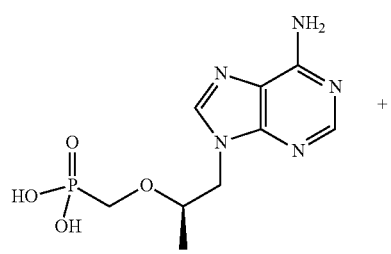

A mixture of PMPA (400 mg, 1.39 mmol), intermediate 92b (1.16 g, 4.18 mmol), 2,2'-dipyridyldisulfide (1.53 g, 6.96 mmol), and triphenylphosphine (1.83 g, 6.96 mmol) was flushed with nitrogen several times and dissolved in pyridine (10 mL). Triethylamine (1.54 mL, 11.10 mmol) were added. The resulting mixture was stirred at 90° C. for 20 h, concentrated in vacuo, co-evaporated with toluene several times, dissolved in EtOAc, vigorously washed with sat. sodium bicarbonate several times, dried with sodium sulfate, concentrated, and purified by silica gel chromatography (MeOH 0 to 10% in DCM) and by prep. HPLC (ACN 100% for 43 min) to afford the title compound (92). $^1$H NMR (400 MHz, Acetonitrile-d$_3$) δ 8.24 (s, 1H), 8.06 (s, 1H), 5.99 (s, 2H), 4.34 (dd, J=14.5, 3.3 Hz, 1H), 4.17 (dd, J=14.5, 7.0 Hz, 1H), 4.01-3.83 (m, 5H), 3.75 (d, J=10.7 Hz, 1H), 3.66 (dd, J=12.7, 8.9 Hz, 1H), 3.57 (d, J=10.8 Hz, 1H), 3.45 (dd, J=12.7, 9.8 Hz, 1H), 1.82-1.68 (m, 8H), 1.60 (m, 2H), 1.53 (s, 3H), 1.50-1.42 (m, 6H), 1.40 (s, 3H), 1.38-1.29 (m, 4H), 1.24-1.10 (m, 9H), 1.09-0.80 (m, 14H). $^{31}$P NMR (162 MHz, Acetonitrile-d$_3$) δ 17.58. LCMS: MS m/z=734.42 [M+1];]; $t_R$=2.15 min; LC system: Dionex Ultimate 3000 UHPLC; Column: Phenomenex Kinetex 2.6µ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min. HPLC: $t_R$=8.35 min; HPLC system: 1290 Infinity II.; Column: Phenomenex 2.6µ C18 100A, 100×4.6 mm; Solvents: Acetonitrile with 0.1% TFA, Water with 0.1% TFA; Gradient: 0 min-8.5 min 2-98% ACN at 1.5 mL/min.

Example 93: Bis(trans-4-phenylcyclohexyl) 2,2'-((((((R)-1-(6-amino-9H-purin-9-yl)propan-2-yl)oxy)methyl)phosphoryl)bis(azanediyl))bis(2-methylpropanoate) (93)

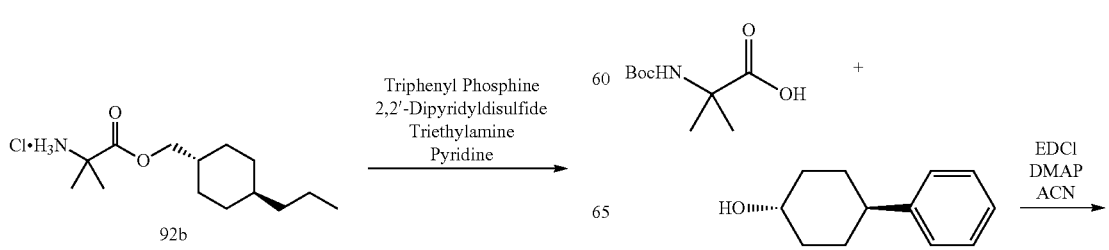

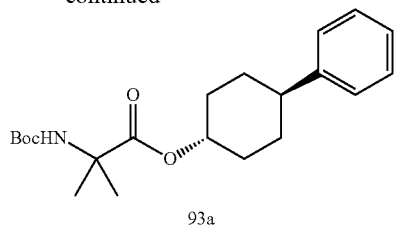

Synthesis of trans-4-phenylcyclohexyl 2-((tert-butoxycarbonyl)amino)-2-methylpropanoate (93a)

To a solution of trans-4-phenylcyclohexanol (1.0 g, 5.67 mmol), 2-((tert-butoxycarbonyl)amino)-2-methylpropanoic acid (1.73 g, 8.51 mmol), and DMAP (1.39 g, 11.3 mmol) in acetonitrile (30 mL) was added 1-ethyl-3-(3-dimethylaminopropyl)carbodiimide, hydrochloride (1.76 g, 11.3 mmol) at room temperature The mixture was stirred at room temperature for 5 h, quenched with water, and concentrated in vacuo. The obtained residue was dissolved in EtOAc, washed with brine, dried with sodium sulfate, and concentrated in vacuo, and purified by silica gel chromatography (EtOAc 0 to 50% hexane) to afford intermediate 93a. $^1$H NMR (400 MHz, Acetonitrile-$d_3$) δ 7.36-7.11 (m, 5H), 5.55 (bs, 1H), 4.76 (m, 1H), 2.59 (m, 1H), 2.10-2.01 (m, 2H), 1.96-1.86 (m, 2H), 1.72-1.58 (m, 2H), 1.57-1.45 (m, 2H), 1.42-1.32 (m, 15H). LCMS: MS m/z=361.84 [M+1];]; $t_R$=1.85 min; LC system::Dionex Ultimate 3000 UHPLC; Column: Phenomenex Kinetex 2.6µ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min.

Synthesis of trans-4-phenylcyclohexyl 2-amino-2-methylpropanoate hydrochloride (93b)

To a mixture of intermediate 93a (1.1 g, 3.04 mmol) in DCM (5 mL) was added 4M HCl in dioxane (2.51 mL) slowly at room temperature. The resulting mixture was stirred at room temperature for 4 h, concentrated in vacuo, co-evaporated with DCM several times, and dried high vacuum for 15 h to afford intermediate 93b. $^1$H NMR (400 MHz, Chloroform-d) δ 9.06 (bs, 3H), 7.34-7.26 (m, 2H), 7.24-7.13 (m, 3H), 4.92 (m, 1H), 2.57 (m, 1H), 2.18 (dd, J=12.9, 4.2 Hz, 2H), 1.98 (m, 2H), 1.89-1.50 (m, 10H).

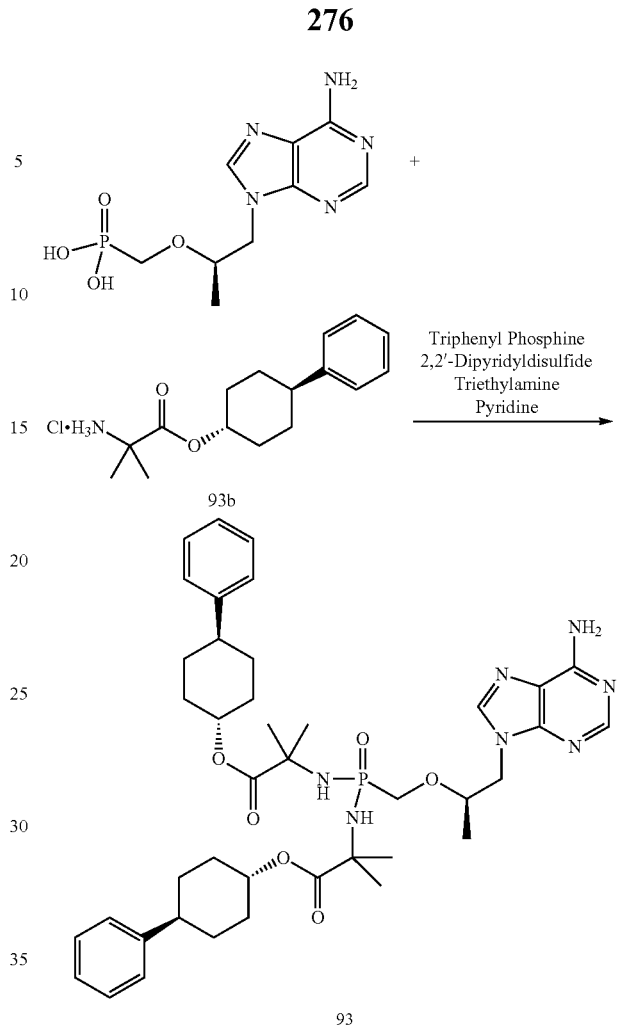

A mixture of PMPA (320 mg, 1.11 mmol), intermediate 93b (929 mg, 3.12 mmol), 2,2'-dipyridyldisulfide (1.23 g, 5.57 mmol), and triphenylphosphine (1.46 g, 5.57 mmol) was flushed with nitrogen several times and dissolved in pyridine (10 mL). TEA (1.54 mL, 11.10 mmol) was added. The resulting mixture was stirred at 90° C. for 20 h, concentrated in vacuo, co-evaporated with toluene several times, dissolved in EtOAc, vigorously washed with sat. sodium bicarbonate solution several times, dried with sodium sulfate, concentrated, and purified by silica gel chromatography (MeOH 0 to 10% in DCM) to afford the title compound (93). $^1$H NMR (400 MHz, Acetonitrile-$d_3$) δ 8.26 (s, 1H), 8.09 (s, 1H), 7.36-7.14 (m, 10H), 6.12 (s, 2H), 4.78 (m, 2H), 4.36 (dd, J=14.5, 3.2 Hz, 1H), 4.19 (dd, J=14.5, 7.0 Hz, 1H), 3.96 (m, 1H), 3.78 (d, J=10.6 Hz, 1H), 3.69 (dd, J=12.6, 8.9 Hz, 1H), 3.60 (d, J=10.7 Hz, 1H), 3.49 (dd, J=12.6, 9.8 Hz, 1H), 2.57 (m, 2H), 2.12-2.01 (m, 4H), 1.96-1.84 (m, 4H), 1.73-1.44 (m, 17H), 1.42 (s, 3H), 1.21 (d, J=6.2 Hz, 3H). $^{31}$P NMR (162 MHz, Acetonitrile-$d_3$) S 17.68. LCMS: MS m/z=774.31 [M+1]; $t_R$=1.90 min; LC system: Thermo Accela 1250 UHPLC; MS system: Thermo LCQ Fleet; Column: Phenomenex Kinetex 2.6µ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min. HPLC: $t_R$=6.99 min; HPLC system: 1290 Infinity II.; Column: Phenomenex 2.6µ C18 100A, 100×4.6 mm; Solvents: Acetonitrile with 0.1% TFA, Water with 0.1% TFA; Gradient: 0 min-8.5 min 2-98% ACN at 1.5 mL/min.

Example 94: Dihexyl 2,2'-(((((1-(6-(((2-(benzoyloxy)ethoxy)carbonyl)amino)-9H-purin-9-yl)propan-2-yl)oxy)methyl)phosphoryl)bis(azanediyl))(R)-bis(2-methylpropanoate) (94)

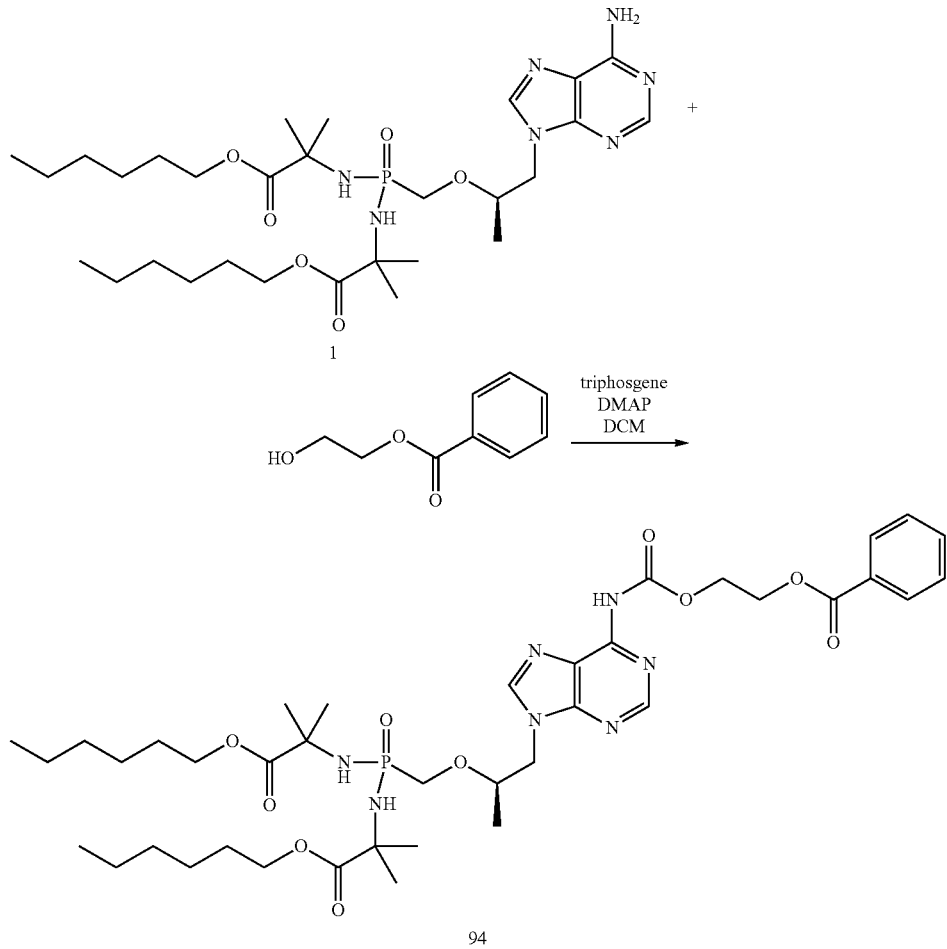

To a mixture of 1 (200 mg, 0.32 mmol) and triphosgene (38 mg, 0.128 mmol) in DCM (4 mL) was added DMAP (234 mg, 1.92 mmol) slowly portion wise at room temperature The resulting mixture was stirred at room temperature for 15 min and 2-benzoyloxy ethanol (60 mg, 0.46 moll) was added at room temperature The resulting mixture was stirred for 2 h, concentrated in vacuo, and purified by silica gel column chromatography to afford the title compound (94). $^1$H NMR (400 MHz, Acetonitrile-d$_3$) δ 9.67 (bs, 1H), 8.61 (s, 1H), 8.32 (s, 1H), 8.01-7.92 (m, 2H), 7.65-7.57 (m, 1H), 7.47-7.40 (m, 2H), 4.59-4.53 (m, 4H), 4.36 (dd, J=14.5, 3.2 Hz, 1H), 4.19 (dd, J=14.5, 7.1 Hz, 1H), 4.16-3.99 (m, 4H), 3.93 (m, 1H), 3.73 (d, J=10.7 Hz, 1H), 3.67 (dd, J=12.8, 8.7 Hz, 1H), 3.55 (d, J=10.8 Hz, 1H), 3.43 (dd, J=12.8, 9.7 Hz, 1H), 1.68-1.55 (m, 4H), 1.49 (s, 3H), 1.44-1.37 (m, 6H), 1.38-1.23 (m, 15H), 1.16 (d, J=6.2 Hz, 3H), 0.92-0.82 (m, 6H). $^{31}$P NMR (162 MHz, Acetonitrile-d$_3$) δ 17.71. LCMS: MS m/z=818.30 [M+1]; t$_R$=1.88 min LC system::Dionex Ultimate 3000 UHPLC; Column: Phenomenex Kinetex 2.6μ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min. HPLC: t$_R$=7.42 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 95: Dihexyl 2,2'-(((((1-(6-(((2-((5-methyl-2-oxo-1,3-dioxol-4-yl)methoxy)-2-oxoethoxy)carbonyl)amino)-9H-purin-9-yl)propan-2-yl)oxy)methyl)phosphoryl)bis(azanediyl))(R)-bis(2-methylpropanoate) (95)

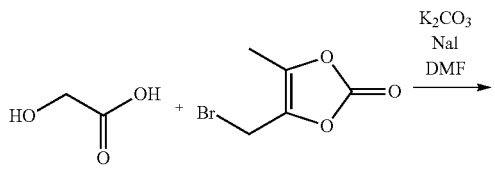

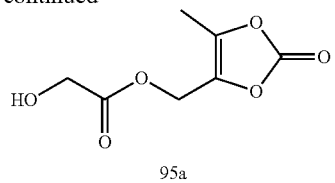

95a

Synthesis of (5-methyl-2-oxo-1,3-dioxol-4-yl) methyl 2-hydroxyacetate (95a)

To a suspension of K$_2$CO$_3$ (716 mg, 5.18 mmol) in DMF (5 mL) was added glycolic acid (197 mg, 2.59 mmol) at room temperature. The resulting mixture was stirred at room temperature for 15 min, and NaI (39 mg, 0.259 mmol) and 4-(bromomethyl)-5-methyl-1,3-dioxol-2-one (500 mg, 2.59 mmol) added. The mixture was stirred at room temperature for 3 h, filtered, the filter cake washed with DCM, the combined filtrate concentrated in vacuo, and the resulting residue purified by silica gel chromatography (EtOAc 0 to 70% in hexane) to afford intermediate 95a. $^1$H NMR (400 MHz, Acetonitrile-d3) δ 4.95 (s, 2H), 4.13 (d, J=6.5 Hz, 2H), 3.25 (t, J=6.5 Hz, 1H), 2.16 (s, 3H).

To a mixture of 1 (100 mg, 0.160 mmol) and triphosgene (31.3 mg, 0.105 mmol) in DCM (2 mL) was added DMAP (117 mg, 0.959 mmol) slowly portion wise at room temperature The resulting mixture was stirred at room temperature for 15 min and intermediate 95a (60 mg, 0.32 mmol) added at room temperature The resulting mixture was stirred for 2 h and additional triphosgene (30 mg) added. The mixture was stirred for 1 h at room temperature, concentrated in vacuo, dissolved in ACN, and purified by prep HPLC (ACN 10 to 100% in water for 5 min and ACN 100% for 10 min) and by silica gel chromatography (MeOH 0 to 10% in DCM) to afford the title compound (95). $^1$H NMR (400 MHz, Acetonitrile-d$_3$) δ 9.10 (bs, 1H), 8.64 (s, 1H), 8.35 (s, 1H), 5.01 (s, 2H), 4.77 (s, 2H), 4.48-4.42 (m, 1H), 4.27 (dd, J=14.6, 7.1 Hz, 1H), 4.17-4.01 (m, 4H), 3.97 (m, 1H), 3.82-3.66 (m, 2H), 3.57 (d, J=10.8 Hz, 1H), 3.45 (dd, J=12.8, 9.7 Hz, 1H), 2.16 (s, 3H), 1.69-1.55 (m, 4H), 1.52 (s, 3H), 1.45 (s, 6H), 1.41-1.26 (m, 15H), 1.20 (d, J=6.2 Hz, 3H), 0.95-0.84 (m, 6H). $^{31}$P NMR (162 MHz, Acetonitrile-d$_3$) δ 17.67. LCMS: MS m/z=840.22 [M+1]; t$_R$=1.99 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: t$_R$=7.10 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

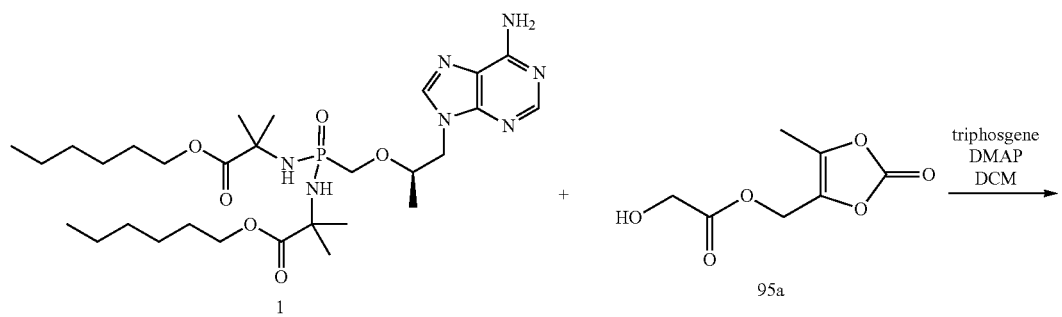

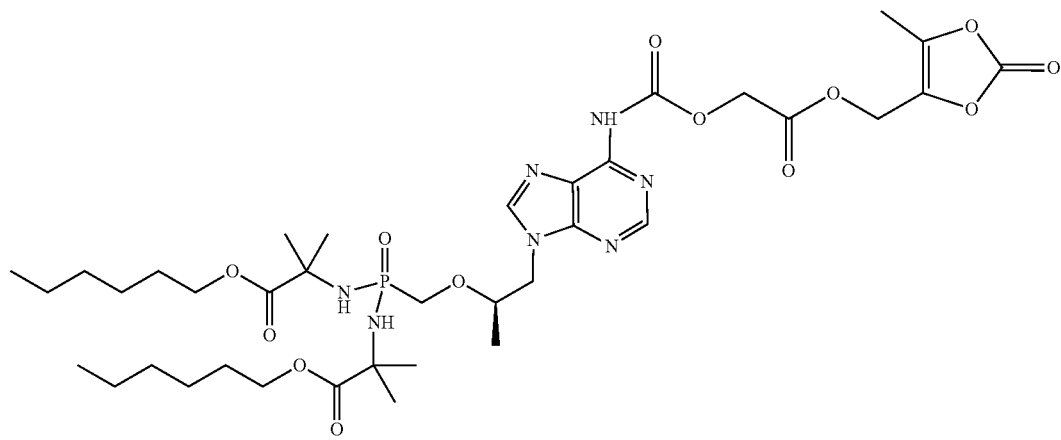

95

Example 96: Dihexyl 2,2'-((((((R)-1-(6-((R)-5-oxo-tetrahydrofuran-2-carboxamido)-9H-purin-9-yl)propan-2-yl)oxy)methyl)phosphoryl)bis(azanediyl))bis(2-methylpropanoate) (96)

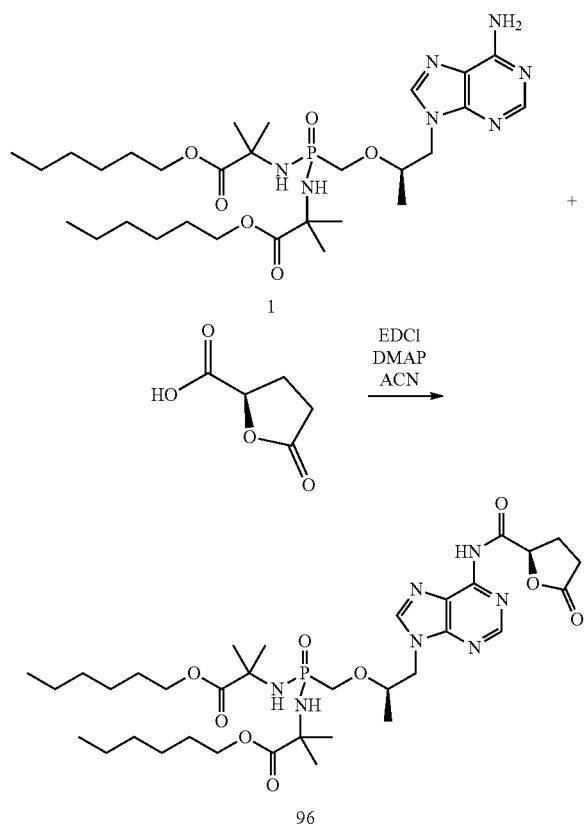

To a mixture of (R)-5-oxotetrahydrofuran-2-carboxylic acid (41.6 mg, 3.2 mmol) and DMAP (39 mg, 0.32 mmol) in ACN (4 mL) was added 1-ethyl-3-(3-dimethylaminopropyl)carbodiimide, hydrochloride (61.3 mg, 3.20 mmol) at room temperature The resulting mixture was stirred at room temperature for 15 min and 1 (100 mg, 0.16 mmol) in DCM (1 mL) added. The resulting mixture was stirred at room temperature for 4 h, quenched by adding water (0.5 mL), and purified by prep HPLC (ACN 10 to 100% in water for 8 min, and ACN 100% for 10 min) to afford the title compound (96). $^1$H NMR (400 MHz, Acetonitrile-$d_3$) δ 9.27 (s, 1H), 8.66 (s, 1H), 8.37 (s, 1H), 5.55 (dd, J=8.6, 5.3 Hz, 1H), 4.45 (dd, J=14.6, 3.2 Hz, 1H), 4.27 (m, 1H), 4.17-4.02 (m, 4H), 3.97 (m, 1H), 3.79-3.62 (m, 2H), 3.58 (d, J=10.8 Hz, 1H), 3.45 (dd, J=12.7, 9.8 Hz, 1H), 2.78-2.66 (m, 1H), 2.62-2.54 (m, 2H), 2.46-2.36 (m, 1H), 1.70-1.56 (m, 4H), 1.52 (s, 3H), 1.45 (s, 6H), 1.41-1.25 (m, 15H), 1.20 (d, J=6.2 Hz, 3H), 0.95-0.85 (m, 6H). $^{31}$P NMR (162 MHz, Acetonitrile-$d_3$) δ 17.73. LCMS: MS m/z=738.24 [M+1]; $t_R$=1.92 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min. HPLC: $t_R$=6.32 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 97: Dihexyl 2,2'-(((((1-(6-(4-(acetylthio)butanamido)-9H-purin-9-yl)propan-2-yl)oxy)methyl)phosphoryl)bis(azanediyl))(R)-bis(2-methylpropanoate) (97)

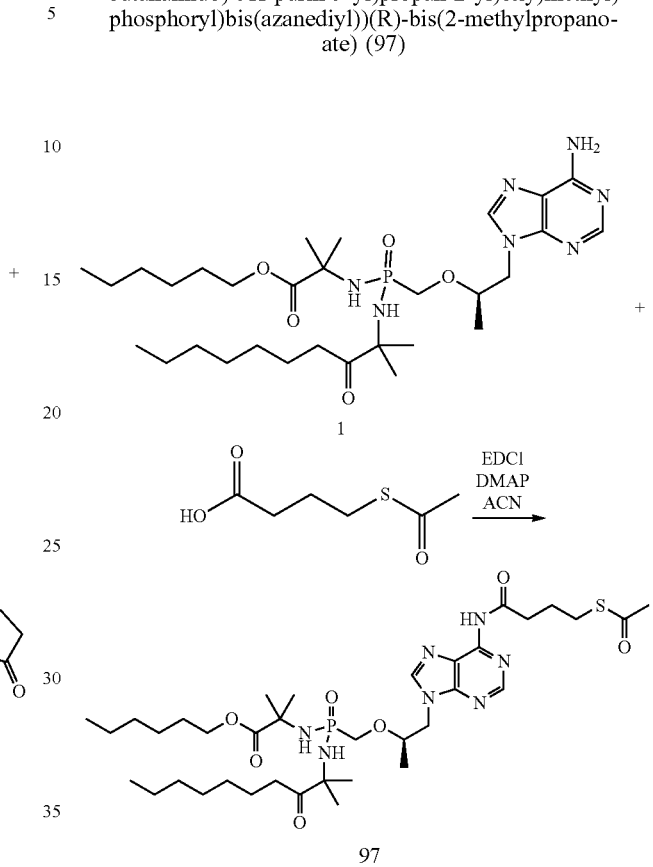

To a mixture of 4-(acetylthio)butanoic acid (41.6 mg, 0.26 mmol) and DMAP (39 mg, 0.32 mmol) in ACN (4 mL) was added 1-ethyl-3-(3-dimethylaminopropyl)carbodiimide, hydrochloride (61.3 mg, 0.32 mmol) at room temperature The resulting mixture was stirred at room temperature for 15 min and 1 (100 mg, 0.16 mmol) in DCM (1 mL) was added. The resulting mixture was stirred at room temperature for 4 h, quenched by adding water (0.5 mL), and purified by prep HPLC (ACN 10 to 100% in water for 5 min, and ACN 100% for 13 min) and by silica gel chromatography (MeOH 0 to 10% in DCM) to afford the title compound (97). $^1$H NMR (400 MHz, Acetonitrile-$d_3$) δ 9.02 (s, 1H), 8.62 (s, 1H), 8.32 (s, 1H), 4.43 (dd, J=14.5, 3.1 Hz, 1H), 4.25 (dd, J=14.5, 7.2 Hz, 1H), 4.18-4.02 (m, 4H), 3.96 (m, 1H), 3.80-3.64 (m, 2H), 3.58 (d, J=10.8 Hz, 1H), 3.44 (dd, J=12.7, 9.9 Hz, 1H), 2.98 (t, J=7.2 Hz, 2H), 2.88 (t, J=7.3 Hz, 2H), 2.33 (s, 3H), 1.97 (m, 2H), 1.63 (m, 4H), 1.52 (s, 3H), 1.45 (s, 6H), 1.42-1.23 (m, 15H), 1.20 (d, J=6.2 Hz, 3H), 0.96-0.85 (m, 6H). $^{31}$P NMR (162 MHz, Acetonitrile-$d_3$) δ 17.79. LCMS: MS m/z=770.36 [M+1]; $t_R$=1.78 min LC system::Dionex Ultimate 3000 UHPLC; Column: Phenomenex Kinetex 2.6μ C18 100A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min. HPLC: $t_R$=7.09 min; HPLC system: 1290 Infinity II.; Column: Phenomenex 2.6μ C18 100A, 100×4.6 mm; Solvents: Acetonitrile with 0.1% TFA, Water with 0.1% TFA; Gradient: 0 min-8.5 min 2-98% ACN at 1.5 mL/min.

Example 98: Dihexyl 2,2'-(((((1-(6-(((2,2-dimethyl-3-((5-methyl-2-oxo-1,3-dioxol-4-yl)methoxy)-3-oxopropoxy)carbonyl)amino)-9H-purin-9-yl)propan-2-yl)oxy)methyl)phosphoryl)bis(azanediyl))(R)-bis(2-methylpropanoate) (98)

Synthesis of (5-methyl-2-oxo-1,3-dioxol-4-yl)methyl 3-hydroxy-2,2-dimethyl-propanoate (98a)

4-(bromomethyl)-5-methyl-1,3-dioxol-2-one (1.20 g, 5.93 mmol), was added to a mixture of 3-hydroxy-2,2-dimethylpropanoic acid (700 mg, 5.93 mmol), potassium carbonate (983 mg, 7.11 mmol), and sodium iodide (888 mg, 5.93 mmol) in N,N-dimethylformamide (10 ml) at 0° C. After 16 h the solids were removed by filtration and washed with ethyl acetate (20 ml). The other liquor was diluted with ethyl acetate (20 ml). The solution was washed with an aqueous solution of lithium chloride (5%, 2×25 ml) and brine (25 ml). The organic phase was dried over sodium sulfate and the solvent was removed under reduced pressure. The residue was subjected to flash chromatography (0-100% ethyl acetate/hexanes with ELSD). The fractions containing product were combined and the solvent was removed under reduced pressure, providing intermediate 98a. $^1$H NMR (400 MHz, Acetonitrile-$d_3$) δ 4.88 (s, 2H), 3.56-3.46 (m, 2H), 2.94 (s, 1H), 2.15 (s, 3H), 1.15 (s, 6H).

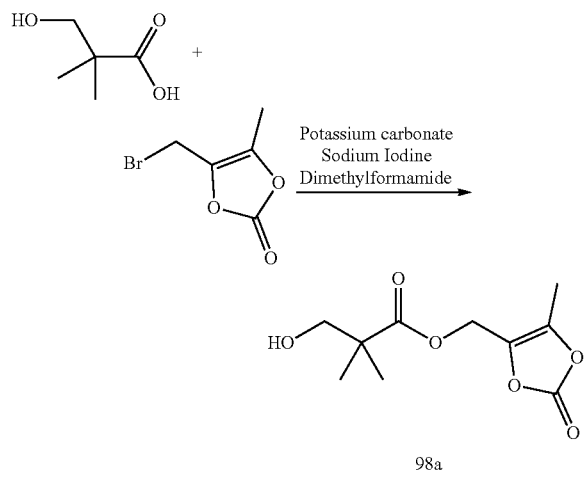

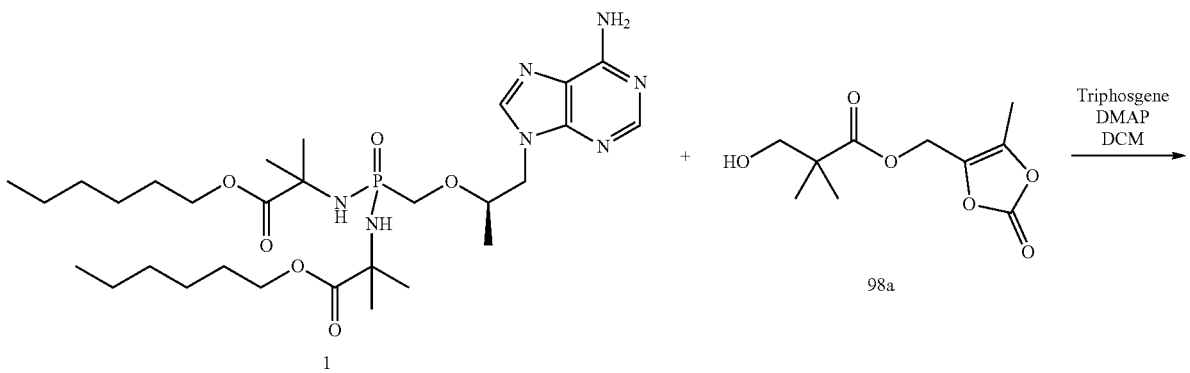

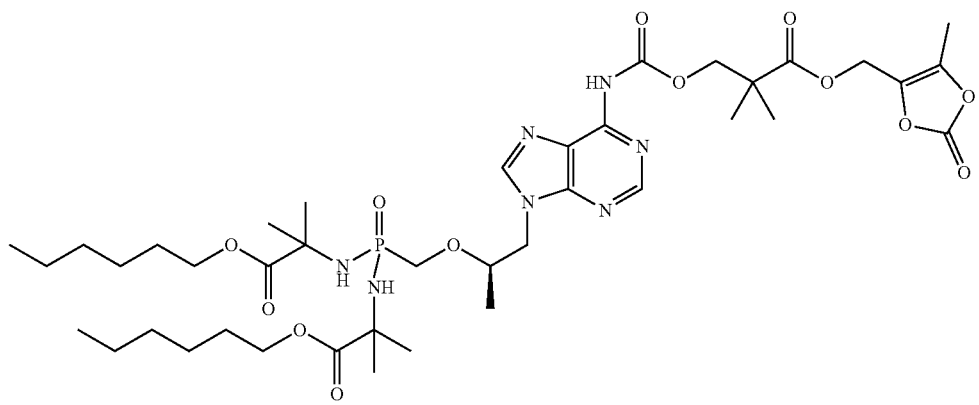

4-Dimethylaminopyridine (58.6 mg, 0.479 mmol) was added to a solution of triphosgene (14.2 mg, 0.0479 mmol) in dichloromethane (4 ml), a solid formed. After 1 minute 1 (100 mg, 0.160 mmol) was added, the solids dissolved. After 15 minutes intermediate 98a (5-methyl-2-oxo-1,3-dioxol-4-yl)methyl 3-hydroxy-2,2-dimethyl-propanoate (73.6 mg, 0.160 mmol) was added. After 20 h the mixture was diluted with dichloromethane (5 ml). The mixture was washed with water (3×5 ml) and saturated ammonium chloride (5 ml). The organic phase was dried over sodium sulfate and the solvent was removed under reduced pressure. The residue was subjected to flash chromatography (0-30% methanol/dichloromethane). The fractions containing product were combined and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization to afford the title compound (98). $^1$H NMR (400 MHz, Acetonitrile-d$_3$) δ 8.71 (s, 1H), 8.61 (s, 1H), 8.30 (s, 1H), 4.90 (s, 2H), 4.44 (dd, J=14.5, 3.2 Hz, 1H), 4.32-4.21 (m, 3H), 4.18-4.01 (m, 4H), 4.01-3.91 (m, 1H), 3.78-3.63 (m, 2H), 3.57 (d, J=10.8 Hz, 1H), 3.45 (dd, J=12.7, 9.8 Hz, 1H), 2.11 (s, 3H), 1.71-1.57 (m, 4H), 1.52 (s, 3H), 1.49-1.42 (m, 6H), 1.42-1.24 (m, 21H), 1.20 (d, J=6.2 Hz, 3H), 0.96-0.85 (m, 6H). $^{31}$P NMR (162 MHz, Acetonitrile-d$_3$) δ 17.63 (p, J=10.0 Hz). LCMS: MS m/z=882.18 [M+1]; $t_R$=1.743 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.888 min; HPLC system: Agilent 1100 series; Column: Gemini 5µ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 99: (5-Methyl-2-oxo-1,3-dioxol-4-yl) methyl 5-[[9-[(2R)-2-[bis[(2-hexoxy-1,1-dimethyl-2-oxo-ethyl)amino]phosphorylmethoxy]propyl]purin-6-yl]amino]-5-oxo-pentanoate (99)

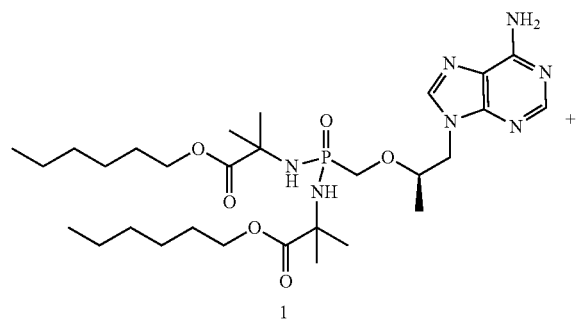

1

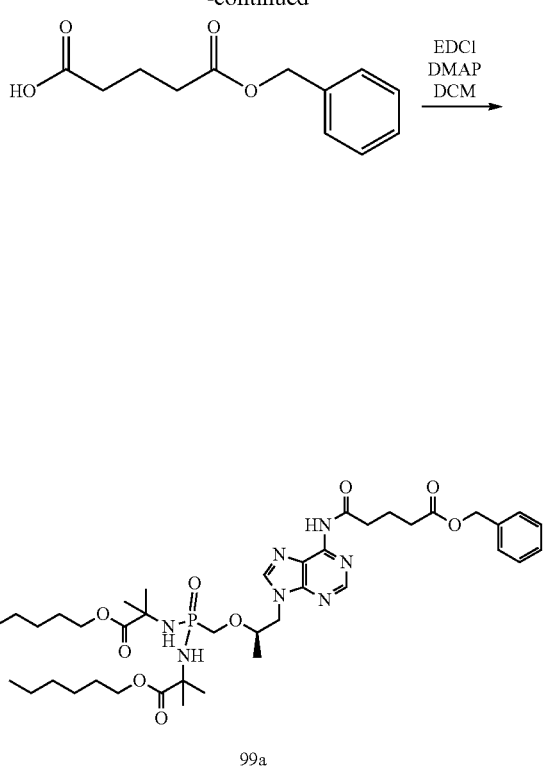

Synthesis of benzyl 5-[[9-[(2R)-2-[bis[(2-hexoxy-1,1-dimethyl-2-oxo-ethyl)amino]phosphorylmethoxy] propyl]purin-6-yl]amino]-5-oxo-pentanoate (99a)

A solution of 1 (200 mg, 0.320 mmol), 5-benzyloxy-5-oxo-pentanoic acid (85.2 mg, 0.384 mmol), 4-dimethylaminopyridine (78.1 mg, 0.639 mmol), and 1-ethyl-3-(3-dimethylaminopropyl)carbodiimide hydrochloride (123 mg, 0.639 mmol) in dichloromethane (4 mL) was stirred for 3 days. The reaction was diluted with dichloromethane (20 ml). The mixture was washed with water (2×10 ml) and saturated ammonium chloride (10 ml). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing intermediate 99a). LCMS: MS m/z=830.24 [M+1]; $t_R$=1.760 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

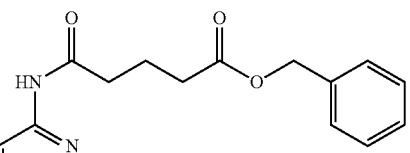
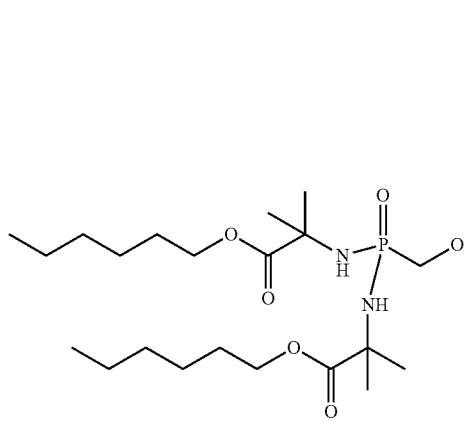

99a

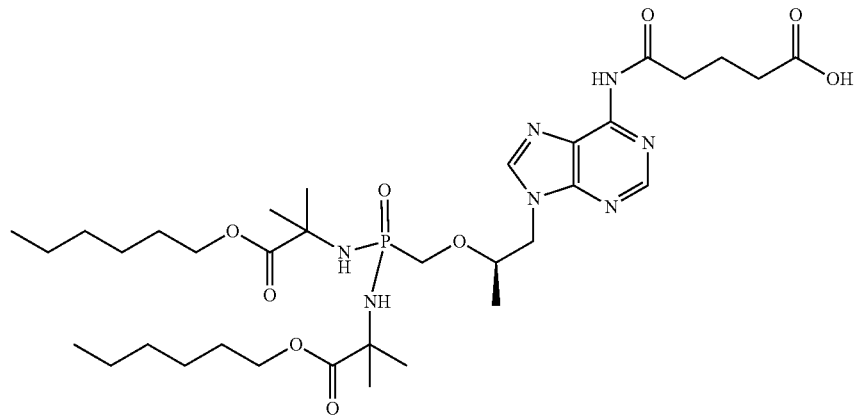

99b

Synthesis of (R)-5-((9-(2-((bis((1-(hexyloxy)-2-methyl-1-oxopropan-2-yl)amino)phosphoryl)methoxy)propyl)-9H-purin-6-yl)amino)-5-oxopentanoic acid (99b)

Palladium on carbon (10%, 90 mg, 0.084 mmol) was added to solution of intermediate 99a (235 mg, 0.283 mmol) in ethyl acetate (5 ml). The atmosphere was flushed with hydrogen via balloon. The mixture was stirred at room temperature under an atmosphere of hydrogen. After 16 hours the hydrogen gas was removed. The palladium on carbon was removed by filtration. The solvent was removed under reduced pressure, providing intermediate 99b. LCMS: MS m/z=740.22 [M+1]; $t_R$=1.573 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

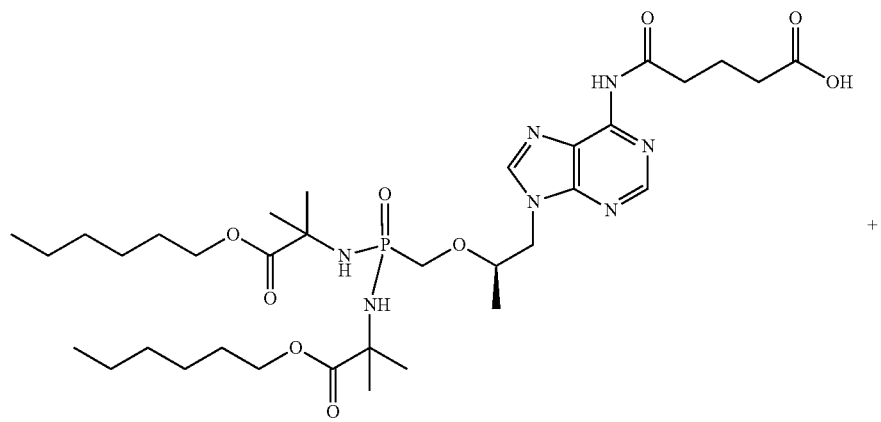

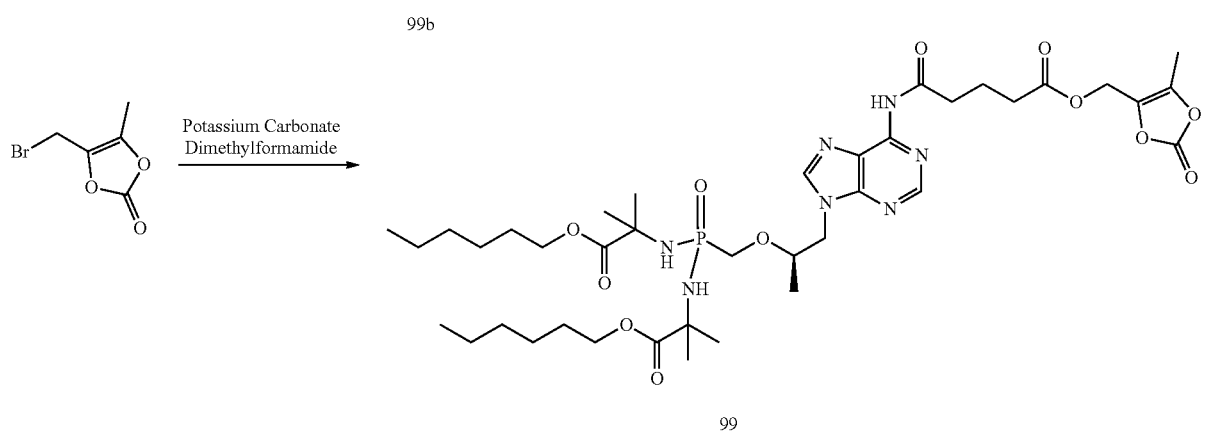

4-(Bromomethyl)-5-methyl-1,3-dioxol-2-one (21.9 mg, 0.114 mmol) was added to a mixture of the intermediate 99b (70.0 mg, 0.0946 mmol) and potassium carbonate (19.6 mg, 0.142 mmol) in dimethylformamide (4 mL). After 90 min the solids were removed by filtration. The filtrate was diluted with ethyl acetate (20 ml) and washed with 5% lithium chloride (3×10 ml) and brine (10 ml). The organic phase was dried over sodium sulfate and the solvent was removed under reduced pressure. The residue was subjected to preparative HPLC (Gemini, 10 uM, NX-C18, 110 Å250×30 mm column, 40%-100% acetonitrile/water gradient over 20 minutes). The fractions containing product were combined and subjected to lyophilization to afford the title compound (99). $^1$H NMR (400 MHz, Acetonitrile-$d_3$) δ 8.95 (s, 1H), 8.61 (s, 1H), 8.32 (s, 1H), 4.88 (s, 2H), 4.43 (dd, J=14.5, 3.2 Hz, 1H), 4.26 (dd, J=14.6, 7.1 Hz, 1H), 4.18-4.01 (m, 4H), 4.01-3.92 (m, 1H), 3.77-3.64 (m, 2H), 3.57 (d, J=10.8 Hz, 1H), 3.45 (dd, J=12.7, 9.8 Hz, 1H), 2.88 (t, J=7.2 Hz, 2H), 2.48 (t, J=7.4 Hz, 2H), 2.14 (s, 3H), 2.04-1.98 (m, 2H), 1.70-1.56 (m, 4H), 1.52 (s, 3H), 1.49-1.41 (m, 6H), 1.41-1.23 (m, 12H), 1.20 (d, J=6.2 Hz, 3H), 0.97-0.83 (m, 6H). $^{31}$P NMR (162 MHz, Acetonitrile-$d_3$) δ 17.69 (p, J=10.0 Hz). LCMS: MS m/z=852.27 [M+1]; $t_R$=1.680 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min. HPLC: $t_R$=3.608 min; HPLC system: Agilent 1100 series; Column: Gemini 5μ C18 110A, 50×4.6 mm; Solvents: A=Acetonitrile with 5% water and 0.1% TFA, B=Water with 5% acetonitrile 0.1% TFA; Gradient: 0 min-4.0 min 2-95% B, 4.0 min-5.0 min 95% B, 5.0 min-5.25 min 95-98% B, 5.25-5.50 min 98%-2% B at 2 mL/min.

Example 100: Dihexyl 2,2'-(((((1-(6-(3-(2-acetoxy-4,6-dimethylphenyl)-3-methylbutanamido)-9H-purin-9-yl)propan-2-yl)oxy)methyl)phosphoryl)bis(azanediyl))(R)-bis(2-methylpropanoate) (100)

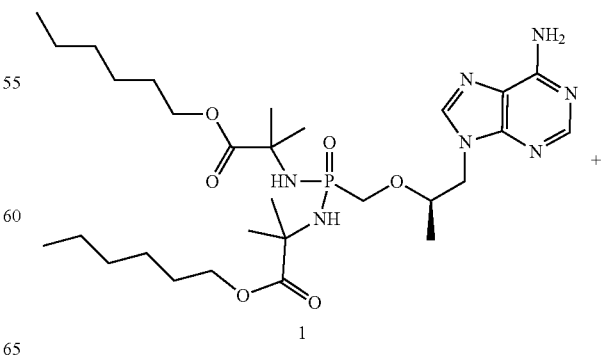

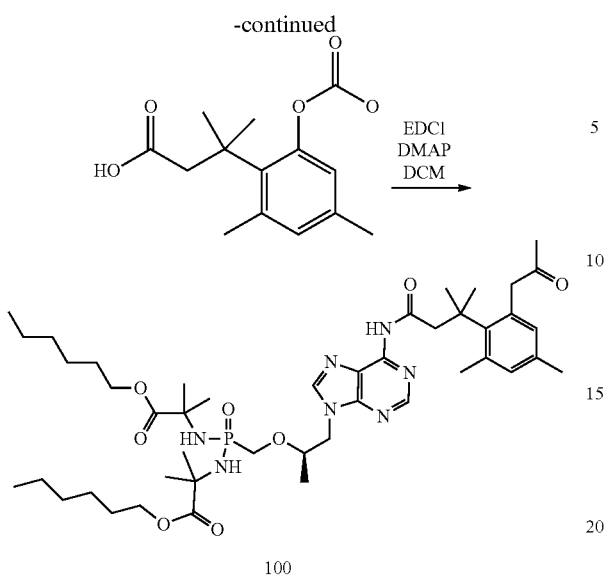

Compound 1 (240 mg, 0.384 mmol), 3-(2-acetoxy-4,6-dimethyl-phenyl)-3-methyl-butanoic acid (406 mg, 1.53 mmol), 4-dimethylaminopyridine (141 mg, 1.15 mmol), 3-(ethyliminomethyleneamino)-N,N-dimethyl-propan-1-amine hydrochloride (221 mg, 1.15 mmol) were taken in 40 mL vial charged with stir bar and added DCM (4 mL), This mixture was flushed with argon, capped and stirred at room temperature 15 h. The reaction mixture was diluted with DCM (15 ml). The solution was washed with water (2×15 ml), and once with saturated ammonium chloride (15 ml) and dried over sodium sulfate. The solvent was concentrated under reduced pressure. The residue was dissolved in Acetonitrile (4 mL), filtered and purified by preparative HPLC (Gemini, 10 uM, NX-C18, 110 Å 250×30 mm column, 40%-100% acetonitrile/water gradient in 20 min run) to afford the title compound (100). $^1$H NMR (400 MHz, Acetonitrile-$d_3$) δ 8.62 (s, 1H), 8.58 (s, 1H), 8.28 (s, 1H), 6.84 (d, J=2.0 Hz, 1H), 6.60 (d, J=2.0 Hz, 1H), 4.42 (dd, J=14.5, 3.1 Hz, 1H), 4.24 (dd, J=14.5, 7.1 Hz, 1H), 4.16-4.00 (m, 4H), 3.98-3.91 (m, 1H), 3.76-3.63 (m, 2H), 3.56 (d, J=10.8 Hz, 1H), 3.44 (dd, J=12.7, 9.8 Hz, 1H), 3.31 (s, 2H), 2.58 (s, 3H), 2.25 (d, J=2.8 Hz, 9H), 2.21 (s, 3H), 1.70-1.56 (m, 12H), 1.52 (s, 3H), 1.45 (d, J=2.1 Hz, 6H), 1.38 (s, 6H), 1.35-1.25 (m, 7H), 1.19 (d, J=6.3 Hz, 3H), 0.96-0.83 (m, 6H). LCMS: MS m/z=872.4 [M+1]; $t_R$=1.82 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 101: Dihexyl 2,2'-((((((1-(6-((((2-methyl-4-((5-methyl-2-oxo-1,3-dioxol-4-yl)methoxy)-4-oxobutan-2-yl)oxy)carbonyl)amino)-9H-purin-9-yl)propan-2-yl)oxy)methyl)phosphoryl)bis(azanediyl))(R)-bis(2-methylpropanoate) (101)

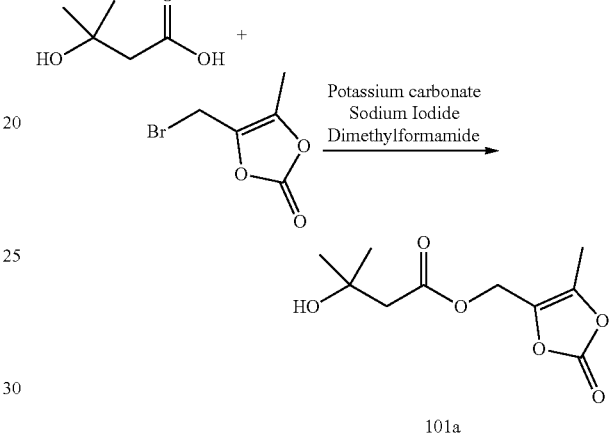

Synthesis of (5-methyl-2-oxo-1,3-dioxol-4-yl) methyl 3-hydroxy-3-methylbutanoate (101a)

To an ice-cold mixture of 3-hydroxy-3-methyl-butanoic acid (1 g, 8.47 mmol), $K_2CO_3$ (1.4 g, 10.2 mmol), NaI (1.27 g, 8.47 mmol) and DMF (15 mL) was added 4-(bromomethyl)-5-methyl-1,3-dioxol-2-one (1.7 mL, 8.47 mmol) drop wise. After 5 minutes ice both was removed and stirred at room temperature for 15 h. The reaction mixture was diluted with EtOAc, washed with water (2×25 mL), and once with 5% LiCl solution (40 mL). The combined organic mixture was dried over sodium sulfate, and concentrated to afford intermediate 101a, which was used in subsequent reactions without purification. $^1$H NMR (400 MHz, Acetonitrile-$d_3$) δ 4.90 (s, 2H), 3.06 (s, 1H), 2.51 (s, 2H), 2.15 (d, J=3.6 Hz, 3H), 1.27 (s, 6H).

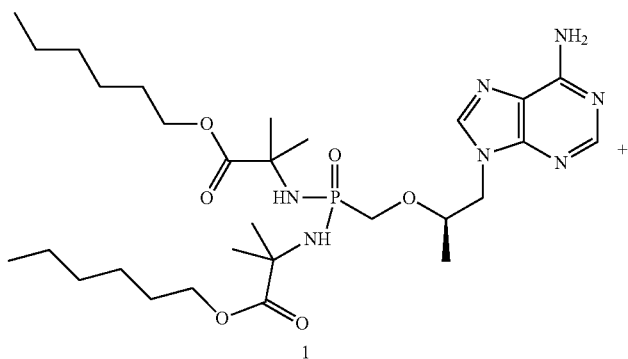

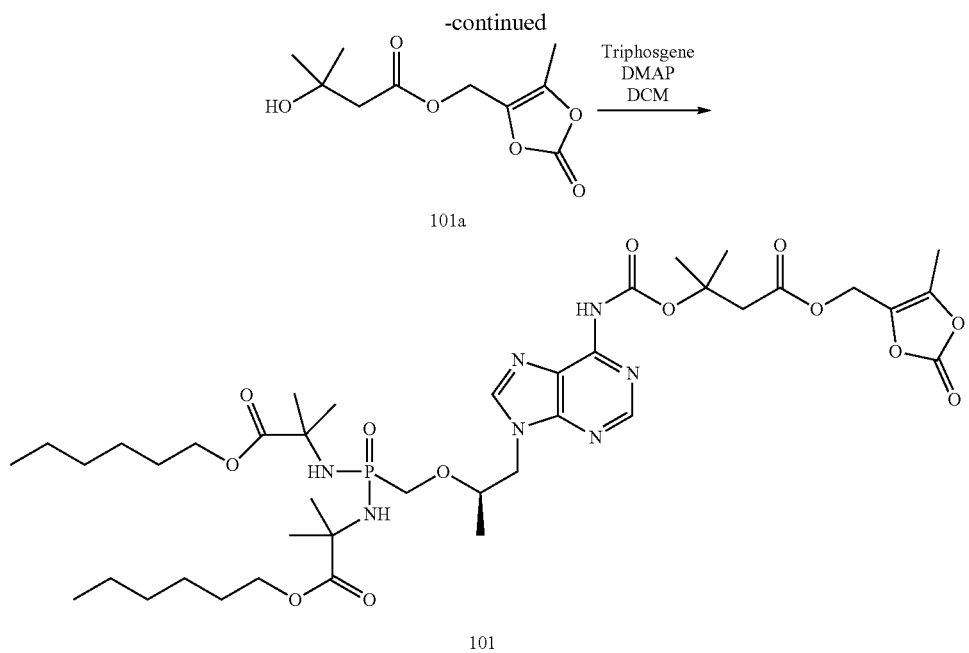

101a

101

Compound 1 (75 mg, 0.12 mmol), Triphosgene (35.6 mg, 0.12 mmol), 4-dimethylaminopyridine (43.9 mg, 0.36 mmol) were taken in 40 mL vial charged with stir bar and added DCM (3 mL) and stirred at room temperature for 15 min. After 15 minutes (5-methyl-2-oxo-1,3-dioxol-4-yl) methyl 3-hydroxy-3-methyl-butanoate (101a, 66.2 mg, 0.14 mmol) was added and stirred at room temperature for 2 h. The solvent was concentrated under reduced pressure. This residue was dissolved in acetonitrile (4 mL), filtered and purified by preparative HPLC (Gemini, 10 uM, NX-C18, 110 Å 250×30 mm column, 50%-100% acetonitrile/water gradient in 20 min run) to afford the title compound (101). $^1$H NMR (400 MHz, Acetonitrile-$d_3$) δ 8.59 (s, 1H), 8.29 (s, 1H), 8.28 (s, 1H), 4.88 (s, 2H), 4.43 (dd, J=14.5, 3.2 Hz, 1H), 4.25 (dd, J=14.5, 7.1 Hz, 1H), 4.15-4.05 (m, 4H), 3.99-3.92 (m, 1H), 3.79-3.62 (m, 2H), 3.62-3.35 (m, 2H), 3.03 (s, 2H), 2.08 (s, 3H), 1.71-1.58 (m, 12H), 1.53 (s, 3H), 1.46 (d, J=1.9 Hz, 7H), 1.39 (s, 4H), 1.32 (td, J=6.0, 3.6 Hz, 8H), 1.20 (d, J=6.2 Hz, 3H), 0.94-0.87 (m, 6H). $^{31}$P NMR (162 MHz, Acetonitrile-$d_3$) δ 17.67. LCMS: MS m/z=882.1 [M+1]; $t_R$=1.72 min; LC system: Thermo Dionex Ultimate 3000 UHPLC+ focused; MS system: Thermo LCQ Fleet; Column: Phenomenex Kinetex 2.6µ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 102: Dihexyl 2,2'-(((((1-(6-(3,3-dimethyl-5-((5-methyl-2-oxo-1,3-dioxol-4-yl)methoxy)-5-oxopentanamido)-9H-purin-9-yl)propan-2-yl)oxy)methyl)phosphoryl)bis(azanediyl))(R)-bis(2-methylpropanoate) (102)

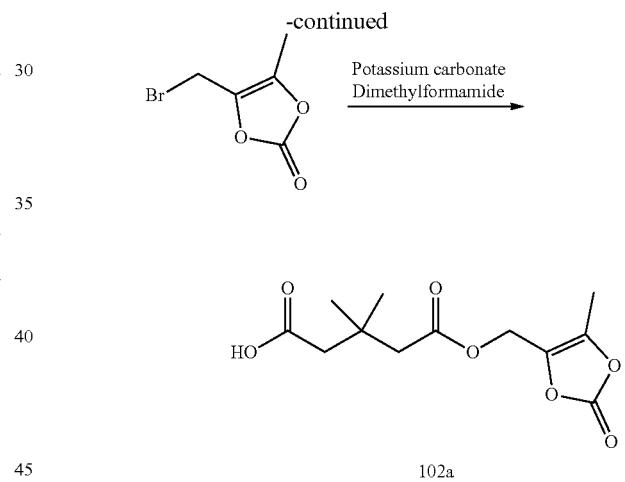

102a

Synthesis of 3,3-dimethyl-5-((5-methyl-2-oxo-1,3-dioxol-4-yl)methoxy)-5-oxopentanoic acid (102a)

To an ice-cold mixture of 3,3-dimethylpentanedioic acid (1 g, 6.24 mmol), $K_2CO_3$ (1.03 g, 7.49 mmol), in DMF (15 mL) was added 4-(bromomethyl)-5-methyl-1,3-dioxol-2-one (1.26 g, 6.24 mmol) drop wise. After 5 minutes ice both was removed and stirred at room temperature for 4 h. The reaction mixture was diluted with EtOAc, washed with water (2×25 mL), and once with 5% LiCl solution (40 mL). The combined organic mixture was dried over sodium sulfate, and concentrated. The residue was purified by flash chromatography (0-20% MeOH/DCM with ELSD). The fractions containing product were combined and the solvent was removed under reduced pressure to afford intermediate 102a. $^1$H NMR (400 MHz, Acetonitrile-$d_3$) 6 8.90 (s, 1H), 4.87 (s, 2H), 2.47 (s, 2H), 2.45 (s, 3H), 2.38 (d, J=3.9 Hz, 2H), 1.11 (s, 6H).

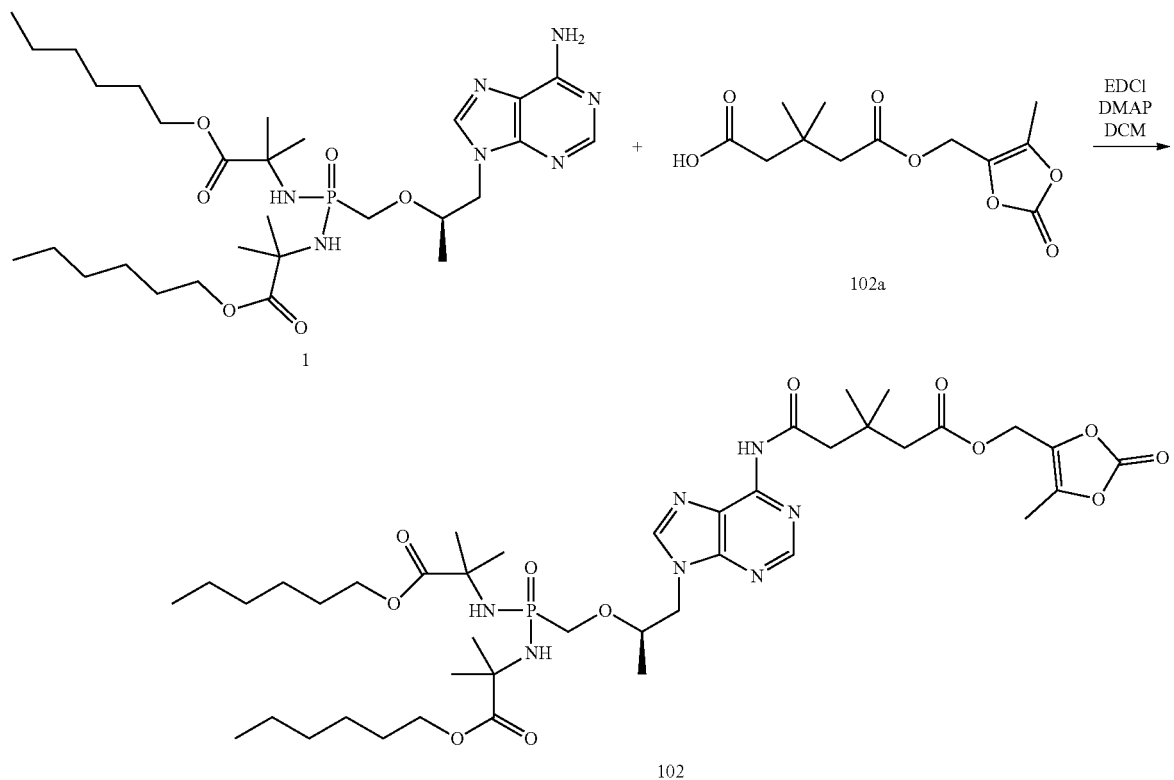

Compound 1 (200 mg, 0.32 mmol), intermediate 102a (338 mg, 1.24 mmol), 4-dimethylaminopyridine (117 mg, 0.95 mmol), 3-(ethyliminomethyleneamino)-N,N-dimethylpropan-1-amine hydrochloride (184 mg, 0.95 mmol) were taken in 40 mL vial charged with stir bar and added DCM (6 mL). This mixture was flushed with argon, capped and stirred at room temperature 15 h. The reaction mixture was diluted with DCM (15 ml). The solution was washed with water (2×15 ml), and once with saturated ammonium chloride (15 ml) and dried over sodium sulfate. The solvent was concentrated under reduced pressure. The residue was dissolved in acetonitrile (6 mL), filtered and purified by preparative HPLC (Gemini, 10 uM, NX-C18, 110 Å250×30 mm column, 50%-100% acetonitrile/water gradient in 20 min run) to afford the title compound (102). $^1$H NMR (400 MHz, Acetonitrile-$d_3$) δ 8.94 (s, 1H), 8.62 (s, 1H), 8.31 (s, 1H), 4.91 (s, 2H), 4.44 (dd, J=14.5, 3.1 Hz, 1H), 4.25 (dd, J=14.5, 7.2 Hz, 1H), 4.17-4.02 (m, 4H), 4.00-3.93 (m, 1H), 3.78-3.63 (m, 2H), 3.55 (d, J=10.8 Hz, 1H), 3.44 (dd, J=12.7, 9.8 Hz, 1H), 2.76 (s, 2H), 2.57 (s, 2H), 2.14 (s, 3H), 1.68-1.59 (m, 5H), 1.52 (s, 3H), 1.45 (d, J=3.2 Hz, 6H), 1.38 (s, 5H), 1.36-1.25 (m, 8H), 1.21-1.17 (m, 10H), 0.96-0.84 (m, 6H). $^{31}$P NMR (162 MHz, Acetonitrile-$d_3$) δ 17.67. LCMS: MS m/z=880.2 [M+1]; $t_R$=1.73 min; LC system: Thermo Dionex Ultimate 3000 UHPLC+ focused; MS system: Thermo LCQ Fleet; Column: Phenomenex Kinetex 2.6μ-C18 100A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Example 103: Diphenethyl 2,2'-(((((1-(6-amino-9H-purin-9-yl)propan-2-yl)oxy)methyl)phosphoryl)bis(azanediyl))(R)-bis(2-methylpropanoate) (103)

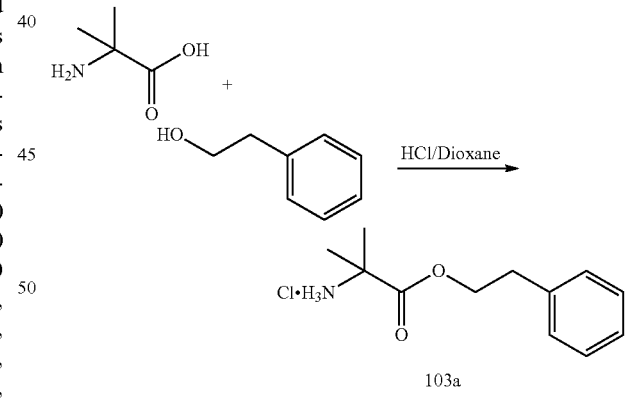

Synthesis of phenethyl 2-amino-2-methylpropanoate hydrochloride (103a)

Intermediate 103a was synthesized in the same manner as intermediate 87a using 2-amino-2-methylpropanoic acid (1 g, 9.7 mmol), 2-phenylethan-1-ol (3.88, 31.8 mmol) and 4N HCl/Dioxane (15 mL) to afford intermediate 103a. LCMS: MS m/z=208.04 [M+1], $t_R$=1.04 min; LC system: Thermo Accela 1250 UHPLC; MS system: Thermo LCQ Fleet; Column: Kinetex 2.6μ XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µl/min.

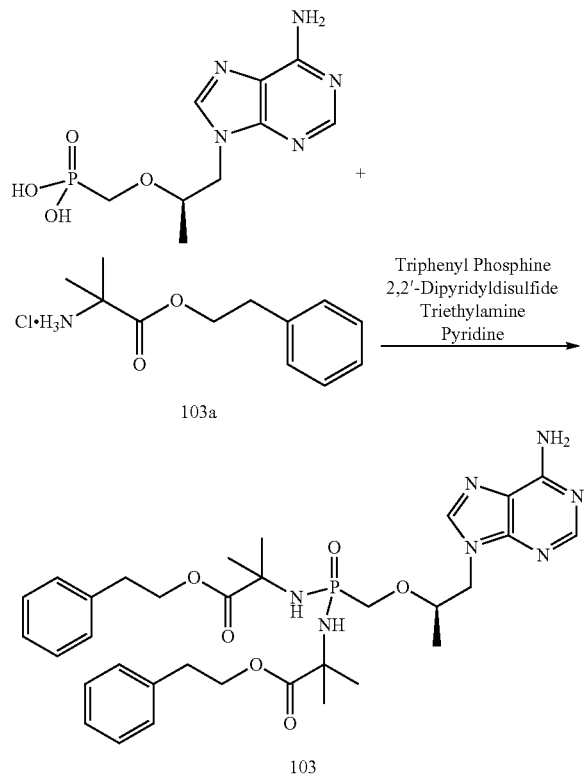

103a

103

PMPA (100 mg, 0.348 mmol), and intermediate 103a (339 mg, 1.39 mmol) were taken in a 8 ml vial, charged with stir bar. To this mixture was added triethylamine (0.5 mL) followed by pyridine (2.5 mL), capped and stirred at 70° C., over 10 min. 2,2'-Dipyridyldisulfide (384 mg, 1.74 mmol) and triphenylphosphine (457 mg, 1.74 mmol) were mixed in another 8 mL vial, added pyridine (2.5 mL), and sonicated to complete dissolution under argon. The clear yellow solution was transferred to stirred suspension of above mixture. Reaction mixture was stirred at 80° C. overnight. Reaction was cooled to room temperature, concentrated under reduced pressure, and co-evaporated with toluene (20 mL×2). The residue was dissolved in DCM, loaded on 24 g flash column, dried the column by passing nitrogen over 2 min (to dry DCM) and elute with 100% EtOAc 6 min, 0-15% MeOH/DCM over 15 min to afford a mixture. This mixture was dissolved in MeOH, filtered and purified by preparative HPLC (Gemini, 10 uM, NX-C18, 110 Å250×30 mm column, 40%-100% acetonitrile/water gradient in 20 min run) to afford the title compound (103). LCMS: MS m/z=666.15 [M+1], $t_R$=1.41 min; LC system: Thermo Accela 1250 UHPLC; MS system: Thermo LCQ Fleet; Column: Kinetex 2.6p XB-C18 100A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µl/min. HPLC: $t_R$=5.19 min; HPLC system: 1290 Infinity II series; Column: Phenomenex Kinetex 2.6µ C18 100A, 100×4.6 mm; Solvents: Acetonitrile with 0.1% TFA, Water with 0.1% TFA; Gradient: 8.5 min, 2-98% ACN, at 1.5 mL/min.

Example 104: Antiviral (HIV) Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (no drug) and positive (5 µM AZT) controls. MT-4 cells were pre-treated with 10 µL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature-controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal and were calculated using a sigmoidal dose-response model to generate curve fits and are shown in Table 1.

Example 105: Cytotoxicity Assay in MT-4 Cells

Assays were performed as described in Example 104 except uninfected MT-4 cells were added to each well containing test compound. In addition, 10 µM puromycin was added to the last column of each assay plate to assess a base level of cytotoxicity. $CC_{50}$ values are shown in Table 1.

Example 106: Antiviral (HBV) Assay in Primary Human Hepatocytes (PHHs)

Cryopreserved PHH were thawed, recovered by centrifugation at 100 g in cryopreserved hepatocyte recovery medium (Thermo Fisher Scientific; CM7500), and plated on collagen matrix (Life Technologies; Catalog Number: R-011-K) coated T225 flasks (Corning CellBIND, Catalog Number: 3293) at a density of 25E6 live cells in 60 mls media. Cells were plated in William's E medium (Thermo Fisher Scientific; A1217601) supplemented with 3.6% hepatocyte thawing and plating supplement (Thermo Fisher Scientific, A15563), 5% fetal bovine serum (Thermo Fisher Scientific; 16000-036), 1 µM dexamethasone (Thermo Fisher Scientific, A15563), and 0.2% Torpedo antibiotic mix (Bioreclamation; Z990008). The plating medium was removed after 14 hours and the cells were subsequently cultured in maintenance medium: William's E medium supplemented with 4% hepatocyte maintenance supplement (Thermo Fisher Scientific; AI15564), 2% fetal bovine serum, 0.1p M dexamethasone, 1.5% DMSO (Sigma-Aldrich, St. Louis, MO; D8418), and 0.2% Torpedo antibiotic mix. Approximately 24 hours after plating, PHH were infected with HepAD38-derived GTD virus at 500 viral genome equivalents per cell in PHH maintenance medium supplemented with 4% PEG 8000 (Promega, Madison, WI; V3011). Infections were allowed to proceed for 24 hours before removing the remaining extracellular virions by washing with maintenance medium three times. After allowing viral infection to take place for 3 days, the infected cells were harvested from the flasks by trypsinization (0.25× in PBS without Ca/Mg, 25 minutes) following a 4 minute 0.5× Versene (Life Technologies Catalog Number: 15040-066) treatment and two PBS washes. Trypsinized cells were inactivated in 10% FBS containing maintenance medium, centrifuged 6 minutes at 50 g, resuspended in hepatocyte maintenance medium, filtered through a 40 uM cell strainer, and adjusted to a density of 0.25E6 cells/ml. Infected cells were seeded on 384 well collagen coated plates (Greiner, Austria) at a density of 20,000 cells/well containing serially diluted compounds of the present disclosure or DMSO (0.5%) in a final volume of 80 µl. The assay plates were incubated for a period of 5 days and the antiviral activity of the test compounds were assayed by detecting the presence of HBV DNA in the culture supernatant using the Quanti-Gene™ 2.0 nucleic acid quantification kit (Affymetrix, Santa Clara, CA).

Example 107: Cytotoxicity Assay in Primary Human Hepatocytes (PHHs)

The HBV-infected primary human hepatocytes are seeded (20K cells/well in 80 uL of Media) in 384well collagen coated plates pre-spotted with compounds. After 5 days, 40 ul of cell supernatant is removed to quantify HBV DNA levels as described in Example 106. Then, 40 ul Cell Titer Glo Reagent (Promega Catalog Number: G7572) is added to the remaining cells and luminescence is measured on the EnVision microplate reader.

Example 108: Kinetic Solubility Analysis

Buffer Preparation: 0.1 N HCl: Hydrochloric acid, 0.1 N standardized solution (MP Biomedicals part number 199569). 1×PBS, pH 7.4: Phosphate Buffered Saline (PBS) solution 10× (Fisher Bioreagent part number BP399-500) 50 mL was added to approximately 450 mL HPLC grade $H_2O$. The volume of the solution was then adjusted to 500 mL for a total dilution factor of 1:10 and a final PBS concentration of 1×. The pH of the final solution was measured and found to be 7.4.

Kinetic Solubility from Compound DMSO Stocks: 100-fold dilutions of each compound DMSO stock solution were prepared in singleton by combining 3 µL of DMSO stock with 297 µL of the appropriate medium in a Millipore solubility filter plate with a 0.45 µM polycarbonate filter membrane using Hamilton STARlet liquid handling. The final DMSO concentration was 1.0% (v/v) and maximum theoretical compound concentration is 100 µM (for compound stock concentration of 10 mM). The filter plate was sealed. Following 24-hour incubation at ambient temperature (24.2-27.5° C.), the samples were vacuum filtered and the filtrates were collected in a 96 well polypropylene plate for analysis. The collection plate was sealed for analysis. Filtrates were injected into the Antek 8060 chemiluminescent nitrogen detector for quantification. The results are reported in µM.

Calculation of Results: The equimolar nitrogen response of the detector was calibrated using standards which spanned the dynamic range of the instrument from 0.08 to 4500 g/mL nitrogen. The filtrates were quantified with respect to this calibration curve. Each calculated solubility value was corrected for background nitrogen present in the DMSO and in the medium used to prepare the sample. All reported values for compounds containing adjacent nitrogen atoms in a ring structure were increased by approximately 25%.

Example 109: TFV-DP Formation in Peripheral Blood Mononuclear Cells (PBMCs)

Compounds were tested in a 96-well assay format for the level of TFV-DP loading in PBMCs in the presence of human serum. PBMCs were activated with 100 units/mL recombinant human TL-2 and 2 µg/mL phytohaemagglutinin (PHA) for 36 hrs. After activation, PBMCs (2 million) were incubated with compounds (1 µM) and cell culture media with 50% serum in a 96 well plate for 2 hrs at 37° C. Cells were transferred to a 96 well deep block plate and spun down. Liquid was removed, and cells were washed 2× with 1 mL of 0.9% saline with spin downs between washes. After a final wash and liquid removal, 500 µL of MeOH+200 nM Cl-ATP+200 nM [adenine-$^{13}C_5$]-tenofovir diphosphate (tetra ammonium salt) was added and thoroughly mixed with the cells. The plate was then spun down and 450 µL of sample was transferred to a new 96 well plate. Supernatants were then evaporated, reconstituted in 80 µl of 1 mM ammonium phosphate and thoroughly vortexed. Blank samples were pooled for serial dilution to construct calibration standards for TFV, TFV-DP and TFV-TP in pmol/million cells. Samples were then transferred to a short-well 96 well plate, centrifuged and injected on an LC-MS/MS for quantification. Values were reported in µM units using an intracellular volume of 0.2 pL/cell.

Example 110: TFV-DP Formation in Primary Human Hepatocytes (PHHs)

Compounds were tested in a 24-well assay format for the level of TFV-DP formation in PHHs. Cells were seeded (4.0×10$^5$ cells/well) in collagen coated plates and incubated at 37° C. After 4-6 hours the liquid was removed, 500 µl of new media (2% FBS, 1.5% DMSO) was added, and the cells were incubated at 37° C. overnight. The media is then replaced (2% FBS, 1.0% DMSO), compounds (1 µM) were added and the cells were incubated at 37° C. in the presence of compounds for 1 hour. Media was then removed and cells were washed 2× with 500 µl of 0.9% saline. After a final wash and liquid removal, 500 µL of MeOH+200 nM Cl-ATP+200 nM [adenine-$^{13}C_5$]-tenofovir diphosphate (tetra ammonium salt) was added and cells were incubated at −80° C. for 30 minutes. The cells were kept on water ice while the MeOH/standard supernatant is pipetted up and down several times and then transferred to a 96 deep-well plate. Supernatants were then evaporated, samples were reconstituted in 80 µl of 1 mM ammonium phosphate and then thoroughly vortexed. Blank samples were pooled for serial dilution to construct calibration standards for TFV, TFV-DP and TFV-TP in pmol/million cells. Samples are then transferred to a short-well 96 well plate, centrifuged and injected on an LC-MS/MS for quantification. Values were reported in µM units using an intracellular volume of 3 pL/cell.

Compounds of the present disclosure demonstrate potent antiviral activity, as shown in Table 1 below.

The compounds of the present disclosure display kinetic solubility, as shown in Table 2 below. Consistent with their antiviral activity, the compounds of the present disclosure demonstrate efficient intracellular formation of TFV-DP in PBMCs and PHHs, as shown in Table 2.

TABLE 1

Results from assays in Examples 104-107

| Example | MT4 HIV EC$_{50}$ (nM)[1] | MT4 CC$_{50}$ (nM)[1] | PHH HBV EC$_{50}$ (nM)[1] | PHH CC$_{50}$ (nM)[1] |
|---|---|---|---|---|
| 1 | 5 | 4990 | 1.96 | >100 |
| 2 | 4 | 6087 | 0.69 | >1000 |
| 3 | 10 | 4460 | | >100 |
| 4 | 6 | 8417 | | >100 |

TABLE 1-continued

Results from assays in Examples 104-107

| Example | MT4 HIV EC$_{50}$ (nM)[1] | MT4 CC$_{50}$ (nM)[1] | PHH HBV EC$_{50}$ (nM)[1] | PHH CC$_{50}$ (nM)[1] |
|---|---|---|---|---|
| 5 | 5 | | | |
| 6 | 2 | | | |
| 7 | 9 | | | |
| 8 | 5 | | | |
| 9 | 169 | | | |
| 10 | 37 | | | |
| 11 | 17 | | | |
| 12 | 172 | | | |
| 13 | 16 | 5473 | | |
| 14 | 7 | 3191 | 2.57 | >100 |
| 15 | 17 | 4359 | | |
| 16 | 35 | 6408 | | |
| 17 | >500 | 8853 | | |
| 18 | 13 | 6567 | | |
| 19 | 30 | 17278 | | |
| 20 | 12 | | | |
| 21 | 7 | 4467 | 3.55 | >100 |
| 22 | 9 | | | |
| 24 | >500 | | | |
| 25 | 8 | | | |
| 26 | 6 | | | |
| 27 | 26 | | | >100 |
| 28 | 65 | | | |
| 29 | 16 | | | |
| 30 | 68 | | | >100 |
| 31 | >500 | 9014 | | >100 |
| 32 | >500 | | | |
| 33 | 7 | 6619 | 2.62 | >100 |
| 34 | 3 | 3666 | | |
| 35 | 5 | 4346 | | |
| 36 | 14 | 8965 | | |
| 37 | 4 | | | |
| 38 | 10 | | | |
| 39 | 24 | 7271 | 4.50 | >100 |
| 40 | 6 | | | |
| 41 | 3 | | | |
| 42 | 2 | | | |
| 43 | 20 | | | |
| 44 | 7 | | | |
| 45 | 3 | | | |
| 46 | 5 | 4158 | 2.51 | >100 |
| 47 | 7 | | | |
| 48 | 6 | 3340 | 4.63 | >100 |
| 49 | 5 | 5215 | 5.45 | >100 |
| 50 | 7 | 8059 | 3.10 | >100 |
| 51 | 8 | 7250 | 6.00 | >100 |
| 52 | 8 | 7187 | 14.36 | >100 |
| 53 | 6 | 7547 | 8.38 | >100 |
| 54 | 4 | 6721 | 4.45 | >100 |
| 55 | 101 | 9419 | 6.26 | >100 |
| 56 | 177 | 9654 | 3.99 | >100 |
| 57 | 23 | 6618 | 4.71 | >100 |
| 58 | 5 | 3676 | 1.26 | >100 |
| 59 | 47 | 6955 | 6.53 | >100 |
| 60 | 3 | 3306 | 1.44 | >100 |
| 61 | 28 | 6002 | | >100 |
| 62 | 7 | 3192 | | >100 |
| 63 | 7 | 2217 | | |
| 64 | >500 | 7343 | | |
| 65 | >500 | 6715 | | >100 |
| 66 | 9 | 4766 | | >100 |
| 67 | 8 | | | |
| 68 | 9 | | | |
| 69 | 24 | | | |
| 70 | >500 | | | |
| 71 | 233 | | | |
| 72 | 16 | | | |
| 77 | >500 | >50000 | | >100 |
| 78 | >500 | | | |
| 79 | 271 | | | |
| 80 | >500 | | | |
| 81 | >500 | | | |
| 82 | 345 | | | |
| 83 | 6 | 6599 | 2.14 | >100 |
| 84 | 229 | 10594 | 3.37 | >100 |
| 85 | 5 | | | |
| 86 | 5 | 3729 | 3.16 | >100 |
| 87 | 6 | 5052 | | >100 |
| 88 | 3 | 7290 | 2.50 | >100 |
| 89 | 6 | 5104 | 2.42 | >100 |
| 90 | 7 | 5514 | 2.95 | >100 |
| 91 | 5 | 4924 | 3.76 | >100 |
| 92 | 23 | 7986 | 4.56 | >100 |
| 93 | 97 | 5471 | | |
| 94 | 130 | 8222 | | >100 |
| 95 | 27 | 14780 | | |
| 96 | 11 | 10974 | | |
| 97 | 13 | 10740 | | |
| 98 | 213 | 24523 | | |
| 99 | 91 | 17240 | | |
| 100 | 22 | | | |
| 101 | 12 | 7681 | | |
| 102 | >500 | 45125 | | |
| 103 | >500 | >42540 | | |

[1]Values are an average of at least two independent experiments

TABLE 2

Results from assays in Examples 108-110

| Example | Kinetic Solubility in pH 7.4 PBS (µg/mL) | Average PBMC TFV-DP (µM)[1] | Average PHH TFV-DP (µM)[1] |
|---|---|---|---|
| 1 | 33 | 5.2 | 2.1 |
| 2 | 65 | 4.4 | 2.5 |
| 3 | 50 | 3.0 | |
| 4 | 53 | 5.0 | |
| 5 | 53 | 3.2 | |
| 6 | 49 | 4.5 | |
| 7 | 7 | 5.4 | |
| 8 | 50 | 6.4 | |
| 9 | | 0.2 | |
| 10 | 7 | 0.8 | |
| 11 | <1 | 1.4 | |
| 12 | <1 | BLQ | |
| 13 | <1 | 2.6 | |
| 14 | 27 | | |
| 15 | 2 | 1.0 | |
| 16 | 12 | | |
| 17 | | | |
| 18 | 22 | 4.1 | |
| 19 | 18 | 1.8 | |
| 20 | 49 | 4.0 | |
| 21 | 39 | 5.8 | |
| 22 | 36 | 5.4 | |
| 24 | 69 | BLQ | |
| 25 | 84 | 4.9 | |
| 26 | 78 | 8.8 | |
| 27 | 1 | 1.0 | |
| 28 | 55 | 0.7 | 2.93 |
| 29 | 26 | 2.2 | |
| 30 | <1 | 0.4 | |
| 31 | 12 | 0.3 | |
| 32 | <1 | 0.3 | 0.26 |
| 33 | 14 | 4.9 | 4.85 |
| 34 | 59 | 0.9 | |
| 35 | 54 | 0.9 | |
| 36 | 60 | 0.3 | |
| 37 | | 1.5 | |
| 38 | 45 | 1.1 | |
| 39 | | 2.1 | 0.9 |
| 40 | 57 | 3.0 | |
| 41 | 54 | 8.1 | |
| 42 | 54 | 7.1 | |
| 43 | 53 | 0.6 | |
| 44 | 10 | 2.0 | |
| 45 | 64 | 5.3 | |

TABLE 2-continued

Results from assays in Examples 108-110

| Example | Kinetic Solubility in pH 7.4 PBS (μg/mL) | Average PBMC TFV-DP (μM)[1] | Average PHH TFV-DP (μM)[1] |
|---|---|---|---|
| 46 | <1 | 6.1 | |
| 47 | 72 | 1.0 | |
| 48 | <1 | 5.6 | |
| 49 | 4 | 4.8 | |
| 50 | <1 | 4.5 | |
| 51 | 6 | 2.9 | |
| 52 | <1 | 2.0 | |
| 53 | <1 | 2.2 | |
| 54 | 12 | 5.7 | |
| 55 | <1 | 0.4 | 0.88 |
| 56 | 5 | 0.3 | 0.91 |
| 57 | <1 | 1.2 | |
| 58 | 51 | 7.8 | 5.75 |
| 59 | <1 | 0.5 | 0.68 |
| 60 | 76 | 1.2 | 5.42 |
| 61 | <1 | 1.2 | 1.08 |
| 62 | <1 | 3.6 | 5.01 |
| 63 | | 2.2 | 2.40 |
| 64 | <1 | 0.3 | |
| 65 | | 0.7 | 0.26 |
| 66 | | 3.9 | |
| 67 | 38 | 5.5 | |
| 68 | 3 | 5.1 | |
| 69 | 1 | 1.9 | |
| 70 | | | |
| 71 | | | |
| 72 | 35 | 2.1 | |
| 77 | 57 | | |
| 78 | 60 | | |
| 79 | 68 | | |
| 80 | 56 | | |
| 81 | 61 | | |
| 82 | 10 | 0.3 | |
| 83 | 33 | 4.0 | 2.66 |
| 84 | 8 | 0.4 | 1.81 |
| 85 | 6 | 9.4 | |
| 86 | 2 | 5.7 | |
| 87 | <1 | 8.4 | |
| 88 | 69 | 8.1 | |
| 89 | <1 | 7.6 | 3.46 |
| 90 | 7 | 5.7 | 3.72 |
| 91 | 1 | 4.6 | |
| 92 | <1 | 1.2 | 0.75 |
| 93 | 1 | 0.4 | 0.21 |
| 94 | 2 | 0.2 | 0.64 |
| 95 | 60 | 0.5 | 0.23 |
| 96 | 92 | 3.1 | 2.53 |
| 97 | 13 | 1.4 | 1.60 |
| 98 | 7 | 1.5 | 0.12 |
| 99 | 25 | 0.4 | 1.78 |
| 100 | | 1.9 | 4.73 |
| 101 | 23 | 3.2 | 0.66 |
| 102 | 10 | BLQ | 0.16 |
| 103 | 64 | 0.4 | |

[1]Values are an average of at least two independent experiments

We claim:

1. A compound of formula (I):

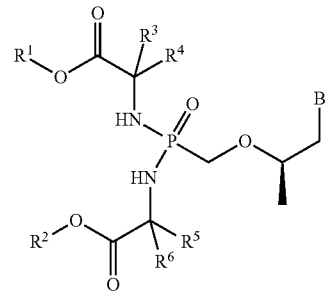

or a pharmaceutically acceptable salt thereof, wherein
$R^1$ and $R^2$ are independently chosen from $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl, bridged $C_{5-10}$bicycloalkyl-$C_{1-4}$alkylene, fused $C_{5-10}$bicycloalkyl, $C_{10-16}$dispirocycloalkyl, $C_{10-16}$dispirocycloalkyl-$C_{1-4}$alkylene, bridged $C_{9-12}$tricycloalkyl, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-12}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three $R^a$;
$R^3$, $R^4$, $R^5$, and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or optionally:
$R^3$ and $R^4$ together with the carbon atom to which they are attached form a 3- to 6-membered saturated or partially unsaturated carbocyclic ring optionally substituted with from one to three $R^b$; and $R^5$ and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; or
$R^3$ and $R^4$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$; or
$R^3$ and $R^4$ together with the carbon atom to which they are attached form a 3- to 6-membered saturated or partially unsaturated carbocyclic ring optionally substituted with from one to three $R^b$; and $R^5$ and $R^6$ together with the carbon atom to which they are attached form a 3- to 6-membered saturated or partially unsaturated carbocyclic ring optionally substituted with from one to three $R^b$;

B is

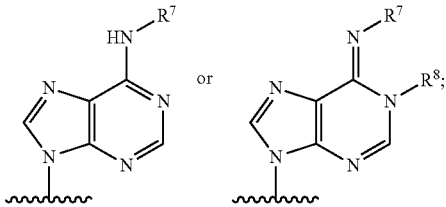

R⁷ is hydrogen or R⁸;
R⁸ is -L¹-(L²)$_m$-(L³)$_n$-R$^{8a}$;
L¹ is chosen from a bond, —C(O)—, and —C(O)O—;
L² is $C_{1-6}$alkylene;
L³ is —C(O)O— or

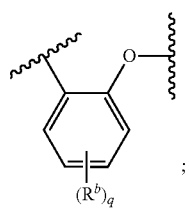

R$^{8a}$ is chosen from $C_{1-12}$alkyl, aryl, —C(O)-aryl, —C(O)—$C_{1-4}$alkyl, —S—C(O)—$C_{1-4}$alkyl,

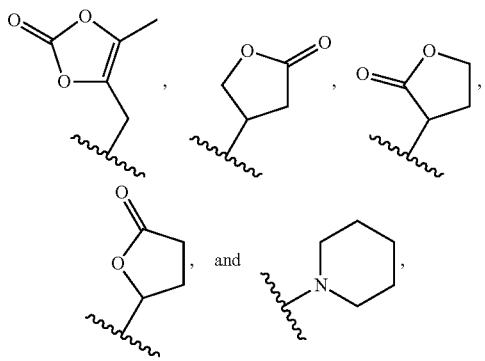

and wherein aryl and —C(O)-aryl are optionally substituted with one or two R$^c$;
each R$^a$ is independently chosen from $C_{1-4}$alkyl, halo, $C_{1-4}$haloalkyl, and —O—$C_{1-4}$alkyl;
each R$^b$ is independently $C_{1-4}$alkyl;
each R$^c$ is independently $C_{1-4}$alkyl or —OC(O)—$C_{1-4}$alkyl;
m and n are independently 0 or 1; and
p is 0, 1, or 2.

2. The compound of claim 1, or a pharmaceutically acceptable salt thereof, wherein R¹ and R² are independently chosen from $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl, bridged $C_{5-10}$bicycloalkyl-$C_{1-4}$alkylene, fused $C_{5-10}$bicycloalkyl, $C_{10-16}$dispirocycloalkyl, $C_{10-16}$dispirocycloalkyl-$C_{1-4}$alkylene, bridged $C_{9-12}$tricycloalkyl, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three R$^a$.

3. The compound of claim 1, or a pharmaceutically acceptable salt thereof, wherein R¹ and R² are independently chosen from $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl-$C_{1-4}$alkylene, fused $C_{5-10}$bicycloalkyl, $C_{10-16}$dispirocycloalkyl-$C_{1-4}$alkylene, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, and $C_{7-12}$spirocycloalkyl-$C_{1-4}$alkylene is optionally substituted with from one to three R$^a$.

4. The compound of claim 1, or a pharmaceutically acceptable salt thereof, wherein R¹ and R² are independently chosen from $C_{1-8}$alkyl, $C_{3-7}$cycloalkyl, $C_{3-7}$cycloalkyl-$C_{1-4}$alkylene, $C_{7-12}$spirocycloalkyl, $C_{7-12}$spirocycloalkyl-$C_{1-4}$alkylene, and bridged $C_{5-10}$bicycloalkyl-$C_{1-4}$alkylene, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three R$^a$.

5. The compound of claim 1, or a pharmaceutically acceptable salt thereof, wherein R¹ and R² are independently chosen from $C_{5-8}$alkyl, $C_{5-7}$cycloalkyl, $C_{5-7}$cycloalkyl-$C_{1-4}$alkylene, $C_{7-9}$spirocycloalkyl, $C_{7-9}$spirocycloalkyl-$C_{1-4}$alkylene, and bridged $C_{5-7}$bicycloalkyl-$C_{1-4}$alkylene, wherein each $C_{5-8}$alkyl, $C_{5-7}$cycloalkyl, $C_{5-7}$cycloalkyl-$C_{1-4}$alkylene, $C_{7-9}$spirocycloalkyl, and $C_{7-9}$spirocycloalkyl-$C_{1-4}$alkylene is optionally substituted with from one to three R$^a$.

6. The compound of claim 1, or a pharmaceutically acceptable salt thereof, wherein R¹ and R² are different.

7. The compound of claim 1, or a pharmaceutically acceptable salt thereof, wherein R¹ and R² are the same.

8. The compound of claim 1, or a pharmaceutically acceptable salt thereof, wherein R¹ and R² are the same and chosen from $C_{1-8}$alkyl, aryl-$C_{1-4}$alkylene, $C_{3-7}$cycloalkyl, $C_{3-7}$cycloalkyl-$C_{1-4}$alkylene, aryl-$C_{3-7}$cycloalkylene, $C_{7-12}$spirocycloalkyl, $C_{7-12}$spirocycloalkyl-$C_{1-4}$alkylene, bridged $C_{5-10}$bicycloalkyl-$C_{1-4}$alkylene, fused $C_{5-10}$bicycloalkyl, $C_{10-16}$dispirocycloalkyl-$C_{1-4}$alkylene, bridged $C_{9-12}$tricycloalkyl-$C_{1-4}$alkylene, $C_{3-7}$cycloalkyl-$C_{3-7}$cycloalkylene, and 5- to 7-membered monocyclic heterocyclyl having from 1 to 3 heteroatoms chosen from N, O, and S, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three R$^a$.

9. The compound of claim 1, or a pharmaceutically acceptable salt thereof, wherein R¹ and R² are the same and chosen from $C_{1-8}$alkyl, $C_{3-7}$cycloalkyl, $C_{3-7}$cycloalkyl-$C_{1-4}$alkylene, $C_{7-12}$spirocycloalkyl, $C_{7-12}$spirocycloalkyl-$C_{1-4}$alkylene, and bridged $C_{5-10}$bicycloalkyl-$C_{1-4}$alkylene, wherein each $C_{1-8}$alkyl, $C_{3-7}$cycloalkyl, $C_{3-7}$cycloalkyl-$C_{1-4}$alkylene, $C_{7-12}$spirocycloalkyl, and $C_{7-12}$spirocycloalkyl-$C_{1-4}$alkylene is optionally substituted with from one to three R$^a$.

10. The compound of claim 1, or a pharmaceutically acceptable salt thereof, wherein R¹ and R² are independently chosen from

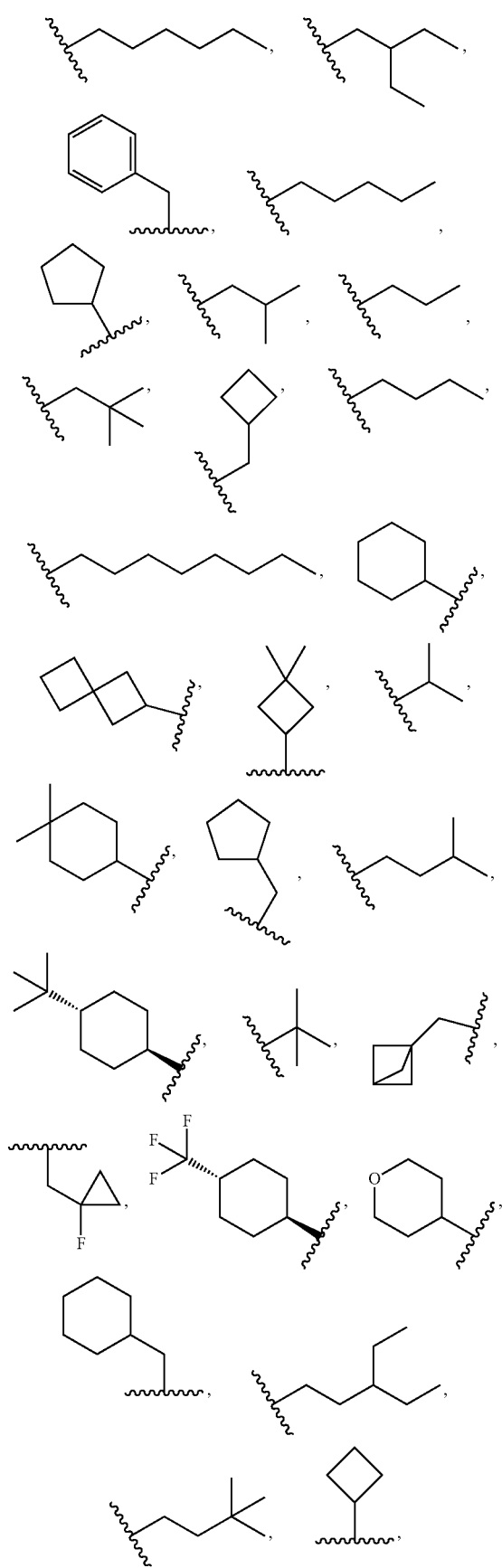
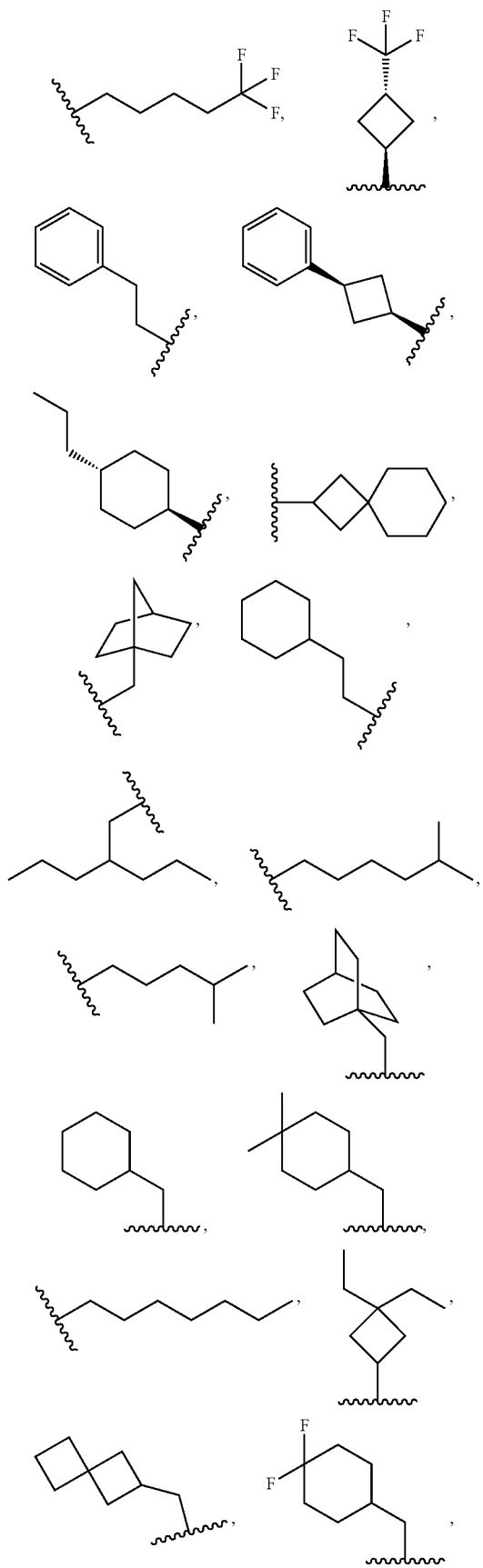

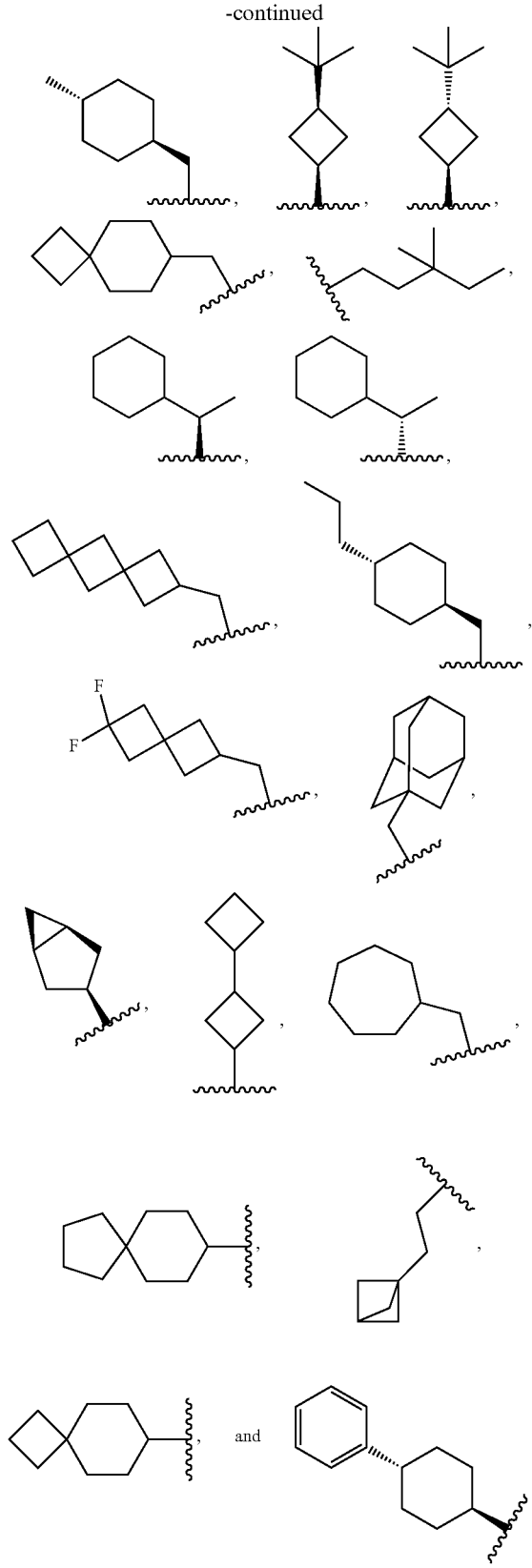
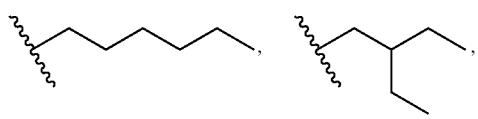
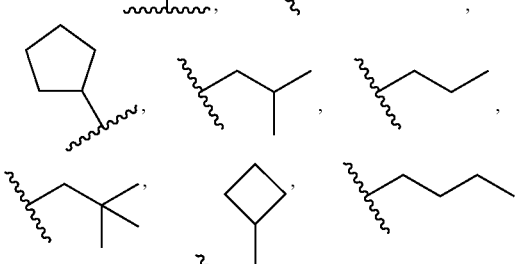
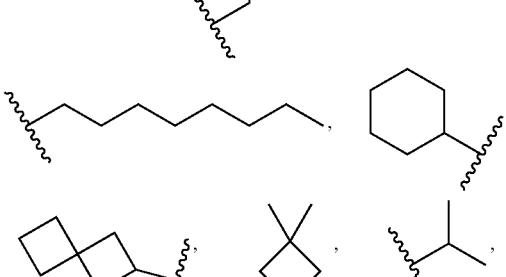
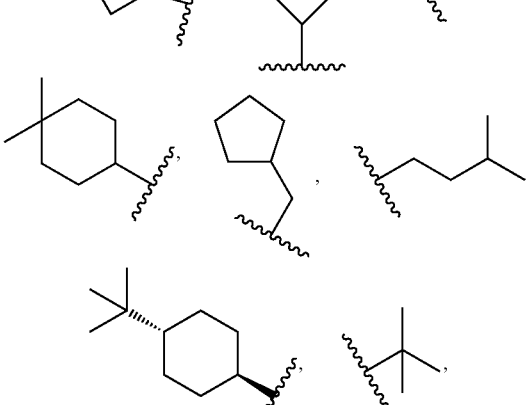
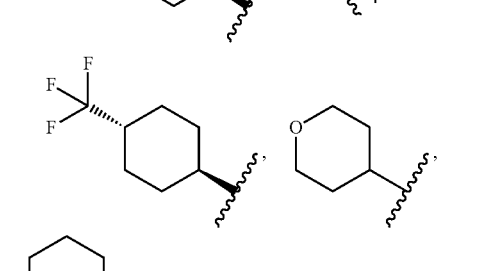
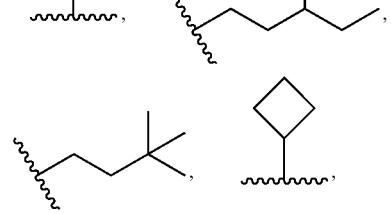
11. The compound of claim 1, or a pharmaceutically acceptable salt thereof, wherein $R^1$ and $R^2$ are the same and chosen from 311
-continued

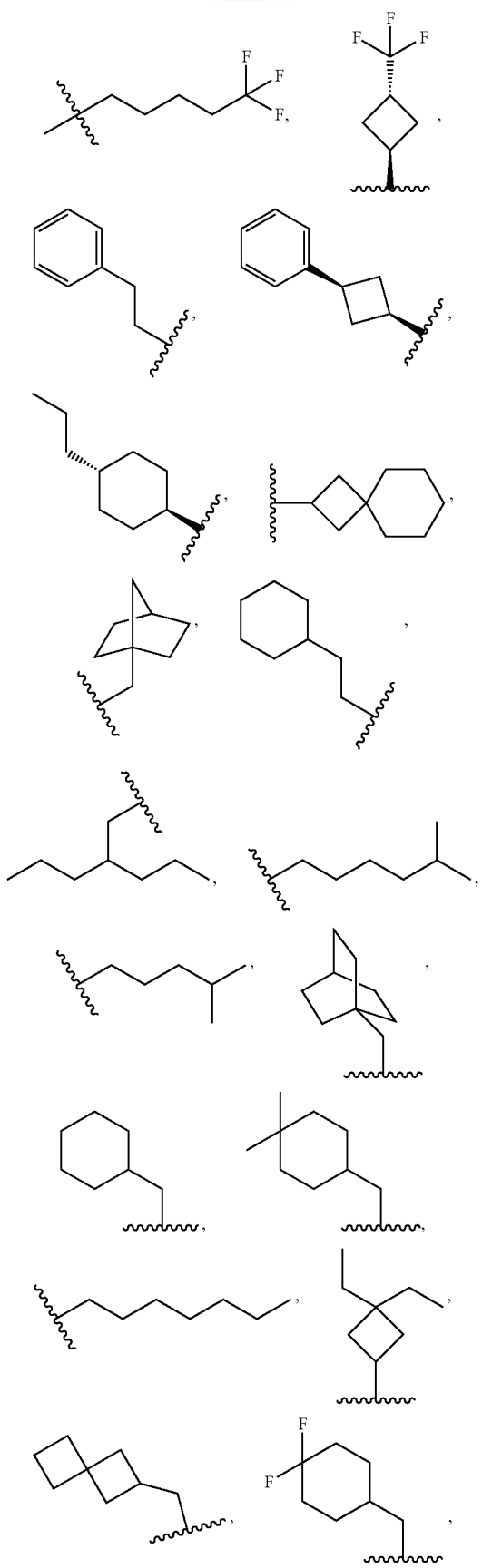

312
-continued

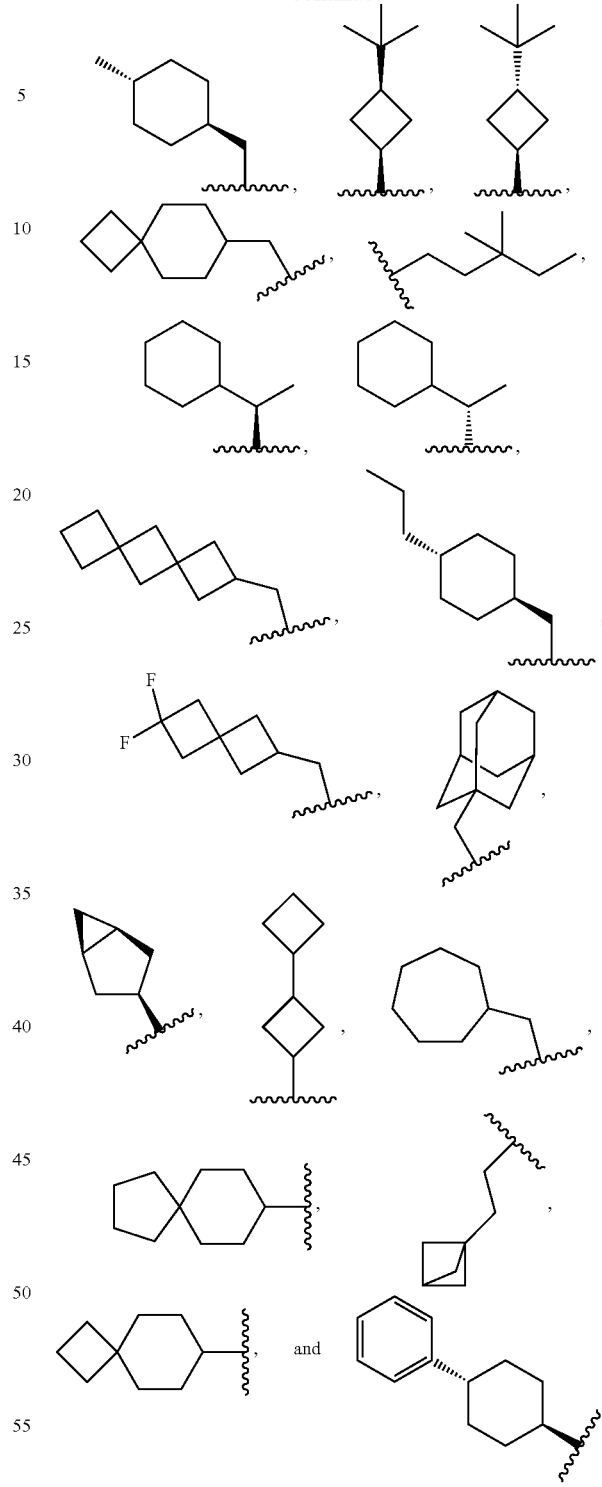

12. The compound of claim 1, or a pharmaceutically acceptable salt thereof, wherein $R^3$, $R^4$, $R^5$, and $R^6$ are each independently chosen from methyl, ethyl, cyclopropyl, and benzyl, wherein each methyl, ethyl, cyclopropyl, and benzyl is optionally substituted with from one to three $R^b$.

13. The compound of claim 1, or a pharmaceutically acceptable salt thereof, wherein $R^3$ and $R^5$ are the same.

14. The compound of claim 1, or a pharmaceutically acceptable salt thereof, wherein $R^3$ and $R^5$ are both methyl.

15. The compound of claim 1, or a pharmaceutically acceptable salt thereof, wherein $R^4$ and $R^6$ are the same.

16. The compound of claim 1, or a pharmaceutically acceptable salt thereof, wherein $R^4$ and $R^6$ are both ethyl or both benzyl.

17. The compound of claim 1, or a pharmaceutically acceptable salt thereof, wherein $R^3$ and $R^4$ are the same.

18. The compound of claim 1, or a pharmaceutically acceptable salt thereof, wherein $R^3$ and $R^4$ are both methyl.

19. The compound of claim 1, or a pharmaceutically acceptable salt thereof, wherein $R^5$ and $R^6$ are the same.

20. The compound of claim 1, or a pharmaceutically acceptable salt thereof, wherein $R^5$ and $R^6$ are both methyl.

21. The compound of claim 1, or a pharmaceutically acceptable salt thereof, wherein $R^3$ and $R^4$ together with the carbon atom to which they are attached form a cyclopropane ring or a cyclobutane ring, wherein the cyclopropane ring or the cyclobutane ring is optionally substituted with from one to three $R^b$; and $R^5$ and $R^6$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$.

22. The compound of claim 21, or a pharmaceutically acceptable salt thereof, wherein $R^5$ and $R^6$ are independently chosen from methyl, ethyl, cyclopropyl, and benzyl, wherein each methyl, ethyl, cyclopropyl, and benzyl is optionally substituted with from one to three $R^b$.

23. The compound of claim 1, or a pharmaceutically acceptable salt thereof, wherein $R^3$ and $R^4$ are independently chosen from $C_{1-4}$alkyl, $C_{3-6}$cycloalkyl, and aryl-$C_{1-4}$alkylene, wherein each $C_{1-4}$alkyl, $C_{3-6}$cycloalkyl, and aryl-$C_{1-4}$alkylene is optionally substituted with from one to three $R^b$; and $R^5$ and $R^6$ together with the carbon atom to which they are attached form a cyclopropane ring or a cyclobutane ring, wherein the cyclopropane ring or the cyclobutane ring is optionally substituted with from one to three $R^b$.

24. The compound of claim 23, or a pharmaceutically acceptable salt thereof, wherein $R^3$ and $R^4$ are independently chosen from methyl, ethyl, cyclopropyl, and benzyl, wherein each methyl, ethyl, cyclopropyl, and benzyl is optionally substituted with from one to three $R^b$.

25. The compound of claim 1, or a pharmaceutically acceptable salt thereof, wherein $R^3$ and $R^4$ together with the carbon atom to which they are attached form a cyclopropane ring or a cyclobutane ring, wherein the cyclopropane ring or the cyclobutane ring is optionally substituted with from one to three $R^b$; and $R^5$ and $R^6$ together with the carbon atom to which they are attached form a cyclopropane ring or a cyclobutane ring, wherein the cyclopropane ring or the cyclobutane ring is optionally substituted with from one to three $R^b$.

26. The compound of claim 1, or a pharmaceutically acceptable salt thereof, wherein each $R^b$ is independently methyl or ethyl.

27. The compound of claim 1, or a pharmaceutically acceptable salt thereof, wherein $R^3$, $R^4$, $R^5$, and $R^6$ are the same.

28. The compound of claim 27, or a pharmaceutically acceptable salt thereof, wherein $R^3$, $R^4$, $R^5$, and $R^6$ are each methyl or cyclopropyl.

29. The compound of claim 27, or a pharmaceutically acceptable salt thereof, wherein $R^3$, $R^4$, $R^5$, and $R^6$ are each methyl.

30. The compound of claim 1, or a pharmaceutically acceptable salt thereof, having the formula (II):

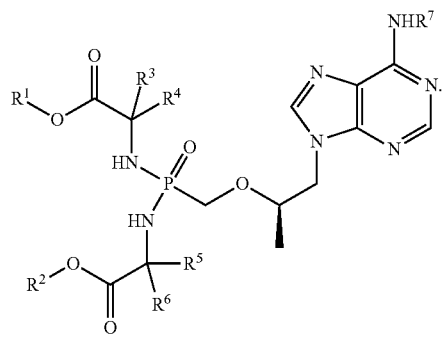

31. The compound of claim 1, or a pharmaceutically acceptable salt thereof, having the formula (III):

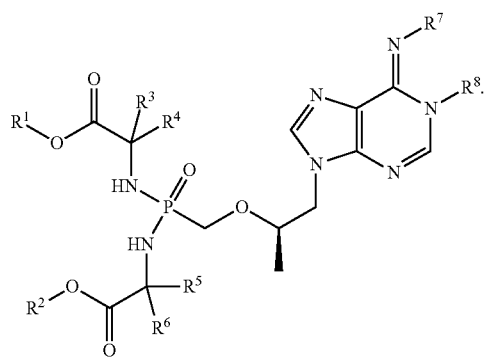

32. The compound of claim 1, or a pharmaceutically acceptable salt thereof, having the formula (IV):

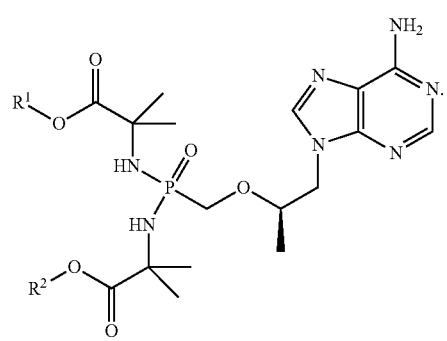

33. The compound of claim 1, or a pharmaceutically acceptable salt thereof, having the formula (V):

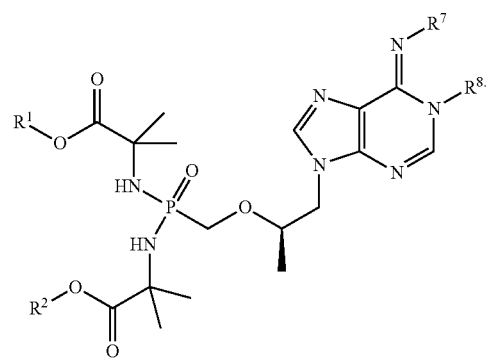

34. A compound of formula:
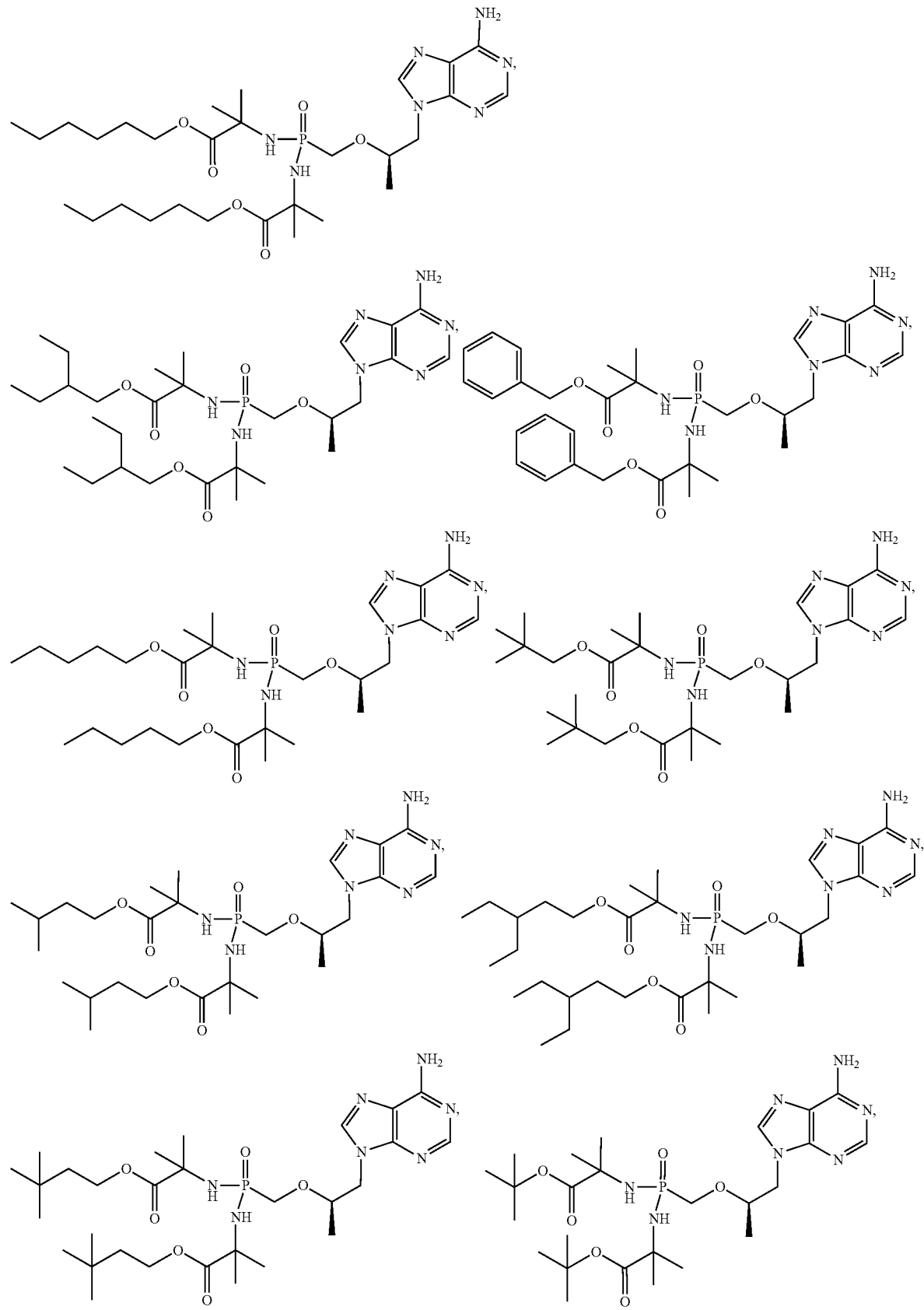

317 318
-continued
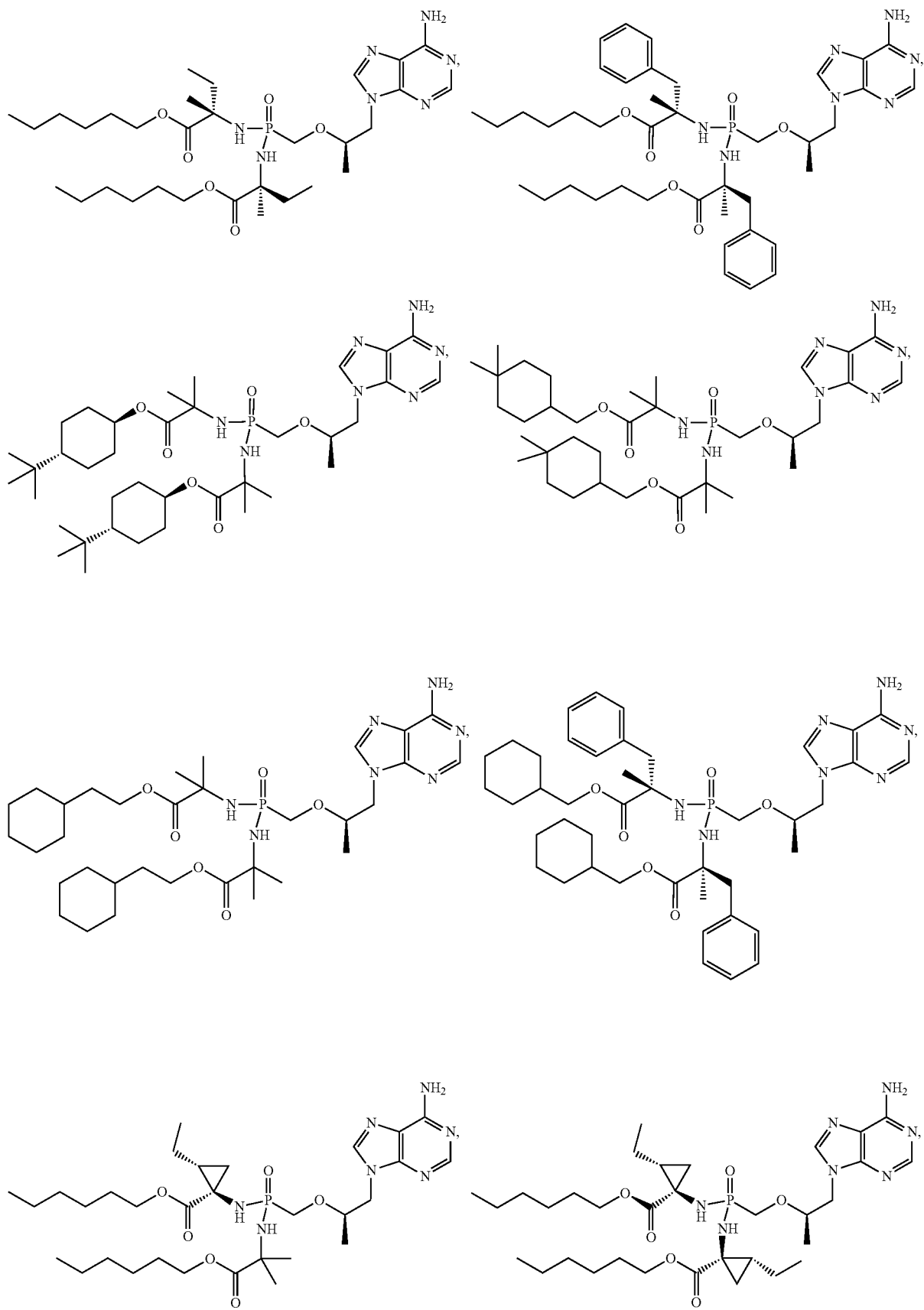

-continued
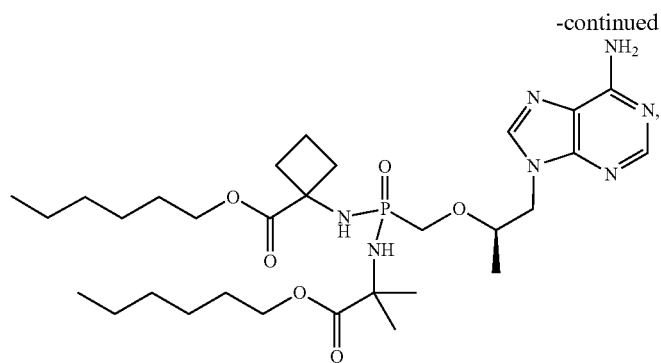
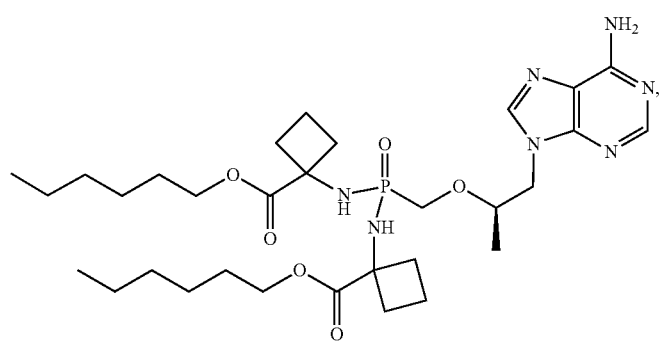
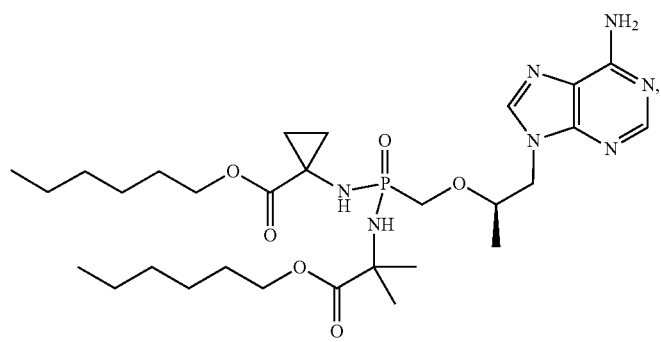
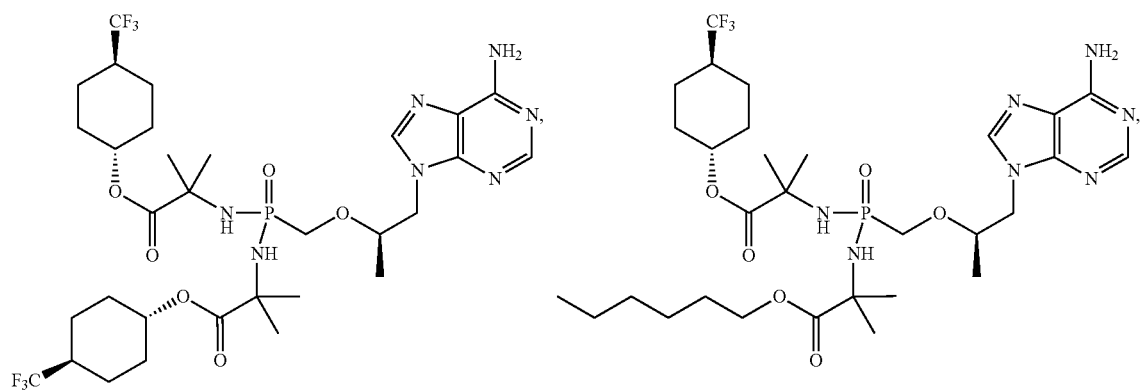

-continued
321
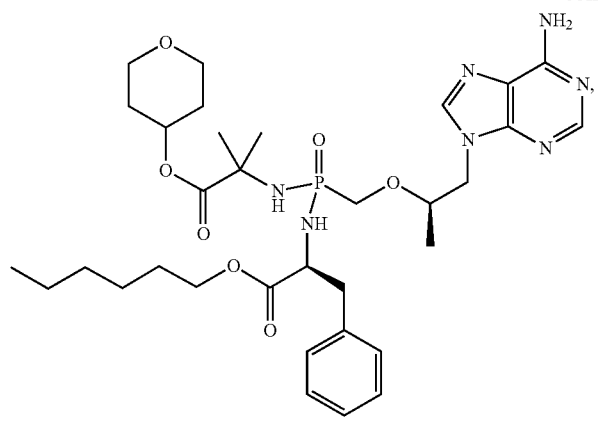
322
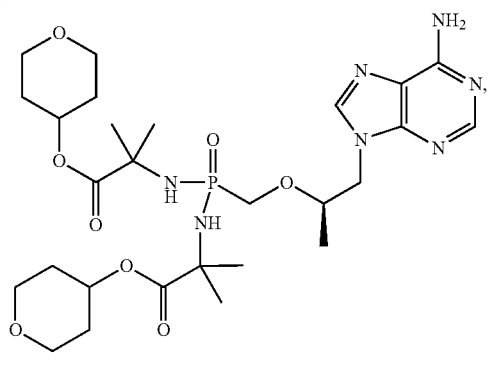
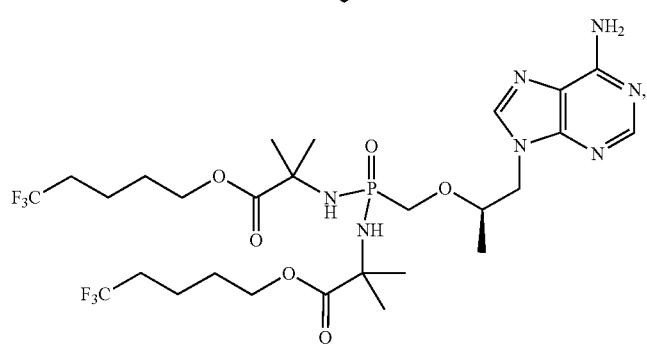
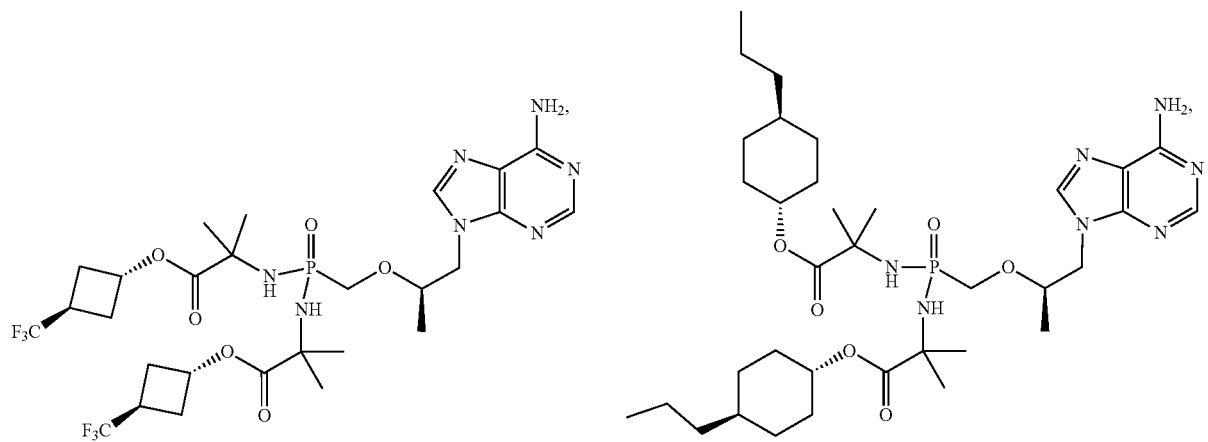
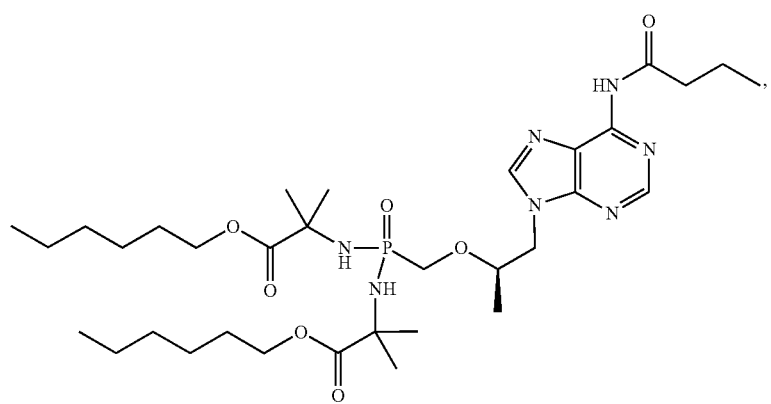

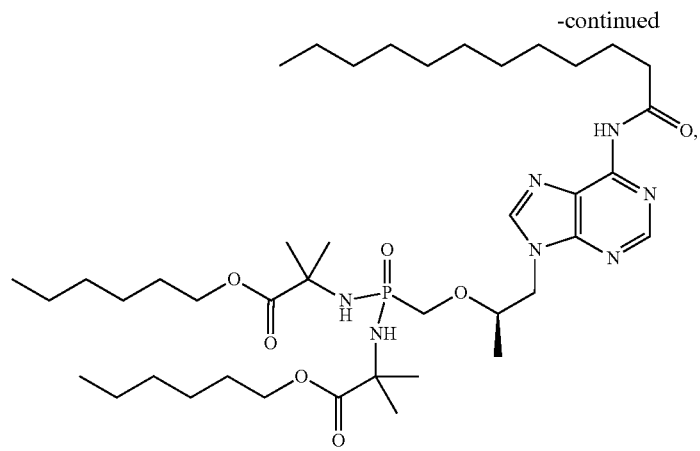
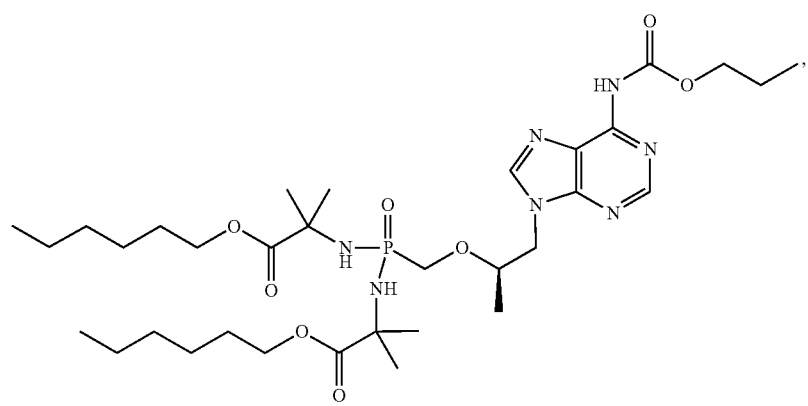
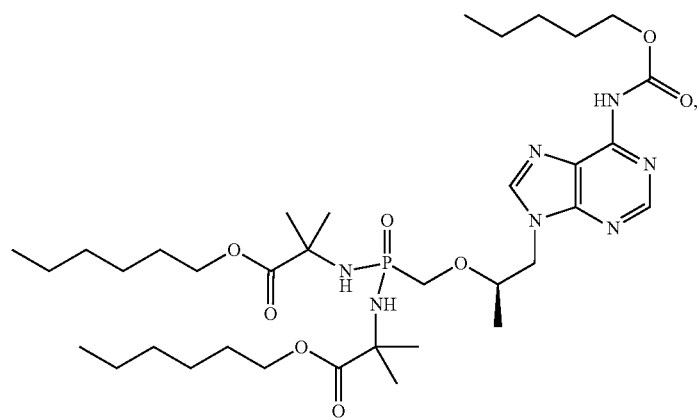
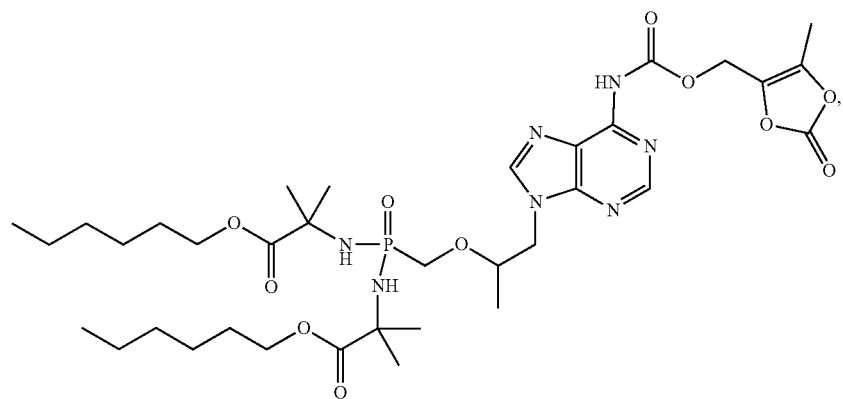

325 326
-continued
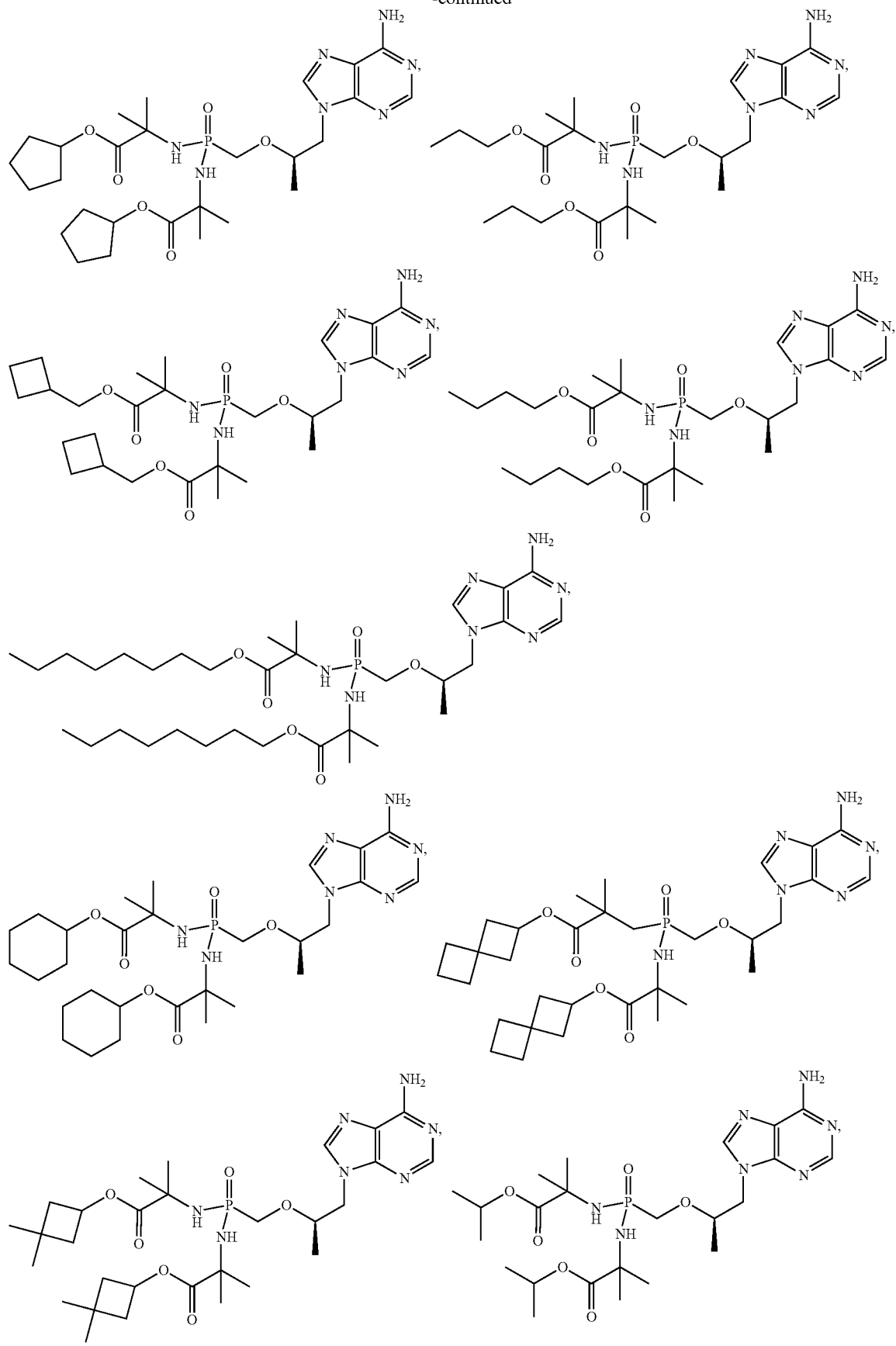

327 328
-continued
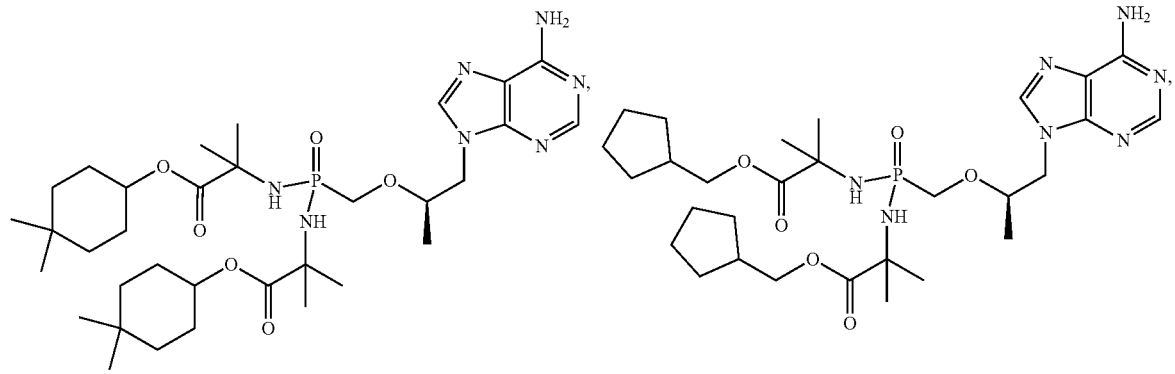
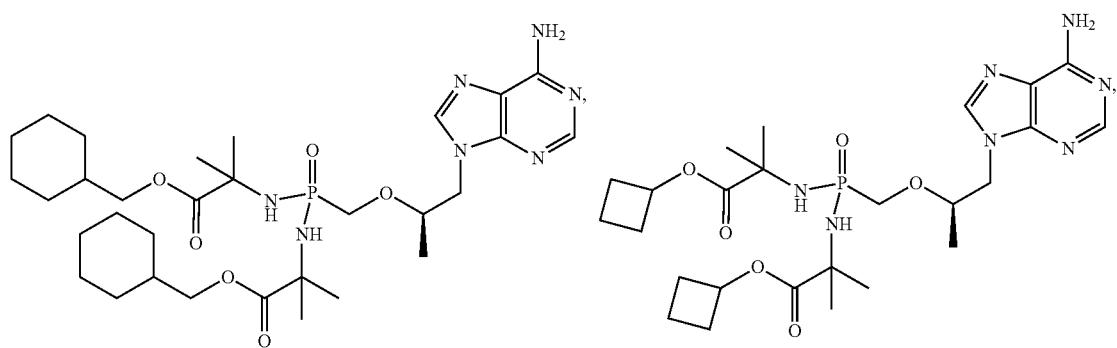
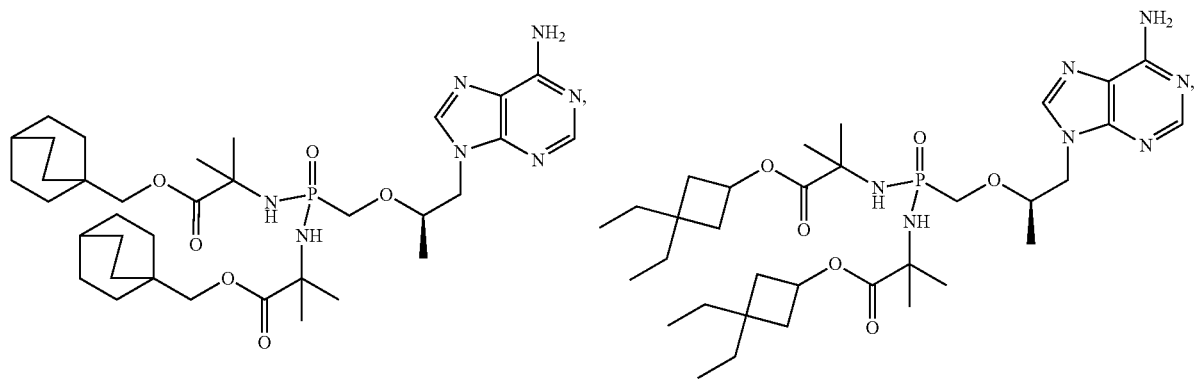
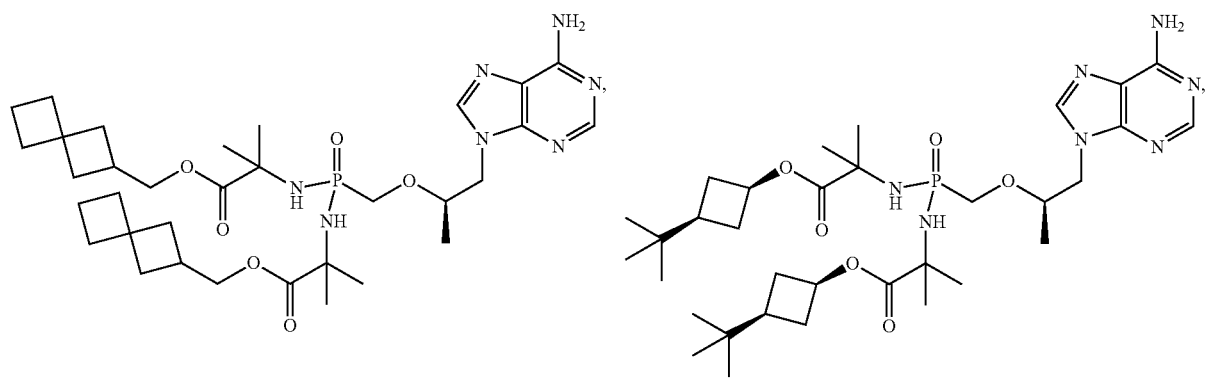

-continued
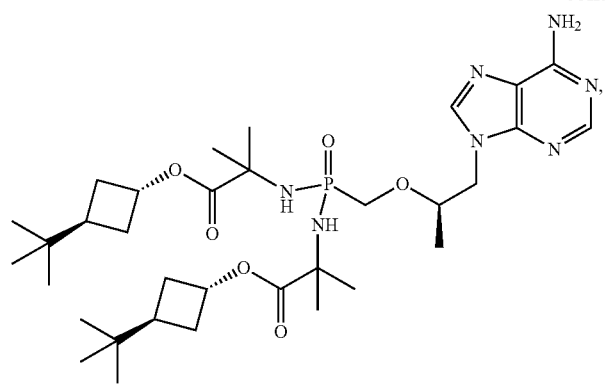
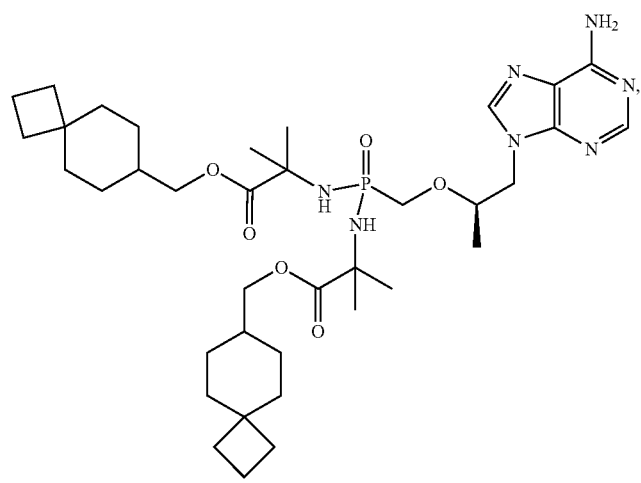
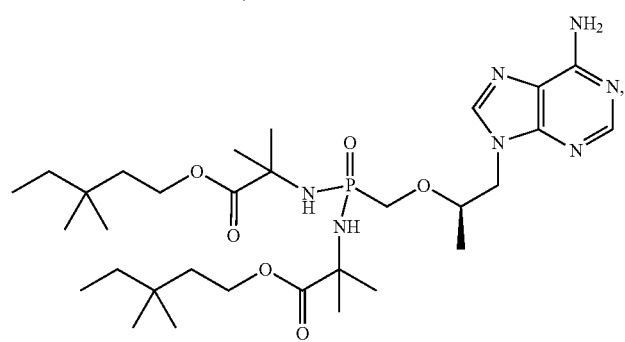
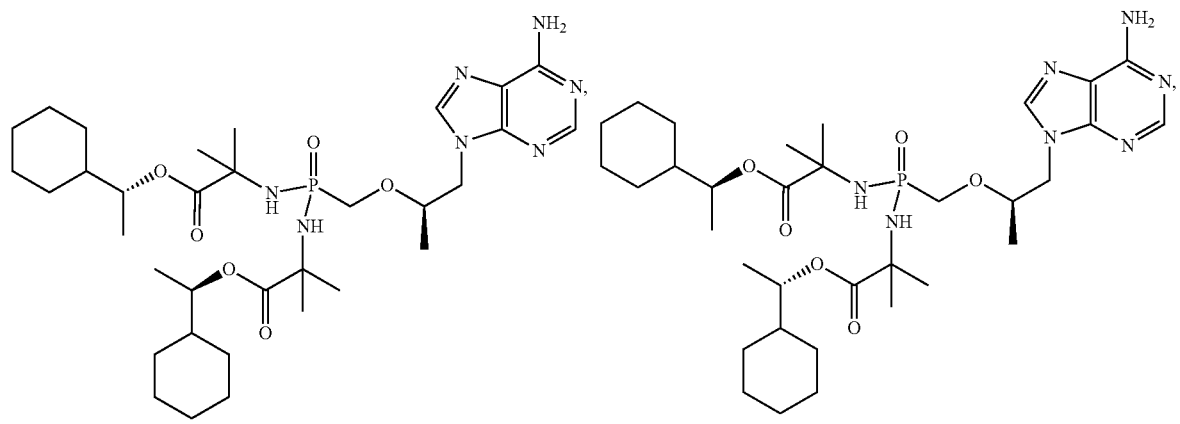

331
332
-continued
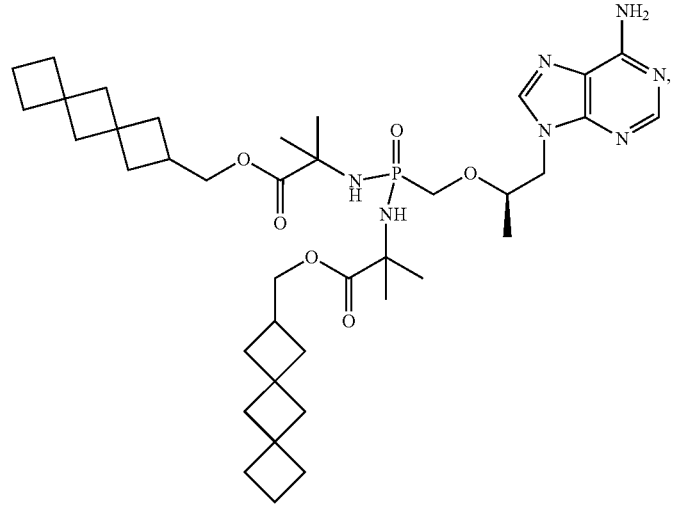
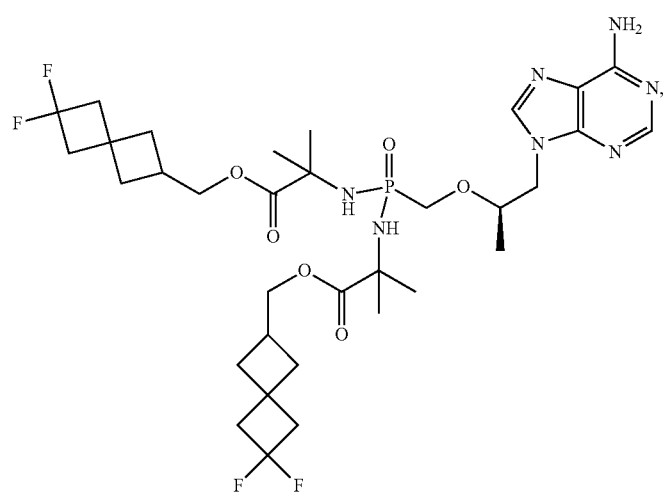
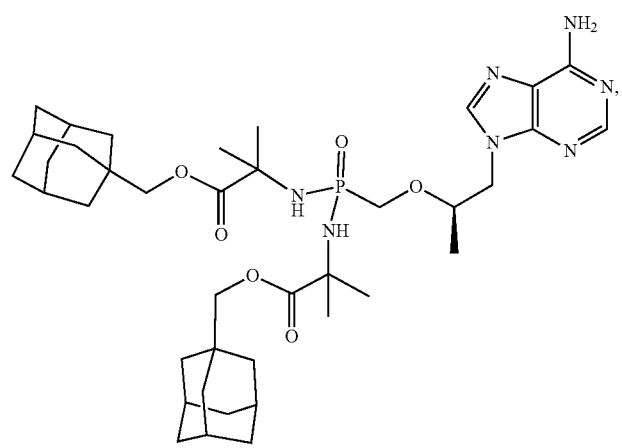

333
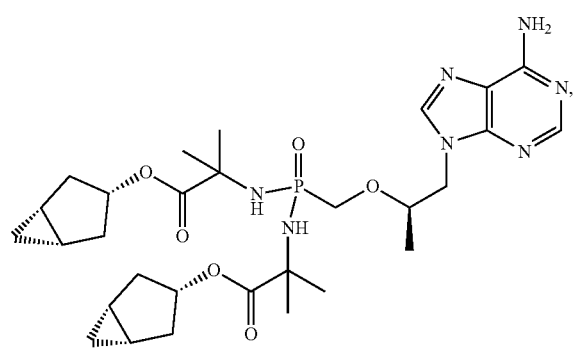
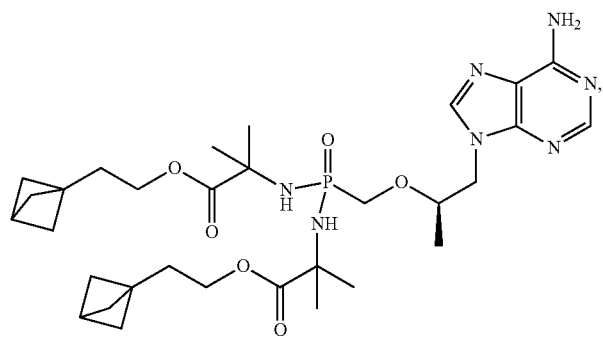
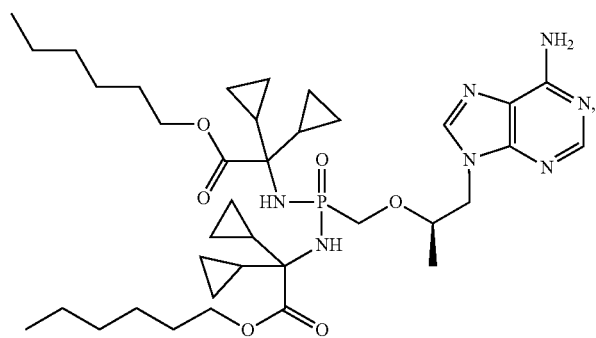
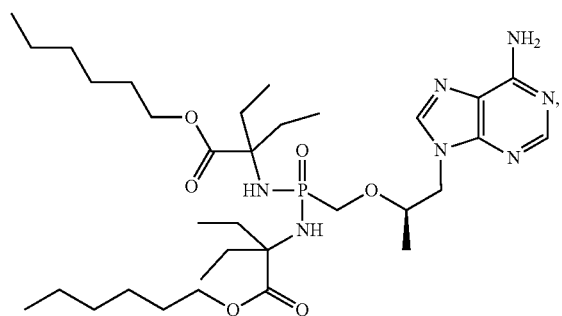
334
-continued
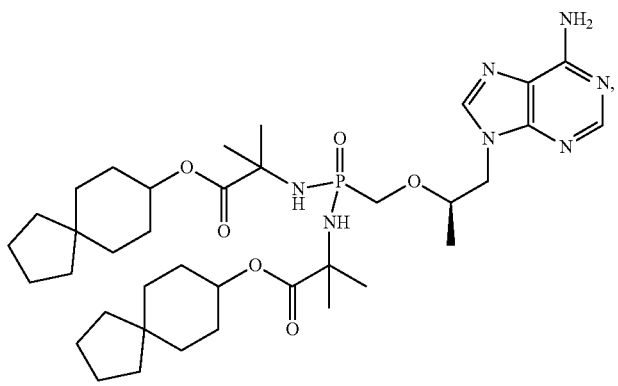
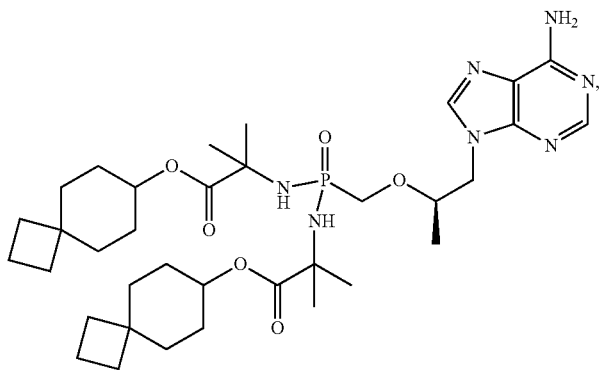
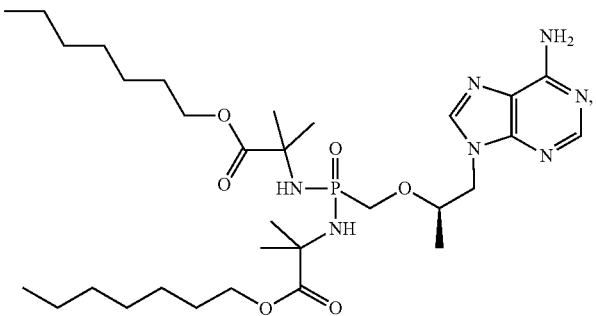

335 336
-continued
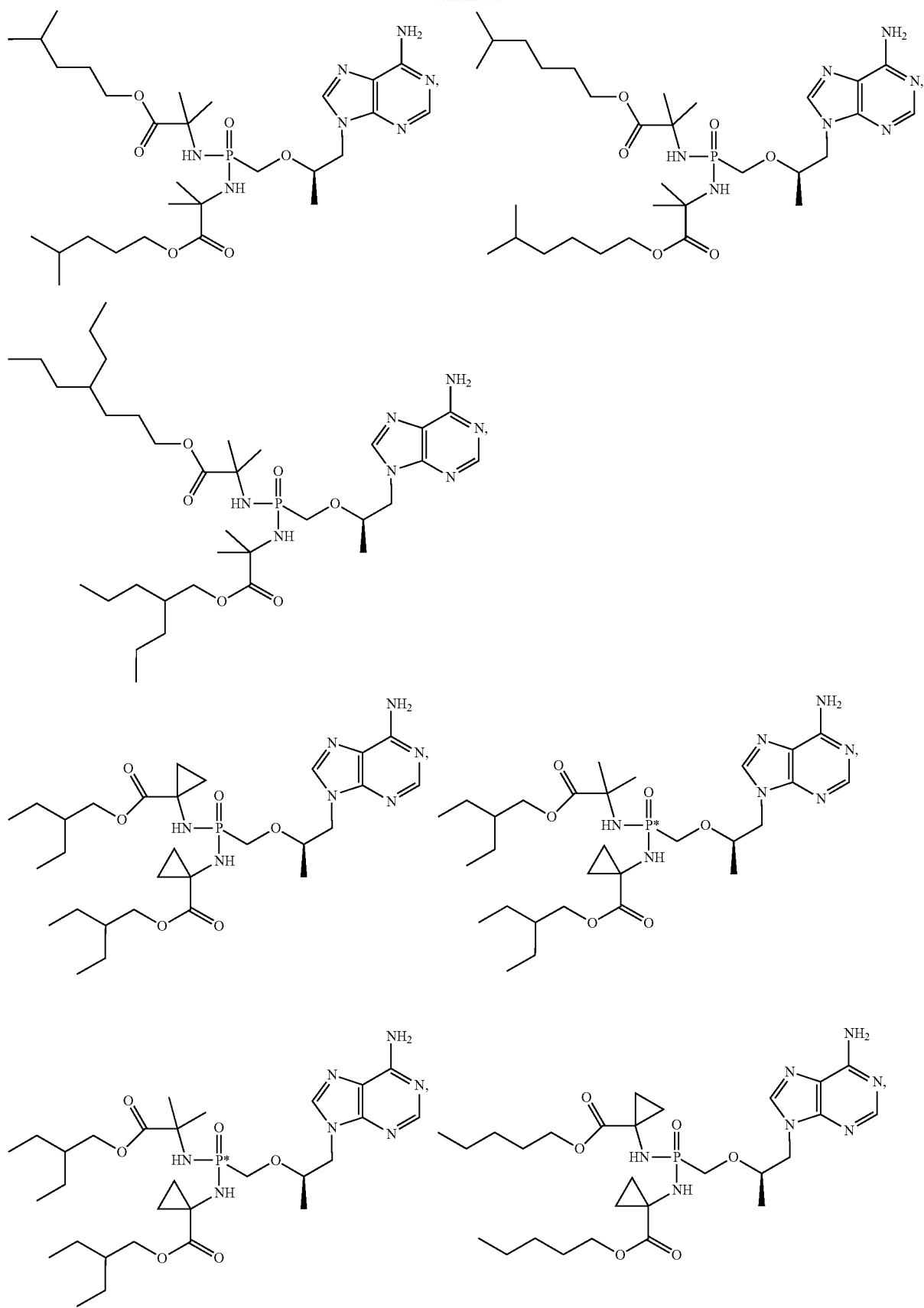

337 338
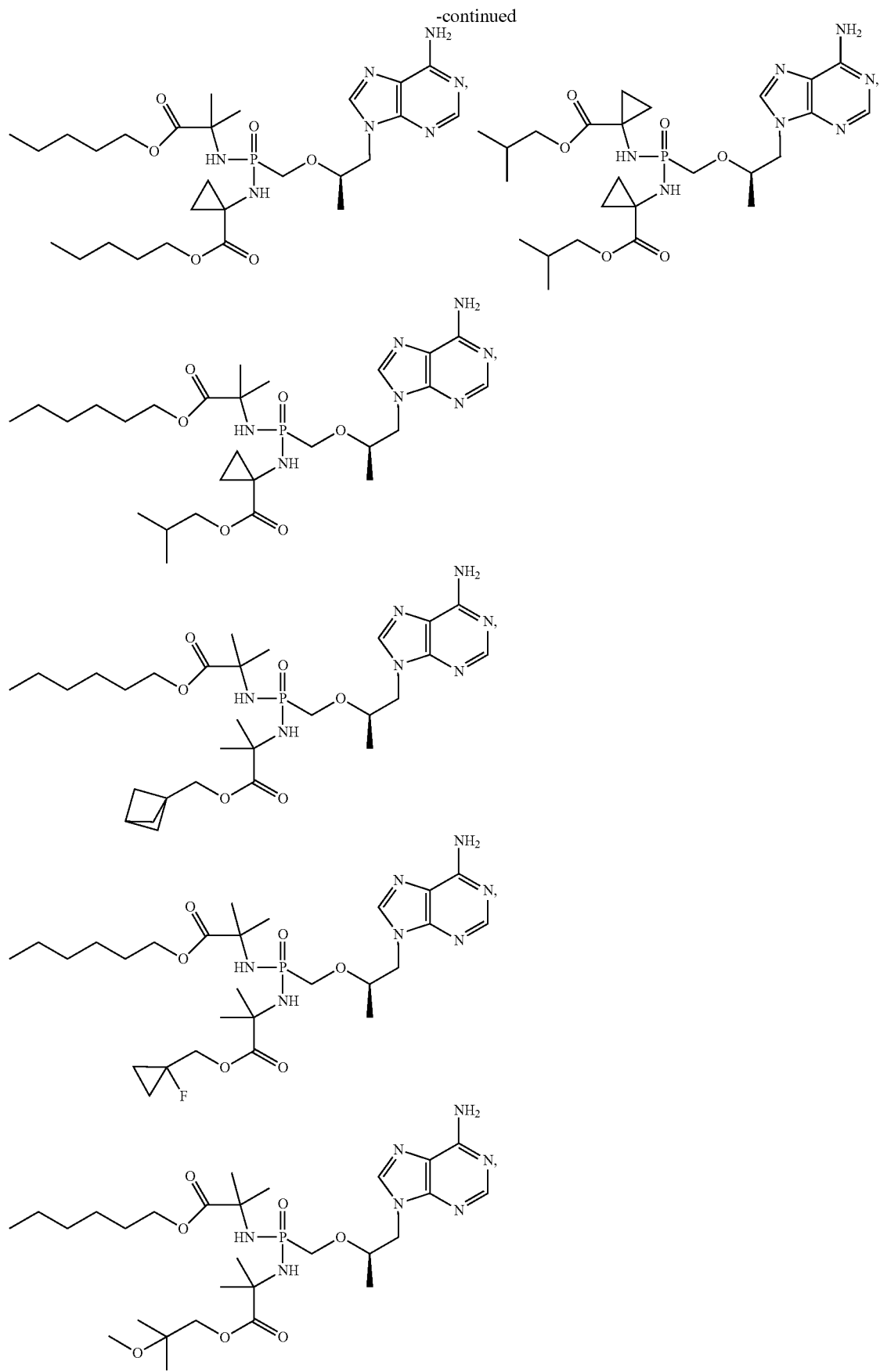
-continued

-continued
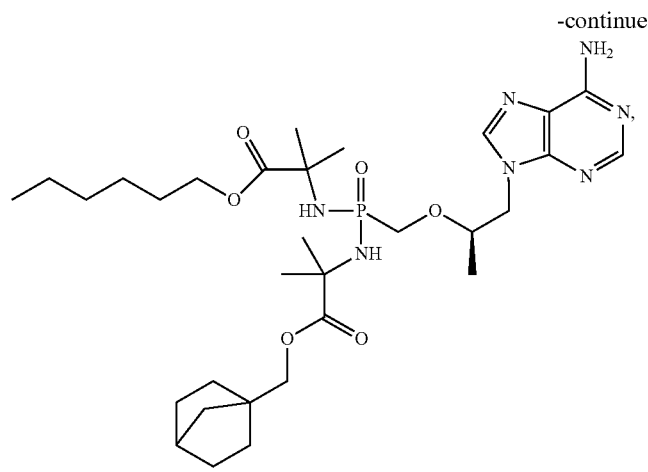
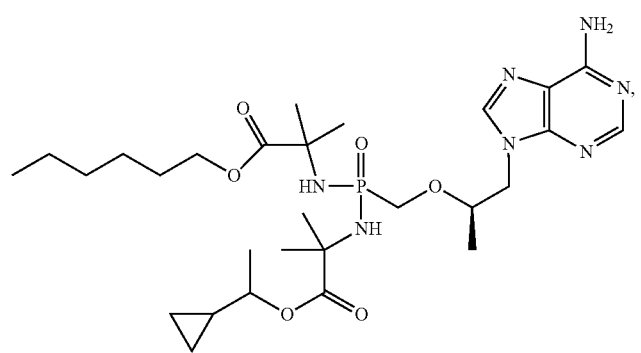
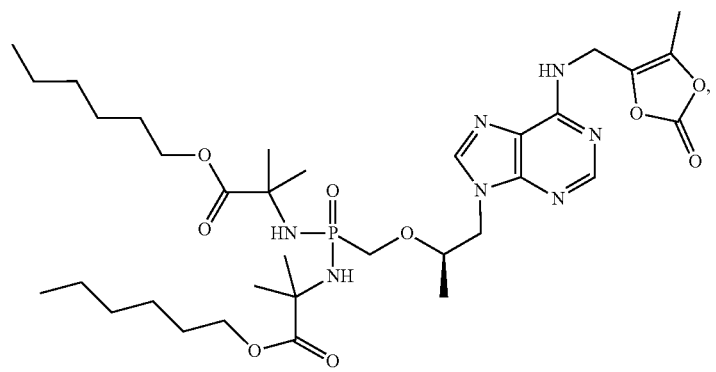
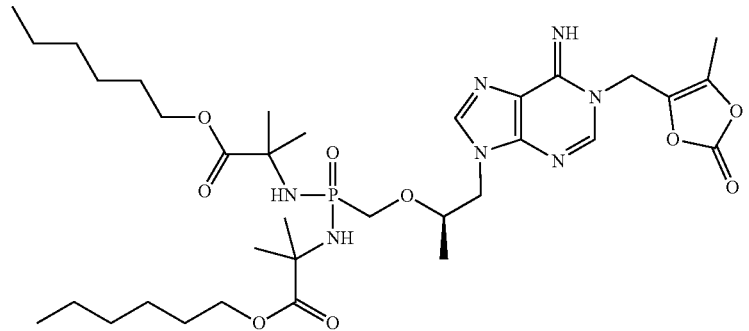

-continued
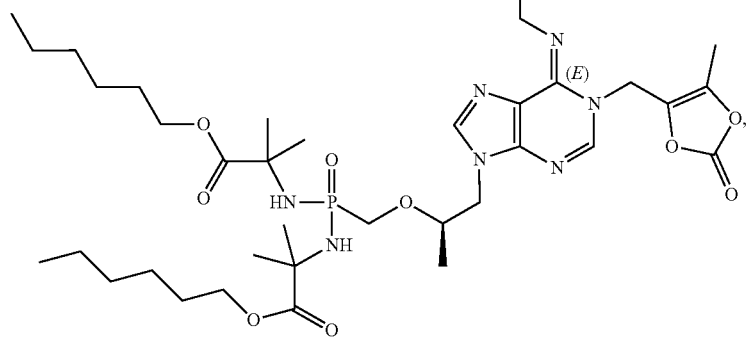
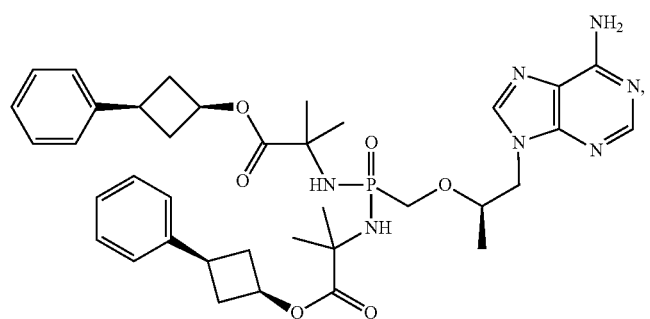
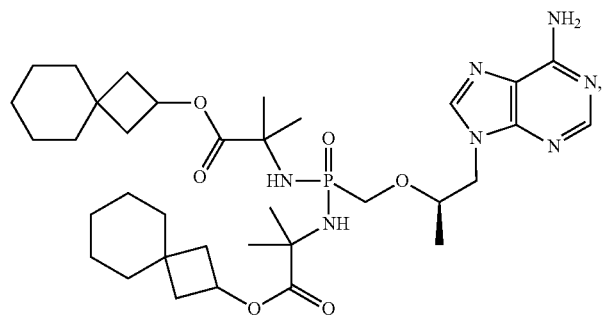
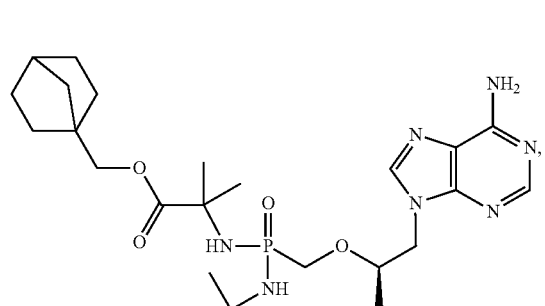
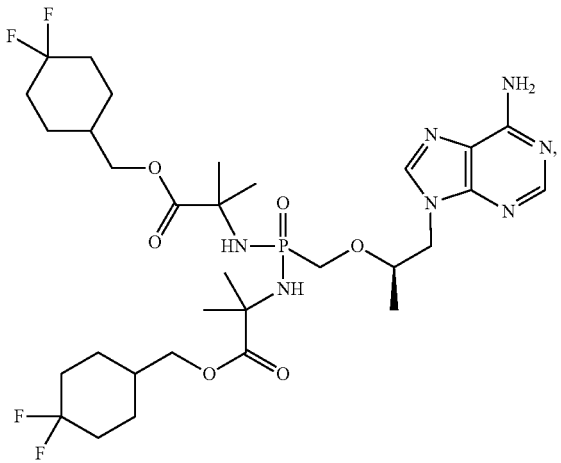

343 344
-continued
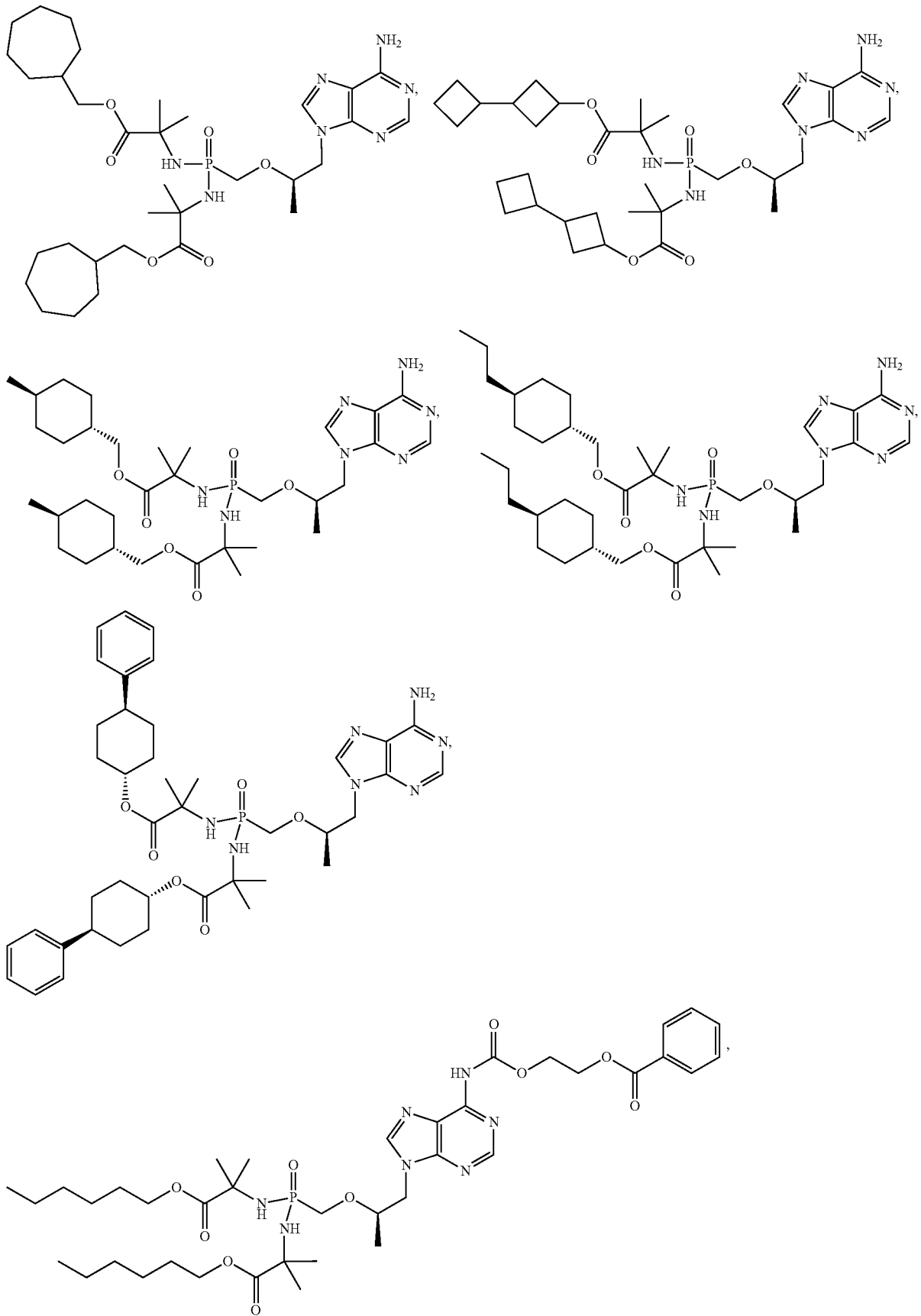

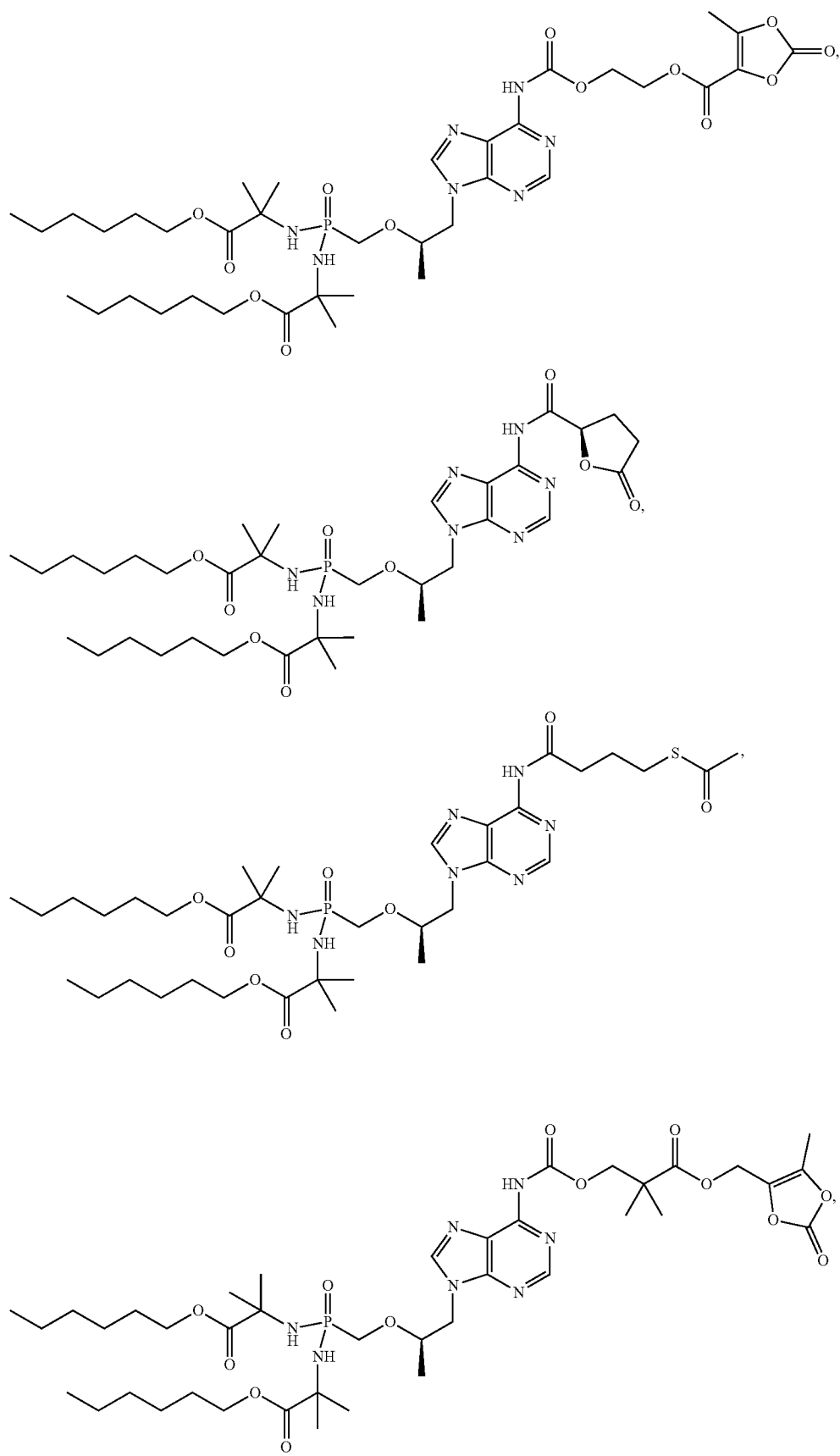

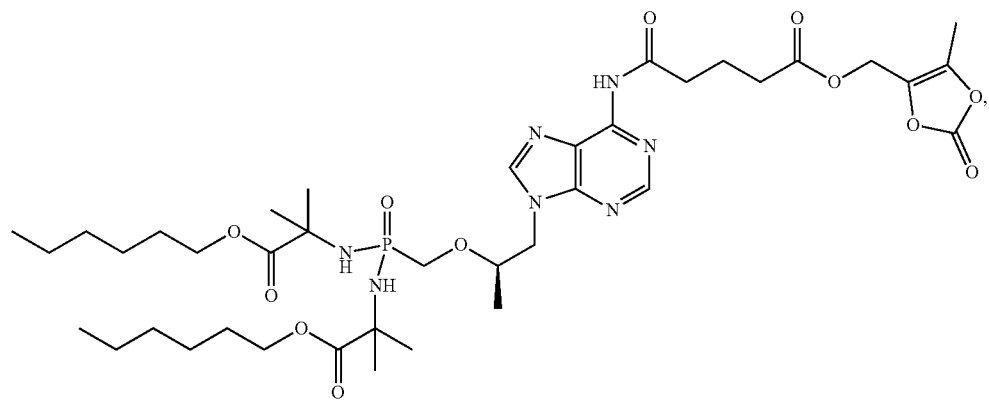
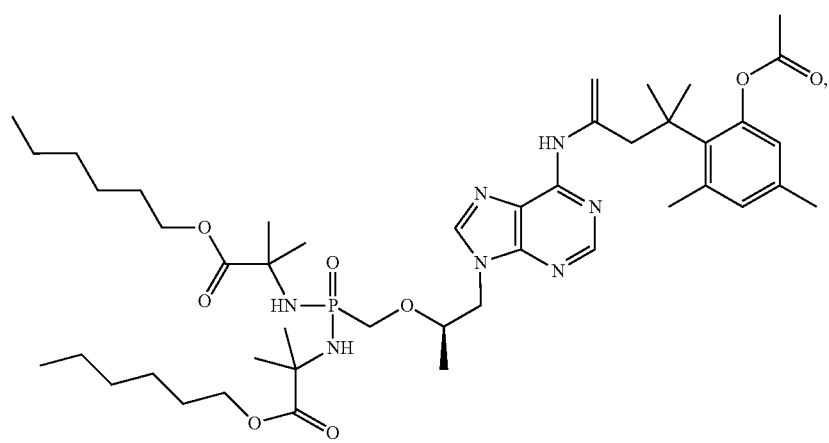
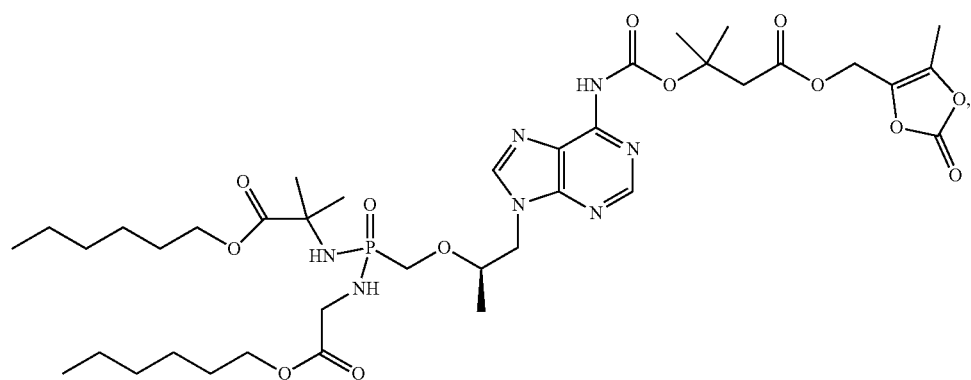
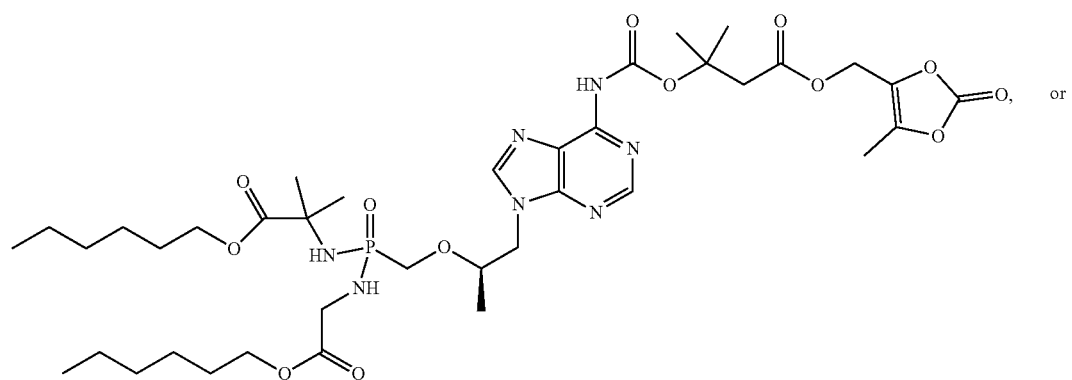

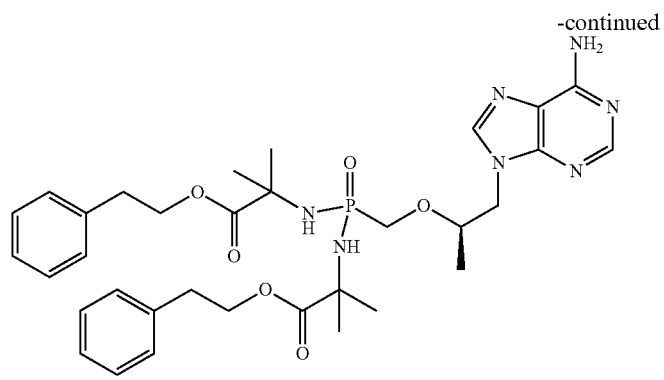
or a pharmaceutically acceptable salt thereof.
35. A compound of formula:
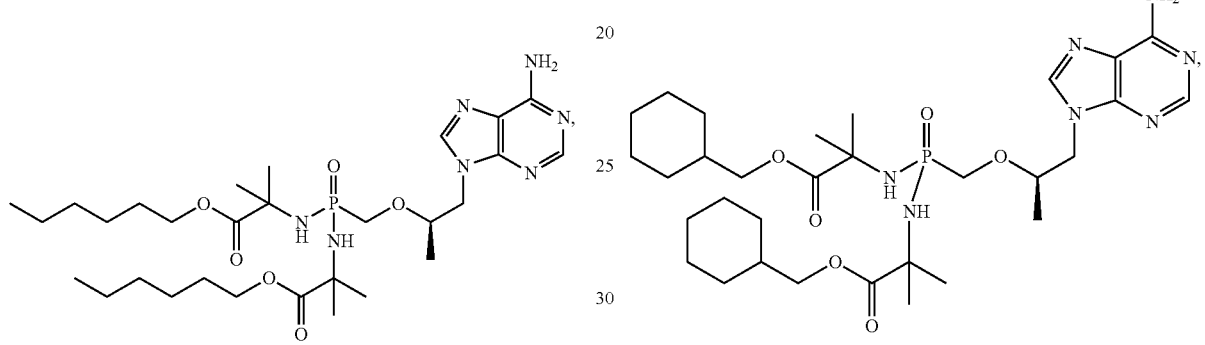
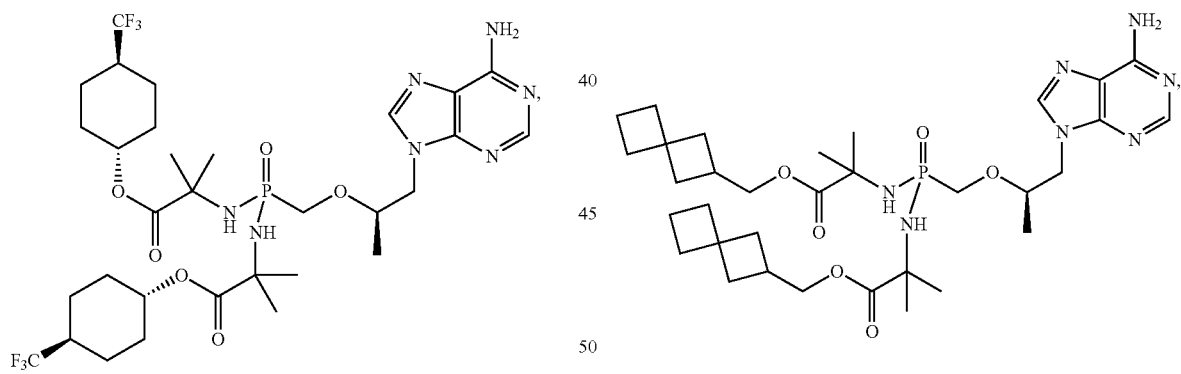
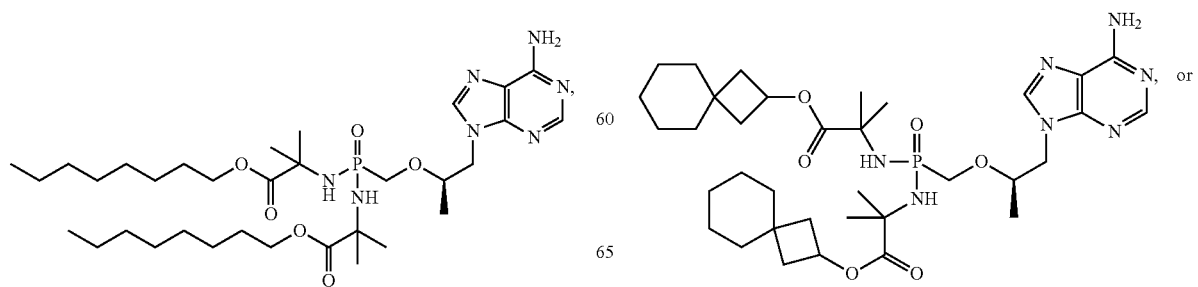

-continued

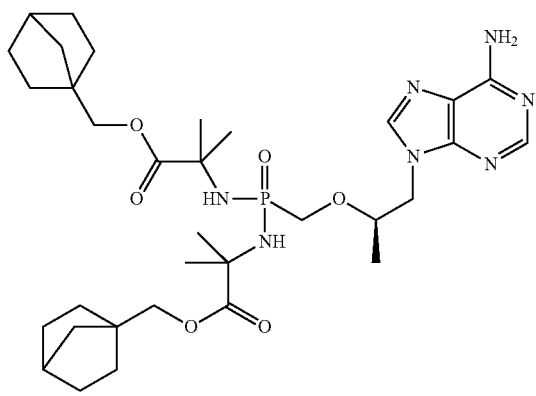

or a pharmaceutically acceptable salt thereof.

36. The compound of claim 1, having the formula

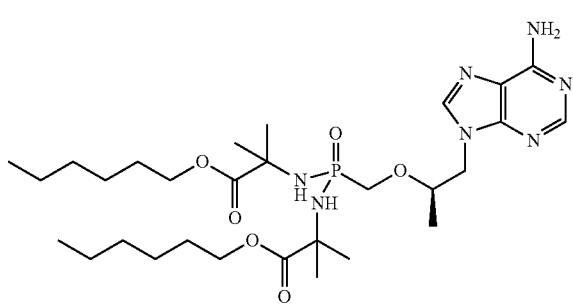 [SMILES: CCCCCCOC(=O)C(C)(C)NP(=O)(CO[C@H](C)Cn1cnc2c(N)ncnc21)NC(C)(C)C(=O)OCCCCCC]

or a pharmaceutically acceptable salt thereof.

37. The compound of claim 1, having the formula

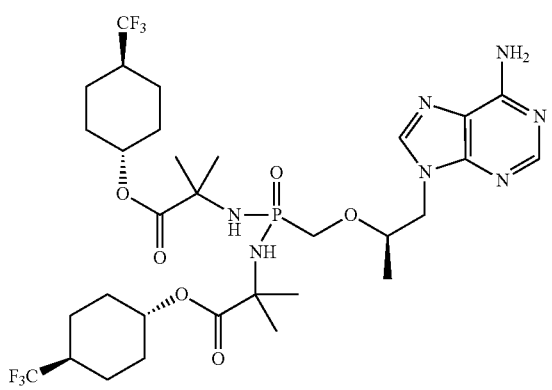 [SMILES: C[C@H](Cn1cnc2c(N)ncnc21)OCP(=O)(NC(C)(C)C(=O)O[C@H]1CC[C@H](C(F)(F)F)CC1)NC(C)(C)C(=O)O[C@H]1CC[C@H](C(F)(F)F)CC1]

or a pharmaceutically acceptable salt thereof.

38. The compound of claim 1, having the formula

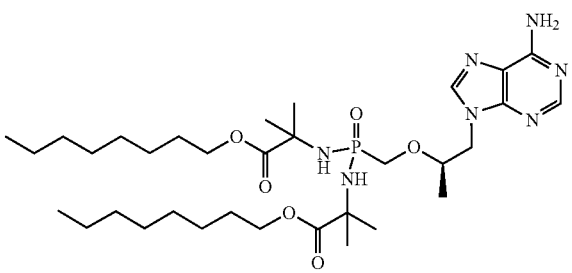 [SMILES: CCCCCCCCOC(=O)C(C)(C)NP(=O)(CO[C@H](C)Cn1cnc2c(N)ncnc21)NC(C)(C)C(=O)OCCCCCCCC]

or a pharmaceutically acceptable salt thereof.

39. The compound of claim 1, having the formula

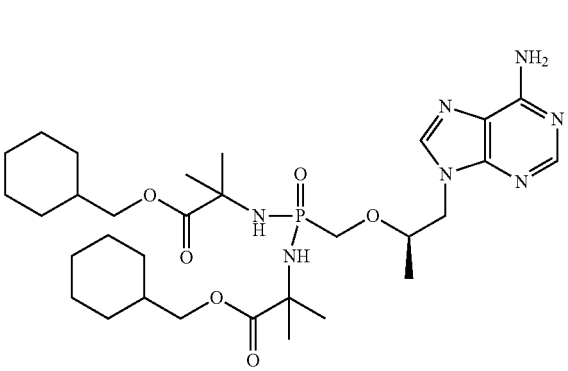 [SMILES: C[C@H](Cn1cnc2c(N)ncnc21)OCP(=O)(NC(C)(C)C(=O)OCC1CCCCC1)NC(C)(C)C(=O)OCC1CCCCC1]

or a pharmaceutically acceptable salt thereof.

40. The compound of claim 1, having the formula

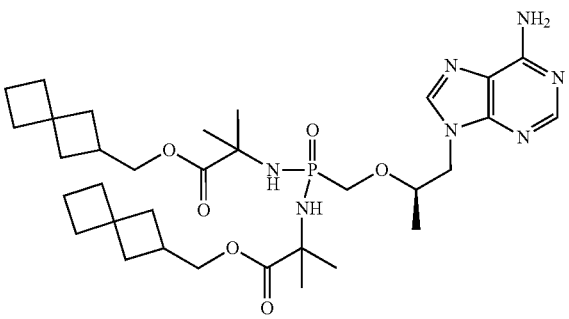 [SMILES: C[C@H](Cn1cnc2c(N)ncnc21)OCP(=O)(NC(C)(C)C(=O)OCC1CC2(CCC2)C1)NC(C)(C)C(=O)OCC1CC2(CCC2)C1]

or a pharmaceutically acceptable salt thereof.

41. The compound of claim 1, having the formula

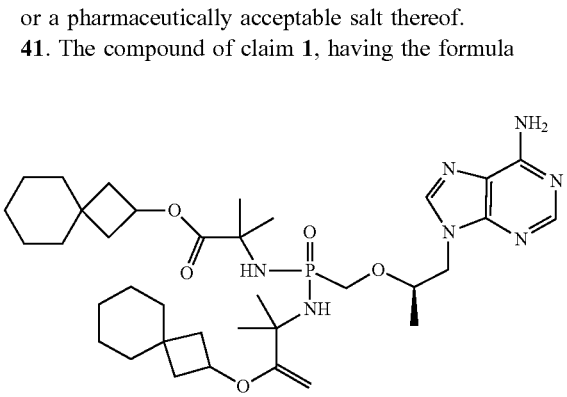

or a pharmaceutically acceptable salt thereof.

42. The compound of claim 1, having the formula

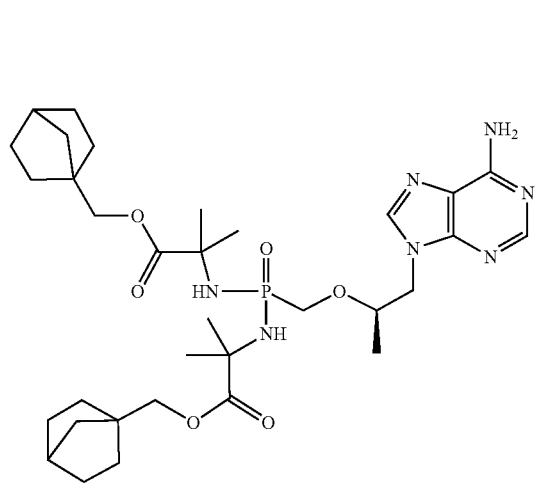 [SMILES: C[C@H](Cn1cnc2c(N)ncnc21)OCP(=O)(NC(C)(C)C(=O)OCC12CCC(CC1)C2)NC(C)(C)C(=O)OCC12CCC(CC1)C2]

or a pharmaceutically acceptable salt thereof.

43. The compound of claim 1, having the formula

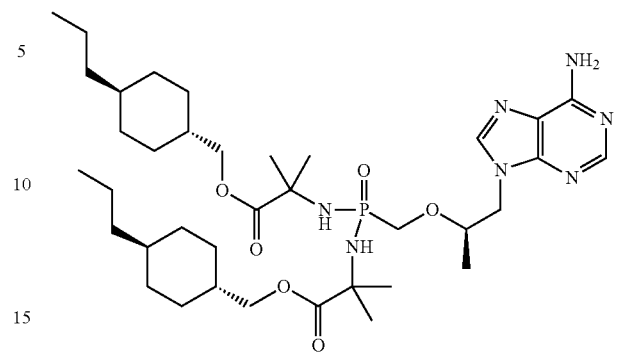

or a pharmaceutically acceptable salt thereof.

44. A pharmaceutical composition comprising a therapeutically effective amount of a compound of claim 1, or a pharmaceutically acceptable salt thereof, and a pharmaceutically acceptable excipient.

45. A method of treating an HIV infection, comprising administering to a subject in need thereof a therapeutically effective amount of a compound of claim 1, or a pharmaceutically acceptable salt thereof.

* * * * *